US011897862B2

(12) United States Patent
Balan et al.

(10) Patent No.: US 11,897,862 B2
(45) Date of Patent: *Feb. 13, 2024

(54) IKAROS ZINC FINGER FAMILY DEGRADERS AND USES THEREOF

(71) Applicant: Gilead Sciences, Inc., Foster City, CA (US)

(72) Inventors: Gayatri Balan, Bellevue, WA (US); Peter A. Blomgren, Issaquah, WA (US); Chen Chen, Newark, CA (US); Julian A. Codelli, Mountlake Terrace, WA (US); Zhimin Du, Belmont, CA (US); Musong Kim, Bellevue, WA (US); Dorothée Saddier Axe, San Carlos, CA (US); Gregg M. Schwarzwalder, Redwood City, CA (US); Rhiannon Thomas-Tran, San Jose, CA (US); Michael T. Tudesco, Chapel Hill, NC (US); Chandrasekar Venkataramani, San Carlos, CA (US); William J. Watkins, Saratoga, CA (US); Brian M. Weist, Dublin, CA (US); Suet C. Yeung, Redmond, WA (US); Helen Yu, Mountain View, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/297,316

(22) Filed: Apr. 7, 2023

(65) Prior Publication Data
US 2023/0295111 A1   Sep. 21, 2023

Related U.S. Application Data

(63) Continuation of application No. 18/184,335, filed on Mar. 15, 2023.

(60) Provisional application No. 63/386,605, filed on Dec. 8, 2022, provisional application No. 63/321,030, filed on Mar. 17, 2022.

(51) Int. Cl.
*C07D 401/04* (2006.01)

(52) U.S. Cl.
CPC ........ *C07D 401/04* (2013.01); *C07B 2200/05* (2013.01)

(58) Field of Classification Search
CPC .................... C07D 401/04; C07B 2200/05
See application file for complete search history.

(56) References Cited

U.S. PATENT DOCUMENTS

| 10,414,755 | B2 | 9/2019 | Beckwith et al. |
| 10,640,489 | B2 | 5/2020 | Beckwith et al. |
| 10,647,701 | B2 | 5/2020 | Beckwith et al. |
| 11,185,537 | B2 | 11/2021 | Beckwith et al. |
| 11,192,877 | B2 | 12/2021 | Adcock et al. |

FOREIGN PATENT DOCUMENTS

| CN | 114835680 A | 8/2022 |
| WO | WO-2009145899 A1 | 12/2009 |
| WO | WO-2018102725 A1 | 6/2018 |
| WO | WO-2018140809 A1 | 8/2018 |
| WO | WO-2019038717 A1 | 2/2019 |
| WO | WO-2019199816 A1 | 10/2019 |
| WO | WO-2019241274 A1 | 12/2019 |
| WO | WO-2020006264 A1 | 1/2020 |
| WO | WO-2020012334 A1 | 1/2020 |
| WO | WO-2020012337 A1 | 1/2020 |
| WO | WO-2020128972 A1 | 6/2020 |
| WO | WO-2020165833 A1 | 8/2020 |
| WO | WO-2020165834 A1 | 8/2020 |
| WO | WO-2020242960 A1 | 12/2020 |
| WO | WO-2020243379 A1 | 12/2020 |
| WO | WO-2021087093 A1 | 5/2021 |
| WO | WO-2021101919 A1 | 5/2021 |
| WO | WO-2021147889 A1 | 7/2021 |
| WO | WO-2021194914 A1 | 9/2021 |
| WO | WO-2021222542 A1 | 11/2021 |
| WO | WO-2021236885 A1 | 11/2021 |
| WO | WO-2021260528 A1 | 12/2021 |
| WO | WO-2022029138 A1 | 2/2022 |
| WO | WO-2022029573 A1 | 2/2022 |
| WO | WO-2022047145 A1 | 3/2022 |
| WO | WO-202268066 A1 | 4/2022 |
| WO | WO-2022081976 A1 | 4/2022 |
| WO | WO-2022187423 A1 | 9/2022 |
| WO | WO-2022216644 A1 | 10/2022 |
| WO | WO-2022219407 A1 | 10/2022 |
| WO | WO-2022219412 A1 | 10/2022 |
| WO | WO-2022232391 A1 | 11/2022 |

(Continued)

OTHER PUBLICATIONS

U.S. Appl. No. 18/184,335, filed Mar. 15, 2023, Gayatri Balan, et al.
U.S. Appl. No. 18/068,700, filed Dec. 20, 2022, Gayatri Balan, et al.
U.S. Appl. No. 18/069,028, filed Dec. 20, 2022, Gayatri Balan, et al.
Hansen et al., "Protein Degradation via CRL4 CRBN Ubiquitin Ligase: Discovery and Structure-Activity Relationships of Novel Glutarimide Analogs That Promote Degradation of Aiolos and/or GSPT1", J Med Chem. Jan. 25, 2018;61(2):492-503.

(Continued)

*Primary Examiner* — Susanna Moore
*Assistant Examiner* — Luisalberto Gonzalez

(57) ABSTRACT

The present disclosure relates generally to compounds that bind to and act as degraders of an IKAROS Family Zinc Finger (IKZF) protein, such as IKZF2 (Helios) and/or IKZF4 (Eos). The disclosure further relates to the use of the compounds for the preparation of a medicament for the treatment of diseases and/or conditions through binding and degradation of an IKZF protein, such as IKZF2 and/or IKZF4, including cancer.

10 Claims, 4 Drawing Sheets

Specification includes a Sequence Listing.

(56) References Cited

FOREIGN PATENT DOCUMENTS

| WO | WO-2022232536 A1 | 11/2022 |
| --- | --- | --- |
| WO | WO-2022253250 A1 | 12/2022 |
| WO | WO-2022254362 A1 | 12/2022 |
| WO | WO-2022257897 A1 | 12/2022 |
| WO | WO-2023283425 A1 | 1/2023 |
| WO | WO-2023283428 A1 | 1/2023 |
| WO | WO-2023283430 A1 | 1/2023 |
| WO | WO-2023288305 A1 | 1/2023 |
| WO | WO-2023056443 A1 | 4/2023 |
| WO | WO-2023116835 A1 | 6/2023 |

OTHER PUBLICATIONS

Hansen et al., "CC-90009: A Cereblon E3 Ligase Modulating Drug That Promotes Selective Degradation of GSPT1 for the Treatment of Acute Myeloid Leukemia", J Med Chem. Feb. 25, 2021;64(4):1835-1843.

Lindner et al., "The molecular mechanism of thalidomide analogs in hematologic malignancies", J Mol Med (Berl). Dec. 2016;94(12):1327-1334.

International Search Report and Written Opinion dated Jun. 6, 2023 for Int'l Appl. No. PCT/US2023/064438.

European Search Report dated Jul. 14, 2023 for European Appl. No. 23162114.5.

IKAROS ZINC FINGER FAMILY DEGRADERS AND USES THEREOF

CROSS-REFERENCES TO RELATED APPLICATIONS

This is a Continuation application of U.S. patent application Ser. No. 18/184,335, filed Mar. 15, 2023, which claims the benefit under 35 U.S.C. § 119(e) of U.S. provisional application No. 63/321,030, filed on Mar. 17, 2022, and of U.S. provisional application No. 63/386,605, filed on Dec. 8, 2022, which are hereby incorporated herein by reference in their entireties for all purposes.

FIELD

The present disclosure relates to compounds that bind to and act as degraders of an IKAROS Family Zinc Finger (IKZF) protein, such as IKZF2 (Helios) and/or IKZF4 (Eos). The disclosure further relates to the use of the compounds for the treatment and/or prophylaxis of diseases and/or conditions associated with one or more IKZF proteins, e.g., an IKZF2 and/or IKZF4 associated disease or condition where reduction of IKZF2 and/or IKZF4 protein levels can ameliorate the disease or disorder.

SEQUENCE LISTING

The instant application contains a Sequence Listing which has been submitted electronically in .XML file format and is hereby incorporated by reference in its entirety. Said .XML copy, created on created on Feb. 21, 2023, is named 1423-US-NP.xml and is 2,745 bytes in size.

BACKGROUND

The IKAROS family of transcription factors includes five members: Ikaros (IKZF1), Helios (IKZF2), Aiolos (IKZF3), Eos (IKZF4), and Pegasus (IKZF5). Helios is about 50% identical with Ikaros, Aiolos, and Eos, and binds to the same DNA consensus site. When co-expressed in cells these four IKZF proteins can heterodimerize with each other. While Ikaros, Helios, and Aiolos are predominantly expressed in hematopoietic cells, Eos and Pegasus are more widely expressed across different tissues.

Regulatory T cells (Tregs) are a subset of CD4+ T cells that maintain normal immune tolerance and homeostasis. Treg activity can also repress antitumor immune responses. Helios is believed to be required to maintain a stable Treg phenotype, especially in the context of inflammatory tumor microenvironments. Genetic Helios knockout in Tregs has been shown to reduce Treg immunosuppressive activity and induce an effector T cell phenotype. A first generation of small molecule Helios degraders has shown similar effects. As such Helios has emerged as a promising immuno-oncology target. Moreover, Helios degraders are expected to be useful for the treatment of chronic viral infections, which are also characterized by the presence of elevated levels of activated Tregs.

A need remains for Helios degraders with desirable selectivity, potency, metabolic stability, or reduced detrimental effects.

SUMMARY

The present disclosure provides compounds useful as degraders of IKAROS Family Zinc Finger (IKZF) protein 2 (IKZF2; Helios). The disclosure further relates to the use of the compounds for the treatment and/or prophylaxis of diseases and/or conditions through binding and degradation of IKZF2 protein by said compounds.

In one embodiment, provided herein is a compound of Formula (I),

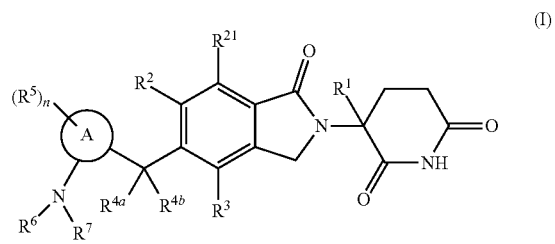

or a pharmaceutically acceptable salt thereof, wherein:
$R^1$ is —H;
$R^2$ is —H, —F, or —Cl;
$R^{21}$ is —H, —F, or —Cl;
$R^3$ is —H, —F, or —Cl;
$R^{4a}$ and $R^{4b}$ are each independently —H, halogen, —OH, or $C_{1-6}$ alkyl;
Ring A is $C_{3-10}$ cycloalkyl or heterocyclyl;
n is 0, 1, 2, 3, or 4;
each $R^5$ is independently halogen, =O, =CH$_2$, —CN, $C_{1-6}$ alkyl, $C_{2-6}$ alkenyl, $C_{1-6}$ haloalkyl, $C_{1-6}$ alkoxy, $C_{1-6}$ haloalkoxy, $C_{3-6}$ cycloalkyl, heterocyclyl, $C_{6-10}$ aryl, heteroaryl, —O—($R^{51}$), or —N($R^{51}$)($R^{52}$);
wherein each =CH$_2$, alkyl, alkenyl, cycloalkyl, alkoxy, haloalkyl, haloalkoxy, heterocyclyl, aryl, or heteroaryl of $R^5$ is optionally substituted with one to four $R^{5a}$, which may be the same or different;
each $R^{5a}$ is independently halogen, —CN, $C_{1-6}$ alkyl, $C_{6-10}$ aryl, or —O($R^{51}$);
wherein each $R^{51}$ and $R^{52}$, which may be the same or different, is independently —H, $C_{1-6}$ alkyl, $C_{3-10}$ cycloalkyl, heterocyclyl, $C_{6-10}$ aryl, or heteroaryl;
$R^6$ is —H, $C_{1-8}$alkyl, $C_{1-6}$ haloalkyl, $C_{3-12}$ cycloalkyl, heterocyclyl, aryl, heteroaryl, —C(O)N($R^{1a}$)($R^{1b}$), —S(O)(NR$^{1a}$)($R^{1b}$), —C(O)$R^{1c}$, —S(O$_2$)$R^{1c}$, or —C(O)OR$^{1d}$,
wherein the alkyl, haloalkyl, cycloalkyl, aryl, heteroaryl, or heterocyclyl of $R^6$ is each optionally substituted with one to four $Z^1$, which may be the same or different;
$R^7$ is —H, $C_{1-8}$alkyl, $C_{1-6}$ haloalkyl, $C_{3-12}$cycloalkyl, heterocyclyl, aryl, heteroaryl, —C(O)N($R^{2a}$)($R^{2b}$), —S(O)(NR$^{2a}$)($R^{2b}$), —C(O)$R^{2c}$, S(O$_2$)$R^{2c}$, or —C(O)OR$^{2d}$,
wherein the alkyl, haloalkyl, cycloalkyl, aryl, heteroaryl, or heterocyclyl of $R^7$ is each optionally substituted with one to four $Z^2$, which may be the same or different; or
$R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 20 membered heterocyclyl having 0 to 3 additional heteroatoms each independently N, O or S;
each $Z^1$, $Z^2$, or $Z^3$ is independently deuterium, $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, =O, imino, —NO$_2$, —N$_3$, —CN, —O—$R^{3a}$, —C(O)—$R^{3a}$, —C(O)O—$R^{3a}$, —C(O)—N($R^{3a}$)($R^{3b}$), —N($R^{3a}$)

($R^{3b}$), —N($R^{3a}$)$_2$($R^{3b}$)$^+$, —N($R^{3a}$)C(O)—$R^{3b}$, —N($R^{3a}$)C(O)O—$R^{3b}$, —N($R^{3a}$)C(O)N($R^{3b}$)($R^{3c}$), —N($R^{3a}$)S(O)$_2$($R^{3b}$), —N$R^{3a}$S(O)$_2$N($R^{3b}$)($R^{3c}$), —N$R^{3a}$S(O)$_2$O($R^{3b}$), —OC(O)$R^{3a}$, —OC(O)O$R^{3b}$, —OC(O)—N($R^{3a}$)($R^{3b}$), —S—$R^{3a}$, —S(O)$R^{3a}$, —S(O)(NH)$R^{3a}$, —S(O)$_2$$R^{3a}$, —S(O)$_2$N($R^{3a}$)($R^{3b}$), —S(O)(N$R^{3a}$)$R^{3b}$, —S(O)(N$R^{3a}$)N($R^{3b}$)($R^{3c}$), —SF$_5$, or —Si($R^{3a}$)$_3$;

wherein the alkyl, haloalkyl, alkenyl, alkynyl, cycloalkyl, heterocyclyl, aryl, or heteroaryl of each $Z^1$, $Z^2$, or $Z^3$ is each optionally substituted with one to four $Z^{1a}$, which may be the same or different;

each $Z^{1a}$ is independently deuterium, $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, =O, —NO$_2$, —CN, —N$_3$, —O—$R^{3a}$, —C(O)$R^{3a}$, —C(O)O—$R^{3a}$, —C(O)N($R^{3a}$)($R^{3b}$), —N($R^{3a}$)($R^{3b}$), —N($R^{3a}$)$_2$($R^{3b}$)$^+$, —N($R^{3a}$)—C(O)$R^{3b}$, —N($R^{3a}$)C(O)O($R^{3b}$), —N($R^{3a}$)C(O)N($R^{3b}$)($R^{3c}$), —N($R^{3a}$)S(O)$_2$($R^{3b}$), —N($R^{3a}$)S(O)$_2$—N($R^{3b}$)($R^{3c}$), —N($R^{3a}$)S(O)$_2$O($R^{3b}$), —OC(O)$R^{3a}$, —OC(O)O$R^{3a}$, —OC(O)—N($R^{3a}$)($R^{3b}$), —S—$R^{3a}$, —S(O)$R^{3a}$, —S(O)(NH)$R^{3a}$, —S(O)$_2$$R^{3a}$, —S(O)$_2$N($R^{3a}$)($R^{3b}$), —S(O)(N$R^{3a}$)$R^{3b}$, or —Si($R^{3a}$)$_3$;

wherein the alkyl, haloalkyl, alkenyl, alkynyl, cycloalkyl, heterocyclyl, aryl, or heteroaryl of $Z^{1a}$ is each optionally substituted with one to four $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl of $Z^{1b}$ is optionally substituted with one to three $C_{1-9}$ alkyl, $C_{1-8}$ haloalkyl, halogen, —OH, —NH$_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH (aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O (heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

each $R^{1a}$, $R^{1b}$, $R^{1c}$, $R^{1d}$, $R^{2a}$, $R^{2b}$, $R^{2c}$, $R^{2a}$, $R^{3a}$, $R^{3b}$, and $R^{3c}$, is independently —H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl, wherein the alkyl, alkenyl, alkynyl, cycloalkyl, heterocyclyl, aryl, or heteroaryl of each $R^{1a}$, $R^{1b}$, $R^{1c}$, $R^{1d}$, $R^{2a}$, $R^{2b}$, $R^{2c}$, $R^{2a}$, $R^{3c}$, $R^{3b}$, and $R^{3c}$, is each optionally substituted with one to four $Z^{1b}$, which may be the same or different;

wherein each aryl of the compound of Formula (I) unless otherwise specified is $C_{6-10}$ aryl;

wherein each heteroaryl of the compound of Formula (I) unless otherwise specified is 5 to 12 membered heteroaryl having one to four heteroatoms each independently N, O, or S;

wherein each heterocyclyl of the compound of Formula (I) unless otherwise specified is 3 to 20 membered heterocyclyl having one to four heteroatoms each independently N, O, or S.

In some embodiments, provided herein are pharmaceutical compositions comprising a compound provided herein, or pharmaceutically acceptable salt thereof, and a pharmaceutically acceptable excipient or carrier. In some embodiments, the pharmaceutical compositions comprise a therapeutically effective amount of a compound provided herein, or pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or pharmaceutically acceptable salts thereof. In some embodiments, the pharmaceutical compositions further comprise a therapeutically effective amount of the one or more (e.g., one, two, three, four, one or two, one to three, or one to four) additional therapeutic agents, or pharmaceutically acceptable salts thereof.

In some embodiments, the present disclosure provides methods of degrading IKZF2 protein in a subject in need thereof, comprising administering to the subject a therapeutically effective amount of a compound provided herein (e.g., a compound of Formula (I), (Ia), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (IVb), (V), (Va), (VI), or (VIa)), or pharmaceutically acceptable salt thereof, or a pharmaceutical composition provided herein.

In some embodiments, the present disclosure provides methods of treating a patient having an IKZF2 protein mediated condition, comprising administering to the patient a therapeutically effective amount of a compound provided herein (e.g., a compound of Formula (I), (Ia), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (IVb), (V), (Va), (VI), or (VIa)), or pharmaceutically acceptable salt thereof, or a pharmaceutical composition provided herein.

In some embodiments, the present disclosure provides methods of treating a cancer patient, comprising administering to the cancer patient a therapeutically effective amount of a compound provided herein (e.g., a compound of Formula (I), (Ia), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (IVb), (V), (Va), (VI), or (VIa)), or pharmaceutically acceptable salt thereof, or a pharmaceutical composition provided herein.

In some embodiments, the present disclosure provides uses of a compound provided herein (e.g., a compound of Formula (I), (Ia), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (IVb), (V), (Va), (VI), or (VIa)), or pharmaceutically acceptable salt thereof, for the manufacture of a medicament for the treatment of an IKFZ2 associated disease or condition.

In some embodiments, the present disclosure provides uses of a compound provided herein (e.g., a compound of Formula (I), (Ia), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (IVb), (V), (Va), (VI), or (VIa)), or pharmaceutically acceptable salt thereof, for the manufacture of a medicament for the treatment of cancer.

In some embodiments, the present disclosure provides a compound provided herein (e.g., a compound of Formula (I), (Ia), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (IVb), (V), (Va), (VI), or (VIa)), or pharmaceutically acceptable salt thereof, or a pharmaceutical composition comprising a compound provided herein for pharmaceutical use.

In some embodiments, the present disclosure provides a compound provided herein (e.g., a compound of Formula (I), (Ia), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (IVb), (V), (Va), (VI), or (VIa)), or pharmaceutically acceptable salt thereof, or a pharmaceutical composition comprising a compound provided herein for the treatment of an IKFZ2 associated disease or condition.

In some embodiments, the present disclosure provides a compound provided herein (e.g., a compound of Formula (I), (Ia), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (IVb), (V), (Va), (VI), or (VIa)), or pharmaceutically acceptable salt thereof, or a pharmaceutical composition comprising a compound provided herein for the treatment of cancer.

DETAILED DESCRIPTION

Figure 1A:
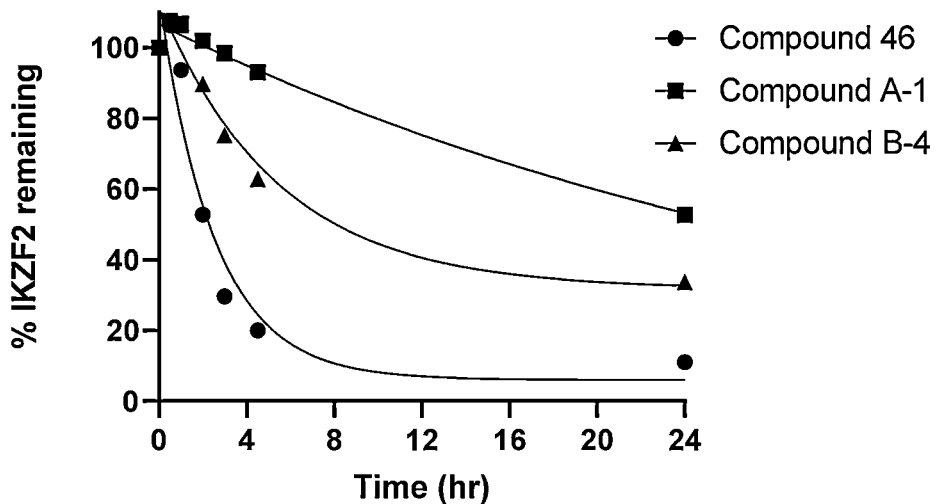
FIG. 1A shows a timecourse for IKZF2 (Helios) degradation in HEK293 cells. The compound of Example 46 (Compound 46; solid circle) and Reference Compounds A-1 (Compound A-1; solid square) and B-4 (Compound B-4; solid triangle) were tested at a concentration of 12 nM. Percent IKZF2 remaining (normalized relative to a DMSO control) is plotted over time.
Figure 1B:
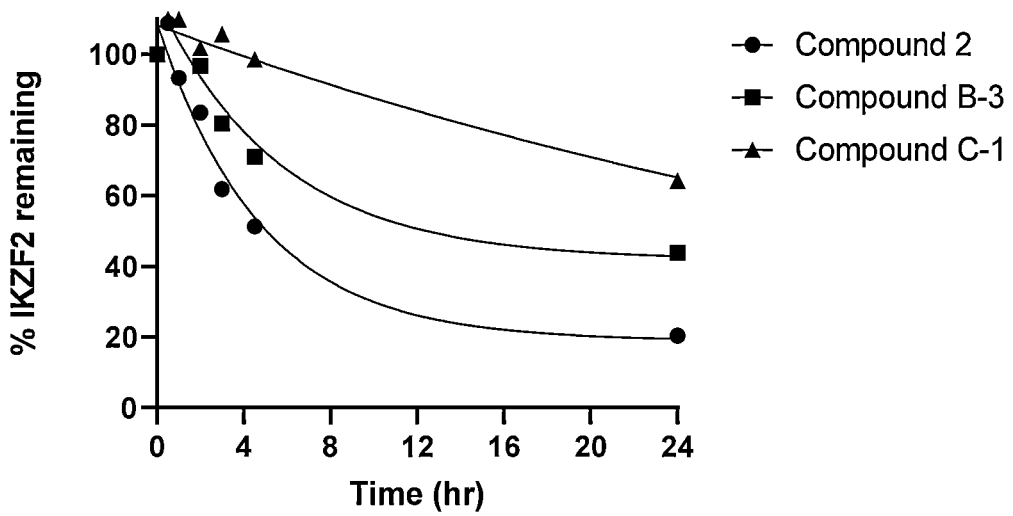
FIG. 1B shows a timecourse for IKZF2 (Helios) degradation in HEK293 cells. The compound of Example 2 (Compound 2; solid circle) and Reference Compounds B-3 (Compound B-3; solid square) and C-1 (Compound C-1; solid triangle) were tested at a concentration of 111 nM. Percent IKZF2 remaining (normalized relative to a DMSO control) is plotted over time.
Figure 2A:
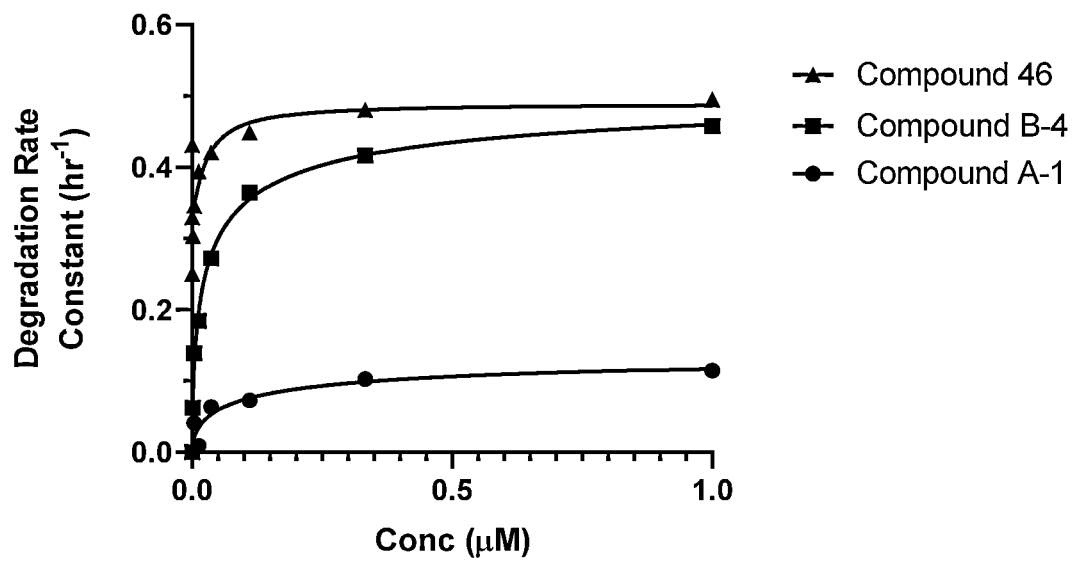
FIG. 2A shows a plot of IKZF2 (Helios) degradation rate constants vs. compound concentrations observed in HEK293 cells for the compound of Example 46 (Compound 46; solid triangle) and Reference Compounds A-1 (Compound A-1; solid circle) and B-4 (Compound B-4; solid square).
Figure 2B:
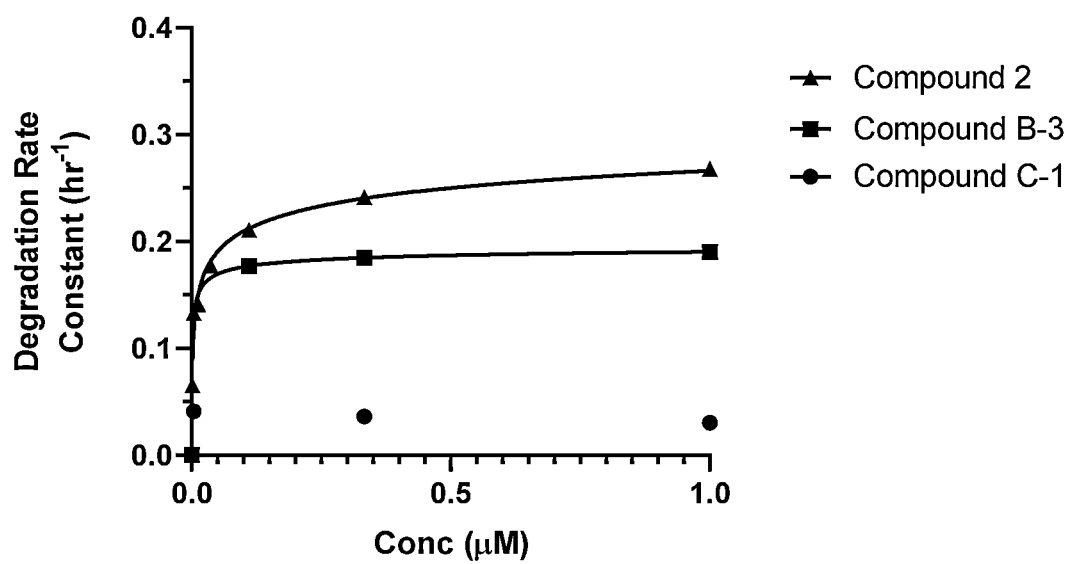
FIG. 2B shows a plot of IKZF2 (Helios) degradation rate constants vs. compound concentrations observed in HEK293 cells for the compound of Example 2 (Compound 2; solid triangle) and Reference Compounds B-3 (Compound B-3; solid square) and C-1 (Compound C-1; solid circle).

The present disclosure relates to degraders of IKAROS Family Zinc Finger (IKZF) proteins, such as IKZF2 (Helios). The disclosure also relates to compositions and methods relating to IKZF2 protein degraders and the use of such compounds for treatment and/or prophylaxis of IKZF2-mediated diseases and conditions. The disclosure also relates to compositions and methods of treating and/or preventing cancer or viral infections that include an IKZF2 protein degrader in combination with one or more additional therapeutic agents.

It is commonly believed that patients with certain IKZF2-mediated diseases, such as cancer and viral infections can benefit from the treatment with an IKZF2 protein degrader and optionally one or more additional therapeutic agents.

DEFINITIONS AND GENERAL PARAMETERS

The description below is made with the understanding that the present disclosure is to be considered as an exemplification of the claimed subject matter and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present specification, the following terms and phrases are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring indicates that the point of attachment for a substituent on the ring can be at any ring atom. For example, Ra in the below structure can be attached to any of the five carbon ring atoms or Ra can replace the hydrogen attached to the nitrogen ring atom:

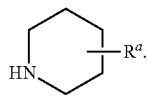

The prefix "C$_{u-v}$" indicates that the following group has from u to v carbon atoms. For example, "C$_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (e.g., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula (I), (Ia), (Ib), or (Ic). Also included are the specific compounds of Examples 1 to 339 provided herein.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 8 carbon atoms (i.e., C$_{1-8}$ alkyl), 1 to 6 carbon atoms (i.e., C$_{1-6}$ alkyl), 1 to 4 carbon atoms (i.e., C$_{1-4}$ alkyl), or 1 to 3 carbon atoms (i.e., C$_{1-3}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

"Alkenyl" refers to an aliphatic group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Alkoxy" refers to an alkyl group having an oxygen atom that connects the alkyl group to the point of attachment: alkyl-O—. As for alkyl group, alkoxy groups will have any suitable number of carbon atoms, such as C$_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers an alkoxy group linked to an alkyl group which is linked to the remainder of the compound. Alkoxyalkyl have any suitable number of carbon, such as from 2 to 6 ($C_{2-6}$ alkoxyalkyl), 2 to 5 ($C_{2-5}$ alkoxyalkyl), 2 to 4 ($C_{2-4}$ alkoxyalkyl), or 2 to 3 ($C_{2-3}$ alkoxyalkyl). The number of carbons refers to the total number of carbons in the alkoxy and the alkyl group. For example, in some embodiments, $C_6$ alkoxyalkyl refers to ethoxy ($C_2$ alkoxy) linked to a butyl ($C_4$ alkyl), and in other embodiments, n-propoxy ($C_3$ alkoxy) linked to isopropyl ($C_3$ alkyl). Alkoxy and alkyl are as defined above where the alkyl is divalent, and can include, but is not limited to, methoxymethyl ($CH_3OCH_2$—), methoxyethyl ($CH_3OCH_2CH_2$—) and others.

"Amino" refers to the group —$NR^yR^z$ wherein $R^y$ and $R^z$ are independently selected from the group consisting of hydrogen, alkyl, haloalkyl, aryl, heteroaryl, cycloalkyl, or heterocyclyl; each of which may be optionally substituted.

"Imino" refers to a group containing a carbon-nitrogen double bond having the structure

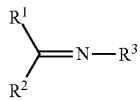

wherein $R^1$, $R^2$, and $R^3$ are independently selected from the group consisting of hydrogen, alkyl, haloalkyl, aryl, heteroaryl, cycloalkyl, or heterocyclyl; each of which may be optionally substituted. Either one of $R^1$, $R^2$, and $R^3$ can serve as points of attachment.

"Aryl" as used herein refers to a single all carbon aromatic ring or a multicyclic all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multicyclicring systems (e.g., ring systems comprising 2, 3 or 4 rings) having 9 to 20 carbon atoms, e.g., 9 to 16 carbon atoms, in which at least one ring is aromatic and wherein the other rings may be aromatic or not aromatic (i.e., carbocycle). Such multicyclicring systems are optionally substituted with one or more (e.g., 1, 2 or 3) oxo groups on any carbocycle portion of the multicyclic ring system. The rings of the multicyclic ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Fused" refers to a ring which is bound to an adjacent ring. In some embodiments the fused ring system is a heterocyclyl. In some embodiments the fused ring system is a oxabicyclohexanyl. In some embodiments the fused ring system is

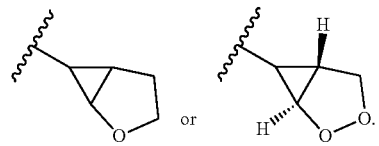 [SMILES: *C1C2CCOC12 ; *C1[C@@H]2COO[C@@H]12]

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems. In some embodiments the bridged ring is a bicyclopentyl (e.g., bicyclo[1.1.1]pentyl), bicycloheptyl (e.g., bicyclo[2.2.1]heptyl, bicyclo[3.1.1]heptyl), or bicyclooctyl (e.g., bicyclo[2.2.2]octyl). In some embodiments, the bridged ring

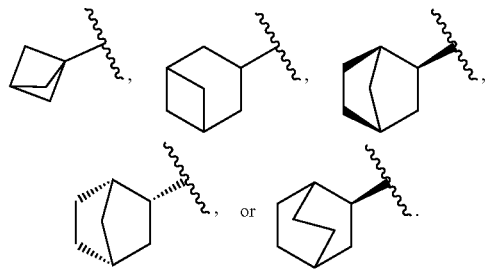

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. In some embodiments the spiro substituent is a spiropentanyl (spiro[a.b]pentanyl), spirohexanyl, spiroheptanyl, spirooctyl (e.g., spiro[2.5]octyl), spirononanyl (e.g., spiro[3.5]nonanyl), spirodecanyl (e.g., spiro[4.5]decanyl), or spiroundecanyl (e.g., spiro[5.5]undecanyl). In some embodiments the spiro substituent is

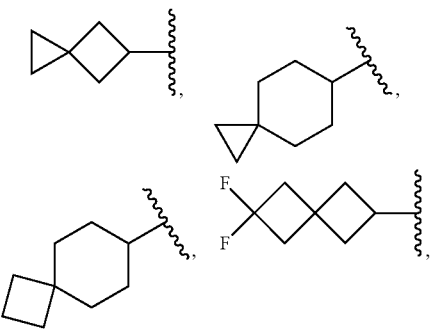

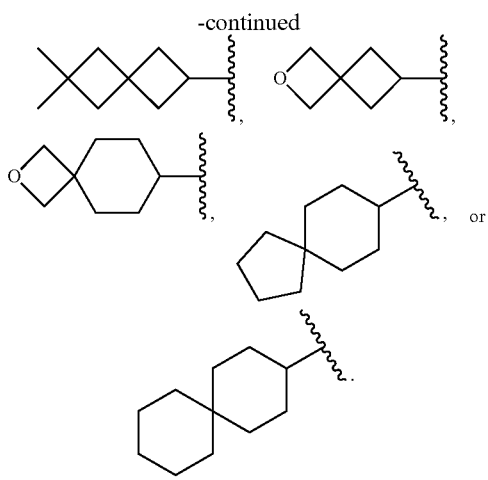

"Halogen" or "halo" includes fluoro, chloro, bromo, and iodo.

"Haloalkyl" as used herein refers to an alkyl as defined herein, wherein one or more hydrogen atoms of the alkyl are independently replaced by a halo substituent, which may be the same or different. For example, $C_{1-4}$ haloalkyl is a $C_{1-4}$ alkyl wherein one or more of the hydrogen atoms of the $C_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2-trifluoroethoxy, perfluoroethoxy, etc.

The term "heteroaryl" as used herein refers to a single aromatic ring or a multicyclic ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multicyclic ring systems (e.g. ring systems comprising 2 or 3 rings) wherein a heteroaryl group, as defined above, can be fused with one or more heteroaryls (e.g. naphthyridinyl), carbocycles (e.g. 5,6,7,8-tetrahydroquinolyl) or aryls (e.g. indazolyl) to form a multicyclic ring. Such multicyclic rings may be optionally substituted with one or more (e.g. 1, 2 or 3) oxo groups on the carbocycle portions of the multicyclic ring. It is to be understood that the point of attachment of a heteroaryl multicyclic ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

"Heterocyclyl" or "heterocyclic ring" or "heterocycle" as used herein refers to a single saturated or partially unsaturated ring or a multicyclic ring. The term includes single saturated or partially unsaturated ring (e.g. 3, 4, 5, 6 or 7-membered ring) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term also includes multicyclic ring systems (e.g. ring systems comprising 2 or 3 rings) wherein a heterocycle group (as defined above) can be connected to two adjacent atoms (fused heterocycle) with one or more heterocycles (e.g. decahydronapthyridinyl), heteroaryls (e.g. 1,2,3,4-tetrahydronaphthyridinyl), carbocycles (e.g. decahydroquinolyl) or aryls. It is to be understood that the point of attachment of a heterocycle multicyclic ring, as defined above, can be at any position of the ring including a heterocyle, heteroaryl, aryl or a carbocycle portion of the ring. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolinyl, benzoxazinyl, dihydrooxazolyl, chromanyl, 1,2-dihydropyridinyl, 2,3-dihydrobenzofuranyl, 1,3-benzodioxolyl and 1,4-benzodioxanyl. Exemplary fused bicyclic heterocycles include, but are not limited to

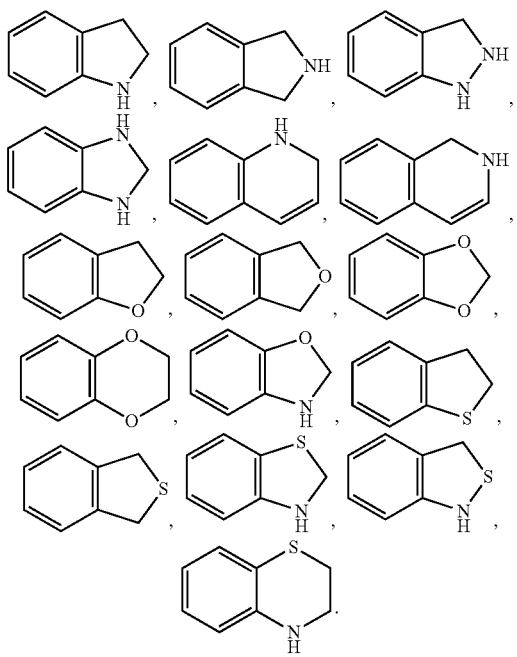

"Hydroxy" or "hydroxyl" refers to the group —OH.

"Oxo" refers to the group (=O) or (O).

"Sulfonyl" refers to the group —S(O)$_2$R$^c$, where R$^c$ is alkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH$_2$ group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl.

Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, amino, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, amino, alkoxy, halo, oxo, and hydroxyl; "substituted heterocyclyl" refers to a heterocyclyl group having one or more substituents including alkyl, amino, haloalkyl, heterocyclyl, cycloalkyl, aryl, heteroaryl, alkoxy, halo, oxo, and hydroxyl; "substituted aryl" refers to an aryl group having one or more substituents including halo, alkyl, amino, haloalkyl, cycloalkyl, heterocyclyl, heteroaryl, alkoxy, and cyano; "substituted heteroaryl" refers to an heteroaryl group having one or more substituents including halo, amino, alkyl, haloalkyl, cycloalkyl, aryl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

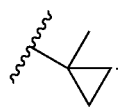

The disclosures illustratively described herein may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. In case the compounds of the present disclosure contain one or more acidic or basic groups, the disclosure also comprises their corresponding pharmaceutically or toxicologically acceptable salts, in particular their pharmaceutically utilizable salts. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine, amino acids, or other bases known to persons skilled in the art. The compounds of the present disclosure which contain one or more basic groups, i.e., groups which can be protonated, can be present and can be used according to the disclosure in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to persons skilled in the art.

If the compounds of the present disclosure simultaneously contain acidic and basic groups in the molecule, the disclosure also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts.

The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources.

Furthermore, compounds disclosed herein may be subject to tautomerism. Where tautomerism, e.g., keto-enol tautomerism, of compounds or their prodrugs may occur, the individual forms, like, e.g., the keto and enol form, are each within the scope of the disclosure as well as their mixtures in any ratio. The same applies for stereoisomers, like, e.g., enantiomers, cis/trans isomers, diastereomers, conformers, and the like.

The term "protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. The term "deprotecting" refers to removing the protecting group.

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

Further the compounds of the present disclosure may be present in the form of solvates, such as those which include as solvate water, or pharmaceutically acceptable solvates, such as alcohols, in particular ethanol. A "solvate" is formed by the interaction of a solvent and a compound.

In certain embodiments, provided are optical isomers, racemates, or other mixtures thereof (e.g., scalemic mixtures) of the compounds described herein or a pharmaceutically acceptable salt or a mixture thereof. If desired, isomers can be separated by methods well known in the art, e.g., by liquid chromatography. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high-pressure liquid chromatography (HPLC) column.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another. "Diastereomers" are stereoisomers that have at least two asymmetric atoms, but which are not mirror-images of each other. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

Compounds disclosed herein and their pharmaceutically acceptable salts may, in some embodiments, include an asymmetric center and may thus give rise to enantiomers, diastereomers, and other stereoisomeric forms that may be defined, in terms of absolute stereochemistry, as (R)- or (S)- or as (D)- or (L)- for amino acids. Some embodiments include all such possible isomers, as well as their racemic, scalemic, and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1. For example, in some embodiments a compound

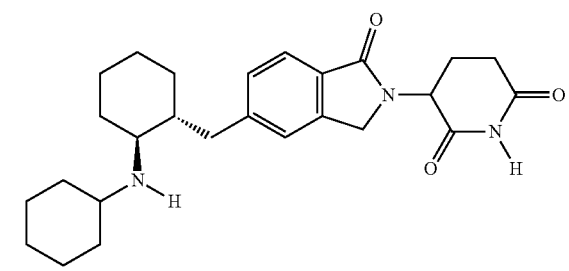 [SMILES: O=C1CCC(N2Cc3cc(C[C@H]4CCCC[C@@H]4NC4CCCCC4)ccc3C2=O)C(=O)N1]

is understood to encompass either the specific diastereomerically or enantiomerically enriched form; or a racemic or scalemic mixture of Isoform A

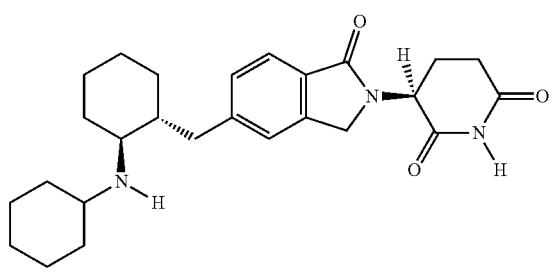 [SMILES: O=C1CC[C@H](N2Cc3cc(C[C@H]4CCCC[C@@H]4NC4CCCCC4)ccc3C2=O)C(=O)N1]

and Isoform B

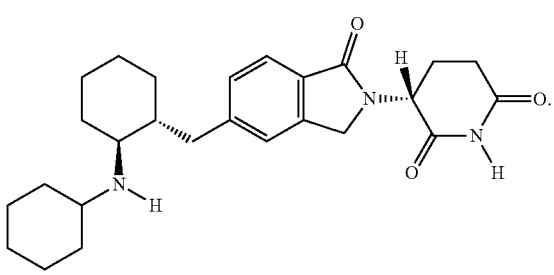 [SMILES: O=C1CC[C@@H](N2Cc3cc(C[C@H]4CCCC[C@@H]4NC4CCCCC4)ccc3C2=O)C(=O)N1]

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphoros, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds disclosed herein, in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula (I) when administered to a mammal, e.g., a human. See, e.g., Foster, "Deuterium Isotope Effects in Studies of Drug Metabolism," Trends Pharmacol. Sci. 5(12): 524-527 (1984). Such compounds are synthesized by means well known in the art, for example by employing starting materials in which one or more hydrogens have been replaced by deuterium.

Deuterium labelled or substituted therapeutic compounds of the disclosure may have beneficial DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Furthermore, the present disclosure provides pharmaceutical compositions comprising a compound of the present disclosure, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure can encompass any composition made by admixing at least one compound of the present disclosure and a pharmaceutically acceptable carrier.

As used herein, "pharmaceutically acceptable carrier" includes excipients or agents such as solvents, diluents, dispersion media, coatings, antibacterial and antifungal agents, isotonic and absorption delaying agents and the like that are not deleterious to the disclosed compound or use thereof. The use of such carriers and agents to prepare compositions of pharmaceutically active substances is well known in the art (see, e.g., Remington's Pharmaceutical Sciences, Mace Publishing Co., Philadelphia, PA 17th Ed. (1985); and Modem Pharmaceutics, Marcel Dekker, Inc. 3rd Ed. (G. S. Banker & C. T. Rhodes, Eds.).

"$IC_{50}$" or "$EC_{50}$" refers to the inhibitory concentration required to achieve 50% of the maximum desired effect. In many cases here the maximum desired effect is the degradation of IKZF2 protein. This term is obtained using an in vitro protein degradation assay, such as a HiBiT protein tagging assay, evaluating the concentration-dependent degradation of IKZF2 protein. "$D_{max}$" refers to the maximum protein (e.g., IKZF2 or IKZF1 protein) degradation at the highest compound concentration tested in the assay.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival. In some embodiments, the term "treatment" or "treating" means administering a compound or pharmaceutically acceptable salt of Formula (I), (Ia), (Ib), or (Ic) for the purpose of: (i) delaying the onset of a disease, that is, causing the clinical symptoms of the disease not to develop or delaying the development thereof; (ii) inhibiting the disease, that is, arresting the development of clinical symptoms; and/or (iii) relieving the disease, that is, causing the regression of clinical symptoms or the severity thereof.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

As used herein, an "IKZF associated disease or condition" (e.g., IKZF2 or IKZF4 associated disease or condition) means a reduction of IKZF protein levels (e.g., IKZF2 or IKZF4 protein levels) can ameliorate the disease or disorder. In some embodiments, in an IKZF associated disease or condition degradation of IKZF2 protein can ameliorate the disease or disorder. In some embodiments, in an IKZF associated disease or condition degradation of IKZF2 protein and one or more additional IKZF proteins (e.g., IKZF4 protein) can ameliorate the disease or disorder. In some embodiments, in an IKZF associated disease or condition degradation of IKZF4 protein can ameliorate the disease or disorder.

"Subject" refers to an animal, such as a mammal (including a human), that has been or will be the object of treatment, observation or experiment. The methods described herein may be useful in human therapy and/or veterinary applications. In some embodiments, the subject is a mammal. In some embodiments, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to IKZF2 degraders. The therapeutically effective amount may vary depending on the subject, and disease or condition being treated, the weight and age of the subject, the severity of the disease or condition, and the manner of administering, which can readily be determined by one or ordinary skill in the art.

As used herein, a "degrader" or "protein degrader" refers to any agent that is capable of binding to and inducing the degradation of a protein. Generally, protein degraders are believed to induce targeted protein degradation through recruitment of the cellular ubiquitinylation and proteasomal protein degradation machinery. For example, as used herein, an "IKZF2 degrader" or "IKZF2 protein degrader" refers to any agent that is capable of binding to and inducing the degradation of IKZF2 protein. In some embodiments, the IKZF2 degrader is IKZF2 selective. In some embodiments, the IKZF2 degrader can induce degradation of IKZF2 protein and one or more additional IKZF2 proteins (e.g., IKZF1 or IKZF4).

IKZF2, also known as Helios, is an IKAROS family zinc finger transcription factor commonly believed to be required to maintain a stable Treg cell phenotype, especially in inflammatory tumor microenvironments. In humans IKZF2 or Helios protein is encoded by the IKZF2 gene. Exemplary reference sequences for IKZF2 (NCBI Gene ID: 22807 (human); 22779 (mouse)) include the NCBI Reference Sequences NP_001072994 (human protein), NP_035900 (mouse protein), NM_001079526 (human mRNA), and NM_0011770 (mouse mRNA). Related family members include IKZF1 (Ikaros; NCBI Gene ID: 10320 (human); 22778 (mouse)) and IKZF4 (Eos; NCBI Gene ID: 64375 (human); 22781 (mouse). The activity of an IKZF (e.g., IKZF2) degrader can be measured by methods known in the art, such as those described and cited in Wang et al., 2021 Nature Chemical Biology 17, 711-717. In some embodiments IKZF protein degradation is measured using a HiBiT protein tagging assay, such as the Nano Glo® HiBiT Extracellular Detection System (Promega).

Spalt-like protein 4 (SALL4) is a member of the Spalt-like (SALL) family of zinc finger transcription factors. In humans SALL4 protein is encoded by the SALL4 gene (NCBI Gene ID: 57167. SALL4 biology is described, e.g., in Donovan et al., 2018 eLife 7:e38430 and Matyskiela et al. 2020 *Nat Struct Mol Biol* 27, 319-322. SALL4 degradation activity can be measured by any method known in the art. In some embodiments SALL4 protein degradation is measured using a HiBiT protein tagging assay, such as the Nano Glo® HiBiT Extracellular Detection System (Promega).

LIST OF ABBREVIATIONS AND ACRONYMS

| Abbreviation | Meaning |
| --- | --- |
| ° C. | degrees Celsius |
| Ac | acetate |
| AcOH | acetic acid |
| Boc | tert-butoxycarbonyl |
| CBz | benzyloxycarbonyl |
| d | doublet |
| DCE | 1,2-dichloroethane |
| DCM | dichloromethane |
| dd | doublet of doublets |
| DIPEA | N,N'-diisopropylethylamine |
| DMA | N,N-dimethylacetamide |
| DME | 1,2-dimethoxyethane |

-continued

| Abbreviation | Meaning |
|---|---|
| DMEDA | 1,2-Dimethylethylenediamine |
| DMF | Dimethylformamide |
| DMP | Dess-Martin periodinane |
| DMSO | Dimethylsulfoxide |
| dtbbpy | 4,4'-Di-tert-butyl-2,2'-dipyridyl |
| equiv or eq. | equivalents |
| ES/MS | electron spray mass spectrometry |
| Et | ethyl |
| EtOH | ethanol |
| g | gram |
| glyme | 1,2-dimethoxyethane |
| H NMR | proton nuclear magnetic resonance |
| h or hr | hour |
| HATU | (1-[Bis(dimethylamino)methylene]-1H-1,2,3-triazolo[4,5-b]pyridinium 3-oxide hexafluorophosphate |
| HEK293 | human embryonic kidney 293 cells |
| IKZF | Ikaros family zinc-finger |
| IPA | isopropanol |
| Ir[(dF(CF$_3$)ppy$_2$)dtbbpy]PF$_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate |
| LC/MS | liquid chromatography/mass spectrometry |
| LED | light emitting diode |
| M | molar |
| m | milli |
| m/z | mass to charge ratio |
| M+ | mass peak |
| M + H | mass peak plus hydrogen |
| Me | methyl |
| MeCN or ACN | acetonitrile |
| MeOH | methanol |
| mg | milligram |
| MHz | megahertz |
| mL | milliliter |
| mol | mole |
| Ms | methanesulfonyl |
| MTBE | methyl tert-butyl ether |
| MW or μW | microwave |
| NaBH$_3$CN | sodium cyanoborohydride |
| nM | nanomolar |
| NMM | N-methylmorpoline |
| Pd(PPh$_3$)$_2$Cl$_2$ | Pd(PPh3)2Cl2 |
| Pd(PPh$_3$)$_4$ | Tetrakis(triphenylphosphine)palladium(0) |
| Pd$_2$dba$_3$ | Tris(dibenzylideneacetone)dipalladium(0) |
| Pg | protecting group |
| Ph | phenyl |
| POC | percentages of control |
| r.t. | room temperature |
| RP-HPLC | reversed-phase high perfomance liquid chromatography |
| s | singlet |
| SEM | 2-(trimethylsilyl)ethoxymethyl |
| SFC | supercritical fluid chromatography |
| STAB | sodium triacetoxyborohydride |
| t | triplet |
| tBu | tert-butyl |
| tBuXPhos Pd G3 | [(2-Di-tert-butylphosphino-2',4',6'-triisopropyl-1,1'-biphenyl)-2-(2'-amino-1,1'-biphenyl)] palladium(II) methanesulfonate |
| Tf | trifluoromethanesulfonate |
| TFA | trifluoroacetic acid |
| TFE | trifluoroethanol |
| THF | tetrahydrofuran |
| TMP | 2,2,6,6-Tetramethylpiperidine |
| TMS | trimethylsilyl |
| Ts | toluenesufonyl |
| XantPhos | (9,9-Dimethyl-9H-xanthene-4,5-diyl)bis(diphenylphosphane) |
| δ | parts per million referenced to residual solvent peak |
| μL | microliter |
| μmol | micromole |

Compounds

In one aspect, the present disclosure provides a compound of Formula (I),

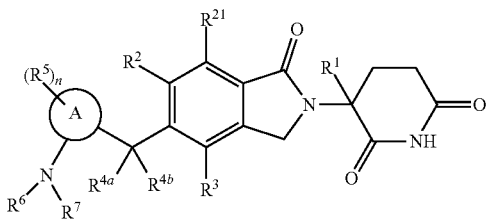

or a pharmaceutically acceptable salt thereof, wherein:
$R^1$ is —H;
$R^2$ is —H, —F, or —Cl;
$R^{21}$ is —H, —F, or —Cl;
$R^3$ is —H, —F, or —Cl;
$R^{4a}$ and $R^{4b}$ are each independently —H, halogen, —OH, or $C_{1-6}$ alkyl;
Ring A is $C_{3-10}$ cycloalkyl or heterocyclyl;
n is 0, 1, 2, 3, or 4;
each $R^5$ is independently halogen, =O, =CH$_2$, —CN, $C_{1-6}$ alkyl, $C_{2-6}$ alkenyl, $C_{1-6}$ haloalkyl, $C_{1-6}$ alkoxy, $C_{1-6}$ haloalkoxy, $C_{3-6}$ cycloalkyl, heterocyclyl, $C_{6-10}$ aryl, heteroaryl, —O—($R^{51}$), or —N($R^{51}$)($R^{52}$) wherein each =CH$_2$, alkyl, alkenyl, cycloalkyl, alkoxy, haloalkyl, haloalkoxy, heterocyclyl, aryl, or heteroaryl of $R^5$ is optionally substituted with one to four $R^{5a}$, which may be the same or different;
each $R^{5a}$ is independently halogen, —CN, $C_{1-6}$ alkyl, $C_{6-10}$ aryl, or —O($R^{51}$);
wherein each $R^{51}$ and $R^{52}$, which may be the same or different, is independently —H, $C_{1-6}$ alkyl, $C_{3-10}$ cycloalkyl, heterocyclyl, $C_{6-10}$ aryl, or heteroaryl;
$R^6$ is —H, $C_{1-8}$alkyl, $C_{1-6}$ haloalkyl, $C_{3-12}$ cycloalkyl, heterocyclyl, aryl, heteroaryl, —C(O)N($R^{1a}$)($R^{1b}$), —S(O)(NR$^{1a}$)($R^{1b}$), —C(O)R$^{1c}$, —S(O$_2$)R$^{1c}$, or —C(O)OR$^{1d}$,
wherein the alkyl, haloalkyl, cycloalkyl, aryl, heteroaryl, or heterocyclyl of $R^6$ is each optionally substituted with one to four $Z^1$, which may be the same or different;
$R^7$ is —H, $C_{1-8}$alkyl, $C_{1-6}$ haloalkyl, $C_{3-12}$cycloalkyl, heterocyclyl, aryl, heteroaryl, —C(O)N($R^{2a}$)($R^{2b}$), —S(O)(NR$^{2a}$)($R^{2b}$), —C(O)R$^{2c}$, S(O$_2$)R$^{2c}$, or —C(O)OR$^{2d}$,
wherein the alkyl, haloalkyl, cycloalkyl, aryl, heteroaryl, or heterocyclyl of $R^7$ is each optionally substituted with one to four $Z^2$, which may be the same or different; or
$R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 20 membered heterocyclyl having 0 to 3 additional heteroatoms each independently N, O or S;
each $Z^1$, $Z^2$, or $Z^3$ is independently deuterium, $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, =O, imino, —NO$_2$, —N$_3$, —CN, —O—R$^{3a}$, —C(O)—R$^{3a}$, —C(O)O—R$^{3a}$, —C(O)—N(R$^{3a}$)(R$^{3b}$), —N(R$^{3a}$)(R$^{3b}$), —N(R$^{3a}$)$_2$(R$^{3b}$)$^+$, —N(R$^{3a}$)C(O)—R$^{3b}$, —N(R$^{3a}$)C(O)O—R$^{3b}$, —N(R$^{3a}$)C(O)N(R$^{3b}$)(R$^{3c}$),
—N(R$^{3a}$)S(O)$_2$(R$^{3b}$), —NR$^{3a}$S(O)$_2$N(R$^{3b}$)(R$^{3c}$), —NR$^{3a}$S(O)$_2$O(R$^{3b}$), —OC(O)R$^{3a}$, —OC(O)OR$^{3a}$, —OC(O)—N(R$^{3a}$)(R$^{3b}$), —S—R$^{3a}$, —S(O)R$^{3a}$, —S(O)(NH)R$^{3a}$, —S(O)$_2$R$^{3a}$, —S(O)$_2$N(R$^{3a}$)(R$^{3b}$), —S(O)(NR$^{3a}$)R$^{3b}$, —S(O)(NR$^{3a}$)N(R$^{3b}$)(R$^{3c}$), —SF$_5$, or —Si(R$^{3a}$)$_3$;
wherein the alkyl, haloalkyl, alkenyl, alkynyl, cycloalkyl, heterocyclyl, aryl, or heteroaryl of each $Z^1$, $Z^2$, or $Z^3$ is each optionally substituted with one to four $Z^{1a}$, which may be the same or different;
each $Z^{1a}$ is independently deuterium, $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, =O, —NO$_2$, —CN, —N$_3$, —O—R$^{3a}$, —C(O)R$^{3a}$, —C(O)O—R$^{3a}$, —C(O)N(R$^{3a}$)(R$^{3b}$), —N(R$^{3a}$)(R$^{3b}$), —N(R$^{3a}$)$_2$(R$^{3b}$)$^+$, —N(R$^{3a}$)—C(O)R$^{3b}$, —N(R$^{3a}$)C(O)O(R$^{3b}$), —N(R$^{3a}$)C(O)N(R$^{3b}$)(R$^{3c}$), —N(R$^{3a}$)S(O)$_2$(R$^{3b}$), —N(R$^{3a}$)S(O)$_2$—N(R$^{3b}$)(R$^{3c}$), —N(R$^{3a}$)S(O)$_2$O(R$^{3b}$), —OC(O)R$^{3a}$, —OC(O)OR$^{3a}$, —OC(O)—N(R$^{3a}$)(R$^{3b}$), —S—R$^{3a}$, —S(O)R$^{3a}$, —S(O)(NH)R$^{3a}$, —S(O)$_2$R$^{3a}$, —S(O)$_2$N(R$^{3a}$)(R$^{3b}$), —S(O)(NR$^{3a}$)R$^{3b}$, or —Si(R$^{3a}$)$_3$;
wherein the alkyl, haloalkyl, alkenyl, alkynyl, cycloalkyl, heterocyclyl, aryl, or heteroaryl of $Z^{1a}$ is each optionally substituted with one to four $Z^{1b}$, which may be the same or different;
each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC (O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl of $Z^{1b}$ is optionally substituted with one to three $C_{1-9}$ alkyl, $C_{1-8}$ haloalkyl, halogen, —OH, —NH$_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

each $R^{1a}$, $R^{1b}$, $R^{1c}$, $R^{1d}$, $R^{2a}$, $R^{2b}$, $R^{2c}$, $R^{2a}$, $R^{3a}$, $R^{3b}$, and $R^{3c}$ is independently —H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl, wherein the alkyl, alkenyl, alkynyl, cycloalkyl, heterocyclyl, aryl, or heteroaryl of each $R^{1a}$, $R^{1b}$, $R^{1c}$, $R^{1d}$, $R^{2a}$, $R^{2b}$, $R^{2c}$, $R^{2a}$, $R^{3a}$, $R^{3b}$, and $R^{3c}$ is each optionally substituted with one to four $Z^{1b}$, which may be the same or different;

wherein each aryl of the compound of Formula (I) unless otherwise specified is $C_{6-10}$ aryl;

wherein each heteroaryl of the compound of Formula (I) unless otherwise specified is 5 to 12 membered heteroaryl having one to four heteroatoms each independently N, O, or S;

wherein each heterocyclyl of the compound of Formula (I) unless otherwise specified is 3 to 20 membered heterocyclyl having one to four heteroatoms each independently N, O, or S.

In some embodiments of the compound of Formula (I), or pharmaceutically acceptable salt thereof, $R^1$ is —H;
$R^2$ is —H, —F, or —Cl;
$R^{21}$ is —H;
$R^3$ is —H, —F, or —Cl;
$R^{4a}$ and $R^{4b}$ are each independently —H, halogen, —OH, or $C_{1-6}$ alkyl;
Ring A is $C_{3-10}$ cycloalkyl or heterocyclyl;
n is 0, 1, 2, 3, or 4;

each $R^5$ is independently halogen, =O, —CN, $C_{1-6}$ alkyl, $C_{1-6}$ haloalkyl, $C_{1-6}$ haloalkoxy, $C_{1-6}$ alkoxy, $C_{3-6}$ cycloalkyl, heterocyclyl, $C_{6-10}$ aryl, heteroaryl, —O—($R^{51}$), or —N($R^{51}$)($R^{52}$);

wherein each alkyl, cycloalkyl, alkoxy, haloalkyl, haloalkoxy, heterocyclyl, aryl, or heteroaryl of $R^5$ is optionally substituted with one to four $R^{5a}$, which may be the same or different;

each $R^{5a}$ is independently halogen, —CN, $C_{1-6}$ alkyl, $C_{6-10}$ aryl, or —O($R^{51}$);

wherein each $R^{51}$ and $R^{52}$, which may be the same or different, is independently —H, $C_{1-6}$ alkyl, $C_{3-10}$ cycloalkyl, $C_{6-10}$ aryl, or heteroaryl;

$R^6$ is —H, $C_{1-8}$ alkyl, $C_{1-6}$ haloalkyl, $C_{3-12}$ cycloalkyl, heterocyclyl, aryl, heteroaryl, —C(O)N($R^{1a}$)($R^{1b}$), —S(O)(N$R^{1a}$)($R^{1b}$), —C(O)$R^{1c}$, —S(O$_2$)$R^{1c}$, or —C(O)O$R^{1d}$, wherein the alkyl, haloalkyl, cycloalkyl, aryl, heteroaryl, or heterocyclyl of $R^6$ is each optionally substituted with one to four $Z^1$, which may be the same or different;

$R^7$ is —H, $C_{1-8}$ alkyl, $C_{1-6}$ haloalkyl, $C_{3-12}$ cycloalkyl, heterocyclyl, aryl, heteroaryl —C(O)N($R^{2a}$)($R^{2b}$), —S(O)(N$R^{2a}$)($R^{2b}$), —C(O)$R^{2c}$, S(O$_2$)$R^{2c}$, or —C(O)O$R^{2d}$, wherein the alkyl, haloalkyl, cycloalkyl, aryl, heteroaryl, or heterocyclyl of $R^7$ is each optionally substituted with one to four $Z^2$, which may be the same or different; or $R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 20 membered heterocyclyl having 0 to 3 additional heteroatoms each independently N, O or S;

each $Z^1$, $Z^2$, or $Z^3$ is independently deuterium, $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, =O, imino, —NO$_2$, —N$_3$, —CN, —O—$R^{3a}$, —C(O)—$R^{3a}$, —C(O)O—$R^{3a}$, —C(O)—N($R^{3a}$)($R^{3b}$), —N($R^{3a}$)($R^{3b}$), —N($R^{3a}$)$_2$($R^{3b}$)$^+$, —N($R^{3a}$)C(O)—$R^{3b}$, —N($R^{3a}$)C(O)O—$R^{3b}$, —N($R^{3a}$)C(O)N($R^{3b}$)($R^{3c}$), —N($R^{3a}$)S(O)$_2$($R^{3b}$), —N$R^{3a}$S(O)$_2$N($R^{3b}$)($R^{3c}$), —N$R^{3a}$S(O)$_2$O($R^{3b}$), —OC(O)$R^{3a}$, —OC(O)O$R^{3a}$, —OC(O)—N($R^{3a}$)($R^{3b}$), —S—$R^{3a}$, —S(O)$R^{3a}$, —S(O)(NH)$R^{3a}$, —S(O)$_2$$R^{3a}$, —S(O)$_2$N($R^{3a}$)($R^{3b}$), —S(O)(N$R^{3a}$)$R^{3b}$, —S(O)(N$R^{3a}$)N($R^{3b}$)($R^{3c}$), —SF$_5$, or —Si($R^{3a}$)$_3$;

wherein the alkyl, haloalkyl, alkenyl, alkynyl, cycloalkyl, heterocyclyl, aryl, or heteroaryl of each $Z^1$, $Z^2$, or $Z^3$ is each optionally substituted with one to four $Z^{1a}$, which may be the same or different;

each $Z^{1a}$ is independently deuterium, $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, =O, —NO$_2$, —CN, —N$_3$, —O—$R^{3a}$, —C(O)$R^{3a}$, —C(O)O—$R^{3a}$, —C(O)N($R^{3a}$)($R^{3b}$), —N($R^{3a}$)($R^{3b}$), —N($R^{3a}$)$_2$($R^{3b}$)$^+$, —N($R^{3a}$)—C(O)O$R^{3b}$, —N($R^{3a}$)C(O)O($R^{3b}$), —N($R^{3a}$)C(O)N($R^{3b}$)($R^{3c}$), —N($R^{3a}$)S(O)$_2$($R^{3b}$), —N($R^{3a}$)S(O)$_2$—N($R^{3b}$)($R^{3c}$), —N($R^{3a}$)S(O)$_2$O($R^{3b}$), —OC(O)$R^{3a}$, —OC(O)O$R^{3a}$, —OC(O)—N($R^{3a}$)($R^{3b}$), —S—$R^{3a}$, —S(O)$R^{3a}$, —S(O)(NH)$R^{3a}$, —S(O)$_2$$R^{3a}$, —S(O)$_2$N($R^{3a}$)($R^{3b}$), —S(O)(N$R^{3a}$)$R^{3b}$, or —Si($R^{3a}$)$_3$;

wherein the alkyl, haloalkyl, alkenyl, alkynyl, cycloalkyl, heterocyclyl, aryl, or heteroaryl of $Z^{1a}$ is each optionally substituted with one to four $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO₂, —NH₂, —N₃, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)₂, —N($C_{1-8}$ haloalkyl)₂, —N($C_{2-6}$ alkenyl)₂, —N($C_{2-6}$ alkynyl)₂, —N($C_{3-15}$ cycloalkyl)₂, —N(heterocyclyl)₂, —N($C_{6-10}$ aryl)₂, —N(heteroaryl)₂, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH₂, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)₂, —C(O)N($C_{1-8}$ haloalkyl)₂, —C(O)N($C_{2-6}$ alkenyl)₂, —C(O)N($C_{2-6}$ alkynyl)₂, —C(O)N($C_{3-15}$ cycloalkyl)₂, —C(O)N(heterocyclyl)₂, —C(O)N($C_{6-10}$ aryl)₂, —C(O)N(heteroaryl)₂, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)₂, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)₂($C_{1-9}$ alkyl), —S(O)₂($C_{1-8}$ haloalkyl), —S(O)₂($C_{2-6}$ alkenyl), —S(O)₂($C_{2-6}$ alkynyl), —S(O)₂($C_{3-15}$ cycloalkyl), —S(O)₂(heterocyclyl), —S(O)₂($C_{6-10}$ aryl), —S(O)₂(heteroaryl), —S(O)(NH)($C_{1-9}$ alkyl), —S(O)₂NH($C_{1-9}$ alkyl), or —S(O)₂N($C_{1-9}$ alkyl)₂;

wherein the alkyl, cycloalkyl, heterocyclyl, aryl, or heteroaryl of $Z^{1b}$ is optionally substituted with one to three $C_{1-9}$ alkyl, $C_{1-8}$ haloalkyl, halogen, —OH, —NH₂, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)₂, —N($C_{3-15}$ cycloalkyl)₂, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)₂($C_{1-9}$ alkyl), —S(O)₂($C_{1-8}$ haloalkyl), —S(O)₂($C_{3-15}$ cycloalkyl), —S(O)₂(heterocyclyl), —S(O)₂(aryl), —S(O)₂(heteroaryl), —S(O)(NH)($C_{1-9}$ alkyl), —S(O)₂NH($C_{1-9}$ alkyl), or —S(O)₂N($C_{1-9}$ alkyl)₂;

each $R^{1a}$, $R^{1b}$, $R^{1c}$, $R^{1d}$, $R^{2a}$, $R^{2b}$, $R^{2c}$, $R^{2a}$, $R^{3a}$, $R^{3b}$, and $R^{3c}$ is independently —H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl, wherein the alkyl, alkenyl, alkynyl, cycloalkyl, heterocyclyl, aryl, or heteroaryl of each $R^{1a}$, $R^{1b}$, $R^{1c}$, $R^{1d}$, $R^{2a}$, $R^{2b}$, $R^{2c}$, $R^{2a}$, $R^{3a}$, $R^{3b}$, and $R^{3c}$ is each optionally substituted with one to four $Z^{1b}$, which may be the same or different;

wherein each aryl of the compound of Formula (I) unless otherwise specified is $C_{6-10}$ aryl;

wherein each heteroaryl of the compound of Formula (I) unless otherwise specified is 5 to 12 membered heteroaryl having one to four heteroatoms each independently N, O, or S;

wherein each heterocyclyl of the compound of Formula (I) unless otherwise specified is 3 to 20 membered heterocyclyl having one to four heteroatoms each independently N, O or S.

In some embodiments of the compound of Formula (I), or pharmaceutically acceptable salt thereof, $R^1$ is —H;

$R^2$ is —H, —F, or —Cl;

$R^3$ is —H, —F, or —Cl;

$R^{4a}$ and $R^{4b}$ are each independently —H, halogen, —OH, or $C_{1-6}$ alkyl;

Ring A is $C_{3-10}$ cycloalkyl or heterocyclyl;

n is 0, 1, 2, 3, or 4;

each $R^5$ is independently halogen, =O, —CN, $C_{1-6}$ alkyl, $C_{1-6}$ haloalkyl, $C_{1-6}$ haloalkoxy, $C_{3-6}$ cycloalkyl, heterocyclyl, $C_{6-10}$ aryl, heteroaryl, —O—($R^{51}$), or —N($R^{51}$)($R^{52}$);

wherein each alkyl, cycloalkyl, alkoxy, haloalkyl, haloalkoxy, heterocyclyl, aryl, or heteroaryl of $R^5$ is optionally substituted with one to four $R^{5a}$, which may be the same or different;

each $R^{5a}$ is independently halogen, —CN, $C_{1-6}$ alkyl, $C_{6-10}$ aryl, or —O($R^{51}$);

wherein each $R^{51}$ and $R^{52}$, which may be the same or different, is independently —H, $C_{1-6}$ alkyl, $C_{3-10}$ cycloalkyl, heterocyclyl, $C_{6-10}$ aryl, or heteroaryl;

$R^6$ is —H, $C_{1-6}$ alkyl, $C_{1-6}$ haloalkyl, $C_{3-10}$ cycloalkyl, heterocyclyl, —C(O)N($R^{1a}$)($R^{1b}$), —S(O)(N$R^{1a}$)($R^{1b}$), —C(O)$R^{1c}$, —S(O)₂$R^{1c}$, or —C(O)O$R^{1d}$, wherein the alkyl, haloalkyl, cycloalkyl, aryl, heteroaryl, or heterocyclyl of $R^6$ is each optionally substituted with one to four $Z^1$, which may be the same or different;

$R^7$ is —H, $C_{1-6}$ alkyl, $C_{1-6}$ haloalkyl, $C_{3-10}$ cycloalkyl, heterocyclyl, —C(O)N($R^{2a}$)($R^{2b}$), —S(O)(N$R^{2a}$)($R^{2b}$), —C(O)$R^{2c}$, S(O)₂$R^{2c}$, or —C(O)O$R^{2d}$, wherein the alkyl, haloalkyl, cycloalkyl, aryl, heteroaryl, or heterocyclyl of $R^7$ is each optionally substituted with one to four $Z^2$, which may be the same or different; or $R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 20 membered heterocyclyl having 0 to 3 additional heteroatoms each independently N, O or S;

each $Z^1$, $Z^2$, or $Z^3$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, =O, imino, —$NO_2$, —$N_3$, —CN, —O—$R^{3a}$, —C(O)—$R^{3a}$, —C(O)O—$R^{3a}$, —C(O)—N($R^{3a}$)($R^{3b}$), —N($R^{3a}$)($R^{3b}$), —N($R^{3a}$)$_2$($R^{3b}$)$^+$, —N($R^{3a}$)C(O)—$R^{3b}$, —N($R^{3a}$)C(O)O—$R^{3b}$, —N($R^{3a}$)C(O)N($R^{3b}$)($R^{3c}$), —N($R^{3a}$)S(O)$_2$($R^{3b}$), —N$R^{3a}$S(O)$_2$N($R^{3b}$)($R^{3c}$), —N$R^{3a}$S(O)$_2$O($R^{3b}$), —OC(O)$R^{3a}$, —OC(O)O$R^{3a}$, —OC(O)—N($R^{3a}$)($R^{3b}$), —S—$R^{3a}$, —S(O)$R^{3a}$, —S(O)(NH)$R^{3a}$, —S(O)$_2$$R^{3a}$, —S(O)$_2$N($R^{3a}$)($R^{3b}$), —S(O)(N$R^{3a}$)$R^{3b}$, —S(O)(N$R^{3a}$)N($R^{3b}$)($R^{3c}$), —$SF_5$, or —Si($R^{3a}$)$_3$;

wherein the alkyl, haloalkyl, alkenyl, alkynyl, cycloalkyl, heterocyclyl, aryl, or heteroaryl of each $Z^1$, $Z^2$, or $Z^3$ is each optionally substituted with one to four $Z^{1a}$, which may be the same or different;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, =O, —$NO_2$, —CN, —$N_3$, —O—$R^{3a}$, —C(O)$R^{3a}$, —C(O)O—$R^{3a}$, —C(O)N($R^{3a}$)($R^{3b}$), —N($R^{3a}$)($R^{3b}$), —N($R^{3a}$)$_2$($R^{3b}$)$^+$, —N($R^{3a}$)—C(O)$R^{3b}$, —N($R^{3a}$)C(O)O($R^{3b}$), —N($R^{3a}$)C(O)N($R^{3b}$)($R^{3c}$), —N($R^{3a}$)S(O)$_2$($R^{3b}$), —N($R^{3a}$)S(O)$_2$—N($R^{3b}$)($R^{3c}$), —N($R^{3a}$)S(O)$_2$O($R^{3b}$), —OC(O)$R^{3a}$, —OC(O)O$R^{3a}$, —OC(O)—N($R^{3a}$)($R^{3b}$), —S—$R^{3a}$, —S(O)$R^{3a}$, —S(O)(NH)$R^{3a}$, —S(O)$_2$$R^{3a}$, —S(O)$_2$N($R^{3a}$)($R^{3b}$), —S(O)(N$R^{3a}$)$R^{3b}$, or —Si($R^{3a}$)$_3$;

wherein the alkyl, haloalkyl, alkenyl, alkynyl, cycloalkyl, heterocyclyl, aryl, or heteroaryl of $Z^{1a}$ is each optionally substituted with one to four $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl of $Z^{1b}$ is optionally substituted with one to three $C_{1-9}$ alkyl, $C_{1-8}$ haloalkyl, halogen, —OH, —$NH_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

each $R^{1a}$, $R^{1b}$, $R^{1c}$, $R^{1d}$, $R^{2a}$, $R^{2b}$, $R^{2c}$, $R^{2a}$, $R^{3a}$, $R^{3b}$, and $R^{3c}$ is independently —H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl, wherein the alkyl, alkenyl, alkynyl, cycloalkyl, heterocyclyl, aryl, or heteroaryl of each $R^{1a}$, $R^{1b}$, $R^{1c}$, $R^{1d}$, $R^{2a}$, $R^{2b}$, $R^{2c}$, $R^{2a}$, $R^{3a}$, $R^{3b}$, and $R^{3c}$ is each optionally substituted with one to four $Z^{1b}$, which may be the same or different;

wherein each aryl of the compound of Formula (I) unless otherwise specified is $C_{6-10}$ aryl;

wherein each heteroaryl of the compound of Formula (I) unless otherwise specified is 5 to 12 membered heteroaryl having one to four heteroatoms each independently N, O, or S;

wherein each heterocyclyl of the compound of Formula (I) unless otherwise specified is 3 to 20 membered heterocyclyl having one to four heteroatoms each independently N, O or S.

In some embodiments of the compound of Formula (I), or pharmaceutically acceptable salt thereof, $R^1$ is —H;

$R^2$ is —H, —F, or —Cl;

$R^3$ is —H, —F, or —Cl;

$R^{4a}$ and $R^{4b}$ are each independently —H, halogen, —OH, or $C_{1-6}$ alkyl;

Ring A is $C_{3-10}$ cycloalkyl or heterocyclyl;

n is 0, 1, 2, 3, or 4;

each $R^5$ is independently halogen, =O, —CN, $C_{1-6}$ alkyl, $C_{1-6}$ haloalkyl, $C_{1-6}$ haloalkoxy, $C_{3-6}$ cycloalkyl, heterocyclyl, $C_{6-10}$ aryl, heteroaryl, —O—($R^{51}$), or —N($R^{51}$)($R^{52}$);

wherein each alkyl, cycloalkyl, alkoxy, haloalkyl, haloalkoxy, heterocyclyl, aryl, or heteroaryl of $R^5$ is optionally substituted with one to four $R^{5a}$, which may be the same or different;

each $R^{5a}$ is independently halogen, —CN, $C_{1-6}$ alkyl, $C_{6-10}$ aryl, or —O($R^{51}$);

wherein each $R^{51}$ and $R^{52}$, which may be the same or different, is independently —H, $C_{1-6}$ alkyl, $C_{3-10}$ cycloalkyl, heterocyclyl, $C_{6-10}$ aryl, or heteroaryl;

$R^6$ is —H, $C_{1-6}$ alkyl, $C_{1-6}$ haloalkyl, $C_{3-12}$ cycloalkyl, heterocyclyl, —C(O)N($R^{1a}$)($R^{1b}$), —S(O)(N$R^{1a}$)($R^{1b}$), —C(O)$R^{1c}$, —S(O$_2$)$R^{1c}$, or —C(O)O$R^{1d}$, wherein the alkyl, haloalkyl, cycloalkyl, aryl, heteroaryl, or heterocyclyl of $R^6$ is each optionally substituted with one to four $Z^1$, which may be the same or different;

$R^7$ is —H, $C_{1-8}$ alkyl, $C_{1-6}$ haloalkyl, $C_{3-12}$ cycloalkyl, heterocyclyl, aryl, heteroaryl —C(O)N($R^{2a}$)($R^{2b}$), —S(O)(N$R^{2a}$)($R^{2b}$), —C(O)$R^{2c}$, S(O$_2$)$R^{2c}$, or —C(O)O$R^{2d}$, wherein the alkyl, haloalkyl, cycloalkyl, aryl, heteroaryl, or heterocyclyl of $R^7$ is each optionally substituted with one to four $Z^2$, which may be the same or different; or $R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 20 membered heterocyclyl having 0 to 3 additional heteroatoms each independently N, O or S;

each $Z^1$, $Z^2$, or $Z^3$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, =O, imino, —NO$_2$, —N$_3$, —CN, —O—$R^{3a}$, —C(O)—$R^{3a}$, —C(O)O—$R^{3a}$, —C(O)—N($R^{3a}$)($R^{3b}$), —N($R^{3a}$)($R^{3b}$), —N($R^{3a}$)$_2$($R^{3b}$)$^+$, —N($R^{3a}$)C(O)—$R^{3b}$, —N($R^{3a}$)C(O)O—$R^{3b}$, —N($R^{3a}$)C(O)N($R^{3b}$)($R^{3c}$), —N($R^{3a}$)S(O)$_2$($R^{3b}$), —N$R^{3a}$S(O)$_2$N($R^{3b}$)($R^{3c}$), —N$R^{3a}$S(O)$_2$O($R^{3b}$), —OC(O)$R^{3a}$, —OC(O)O$R^{3a}$, —OC(O)—N($R^{3a}$)($R^{3b}$), —S—$R^{3a}$, —S(O)$R^{3a}$, —S(O)(NH)$R^{3a}$, —S(O)$_2$$R^{3a}$, —S(O)$_2$N($R^{3a}$)($R^{3b}$), —S(O)(N$R^{3a}$)$R^{3b}$, —S(O)(N$R^{3a}$)N($R^{3b}$)($R^{3c}$), —SF$_5$, or —Si($R^{3a}$)$_3$;

wherein the alkyl, haloalkyl, alkenyl, alkynyl, cycloalkyl, heterocyclyl, aryl, or heteroaryl of each $Z^1$, $Z^2$, or $Z^3$ is each optionally substituted with one to four $Z^{1a}$, which may be the same or different;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, =O, —NO$_2$, —CN, —N$_3$, —O—$R^{3a}$, —C(O)$R^{3a}$, —C(O)O—$R^{3a}$, —C(O)N($R^{3a}$)($R^{3b}$), —N($R^{3a}$)($R^{3b}$), —N($R^{3a}$)$_2$($R^{3b}$)$^+$, —N($R^{3a}$)—C(O)$R^{3b}$, —N($R^{3a}$)C(O)O($R^{3b}$), —N($R^{3a}$)C(O)N($R^{3b}$)($R^{3c}$), —N($R^{3a}$)S(O)$_2$($R^{3b}$), —N($R^{3a}$)S(O)$_2$N($R^{3b}$)($R^{3c}$), —N($R^{3a}$)S(O)$_2$O($R^{3b}$), —OC(O)$R^{3a}$, —OC(O)O$R^{3a}$, —OC(O)—N($R^{3a}$)($R^{3b}$), —S—$R^{3a}$, —S(O)$R^{3a}$, —S(O)(NH)$R^{3a}$, —S(O)$_2$$R^{3a}$, —S(O)$_2$N($R^{3a}$)($R^{3b}$), —S(O)(N$R^{3a}$)$R^{3b}$, or —Si($R^{3a}$)$_3$;

wherein the alkyl, haloalkyl, alkenyl, alkynyl, cycloalkyl, heterocyclyl, aryl, or heteroaryl of $Z^{1a}$ is each optionally substituted with one to four $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$(C$_{2-6}$ alkynyl), —S(O)$_2$(C$_{3-15}$ cycloalkyl), —S(O)$_2$(heterocyclyl), —S(O)$_2$(C$_{6-10}$ aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

wherein the alkyl, cycloalkyl, heterocyclyl, aryl, or heteroaryl of Z$^{1b}$ is optionally substituted with one to three C$_{1-9}$ alkyl, C$_{1-8}$ haloalkyl, halogen, —OH, —NH$_2$, —O(C$_{1-9}$ alkyl), —O(C$_{1-8}$ haloalkyl), —O(C$_{3-15}$ cycloalkyl), —O(heterocyclyl), —O(aryl), —O(heteroaryl), —NH(C$_{1-9}$ alkyl), —NH(C$_{1-8}$ haloalkyl), —NH(C$_{3-15}$ cycloalkyl), —NH(heterocyclyl), —NH(aryl), —NH(heteroaryl), —N(C$_{1-9}$ alkyl)$_2$, —N(C$_{3-15}$ cycloalkyl)$_2$, —NHC(O)(C$_{1-8}$ haloalkyl), —NHC(O)(C$_{3-15}$ cycloalkyl), —NHC(O)(heterocyclyl), —NHC(O)(aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkynyl), —NHC(O)O(C$_{3-15}$ cycloalkyl), —NHC(O)O(heterocyclyl), —NHC(O)O(aryl), —NHC(O)O(heteroaryl), —NHC(O)NH(C$_{1-9}$ alkyl), S(O)$_2$(C$_{1-9}$ alkyl), —S(O)$_2$(C$_{1-8}$ haloalkyl), —S(O)$_2$(C$_{3-15}$ cycloalkyl), —S(O)$_2$(heterocyclyl), —S(O)$_2$(aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

each R$^{1a}$, R$^{1b}$, R$^{1c}$, R$^{1d}$, R$^{2a}$, R$^{2b}$, R$^{2c}$, R$^{2a}$, R$^{3a}$, R$^{3b}$, and R$^{3c}$ is independently —H, C$_{1-9}$ alkyl, C$_{2-6}$ alkenyl, C$_{2-6}$ alkynyl, C$_{3-15}$ cycloalkyl, heterocyclyl, C$_{6-10}$ aryl, or heteroaryl, wherein the alkyl, alkenyl, alkynyl, cycloalkyl, heterocyclyl, aryl, or heteroaryl of each R$^{1a}$, R$^{1b}$, R$^{1c}$, R$^{1d}$, R$^{2a}$, R$^{2b}$, R$^{2c}$, R$^{2a}$, R$^{3a}$, R$^{3b}$, and R$^{3c}$ is each optionally substituted with one to four Z$^{1b}$, which may be the same or different;

wherein each heteroaryl of the compound of Formula (I) unless otherwise specified is 5 to 12 membered heteroaryl having one to four heteroatoms each independently N, O, or S;

wherein each heterocyclyl of the compound of Formula (I) unless otherwise specified is 3 to 20 membered heterocyclyl having one to four heteroatoms each independently N, O or S.

In some embodiments of the compound of Formula (I), or pharmaceutically acceptable salt thereof, R$^1$ is —H;
R$^2$ is —H or —F;
R$^{21}$ is —H;
R$^3$ is —H or —F;
R$^{4a}$ and R$^{4b}$ are each independently —H, —F, or —CH$_3$;
Ring A is a cyclopentyl, cyclohexyl, cycloheptyl, cyclohexenyl, or tetrahydropyranyl ring;
n is 0, 1, or 2;
each R$^5$ is independently —F, —OH, —CH$_3$, =CH$_2$, —CH$_2$—OH, or —O—CH$_3$;
R$^6$ is —H, C$_{1-6}$ alkyl, C$_{1-6}$ haloalkyl, C$_{3-10}$ cycloalkyl, heterocyclyl, C$_{6-10}$ aryl, or heteroaryl,
wherein each alkyl, haloalkyl, cycloalkyl, aryl, heteroaryl, or heterocyclyl of R$^6$ is optionally substituted with one to four Z$^1$, which may be the same or different;
R$^7$ is —H, C$_{1-8}$ alkyl, C$_{1-6}$ haloalkyl, C$_{3-12}$ cycloalkyl, heterocyclyl, C$_{6-10}$ aryl, or heteroaryl,
wherein each alkyl, haloalkyl, cycloalkyl, aryl, heteroaryl, or heterocyclyl of R$^7$ is optionally substituted with one to four Z$^2$, which may be the same or different; or
R$^6$ and R$^7$ together with the nitrogen to which they are attached form a heterocyclyl, which is optionally substituted with one to four Z$^3$, which may be the same or different; wherein the heterocyclyl formed by R$^6$ and R$^7$ is 3 to 12 membered heterocyclyl having 0 to 3 additional heteroatoms each independently N, O, or S;

each Z$^1$, Z$^2$, or Z$^3$ is independently deuterium, halogen, =O, —CN, C$_{1-9}$ alkyl, C$_{1-8}$ haloalkyl, C$_{1-6}$ alkoxy, C$_{1-6}$ haloalkoxy, C$_{2-6}$ alkoxyalkyl, C$_{2-6}$ alkenyl, C$_{2-6}$ alkynyl, C$_{3-15}$ cycloalkyl, heterocyclyl, C$_{6-10}$ aryl, heteroaryl, or —O—R$^{3a}$;

wherein each alkyl, haloalkyl, alkenyl, alkynyl, cycloalkyl, heterocyclyl, aryl, or heteroaryl of each Z$^1$, Z$^2$, or Z$^3$ is optionally substituted with one to four Z$^{1a}$, which may be the same or different;

each Z$^{1a}$ is independently deuterium, C$_{1-9}$ alkyl, C$_{1-8}$ haloalkyl, C$_{1-6}$ alkoxy, C$_{1-6}$ haloalkoxy, C$_{2-6}$ alkoxyalkyl, C$_{2-6}$ alkenyl, C$_{2-6}$ alkynyl, halogen, C$_{3-15}$ cycloalkyl, heterocyclyl, C$_{6-10}$ aryl, heteroaryl, —CN, —O—R$^{3a}$, or —S(O)$_2$R$^{3a}$, wherein each alkyl, haloalkyl, alkenyl, alkynyl, cycloalkyl, heterocyclyl, aryl, or heteroaryl of Z$^{1a}$ is optionally substituted with one to four Z$^{1b}$, which may be the same or different;

each Z$^{1b}$ is independently C$_{1-9}$ alkyl, C$_{1-8}$ haloalkyl, C$_{2-6}$ alkenyl, C$_{2-6}$ alkynyl, halogen, C$_{3-15}$ cycloalkyl, heterocyclyl, C$_{6-10}$ aryl, heteroaryl, or —CN, wherein each alkyl, alkenyl, alkynyl, cycloalkyl, heterocyclyl, aryl, or heteroaryl of Z$^{1b}$ is unsubstituted;

each R$^{3a}$ is independently —H, C$_{1-9}$ alkyl, C$_{6-10}$ aryl, or heteroaryl, wherein each alkyl, alkenyl, alkynyl, cycloalkyl, heterocyclyl, aryl, or heteroaryl of R$^{3a}$ is optionally substituted with one to four Z$^{1b}$, which may be the same or different;

wherein each heteroaryl of the compound of Formula (I) or Formula (Ia) is 5 to 12 membered heteroaryl having one to four heteroatoms each independently N, O, or S;

wherein each heterocyclyl of the compound of Formula (I) or Formula (Ia) is 3 to 20 membered heterocyclyl having one to four heteroatoms each independently N, O, or S.

In some embodiments of the compound of Formula (I), or pharmaceutically acceptable salt thereof, R$^1$ is —H;
R$^2$ is —H or —F;
R$^{21}$ is —H or —F;
R$^3$ is —H or —F;
R$^{4a}$ is —H, —F, or —CH$_3$, and R$^{4b}$ is —H;

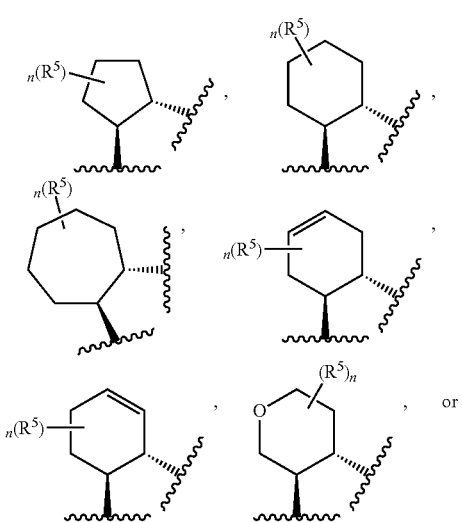

-continued

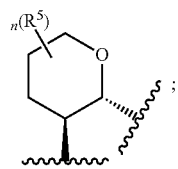

n is 0, 1, or 2;
each $R^5$ is independently —F, —OH, —CH$_3$, =CH$_2$, —CH$_2$—OH, or —O—CH$_3$;
$R^6$ is —H or C$_{1-6}$ alkyl optionally substituted with one $Z^1$, wherein $Z^1$ is unsubstituted;
$R^7$ is —H, C$_{1-8}$ alkyl, C$_{3-12}$ cycloalkyl, C$_{6-10}$ aryl, 4 to 12 membered heterocyclyl having 1 to 2 heteroatoms each independently selected from nitrogen, oxygen, and sulfur, or 5 to 12 membered heteroaryl having 1 to 3 heteroatoms each independently selected from nitrogen, oxygen, and sulfur,
wherein each alkyl, cycloalkyl, aryl, heterocyclyl or heteroaryl of $R^7$ is optionally substituted with one to four $Z^2$, which may be the same or different; or
$R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 7 membered heterocyclyl optionally having an additional N;
each $Z^1$, $Z^2$, or $Z^3$ is independently deuterium, halogen, =O, C$_{1-9}$ alkyl, C$_{1-8}$ haloalkyl, C$_{1-6}$ alkoxy, C$_{1-6}$ haloalkoxy, C$_{3-15}$ cycloalkyl, C$_{6-10}$ aryl, heterocyclyl, heteroaryl or —O—R$^{3a}$;
wherein each alkyl, haloalkyl, alkoxy, haloalkoxy, cycloalkyl, heterocyclyl, aryl, or heteroaryl of $Z^1$, $Z^2$, or $Z^3$ is optionally substituted with one to four $Z^{1a}$, which may be the same or different;
each $Z^{1a}$ is independently deuterium, C$_{1-9}$ alkyl, C$_{1-8}$ haloalkyl, C$_{1-6}$ alkoxy, halogen, —CN, or —S(O)$_2$R$^{3a}$;
wherein each alkyl of $Z^{1a}$ is optionally substituted with one to four $Z^{1b}$, which may be the same or different;
each $Z^{1b}$ is independently halogen, C$_{3-15}$ cycloalkyl, or C$_{6-10}$ aryl,
wherein each cycloalkyl or aryl of $Z^{1b}$ is unsubstituted;
each R$^{3a}$ is independently C$_{1-9}$ alkyl or C$_{6-10}$ aryl, wherein each alkyl or aryl of R$^{3a}$ is optionally substituted with one to four $Z^{1b}$, which may be the same or different;
wherein each heteroaryl of the compound of Formula (I) or Formula (Ia) is 5 to 6 membered heteroaryl having one or two heteroatoms each independently N or S;
wherein each heterocyclyl of the compound of Formula (I) or Formula (Ia) is 3 to 7 membered heterocyclyl having one to two heteroatoms each independently N or O.

In some embodiments, the compound of Formula (I), or pharmaceutically acceptable salt thereof, is a compound of Formula (Ia),

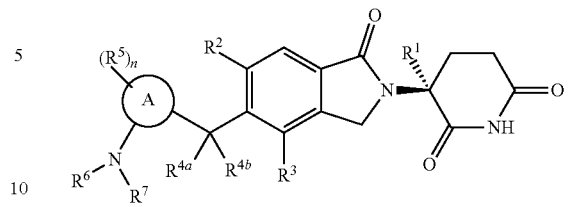

or a pharmaceutically acceptable salt thereof.
In some embodiments, the compound of of Formula (I), or pharmaceutically acceptable salt thereof, is a compound of Formula (Ib),

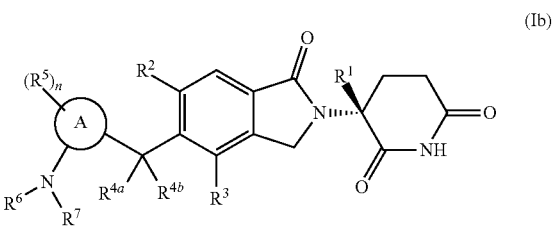

or a pharmaceutically acceptable salt thereof.
In some embodiments of the compound of Formula (I), Formula (Ia), or Formula (Ib), or pharmaceutically acceptable salt thereof,
$R^1$ is —H;
$R^2$ is —H or —F;
$R^3$ is —H or —F;
$R^{4a}$ and $R^{4b}$ are each independently —H—F, or —CH$_3$;
Ring A is a cyclopentyl, cyclohexyl, cycloheptyl, cyclohexenyl, or tetrahydropyranyl ring;
n is 0, 1, or 2;
each $R^5$ is independently —F, —OH, —CH$_3$, =CH$_2$, —CH$_2$—OH, or —O—CH$_3$;
$R^6$ is —H, C$_{1-6}$ alkyl, C$_{1-6}$ haloalkyl, C$_{3-10}$ cycloalkyl, heterocyclyl, C$_{6-10}$ aryl, or heteroaryl,
wherein each alkyl, haloalkyl, cycloalkyl, aryl, heteroaryl, or heterocyclyl of $R^6$ is optionally substituted with one to four $Z^1$, which may be the same or different;
$R^7$ is —H, C$_{1-8}$ alkyl, C$_{1-6}$ haloalkyl, C$_{3-12}$ cycloalkyl, heterocyclyl, C$_{6-10}$ aryl, or heteroaryl,
wherein each alkyl, haloalkyl, cycloalkyl, aryl, heteroaryl, or heterocyclyl of $R^7$ is optionally substituted with one to four $Z^2$, which may be the same or different; or
$R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 12 membered heterocyclyl having 0 to 3 additional heteroatoms each independently N, O, or S;
each $Z^1$, $Z^2$, or $Z^3$ is independently deuterium, halogen, =O, —CN, C$_{1-9}$ alkyl, C$_{1-8}$ haloalkyl, C$_{1-6}$ alkoxy, C$_{1-6}$ haloalkoxy, C$_{2-6}$ alkoxyalkyl, C$_{2-6}$ alkenyl, C$_{2-6}$ alkynyl, C$_{3-15}$ cycloalkyl, heterocyclyl, C$_{6-10}$ aryl, heteroaryl, or —O—R$^{3a}$;
wherein each alkyl, haloalkyl, alkenyl, alkynyl, cycloalkyl, heterocyclyl, aryl, or heteroaryl of each $Z^1$, $Z^2$, or $Z^3$ is optionally substituted with one to four $Z^{1a}$, which may be the same or different;

each $Z^{1a}$ is independently deuterium, $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, —CN, —O—$R^{3a}$, or —S(O)$_2$$R^{3a}$, wherein each alkyl, haloalkyl, alkenyl, alkynyl, cycloalkyl, heterocyclyl, aryl, or heteroaryl of $Z^{1a}$ is optionally substituted with one to four $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, or —CN, wherein each alkyl, alkenyl, alkynyl, cycloalkyl, heterocyclyl, aryl, or heteroaryl of $Z^{1b}$ is unsubstituted;

each $R^{3a}$ is independently —H, $C_{1-9}$ alkyl, $C_{6-10}$ aryl, or heteroaryl, wherein each alkyl, alkenyl, alkynyl, cycloalkyl, heterocyclyl, aryl, or heteroaryl of $R^{3a}$ is optionally substituted with one to four $Z^{1b}$, which may be the same or different;

wherein each heteroaryl of the compound of Formula (I) or Formula (Ia) is 5 to 12 membered heteroaryl having one to four heteroatoms each independently N, O, or S;

wherein each heterocyclyl of the compound of Formula (I) or Formula (Ia) is 3 to 20 membered heterocyclyl having one to four heteroatoms each independently N, O, or S.

In some embodiments of the compound of Formula (I), Formula (Ia), or Formula (Ib), or pharmaceutically acceptable salt thereof, $R^1$ is —H;
$R^2$ is —H or —F;
$R^3$ is —H or —F;
$R^{4a}$ and $R^{4b}$ are each independently —H—F, or —CH$_3$;
Ring A is a cyclopentyl, cyclohexyl, cyclohexenyl, or tetrahydropyranyl ring;
n is 0, 1, or 2;
each $R^5$ is independently —F, —OH, —CH$_3$, or —O—CH$_3$;
$R^6$ is —H, $C_{1-6}$ alkyl, $C_{1-6}$ haloalkyl, $C_{3-10}$ cycloalkyl, heterocyclyl, $C_{6-10}$ aryl, or heteroaryl,
wherein each alkyl, haloalkyl, cycloalkyl, aryl, heteroaryl, or heterocyclyl of $R^6$ is optionally substituted with one to four $Z^1$, which may be the same or different;
$R^7$ is —H, $C_{1-8}$ alkyl, $C_{1-6}$ haloalkyl, $C_{3-12}$ cycloalkyl, heterocyclyl, $C_{6-10}$ aryl, or heteroaryl,
wherein each alkyl, haloalkyl, cycloalkyl, aryl, heteroaryl, or heterocyclyl of $R^7$ is optionally substituted with one to four $Z^2$, which may be the same or different; or
$R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 12 membered heterocyclyl having 0 to 3 additional heteroatoms each independently N, O, or S;
each $Z^1$, $Z^2$, or $Z^3$ is independently deuterium, halogen, =O, —CN, $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, $C_{3-15}$ cycloalkyl, heterocyclyl, $C_{6-10}$ aryl, heteroaryl, or —O—$R^{3a}$;
wherein each alkyl, haloalkyl, alkenyl, alkynyl, cycloalkyl, heterocyclyl, aryl, or heteroaryl of each $Z^1$, $Z^2$, or $Z^3$ is optionally substituted with one to four $Z^{1a}$, which may be the same or different;
each $Z^{1a}$ is independently deuterium, $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{1-10}$ aryl, heteroaryl, —CN, —O—$R^{3a}$, or —S(O)$_2$$R^{3a}$, wherein each alkyl, haloalkyl, alkenyl, alkynyl, cycloalkyl, heterocyclyl, aryl, or heteroaryl of $Z^{1a}$ is optionally substituted with one to four $Z^{1b}$, which may be the same or different; each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, or —CN, wherein each alkyl, alkenyl, alkynyl, cycloalkyl, heterocyclyl, aryl, or heteroaryl of $Z^{1b}$ is unsubstituted;

each $R^{3a}$ is independently —H, $C_{1-9}$ alkyl, $C_{6-10}$ aryl, or heteroaryl, wherein each alkyl, alkenyl, alkynyl, cycloalkyl, heterocyclyl, aryl, or heteroaryl of $R^{3a}$ is optionally substituted with one to four $Z^{1b}$, which may be the same or different;

wherein each heteroaryl of the compound of Formula (I) or Formula (Ia) is 5 to 12 membered heteroaryl having one to four heteroatoms each independently N, O, or S;

wherein each heterocyclyl of the compound of Formula (I) or Formula (Ia) is 3 to 20 membered heterocyclyl having one to four heteroatoms each independently N, O, or S.

In some embodiments, in the compound of Formula (I), Formula (Ia) or Formula (Ib), or pharmaceutically acceptable salt thereof, $R^1$ is —H;
$R^2$ is —H or —F;
$R^3$ is —H or —F;
$R^{4a}$ and $R^{4b}$ are each independently —H or —F;
Ring A is a cyclohexyl, cyclohexenyl, or tetrahydropyranyl ring;
n is 0;
$R^6$ is —H, $C_{1-6}$ alkyl, $C_{1-6}$ haloalkyl, $C_{3-10}$ cycloalkyl, heterocyclyl, $C_{6-10}$ aryl, or heteroaryl,
wherein each alkyl, haloalkyl, cycloalkyl, aryl, heteroaryl, or heterocyclyl of $R^6$ is optionally substituted with one to four $Z^1$, which may be the same or different;
$R^7$ is —H, $C_{1-6}$ alkyl, $C_{1-6}$ haloalkyl, $C_{3-10}$ cycloalkyl, heterocyclyl, $C_{6-10}$ aryl, or heteroaryl,
wherein each alkyl, haloalkyl, cycloalkyl, aryl, heteroaryl, or heterocyclyl of $R^7$ is optionally substituted with one to four $Z^2$, which may be the same or different; or
$R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 12 membered heterocyclyl having 0 to 3 additional heteroatoms each independently N, O, or S;
each $Z^1$, $Z^2$, or $Z^3$ is independently halogen, =O, —CN, $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, $C_{3-15}$ cycloalkyl, heterocyclyl, $C_{6-10}$ aryl, heteroaryl, or —O—$R^{3a}$;
wherein each alkyl, haloalkyl, alkenyl, alkynyl, cycloalkyl, heterocyclyl, aryl, or heteroaryl of each $Z^1$, $Z^2$, or $Z^3$ is optionally substituted with one to four $Z^{1a}$, which may be the same or different;
each $Z^{1a}$ is independently -D, $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, —CN, —O—$R^{3a}$, or —S(O)$_2$$R^{3a}$;

wherein each alkyl, haloalkyl, alkenyl, alkynyl, cycloalkyl, heterocyclyl, aryl, or heteroaryl of $Z^{1a}$ is optionally substituted with one to four $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, or —CN, wherein each alkyl, alkenyl, alkynyl, cycloalkyl, heterocyclyl, aryl, or heteroaryl of $Z^{1b}$ is unsubstituted;

each $R^{3a}$ is independently —H, $C_{1-9}$ alkyl, $C_{6-10}$ aryl, or heteroaryl, wherein each alkyl, alkenyl, alkynyl, cycloalkyl, heterocyclyl, aryl, or heteroaryl of $R^{3a}$ is optionally substituted with one to four $Z^{1b}$, which may be the same or different;

wherein each heteroaryl of the compound of Formula (I) or Formula (Ia) is 5 to 12 membered heteroaryl having one to four heteroatoms each independently N, O, or S; and wherein each heterocyclyl of the compound of Formula (I) or Formula (Ia) is 3 to 20 membered heterocyclyl having one to four heteroatoms each independently N, O or S.

In some embodiments of the compound of Formula (I), Formula (Ia), or Formula (Ib), or pharmaceutically acceptable salt thereof, $R^1$ is —H;
$R^2$ is —H or —F;
$R^3$ is —H or —F;
$R^{4a}$ is —H, —F, or —CH$_3$, and $R^{4b}$ is —H;
Ring A is

[structures]

n is 0, 1, or 2;
each $R^5$ is independently —F, —OH, —CH$_3$, =CH$_2$, —CH$_2$—OH, or —O—CH$_3$;
$R^6$ is —H or $C_{1-6}$ alkyl optionally substituted with one $Z^1$, wherein $Z^1$ is unsubstituted;
$R^7$ is —H, $C_{1-8}$ alkyl, $C_{3-12}$ cycloalkyl, $C_{6-10}$ aryl, 4 to 12 membered heterocyclyl having 1 to 2 heteroatoms each independently selected from nitrogen, oxygen, and sulfur, or 5 to 12 membered heteroaryl having 1 to 3 heteroatoms each independently selected from nitrogen, oxygen, and sulfur, wherein each alkyl, cycloalkyl, aryl, heterocyclyl or heteroaryl of $R^7$ is optionally substituted with one to four $Z^2$, which may be the same or different; or $R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 7 membered heterocyclyl optionally having an additional N;

each $Z^1$, $Z^2$, or $Z^3$ is independently deuterium, halogen, =O, $C_{1-9}$ alkyl, $C_{1-8}$ haloalkyl, $C_{1-6}$ alkoxy, $C_{1-6}$ haloalkoxy, $C_{3-15}$ cycloalkyl, $C_{6-10}$ aryl, heterocyclyl, heteroaryl or —O—$R^{3a}$;

wherein each alkyl, haloalkyl, alkoxy, haloalkoxy, cycloalkyl, heterocyclyl, aryl, or heteroaryl of $Z^1$, $Z^2$, or $Z^3$ is optionally substituted with one to four $Z^{1a}$, which may be the same or different;

each $Z^{1a}$ is independently deuterium, $C_{1-9}$ alkyl, $C_{1-8}$ haloalkyl, $C_{1-6}$ alkoxy, halogen, —CN, or —S(O)$_2$R$^{3a}$;

wherein each alkyl of $Z^{1a}$ is optionally substituted with one to four $Z^{1b}$, which may be the same or different;

each $Z^{1b}$ is independently halogen, $C_{3-15}$ cycloalkyl, or $C_{6-10}$ aryl, wherein each cycloalkyl or aryl of $Z^{1b}$ is unsubstituted;

each $R^{3a}$ is independently $C_{1-9}$ alkyl or $C_{6-10}$ aryl, wherein each alkyl or aryl of $R^{3a}$ is optionally substituted with one to four $Z^{1b}$, which may be the same or different;

wherein each heteroaryl of the compound of Formula (I) or Formula (Ia) is 5 to 6 membered heteroaryl having one or two heteroatoms each independently N or S;

wherein each heterocyclyl of the compound of Formula (I) or Formula (Ia) is 3 to 7 membered heterocyclyl having one to two heteroatoms each independently N or O.

In some embodiments of the compound of Formula (I), Formula (Ia), or Formula (Ib), or pharmaceutically acceptable salt thereof, $R^1$ is —H;
$R^2$ is —H or —F;
$R^3$ is —H or —F;
$R^{4a}$ is —H, —F, or —CH$_3$, and $R^{4b}$ is —H;
Ring A is

[structures]

n is 0, 1, or 2;

each $R^5$ is independently —F, —OH, —CH$_3$, or —O—CH$_3$;

$R^6$ is —H or C$_{1-6}$ alkyl optionally substituted with one $Z^1$, wherein $Z^1$ is unsubstituted;

$R^7$ is —H, C$_{1-8}$ alkyl, C$_{3-12}$ cycloalkyl, C$_{6-10}$ aryl, 4 to 12 membered heterocyclyl having 1 to 2 heteroatoms each independently selected from nitrogen, oxygen, and sulfur, or 5 to 12 membered heteroaryl having 1 to 3 heteroatoms each independently selected from nitrogen, oxygen, and sulfur, wherein each alkyl, cycloalkyl, aryl, heterocyclyl or heteroaryl of $R^7$ is optionally substituted with one to four $Z^2$, which may be the same or different; or $R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 7 membered heterocyclyl optionally having an additional N;

each $Z^1$, $Z^2$, or $Z^3$ is independently deuterium, halogen, =O, C$_{1-9}$ alkyl, C$_{1-8}$ haloalkyl, C$_{1-6}$ alkoxy, C$_{1-6}$ haloalkoxy, C$_{3-15}$ cycloalkyl, C$_{6-10}$ aryl, heterocyclyl, heteroaryl or —O—R$^{3a}$;

wherein each alkyl, haloalkyl, alkoxy, haloalkoxy, cycloalkyl, heterocyclyl, aryl, or heteroaryl of $Z^1$, $Z^2$, or $Z^3$ is optionally substituted with one to four $Z^{1a}$, which may be the same or different;

each $Z^{1a}$ is independently deuterium, C$_{1-9}$ alkyl, Cis haloalkyl, C$_{1-6}$ alkoxy, halogen, —CN, or —S(O)$_2$R$^{3a}$;

wherein each alkyl of $Z^{1a}$ is optionally substituted with one to four $Z^{1b}$, which may be the same or different;

each $Z^{1b}$ is independently halogen, C$_{3-15}$ cycloalkyl, or C$_{6-10}$ aryl, wherein each cycloalkyl or aryl of $Z^{1b}$ is unsubstituted;

each $R^{3a}$ is independently C$_{1-9}$ alkyl or C$_{6-10}$ aryl, wherein each alkyl or aryl of $R^{3a}$ is optionally substituted with one to four $Z^{1b}$, which may be the same or different;

wherein each heteroaryl of the compound of Formula (I) or Formula (Ia) is 5 to 6 membered heteroaryl having one or two heteroatoms each independently N or S;

wherein each heterocyclyl of the compound of Formula (I) or Formula (Ia) is 3 to 7 membered heterocyclyl having one to two heteroatoms each independently N or O.

In some embodiments of the compound of Formula (I), Formula (Ia), or Formula (Ib), or pharmaceutically acceptable salt thereof, $R^1$ is —H;
$R^2$ is —H or —F;
$R^3$ is —H or —F;
$R^{4a}$ and $R^{4b}$ are each —H; Ring A is

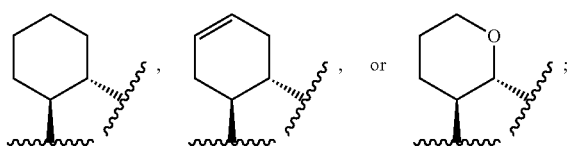

n is 0;

$R^6$ is —H or C$_{1-6}$ alkyl optionally substituted with one $Z^1$, wherein $Z^1$ is unsubstituted;

$R^7$ is —H, C$_{1-6}$ alkyl, C$_{3-10}$ cycloalkyl, or heterocyclyl, wherein each alkyl, cycloalkyl, or heterocyclyl of $R^7$ is optionally substituted with one to four $Z^2$, which may be the same or different; or $R^6$ and $R^7$ together with the nitrogen to which they are attached form a heterocyclyl, which is optionally substituted with one to four $Z^3$, which may be the same or different; wherein the heterocyclyl formed by $R^6$ and $R^7$ is 3 to 7 membered heterocyclyl optionally having an additional N;

each $Z^1$, $Z^2$, or $Z^3$ is independently halogen, =O, C$_{1-9}$ alkyl, C$_{1-8}$ haloalkyl, C$_{1-6}$ alkoxy, C$_{3-15}$ cycloalkyl, heterocyclyl, C$_{6-10}$ aryl, heteroaryl, or —O—R$^{3a}$;

wherein each alkyl, cycloalkyl, heterocyclyl, aryl, or heteroaryl of $Z^1$, $Z^2$, or $Z^3$ is optionally substituted with one to four $Z^{1a}$, which may be the same or different;

each $Z^{1a}$ is independently C$_{1-9}$ alkyl, C$_{1-8}$ haloalkyl, C$_{1-6}$ alkoxy, halogen, —CN, or —S(O)$_2$R$^{3a}$;

wherein each alkyl of $Z^{1a}$ is optionally substituted with one to four $Z^{1b}$, which may be the same or different;

each $Z^{1b}$ is independently halogen, C$_{3-15}$ cycloalkyl, or C$_{6-10}$ aryl;

wherein each cycloalkyl or aryl of $Z^{1b}$ is unsubstituted;

each $R^{3a}$ is independently C$_{1-9}$ alkyl or C$_{6-10}$ aryl, wherein each alkyl or aryl of $R^{3a}$ is optionally substituted with one to four $Z^{1b}$, which may be the same or different;

wherein each heteroaryl of the compound of Formula (I) or Formula (Ia) is 5 to 6 membered heteroaryl having one or two heteroatoms each independently N or S;

wherein each heterocyclyl of the compound of Formula (I) or Formula (Ia) is 3 to 7 membered heterocyclyl having one to two heteroatoms each independently N or O.

In some embodiments, the compound of Formula (I), or pharmaceutically acceptable salt thereof, is a compound of Formula (IIa)

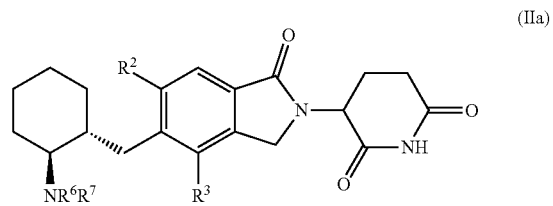

or pharmaceutically acceptable salt thereof.

In some embodiments, the compound of Formula (I), or pharmaceutically acceptable salt thereof, is a compound of Formula (IIb)

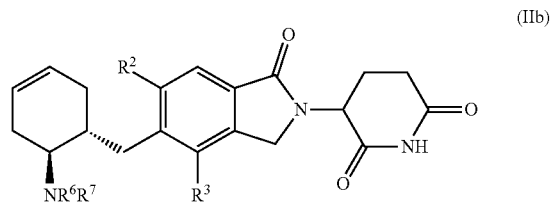

or pharmaceutically acceptable salt thereof.

In some embodiments, the compound of Formula (I), or pharmaceutically acceptable salt thereof, is a compound of Formula (IIc)

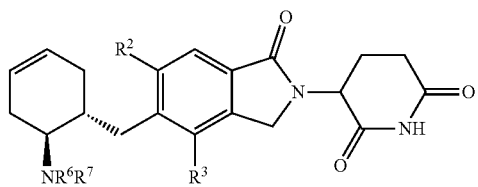

(IIc)

or pharmaceutically acceptable salt thereof.

In some embodiments, the compound of Formula (I), or pharmaceutically acceptable salt thereof, is a compound of Formula (IId)

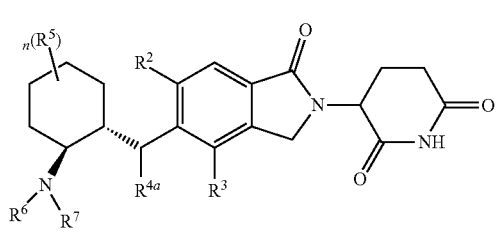

(IId)

or a pharmaceutically acceptable salt thereof.

In some embodiments, the compound of Formula (I), or pharmaceutically acceptable salt thereof, is a compound of Formula (IIe)

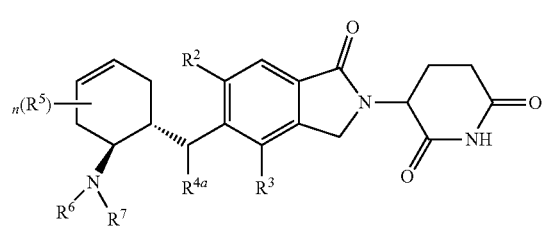

(IIe)

or a pharmaceutically acceptable salt thereof.

In some embodiments, the compound of Formula (I), or pharmaceutically acceptable salt thereof, is a compound of Formula (IIf)

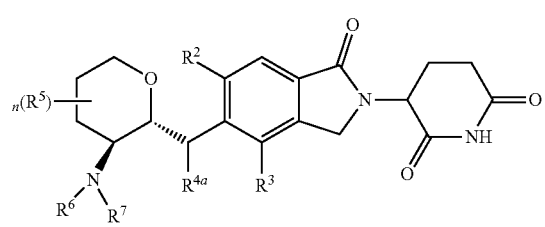

(IIf)

or a pharmaceutically acceptable salt thereof.

In some embodiments, the compound of Formula (I), or pharmaceutically acceptable salt thereof, is a compound of Formula (IIg)

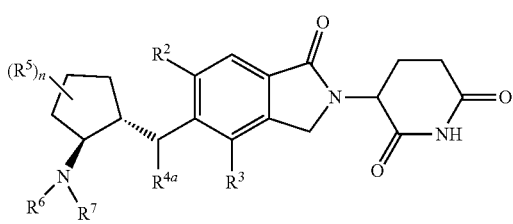

(IIg)

or a pharmaceutically acceptable salt thereof.

In some embodiments, the compound of Formula (I), or pharmaceutically acceptable salt thereof, is a compound of Formula (IIh)

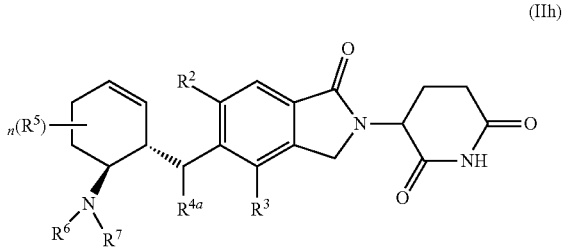

(IIh)

or a pharmaceutically acceptable salt thereof.

In some embodiments, the compound of Formula (I), or pharmaceutically acceptable salt thereof, is a compound of Formula (IIi)

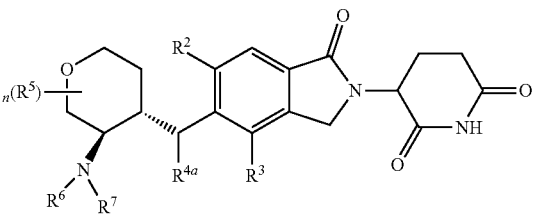

(IIi)

or a pharmaceutically acceptable salt thereof.

In some embodiments, the compound of Formula (I), or pharmaceutically acceptable salt thereof, is a compound of Formula (IIj)

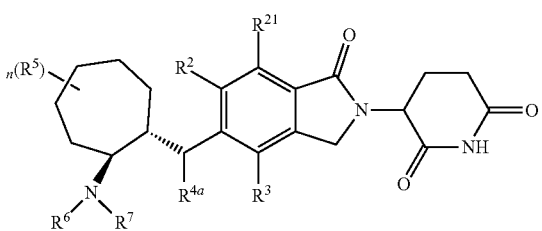

(IIj)

or a pharmaceutically acceptable salt thereof.

In some embodiments, the compound of Formula (I), or pharmaceutically acceptable salt thereof, is a compound of Formula (IIk)

(IIk)

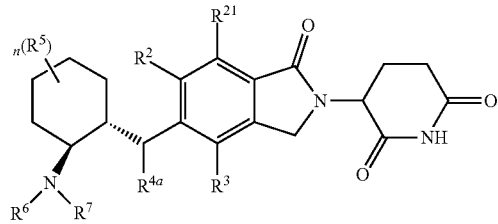

or a pharmaceutically acceptable salt thereof.

In some embodiments of the compounds of Formula (I), (Ia), (Ib), (IId), (IIe), (IIf), (IIg), (IIh), (IIi), (IIj), or (IIk), or pharmaceutically acceptable salt thereof, $R^{4b}$ is —F or —CH$_3$. In some embodiments of the compounds of Formula (I), (Ia), (Ib), (IId), (IIe), (IIf), (IIg), (IIh), (IIi), (IIj), or (IIk), or pharmaceutically acceptable salt thereof, each $R^5$ is independently —F, —OH, —CH$_3$, or —O—CH$_3$. In some embodiments of the compounds of Formula (I), (Ia), (Ib), (IId), (IIe), (IIf), (IIg), (IIh), (IIi), (IIj), or (IIk), or pharmaceutically sal thereof, $R^6$ is —H.

In some embodiments of the compound of Formula (I), (Ia), (Ib), (IIa), (IIb), (IIc), (IId), (IIe), (IIf), (IIg), (IIh), (IIi), (IIj), or (IIk), or pharmaceutically acceptable salt thereof, $R^6$ is $C_{1-6}$ alkyl or $C_{1-6}$ haloalkyl. In some embodiments of the compound of Formula (I), (Ia), (Ib), (IIa), (IIb), (IIc), (IId), (IIe), (IIf), (IIg), (IIh), (IIi), (IIj), or (IIk), or pharmaceutically acceptable salt thereof, $R^6$ is unsubstituted $C_{1-6}$ alkyl. In some embodiments of the compound of Formula (I), (Ia), (Ib), (IIa), (IIb), (IIc), (IId), (IIe), (IIf), (IIg), (IIh), (IIi), (IIj), or (IIk), or pharmaceutically acceptable salt thereof, $R^6$ is

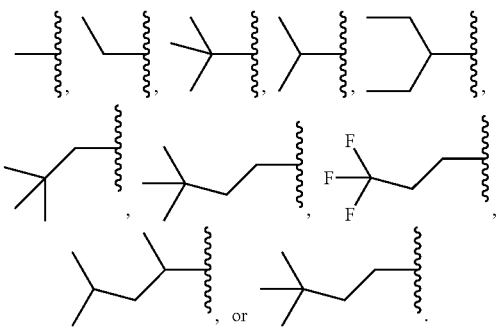

In some embodiments of the compound of Formula (I), (Ia), (Ib), (IIa), (IIb), (IIc), (IId), (IIe), (If), (IIg), (IIh), (IIi), (IIj), or (IIk), or pharmaceutically acceptable salt thereof, $R^6$ is —CH$_3$ or

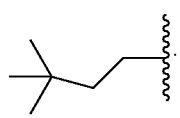 [SMILES: *CCC(C)(C)C]

In some embodiments of the compound of Formula (I), (Ia), (Ib), (IIa), (IIb), (IIc), (IId), (IIe), (IIf), (IIg), (IIh), (IIi), (IIj), or (IIk), or pharmaceutically acceptable salt thereof, $R^7$ is $C_{1-6}$ alkyl or $C_{3-10}$ cycloalkyl, each optionally substituted with one or two halogen or $C_{6-10}$ aryl of $Z^2$. In some embodiments of the compound of Formula (I), (Ia), (Ib), (IIa), (IIb), (IIc), (IId), (IIe), (IIf), (IIg), (IIh), or (IIi), or pharmaceutically acceptable salt thereof, $R^7$ is $C_{1-6}$ alkyl or cyclohexyl, each optionally substituted with one or two —F or phenyl of $Z^2$. In some embodiments of the compound of Formula (I), (Ia), (Ib), (IIa), (IIb), (IIc), (IId), (IIe), (IIf), (IIg), (IIh), (IIi), (IIj), or (IIk), or pharmaceutically acceptable salt thereof, $R^7$ is

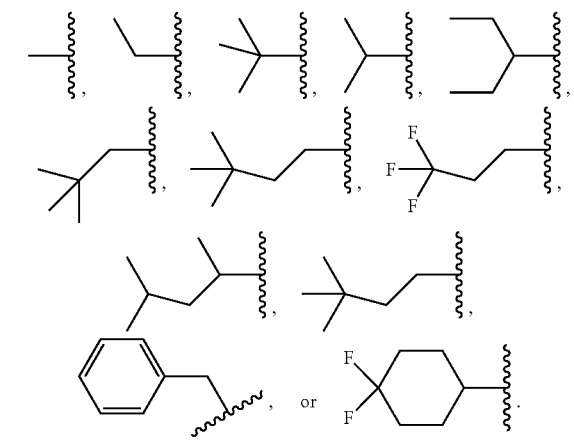

In some embodiments of the compound of Formula (I), (Ia), (Ib), (IIa), (IIb), (IIc), (IId), (IIe), (IIf), (IIg), (IIh), (IIi), (IIj), or (IIk), or pharmaceutically acceptable salt thereof, $R^7$ is

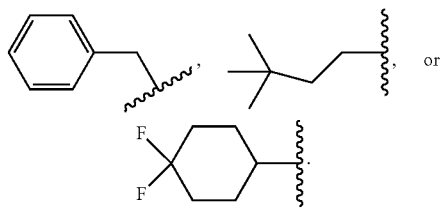

In some embodiments of the compound of Formula (I), (Ia), (Ib), (IIa), (IIb), (IIc), (IId), (IIe), (IIf), (IIg), (IIh), (IIi), (IIj), or (IIk), or pharmaceutically acceptable salt thereof, $R^7$ is

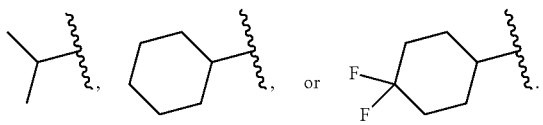

In some embodiments the compound of Formula (I) or (IIa), or pharmaceutically acceptable salt thereof, is a compound of Formula (IIIa)

(IIIa)

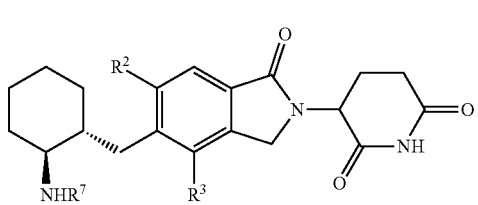

or pharmaceutically acceptable salt thereof.

In some embodiments the compound of Formula (I), or pharmaceutically acceptable salt thereof, is a compound of Formula (IIIa-1)

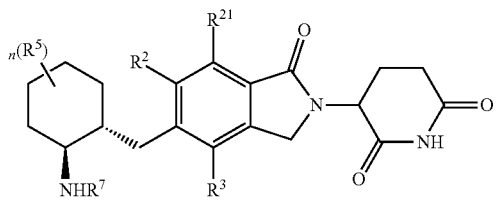

(IIIa-1)

or pharmaceutically acceptable salt thereof.

In some embodiments the compound of Formula (I), or pharmaceutically acceptable salt thereof, is a compound of Formula (IIIa-2)

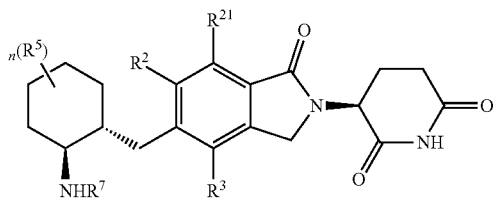

(IIIa-2)

or pharmaceutically acceptable salt thereof.

In some embodiments the compound of Formula (I), or pharmaceutically acceptable salt thereof, is a compound of Formula (IIIa-3)

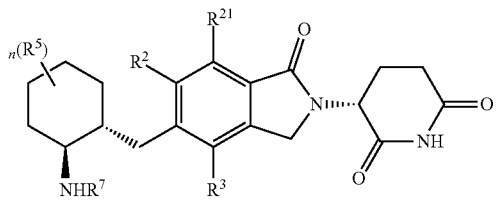

(IIIa-3)

In some embodiments of the compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), or (IIIa-3), or pharmaceutically acceptable salt thereof, $R^7$ is —H, $C_{1-8}$ alkyl, $C_{3-12}$ cycloalkyl, $C_{6-10}$ aryl, 4 to 12 membered heterocyclyl having 1 to 2 heteroatoms each independently selected from nitrogen, oxygen, and sulfur, or 5 to 12 membered heteroaryl having 1 to 3 heteroatoms each independently selected from nitrogen, oxygen, and sulfur, wherein each alkyl, cycloalkyl, aryl, heterocyclyl, or heteroaryl of $R^7$ is optionally substituted with 1 to 3 $Z^2$, which may be the same or different, wherein each $Z^2$ is independently, deuterium, halogen, =O, —CN, $C_{1-8}$ alkyl, $C_{1-8}$ haloalkyl, $C_{1-6}$ alkoxy, $C_{1-6}$ haloalkoxy, $C_{3-10}$ cycloalkyl, $C_{6-10}$ aryl, 5 to 12 membered heteroaryl having 1 to 3 heteroatoms each independently selected from nitrogen, oxygen, and sulfur, or —C(O)—$R^{3a}$, wherein $R^{3a}$ is —H or unsubstituted $C_{1-6}$ alkyl, wherein each $C_{1-6}$ alkyl of $Z^2$ is optionally substituted with 1 to 3 Zia, wherein each $Z^{1a}$ is independently cyano or $C_{1-6}$ alkoxy. In some embodiments of the compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), or (IIIa-3), or pharmaceutically acceptable salt thereof, $R^7$ is —H, $C_{1-8}$ alkyl, $C_{3-12}$ cycloalkyl, $C_{6-10}$ aryl, 4 to 12 membered heterocyclyl having 1 to 2 heteroatoms each independently selected from nitrogen, oxygen, and sulfur, or 5 to 12 membered heteroaryl having 1 to 3 heteroatoms each independently selected from nitrogen, oxygen, and sulfur, wherein each alkyl, cycloalkyl, aryl, heterocyclyl, or heteroaryl of $R^7$ is optionally substituted with 1 to 3 $Z^2$, which may be the same or different, wherein each $Z^2$ is independently, deuterium, halogen, =O, —CN, $C_{1-8}$ alkyl, $C_{1-8}$ haloalkyl, $C_{1-6}$ alkoxy, $C_{1-6}$ haloalkoxy, $C_{3-10}$ cycloalkyl, $C_{6-10}$ aryl, or —C(O)—$R^{3a}$, wherein $R^{3a}$ is —H or unsubstituted $C_{1-6}$ alkyl, wherein each $C_{1-6}$ alkyl of $Z^2$ is optionally substituted with 1 to 3 $Z^{1a}$, wherein each $Z^{1a}$ is independently cyano or $C_{1-6}$ alkoxy. In some embodiments of the compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), or (IIIa-3), or pharmaceutically acceptable salt thereof, $R^7$ is —H, $C_{1-6}$ alkyl, $C_{3-12}$ cycloalkyl, or 4 to 12 membered heterocyclyl having a heteroatom selected from nitrogen and oxygen, wherein each alkyl, cycloalkyl or heterocyclyl of $R^7$ is optionally substituted with 1 to 3 $Z^2$, which may be the same or different, wherein each $Z^2$ is independently halogen, =O, $C_{1-6}$ alkyl, $C_{1-8}$ haloalkyl, $C_{1-6}$ alkoxy, or —C(O)—$R^{3a}$, wherein $R^{3a}$ is —H or unsubstituted $C_{1-6}$ alkyl. In some embodiments of the compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), or (IIIa-3), or pharmaceutically acceptable salt thereof, $R^7$ is —H, $C_{1-8}$ alkyl, cyclopropyl, cyclobutyl, cyclopentyl, cyclohexyl, cycloheptyl, spiro[2.3]hexyl, bicyclo[3.1.1]heptyl, spiro[3.3]heptyl, spiro[2.5]octyl, oxetanyl, oxepanyl, dioxanyl, oxaspiro[3.3]heptyl, oxaspiro[3.5]nonyl, oxabicyclo[3.2.1]octyl, (3aR,6aS)-hexahydro-1H-cyclopenta[c]furanyl, bicyclo[3.2.1]octyl, (1R,5S)bicyclo[3.1.0]hexyl, (1R,5S)bicyclo[3.2.0]heptyl, (3aR,6aS)-2-methyloctahydropentalenyl, (1R,5S)-6,6-dimethylbicyclo[3.1.0]hexyl, spiro[2.4]heptyl, 7,7-difluoro-spiro[3.5]nonanyl, (4s,7s)-1-oxaspiro[3.5]nonanyl, (4r,7r)-oxaspiro[3.5]nonanyl, oxabicyclo[2.2.1]heptanyl, 3-oxabicyclo[3.2.1]octanyl, tetrahydrofuranyl, tetrahydropyranyl, piperidyl, tetrahydrothiopyranyl, -2,3-dihydro-1H-indyl, chromane, or 4,5,6,7-tetrahydro-1H-indazolyl, each optionally substituted with 1 to 3 $Z^2$, which may be the same or different, wherein each $Z^2$ is independently deuterium, =O, —CN, —CH$_3$, —CH$_2$—O—CH$_3$, —CH$_2$—CN, —O—CH$_3$, —O—CF$_3$, —CF$_3$, —O—C$_2$H$_5$, —O—C$_3$H$_7$, —C(O)—CH$_3$, —F, cyclopropyl, phenyl, triazolyl, or pyridyl. In some embodiments of the compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), or (IIIa-3), or pharmaceutically acceptable salt thereof, $R^7$ is-H, $C_{1-8}$ alkyl, cyclopropyl, cyclobutyl, cyclopentyl, cyclohexyl, cycloheptyl, spiro[2.3]hexyl, bicyclo[3.1.1]heptyl, spiro[3.3]heptyl, spiro[2.5]octyl, oxetanyl, oxepanyl, dioxanyl, oxaspiro[3.3]heptyl, oxaspiro[3.5]nonyl, oxabicyclo[3.2.1]octyl, (3aR,6aS)-hexahydro-1H-cyclopenta[c]furanyl, bicyclo[3.2.1]octyl, (1R,5S)bicyclo[3.1.0]hexyl, (1R,5S)bicyclo[3.2.0]heptyl, (3aR,6aS)-2-methyloctahydropentalene, (1R,5S)-6,6-dimethylbicyclo[3.1.0]hexyl, spiro[2.4]heptyl, 7,7-difluoro-spiro[3.5]nonanyl, (4s,7s)-1-oxaspiro[3.5]nonanyl, (4r,7r)-oxaspiro[3.5]nonanyl, oxabicyclo[2.2.1]heptanyl, 3-oxabicyclo[3.2.1]octanyl, tetrahydrofuranyl, tetrahydropyranyl, piperidyl, tetrahydrothiopyranyl, 2,3-dihydro-1H-indyl, chromane, or 4,5,6,7-tetrahydro-1H-indazolyl, each optionally substituted with 1 to 3 $Z^2$, which may be the same or different, wherein each $Z^2$ is independently deuterium, =O, —CN, —CH$_3$, —CH$_2$—O—CH$_3$, —CH$_2$—CN, —O—CH$_3$, —O—CF$_3$, —CF$_3$, —O—C$_2$H$_5$, —O—C$_3$H$_7$, —C(O)—CH$_3$, —F, cyclopropyl, or phenyl. In some embodiments of the compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), or (IIIa-3), or pharmaceutically acceptable salt thereof, $R^7$ is —H, $C_{1-6}$ alkyl, cyclopropyl, cyclobutyl, cyclopentyl, cyclohexyl, spiro[2.3]hexyl, bicyclo[3.1.1]heptyl, spiro[3.3]heptyl, spiro[2.5]octyl, oxetanyl, oxaspiro[3.3]heptyl, oxaspiro[3.5]nonyl, oxabicyclo[3.2.1]octyl, tetrahydrofuranyl, tetrahydropyranyl, piperidyl, or tetrahydrothiopyranyl, each optionally substituted with 1 to 3 $Z^2$, which may be the same or different, wherein each $Z^2$ is independently =O, —CH$_3$, —CF$_3$, —O—C$_2$H$_5$, —C(O)—CH$_3$, or —F. In some embodiments of the compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), or (IIIa-3), or pharmaceutically acceptable salt thereof, $R^7$ is —H,

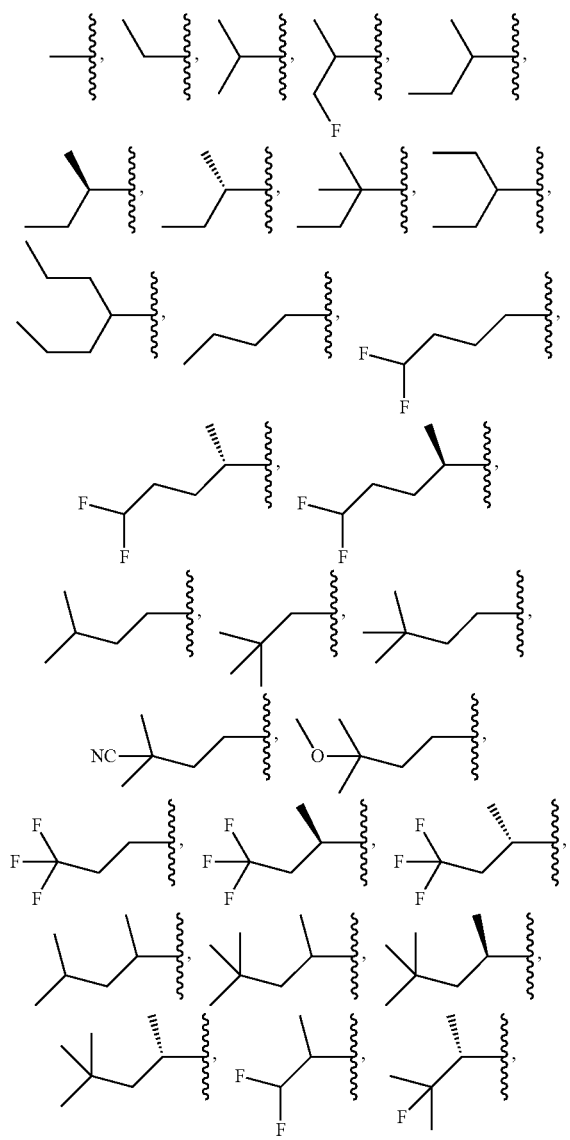

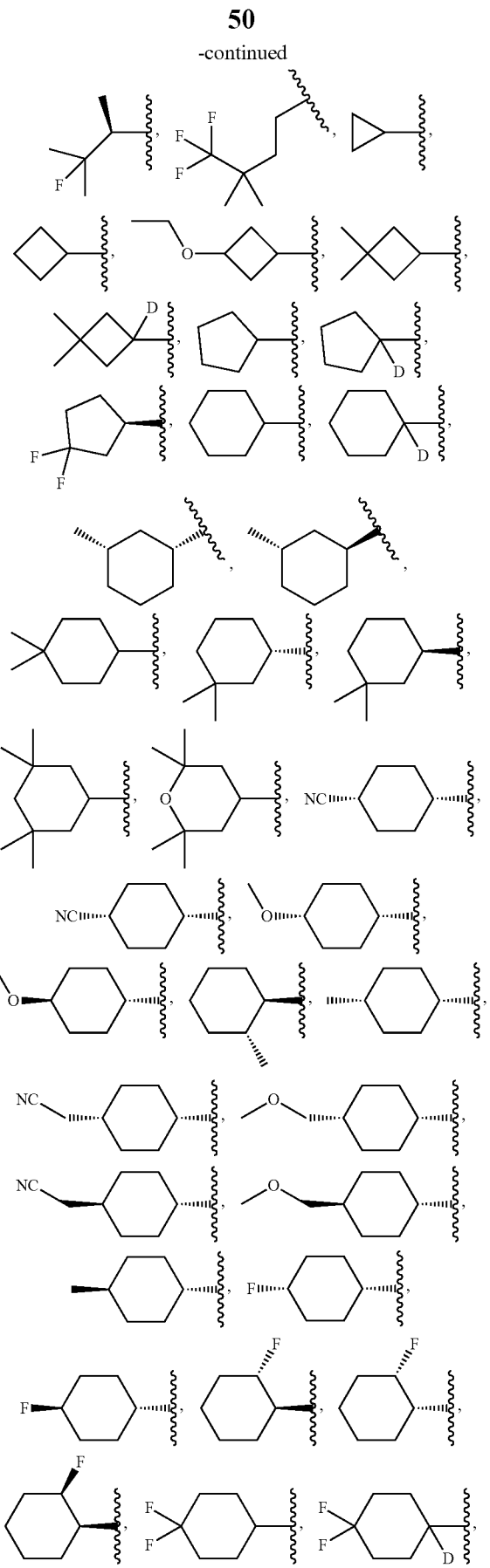

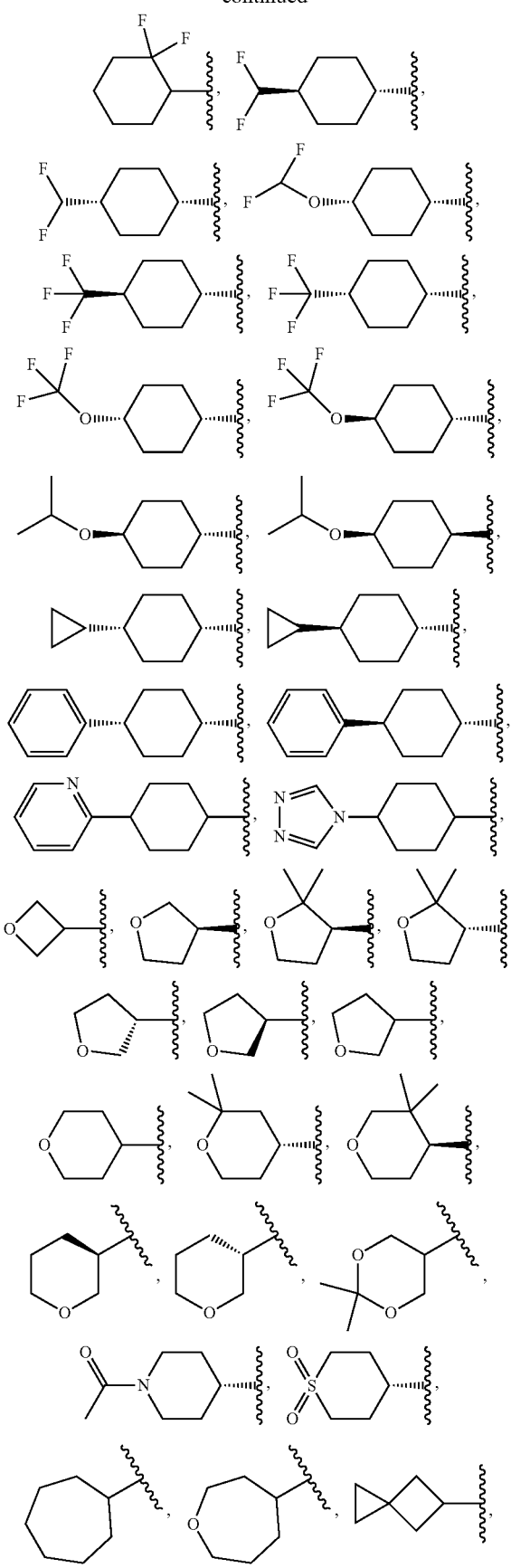
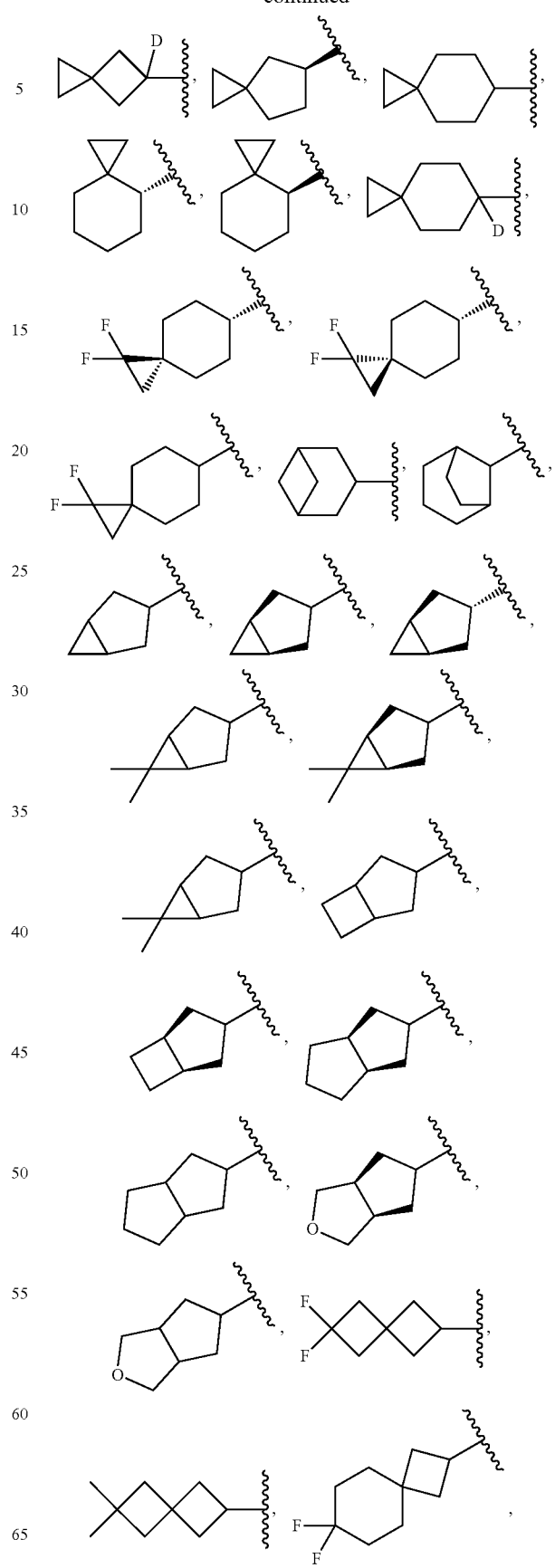

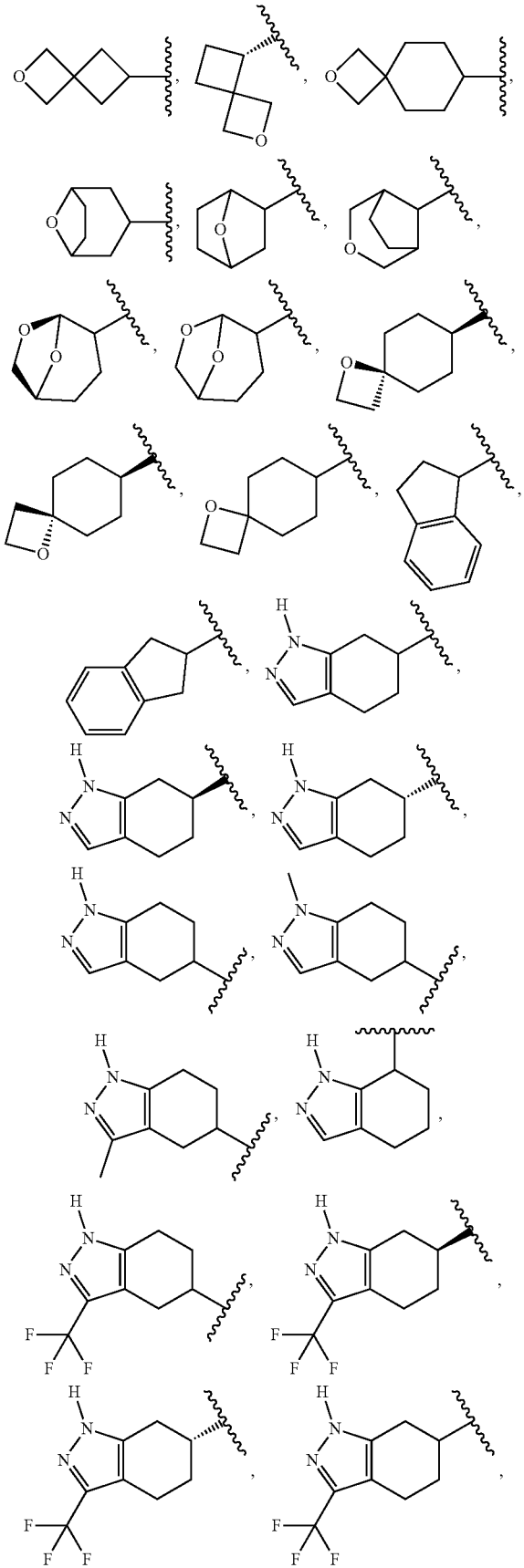
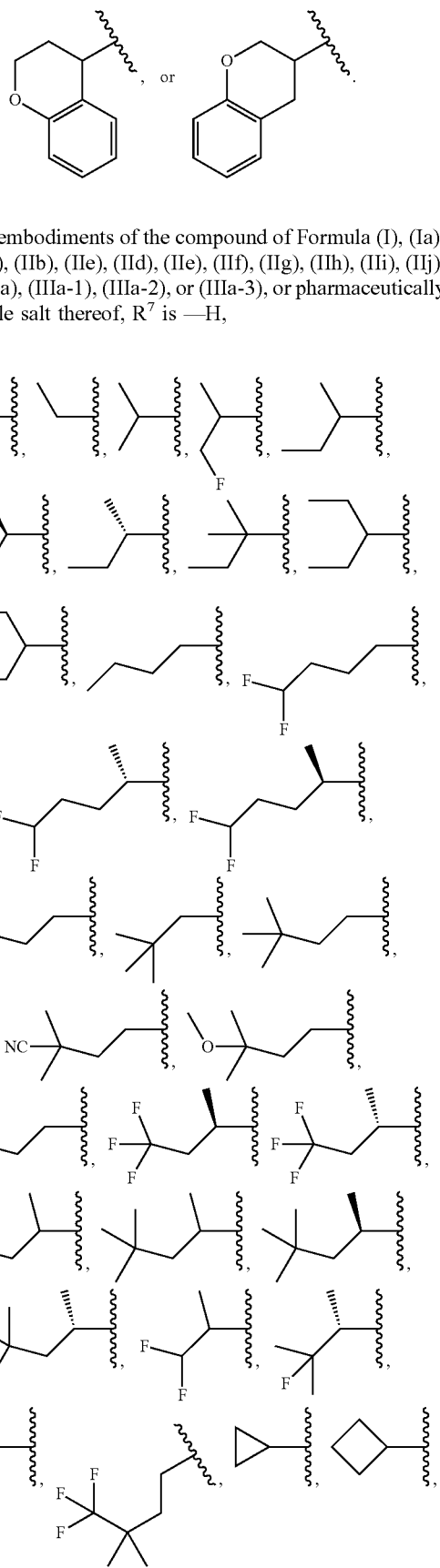
In some embodiments of the compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), or (IIIa-3), or pharmaceutically acceptable salt thereof, R$^7$ is —H,

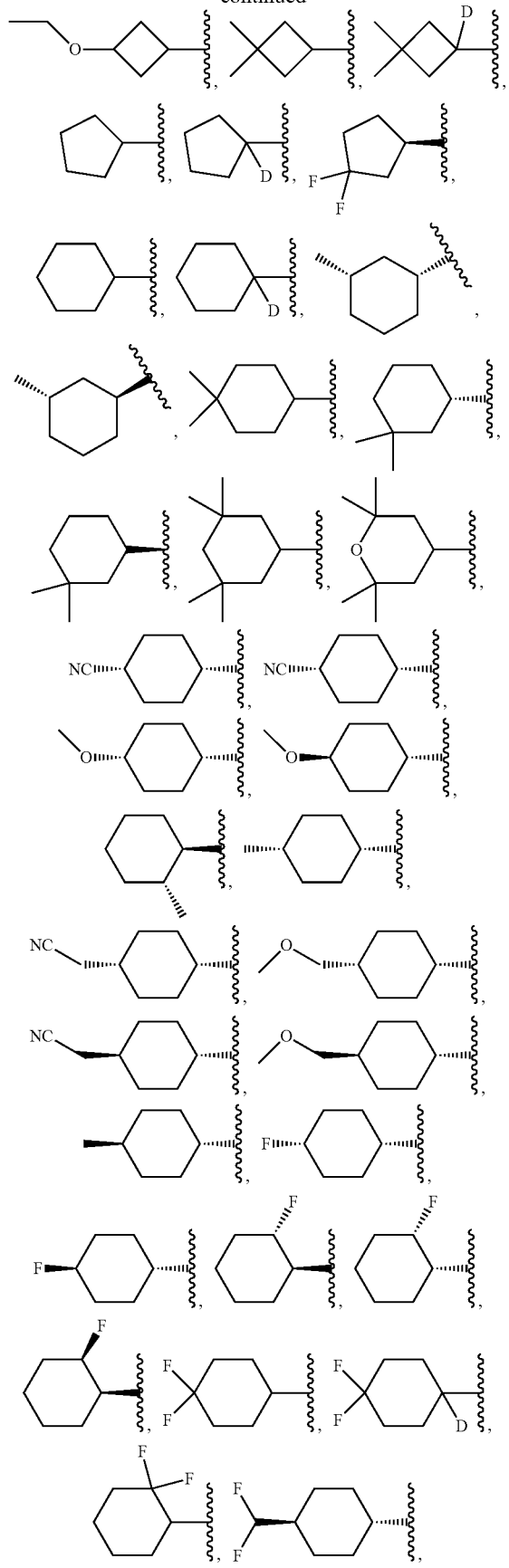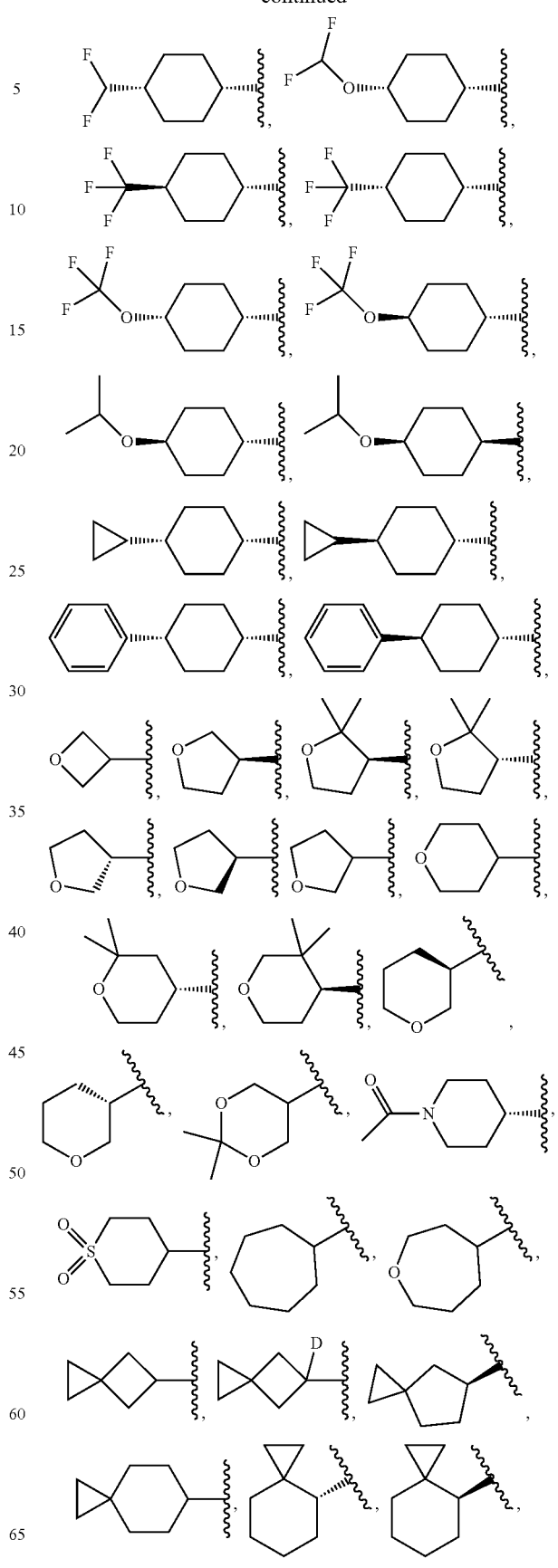

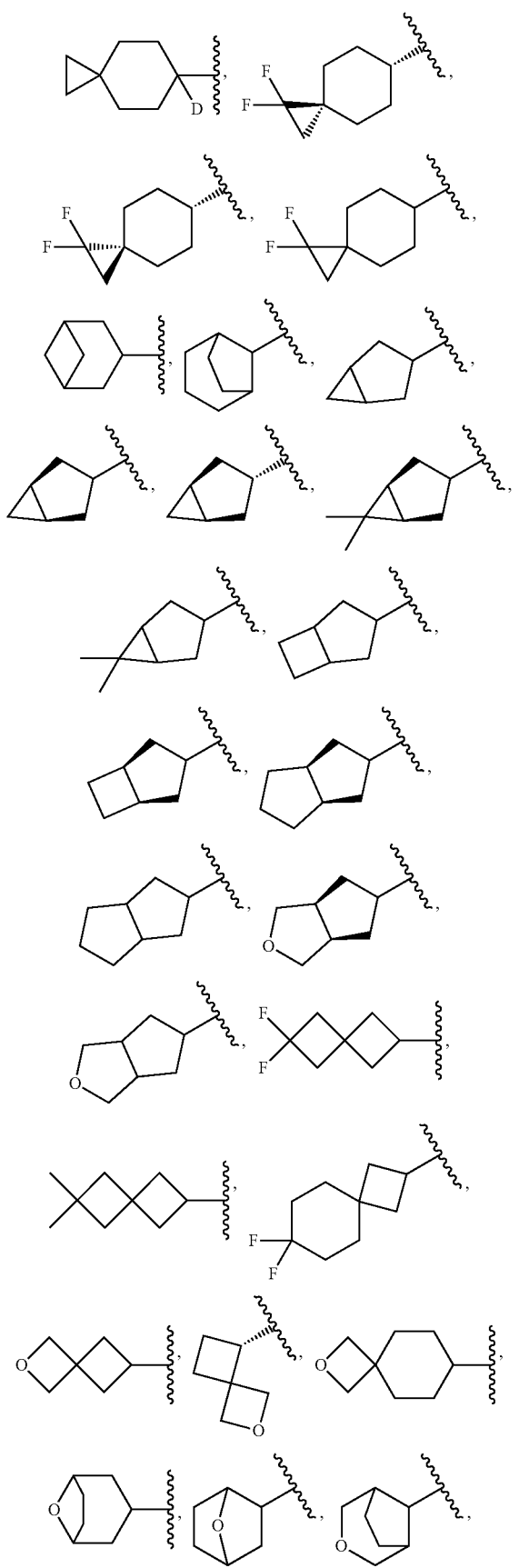
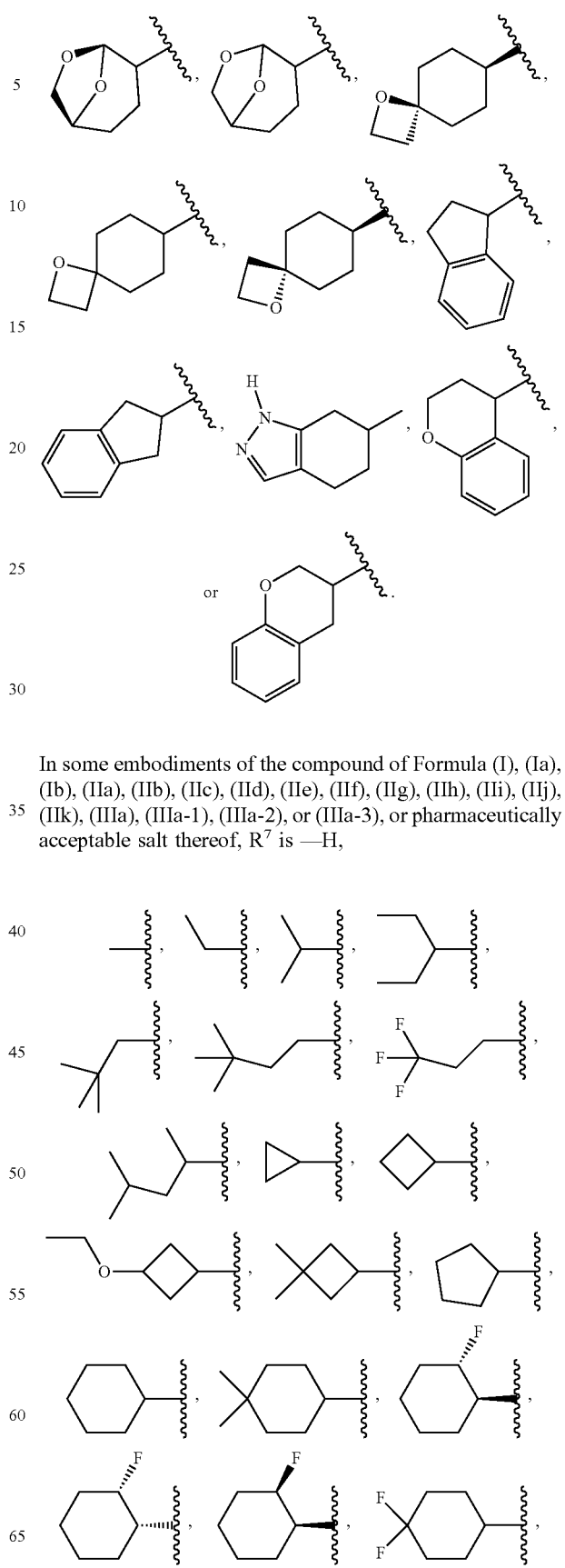
In some embodiments of the compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), or (IIIa-3), or pharmaceutically acceptable salt thereof, $R^7$ is —H, -continued

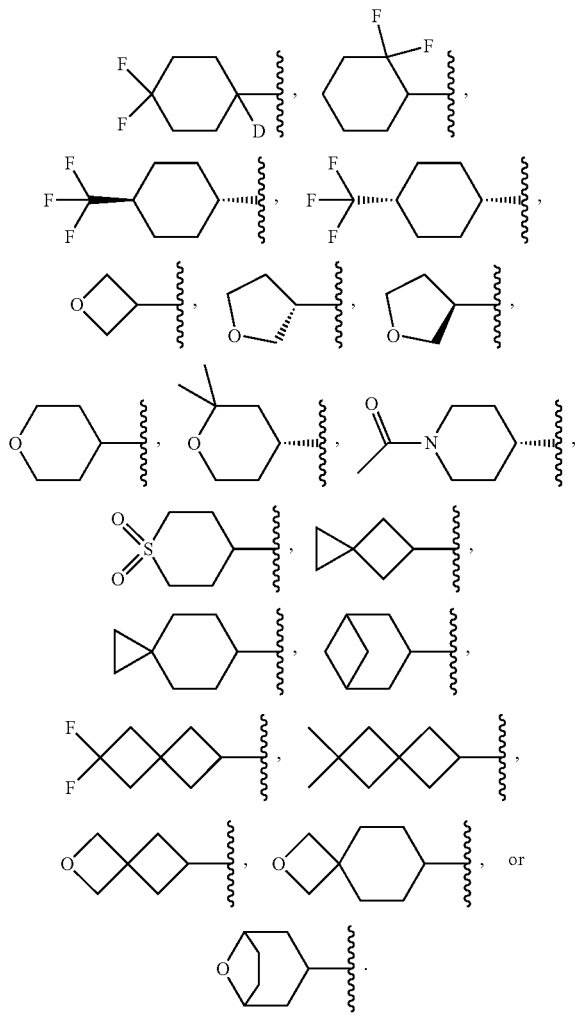

In some embodiments the compound of Formula (I), (IIa), (IId), or (IIIa), or pharmaceutically acceptable salt thereof, is a compound of Formula (Va)

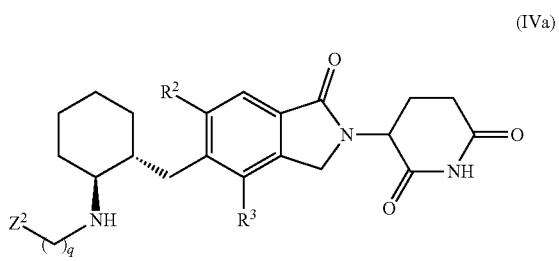

wherein q is 1, 2, or 3, or a pharmaceutically acceptable salt thereof.

In some embodiments of the compound of Formula (IVa), or pharmaceutically acceptable salt thereof, q is 1 or 2. In some embodiments of the compound of Formula (IVa), or pharmaceutically acceptable salt thereof, q is 1.

In some embodiments the compound of Formula (I), (IIa), (IId), (IIIa), or (IVa), or pharmaceutically acceptable salt thereof, is a compound of Formula (IVa-1)

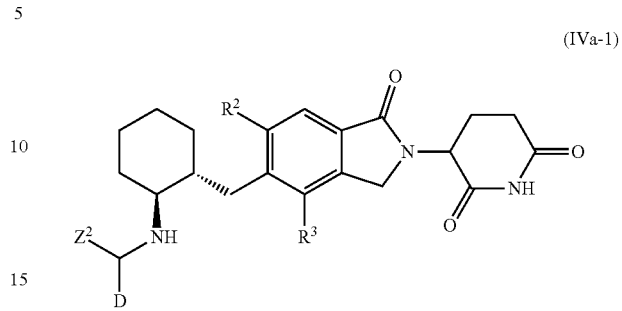

or a pharmaceutically acceptable salt thereof.

In some embodiments the compound of Formula (I), (IIa), (IId), (IIIa), or (IVa), or pharmaceutically acceptable salt thereof, is a compound of Formula (IVa-2)

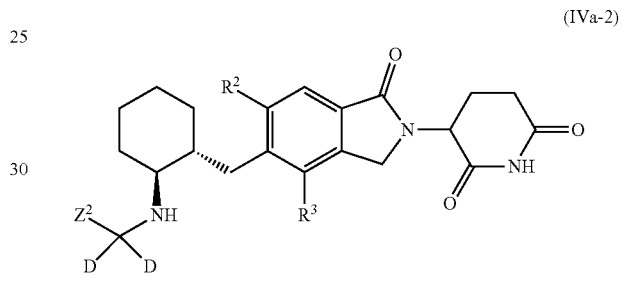

or a pharmaceutically acceptable salt thereof.

In some embodiments of the compound of Formula (I), (Ia), (Ib), (IIa), (IIb), (IIc), (IId), (IIe), (IIf), (IIg), (IIh), (IIi), or (IIIa), (IVa), (IVa-1), or (IVa-2), or pharmaceutically acceptable salt thereof, $Z^2$ is —O—$R^{3a}$, $C_{3-15}$ cycloalkyl, 4 to 14 membered heterocyclyl having 1-2 heteroatoms selected from nitrogen, oxygen, and sulfur, $C_{6-10}$ aryl, 5 to 14 membered heteroaryl having 1-2 heteroatoms selected from nitrogen, oxygen, and sulfur, wherein each $Z^2$ is optionally substituted with one to four $Z^{1a}$, which may be the same or different, wherein each $Z^{1a}$ is independently deuterium, cyano, halogen, $C_{1-6}$ alkyl, $C_{1-8}$ haloalkyl, $C_{1-6}$ alkoxy, or —S(O)$_2$$R^{3a}$, and each wherein each $R^{3a}$ is independently $C_{1-9}$ alkyl or $C_{6-10}$ aryl, wherein each alkyl or aryl of $R^{3a}$ optionally substituted with one to four halogens. In some embodiments of the compound of Formula (I), (Ia), (Ib), (IIa), (IIb), (IIc), (IId), (IIe), (IIf), (IIg), (IIh), (IIi), or (IIIa), (IVa), (IVa-1), or (IVa-2), or pharmaceutically acceptable salt thereof, $Z^2$ is —O—$R^{3a}$, cyclopropyl, cyclobutyl, cyclohexyl, bicyclo[1.1.1]pentyl, bicyclo[2.2.2]octyl, oxetanyl, tetrahydrofuranyl, tetrahydropyranyl, 1,3-dioxolanyl, phenyl, naphthyl, thiazolyl, pyrazolyl, pyridyl, or pyrazinyl, each optionally substituted with 1 or 3 $Z^{1a}$, wherein each $Z^{1a}$ is independently cyano, —F, —Cl, —OCH$_3$, —CF$_3$, or phenyl, and wherein each $R^{3a}$ is independently methyl, ethyl, or phenyl, wherein each phenyl of $R^{3a}$ is optionally substituted with —Cl. In some embodiments of the compound of Formula (I), (Ia), (Ib), (IIa), (IIb), (IIc), (IId), (IIe), (IIf), (IIg), (IIh), (IIi), or (IIIa), (IVa), (IVa-1), or (IVa-2), or pharmaceutically acceptable salt thereof, $Z^2$ is —O—$R^{3a}$, cyclopropyl, cyclobutyl, cyclohexyl, bicyclo[1.1.1]pentyl, bicyclo[2.2.2]octyl, oxetanyl, tetrahydrofuranyl, tetrahydropyranyl, 1,3-dioxolanyl, phenyl, naphthyl, thiazolyl, pyrazolyl, pyridyl, or pyrazinyl, each optionally substituted with 1 or 2 $Z^{1a}$, wherein each $Z^{1a}$ is independently cyano, —F, —Cl, —OCH$_3$, —CF$_3$, and wherein each $R^{3a}$ is independently methyl, ethyl, or phenyl, wherein each phenyl of $R^{3a}$ is optionally substituted with —Cl. In some embodiments of the compound of Formula (I), (Ia), (Ib), (IIa), (IIb), (IIc), (IId), (IIe), (IIf), (IIg), (IIh), (IIi), or (IIIa), (IVa), (IVa-1), or (IVa-2), or pharmaceutically acceptable salt thereof, $Z^2$ is

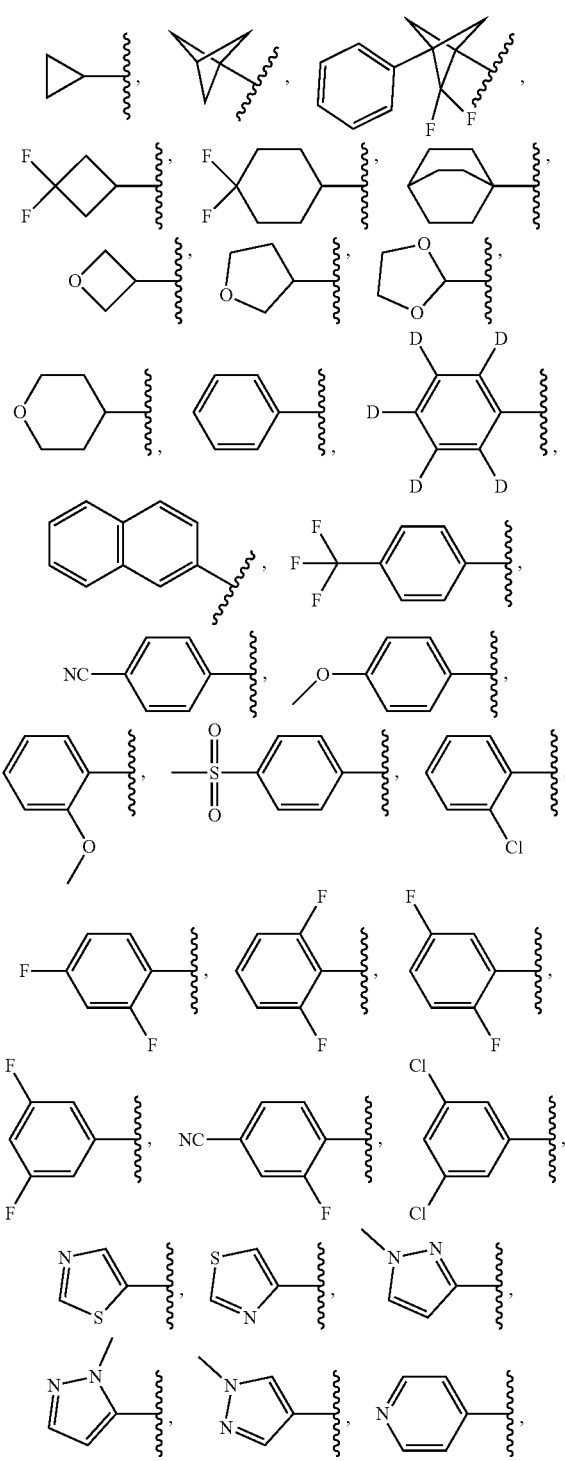

In some embodiments of the compound of Formula (I), (Ia), (Ib), (IIa), (IIb), (IIc), (IId), (IIe), (IIf), (IIg), (IIh), (IIi), or (IIIa), (IVa), (IVa-1), or (IVa-2), or pharmaceutically acceptable salt thereof, $Z^2$ is

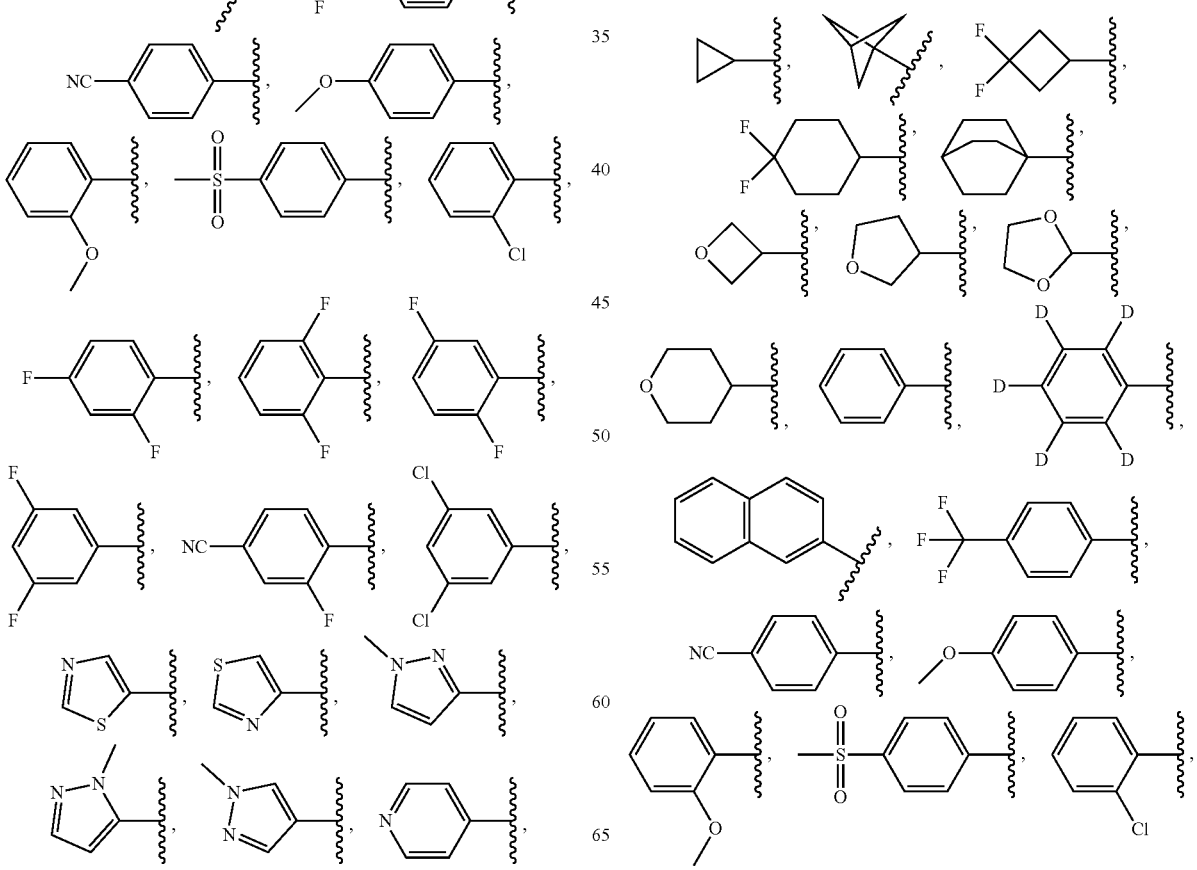

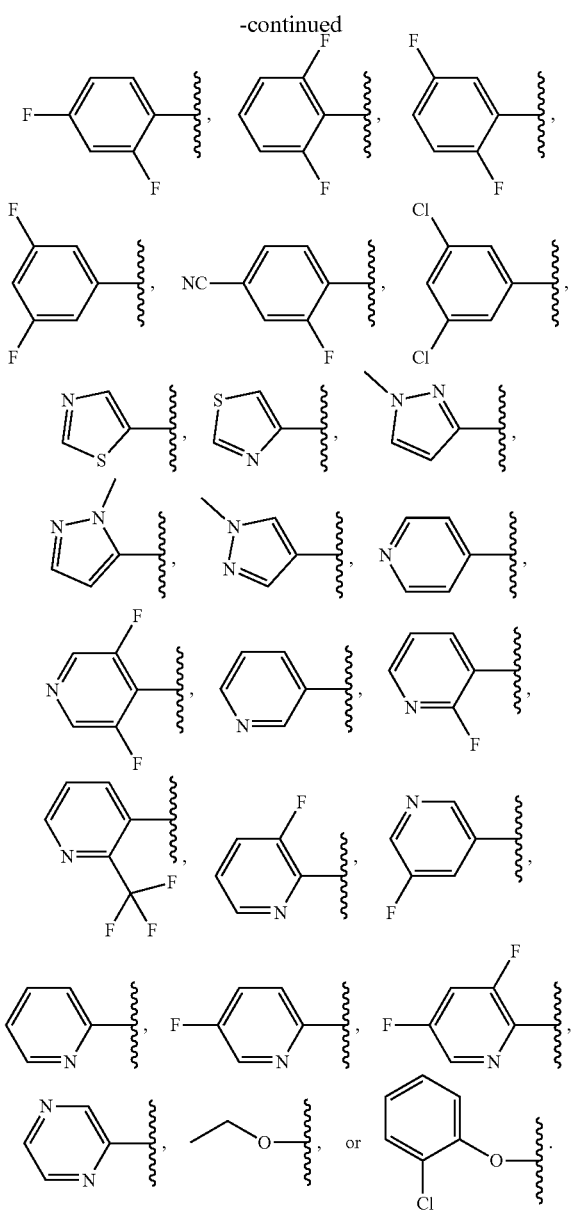

In some embodiments the compound of Formula (I), (IIa), (IId), or (IIIa), or pharmaceutically acceptable salt thereof, is a compound of Formula (IVb)

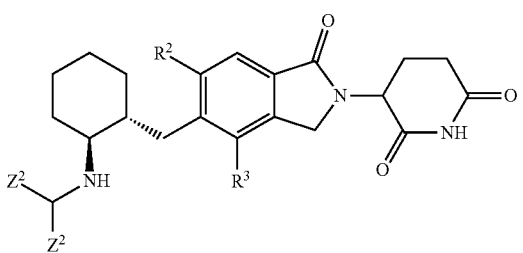

wherein each $Z^2$ may be the same or different, or a pharmaceutically acceptable salt thereof.

In some embodiments of the compound of Formula (I), (Ia), (Ib), (IIa), (IIb), (IIc), (IId), (IIe), (IIf), (IIg), (IIh), (IIi), or (IIIa), or (IVb), or pharmaceutically acceptable salt thereof, each $Z^2$, which may be the same or different, is independently $C_{1-6}$ alkyl, $C_{3-15}$ cycloalkyl, 4 to 14 membered heterocyclyl having 1-2 heteroatoms selected from nitrogen, oxygen, and sulfur, $C_{6-14}$ aryl, or $C_{1-6}$ alkoxy, each optionally substituted with 1 or 3 $Z^{1a}$, wherein each $Z^{1a}$ is independently halogen, cyano, =O, $C_{1-6}$ haloalkyl, $C_{3-10}$ cycloalkyl, or $C_{6-14}$ aryl. In some embodiments of the compound of Formula (I), (Ia), (Ib), (IIa), (IIb), (IIc), (IId), (IIe), (IIf), (IIg), (IIh), (IIi), or (IIIa), or (IVb), or pharmaceutically acceptable salt thereof, each $Z^2$, which may be the same or different, is independently $C_{1-6}$ alkyl, $C_{3-15}$ cycloalkyl, 4 to 14 membered heterocyclyl having 1 to 2 heteroatoms selected from nitrogen, oxygen, and sulfur, $C_{6-14}$ aryl, or $C_{1-6}$ alkoxy, each optionally substituted with 1 or 3 $Z^{1a}$, wherein each $Z^{1a}$ is independently halogen, cyano, $C_{1-6}$haloalkyl, $C_{3-10}$ cycloalkyl, $C_{6-14}$ aryl. In some embodiments of the compound of Formula (I), (Ia), (Ib), (IIa), (IIb), (IIc), (IId), (IIe), (IIf), (IIg), (IIh), (IIi), or (IIIa), or (IVb), or pharmaceutically acceptable salt thereof, each $Z^2$, which may be the same or different, is independently $C_{1-6}$ alkyl, $C_{3-15}$ cycloalkyl, $C_{6-14}$ aryl, or $C_{1-6}$ alkoxy. In some embodiments of the compound of Formula (I), (Ia), (Ib), (IIa), (IIb), (IIc), (IId), (IIe), (IIf), (IIg), (IIh), (IIi), or (IIIa), or (IVb), or pharmaceutically acceptable salt thereof, each $Z^2$, which may be the same or different, is independently methyl, ethyl, ethoxy, cyclopropyl, cyclobutyl, cyclopentyl, cyclohexyl, tetrahyrdofuranyl, tetrahydropyranyl, bicyclo[1.1.1]pentanyl, phenyl, or thiopyranyl, each optionally substituted with 1 or 3 $Z^{1a}$, wherein each $Z^{1a}$ is independently —F, —CH₃, —CHF₂, —CN, =O, or cyclopropyl. In some embodiments of the compound of Formula (I), (Ia), (Ib), (IIa), (IIb), (IIc), (IId), (IIe), (IIf), (IIg), (IIh), (IIi), or (IIIa), or (IVb), or pharmaceutically acceptable salt thereof, each $Z^2$, which may be the same or different, is independently methyl, ethyl, ethoxy, cyclopropyl, cyclobutyl, cyclopentyl, cyclohexyl, tetrahyrdofuranyl, tetrahydropyranyl, bicyclo[1.1.1]pentanyl, or phenyl, each optionally substituted with 1 or 3 $Z^{1a}$, wherein each $Z^{1a}$ is independently —F, —CH₃, —CHF₂, —CN, or cyclopropyl. In some embodiments of the compound of Formula (I), (Ia), (Ib), (IIa), (IIb), (IIc), (IId), (IIe), (IIf), (IIg), (IIh), (IIi), or (IIIa), or (IVb), or pharmaceutically acceptable salt thereof, each $Z^2$, which may be the same or different, is independently

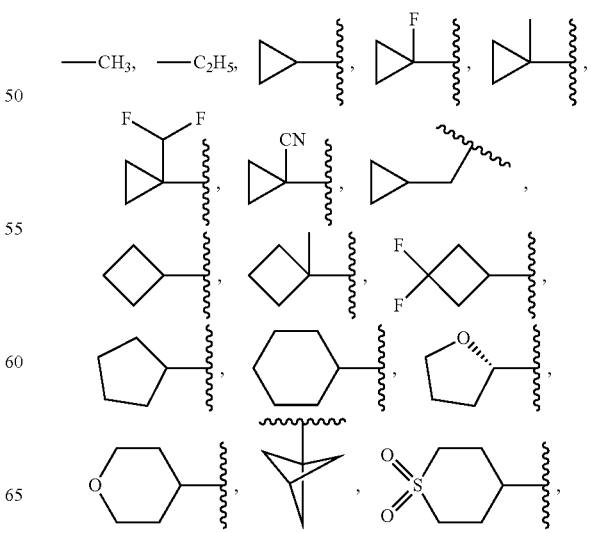

-continued

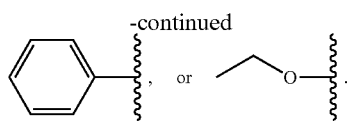

In some embodiments of the compound of Formula (I), (Ia), (Ib), (IIa), (IIb), (IIc), (IId), (IIe), (IIf), (IIg), (IIh), (IIi), or (IIIa), or (IVb), or pharmaceutically acceptable salt thereof, each $Z^2$, which may be the same or different, is independently

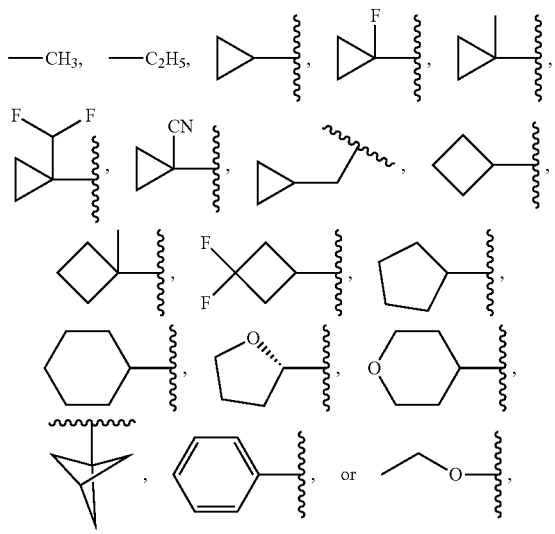

In some embodiments of the compound of Formula (I), (Ia), (Ib), (IIa), (IIb), (IIc), (IId), (IIe), (IIf), (IIg), (IIh), (IIi), or (IIIa), or (IVb), or pharmaceutically acceptable salt thereof, each $Z^2$, which may be the same or different, is independently

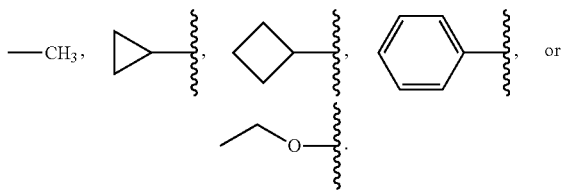

In some embodiments the compound of Formula (I), (IIa), or (IId), or pharmaceutically acceptable salt thereof, is a compound of Formula (IIIb)

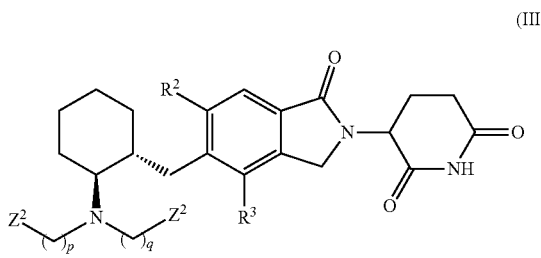

wherein each p or q, which may be the same or different, is independently 1, 2, or 3,
or a pharmaceutically acceptable salt thereof.

In some embodiments of the compound of Formula (IIIb), or pharmaceutically acceptable salt thereof, p and q are each 1. In some embodiments of the compound of Formula (IIIb), or pharmaceutically acceptable salt thereof, each $Z^1$ or $Z^2$, which may be the same or different, is independently —H, $C_{6-10}$ aryl, or 4 to 10 membered heterocyclyl having 1 to 2 heteroatoms selected from nitrogen, oxygen, and sulfur, wherein each aryl or heterocyclyl of $Z^1$ or $Z^2$ is unsubstituted. In some embodiments of the compound of Formula (IIIb), or pharmaceutically acceptable salt thereof, each $Z^1$ or $Z^2$, which may be the same or different, is independently hydrogen, unsubstituted phenyl, or unsubstituted tetrahydropyranyl. In some embodiments of the compound of Formula (IIIb), or pharmaceutically acceptable salt thereof, each $Z^1$ or $Z^2$, which may be the same or different, is independently

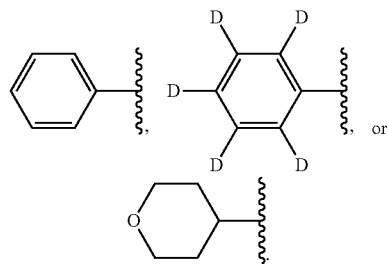

In some embodiments the compound of Formula (I), (IIa), or (IId), or pharmaceutically acceptable salt thereof, is a compound of Formula (IIIc)

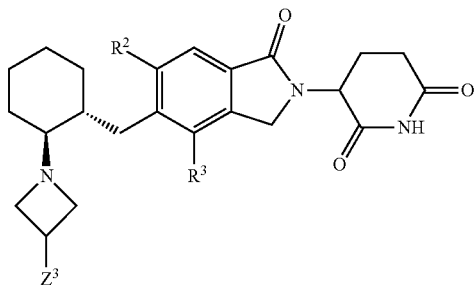

or pharmaceutically acceptable salt thereof.

In some embodiments of the compound of Formula (IIIc), or pharmaceutically acceptable salt thereof, $Z^3$ is —H, $C_{6-10}$ aryl, or —O—$R^{3a}$, wherein $R^{3a}$ is —H, $C_{1-6}$ alkyl or $C_{6-10}$ aryl, wherein the $R^{3a}$ alkyl or aryl is each optionally substituted with halogen, $C_{3-10}$ cycloalkyl, or $C_{6-10}$ aryl. In some embodiments of the compound of Formula (IIIc), or pharmaceutically acceptable salt thereof, $Z^3$ is methyl, phenyl, or —O—$R^{3a}$, wherein $R^{3a}$ is methyl, ethyl, or phenyl, wherein the $R^{3a}$ methyl or phenyl is each optionally substituted with —Cl, cyclopropyl, or phenyl. In some embodiments of the compound of Formula (IIIc), or pharmaceutically acceptable salt thereof, $Z^3$ is

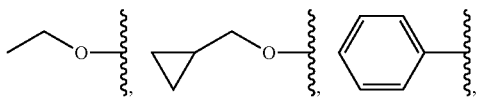

-continued

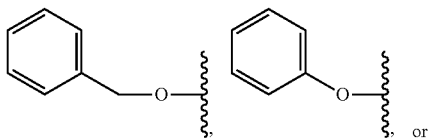, or

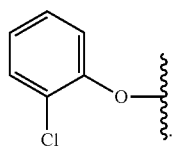 [SMILES: *Cc1ccccc1Cl]

In some embodiments the compound of Formula (I), (IIa), or (IId), or pharmaceutically acceptable salt thereof, is a compound of Formula (IIId)

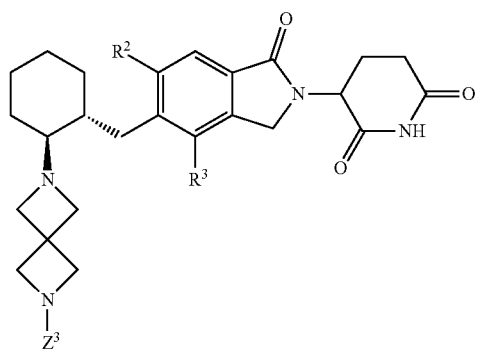

(IIId)

or pharmaceutically acceptable salt thereof.

In some embodiments of the compound of Formula (I), (Ia), (Ib), (IIa), (IIb), (IIc), (IId), (IIe), (IIf), (IIg), (IIh), (IIi), or (IIId), or pharmaceutically acceptable salt thereof, $Z^3$ is $C_{1-6}$ alkyl optionally substituted with one $C_{6-10}$ aryl of $Z^{1a}$, wherein the $C_{6-10}$ aryl of $Z^{1a}$ is optionally substituted with one halogen of $Z^{1b}$. In some embodiments of the compound of Formula (I), (Ia), (Ib), (IIa), (IIb), (IIc), (IId), (IIe), (IIf), (IIg), (IIh), (IIi), or (IIId), or pharmaceutically acceptable salt thereof, $Z^3$ is methyl, optionally substituted with one phenyl of $Z^{1a}$, wherein the phenyl of $Z^{1a}$ is optionally substituted with one —Cl of $Z^{1b}$. In some embodiments of the compound of Formula (I), (Ia), (Ib), (IIa), (IIb), (IIc), (IId), (IIe), (IIf), (IIg), (IIh), (IIi), or (IIId), or pharmaceutically acceptable salt thereof, $Z^3$ is

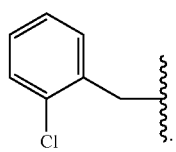

In some embodiments the compound of Formula (I) or (IIa), or pharmaceutically acceptable salt thereof, is a compound of Formula (IIIe)

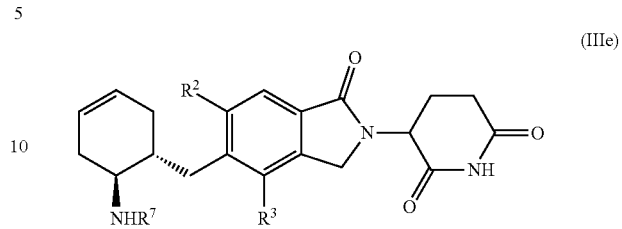

(IIIe)

or pharmaceutically acceptable salt thereof.

In some embodiments of the compound of Formula (I), (Ia), (Ib), (IIa), (IIb), (IIc), (IId), (IIe), (IIf), (IIg), (IIh), (IIi), or (IIIe), or pharmaceutically acceptable salt thereof, $R^7$ is $C_{1-6}$ alkyl.

In some embodiments of the compound of Formula (I), (Ia), (Ib), (IIa), (IIb), (IIc), (IId), (IIe), (IIf), (IIg), (IIh), (IIi), or (IIIe), or pharmaceutically acceptable salt thereof, $R^7$ is

In some embodiments the compound of Formula (I), (IIc), or (IIf), or pharmaceutically acceptable salt thereof, is a compound of Formula (IIIf)

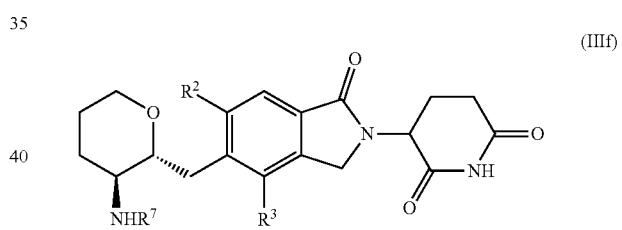

(IIIf)

or pharmaceutically acceptable salt thereof.

In some embodiments of the compound of Formula (I), (Ia), (Ib), (IIa), (IIb), (IIc), (IId), (IIe), (IIf), (IIg), (IIh), (IIi), or (IIIf), or pharmaceutically acceptable salt thereof, $R^7$ is $C_{1-8}$ alkyl, $C_{3-12}$ cycloalkyl, or 4 to 12 membered heterocyclyl having 1 to 2 heteroatoms each independently selected from nitrogen, oxygen, and sulfur, wherein each alkyl, cycloalkyl, or heterocyclyl of $R^7$ is optionally substituted with 1 to 3 $Z^2$, which may be the same or different, wherein each $Z^2$ is independently, deuterium, halogen, $C_{3-10}$ cycloalkyl, $C_{1-8}$ alkyl, $C_{1-8}$ haloalkyl, $C_{1-6}$ alkoxy, $C_{1-6}$ haloalkoxy, or 4 to 12 membered heterocyclyl having 1 to 2 heteroatoms each independently selected from nitrogen, oxygen, and sulfur, wherein each $C_{1-6}$ alkyl of $Z^2$ is optionally substituted with 1 to 3 $Z^{1a}$, wherein each $Z^{1a}$ is independently halogen or $C_{1-6}$ alkoxy. In some embodiments of the compound of Formula (I), (Ia), (Ib), (IIa), (IIb), (IIc), (IId), (IIe), (IIf), (IIg), (IIh), (IIi), or (IIIf), or pharmaceutically acceptable salt thereof, $R^7$ is $C_{1-8}$ alkyl, cyclobutyl, cyclopentyl, cyclohexyl, spiro[3.3]heptanyl, spiro[2.5]octanyl, spiro[3.5]nonanyl, tetrahydrofuranyl, tetrahydropyranyl, oxepanyl, piperidyl, or tetrahydroindazolyl, each optionally substituted with 1 to 3 $Z^2$, which may be the same or different, wherein each $Z^2$ is independently, deuterium, —F, —$CH_3$, —$CHF_2$, —$CH_2$—$CHF_2$, —$CF_3$, —$CH_2$—$CF_3$, —O—$CH_3$, —O—$CHF_2$, —$CH_2$—O—$CH_3$, —O—$C_3H_7$, cyclobutyl, oxetanyl, or tetrahydropyranyl, wherein each cyclobutyl, oxetanyl, or tetrahydropyranyl is optionally substituted with 1 to 3-F. In some embodiments of the compound of Formula (I), (Ia), (Ib), (IIa), (IIb), (IIc), (IId), (IIe), (IIf), (IIg), (IIh), (IIi), or (IIIf), or pharmaceutically acceptable salt thereof, $R^7$ is $C_{1-8}$ alkyl, cyclobutyl, cyclopentyl, cyclohexyl, spiro[3.3]heptanyl, spiro[3.5]nonanyl, tetrahydrofuranyl, tetrahydropyranyl, oxepanyl, or piperidyl, each optionally substituted with 1 to 3 $Z^2$, which may be the same or different, wherein each $Z^2$ is independently, deuterium, —F, —$CH_3$, —$CHF_2$, —$CH_2$—$CHF_2$, —$CF_3$, —$CH_2$—$CF_3$, —O—$CH_3$, —O—$CHF_2$, —$CH_2$—O—$CH_3$, —O—$C_3H_7$, cyclobutyl, oxetanyl, or tetrahydropyranyl, wherein each cyclobutyl, oxetanyl, or tetrahydropyranyl is optionally substituted with 1 to 3-F. In some embodiments of the compound of Formula (I), (Ia), (Ib), (IIa), (IIb), (IIc), (IId), (IIe), (IIf), (IIg), (IIh), (IIi), or (IIIf), or pharmaceutically acceptable salt thereof, $R^7$ is $C_{3-12}$ cycloalkyl optionally substituted with 1 to 3 halogens. In some embodiments of the compound of Formula (I), (Ia), (Ib), (IIa), (IIb), (IIc), (IId), (IIe), (IIf), (IIg), (IIh), (IIi), or (IIIf), or pharmaceutically acceptable salt thereof, $R^7$ is cyclohexyl optionally substituted with 1 to 3-F. In some embodiments of the compound of Formula (I), (Ia), (Ib), (IIa), (IIb), (IIc), (IId), (IIe), (IIf), (IIg), (IIh), (IIi), or (IIIf), or pharmaceutically acceptable salt thereof, $R^7$ is

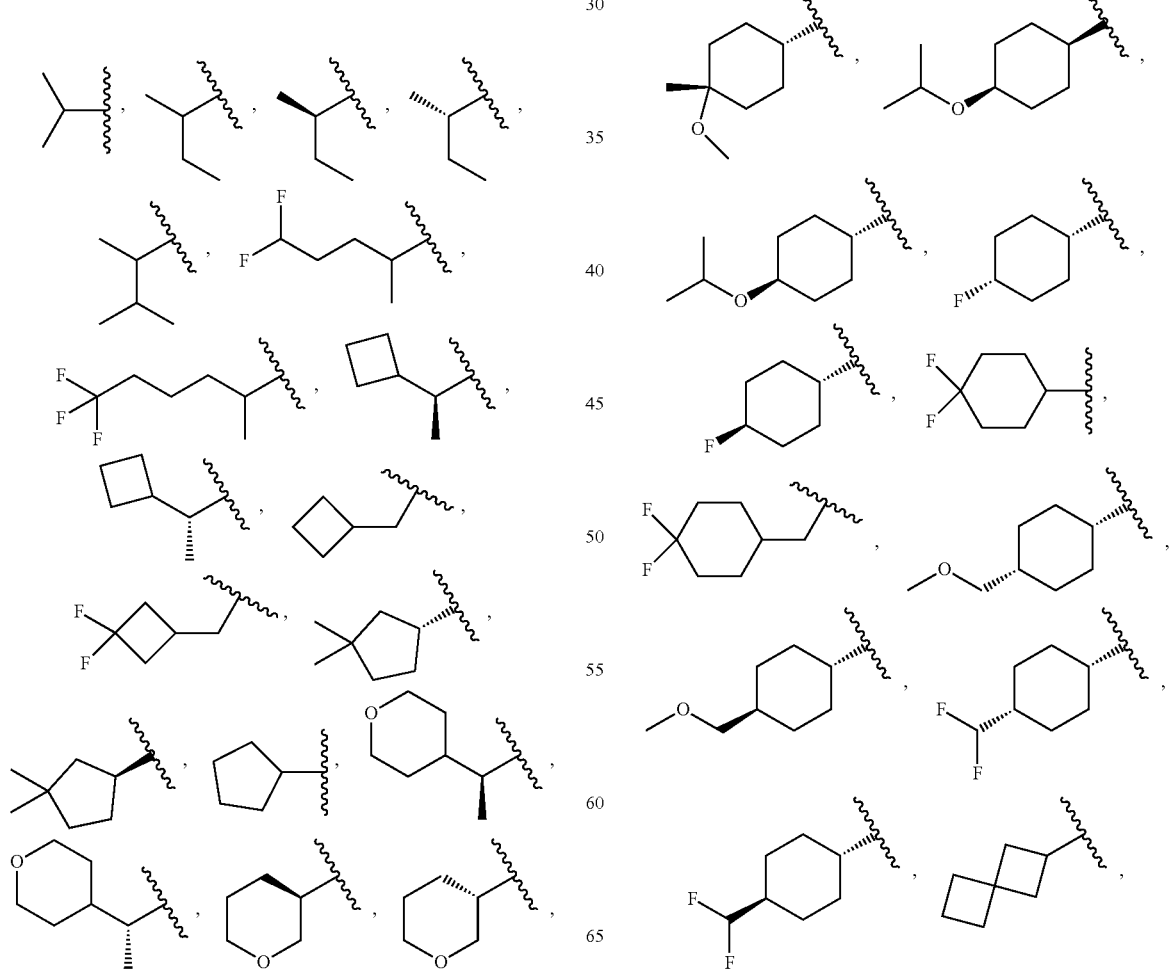

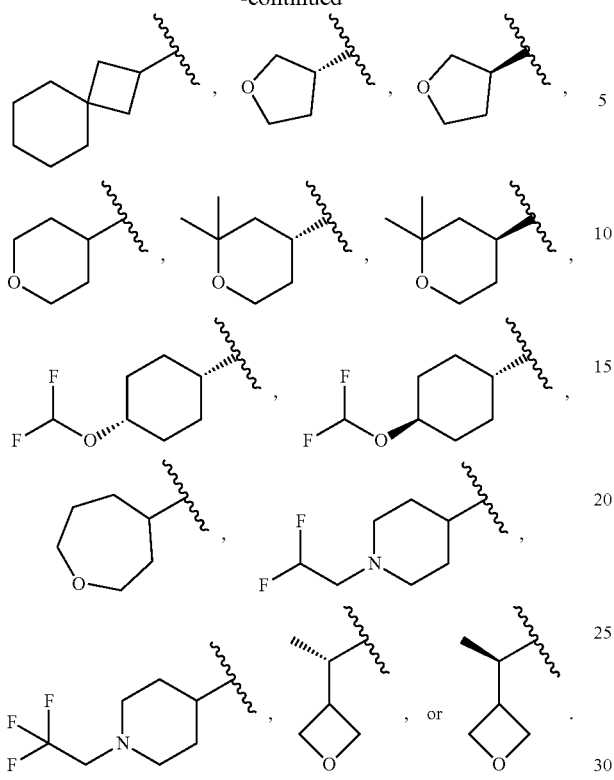
In some embodiments of the compound of Formula (I), (Ia), (Ib), (IIa), (IIb), (IIc), (IId), (IIe), (IIf), (IIg), (IIh), (IIi), or (IIIf), or pharmaceutically acceptable salt thereof, $R^7$ is
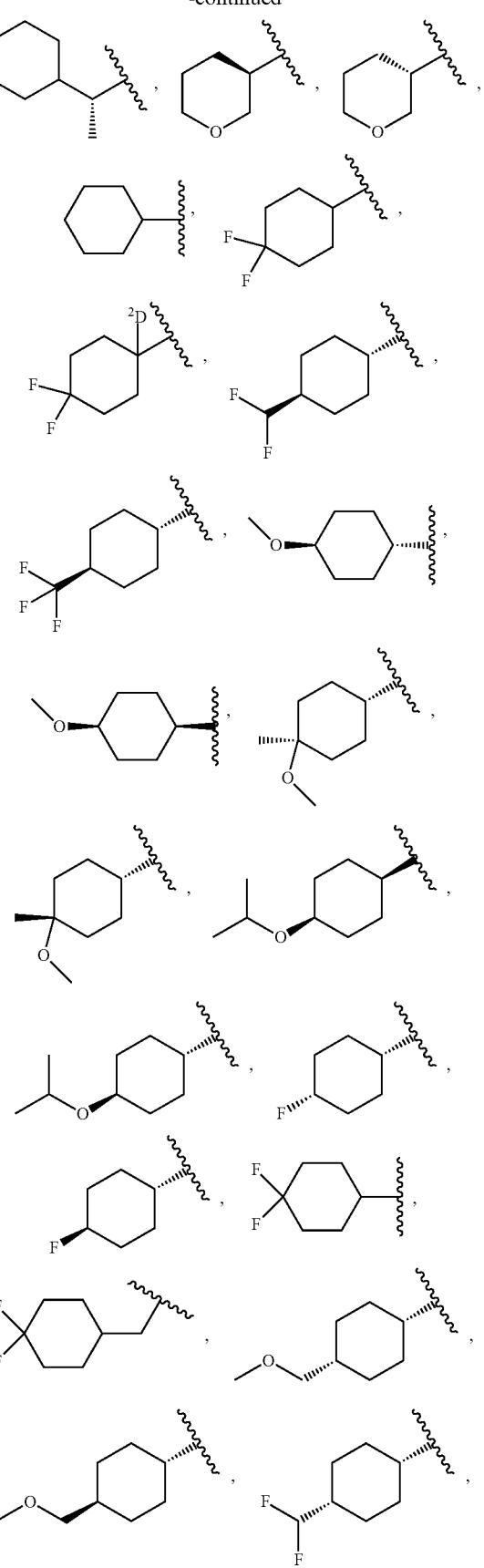

-continued

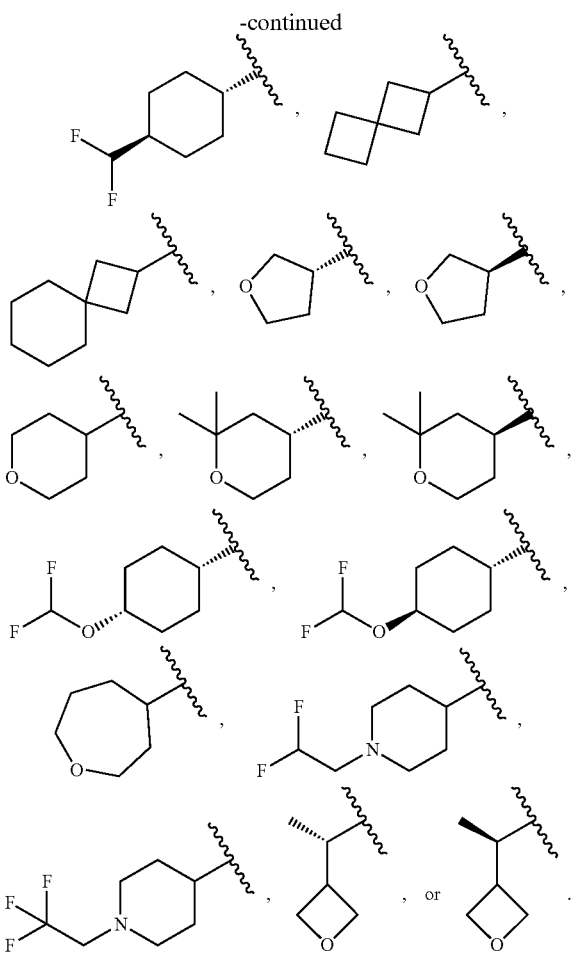

In some embodiments of the compound of Formula (I), (Ia), (Ib), (IIa), (IIb), (IIc), (IId), (IIe), (IIf), (IIg), (IIh), (IIi), or (IIIf), or pharmaceutically acceptable salt thereof, R⁷ is

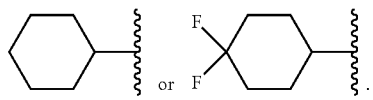

In some embodiments of the compound of Formula (I), (Ia), or (IIa), or pharmaceutically acceptable salt thereof, R¹ is -D. In some embodiments of the compound of Formula (I), (Ia), (IIb), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), or (IVa-2), or pharmaceutically acceptable salt thereof, R² is —H or —F. In some embodiments of the compound of Formula (I), (Ia), (IIb), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), or (IVa-2), or pharmaceutically acceptable salt thereof, R² is —H. In some embodiments of the compound of Formula (I), (Ia), (IIb), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), or (IVa-2), or pharmaceutically acceptable salt thereof, R² is —F. In some embodiments of the compound of Formula (I), (Ia), (IIb), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), or (IVa-2), or pharmaceutically acceptable salt thereof, R³ is —H or —F. In some embodiments of the compound of Formula (I), (Ia), (IIb), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), or (IVa-2), or pharmaceutically acceptable salt thereof, R³ is —H. In some embodiments of the compound of Formula (I), (Ia), (IIb), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), or (IVa-2), or pharmaceutically acceptable salt thereof, R³—F. In some embodiments of the compound of Formula (I), (Ia), (Ib), (IId), (IIe), (IIf), (IIg), (IIh), or (IIi), or pharmaceutically acceptable salt thereof, $R^{4a}$ and $R^{4b}$ are each —H.

In some embodiments the compound of Formula (I), or pharmaceutically acceptable salt thereof, is a compound of Formula (V)

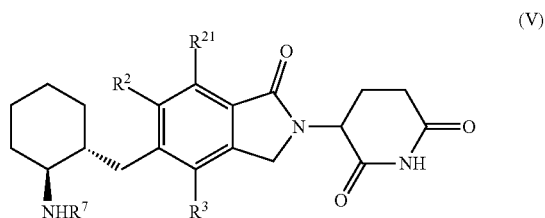

(V)

or pharmaceutically acceptable salt thereof, wherein
R² is —H or —F;
R²¹ is —H or —F;
R³ is —H or —F;
R⁷ is $C_{1-8}$ alkyl or $C_{3-12}$ cycloalkyl,
wherein each alkyl or cycloalkyl of R⁷ is optionally substituted with one to four Z², which may be the same or different; and
each Z² is independently deuterium, halogen, $C_{1-3}$ alkyl, $C_{1-3}$ haloalkyl, or $C_{6-10}$ aryl.

In some embodiments the compound of Formula (V), or pharmaceutically acceptable salt thereof, is a compound of Formula (Va):

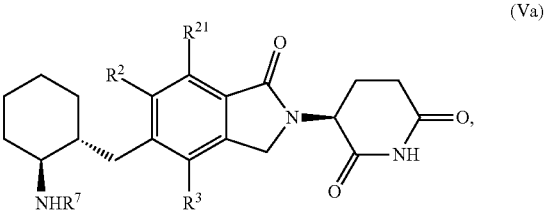

(Va)

or pharmaceutically acceptable salt thereof.

In some embodiments of the compound of Formula (V) or (Va), or pharmaceutically acceptable salt thereof, R² is —H; $R^{2a}$ is —H; and R³ is —H or —F. In some embodiments of the compound of Formula (V) or (Va), or pharmaceutically acceptable salt thereof, R⁷ is $C_{1-8}$ alkyl, cyclopropyl, cyclobutyl, cyclopentyl, cyclohexyl, cycloheptyl, spiro[2.3]hexyl, bicyclo[3.1.1]heptyl, spiro[3.3]heptyl, spiro[2.5]octyl, bicyclo[3.2.1]octyl, (1R,5S)bicyclo[3.1.0]hexyl, (1R,5S)bicyclo[3.2.0]heptyl, spiro[2.4]heptyl, each optionally substituted with 1 to 3 Z², which may be the same or different, wherein each Z² is independently deuterium, —CH₃, —C₂F, —CHF₂, —CF₃, —F, or phenyl. In some embodiments of the compound of Formula (V) or (Va), or pharmaceutically acceptable salt thereof, $R^7$ is $C_{1-3}$ alkyl or cyclohexyl, each optionally substituted with 1 to 2 $Z^2$, which may be the same or different, wherein each $Z^2$ is independently —F or phenyl. In some embodiments of the compound of Formula (V) or (Va), or pharmaceutically acceptable salt thereof, $R^7$ is

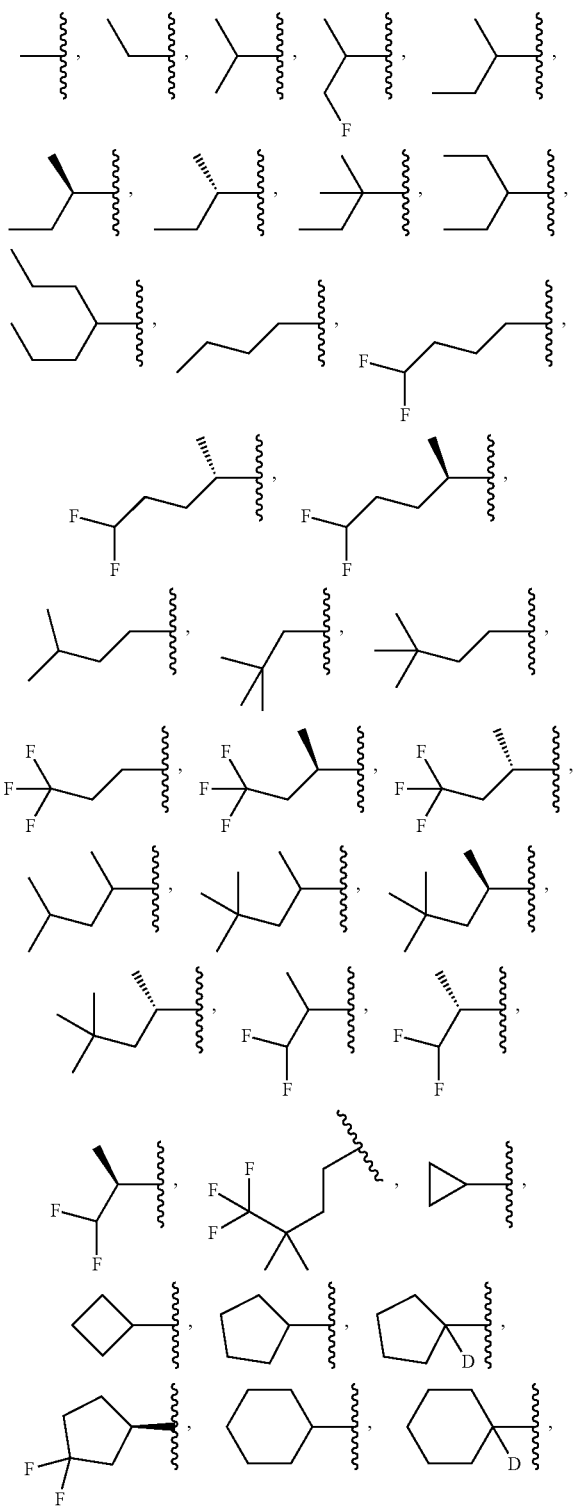

-continued

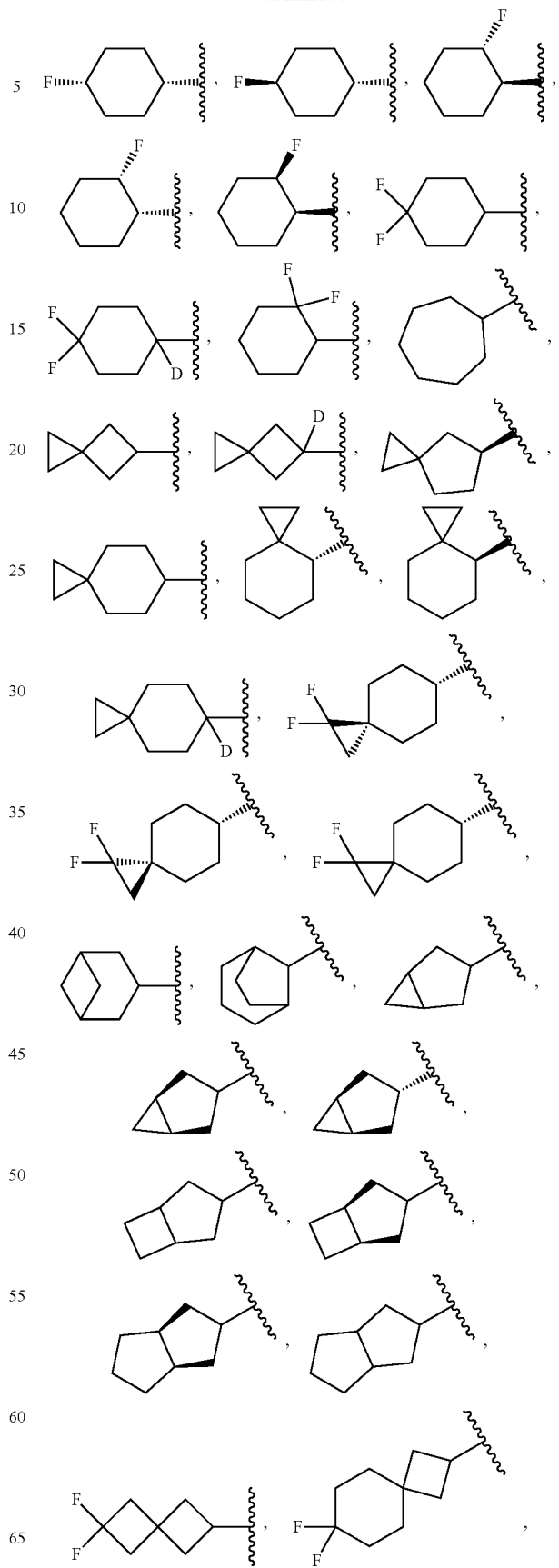

-continued
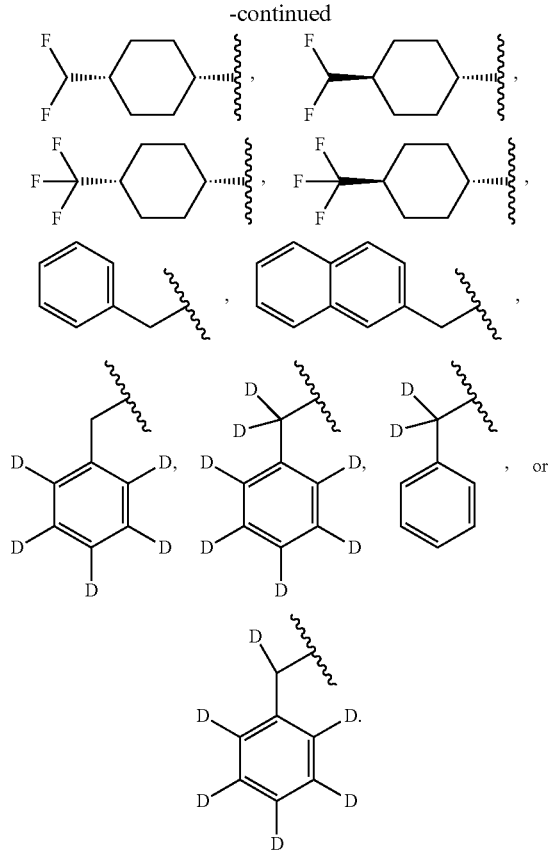
In some embodiments of the compound of Formula (V) or (Va), or pharmaceutically acceptable salt thereof, R⁷ is
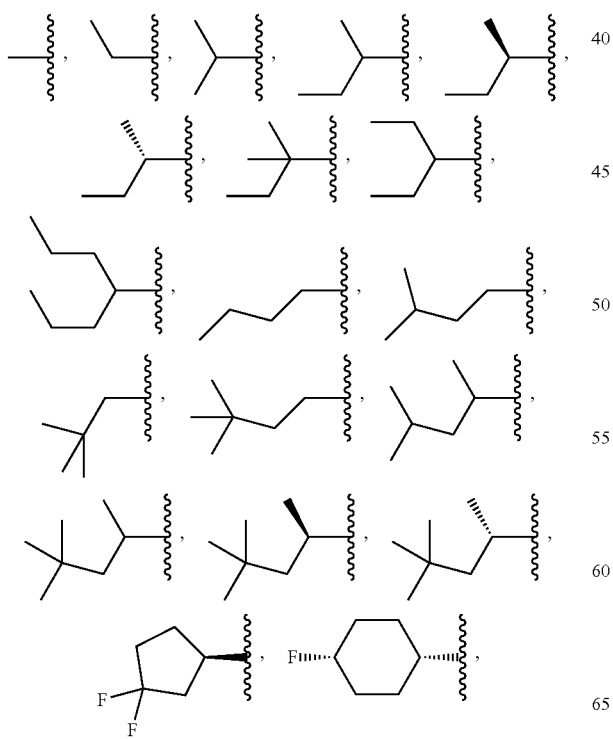
-continued
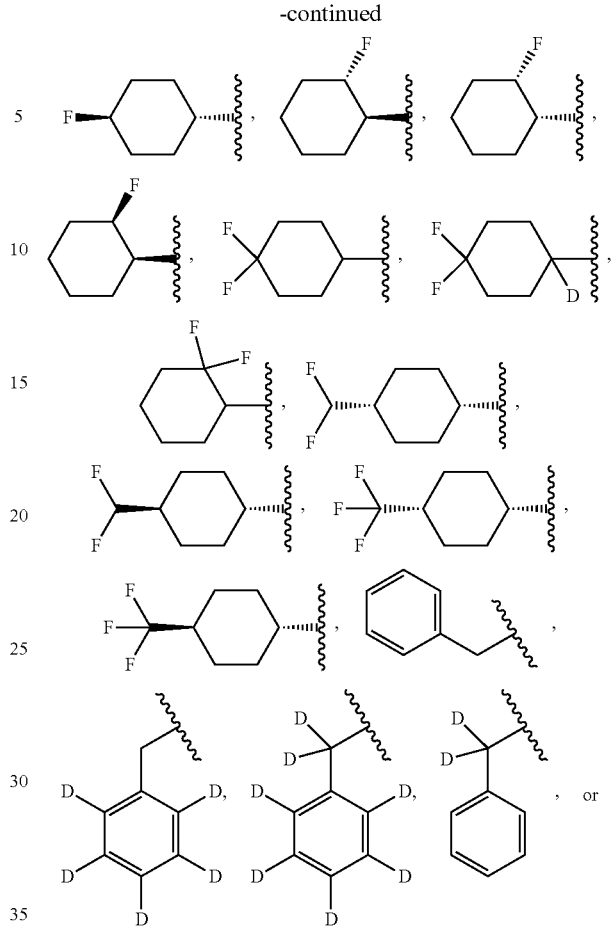
In some embodiments the compound of Formula (V), or pharmaceutically acceptable salt thereof is
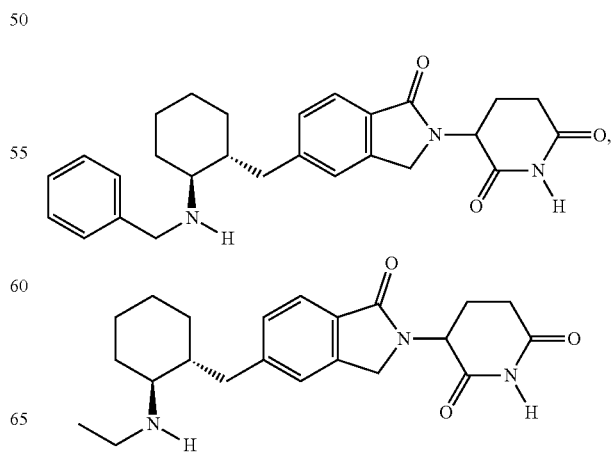

-continued
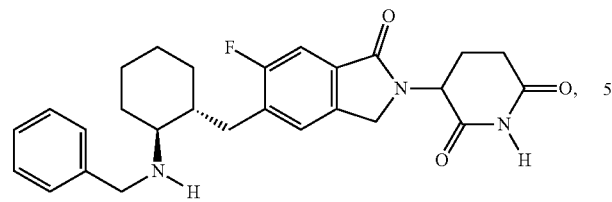
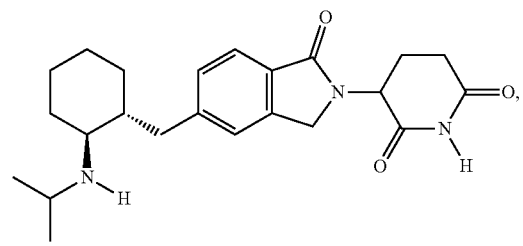
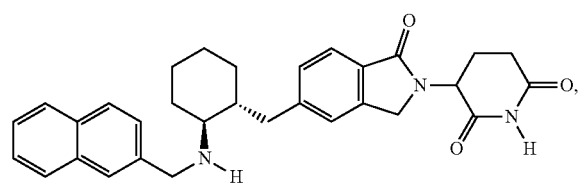
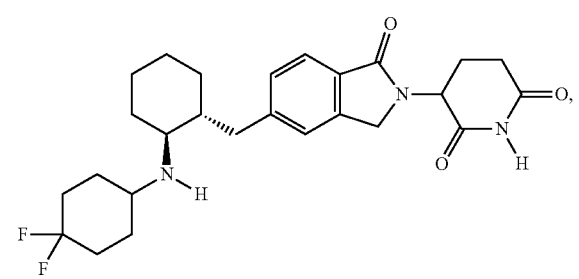
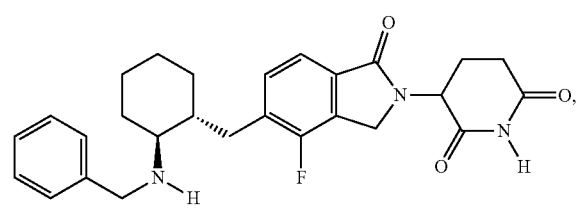
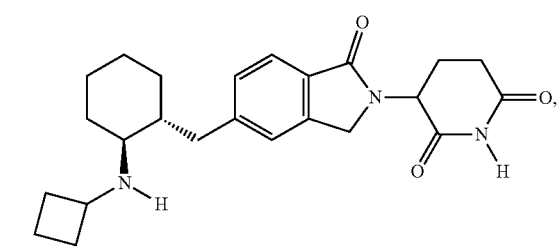
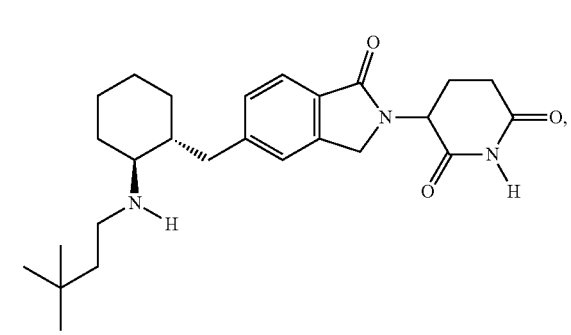
-continued
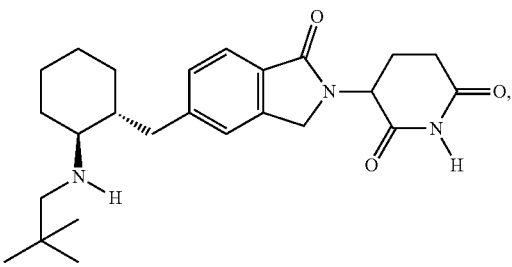
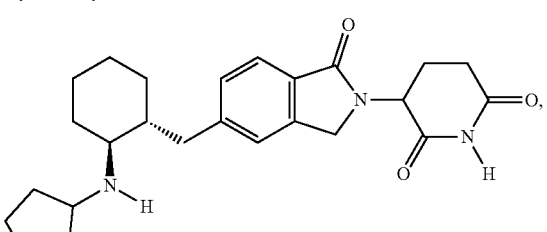
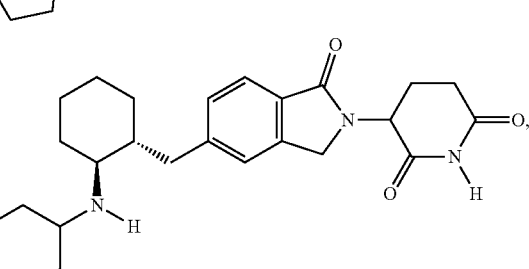
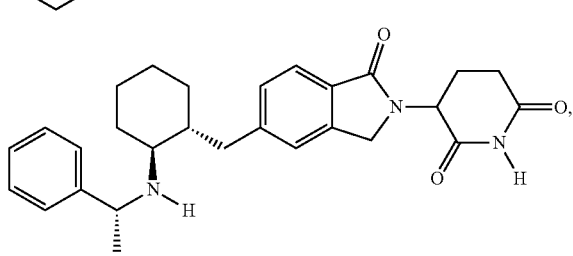
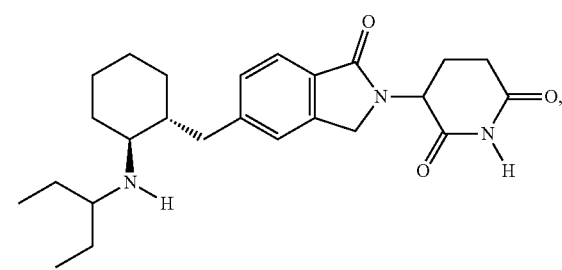
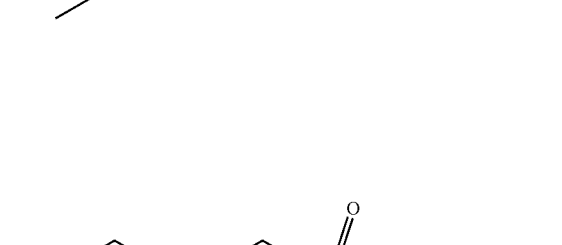
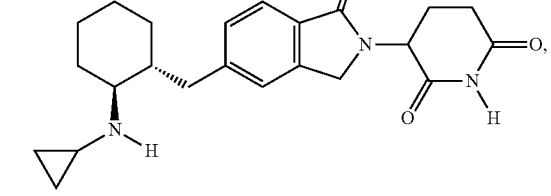

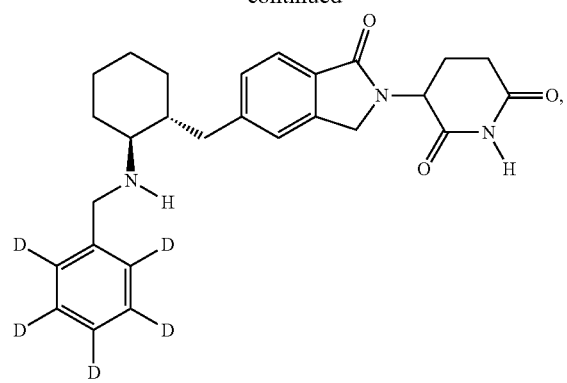
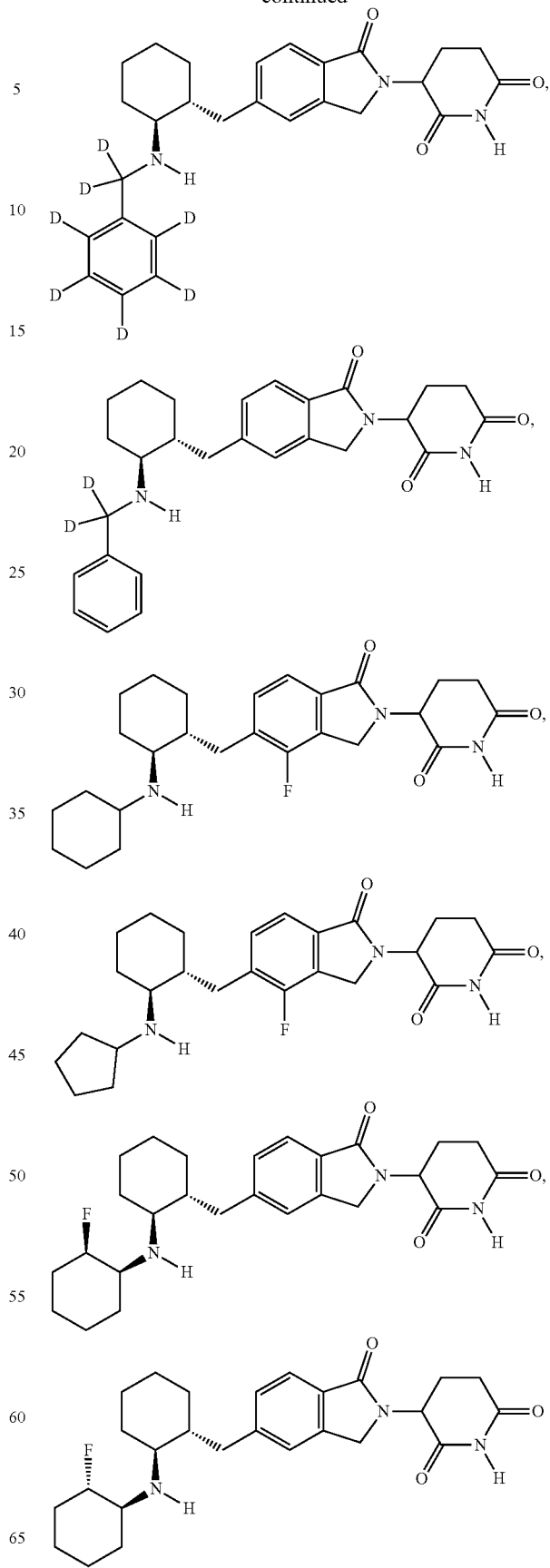

83
-continued
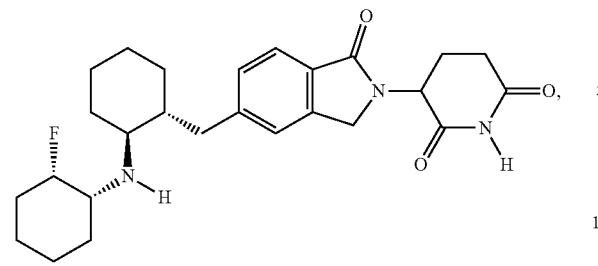
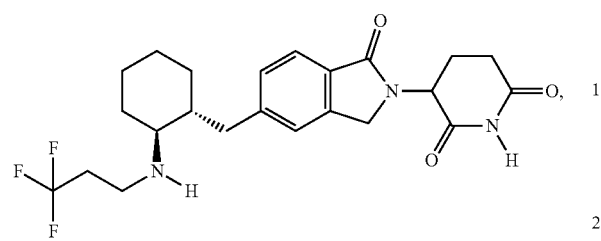

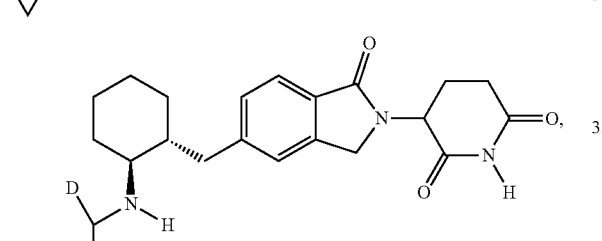
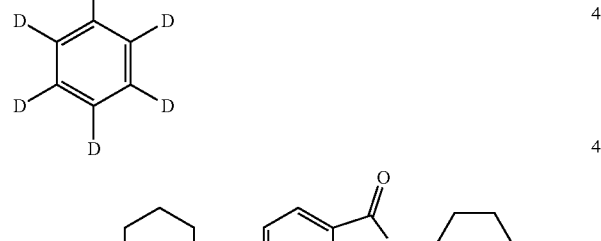
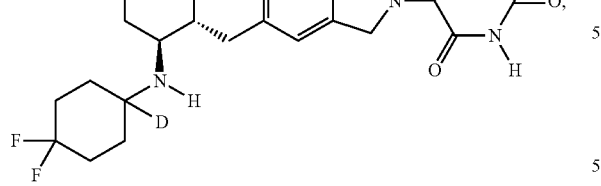
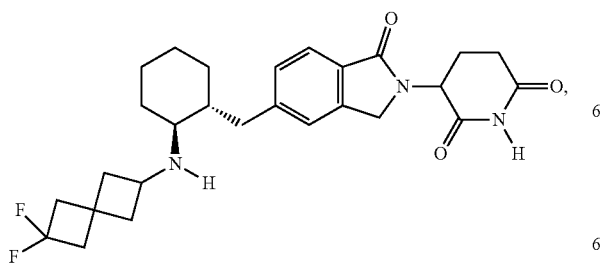
84
-continued
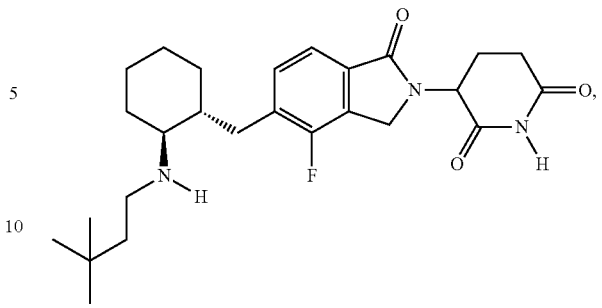
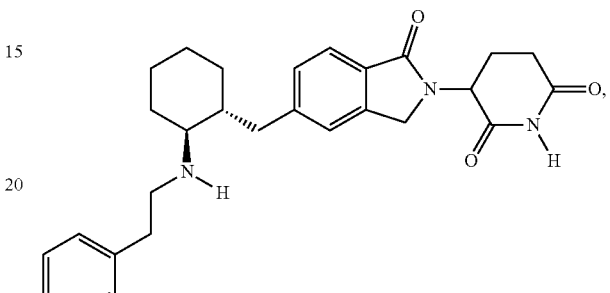
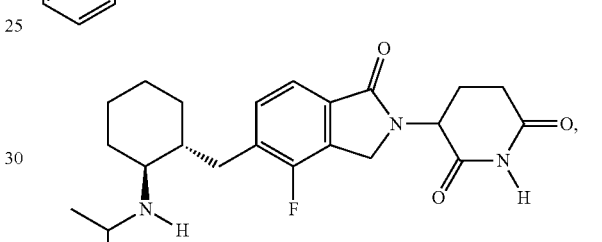
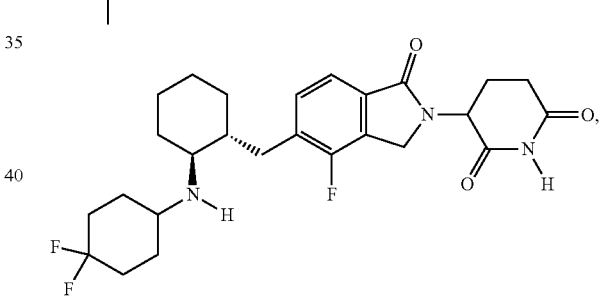
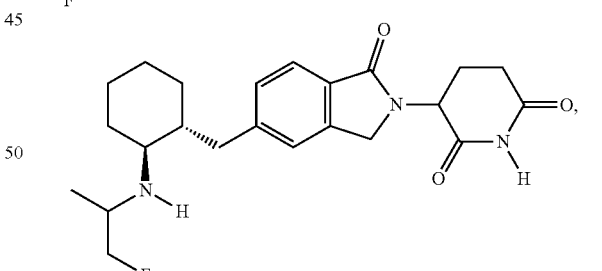
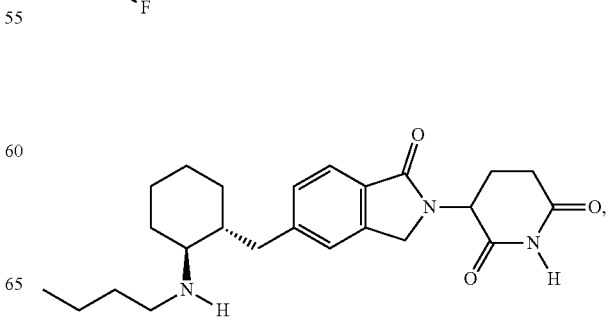

85
-continued
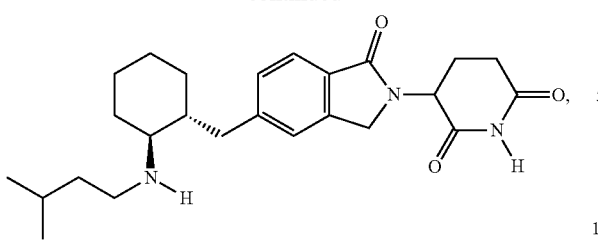
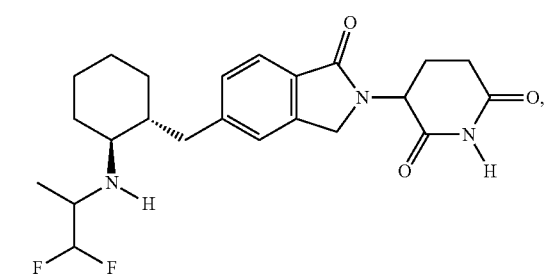
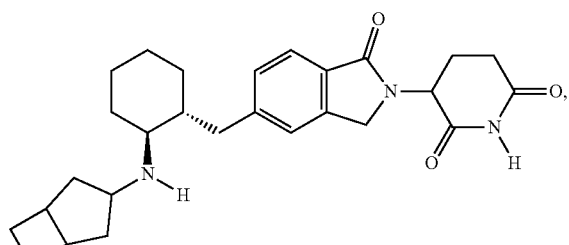
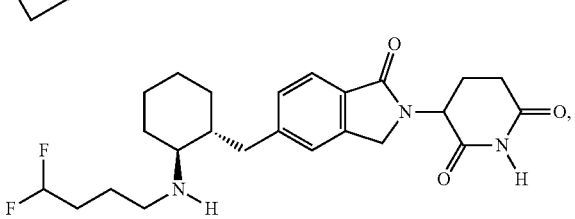
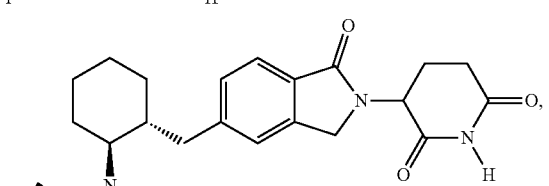
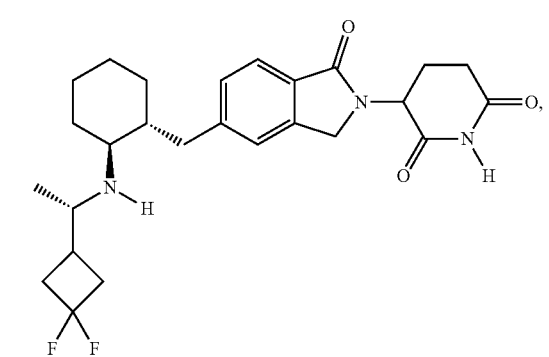
86
-continued
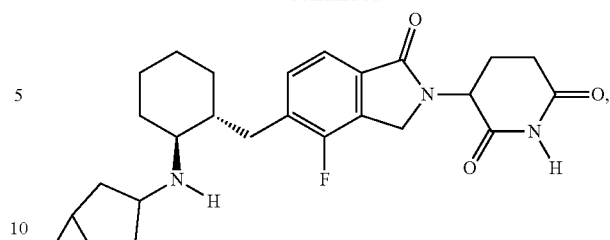
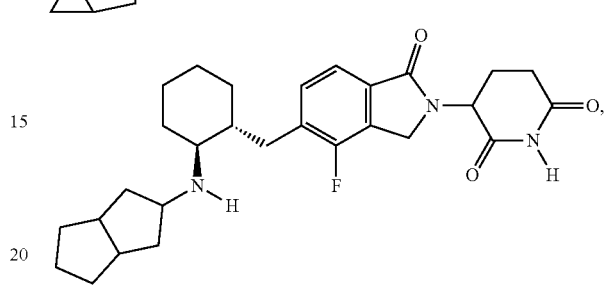
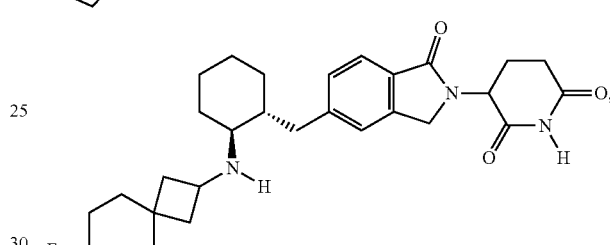
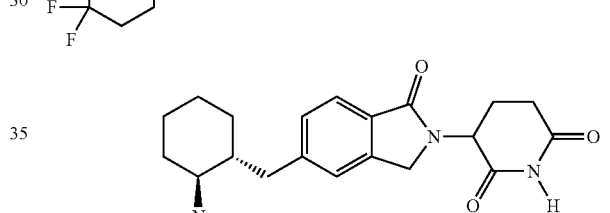
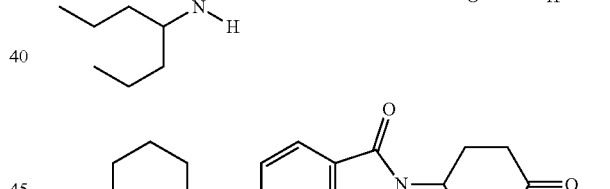
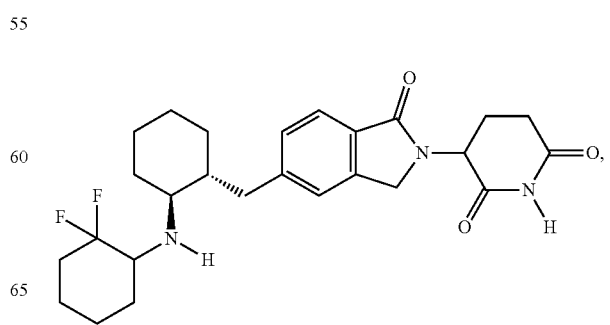

87
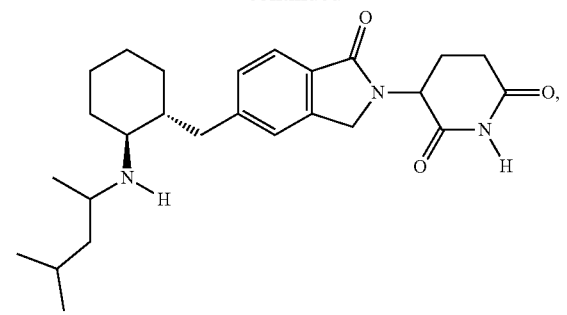
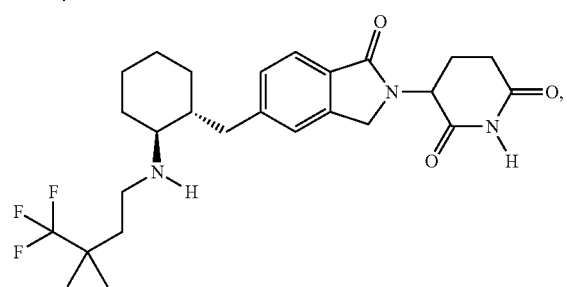
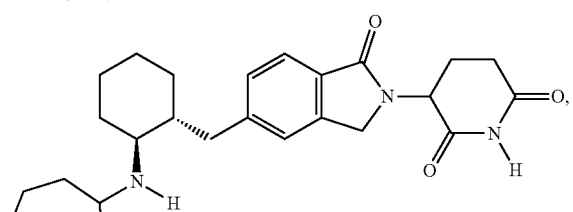
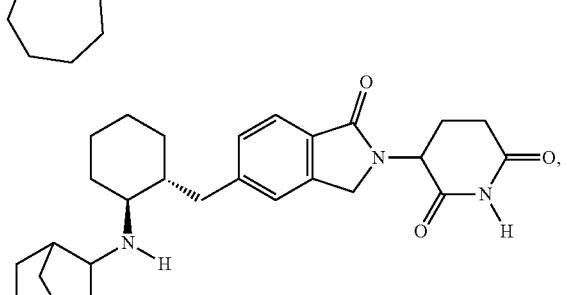
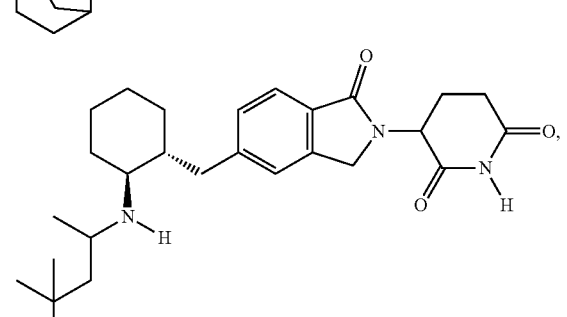
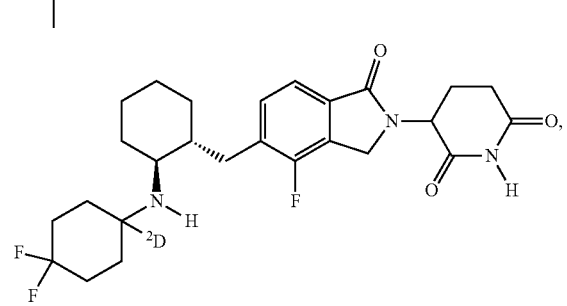
88
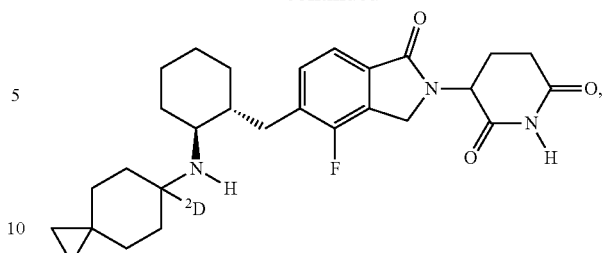
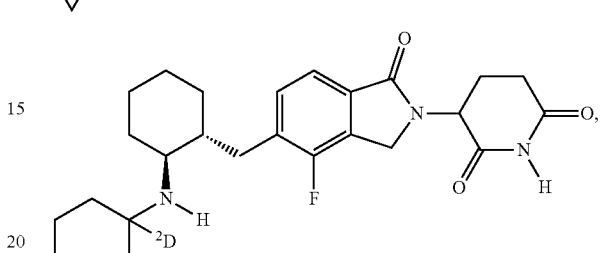
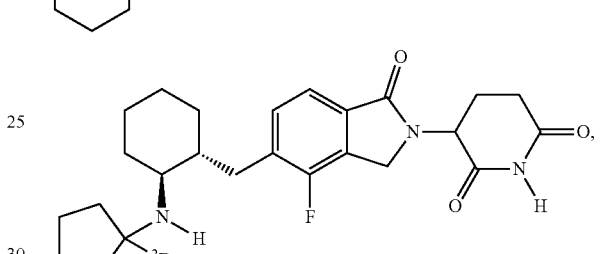
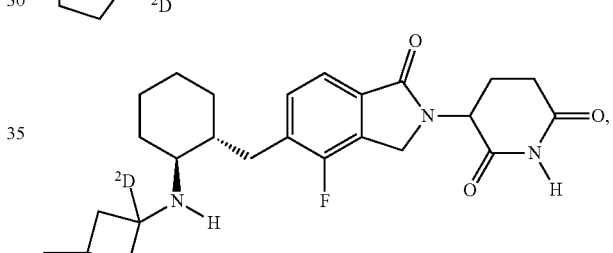
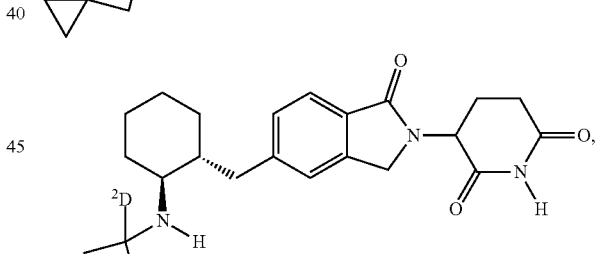
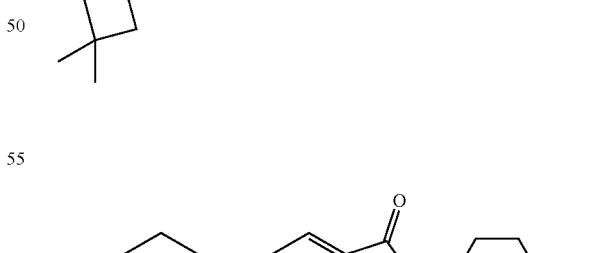
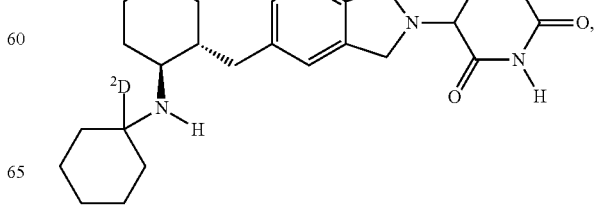

89
-continued
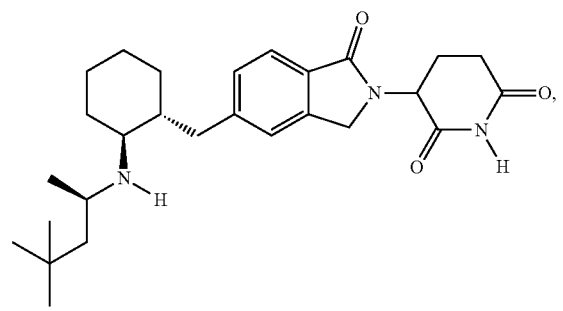
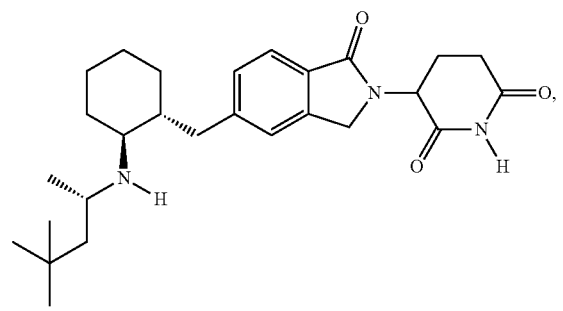
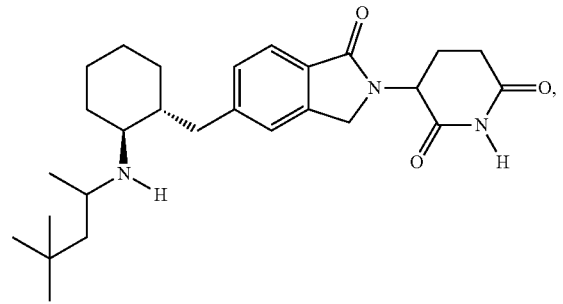
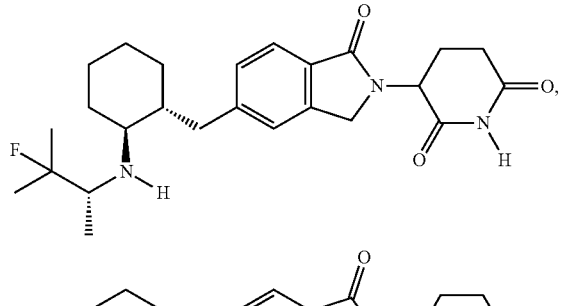
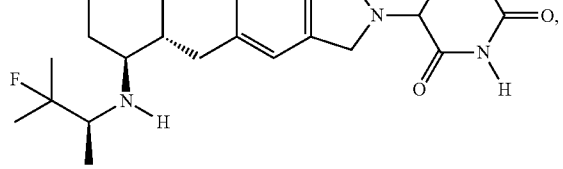
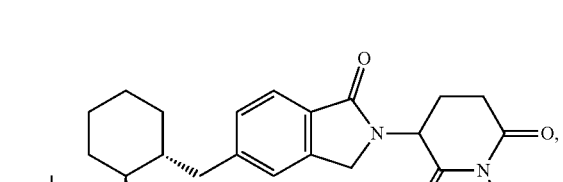
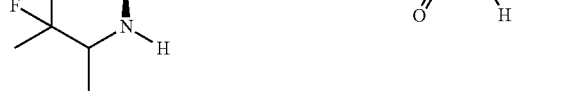
90
-continued
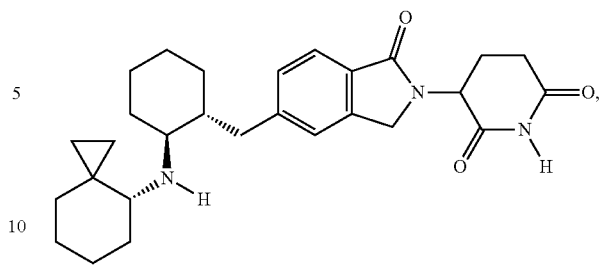

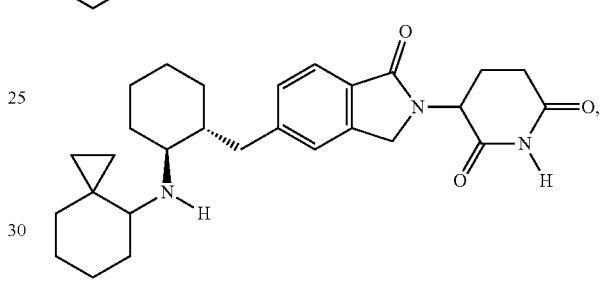
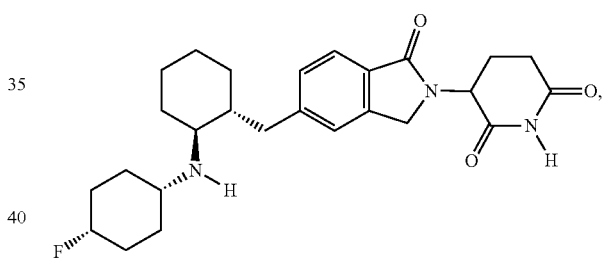
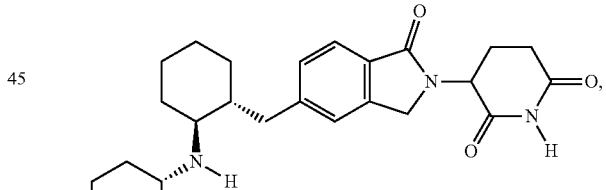
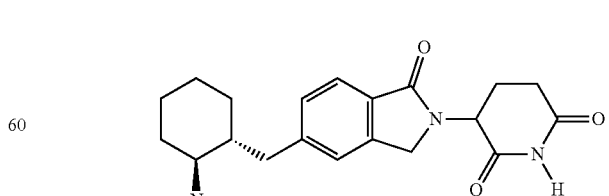

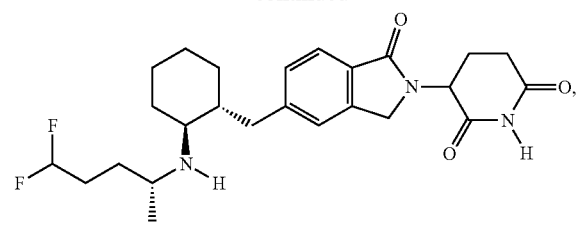
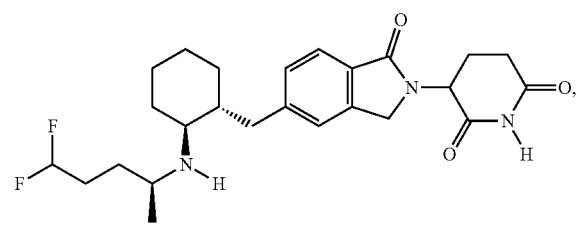
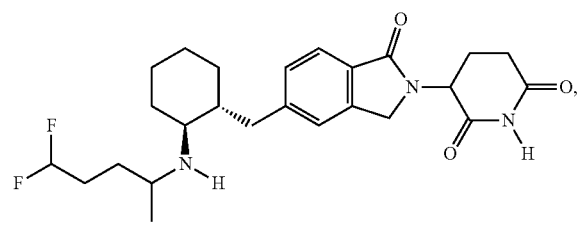
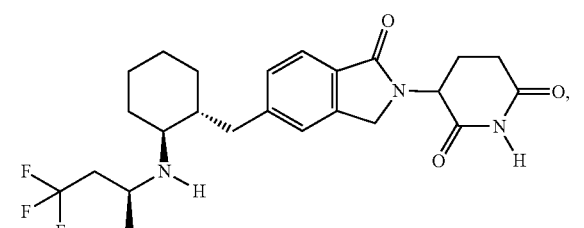
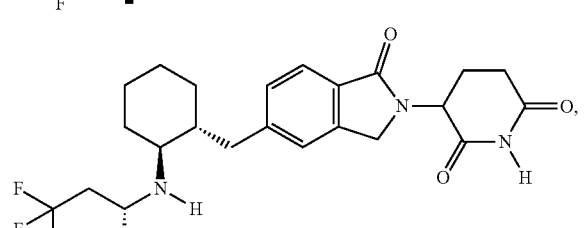
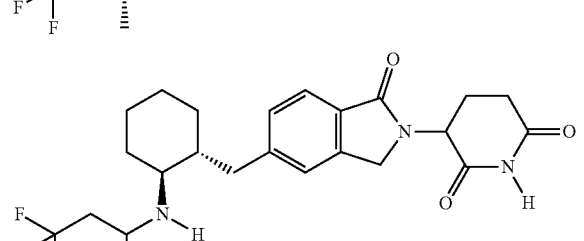
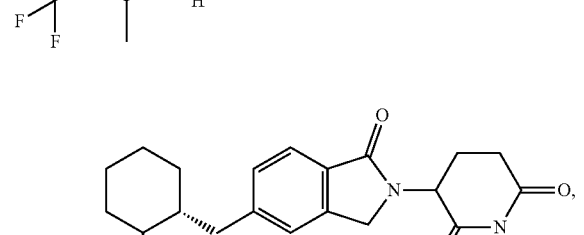
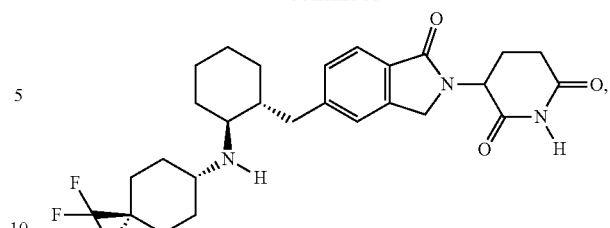
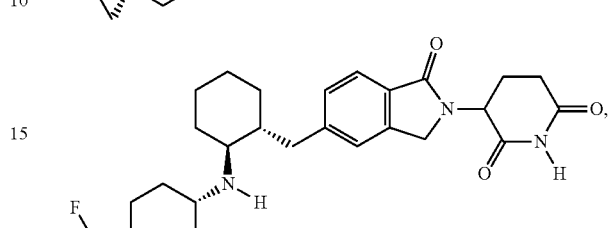
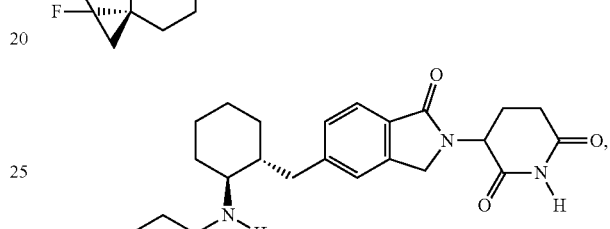
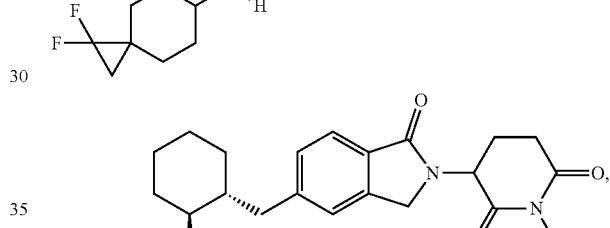
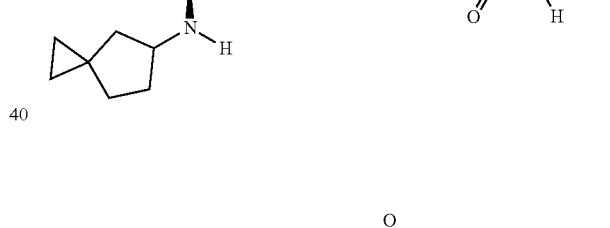
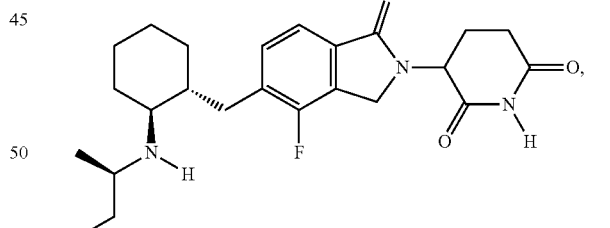
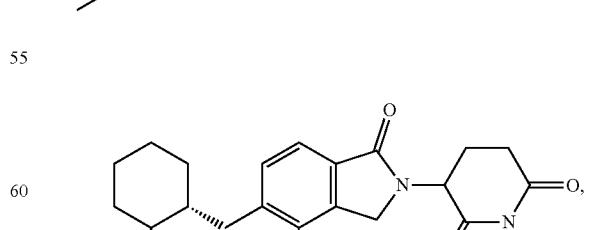
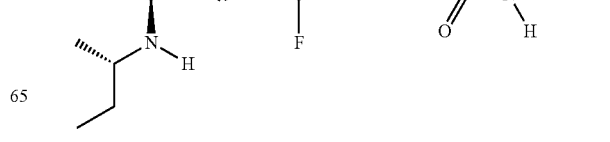

93
-continued
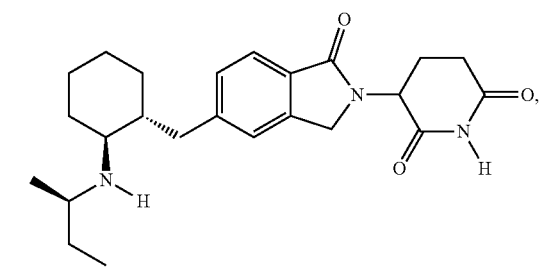
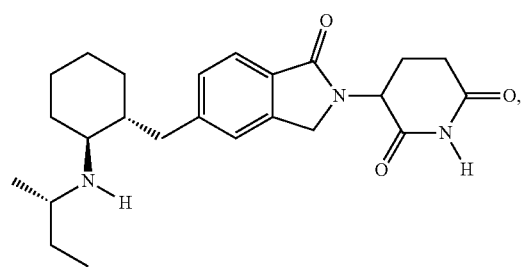
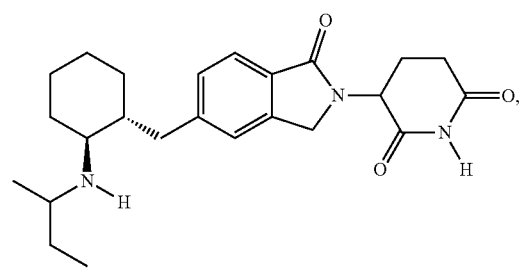
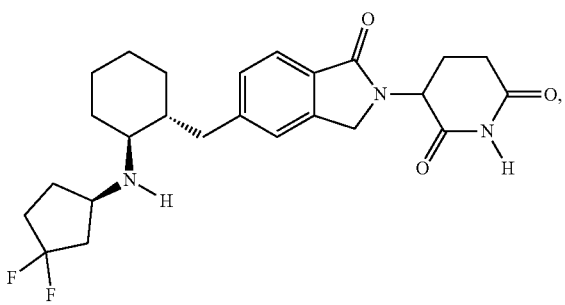
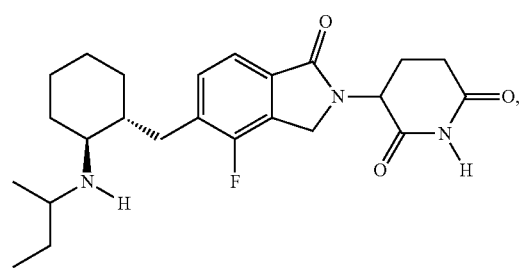
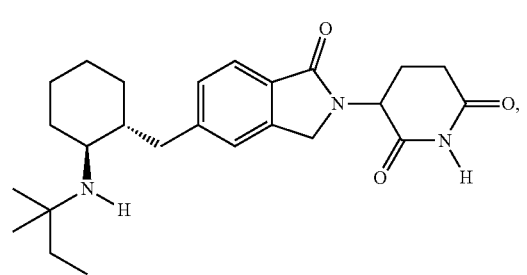
94
-continued
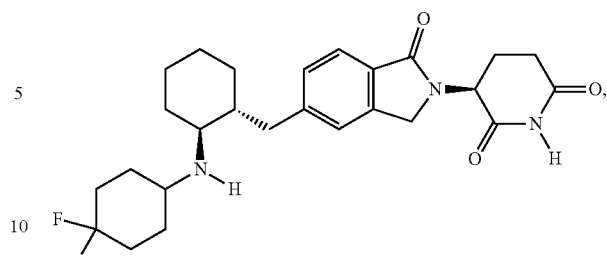
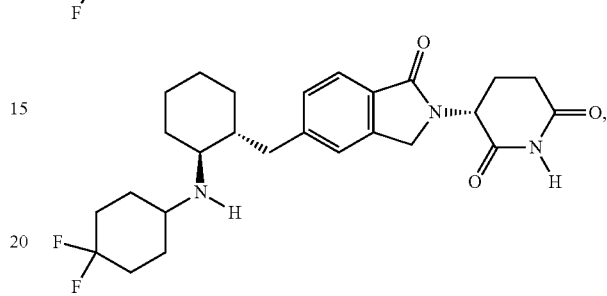
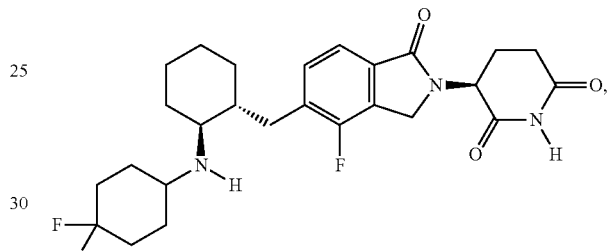
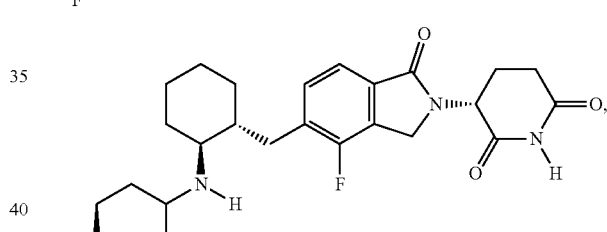
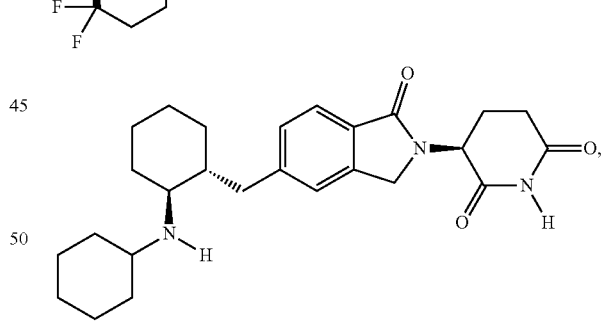
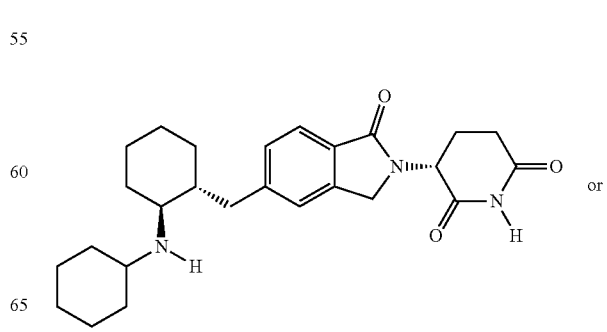

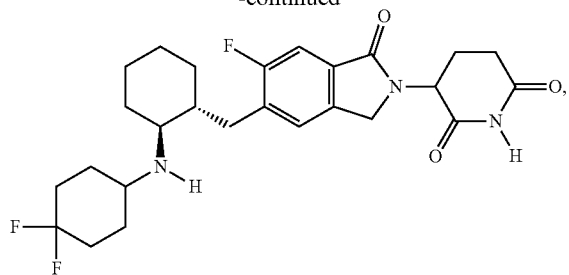
or a pharmaceutically acceptable salt thereof.
In some embodiments the compound of Formula (V), or pharmaceutically acceptable salt thereof is
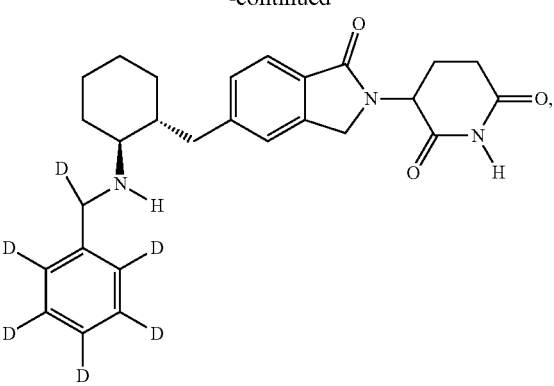
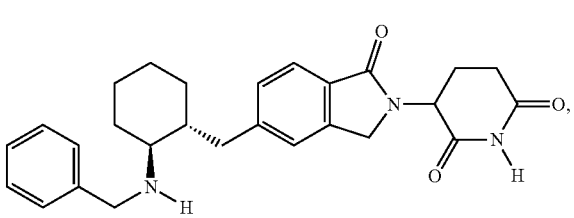
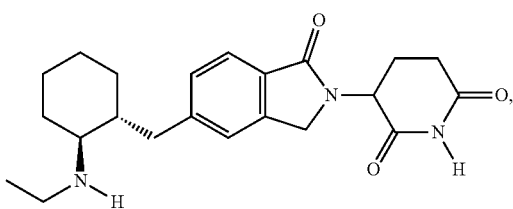
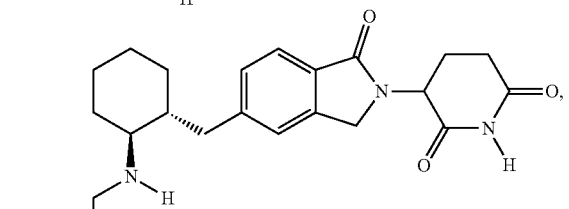
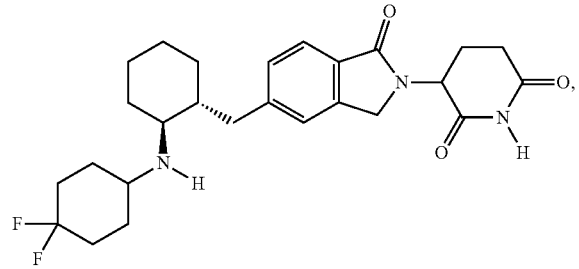
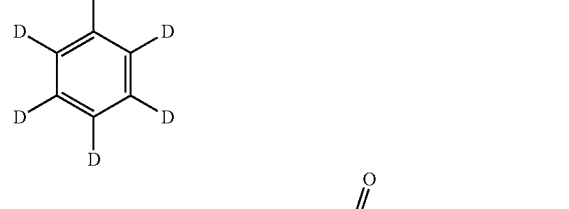
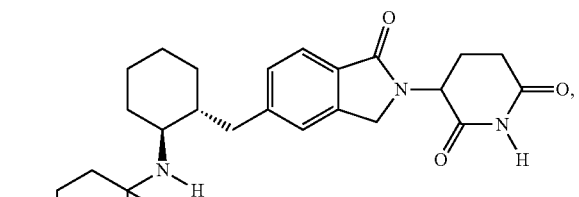
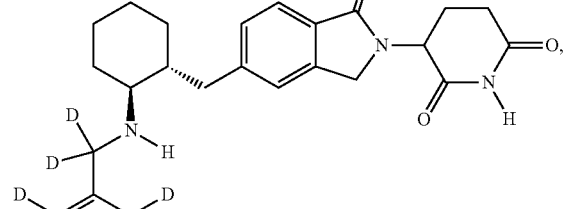
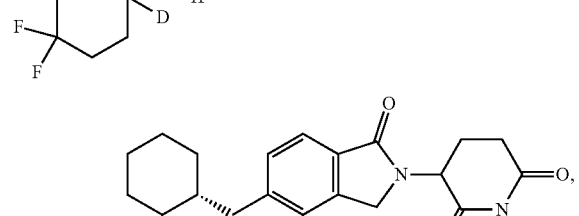
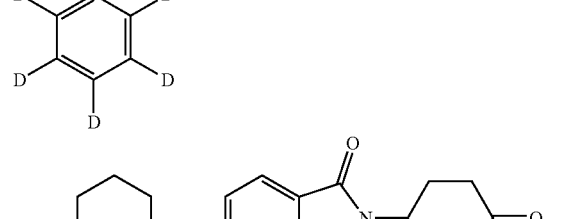
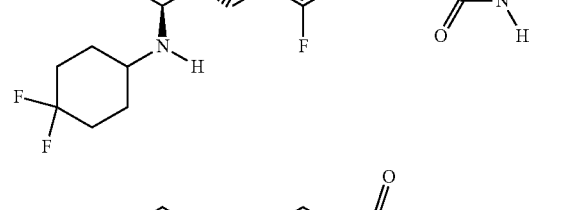

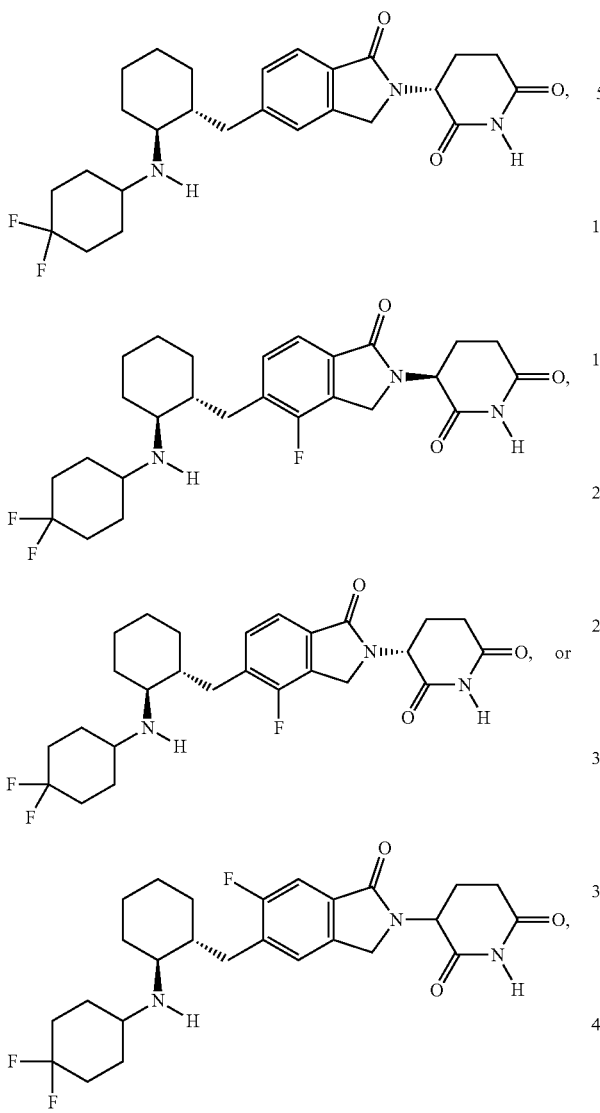

or a pharmaceutically acceptable salt thereof.

In some embodiments the compound of Formula (I), or pharmaceutically acceptable salt thereof, is a compound of Formula (VI)

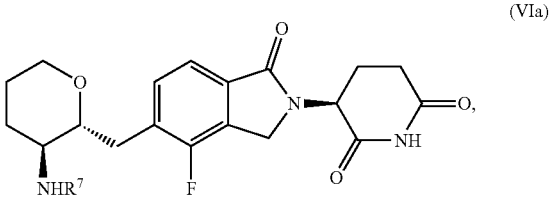

(VI)

or pharmaceutically acceptable salt thereof, wherein $R^7$ is $C_{3-12}$ cycloalkyl, optionally substituted with one to four $Z^2$, which may be the same or different; and each $Z^2$ is independently deuterium, halogen, $C_{1-3}$ alkyl, $C_{1-3}$ haloalkyl.

In some embodiments the compound of Formula (VI), or pharmaceutically acceptable salt thereof, is a compound of Formula (VIa):

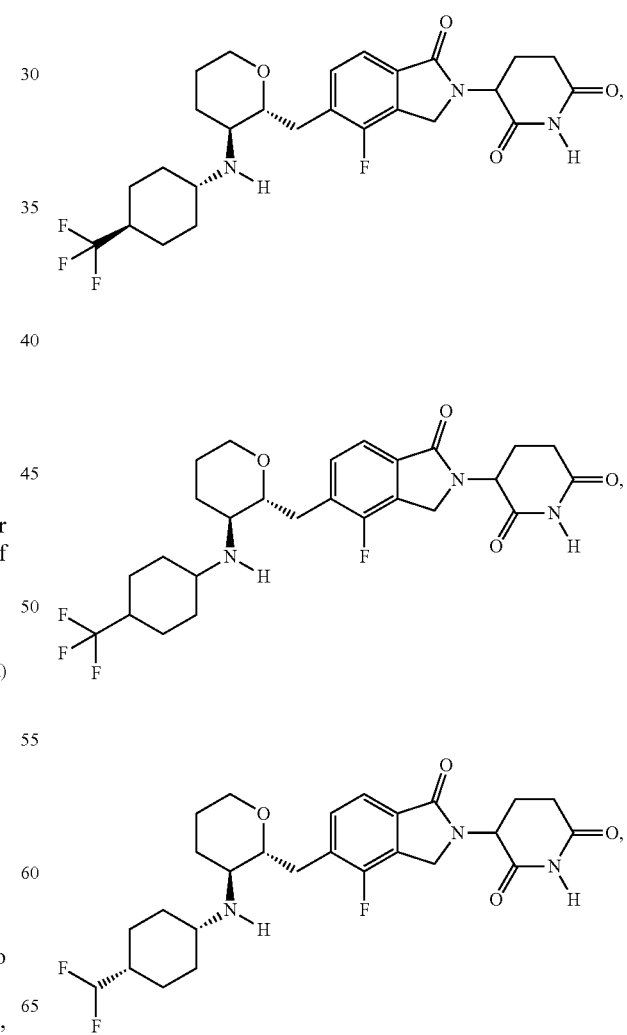

(VIa)

or a pharmaceutically acceptable salt thereof.

In some embodiments of the compound of Formula (VI) or (VIa), or pharmaceutically acceptable salt thereof, $R^7$ is cyclohexyl optionally substituted with 1 to 4 $Z^2$, which may be the same or different, wherein each $Z^2$ is independently deuterium, —$CH_3$, —$C_2F$, —$CHF_2$, —$CF_3$, or —F. In some embodiments of In some embodiments the compound of Formula (VI), or pharmaceutically acceptable salt thereof, is 99
-continued
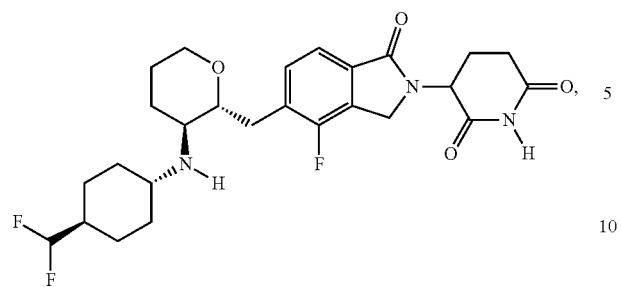
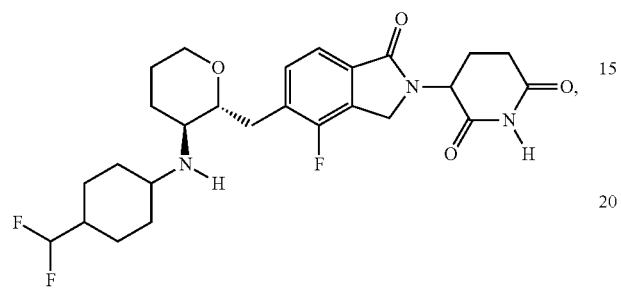
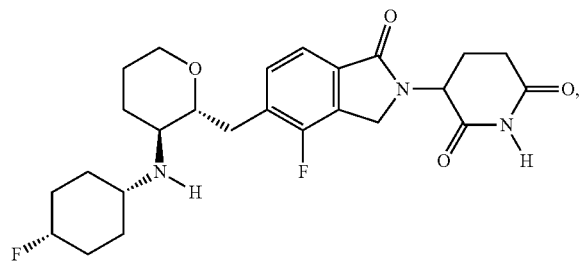
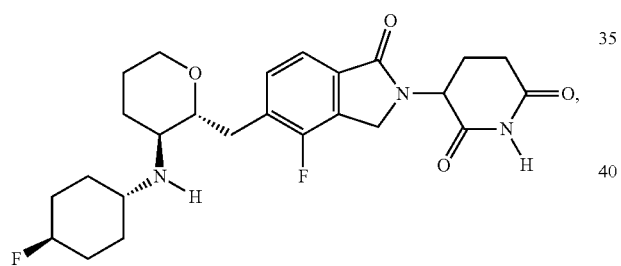
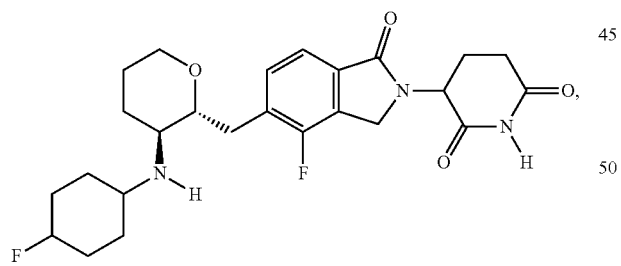
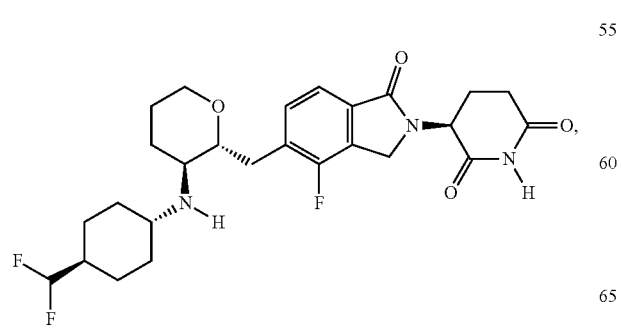
100
-continued
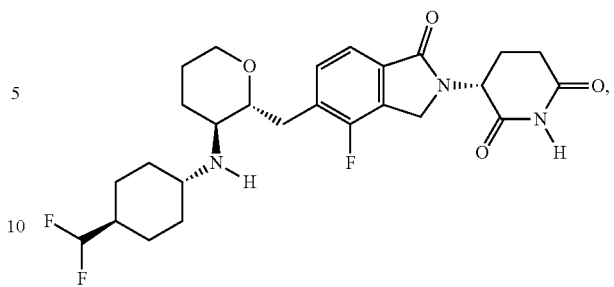
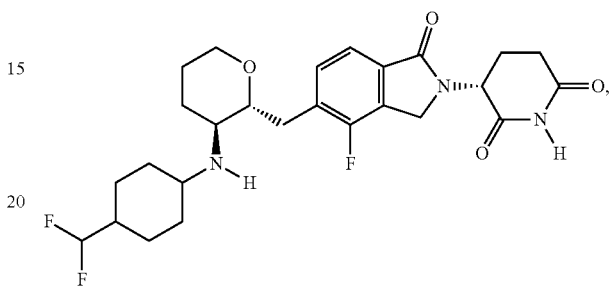
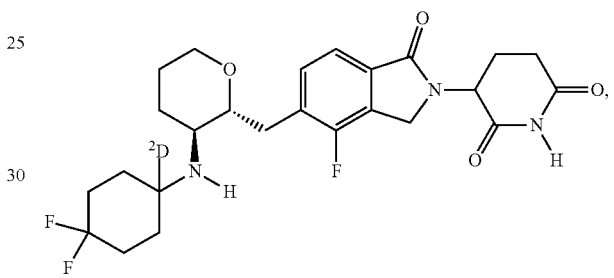
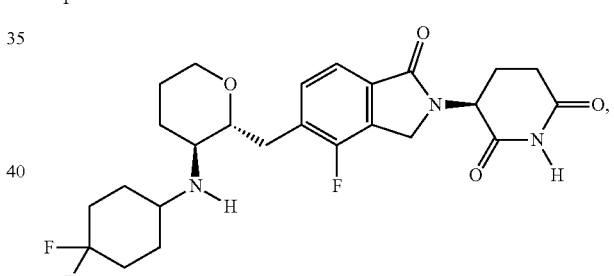
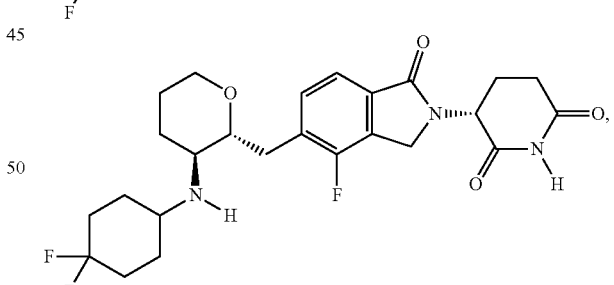
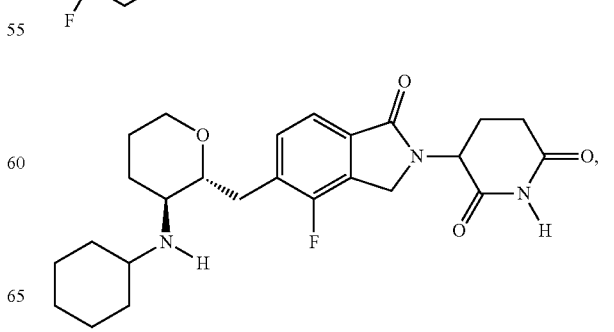

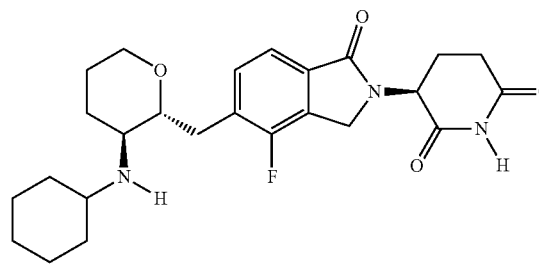
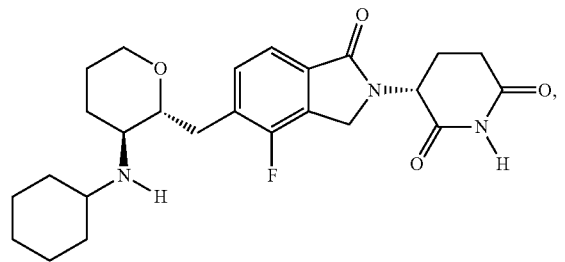
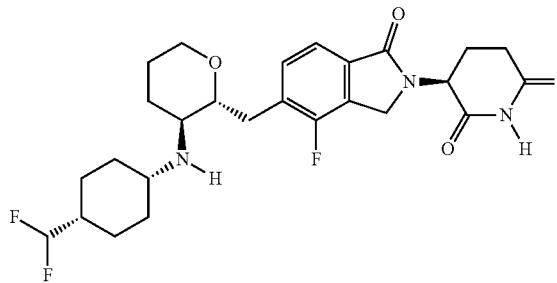
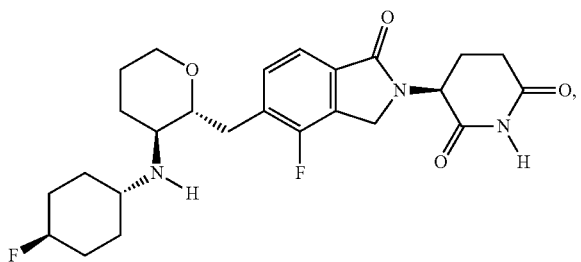
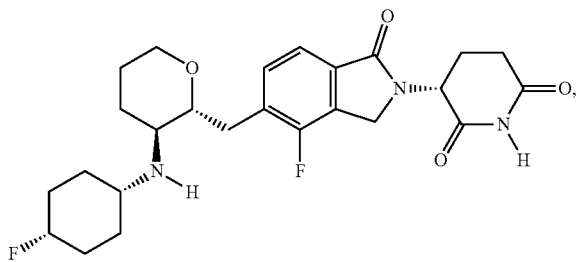
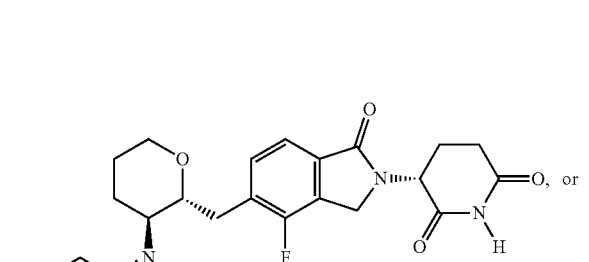
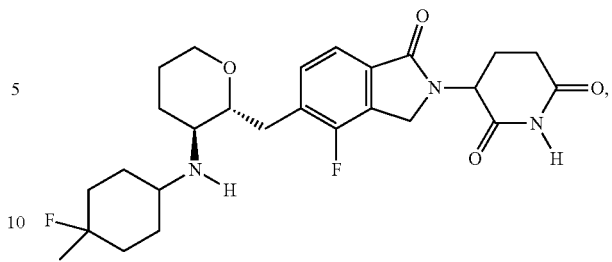
or a pharmaceutically acceptable salt thereof.
In some embodiments the compound of Formula (VI), or pharmaceutically acceptable salt thereof, is
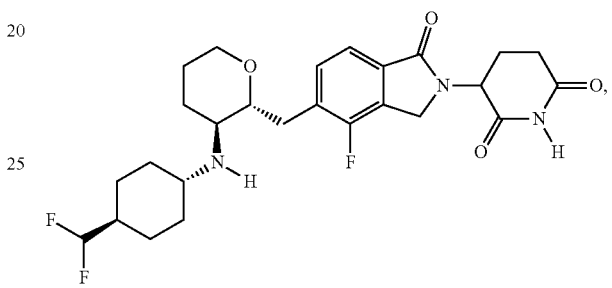
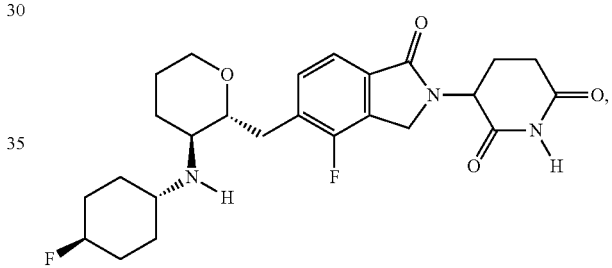
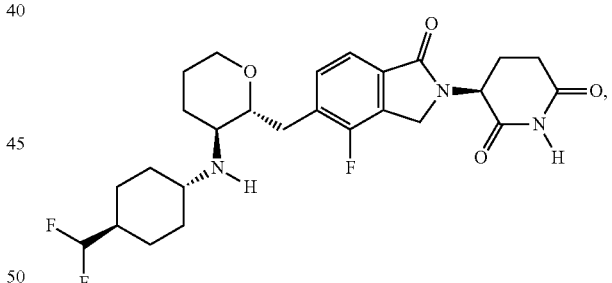
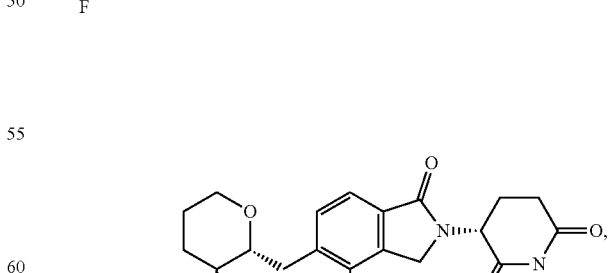
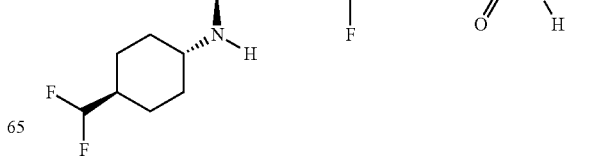

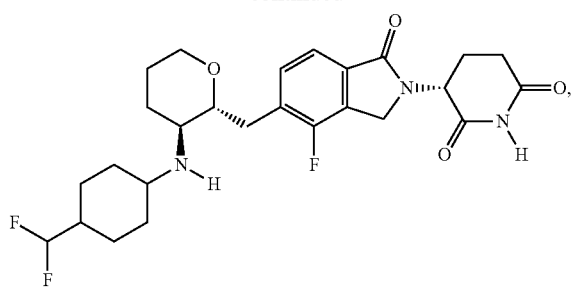
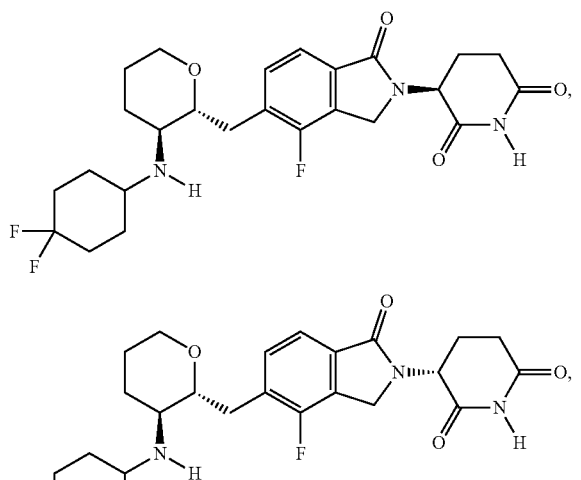
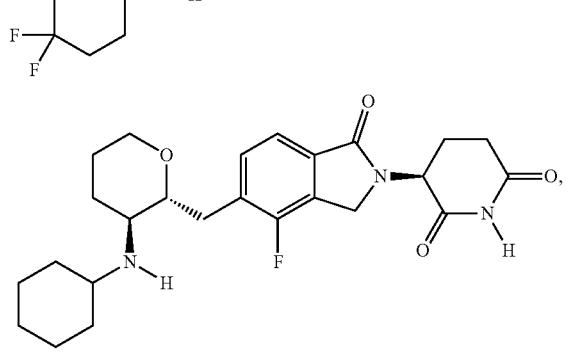
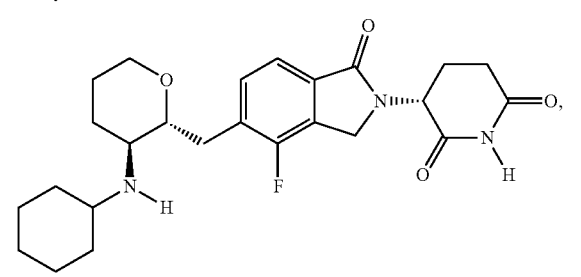
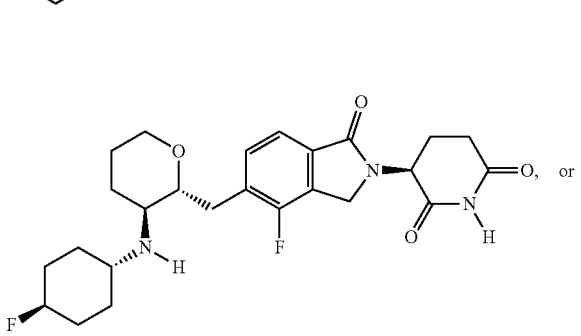
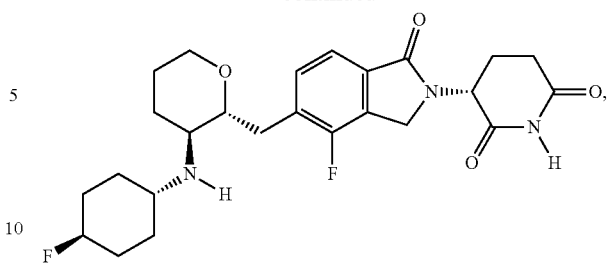
or a pharmaceutically acceptable salt thereof.
In some embodiments the compound of Formula (I) or (IIa), or pharmaceutically acceptable salt thereof, is

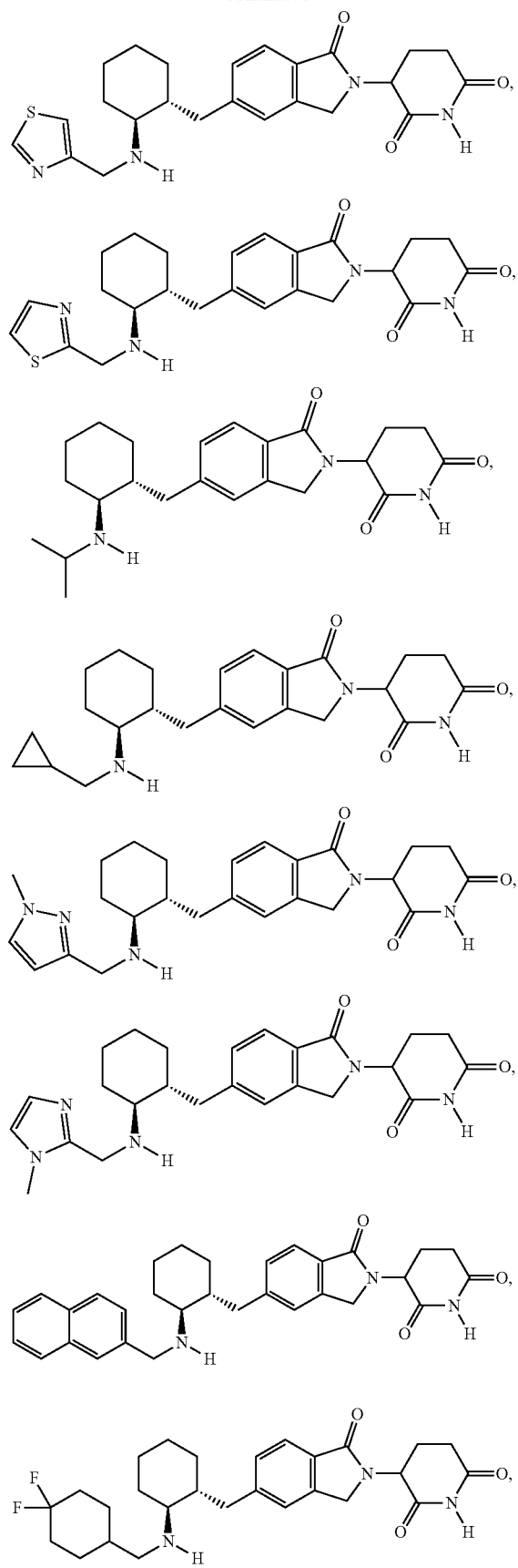
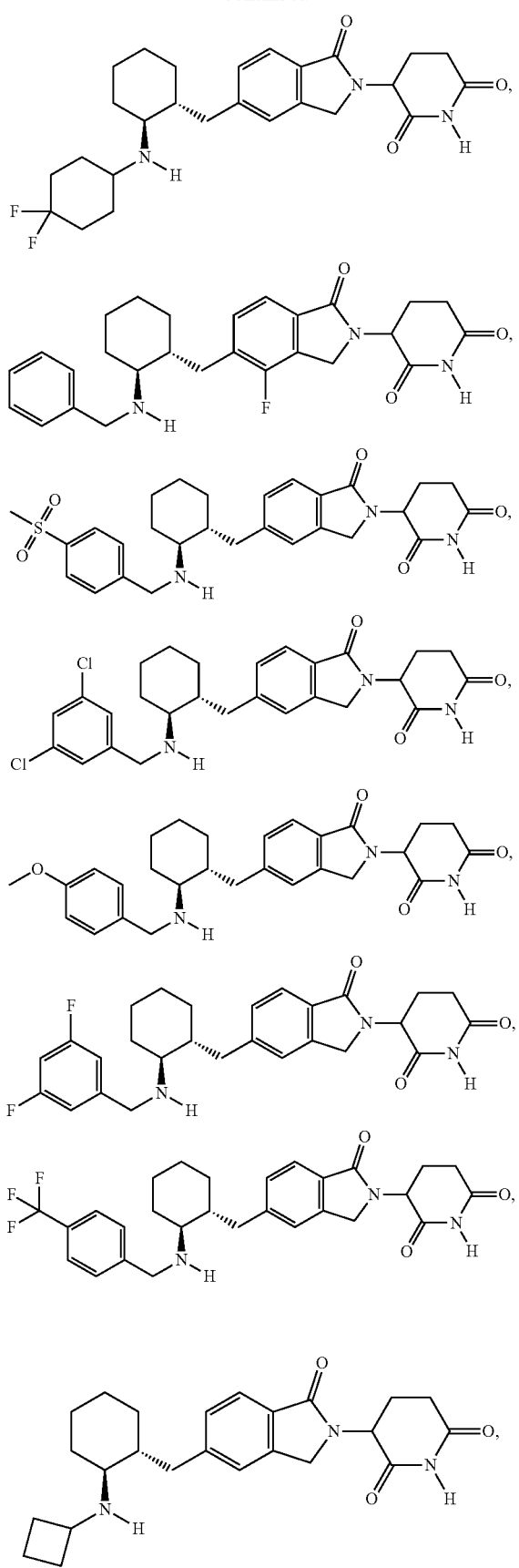

107
-continued
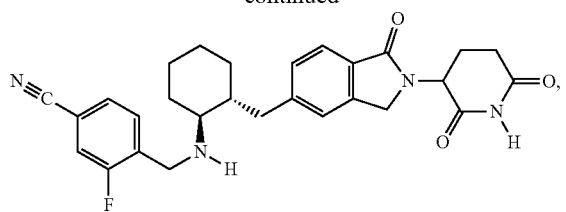
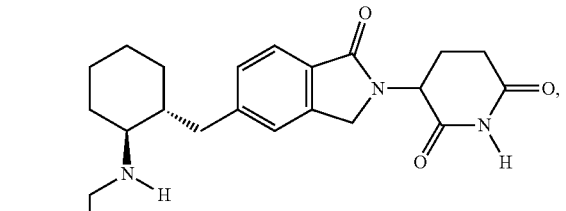
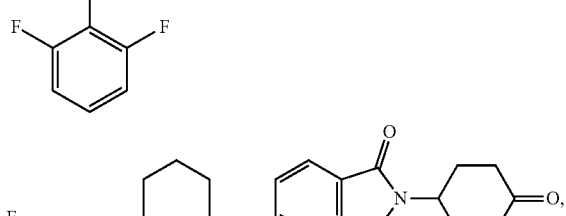
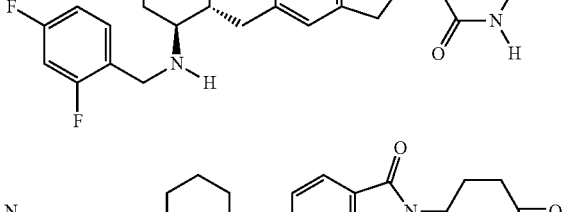

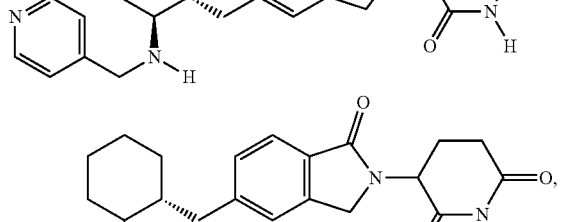

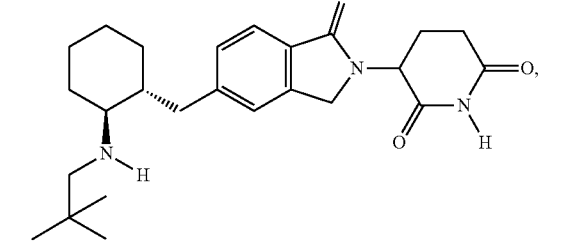
108
-continued
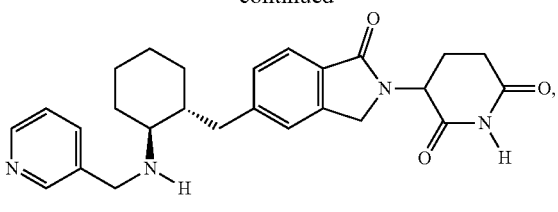
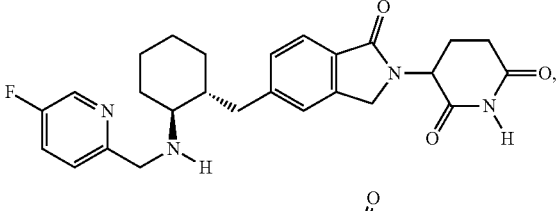
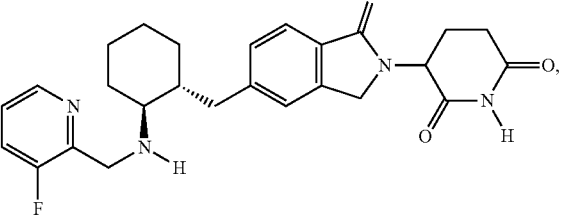
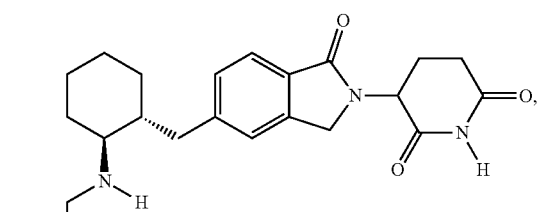
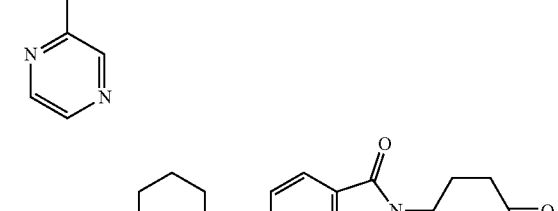
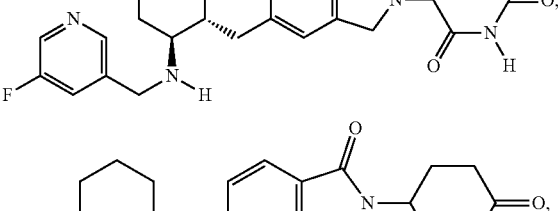
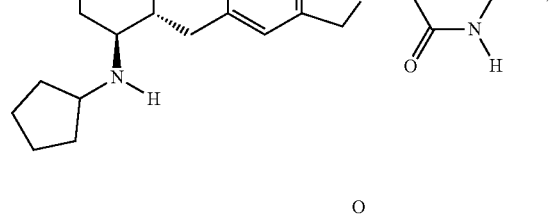
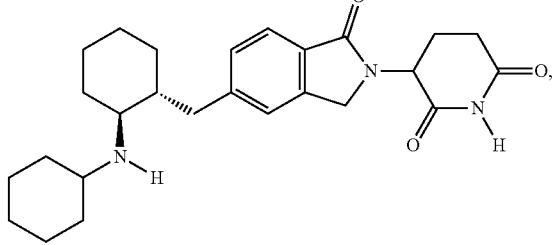

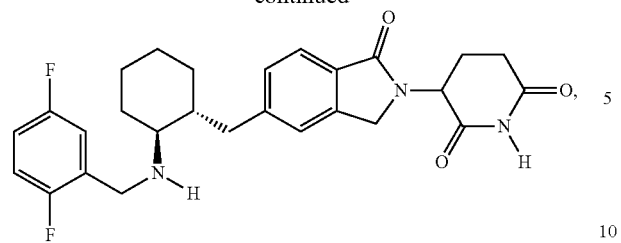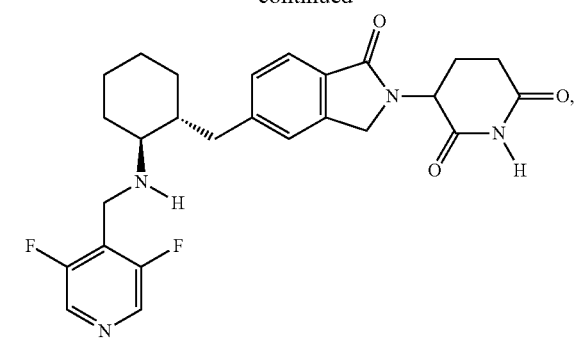

111
-continued
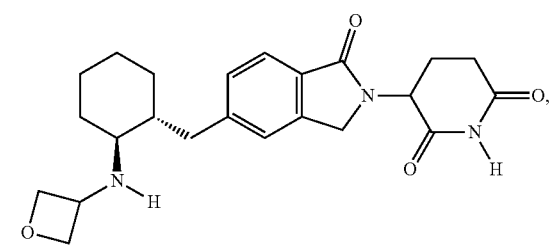
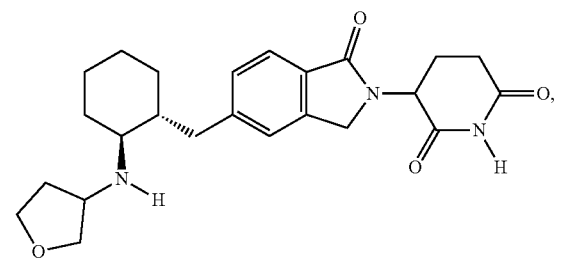
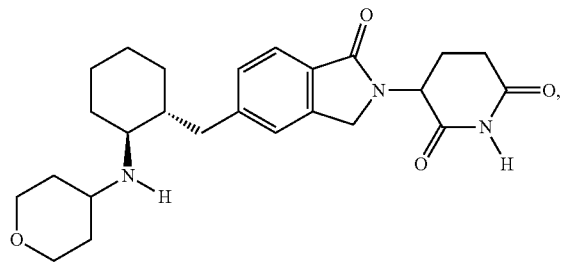
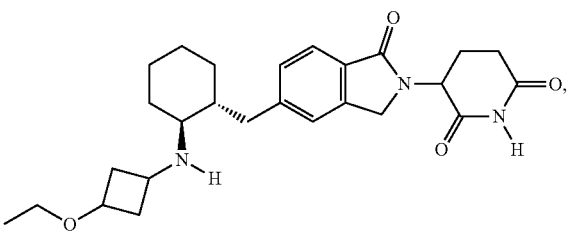
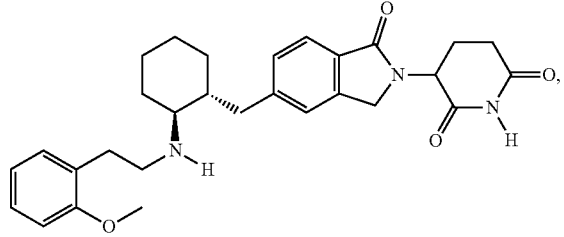
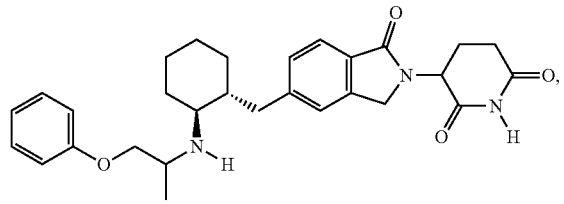
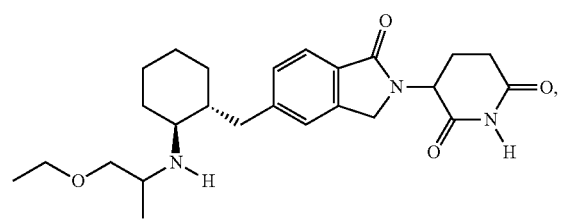
112
-continued
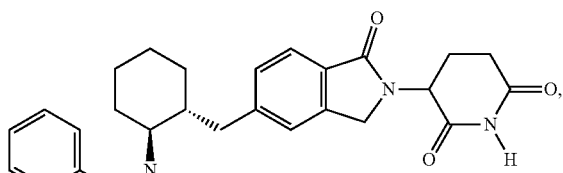
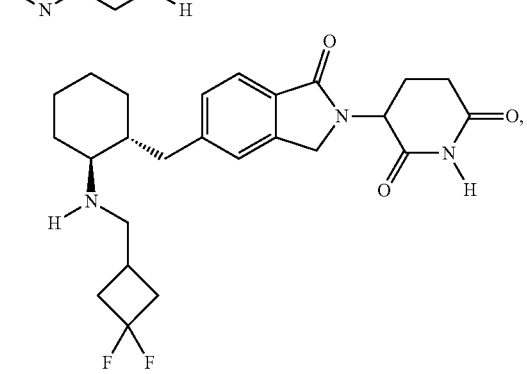
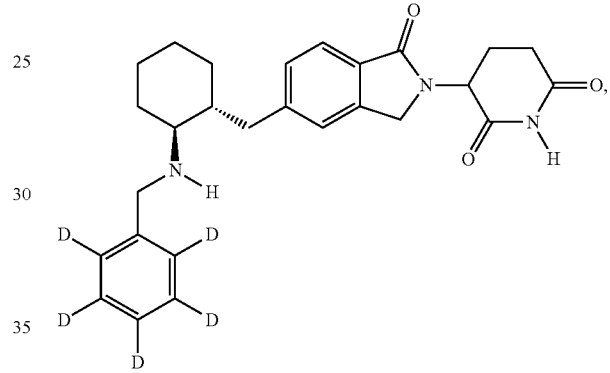
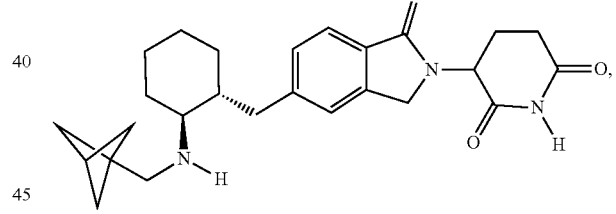
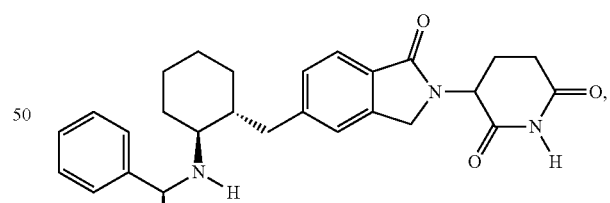
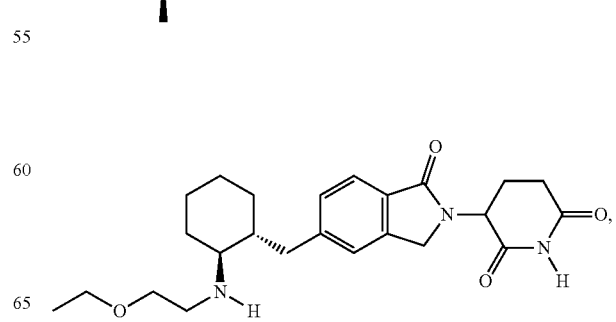

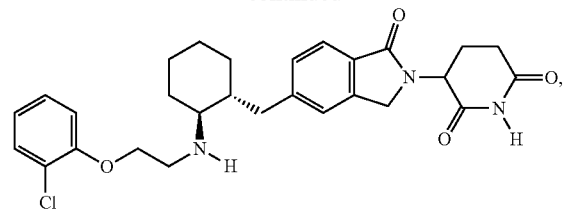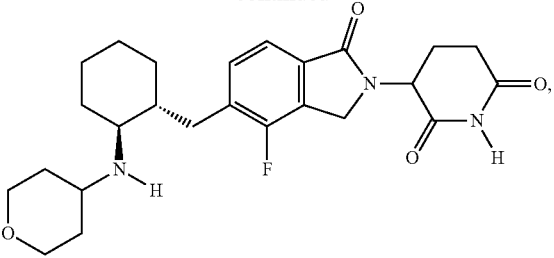

115
-continued
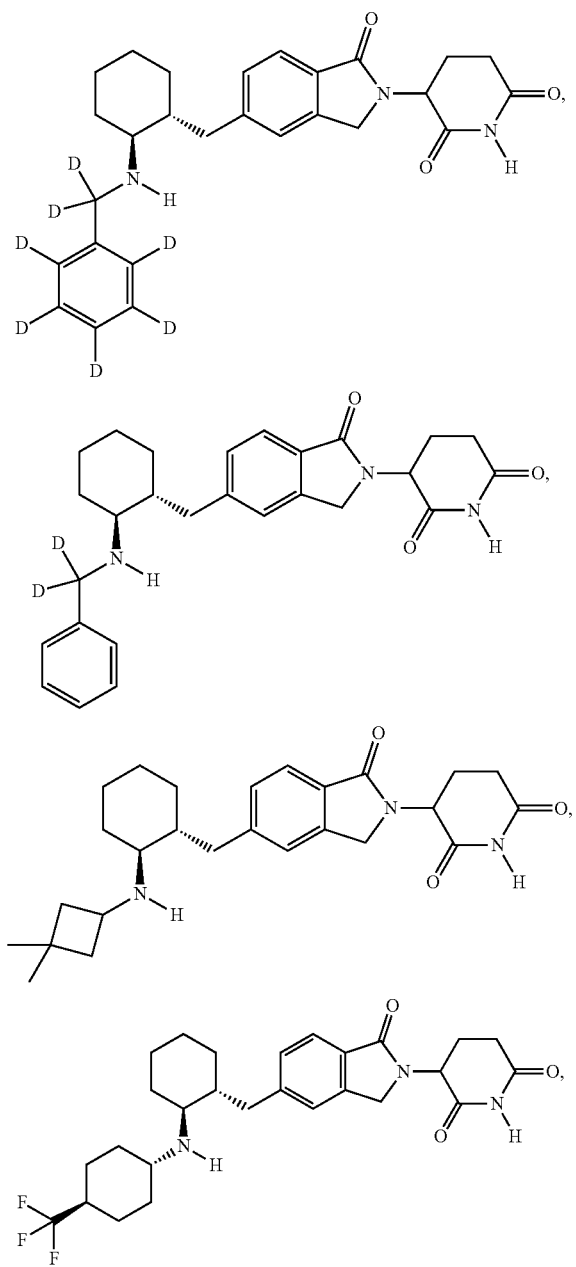
116
-continued
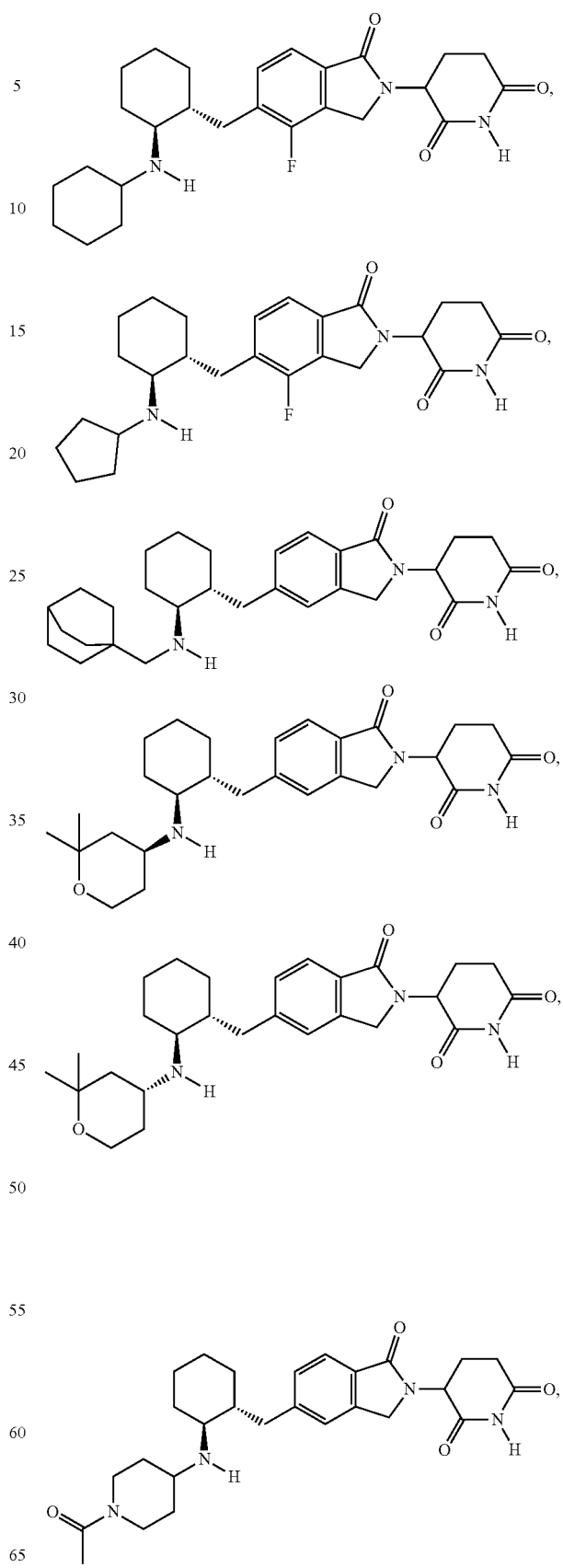

117
-continued
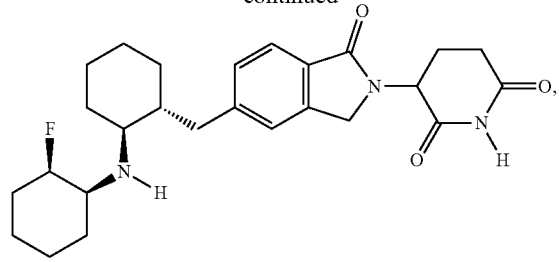
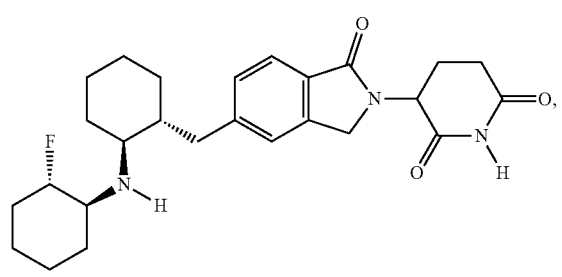
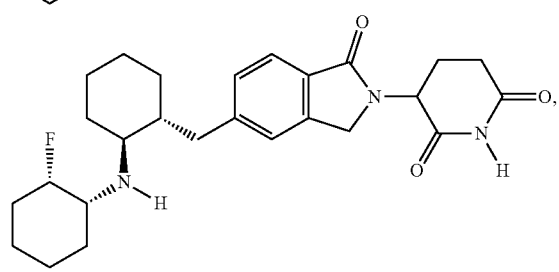
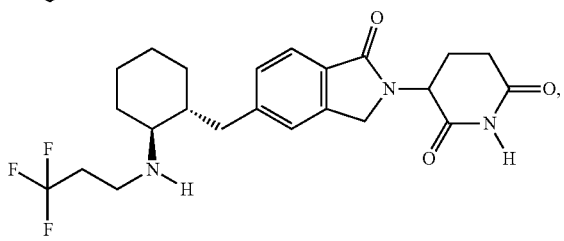
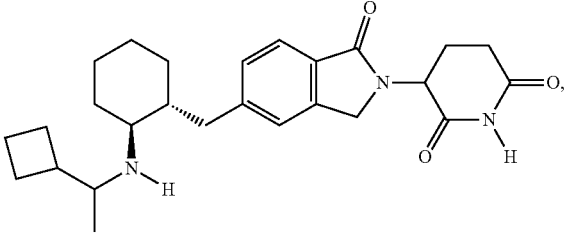
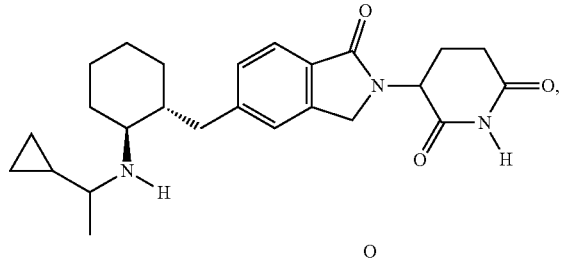
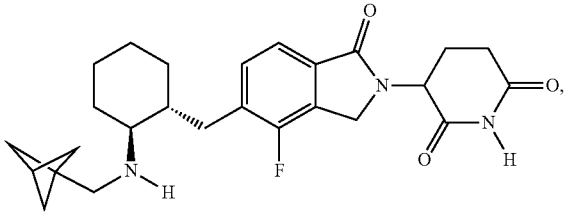
118
-continued
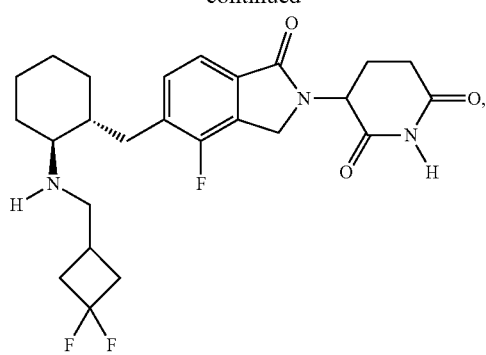
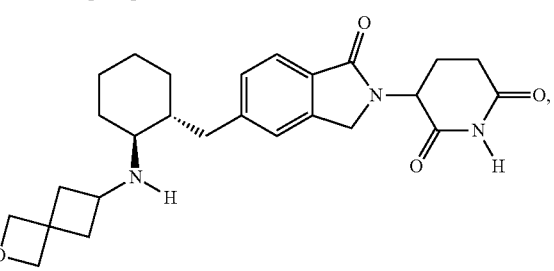
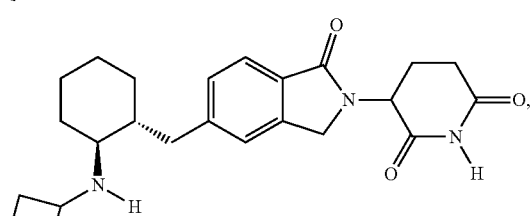
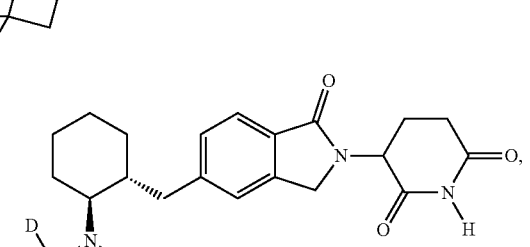
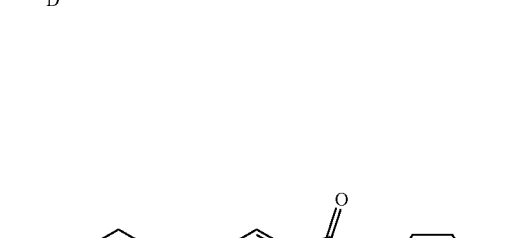
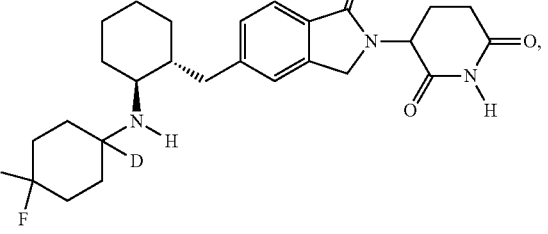

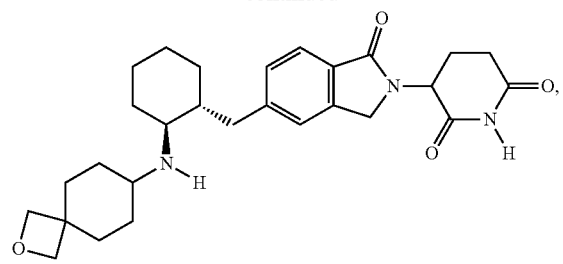
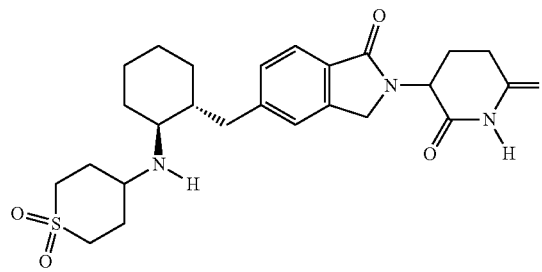
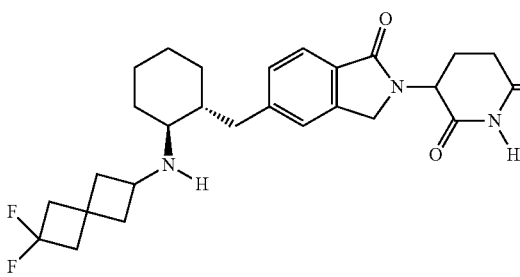
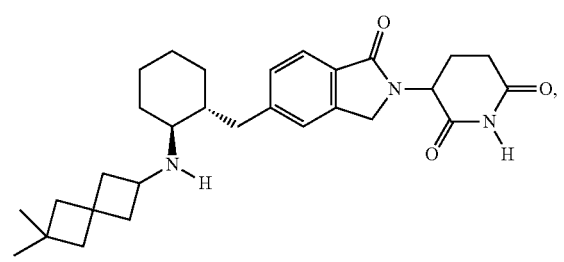
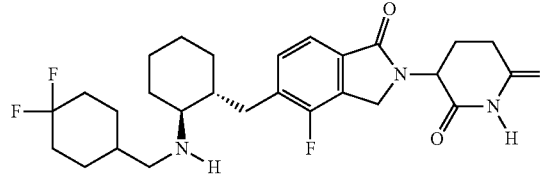
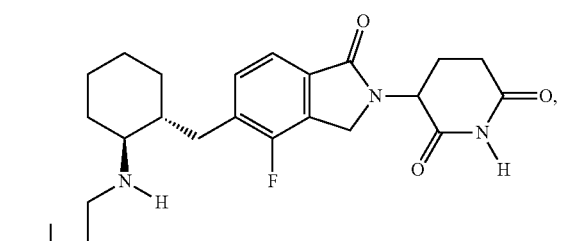
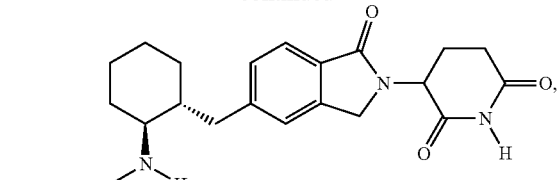
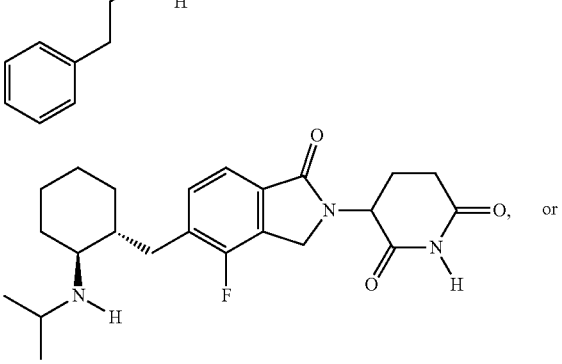
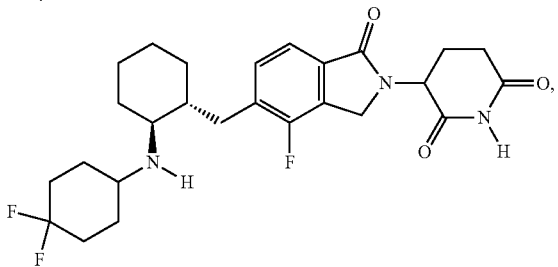
or a pharmaceutically acceptable salt thereof.
In some embodiments the compound of Formula (I) or (IIa), or pharmaceutically acceptable salt thereof, is
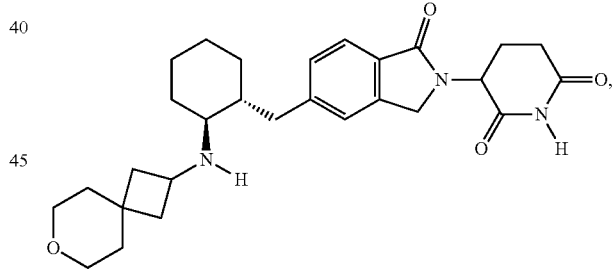
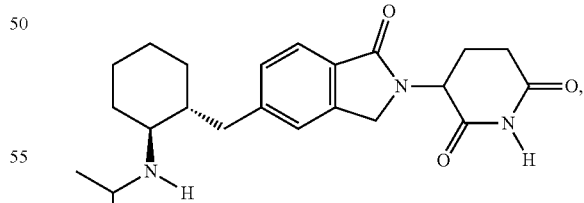
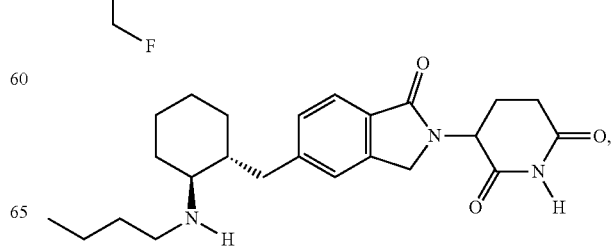

121
-continued
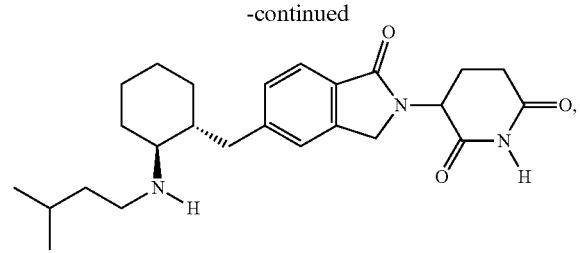
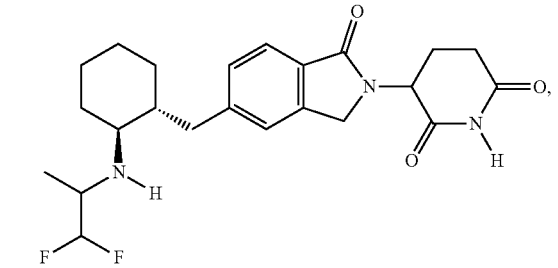
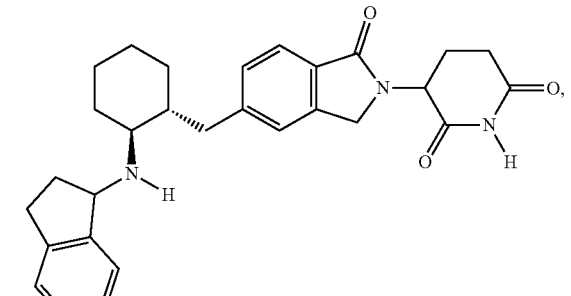
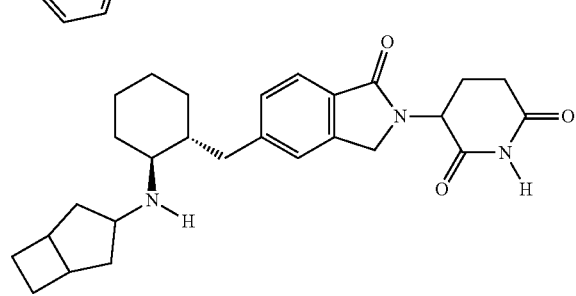
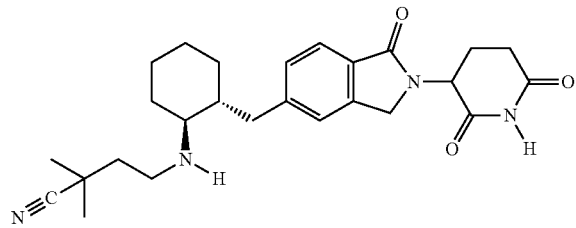
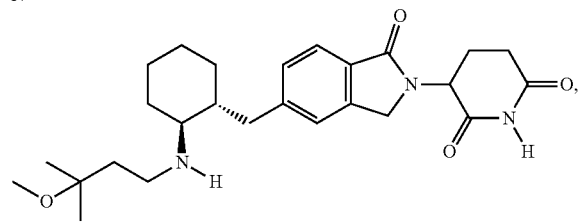
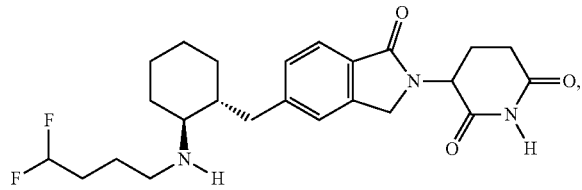
122
-continued
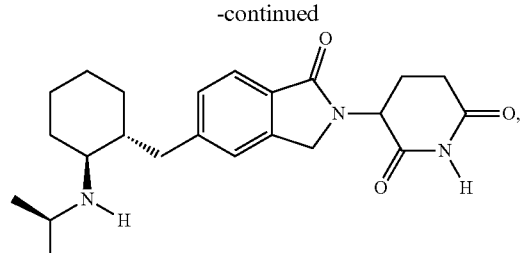
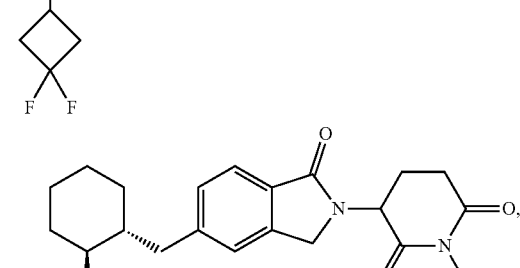
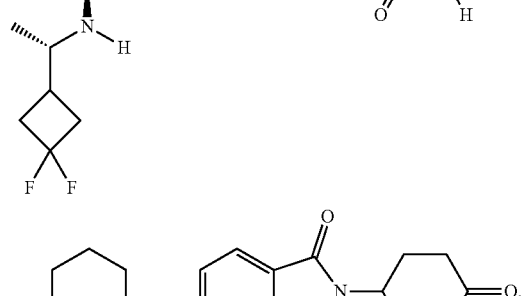
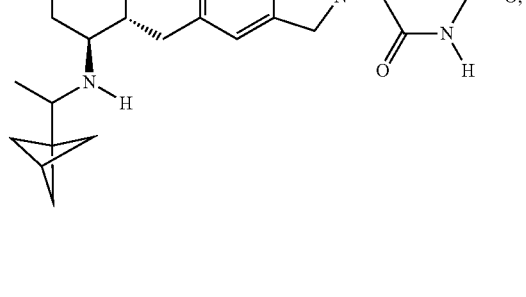
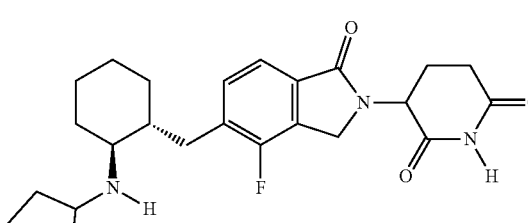
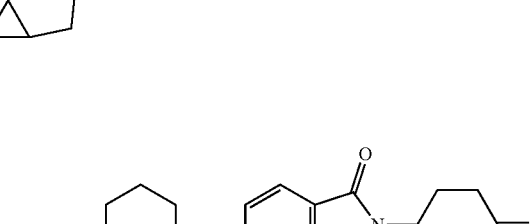
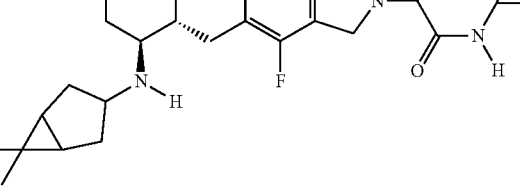

123
-continued
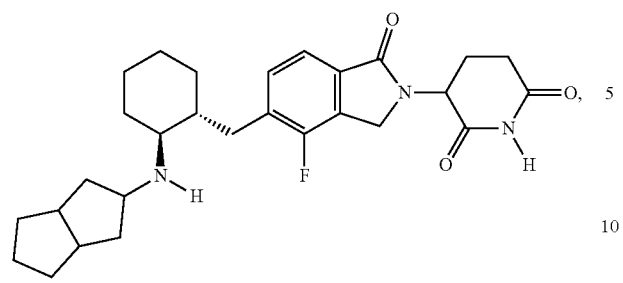
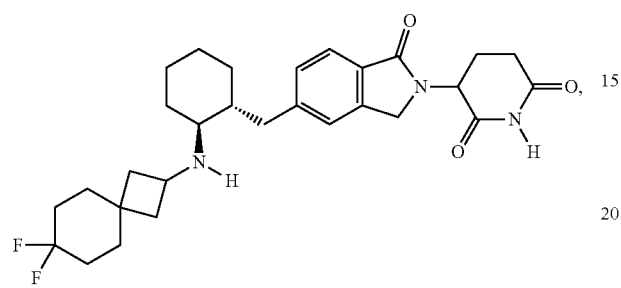
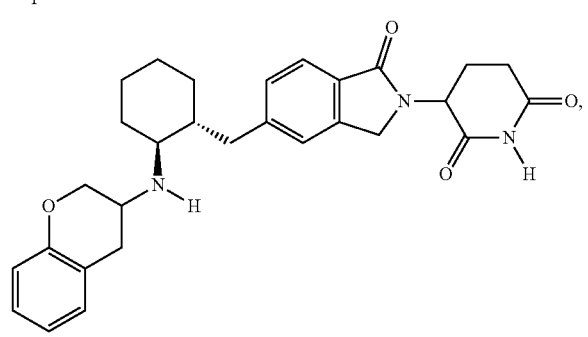
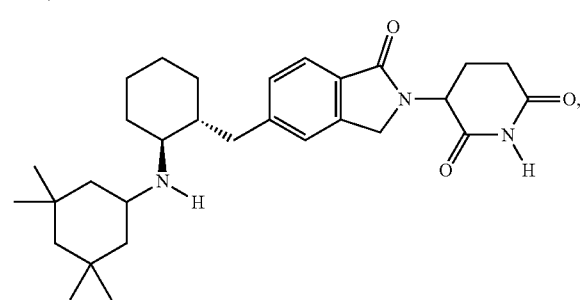
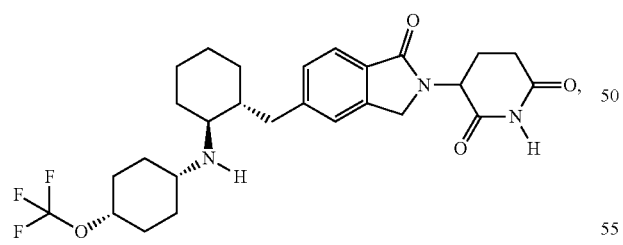
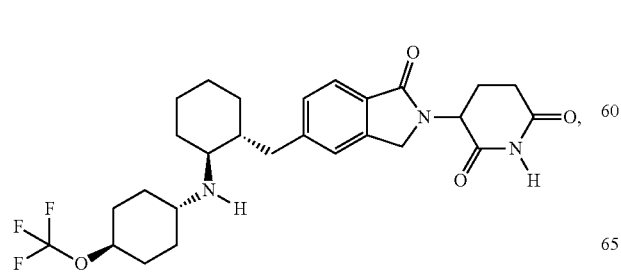
124
-continued
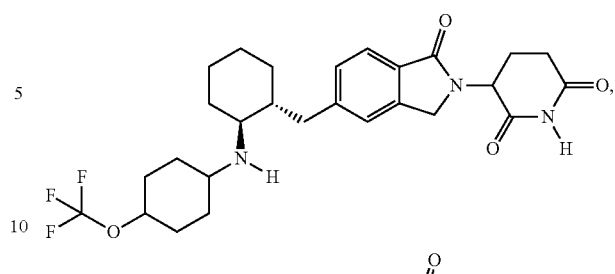
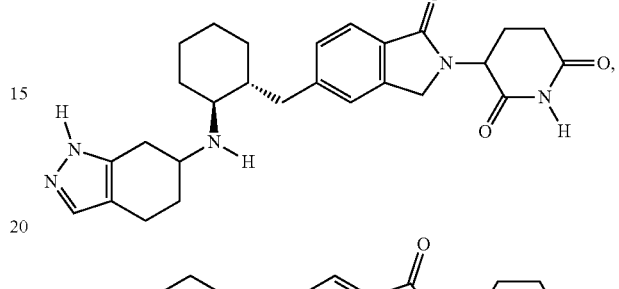
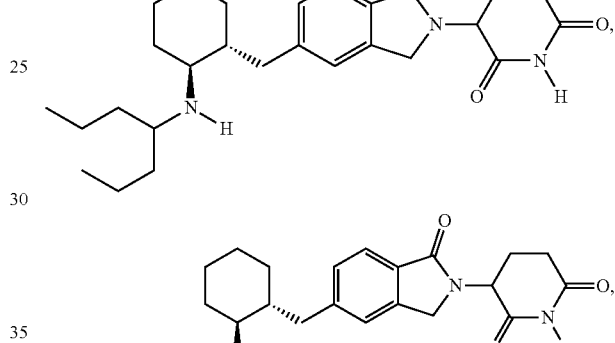
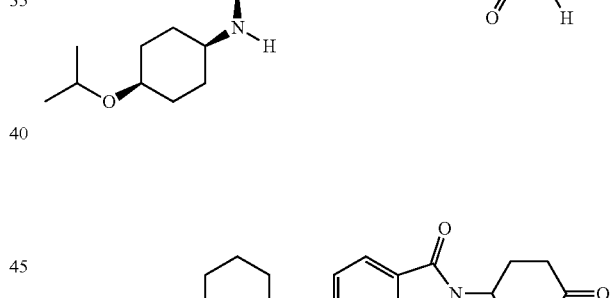
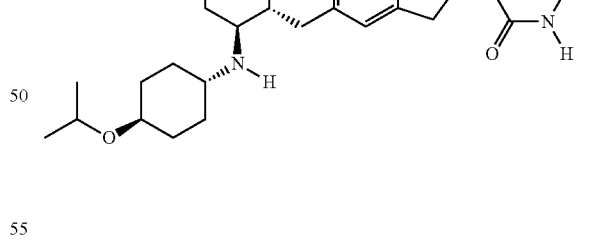
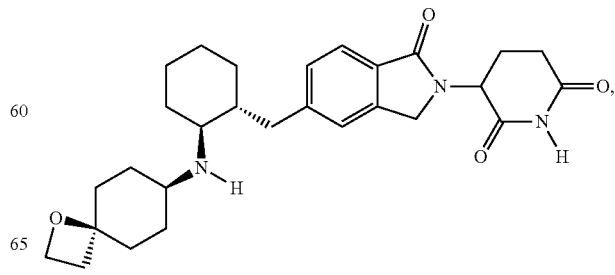

125
-continued

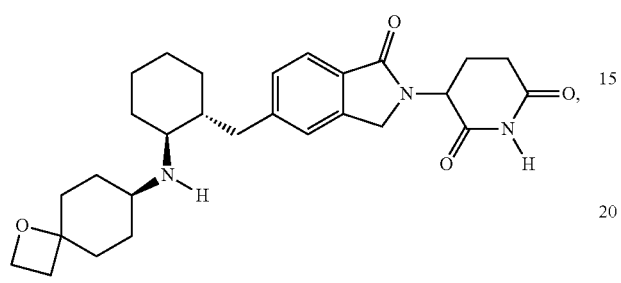
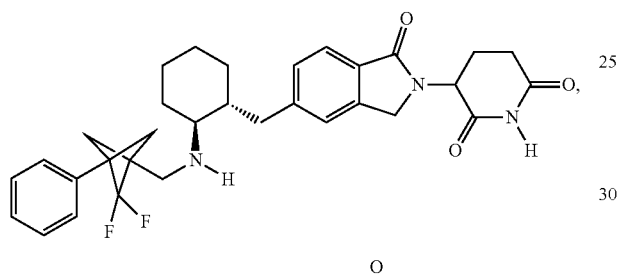
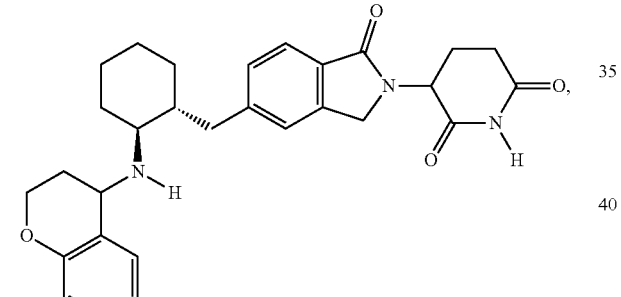
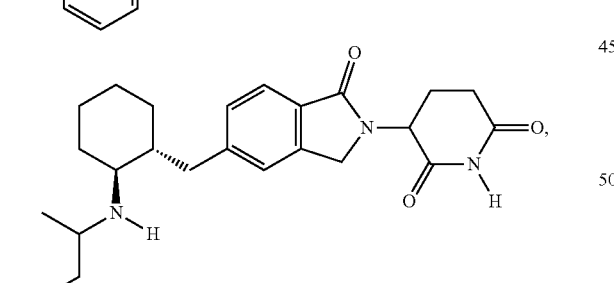
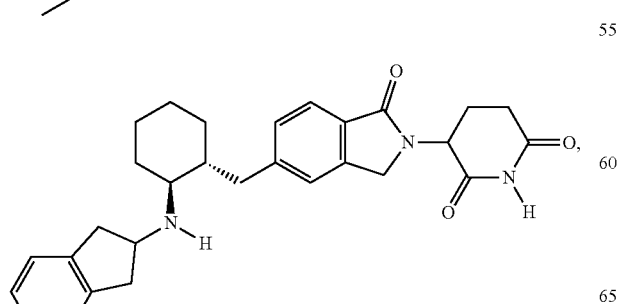
126
-continued
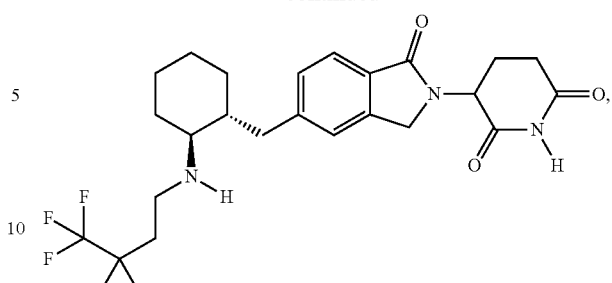
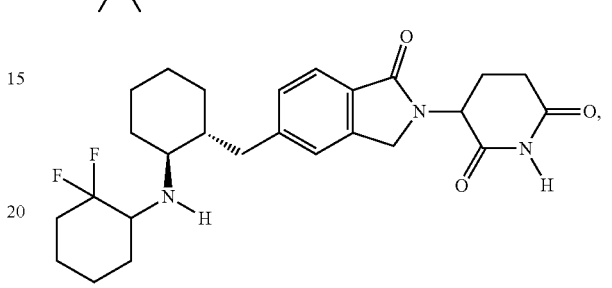
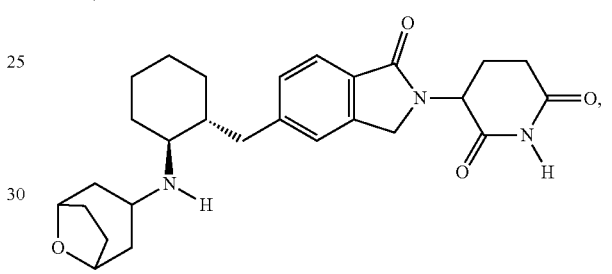
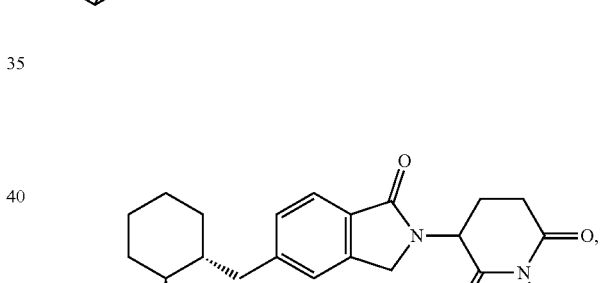
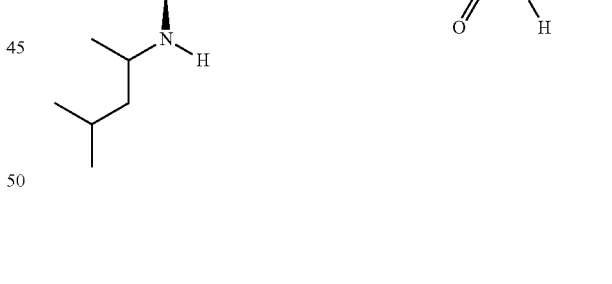
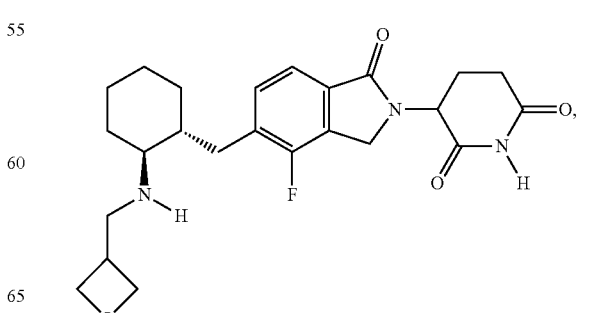

127
-continued
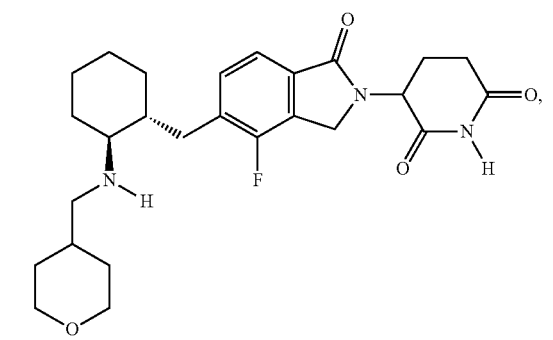
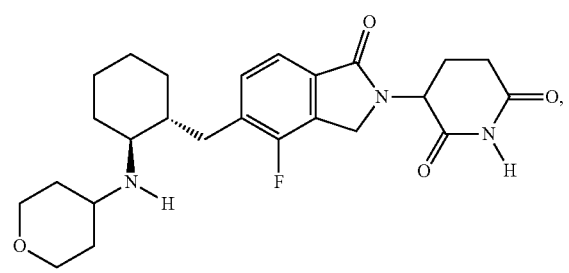
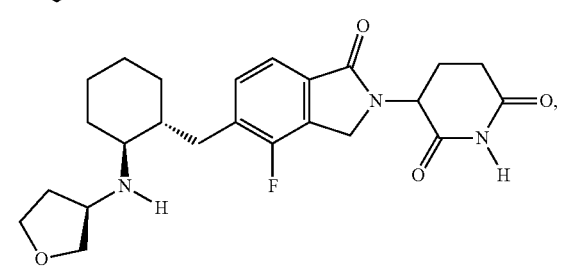
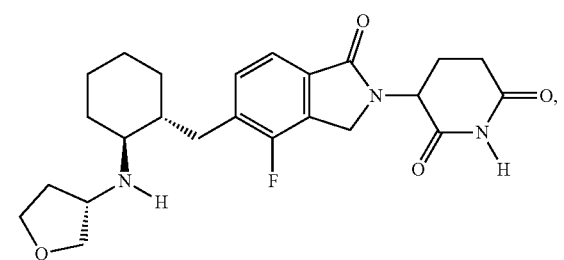
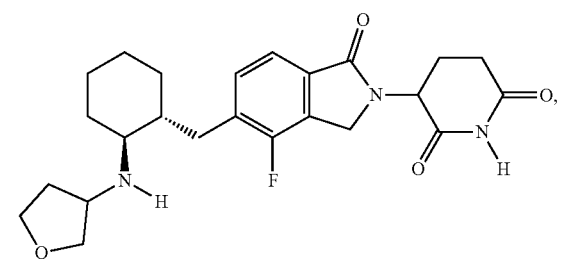
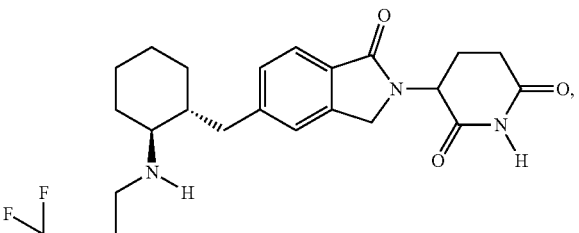
128
-continued
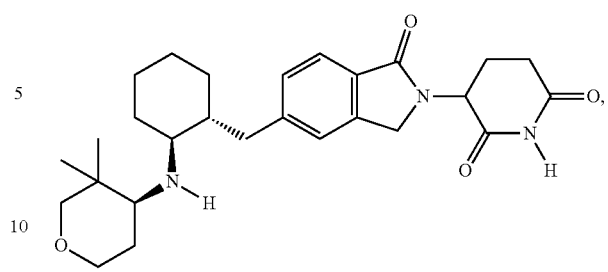
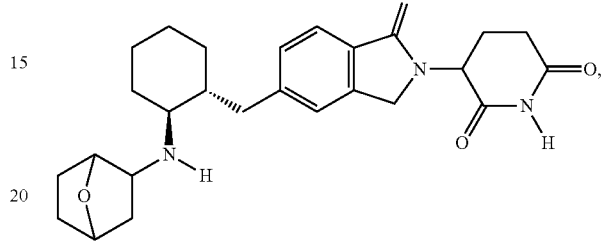
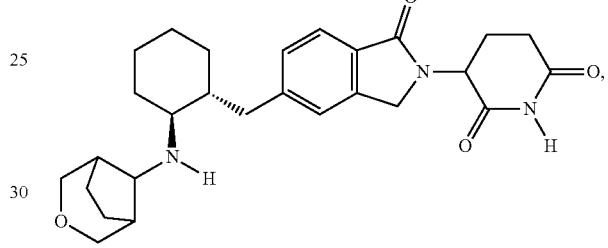
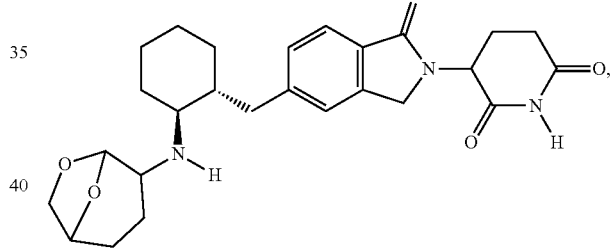
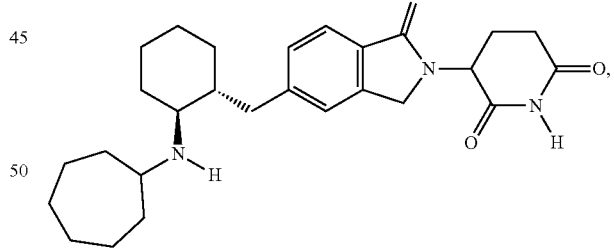
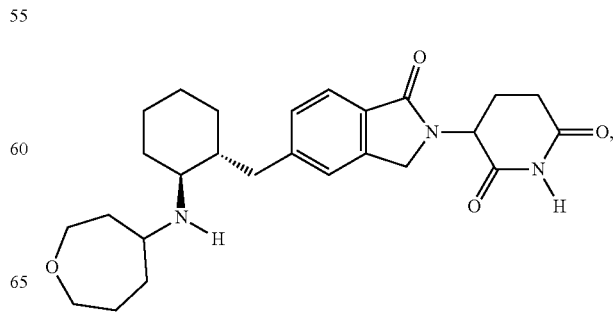

129
-continued
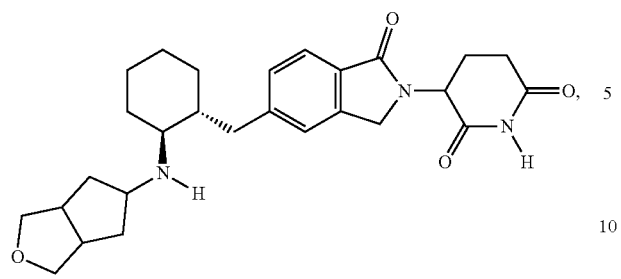
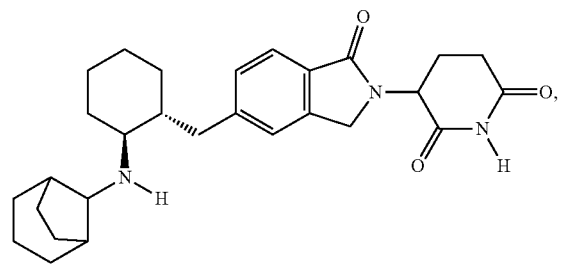
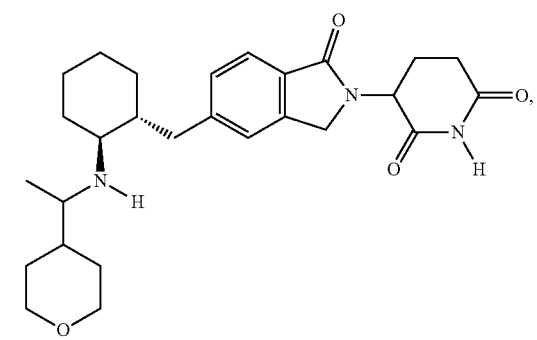
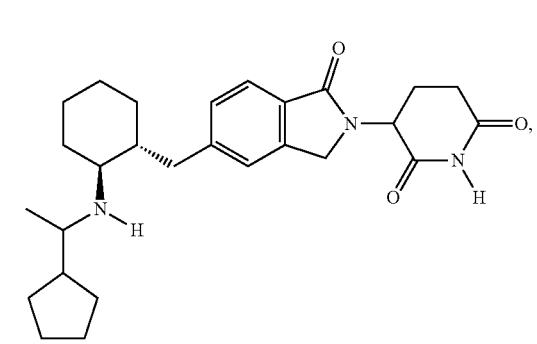
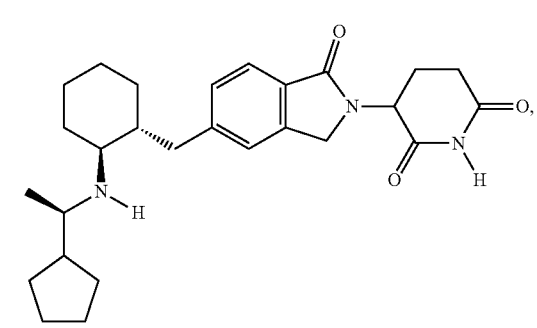
130
-continued
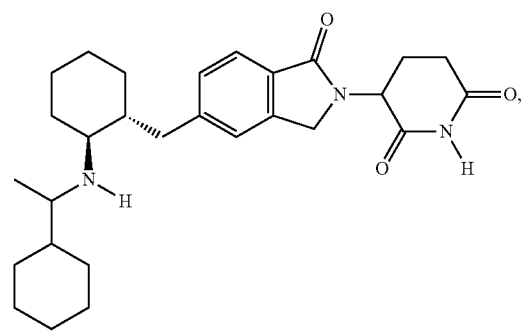
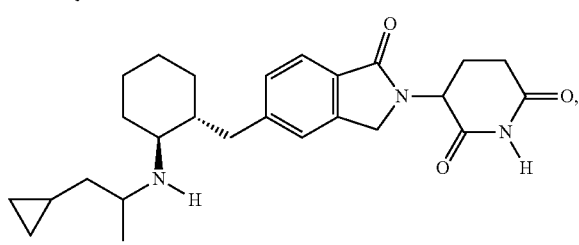
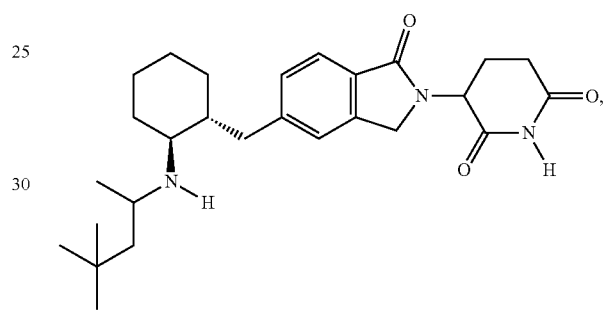
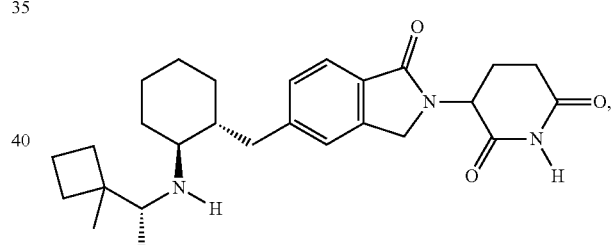
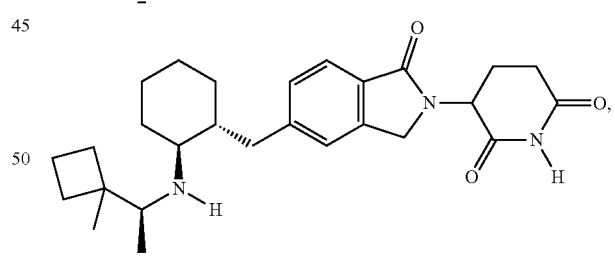
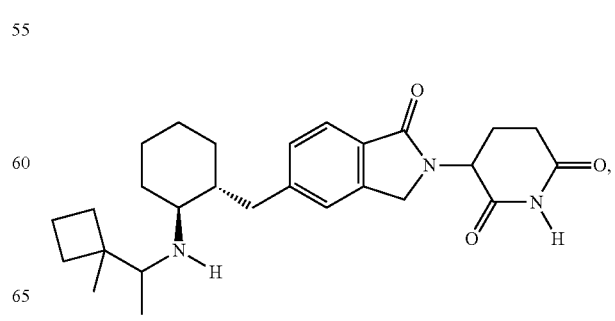

131
-continued
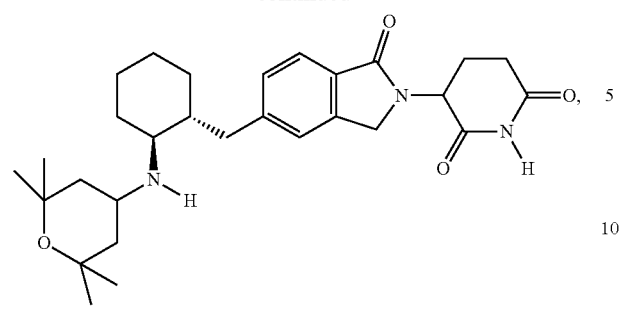
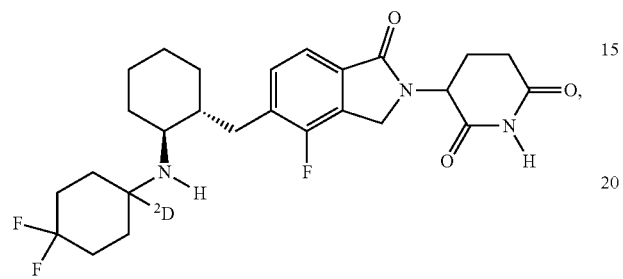
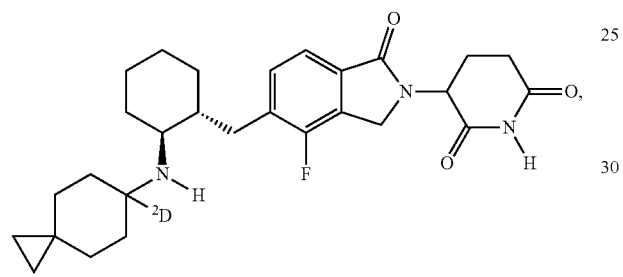
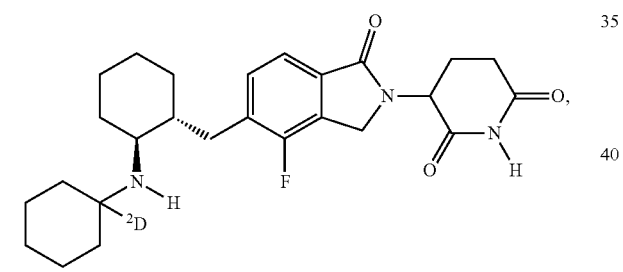
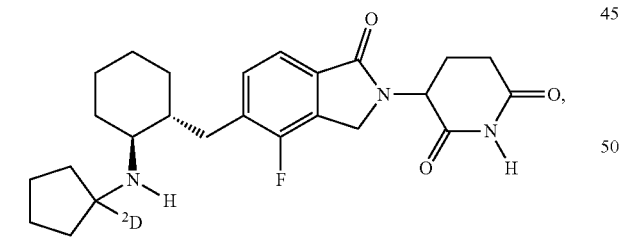
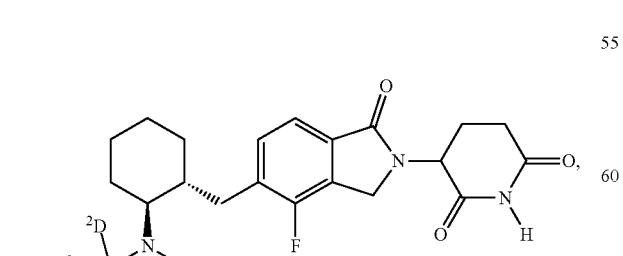
132
-continued
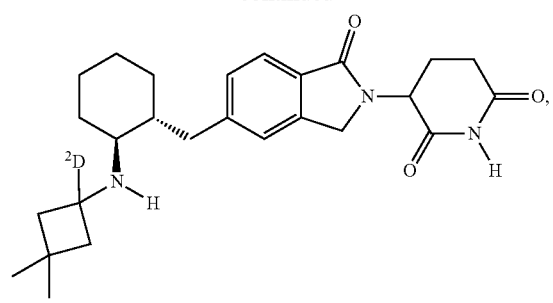
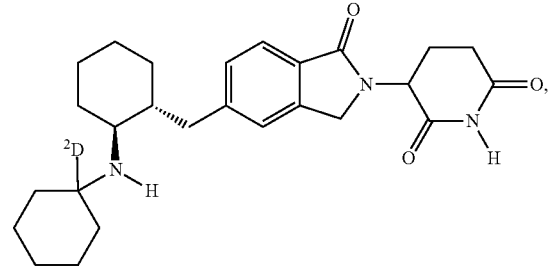
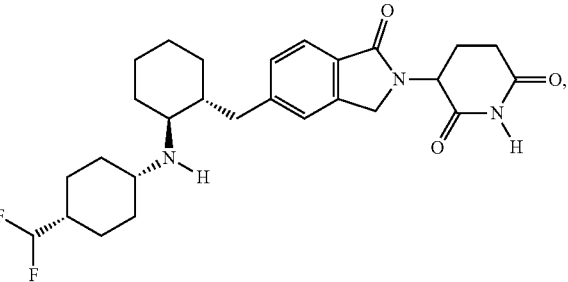
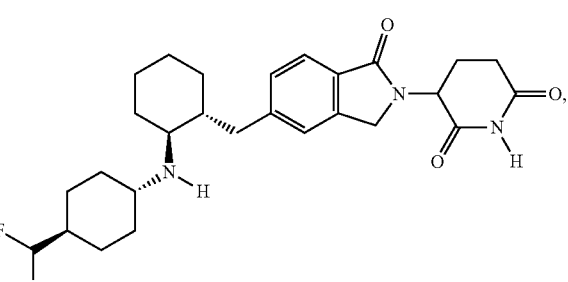
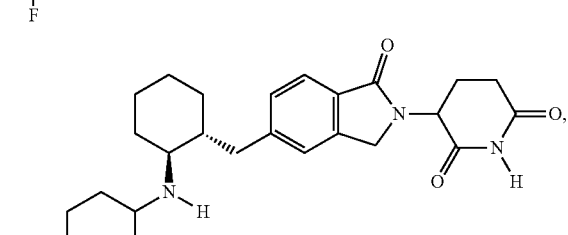
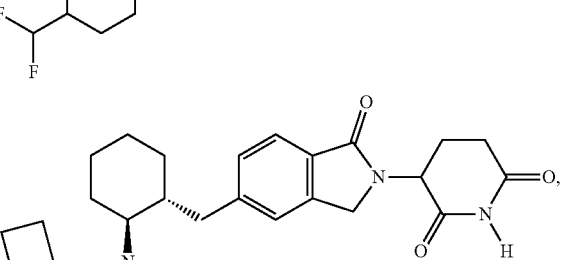

133
-continued
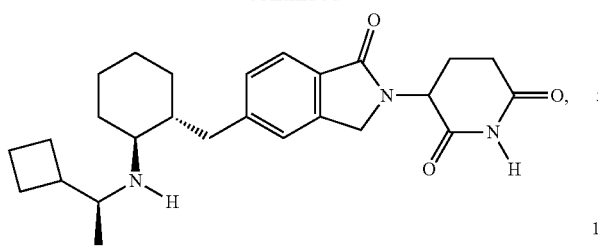
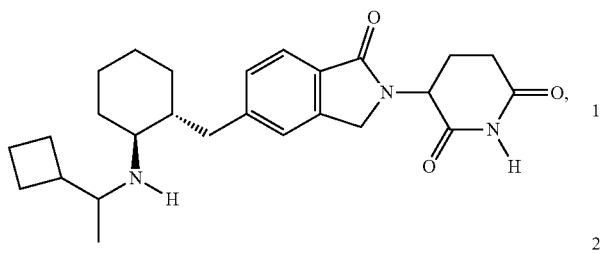
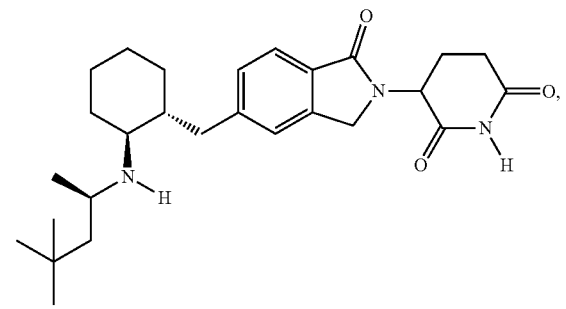
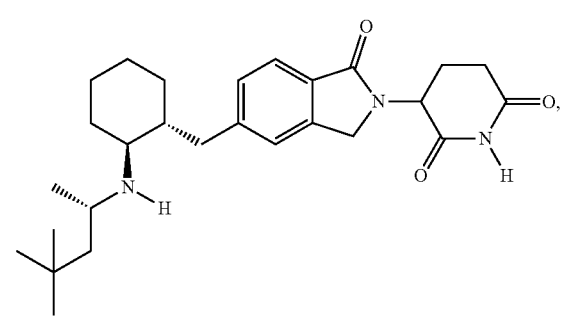
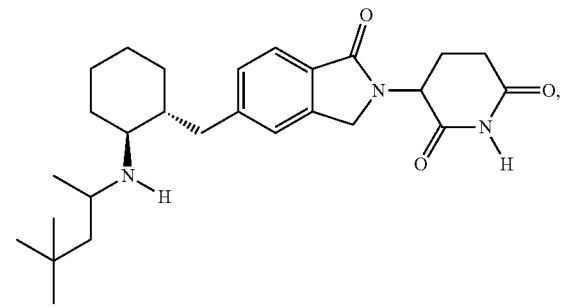
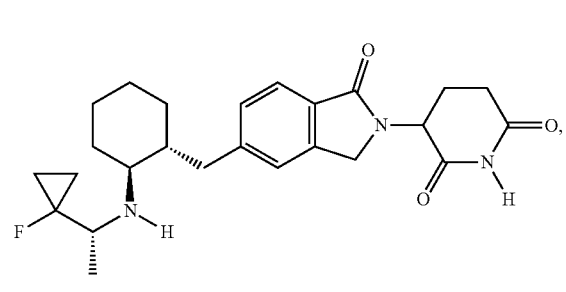
134
-continued
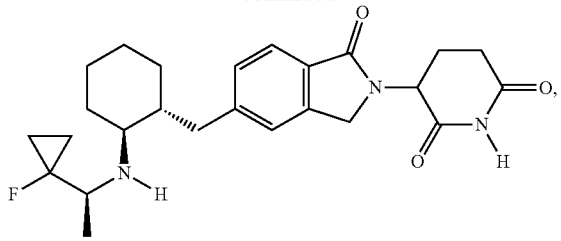
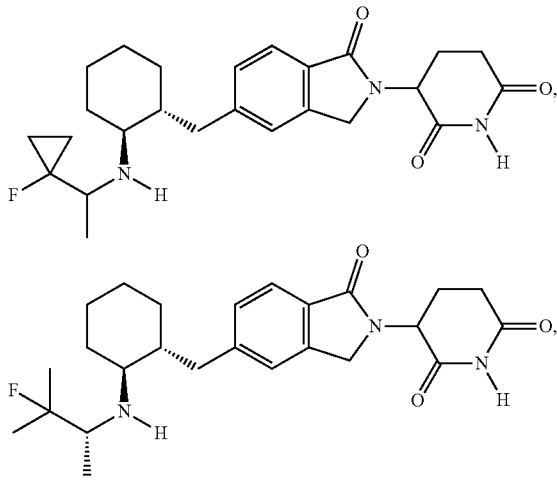
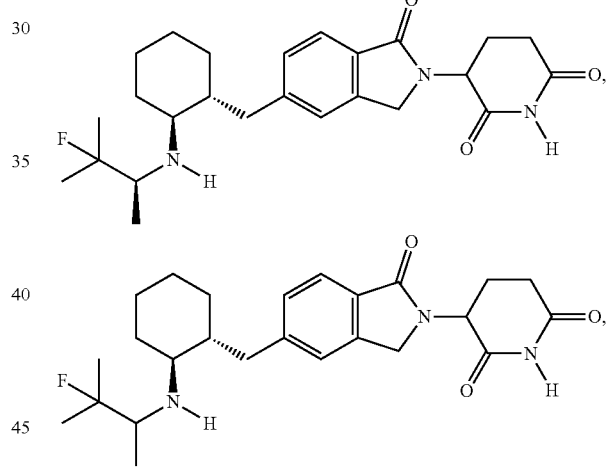
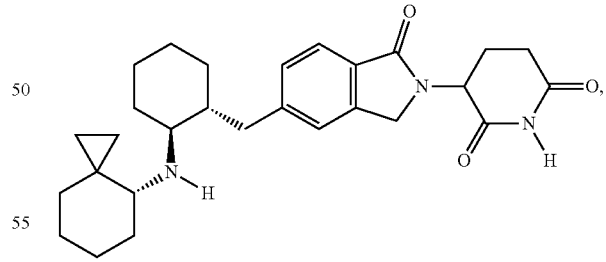
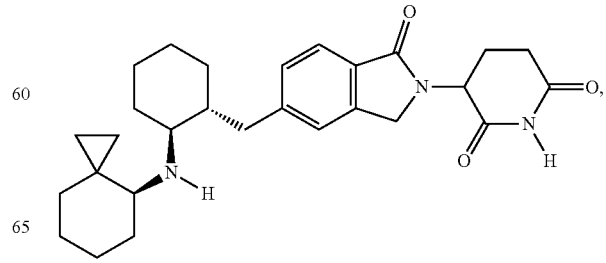

135
-continued
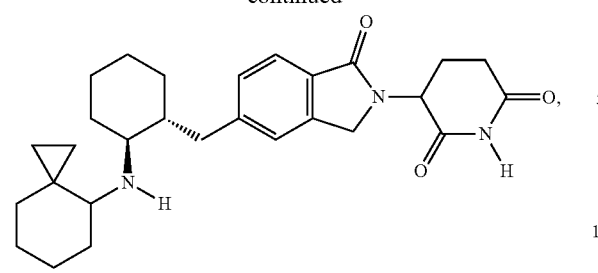
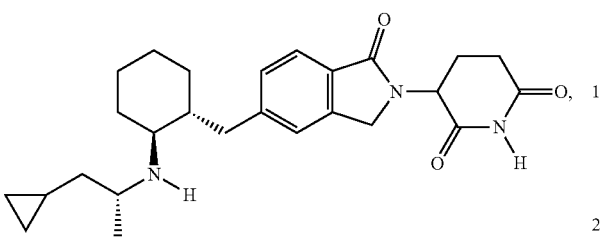
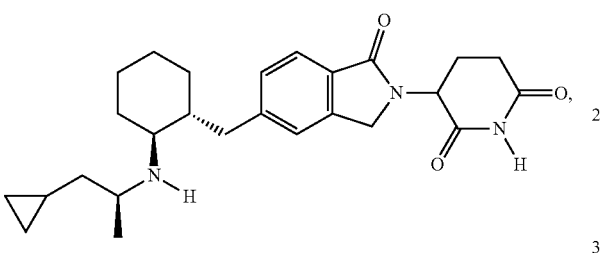
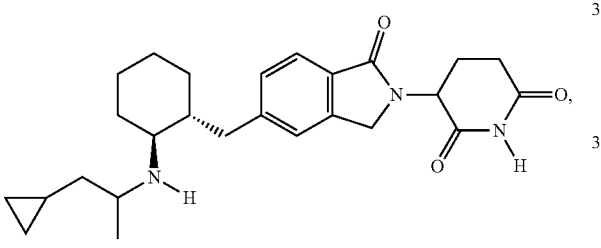
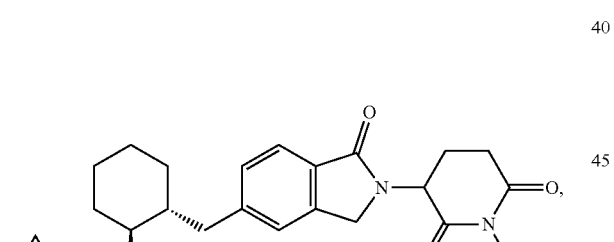
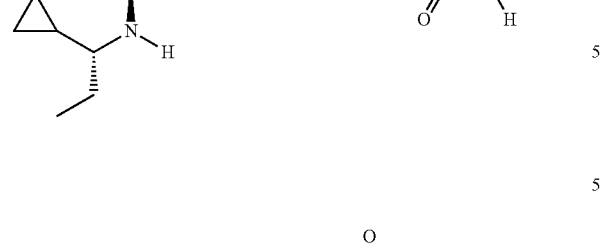
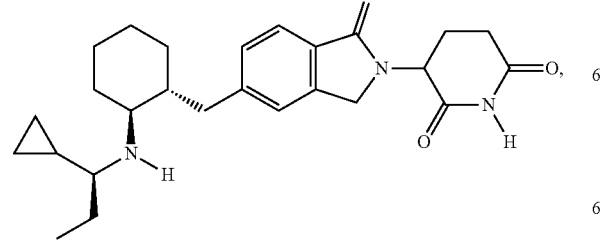
136
-continued
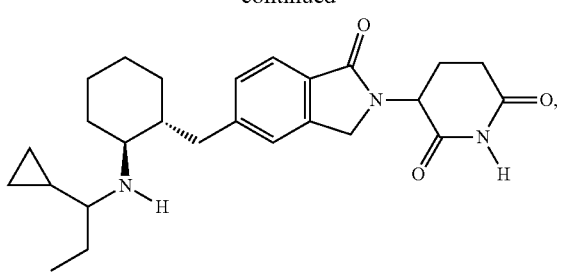
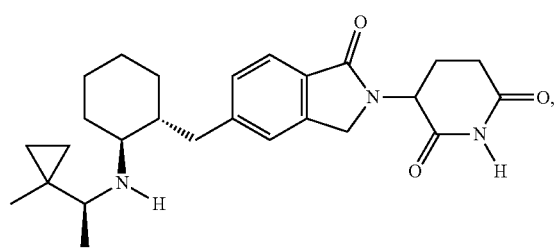
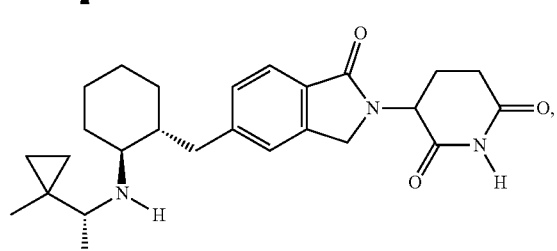
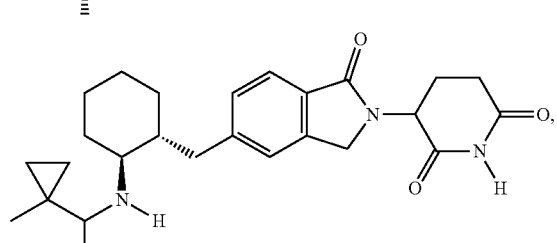
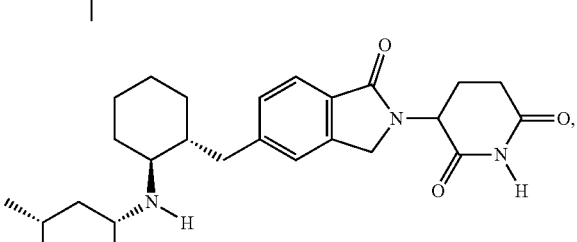
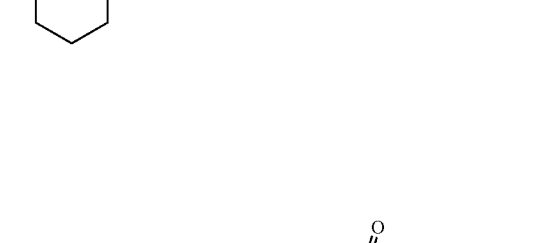
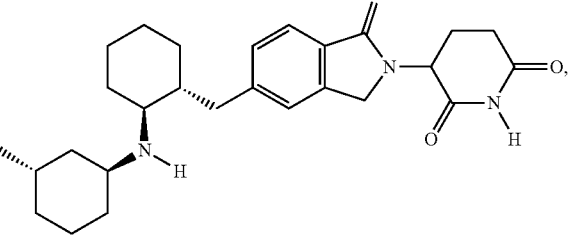

137
-continued
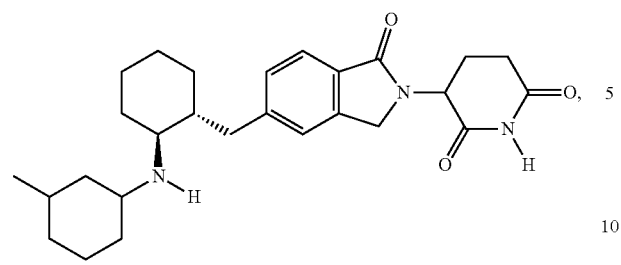

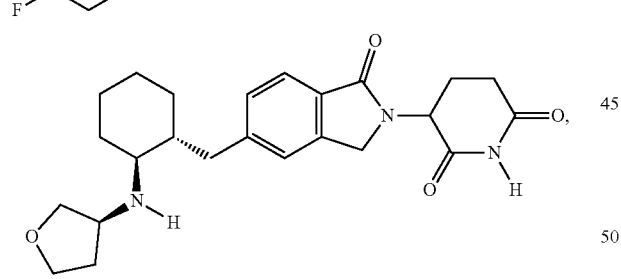
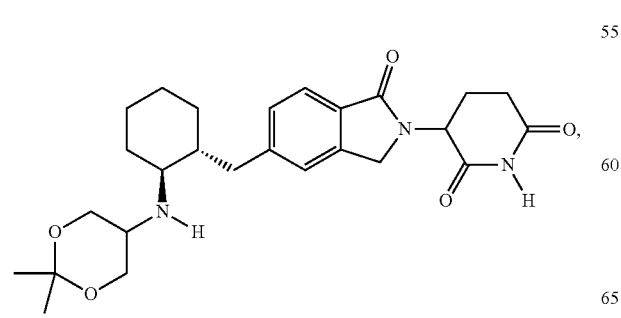
138
-continued
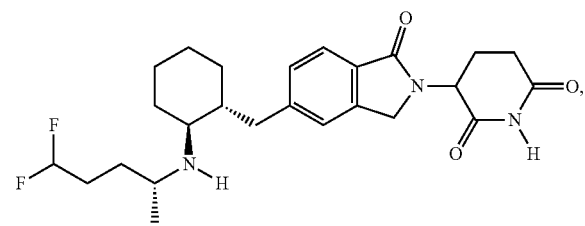
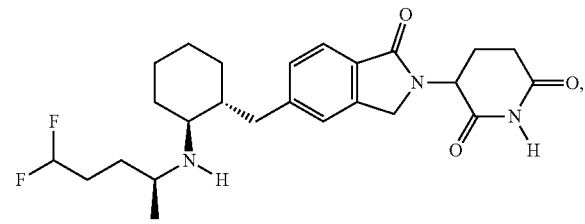
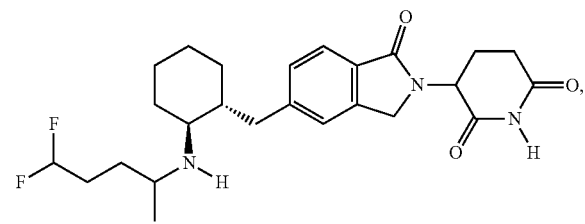
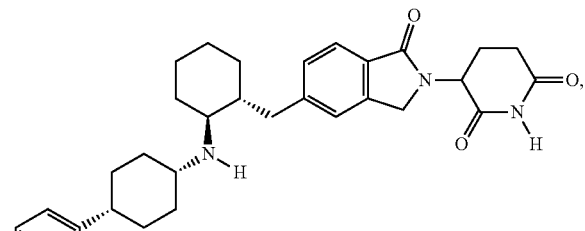
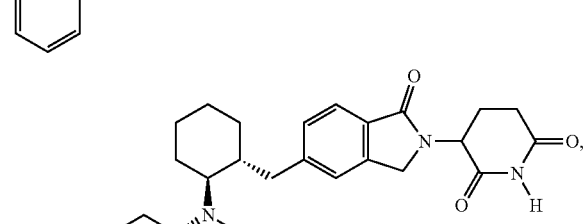
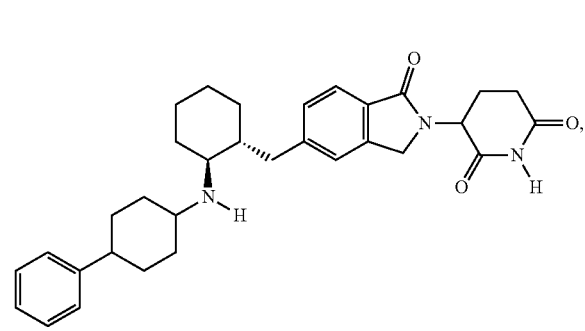

139
-continued
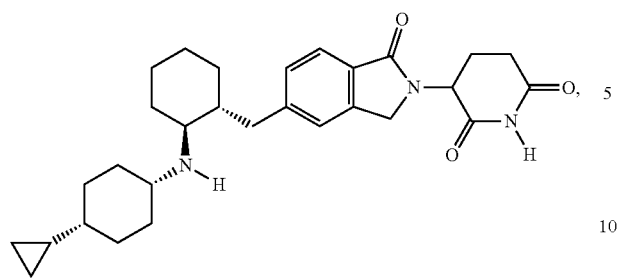
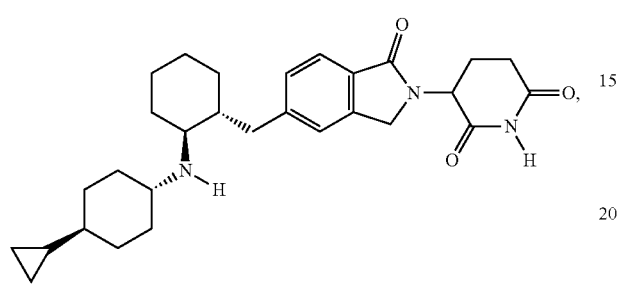
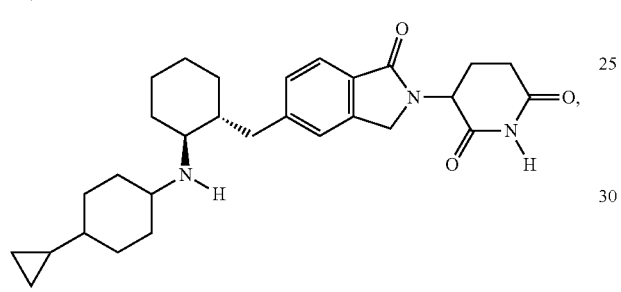
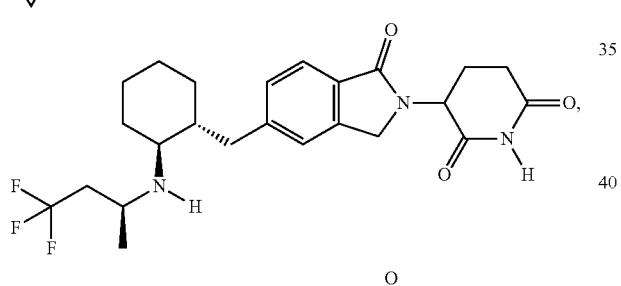
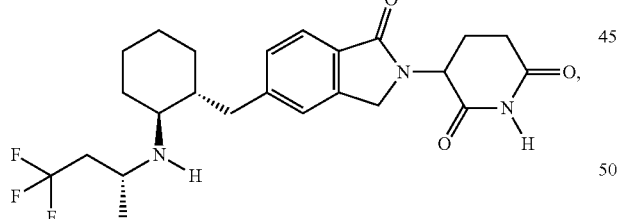
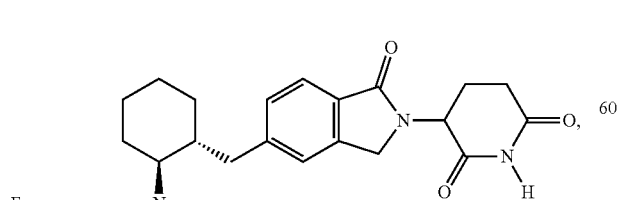
140
-continued
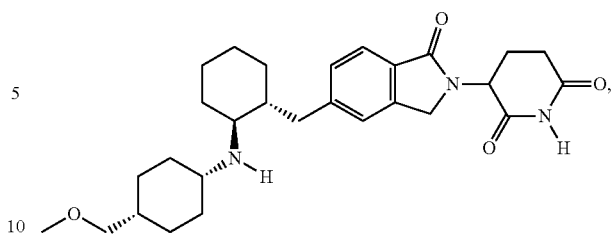
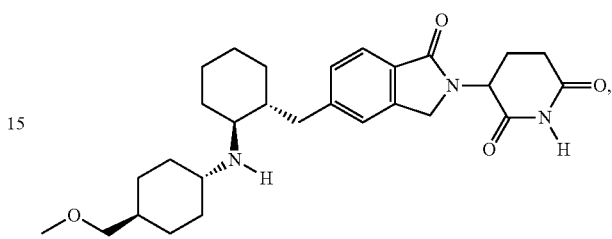
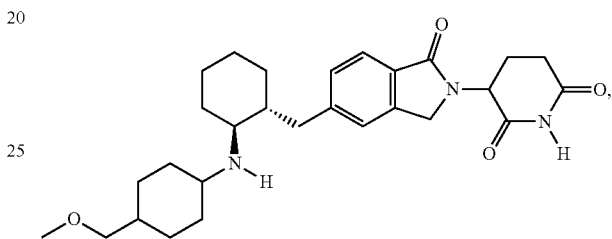
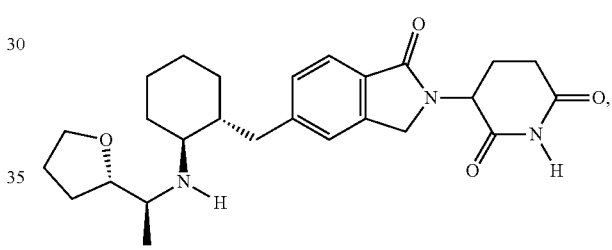
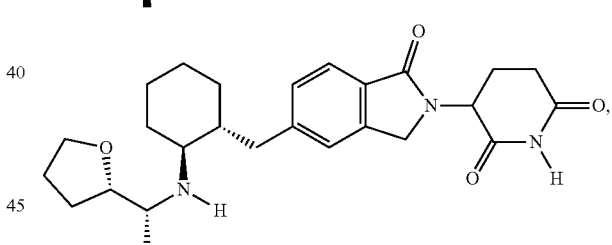
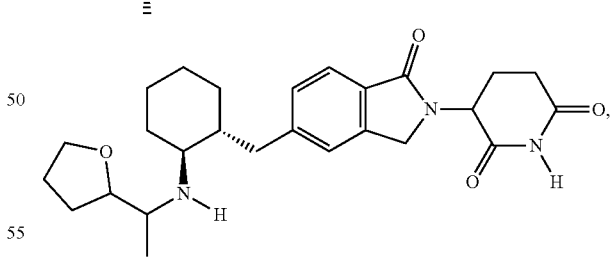
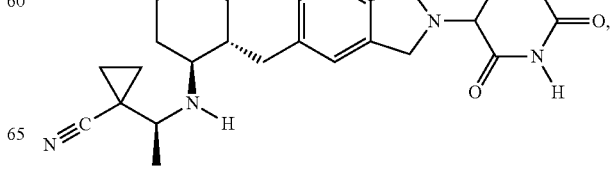

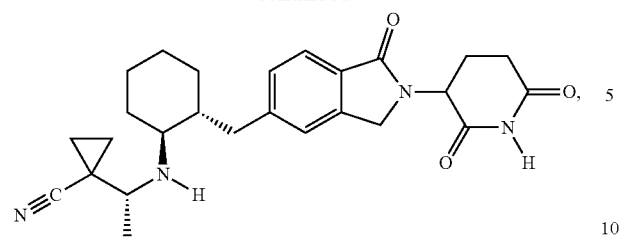
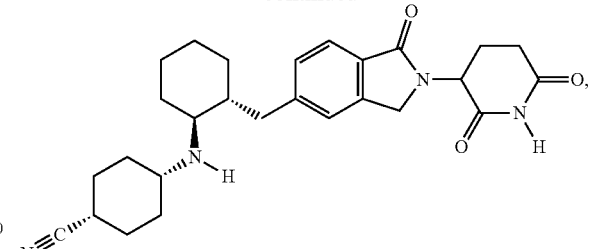
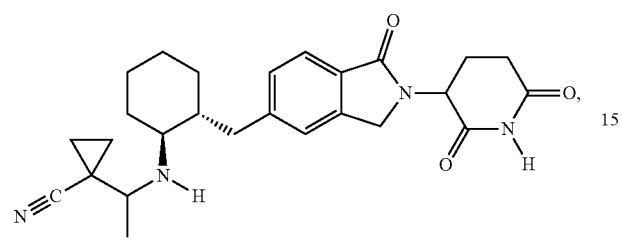
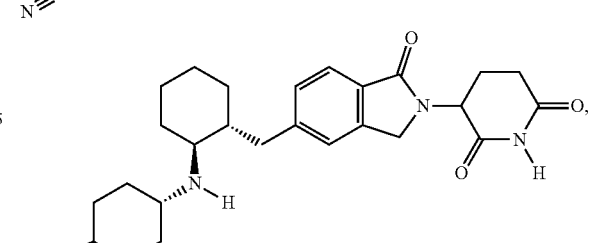
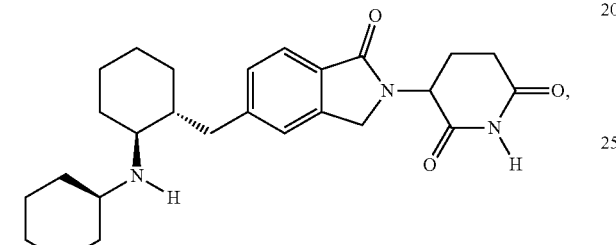
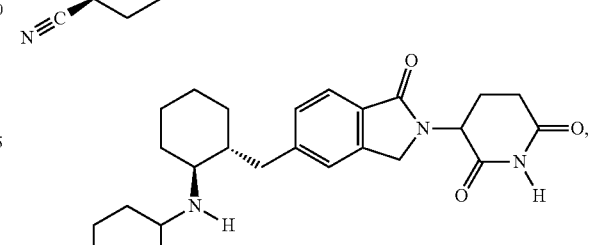
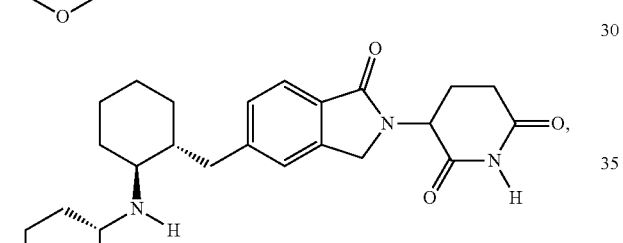
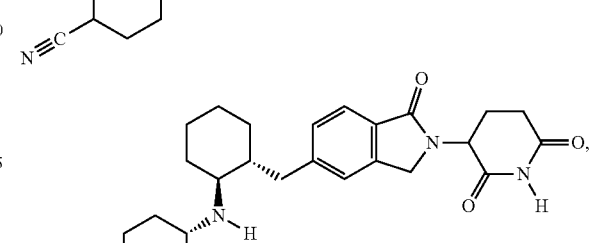
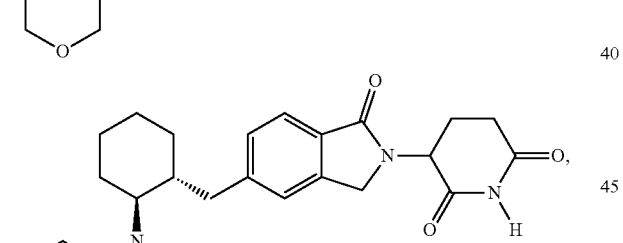
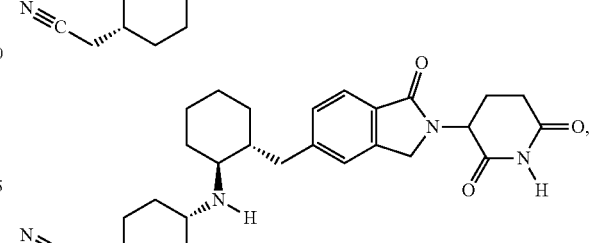
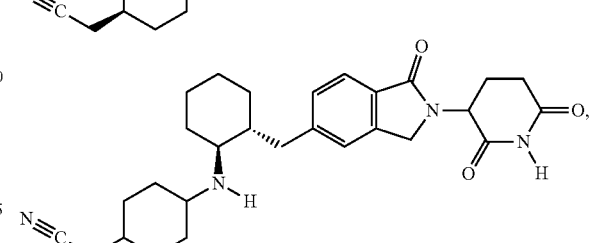
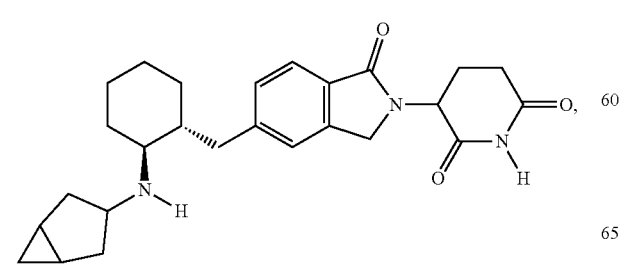
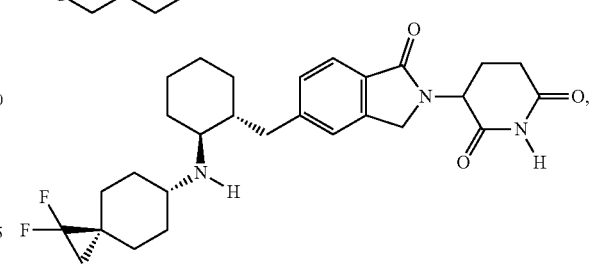

143
-continued
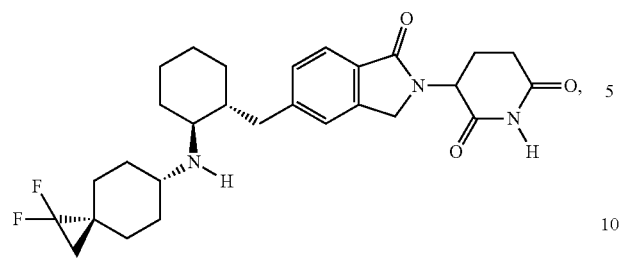
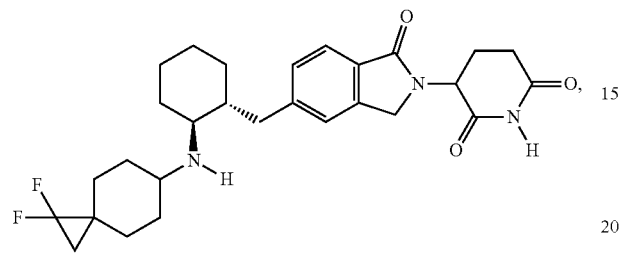
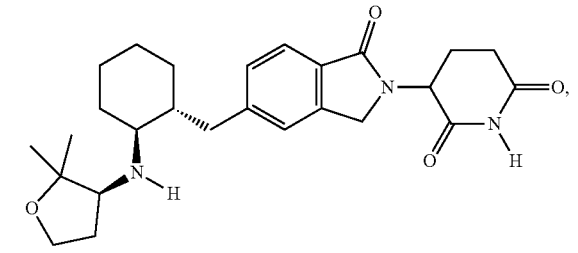
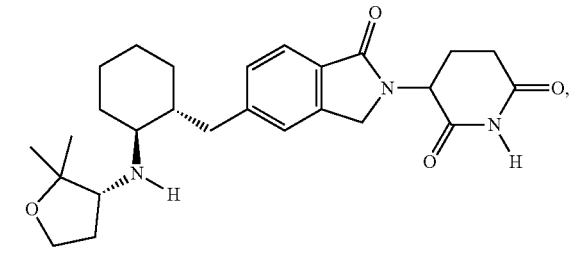
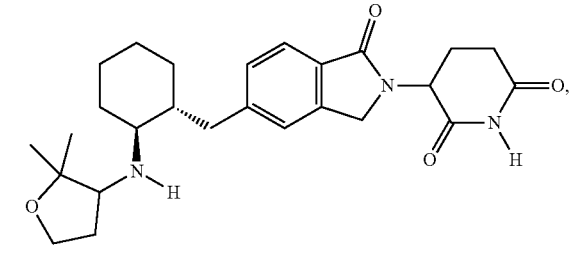
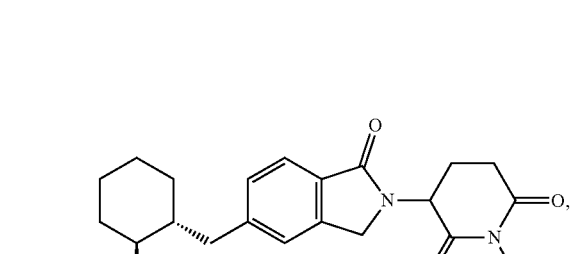
144
-continued
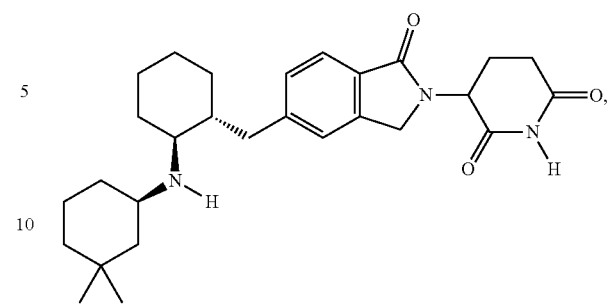
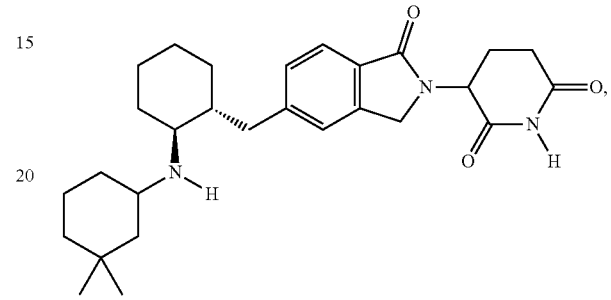
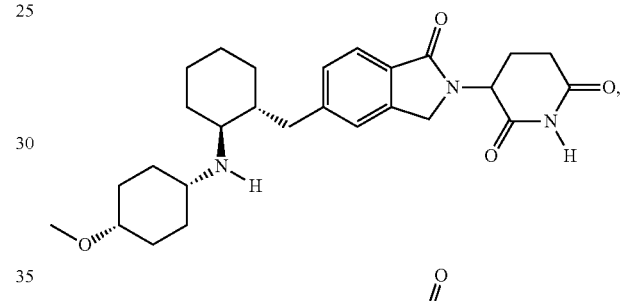
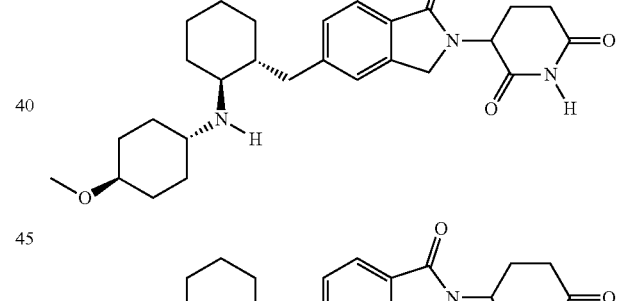
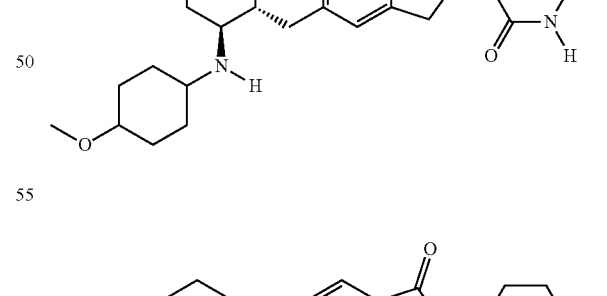
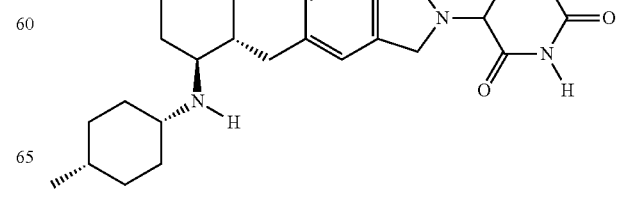

145
-continued
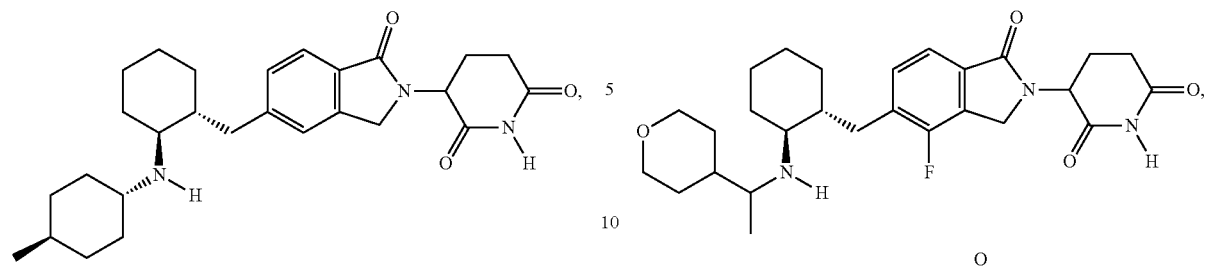
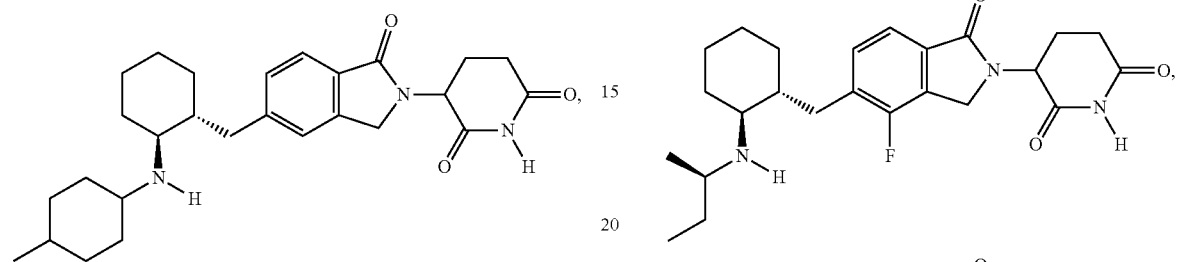
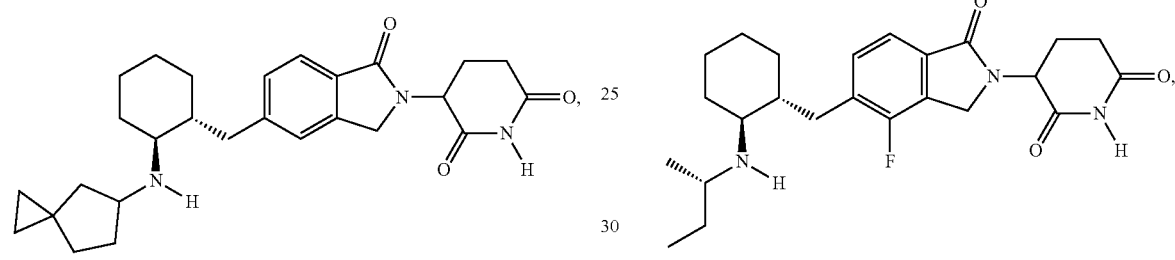
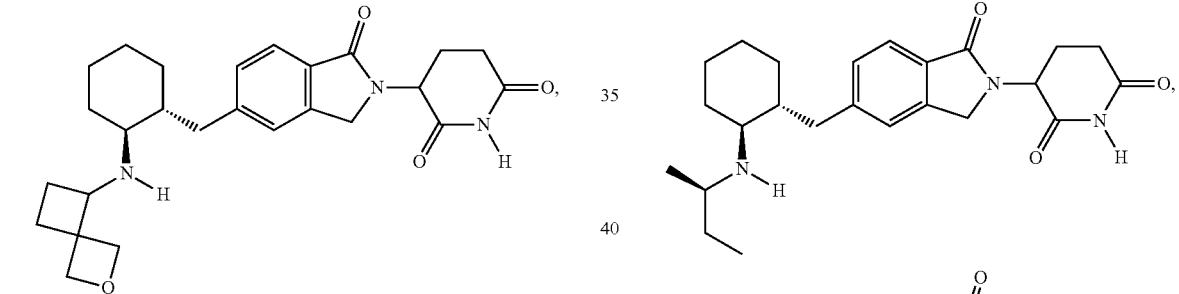
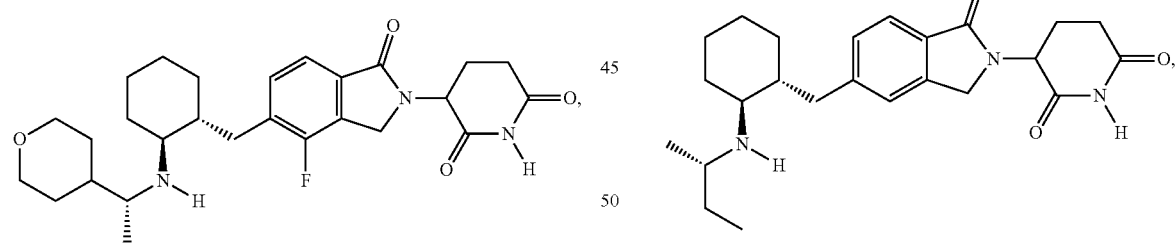
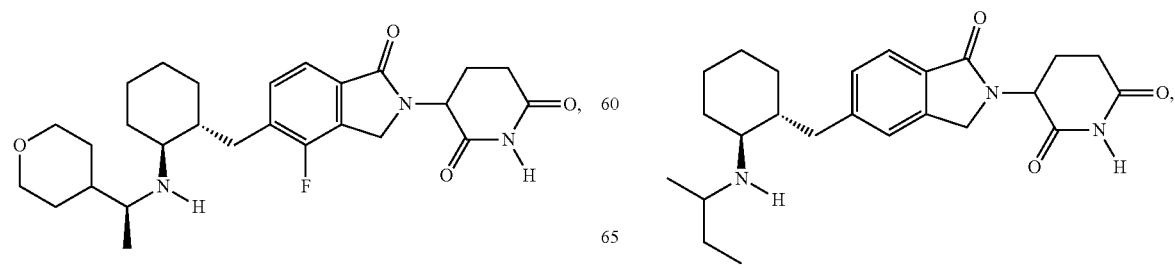
146
-continued
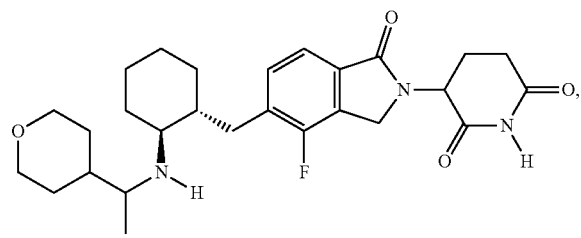
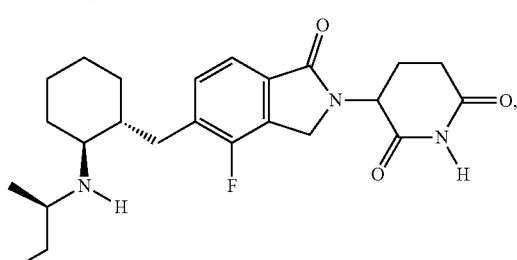
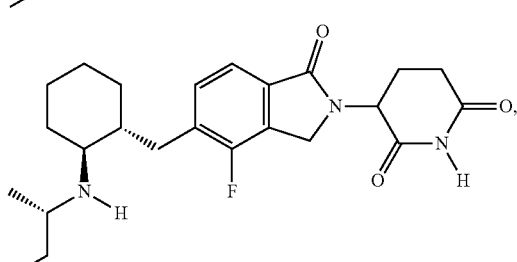
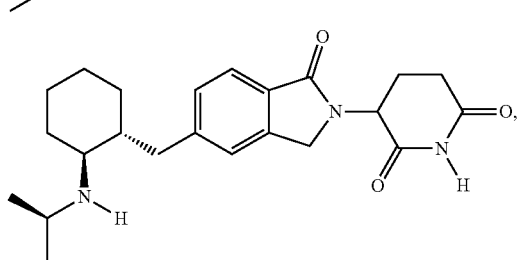
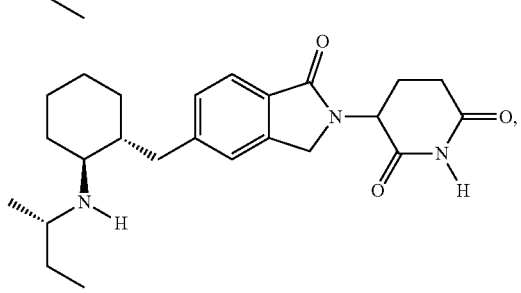

147
-continued
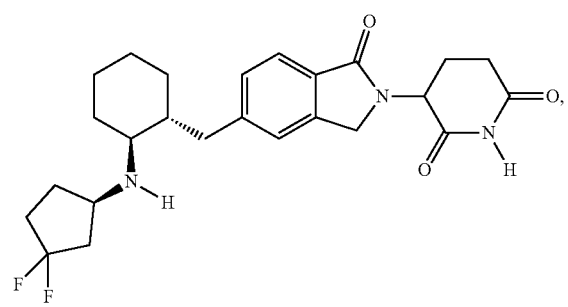
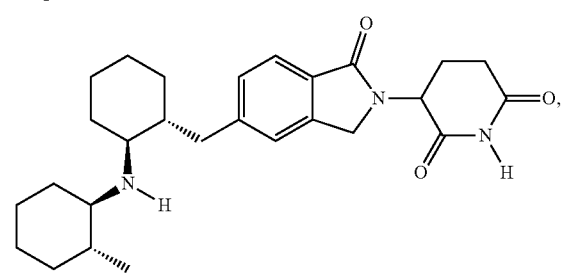
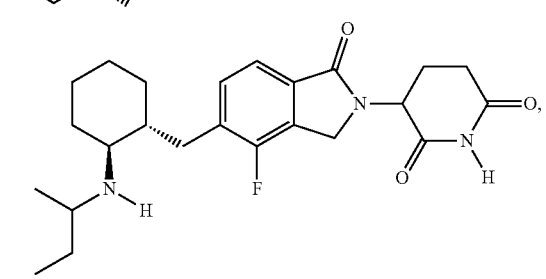
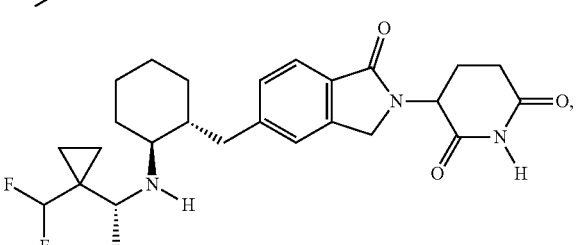
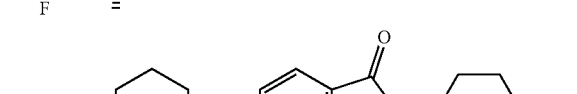
148
-continued
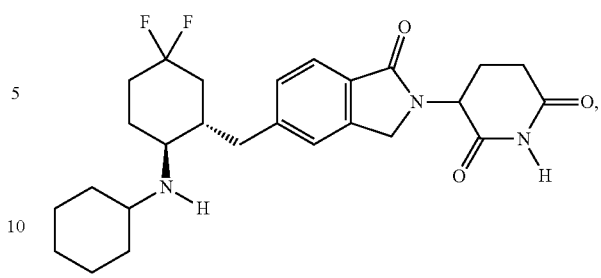
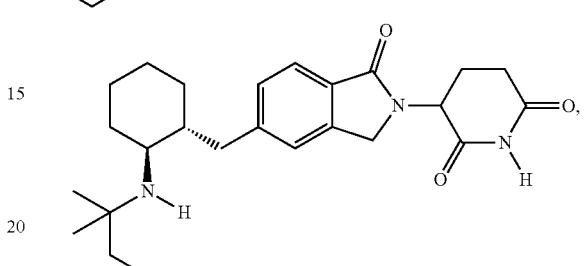
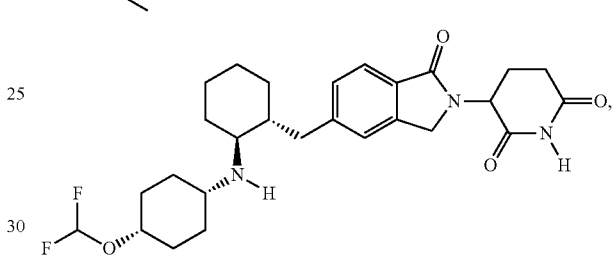
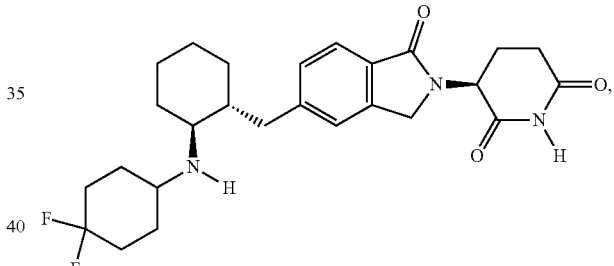
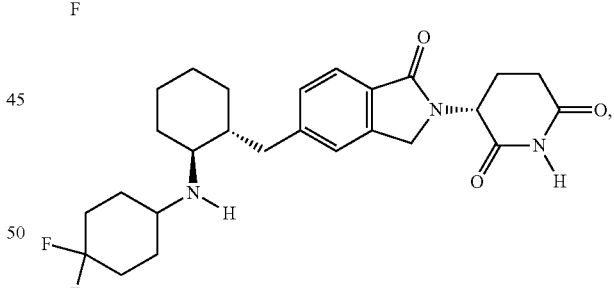

149
-continued
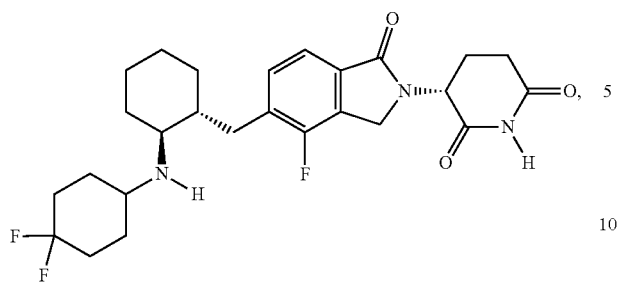
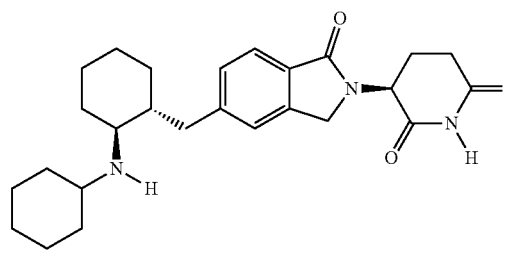
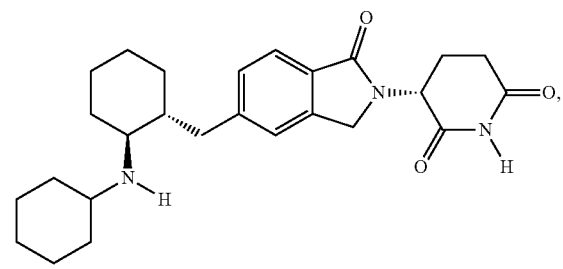
or a pharmaceutically acceptable salt thereof.
In some embodiments, the compound of Formula (I) or (IId), or pharmaceutically acceptable salt thereof, is
150
-continued
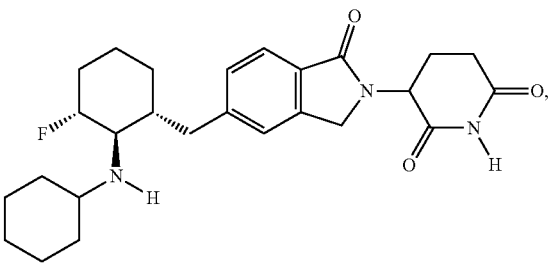, or
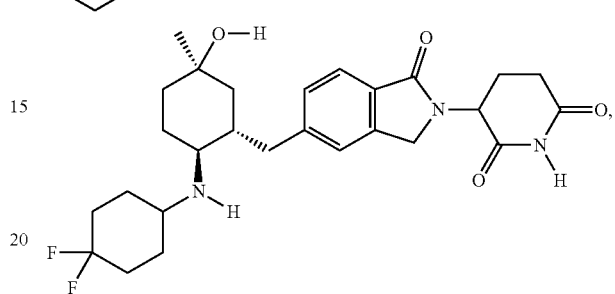
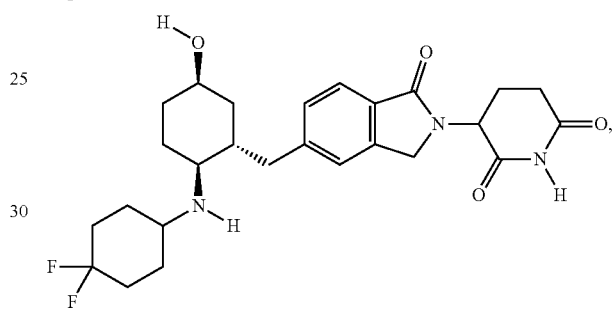
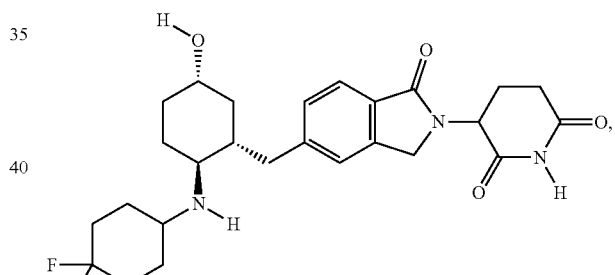
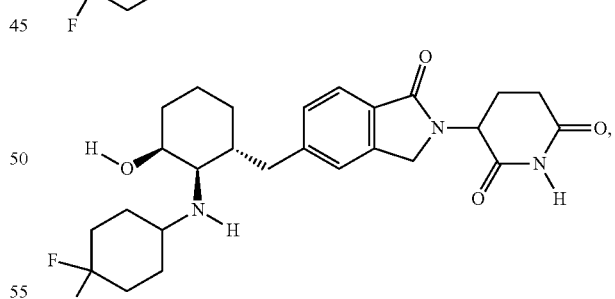
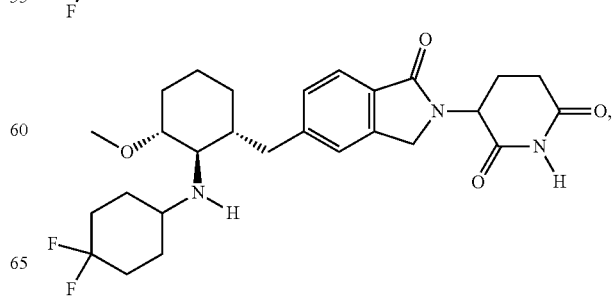

-continued
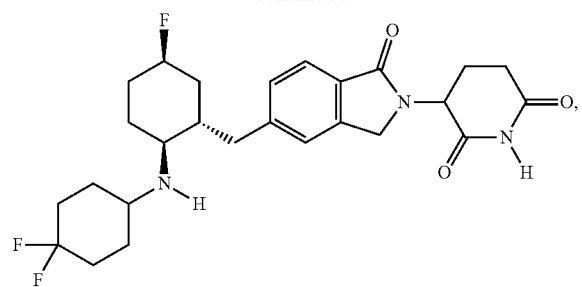
or a pharmaceutically acceptable salt thereof.
In some embodiments the compound of Formula (I), (IIk), or (IIIa-1), or pharmaceutically acceptable salt thereof, is
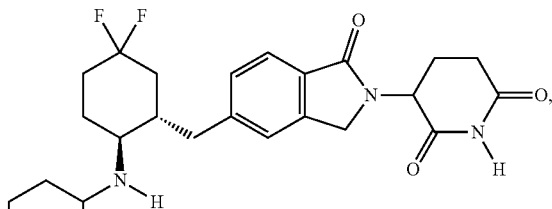

153
-continued
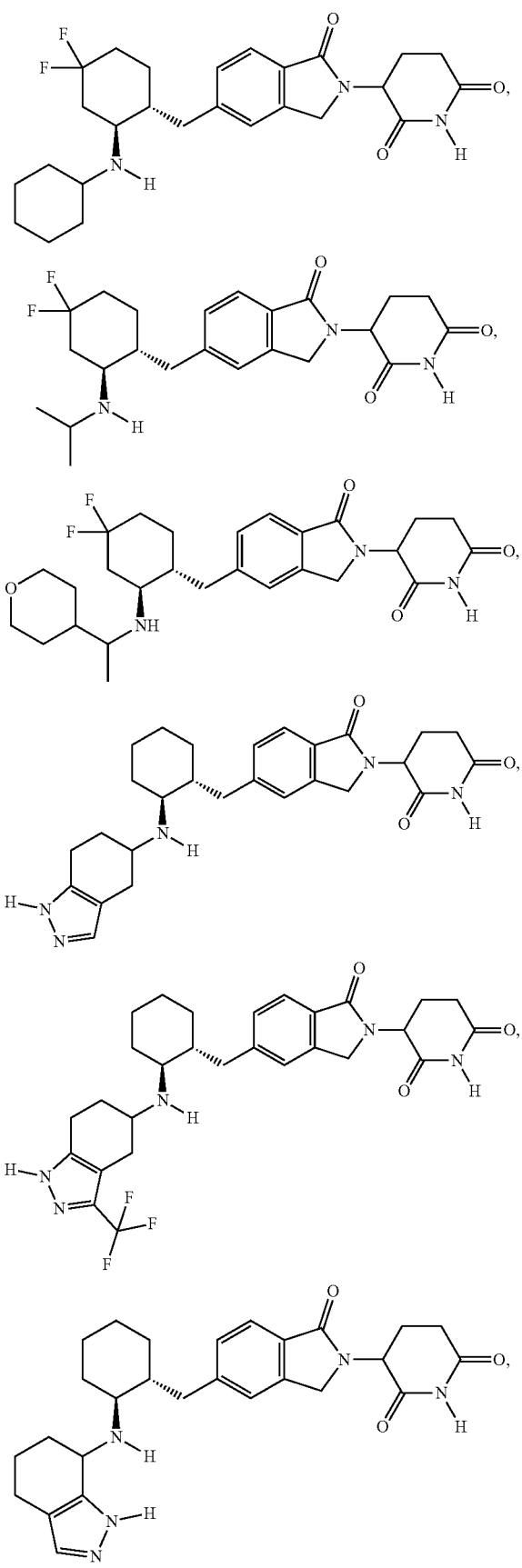
154
-continued
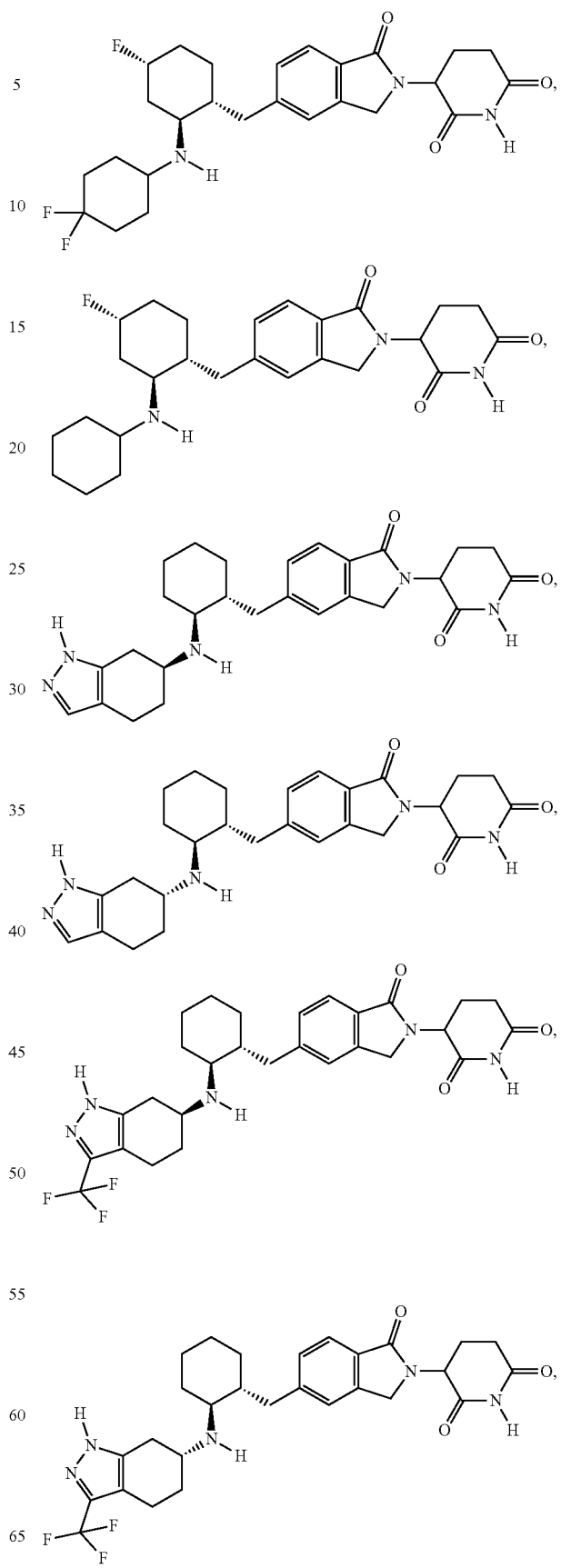

155
-continued
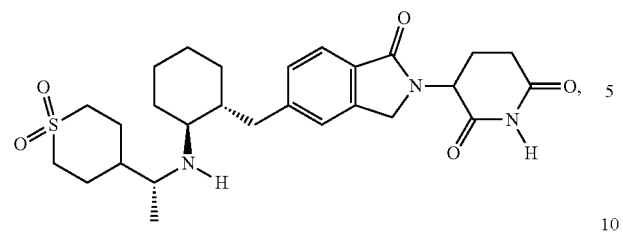
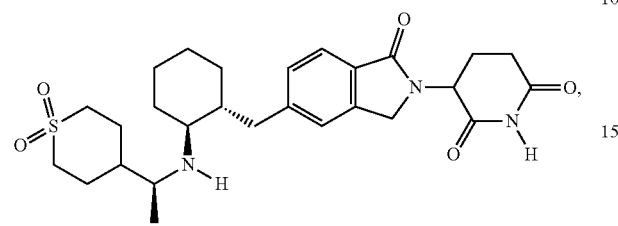
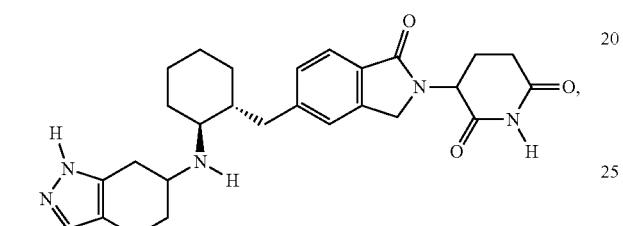
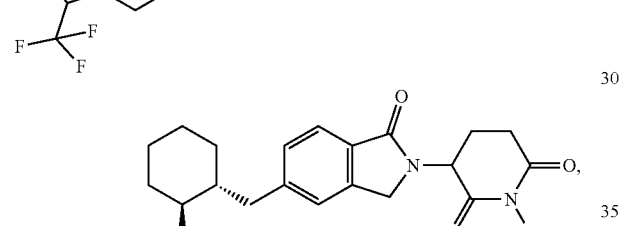
156
-continued
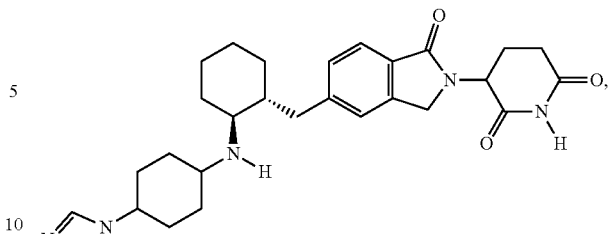
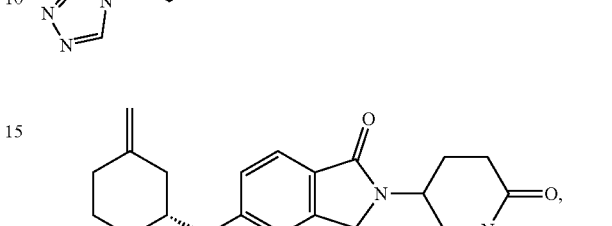
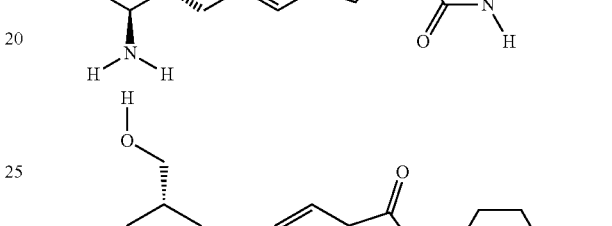
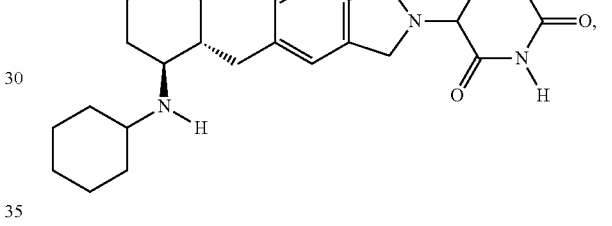
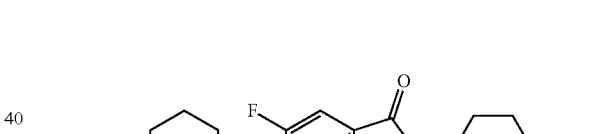
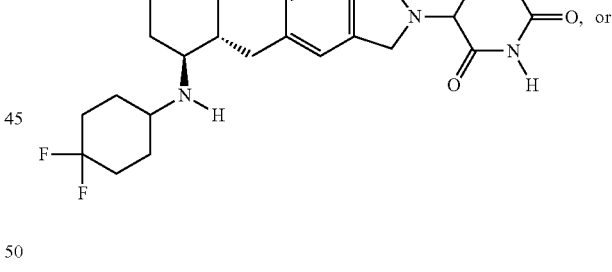
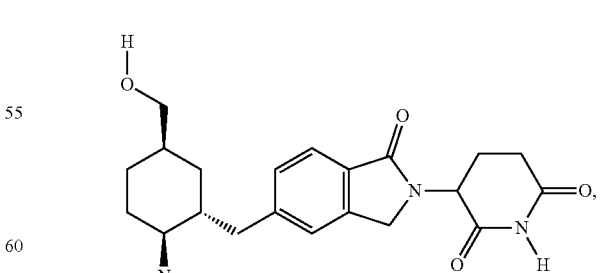
or a pharmaceutically acceptable salt thereof.

In some embodiments the compound of Formula (I) or (IIa), or pharmaceutically acceptable salt thereof, is
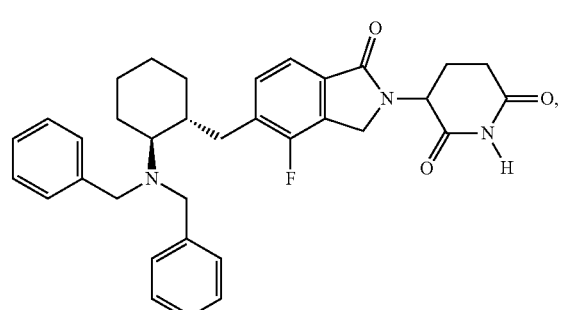
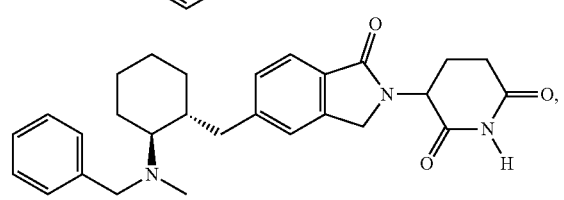
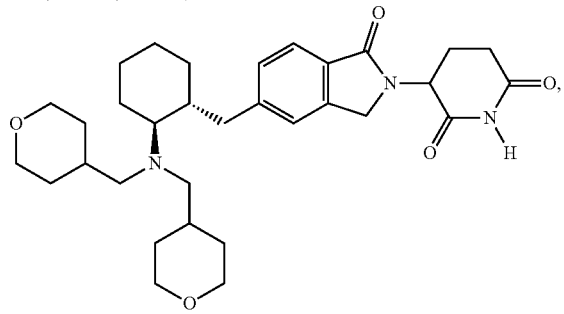
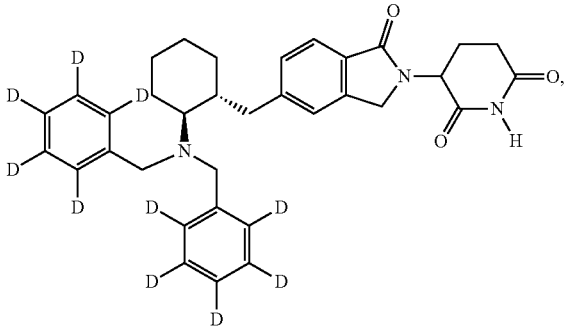
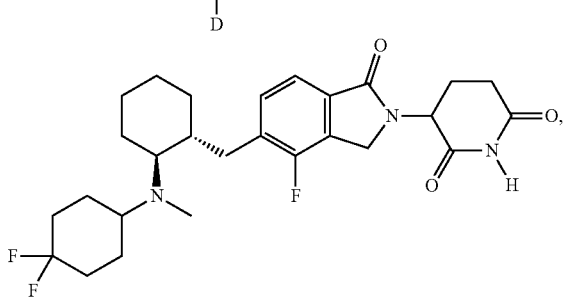
, or
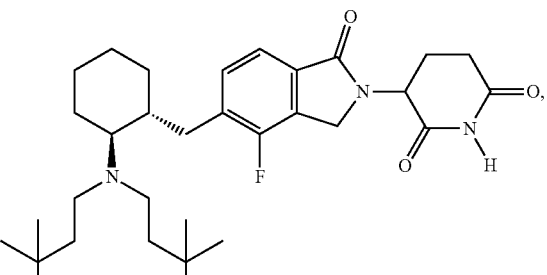
or a pharmaceutically acceptable salt thereof.
In some embodiments the compound of Formula (I) or (IIa), or pharmaceutically acceptable salt thereof, is
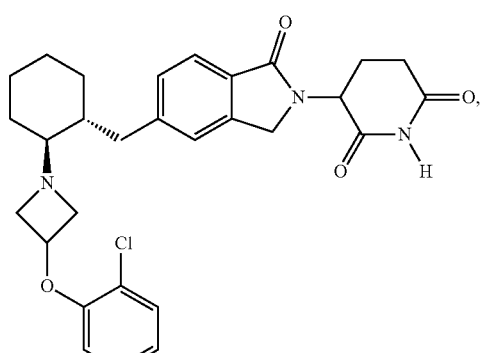
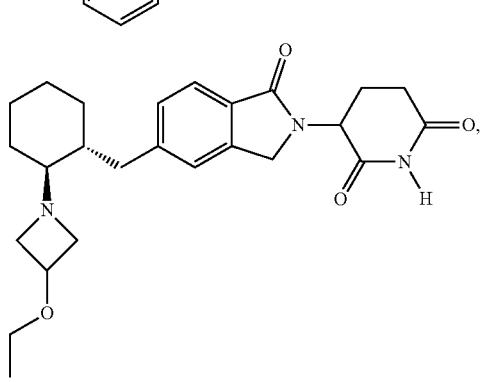
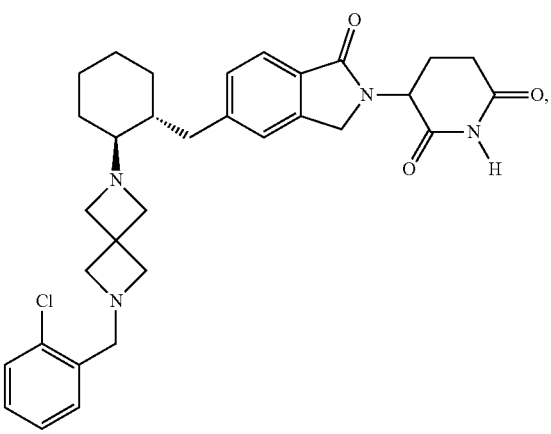

-continued

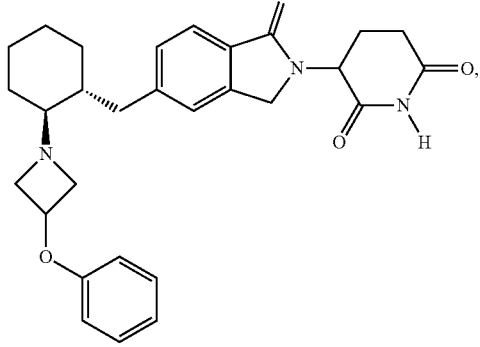

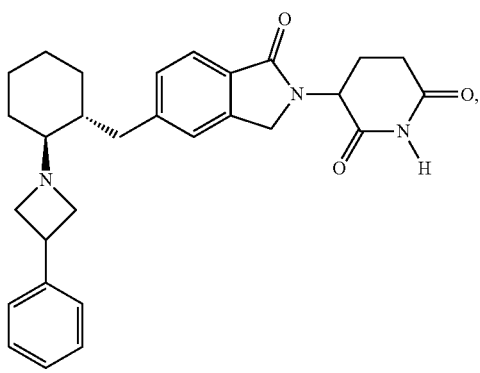

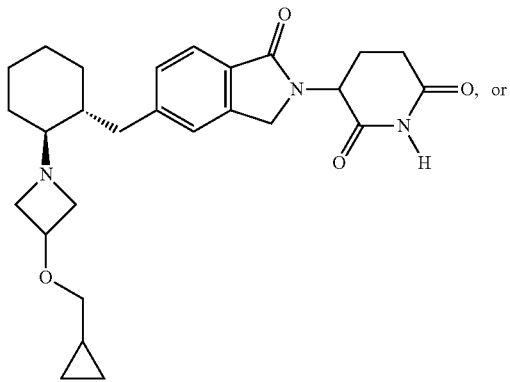

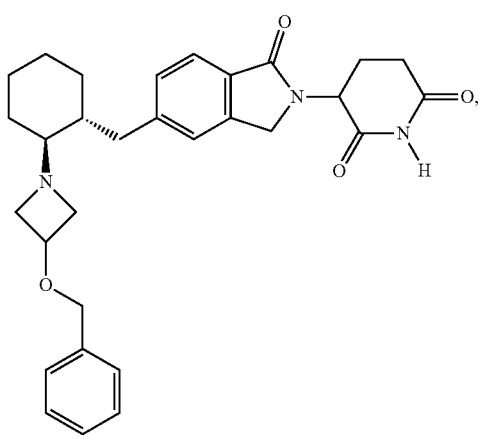

or a pharmaceutically acceptable salt thereof.

In some embodiments the compound of Formula (I) or (IIb), or pharmaceutically acceptable salt thereof, is

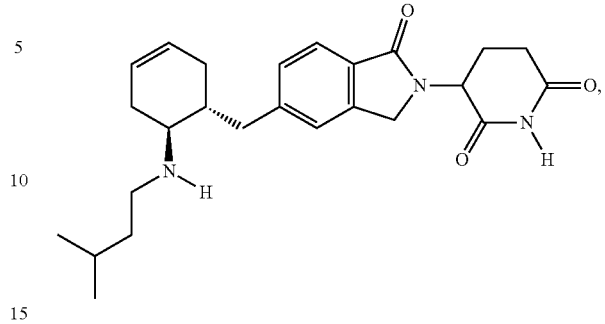

or a pharmaceutically acceptable salt thereof.

In some embodiments the compound of Formula (I) or (IIc), or pharmaceutically acceptable salt thereof, is

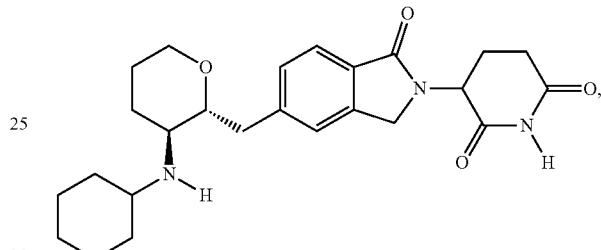

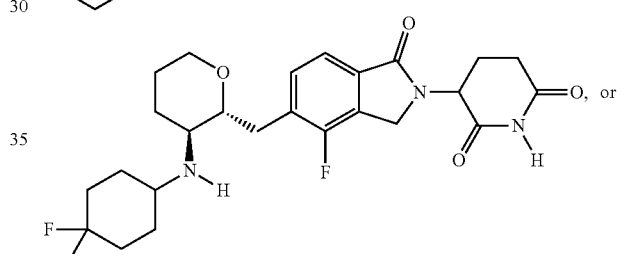

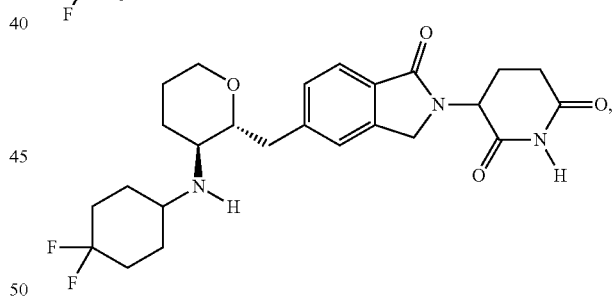

or a pharmaceutically acceptable salt thereof.

In some embodiments the compound of Formula (I) or (IIc), or pharmaceutically acceptable salt thereof, is

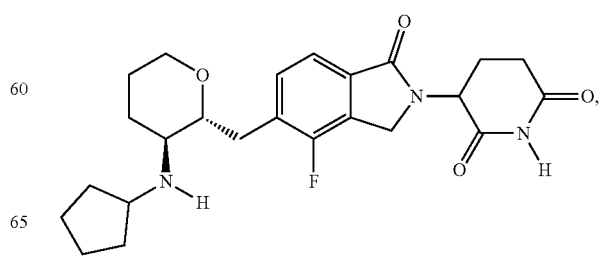

-continued
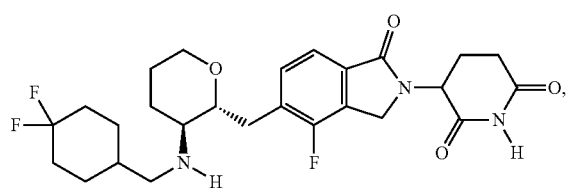
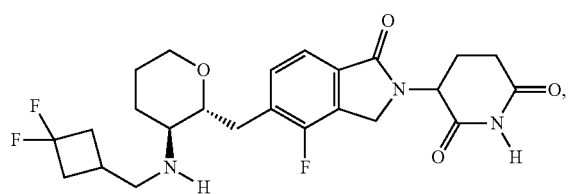
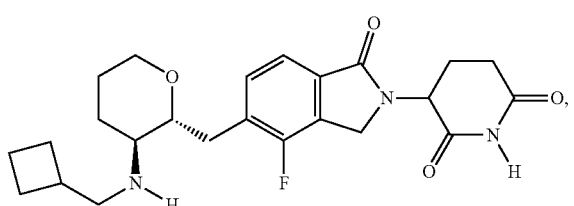
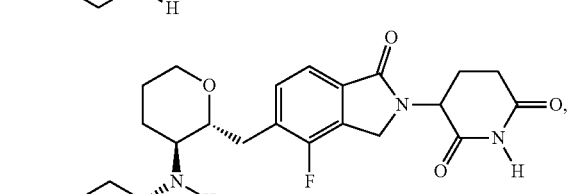

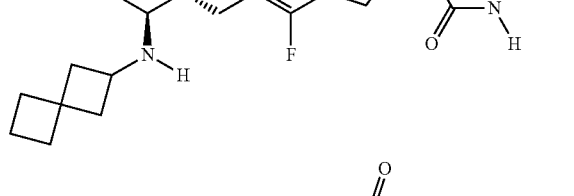
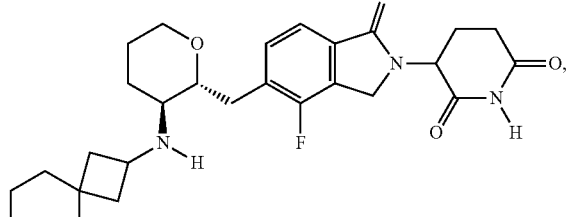
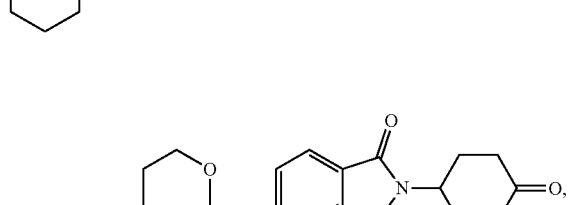
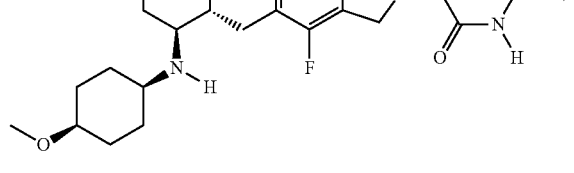
-continued
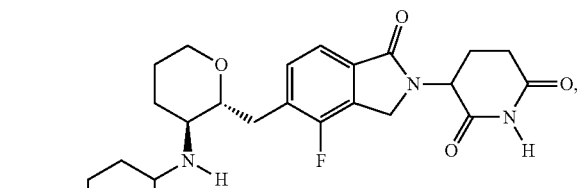
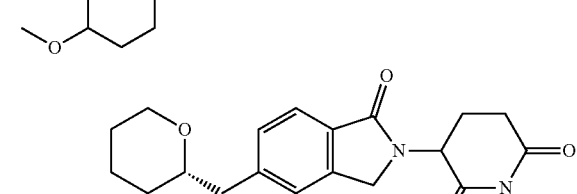
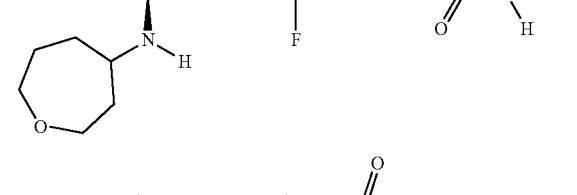
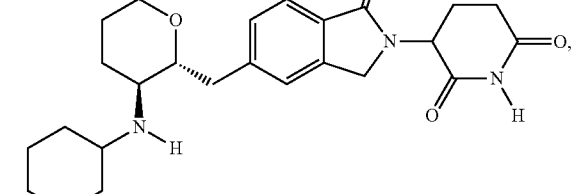
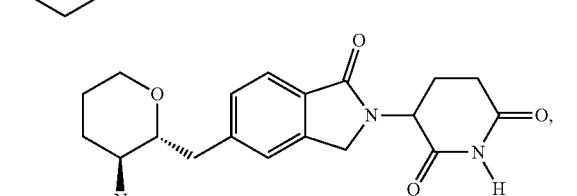
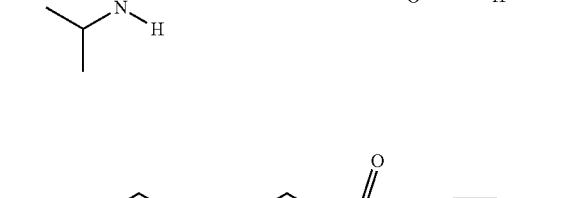
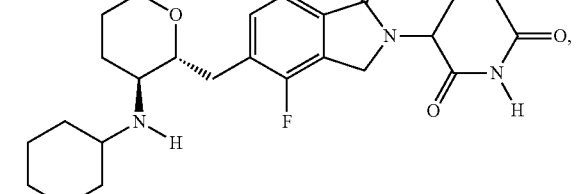
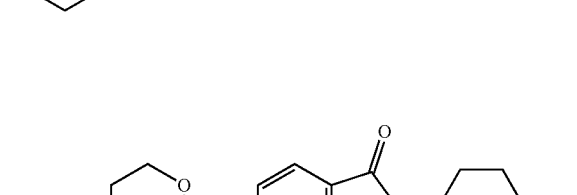
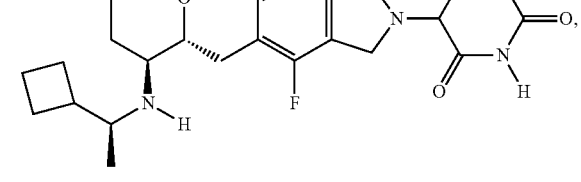

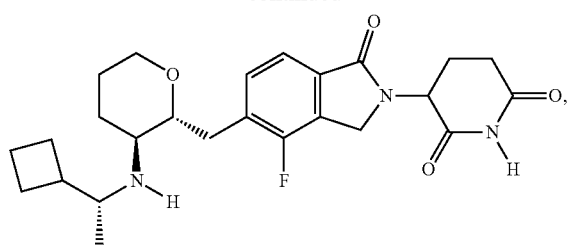
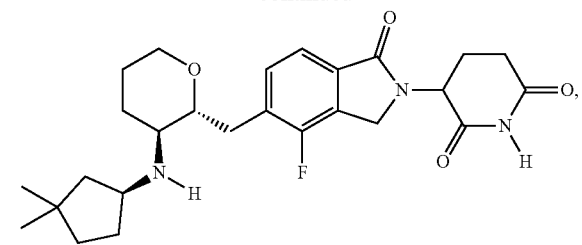
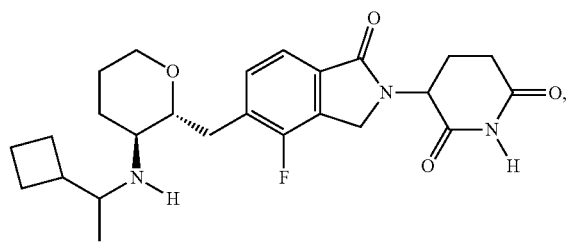
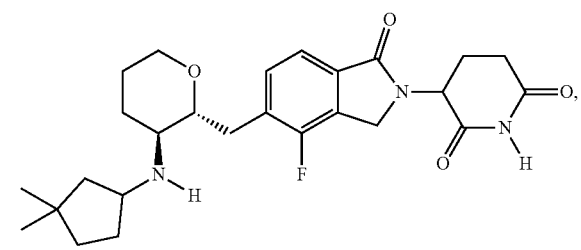
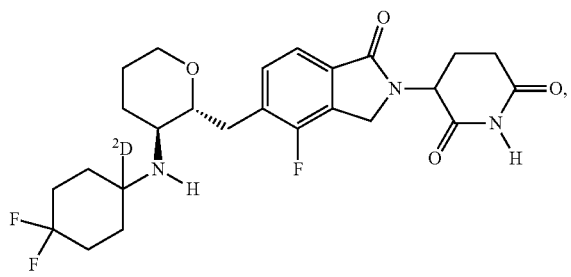
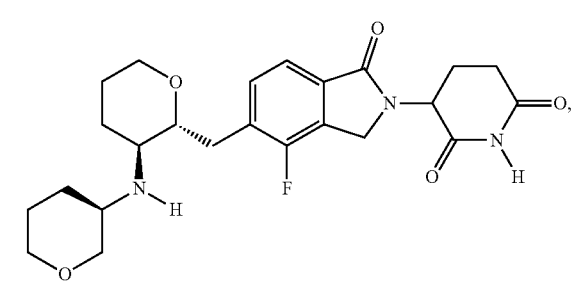
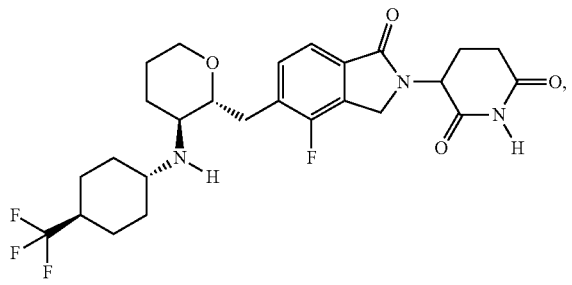
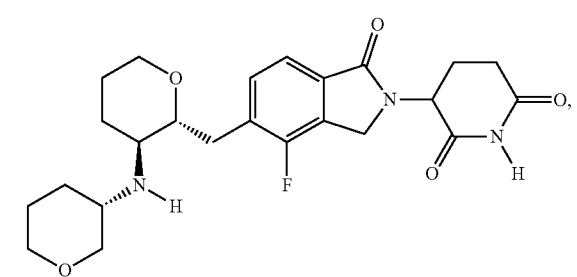
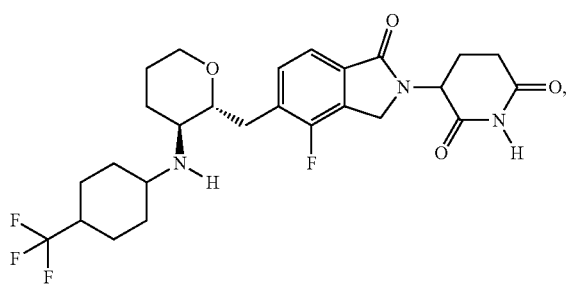
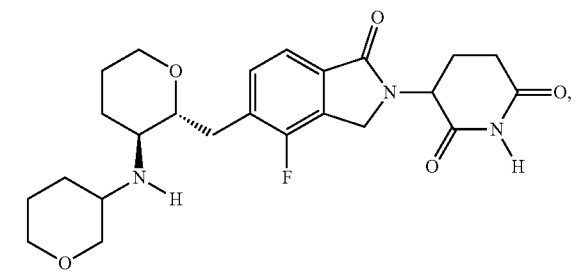
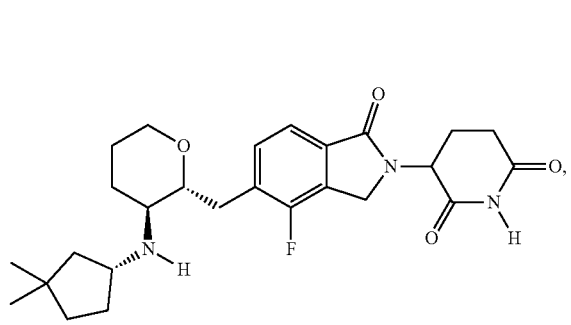
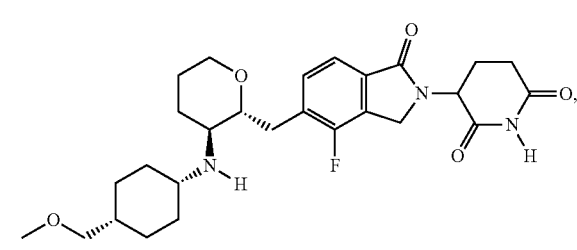

-continued
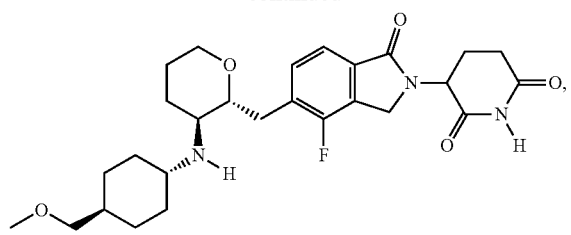
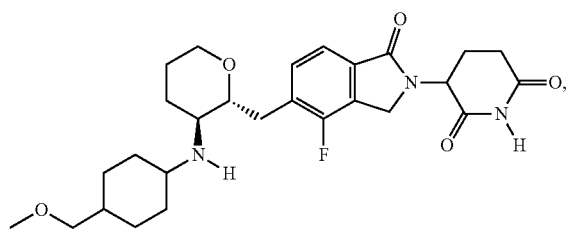
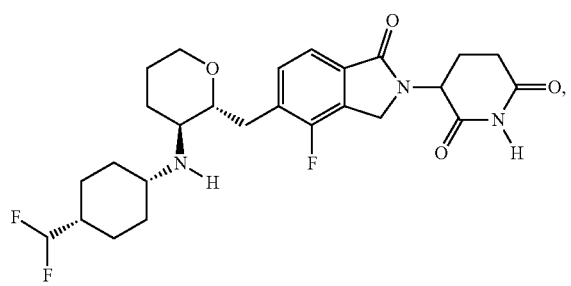
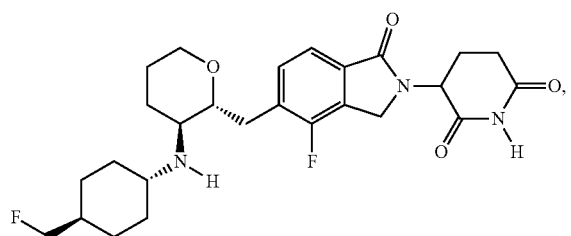
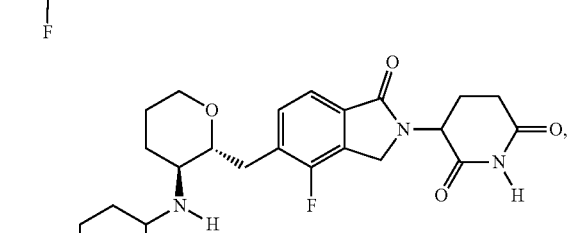
-continued
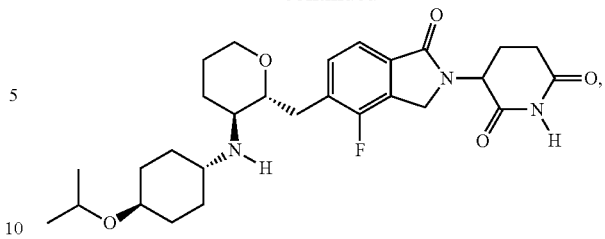
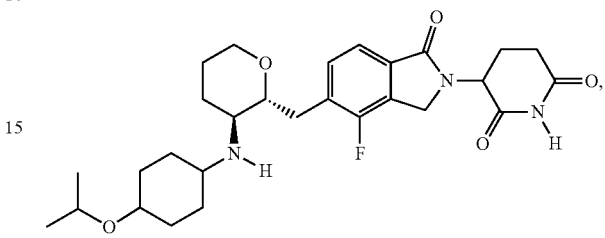
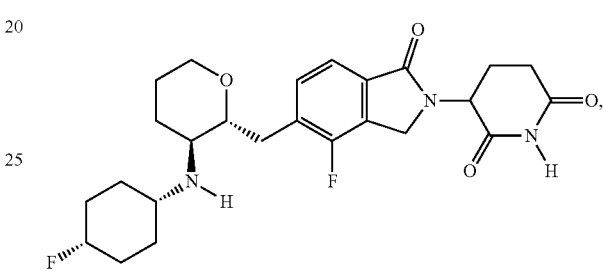
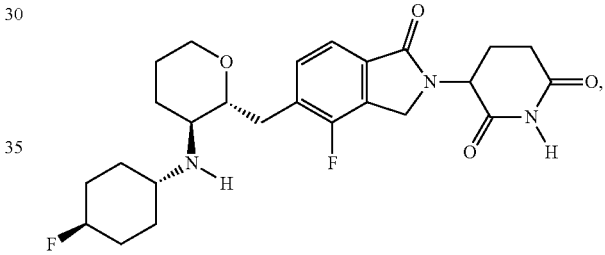
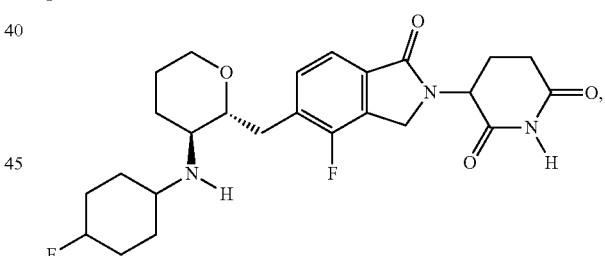
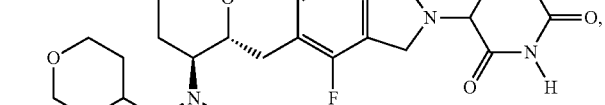

167
-continued
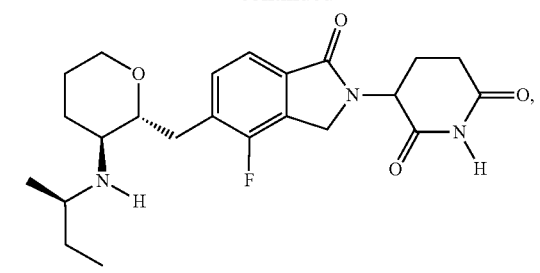
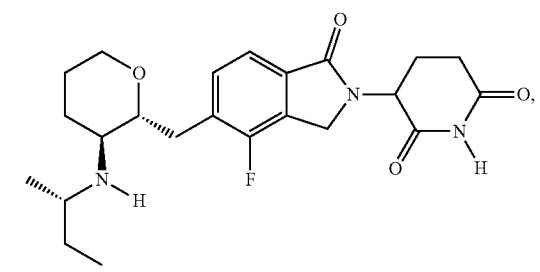
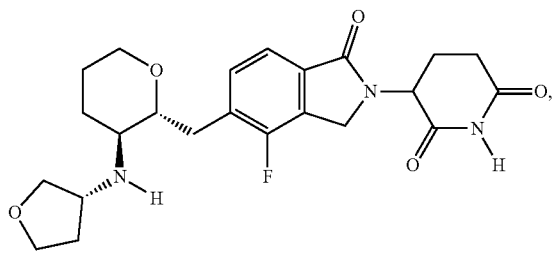
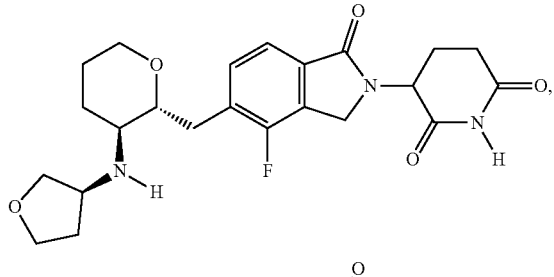
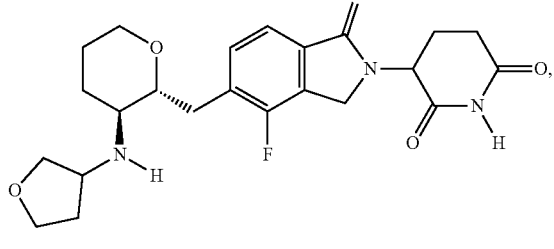

168
-continued
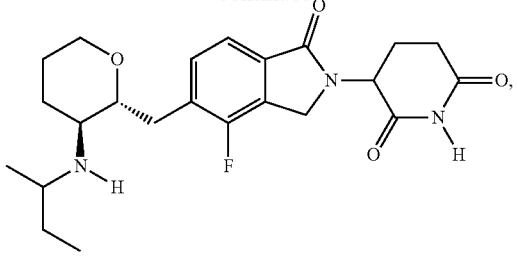
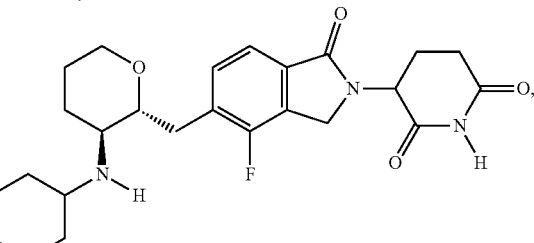
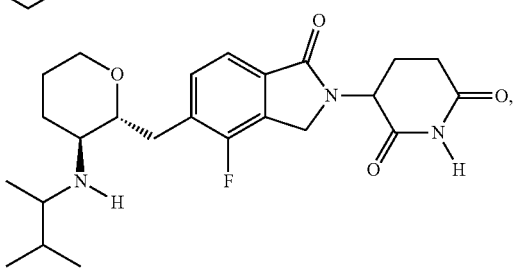
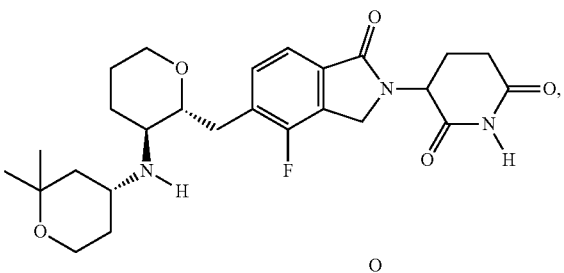
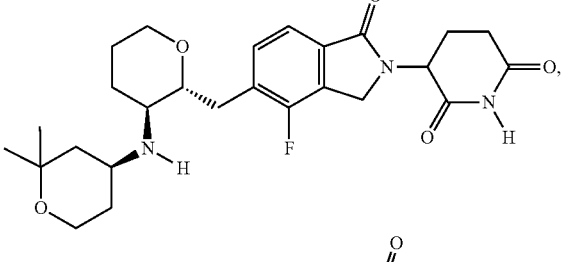
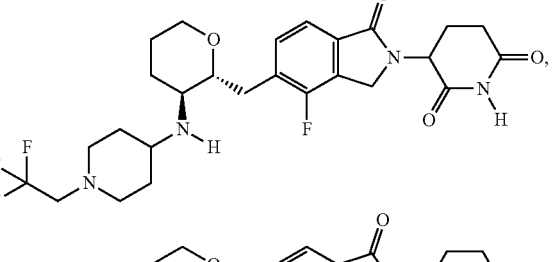
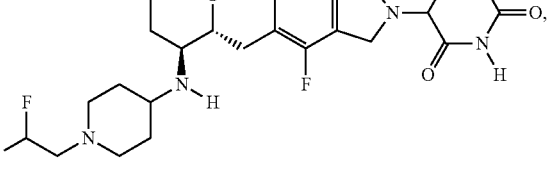

169
-continued
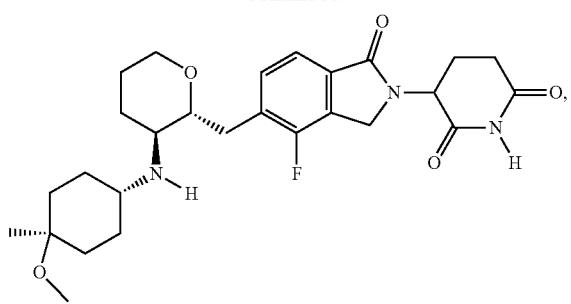
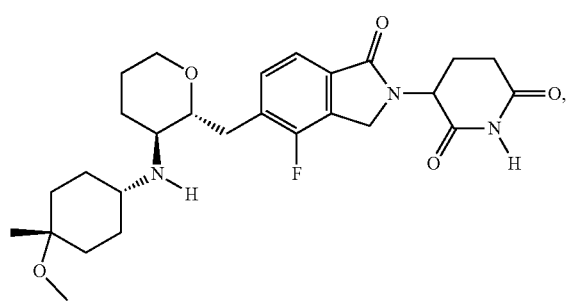
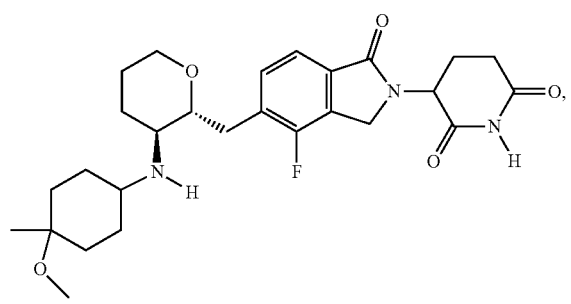
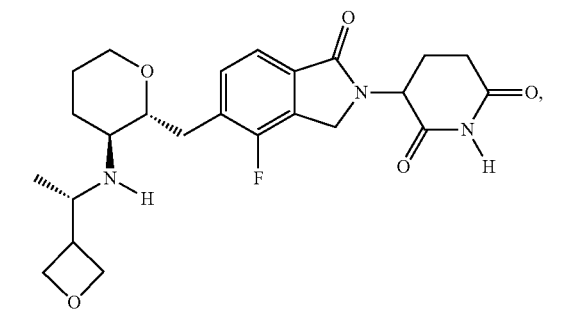

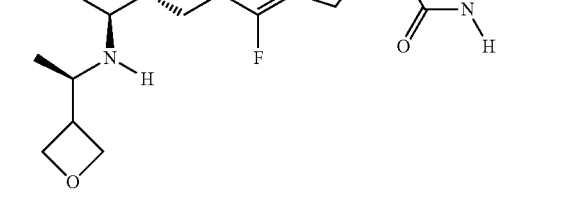
170
-continued
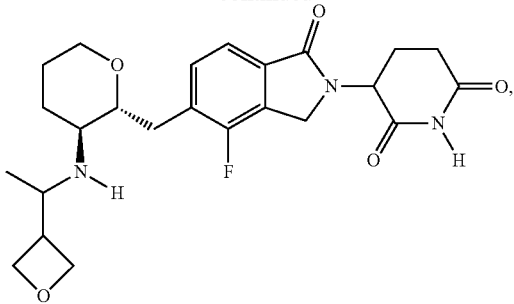
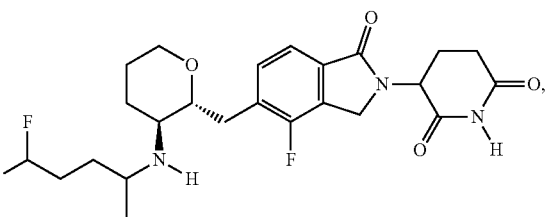
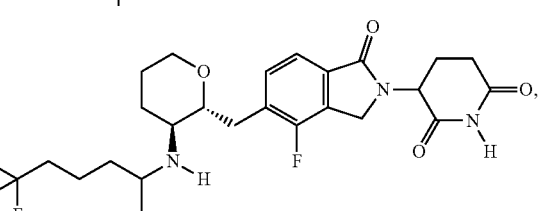
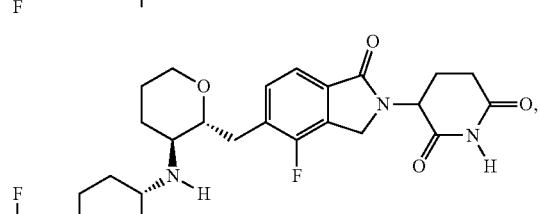
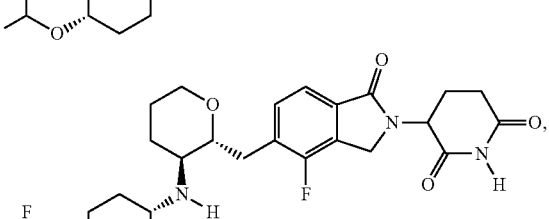
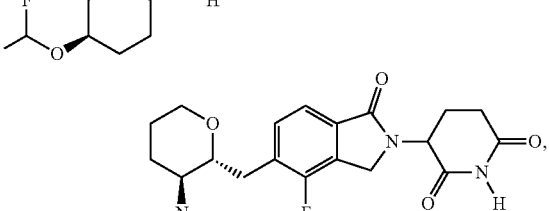
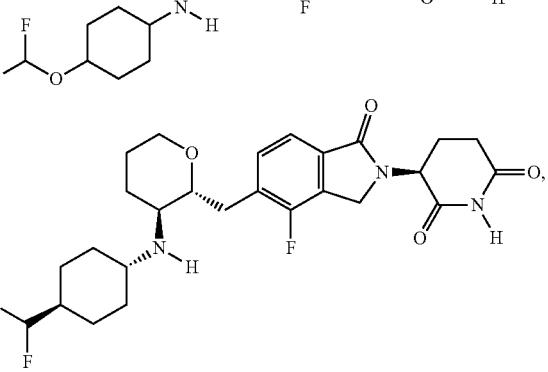

-continued
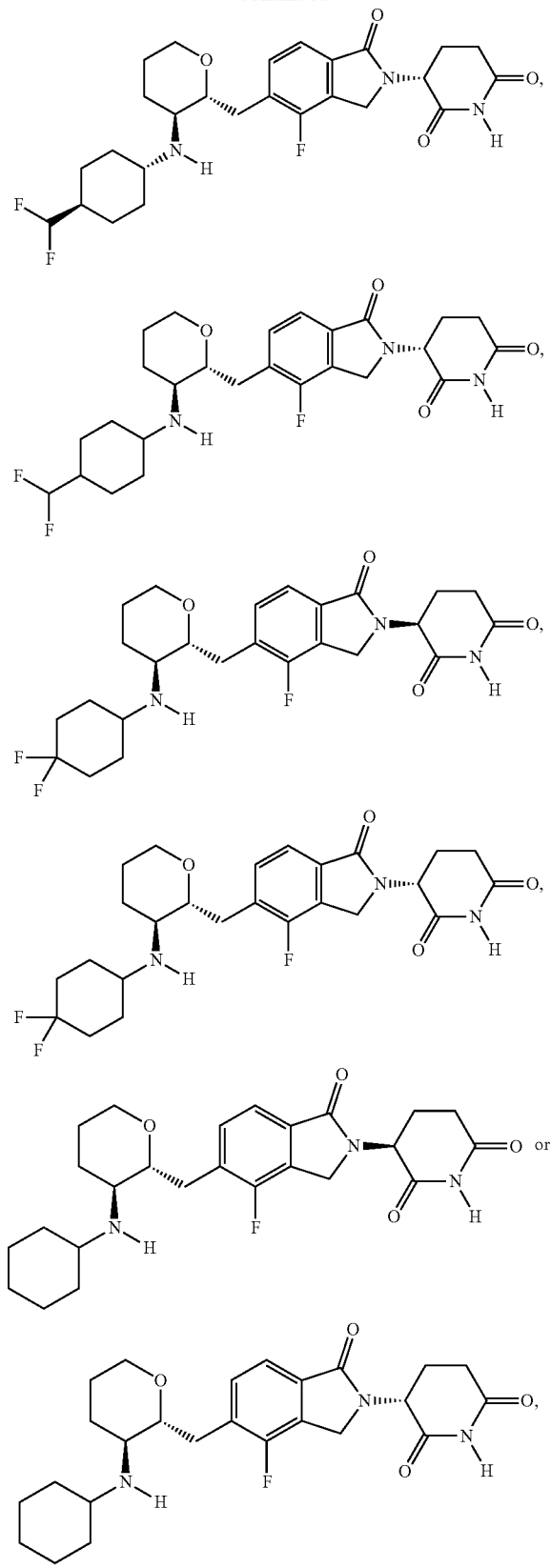
or a pharmaceutically acceptable salt thereof.
In some embodiments the compound of Formula (I) or (IIc), or pharmaceutically acceptable salt thereof, is
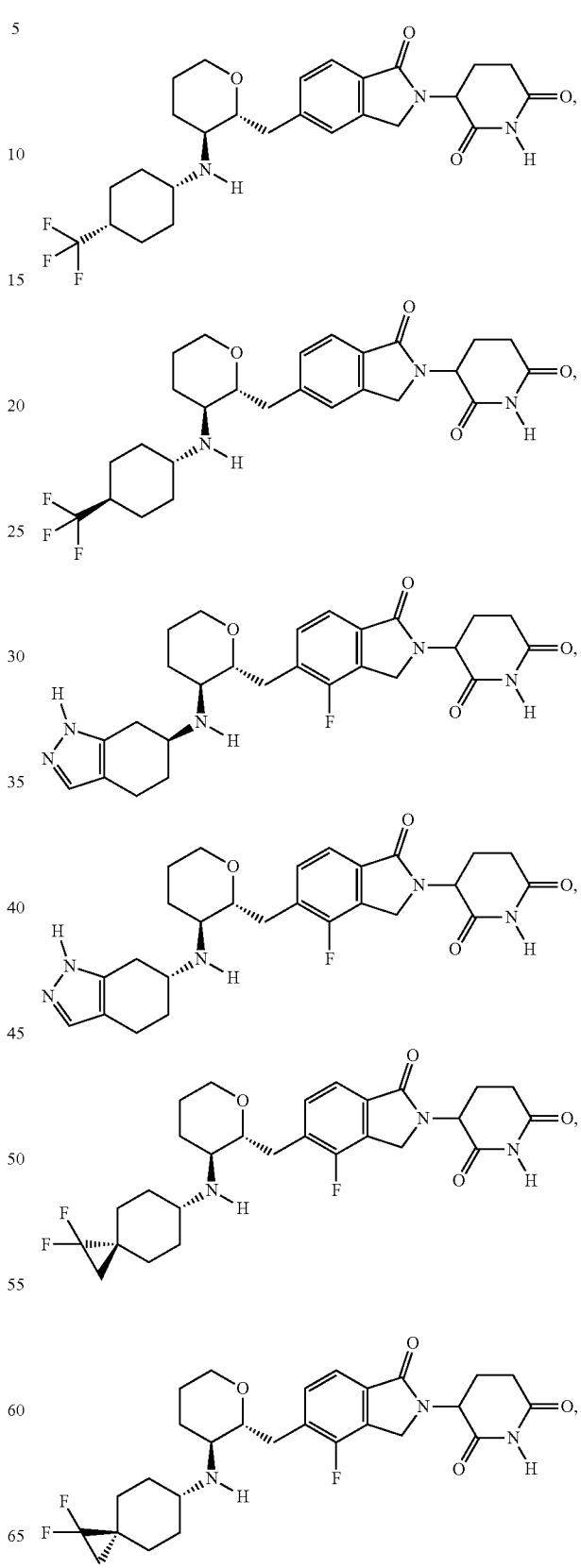

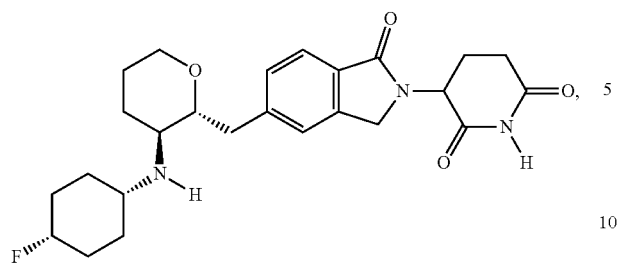
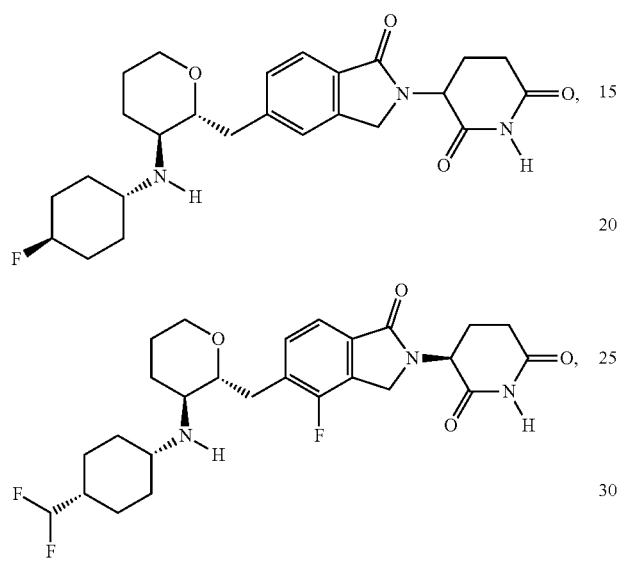
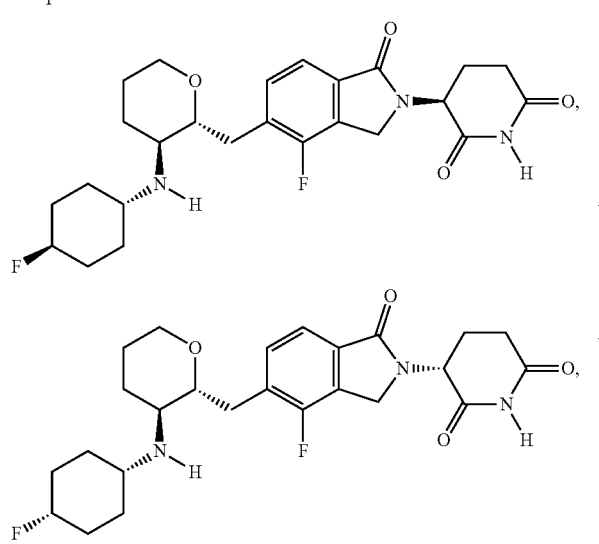
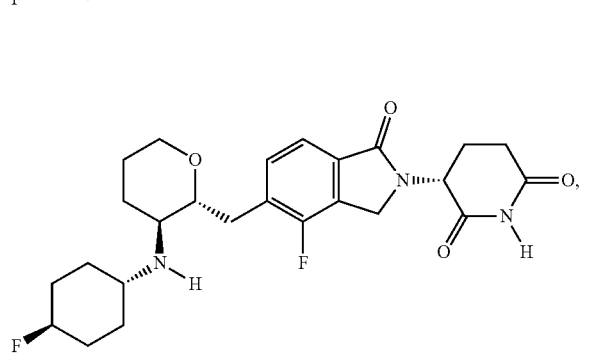
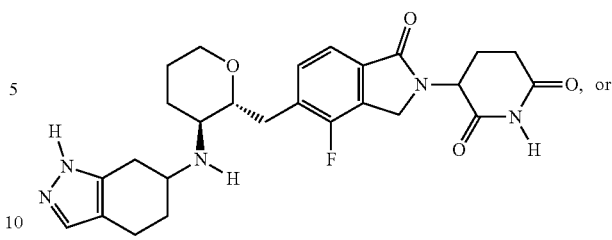
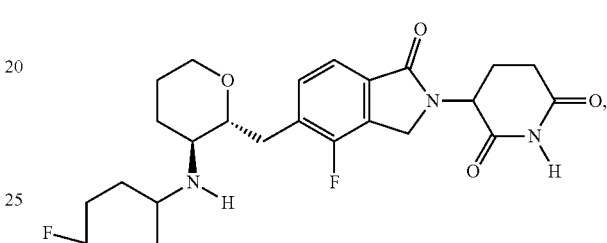
or a pharmaceutically acceptable salt thereof.
In some embodiments, the compound of Formula (I) or (IIg), or pharmaceutically acceptable salt thereof, is
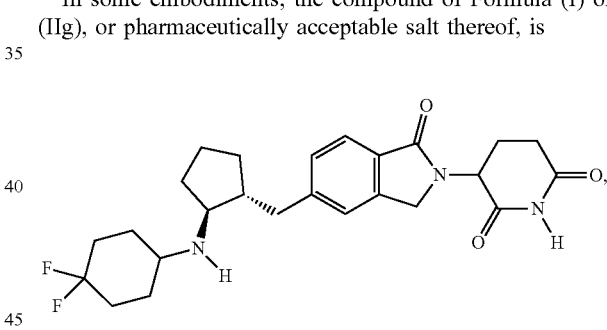
or a pharmaceutically acceptable salt thereof.
In some embodiments, the compound of Formula (I) or (IIh), or pharmaceutically acceptable salt thereof, is
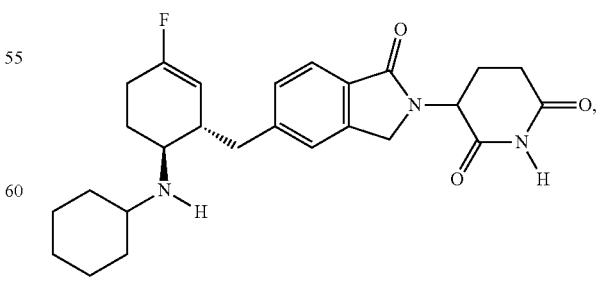
or a pharmaceutically acceptable salt thereof.

In some embodiments, the compound of Formula (I) or (IIi), or pharmaceutically acceptable salt thereof, is

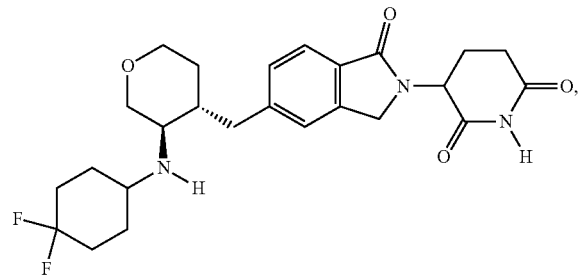 [SMILES: O=C1CCC(N2Cc3cc(C[C@H]4CCOC[C@@H]4NC4CCC(F)(F)CC4)ccc3C2=O)C(=O)N1]

or a pharmaceutically acceptable salt thereof.

In some embodiments, the compound of Formula (I) or (IIj), or pharmaceutically acceptable salt thereof, is

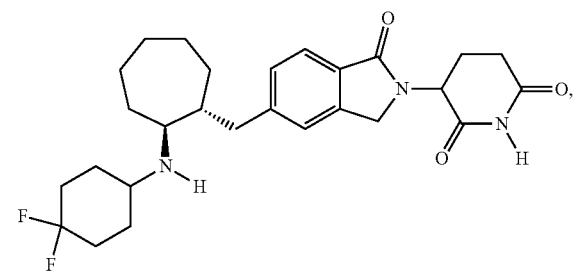 [SMILES: O=C1CCC(N2Cc3cc(C[C@H]4CCCCC[C@@H]4NC4CCC(F)(F)CC4)ccc3C2=O)C(=O)N1]

or a pharmaceutically acceptable salt thereof.

In some embodiments, the compound of Formula (I) or (IIk), or pharmaceutically acceptable salt thereof, is

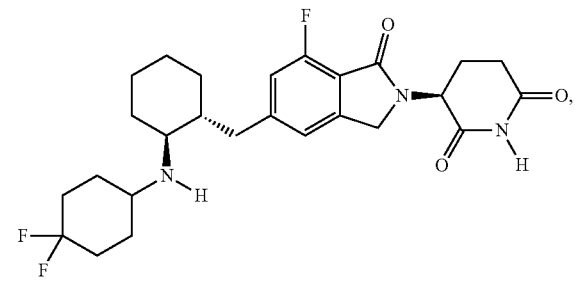 [SMILES: O=C1CC[C@H](N2Cc3cc(C[C@H]4CCCC[C@@H]4NC4CCC(F)(F)CC4)cc(F)c3C2=O)C(=O)N1]

or a pharmaceutically acceptable salt thereof.

In some embodiments, the compound of Formula (I) or (IIa), or pharmaceutically acceptable salt thereof, is

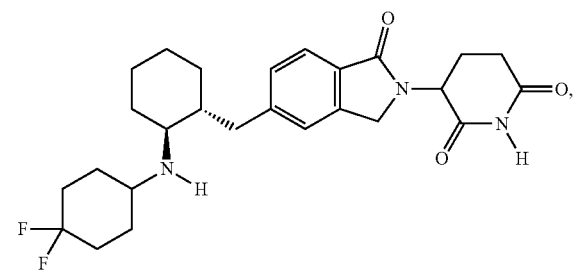 [SMILES: O=C1CCC(N2Cc3cc(C[C@H]4CCCC[C@@H]4NC4CCC(F)(F)CC4)ccc3C2=O)C(=O)N1]

or a pharmaceutically acceptable salt thereof.

In some embodiments, the compound of Formula (I), (Ia), or (IIa), or pharmaceutically acceptable salt thereof, is

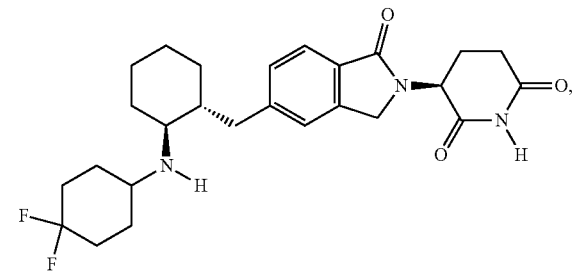 [SMILES: O=C1CC[C@H](N2Cc3cc(C[C@H]4CCCC[C@@H]4NC4CCC(F)(F)CC4)ccc3C2=O)C(=O)N1]

or a pharmaceutically acceptable salt thereof.

In some embodiments, the compound of Formula (I), (Ib), or (IIa), or pharmaceutically acceptable salt thereof, is
or a pharmaceutically acceptable salt thereof.

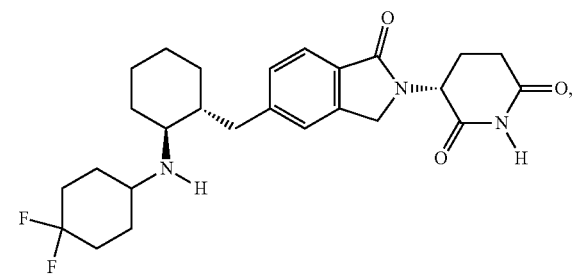

In some embodiments, the compound of Formula (I) or (IIa), or pharmaceutically acceptable salt thereof, is

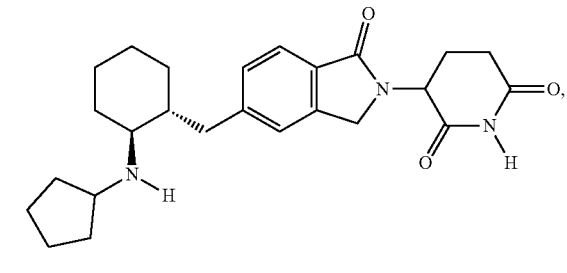 [SMILES: O=C1CCC(N2Cc3cc(C[C@H]4CCCC[C@@H]4NC4CCCC4)ccc3C2=O)C(=O)N1]

or a pharmaceutically acceptable salt thereof.

In some embodiments, the compound of Formula (I) or (IIa), or pharmaceutically acceptable salt thereof, is

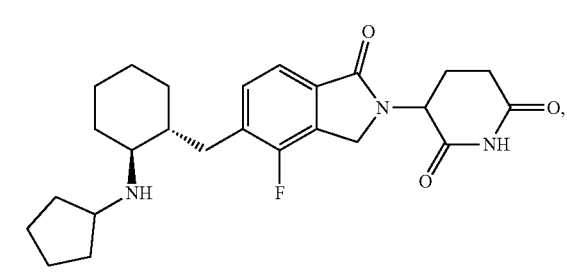 [SMILES: O=C1CCC(N2Cc3c(ccc(C[C@H]4CCCC[C@@H]4NC4CCCC4)c3F)C2=O)C(=O)N1]

or a pharmaceutically acceptable salt thereof.

In some embodiments, the compound of Formula (I) or (IIa), or pharmaceutically acceptable salt thereof, is

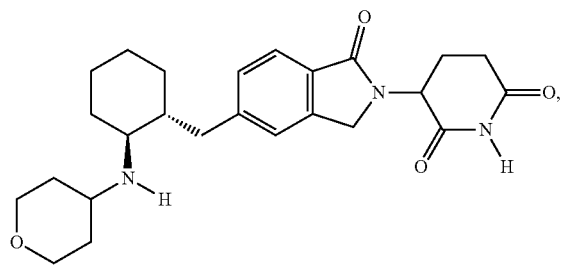 [SMILES: O=C1CCC(N2Cc3cc(C[C@H]4CCCC[C@@H]4NC4CCOCC4)ccc3C2=O)C(=O)N1]

or a pharmaceutically acceptable salt thereof.

In some embodiments, the compound of Formula (I) or (IIa), or pharmaceutically acceptable salt thereof, is

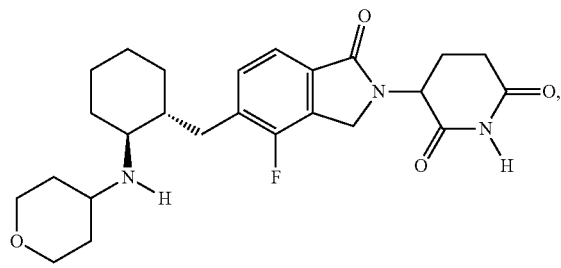 [SMILES: O=C1CCC(N2Cc3c(ccc(C[C@H]4CCCC[C@@H]4NC4CCOCC4)c3F)C2=O)C(=O)N1]

or a pharmaceutically acceptable salt thereof.

In some embodiments, the compound of Formula (I) or (IIa), or pharmaceutically acceptable salt thereof, is

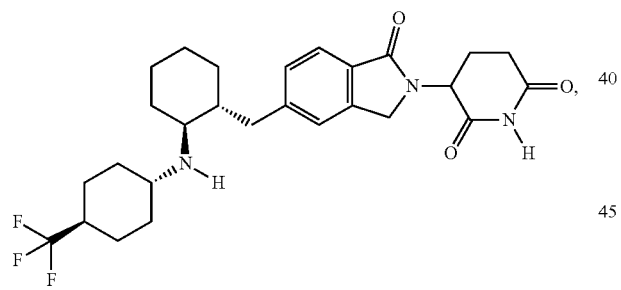

or a pharmaceutically acceptable salt thereof.

In some embodiments, the compound of Formula (I) or (IIa), or pharmaceutically acceptable salt thereof, is

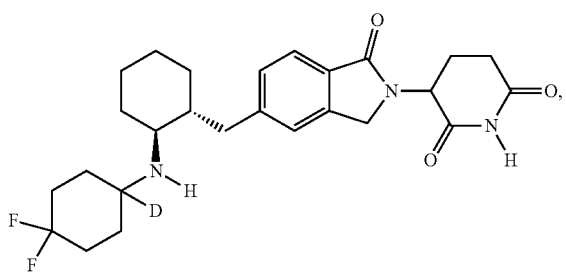 [SMILES: [2H]C1(N[C@H]2CCCC[C@@H]2Cc2ccc3c(c2)CN(C2CCC(=O)NC2=O)C3=O)CCC(F)(F)CC1]

or a pharmaceutically acceptable salt thereof.

In some embodiments, the compound of Formula (I) or (IIa), or pharmaceutically acceptable salt thereof, is

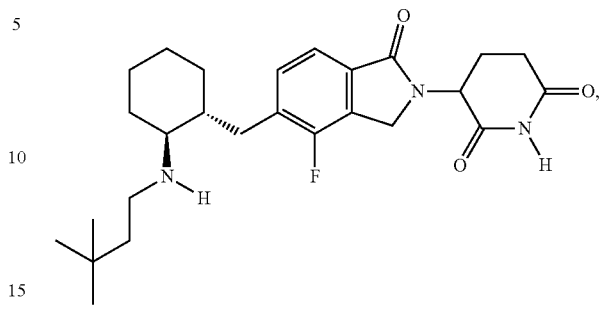

or a pharmaceutically acceptable salt thereof.

In some embodiments, the compound of Formula (I) or (IIa), or pharmaceutically acceptable salt thereof, is

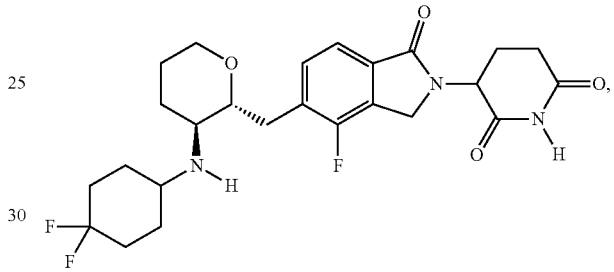

or a pharmaceutically acceptable salt thereof.

In some embodiments, the compound of Formula (I), (Ia), or (IIc), or pharmaceutically acceptable salt thereof, is

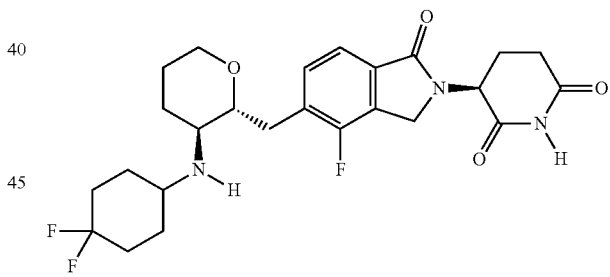

or a pharmaceutically acceptable salt thereof.

In some embodiments, the compound of Formula (I), (Ib), or (IIc), or pharmaceutically acceptable salt thereof, is

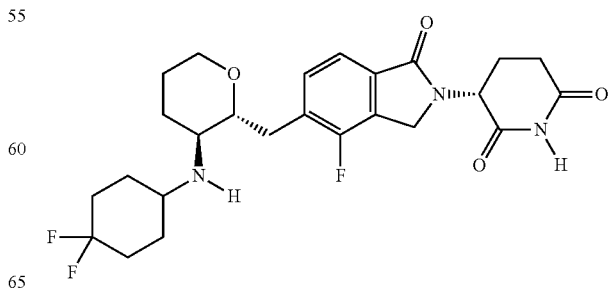

or a pharmaceutically acceptable salt thereof.

In some embodiments, the compound of Formula (I), (Ia), or (IIc), or pharmaceutically acceptable salt thereof, is

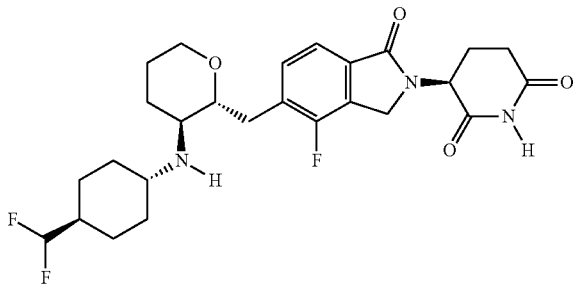 [SMILES: O=C1CC[C@H](N2Cc3c(ccc(C[C@H]4OCCC[C@@H]4N[C@H]4CC[C@H](C(F)F)CC4)c3F)C2=O)C(=O)N1]

or a pharmaceutically acceptable salt thereof.

In some embodiments, the compound of Formula (I), (Ib), or (IIc), or pharmaceutically acceptable salt thereof, is

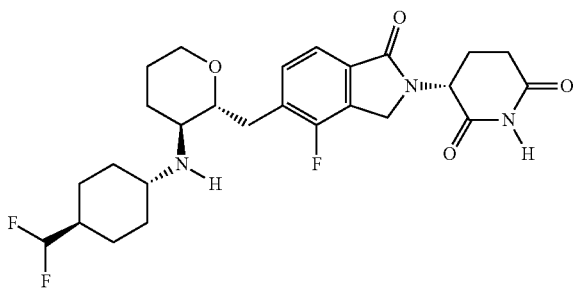 [SMILES: O=C1CC[C@@H](N2Cc3c(ccc(C[C@H]4OCCC[C@@H]4N[C@H]4CC[C@H](C(F)F)CC4)c3F)C2=O)C(=O)N1]

or a pharmaceutically acceptable salt thereof.

In some embodiments, the compound of Formula (I), (Ia), or (IIc), or pharmaceutically acceptable salt thereof, is

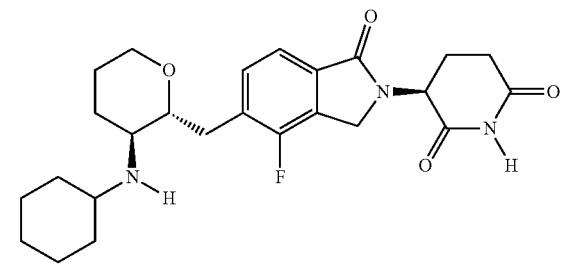 [SMILES: O=C1CC[C@H](N2Cc3c(ccc(C[C@H]4OCCC[C@@H]4NC4CCCCC4)c3F)C2=O)C(=O)N1]

or a pharmaceutically acceptable salt thereof.

In some embodiments, the compound of Formula (I), (Ib), or (IIc), or pharmaceutically acceptable salt thereof, is

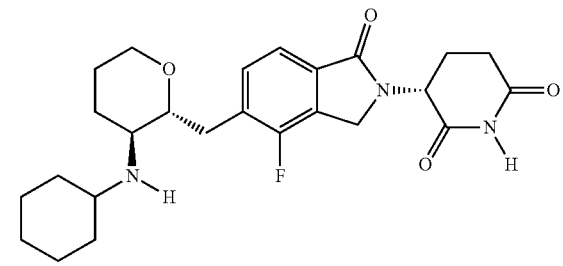 [SMILES: O=C1CC[C@@H](N2Cc3c(ccc(C[C@H]4OCCC[C@@H]4NC4CCCCC4)c3F)C2=O)C(=O)N1]

or a pharmaceutically acceptable salt thereof.

In some embodiments, the present disclosure provides a racemic mixture comprising the compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), or a pharmaceutically acceptable salt thereof. In some embodiments, the present disclosure provides a racemic mixture comprising the compound disclosed herein, or a pharmaceutically acceptable salt thereof. In some embodiments, the present disclosure provides a scalemic mixture comprising the compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), or a pharmaceutically acceptable salt thereof. In some embodiments, the present disclosure provides a scalemic mixture comprising the compound disclosed herein, or a pharmaceutically acceptable salt thereof.

One of skill in the art is aware that each and every embodiment of a group (e.g., $R^1$) disclosed herein may be combined with any other embodiment of each of the remaining groups (e.g., $R^2$, $R^3$, $Z^1$, $Z^2$, etc.) to generate a complete compound of Formula (I), or any Formula described herein or a pharmaceutically acceptable salt, stereoisomer, mixture of stereoisomers, or tautomer thereof, each of which is deemed within the ambit of the present disclosure.

PHARMACEUTICAL COMPOSITIONS AND MODES OF ADMINISTRATION

Furthermore, the present disclosure provides pharmaceutical compositions comprising at least one compound of the present disclosure, or a prodrug compound thereof, or a pharmaceutically acceptable salt or solvate thereof as active ingredient together with a pharmaceutically acceptable carrier.

The pharmaceutical composition of the present disclosure may additionally comprise one or more other compounds as active ingredients like a prodrug compound or other enzyme inhibitors.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the present disclosure can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

In some embodiments, the compounds of the present disclosure may also be used as salts with various countercations to yield an orally available formulation.

The compounds of the present disclosure may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In some embodiments, compounds of the present disclosure are administered orally.

Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Treatment Methods and Uses

The compounds or pharmaceutically acceptable salts thereof provided herein, or compositions comprising a compound or pharmaceutically acceptable salt thereof provided herein can be put to pharmaceutical use. In some embodiments the compounds or pharmaceutically acceptable salts thereof provided herein, or compositions comprising a compound or pharmaceutically acceptable salt thereof provided herein are for treating an IKFZ2 associated disease or condition. In some embodiments the compounds or pharmaceutically acceptable salts thereof provided herein, or compositions comprising a compound or pharmaceutically acceptable salt thereof provided herein are for treating cancer. In some embodiments, the compounds or pharmaceutically acceptable salts thereof provided herein, or compositions comprising a compound or pharmaceutically acceptable salt thereof provided herein can be used for the manufacture of a medicament for the treatment of an IKFZ2 associated disease or condition. In some embodiments, the compounds or pharmaceutically acceptable salts thereof provided herein, or compositions comprising a compound or pharmaceutically acceptable salt thereof provided herein can be used for the manufacture of a medicament for the treatment of cancer.

The disclosure further relates to the use of compounds or pharmaceutically acceptable salts thereof disclosed herein for the treatment and/or prophylaxis of diseases and/or conditions through binding and degradation of an IKZF protein (e.g., IKZF2 or IKZF4 protein) by said compounds. Further, the present disclosure relates to the use of said compounds or pharmaceutically acceptable salts thereof for the preparation of a medicament for the treatment and/or prophylaxis of an IKZF associated disease and/or condition through binding and degradation of an IKZF protein (e.g., IKZF2 or IKZF4 protein) by said compounds. In some embodiments the IKZF associated disease or condition is alleviated by selective degradation of IKZF2 protein. In some embodiments, the IKZF associated disease or condition is alleviated by degradation of IKZF2 protein. In some embodiments, the IKZF associated disease or condition is alleviated by degradation of IKZF2 protein and one or more additional IKZF2 proteins (e.g., IKZF1 and/or IKZF4 proteins). In some embodiments, the IKZF associated disease or condition is alleviated by degradation of IKZF4 protein.

In some embodiments the IKZF associated disease and/or condition is an IKZF2 associated disease and/or condition. In some embodiments the IKZF2 associated disease or condition is alleviated by selective degradation of IKZF2 protein. In some embodiments the IKZF2 associated disease and/or condition is alleviated by degradation of IKZF2 protein and one or more additional IKZF proteins (e.g., IKZF1 and/or IKZF4 proteins).

Medicaments as referred to herein can be prepared by conventional processes, including the combination of a compound according to the present disclosure and a pharmaceutically acceptable carrier.

In some embodiments, provided herein is a method of treating and/or preventing an IKZF protein (e.g., IKZF2 protein) associated disease or condition in a patient in need thereof, comprising administering to the patient a therapeutically effective amount of a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), or pharmaceutically acceptable salt thereof, or a composition comprising a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), or a pharmaceutically acceptable salt thereof.

In some embodiments, provided herein is a method of degrading an IKZF protein (e.g., IKZF2 protein) comprising administering to a patient in need thereof (e.g., a patient having an IKZF protein associated disease or condition) a therapeutically effective amount of a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), or a pharmaceutically acceptable salt thereof, or a composition comprising a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), or a pharmaceutically acceptable salt thereof.

In some embodiments, provided herein is a method of reducing the proliferation of a cell comprising contacting the cell with a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), or a pharmaceutically acceptable salt thereof, and reducing IKZF protein (e.g., IKZF2 protein) levels in the cell.

In some embodiments, provided herein is a method of reducing IKFZ protein (e.g., IKZF2 protein) levels in a patient in need thereof (e.g., a patient having an IKZF2 associated disease or condition) comprising administering to the patient a therapeutically effective amount of a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), or a pharmaceutically acceptable salt thereof, or a composition comprising a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), or a pharmaceutically acceptable salt thereof.

In some embodiments, the IKZF protein (e.g., IKZF2 protein) associated disease or condition includes cancer. In some embodiments, the cancer is a hematological cancer. In some embodiments, the cancer includes a solid tumor. In some embodiments, the cancer includes a malignant tumor. In some embodiments the cancer includes a metastatic cancer. In some embodiments, the cancer is resistant or refractory to one or more anticancer therapies. In some embodiments, greater than about 50% of the cancer cells detectably express one or more cell surface immune checkpoint receptors (e.g., so-called "hot" cancer or tumor). In some embodiments, greater than about 1% and less than about 50% of the cancer cells detectably express one or more cell surface immune checkpoint receptors (e.g., so called "warm" cancer or tumor). In some embodiments, less than about 1% of the cancer cells detectably express one or more cell surface immune checkpoint receptors (e.g., so called "cold" cancer or tumor).

In some embodiments, the IKZF protein (e.g., IKZF2 protein) associated disease or condition is a hematological cancer, e.g., a leukemia (e.g., Acute Myelogenous Leukemia (AML), Acute Lymphoblastic Leukemia (ALL), B-cell ALL, Myelodysplastic Syndrome (MDS), myeloproliferative disease (MPD), Chronic Myelogenous Leukemia (CML), Chronic Lymphocytic Leukemia (CLL), undifferentiated leukemia), a lymphoma (e.g., small lymphocytic lymphoma (SLL), mantle cell lymphoma (MCL), follicular lymphoma (FL), T-cell lymphoma, B-cell lymphoma, diffuse large B-cell lymphoma (DLBCL), marginal zone lymphoma (MZL), Waldestrom's macroglobulinemia (WM)) and/or a myeloma (e.g., multiple myeloma (MM)).

In some embodiments, the IKZF protein (e.g., IKZF2 protein) associated disease or condition is an epithelial tumor (e.g., a carcinoma, a squamous cell carcinoma, a basal cell carcinoma, a squamous intraepithelial neoplasia), a glandular tumor (e.g., an adenocarcinoma, an adenoma, an adenomyoma), a mesenchymal or soft tissue tumor (e.g., a sarcoma, a rhabdomyosarcoma, a leiomyosarcoma, a liposarcoma, a fibrosarcoma, a dermatofibrosarcoma, a neurofibrosarcoma, a fibrous histiocytoma, an angiosarcoma, an angiomyxoma, a leiomyoma, a chondroma, a chondrosarcoma, an alveolar soft-part sarcoma, an epithelioid hemangioendothelioma, a Spitz tumor, a synovial sarcoma), or a lymphoma.

In some embodiments, the IKZF protein (e.g., IKZF2 protein) associated disease or condition includes a solid tumor in or arising from a tissue or organ, such as:
  bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma);
  lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors);
  esophagus (e.g., Barrett's esophagus, dysplasia and adenocarcinoma);
  gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus;
  pancreas (e.g., serous neoplasms, including microcystic or macrocystic serous cystadenoma, solid serous cystadenoma, Von Hippel-Landau (VHL)-associated serous cystic neoplasm, serous cystadenocarcinoma; mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma);

gall bladder (e.g. carcinoma of the gallbladder and extrahepatic bile ducts, intrahepatic cholangiocarcinoma);

neuro-endocrine (e.g., adrenal cortical carcinoma, carcinoid tumors, phaeochromocytoma, pituitary adenomas);

thyroid (e.g., anaplastic (undifferentiated) carcinoma, medullary carcinoma, oncocytic tumors, papillary carcinoma, adenocarcinoma);

liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma; hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor);

kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma);

breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma; lobular carcinoma, including without limitation, pleomorphic carcinoma, signet ring cell carcinoma;

peritoneum (e.g., mesothelioma; primary peritoneal cancer);

female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, Müllerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina;

male sex organ tissues, including prostate, testis (e.g., germ cell tumors, spermatocytic seminoma), penis;

bladder (e.g., squamous cell carcinoma, urothelial carcinoma, bladder urothelial carcinoma);

brain, (e.g., gliomas (e.g., astrocytomas, including non-infiltrating, low-grade, anaplastic, glioblastomas; oligodendrogliomas, ependymomas), meningiomas, ganglioglioma, schwannomas (neurilemmomas), craniopharyngiomas, chordomas, Non-Hodgkin lymphomas (NHLs), indolent non-Hodgkin's lymphoma (iNHL), refractory iNHL, pituitary tumors;

eye (e.g., retinoma, retinoblastoma, ocular melanoma, posterior uveal melanoma, iris hamartoma);

head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal);

thymus (e.g., thymoma);

heart (e.g., cardiac myxoma);

lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma);

lymph (e.g., lymphomas, including Hodgkin's lymphoma, non-Hodgkin's lymphoma (NHL), indolent non-Hodgkin's lymphoma (iNHL), refractory iNHL, Epstein-Barr virus (EBV)-associated lymphoproliferative diseases, including B cell lymphomas and T cell lymphomas (e.g., Burkitt lymphoma; large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis);

central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, Pituitary adenomas, cranial and paraspinal nerve tumors, stellar region tumors); neurofibroma, meningioma, peripheral nerve sheath tumors, peripheral neuroblastic tumours (including without limitation neuroblastoma, ganglioneuroblastoma, ganglioneuroma), trisomy 19 ependymoma);

neuroendocrine tissues (e.g., paraganglionic system including adrenal medulla (pheochromocytomas) and extra-adrenal paraganglia ((extra-adrenal) paragangliomas);

skin (e.g., clear cell hidradenoma, cutaneous benign fibrous histiocytomas, cylindroma, hidradenoma, melanoma (including cutaneous melanoma, mucosal melanoma), pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, lipoblastoma, lipoma, chondroid lipoma, liposarcoma/malignant lipomatous tumors, liposarcoma, myxoid liposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non-rhabdomyosarcoma soft tissue sarcoma (NRSTS), soft tissue leiomyosarcoma, undifferentiated sarcoma, well-differentiated liposarcoma.

In some embodiments, the IKZF protein (e.g., IKZF2 protein) associated disease or condition is a cancer selected from a lung cancer, a colorectal cancer, a breast cancer, a prostate cancer, a cervical cancer, a pancreatic cancer and a head and neck cancer. In some embodiments, the cancer is metastatic.

In some embodiments, the IKZF protein (e.g., IKZF2 protein) associated disease or condition is a cancer selected from non-small lung cancer (NSCLC), melanoma, triple-negative breast cancer (TNBC), nasopharyngeal cancer (NPC), microsatellite stable colorectal cancer (mssCRC), thymoma, and gastrointestinal stromal tumor (GIST). In some embodiments, the cancer is metastatic.

Dosage

The effective dosage of active ingredient employed may vary depending on the particular compound employed, the mode of administration, the condition being treated and the severity of the condition being treated. Such dosage may be ascertained readily by a person skilled in the art.

When treating or preventing an IKZF protein (e.g., IKZF2 protein) associated disease or condition for which compounds of the present disclosure are indicated, generally satisfactory results are obtained when the compounds of the present disclosure are administered at a daily dosage of from about 0.1 milligram to about 300 milligram per kilogram of animal body weight. In some embodiments, the compounds of the present disclosure are given as a single daily dose or in divided doses two to six times a day, or in sustained release form. For most large mammals, the total daily dosage is from about 1 milligram to about 1000 milligrams, or from about 1 milligram to about 50 milligrams. In the case of a 70 kg adult human, the total daily dose will generally be from about 0.1 milligrams to about 200 milligrams. This dosage regimen may be adjusted to provide the optimal therapeutic response. In some embodiments, the total daily dosage is from about 1 milligram to about 900 milligrams, about 1 milligram to about 800 milligrams, about 1 milligram to about 700 milligrams, about 1 milligram to about 600 milligrams, about 1 milligram to about 400 milligrams, about 1 milligram to about 300 milligrams, about 1 milligram to about 200 milligrams, about 1 milligram to about 100 milligrams, about 1 milligram to about 50 milligrams, about 1 milligram to about 20 milligram, or about 1 milligram to about 10 milligrams.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are frequently alternated with resting periods of about 1 to 28 days, commonly about 7 days or about 14 days, between cycles. The treatment cycles, in other embodiments, may also be continuous.

In some embodiments, the methods provided herein comprise administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Combinations

In some embodiments, a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered in combination with one or more additional therapeutic agents to treat or prevent a disease or condition disclosed herein. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the pharmaceutical compositions provided herein have a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, and one or more additional therapeutic agents. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments the one or more additional therapeutic agents include, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (e.g., a mono- and multi-specific antibody, or fragment thereof, in any format, such as DART®, Duobody®, BiTE®, BiKE, TriKE, XmAb®, TandAb®, scFv, Fab, Fab derivative), a bi-specific antibody, a non-immunoglobulin antibody mimetic (e.g., including adnectin, affibody, affilin, affimer, affitin, alphabody, anticalin, peptide aptamer, armadillo repeat protein (ARM), atrimer, avimer, designed ankyrin repeat protein (DARPin®), fynomer, knottin, Kunitz domain peptide, monobody, and nanoCLAMPs), an antibody-drug conjugate (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, e.g., an inhibitor, agonist, antagonist, ligand, modulator, stimulator, blocker, activator or suppressor of a target (e.g., polypeptide or polynucleotide), such as: 2'-5'-oligoadenylate synthetase (OAS1; NCBI Gene ID: 4938); 5'-3' exoribonuclease 1 (XRN1; NCBI Gene ID: 54464); 5'-nucleotidase ecto (NT5E, CD73; NCBI Gene ID: 4907); ABL proto-oncogene 1, non-receptor tyrosine kinase (ABL1, BCR-ABL, c-ABL, v-ABL; NCBI Gene ID: 25); absent in melanoma 2 (AIM2; NCBI Gene ID: 9447); acetyl-CoA acyltransferase 2 (ACAA2; NCBI Gene ID: 10499); acid phosphatase 3 (ACP3; NCBI Gene ID: 55); adenosine deaminase (ADA, ADA1; NCBI Gene ID: 100); adenosine receptors (e.g., ADORA1 (A1), ADORA2A (A2a, A2AR), ADORA2B (A2b, A2BR), ADORA3 (A3); NCBI Gene IDs: 134, 135, 136, 137); AKT serine/threonine kinase 1 (AKT1, AKT, PKB; NCBI Gene ID: 207); alanyl aminopeptidase, membrane (ANPEP, CD13; NCBI Gene ID: 290); ALK receptor tyrosine kinase (ALK, CD242; NCBI Gene ID: 238); alpha fetoprotein (AFP; NCBI Gene ID: 174); amine oxidase copper containing (e.g., AOC1 (DAO1), AOC2, AOC3 (VAP1); NCBI Gene IDs: 26, 314, 8639); androgen receptor (AR; NCBI Gene ID: 367); angiopoietins (ANGPT1, ANGPT2; NCBI Gene IDs: 284, 285); angiotensin II receptor type 1 (AGTR1; NCBI Gene ID: 185); angiotensinogen (AGT; NCBI Gene ID: 183); apolipoprotein A1 (APOA1; NCBI Gene ID: 335); apoptosis inducing factor mitochondria associated 1 (AIFM1, AIF; NCBI Gene ID: 9131); arachidonate 5-lipoxygenase (ALOX5; NCBI Gene ID: 240); asparaginase (ASPG; NCBI Gene ID: 374569); asteroid homolog 1 (ASTE1; NCBI Gene ID: 28990); ATM serine/threonine kinase (ATM; NCBI Gene ID: 472); ATP binding cassette subfamily B member 1 (ABCB1, CD243, GP170; NCBI Gene ID: 5243); ATP-dependent Clp-protease (CLPP; NCBI Gene ID: 8192); ATR serine/threonine kinase (ATR; NCBI Gene ID: 545); AXL receptor tyrosine kinase (AXL; NCBI Gene ID: 558); B and T lymphocyte associated (BTLA, CD272; NCBI Gene ID: 151888); baculoviral IAP repeat containing proteins (BIRC2 (cIAP1), BIRC3 (cIAP2), XIAP (BIRC4, IAP3), BIRC5 (survivin); NCBI Gene IDs: 329, 330, 331, 332); basigin (Ok blood group) (BSG, CD147; NCBI Gene ID: 682); B-cell lymphoma 2 (BCL2; NCBI Gene ID: 596); BCL2 binding component 3 (BBC3, PUMA; NCBI Gene ID: 27113); BCL2 like (e.g., BCL2L1 (Bcl-x), BCL2L2 (BIM); Bcl-x; NCBI Gene IDs: 598, 10018); beta 3-adrenergic receptor (ADRB3; NCBI Gene ID: 155); bone gamma-carboxyglutamate protein (BGLAP; NCBI Gene ID: 632); bone morphogenetic protein-10 ligand (BMP10; NCBI Gene ID: 27302); bradykinin receptors (e.g., BDKRB1, BDKRB2; NCBI Gene IDs: 623, 624); B-RAF (BRAF; NCBI Gene ID: 273); breakpoint cluster region (BCR; NCBI Gene ID: 613); bromodomain and external domain (BET) bromodomain containing proteins (e.g., BRD2, BRD3, BRD4, BRDT; NCBI Gene IDs: 6046, 8019, 23476, 676); Bruton's tyrosine kinase (BTK; NCBI Gene ID: 695); cadherins (e.g., CDH3 (p-cadherin), CDH6 (k-cadherin); NCBI Gene IDs: 1001, 1004); cancer/testis antigens (e.g., CTAG1A, CTAG1B, CTAG2; NCBI Gene IDs: 1485, 30848, 246100); cannabinoid receptors (e.g., CNR1 (CB1), CNR2 (CB2); NCBI Gene IDs: 1268, 1269); carbohydrate sulfotransferase 15 (CHST15; NCBI Gene ID: 51363); carbonic anhydrases (e.g., CA1, CA2, CA3, CA4, CA5A, CA5B, CA6, CA7, CA8, CA9, CA10, CA11, CA12, CA13, CA14; NCBI Gene IDs: 759, 760, 761, 762, 763, 765, 766, 767, 768, 770, 771, 11238, 23632, 56934, 377677); carcinoembryonic antigen related cell adhesion molecules (e.g., CEACAM3 (CD66d), CEACAM5 (CD66e), CEACAM6 (CD66c); NCBI Gene IDs: 1048, 1084, 4680); casein kinases (e.g., CSNK1A1 (CK1), CSNK2A1 (CK2); NCBI Gene IDs: 1452, 1457); caspases (e.g., CASP3, CASP7, CASP8; NCBI Gene IDs: 836, 840, 841, 864); catenin beta 1 (CTNNB1; NCBI Gene ID: 1499); cathepsin G (CTSG; NCBI Gene ID: 1511); Cbl proto-oncogene B (CBLB, Cbl-b; NCBI Gene ID: 868); C-C motif chemokine ligand 21 (CCL21; NCBI Gene ID: 6366); C-C motif chemokine receptor 2 (CCR2; NCBI Gene ID: 729230); C-C motif chemokine receptors (e.g., CCR3 (CD193), CCR4 (CD194), CCR5 (CD195), CCR8 (CDw198); NCBI Gene IDs: 1232, 1233, 1234, 1237); CCAAT enhancer binding protein alpha (CEBPA, CEBP; NCBI Gene ID: 1050); cell adhesion molecule 1 (CADM1; NCBI Gene ID: 23705); cell division cycle 7 (CDC7; NCBI Gene ID: 8317); cellular communication network factor 2 (CCN2; NCBI Gene ID: 1490); cereblon (CRBN; NCBI Gene ID: 51185); checkpoint kinases (e.g., CHEK1 (CHK1), CHEK2 (CHK2); NCBI Gene IDs: 1111, 11200); cholecystokinin B receptor (CCKBR; NCBI Gene ID: 887); chorionic somatomammotropin hormone 1 (CSH1; NCBI Gene ID: 1442); claudins (e.g., CLDN6, CLDN18; NCBI Gene IDs: 9074, 51208); cluster of differentiation markers (e.g., CD1A, CD1C, CD1D, CD1E, CD2, CD3 alpha (TRA), CD beta (TRB), CD gamma (TRG), CD delta (TRD), CD4, CD8A, CD8B, CD19, CD20 (MS4A1), CD22, CD24, CD25 (IL2RA, TCGFR), CD28, CD33 (SIGLEC3), CD37, CD38, CD39 (ENTPD1), CD40 (TNFRSF5), CD44 (MIC4, PGP1), CD47 (IAP), CD48 (BLAST1), CD52, CD55 (DAF), CD58 (LFA3), CD74, CD79a, CD79b, CD80 (B7-1), CD84, CD86 (B7-2), CD96 (TACTILE), CD99 (MIC2), CD115 (CSF1R), CD116 (GMCSFR, CSF2RA), CD122 (IL2RB), CD123 (IL3RA), CD128 (IL8R1), CD132 (IL2RG), CD135 (FLT3), CD137 (TNFRSF9, 4-1BB), CD142 (TF, TFA), CD152 (CTLA4), CD160, CD182 (IL8R2), CD193 (CCR3), CD194 (CCR4), CD195 (CCR5), CD207, CD221 (IGF1R), CD222

(IGF2R), CD223 (LAG3), CD226 (DNAM1), CD244, CD247, CD248, CD276 (B7-H3), CD331 (FGFR1), CD332 (FGFR2), CD333 (FGFR3), CD334 (FGFR4); NCBI Gene IDs: 909, 911, 912, 913, 914, 919, 920, 923, 925, 926, 930, 931, 933, 940, 941, 942, 945, 951, 952, 953, 958,960, 961, 962, 965, 972, 973, 974, 1043, 1232, 1233, 1234, 1237, 1436, 1438, 1493, 1604, 2152, 2260, 2261, 2263, 2322, 3480, 3482, 3559, 3560, 3561, 3563, 3577, 3579, 3604, 3902, 4267, 6955, 6957, 6964, 6965, 8832, 10666, 11126, 50489, 51744, 80381, 100133941); clusterin (CLU; NCBI Gene ID: 1191); coagulation factors (e.g., F7, FXA, NCBI Gene IDs: 2155, 2159); collagen type IV alpha chains (e.g., COL4A1, COL4A2, COL4A3, COL4A4, COL4A5; NCBI Gene IDs: 1282, 1284, 1285, 1286, 1287); collectin subfamily member 10 (COLEC10; NCBI Gene ID: 10584); colony stimulating factors (e.g., CSF1 (MCSF), CSF2 (GMCSF), CSF3 (GCSF); NCBI Gene IDs: 1435, 1437, 1440); complement factors (e.g., C3, C5; NCBI Gene IDs: 718, 727); COP9 signalosome subunit 5 (COPS5; NCBI Gene ID: 10987); C-type lectin domain family member (e.g., CLEC4C (CD303), CLEC9A (CD370), CLEC12A (CD371); CD371; NCBI Gene ID: 160364, 170482, 283420); C-X-C motif chemokine ligand 12 (CXCL12; NCBI Gene ID: 6387); C-X-C motif chemokine receptors (CXCR1 (IL8R1, CD128), CXCR2 (IL8R2, CD182), CXCR3 (CD182, CD183, IP-10R), CXCR4 (CD184); NCBI Gene ID: 2833, 3577, 3579, 7852); cyclin D1 (CCND1, BCL1; NCBI Gene ID: 595); cyclin dependent kinases (e.g., CDK1, CDK2, CDK3, CDK4, CDK5, CDK6, CDK7, CDK8, CDK9, CDK10, CDK12; NCBI Gene ID: 983, 1017, 1018, 1019, 1020, 1021, 1022, 1024, 1025, 8558, 51755); cyclin G1 (CCNG1; NCBI Gene ID: 900); cytochrome P450 family members (e.g., CYP2D6, CYP3A4, CYP11A1, CYP11B2, CYP17A1, CYP19A1, CYP51A1; NCBI Gene IDs: 1565, 1576, 1583, 1585, 1586, 1588, 1595); cytochrome P450 oxidoreductase (POR; NCBI Gene ID: 5447); cytokine inducible SH2 containing protein (CISH; NCBI Gene ID: 1154); cytotoxic T-lymphocyte associated protein 4 (CTLA4, CD152; NCBI Gene ID: 1493); DEAD-box helicases (e.g., DDX5, DDX6, DDX58; NCBI Gene IDs: 1655, 1656, 23586); delta like canonical Notch ligands (e.g., DLL3, DLL4; NCBI Gene IDs: 10683, 54567); diablo IAP-binding mitochondrial protein (DIABLO, SMAC; NCBI Gene ID: 56616); diacylglycerol kinases (e.g., DGKA, DGKZ; NCBI Gene IDs: 1606, 8525); dickkopf WNT signaling pathway inhibitors (e.g., DKK1, DKK3; NCBI Gene ID: 22943, 27122); dihydrofolate reductase (DHFR; NCBI Gene ID: 1719); dihydropyrimidine dehydrogenase (DPYD; NCBI Gene ID: 1806); dipeptidyl peptidase 4 (DPP4; NCBI Gene ID: 1803); discoidin domain receptor tyrosine kinases (e.g., DDR1 (CD167), DDR2; CD167; NCBI Gene ID: 780, 4921); DNA dependent protein kinase (PRKDC; NCBI Gene ID: 5591); DNA topoisomerases (e.g., TOP1, TOP2A, TOP2B, TOP3A, TOP3B; NCBI Gene ID: 7150, 7153, 7155, 7156, 8940); dopachrome tautomerase (DCT; NCBI Gene ID: 1638); dopamine receptor D2 (DRD2; NCBI Gene ID: 1318); DOT1 like histone lysine methyltransferase (DOT 1L; NCBI Gene ID: 84444); ectonucleotide pyrophosphatase/phosphodiesterase 3 (ENPP3, CD203c; NCBI Gene ID: 5169); EMAP like 4 (EML4; NCBI Gene ID: 27436); endoglin (ENG; NCBI Gene ID: 2022); endoplasmic reticulum aminopeptidases (e.g., ERAP1, ERAP2; NCBI Gene ID: 51752, 64167); enhancer of zeste 2 polycomb repressive complex 2 subunit (EZH2; NCBI Gene ID: 2146); ephrin receptors (e.g., EPHA1, EPHA2EPHA3, EPHA4, EPHA5, EPHA7, EPHB4; NCBI Gene ID: 1969, 2041, 2042, 2043, 2044, 2045, 2050); ephrins (e.g., EFNA1, EFNA4, EFNB2; NCBI Gene ID: 1942, 1945, 1948); epidermal growth factor receptors (e.g., ERBB1 (HER1, EGFR), ERBB1 variant III (EGFRvIII), ERBB2 (HER2, NEU, CD340), ERBB3 (HER3), ERBB4 (HER4); NCBI Gene ID: 1956, 2064, 2065, 2066); epithelial cell adhesion molecule (EPCAM; NCBI Gene ID: 4072); epithelial mitogen (EPGN; NCBI Gene ID: 255324); eukaryotic translation elongation factors (e.g., EEF1A2, EEF2; NCBI Gene ID: 1917, 1938); eukaryotic translation initiation factors (e.g., EIF4A1, EIF5A; NCBI Gene ID: 1973, 1984); exportin-1 (XPO1; NCBI Gene ID: 7514); farnesoid X receptor (NR1H4, FXR; NCBI Gene ID: 9971); Fas ligand (FASLG, FASL, CD95L, CD178, TNFSF6; NCBI Gene ID: 356); fatty acid amide hydrolase (FAAH; NCBI Gene ID: 2166); fatty acid synthase (FASN; FAS; NCBI Gene ID: 2194); Fc fragment of Ig receptors (e.g., FCER1A, FCGRT, FCGR3A (CD16); NCBI Gene IDs: 2205, 2214, 2217); Fc receptor like 5 (FCRL5, CD307; NCBI Gene ID: 83416); fibroblast activation protein alpha (FAP; NCBI Gene ID: 2191); fibroblast growth factor receptors (e.g., FGFR1 (CD331), FGFR2 (CD332), FGFR3 (CD333), FGFR4 (CD334); NCBI Gene IDs: 2260, 2261, 2263, 2264); fibroblast growth factors (e.g., FGF1 (FGF alpha), FGF2 (FGF beta), FGF4, FGF5; NCBI Gene IDs: 2246, 2247, 2249, 2250); fibronectin 1 (FN1, MSF; NCBI Gene ID: 2335); fms related receptor tyrosine kinases (e.g., FLT1 (VEGFR1), FLT3 (STK1, CD135), FLT4 (VEGFR2); NCBI Gene IDs: 2321, 2322, 2324); fms related receptor tyrosine kinase 3 ligand (FLT3LG; NCBI Gene ID: 2323); focal adhesion kinase 2 (PTK2, FAK1; NCBI Gene ID: 5747); folate hydrolase 1 (FOLH1, PSMA; NCBI Gene ID: 2346); folate receptor 1 (FOLR1; NCBI Gene ID: 2348); forkhead box protein M1 (FOXM1; NCBI Gene ID: 2305); FURIN (FURIN, PACE; NCBI Gene ID: 5045); FYN tyrosine kinase (FYN, SYN; NCBI Gene ID: 2534); galectins (e.g., LGALS3, LGALS8 (PCTA1), LGALS9; NCBI Gene ID: 3958, 3964, 3965); glucocorticoid receptor (NR3C1, GR; NCBI Gene ID: 2908); glucuronidase beta (GUSB; NCBI Gene ID: 2990); glutamate metabotropic receptor 1 (GRM1; NCBI Gene ID: 2911); glutaminase (GLS; NCBI Gene ID: 2744); glutathione S-transferase Pi (GSTP1; NCBI Gene ID: 2950); glycogen synthase kinase 3 beta (GSK3B; NCBI Gene ID: 2932); glypican 3 (GPC3; NCBI Gene ID: 2719); gonadotropin releasing hormone 1 (GNRH1; NCBI Gene ID: 2796); gonadotropin releasing hormone receptor (GNRHR; NCBI Gene ID: 2798); GPNMB glycoprotein nmb (GPNMB, osteoactivin; NCBI Gene ID: 10457); growth differentiation factor 2 (GDF2, BMP9; NCBI Gene ID: 2658); growth factor receptor-bound protein 2 (GRB2, ASH; NCBI Gene ID: 2885); guanylate cyclase 2C (GUCY2C, STAR, MECIL, MUCIL, NCBI Gene ID: 2984); H19 imprinted maternally expressed transcript (H19; NCBI Gene ID: 283120); HCK proto-oncogene, Src family tyrosine kinase (HCK; NCBI Gene ID: 3055); heat shock proteins (e.g., HSPA5 (HSP70, BIP, GRP78), HSPB1 (HSP27), HSP90B1 (GP96); NCBI Gene IDs: 3309, 3315, 7184); heme oxygenases (e.g., HMOX1 (HO1), HMOX2 (HO1); NCBI Gene ID: 3162, 3163); heparanase (HPSE; NCBI Gene ID: 10855); hepatitis A virus cellular receptor 2 (HAVCR2, TIM3, CD366; NCBI Gene ID: 84868); hepatocyte growth factor (HGF; NCBI Gene ID: 3082); HERV-H LTR-associating 2 (HHLA2, B7-H7; NCBI Gene ID: 11148); histamine receptor H2 (HRH2; NCBI Gene ID: 3274); histone deacetylases (e.g., HDAC1, HDAC7, HDAC9; NCBI Gene ID: 3065, 9734, 51564); HRas proto-oncogene, GTPase (HRAS; NCBI Gene ID: 3265); hypoxia-inducible factors (e.g., HIF1A, HIF2A (EPAS1); NCBI Gene IDs: 2034, 3091); I-Kappa-B kinase (IKK beta; NCBI Gene IDs: 3551, 3553); IKAROS family zinc fingers (IKZF1 (LYF1), IKZF3; NCBI Gene ID: 10320, 22806); immunoglobulin superfamily member 11 (IGSF11; NCBI Gene ID: 152404); indoleamine 2,3-dioxygenases (e.g., IDO1, ID2; NCBI Gene IDs: 3620, 169355); inducible T cell costimulator (ICOS, CD278; NCBI Gene ID: 29851); inducible T cell costimulator ligand (ICOSLG, B7-H2; NCBI Gene ID: 23308); insulin like growth factor receptors (e.g., IGF1R, IGF2R; NCBI Gene ID: 3480, 3482); insulin like growth factors (e.g., IGF1, IGF2; NCBI Gene IDs: 3479, 3481); insulin receptor (INSR, CD220; NCBI Gene ID: 3643); integrin subunits (e.g., ITGA5 (CD49e), ITGAV (CD51), ITGB1 (CD29), ITGB2 (CD18, LFA1, MAC1), ITGB7; NCBI Gene IDs: 3678, 3685, 3688, 3695, 3698); intercellular adhesion molecule 1 (ICAM1, CD54; NCBI Gene ID: 3383); interleukin 1 receptor associated kinase 4 (IRAK4; NCBI Gene ID: 51135); interleukin receptors (e.g., IL2RA (TCGFR, CD25), IL2RB (CD122), IL2RG (CD132), IL3RA, IL6R, IL13RA2 (CD213A2), IL22RA1; NCBI Gene IDs: 3598, 3559, 3560, 3561, 3563, 3570, 58985); interleukins (e.g., IL1A, IL1B, IL2, IL3, IL6 (HGF), IL7, IL8 (CXCL8), IL10 (TGIF), IL12A, IL12B, IL15, IL17A (CTLA8), IL18, IL23A, IL24, IL-29 (IFNL1); NCBI Gene IDs: 3552, 3553, 3558, 3562, 3565, 3569, 3574, 3586, 3592, 3593, 3600, 3605, 3606, 11009, 51561, 282618); isocitrate dehydrogenases (NADP(+)1) (e.g., IDH1, IDH2; NCBI Gene IDs: 3417, 3418); Janus kinases (e.g., JAK1, JAK2, JAK3; NCBI Gene IDs: 3716, 3717, 3718); kallikrein related peptidase 3 (KLK3; NCBI Gene ID: 354); killer cell immunoglobulin like receptor, Ig domains and long cytoplasmic tails (e.g., KIR2DL1 (CD158A), KIR2DL2 (CD158B1), KIR2DL3 (CD158B), KIR2DL4 (CD158D), KIR2DL5A (CD158F), KIR2DL5B, KIR3DL1 (CD158E1), KIR3DL2 (CD158K), KIR3DP1 (CD158c), KIR2DS2 (CD158J); NCBI Gene IDs: 3802, 3803, 3804, 3805, 3811, 3812, 57292, 553128, 548594, 100132285); killer cell lectin like receptors (e.g., KLRC1 (CD159A), KLRC2 (CD159c), KLRC3, KLRRC4, KLRD1 (CD94), KLRG1, KLRK1 (NKG2D, CD314); NCBI Gene IDs: 3821, 3822, 3823, 3824, 8302, 10219, 22914); kinase insert domain receptor (KDR, CD309, VEGFR2; NCBI Gene ID: 3791); kinesin family member 11 (KIF11; NCBI Gene ID: 3832); KiSS-1 metastasis suppressor (KISS1; NCBI Gene ID: 3814); KIT proto-oncogene, receptor tyrosine kinase (KIT, C-KIT, CD117; NCBI Gene ID: 3815); KRAS proto-oncogene, GTPase (KRAS; NCBI Gene ID: 3845); lactotransferrin (LTF; NCBI Gene ID: 4057); LCK proto-oncogene, Src family tyrosine kinase (LCK; NCBI Gene ID: 3932); LDL receptor related protein 1 (LRP1, CD91, IGFBP3R; NCBI Gene ID: 4035); leucine rich repeat containing 15 (LRRC15; NCBI Gene ID: 131578); leukocyte immunoglobulin like receptors (e.g., LILRB1 (ILT2, CD85J), LILRB2 (ILT4, CD85D); NCBI Gene ID: 10288, 10859); leukotriene A4 hydrolase (LTA4H; NCBI Gene ID: 4048); linker for activation of T-cells (LAT; NCBI Gene ID: 27040); luteinizing hormone/choriogonadotropin receptor (LHCGR; NCBI Gene ID: 3973); LY6/PLAUR domain containing 3 (LYPD3; NCBI Gene ID: 27076); lymphocyte activating 3 (LAG3; CD223; NCBI Gene ID: 3902); lymphocyte antigens (e.g., LY9 (CD229), LY75 (CD205); NCBI Gene IDs: 4063, 17076); LYN proto-oncogene, Src family tyrosine kinase (LYN; NCBI Gene ID: 4067); lypmphocyte cytosolic protein 2 (LCP2; NCBI Gene ID: 3937); lysine demethylase 1A (KDM1A; NCBI Gene ID: 23028); lysophosphatidic acid receptor 1 (LPAR1, EDG2, LPA1, GPR26; NCBI Gene ID: 1902); lysyl oxidase (LOX; NCBI Gene ID: 4015); lysyl oxidase like 2 (LOXL2; NCBI Gene ID: 4017); macrophage migration inhibitory factor (MIF, GIF; NCBI Gene ID: 4282); macrophage stimulating 1 receptor (MST1R, CD136; NCBI Gene ID: 4486); MAGE family members (e.g., MAGEA1, MAGEA2, MAGEA2B, MAGEA3, MAGEA4, MAGEA5, MAGEA6, MAGEA10, MAGEA11, MAGEC1, MAGEC2, MAGED1, MAGED2; NCBI Gene IDs: 4100, 4101, 4102, 4103, 4104, 4105, 4109, 4110, 9500, 9947, 10916, 51438, 266740); major histocompatibility complexes (e.g., HLA-A, HLA-E, HLA-F, HLA-G; NCBI Gene IDs: 3105, 3133, 3134, 3135); major vault protein (MVP, VAULTi; NCBI Gene ID: 9961); MALT1 paracaspase (MALT1; NCBI Gene ID: 10892); MAPK activated protein kinase 2 (MAPKAPK2; NCBI Gene ID: 9261); MAPK interacting serine/threonine kinases (e.g., MKNK1, MKNK2; NCBI Gene IDs: 2872, 8569); matrix metallopeptidases (e.g., MMP1, MMP2, MMP3, MMP7, MMP8, MMP9, MMP10, MMP11, MMP12, MMP13, MMP14, MMP15, MMP16, MMP17, MMP19, MMP20, MMP21, MMP24, MMP25, MMP26, MMP27, MMP28; NCBI Gene IDs: 4312, 4313, 4314, 4316, 4317, 4318, 4319, 4320, 4321, 4322, 4323, 4324, 4325, 4326, 4327, 9313, 10893, 56547, 64066, 64386, 79148, 118856); MCL1 apoptosis regulator, BCL2 family member (MCL1; NCBI Gene ID: 4170); MDM2 proto-oncogene (MDM2; NCBI Gene ID: 4193); MDM4 regulator of p53 (MDM4; BMFS6; NCBI Gene ID: 4194); mechanistic target of rapamycin kinase (MTOR, FRAP1; NCBI Gene ID: 2475); melan-A (MLANA; NCBI Gene ID: 2315); melanocortin receptors (MC1R, MC2R; NCBI Gene IDs: 4157, 4148); MER proto-oncogene, tyrosine kinase (MERTK; NCBI Gene ID: 10461); mesothelin (MSLN; NCBI Gene ID: 10232); MET proto-oncogene, receptor tyrosine kinase (MET, c-Met, HGFR; NCBI Gene ID: 4233); methionyl aminopeptidase 2 (METAP2, MAP2; NCBI Gene ID: 10988); MHC class I polypeptide-related sequences (e.g., MICA, MICB; NCBI Gene IDs: 4277, 100507436); mitogen activated protein kinases (e.g., MAPK1 (ERK2), MAPK3 (ERK1), MAPK8 (JNK1), MAPK9 (JNK2), MAPK10 (JNK3), MAPK11 (p38 beta), MAPK12; NCBI Gene IDs: 5594, 5595, 5599, 5600, 5601, 5602, 819251); mitogen-activated protein kinase kinases (e.g., MAP3K5 (ASK1), MAP3K8 (TPL2, AURA2); NCBI Gene IDs: 4217, 1326); mitogen-activated protein kinase kinase kinase kinase 1 (MAP4K1, HPK1; NCBI Gene ID: 11184); mitogen-activated protein kinases (e.g., MAP2K1 (MEK1), MAP2K2 (MEK2), MAP2K7 (MEK7); NCBI Gene IDs: 5604, 5605, 5609); MPL proto-oncogene, thrombopoietin receptor (MPL; NCBI Gene ID: 4352); mucins (e.g., MUC1 (including splice variants thereof (e.g., including MUC1/A, C, D, X, Y, Z and REP)), MUC5AC, MUC16 (CA125); NCBI Gene IDs: 4582, 4586, 94025); MYC proto-oncogene, bHLH transcription factor (MYC; NCBI Gene ID: 4609); myostatin (MSTN, GDF8; NCBI Gene ID: 2660); myristoylated alanine rich protein kinase C substrate (MARCKS; NCBI Gene ID: 4082); natriuretic peptide receptor 3 (NPR3; NCBI Gene ID: 4883); natural killer cell cytotoxicity receptor 3 ligand 1 (NCR3LG1, B7-H6; NCBI Gene ID: 374383); necdin, MAGE family member (NDN; NCBI Gene ID: 4692); nectin cell adhesion molecules (e.g., NECTIN2 (CD112, PVRL2), NECTIN4 (PVRL4); NCBI Gene IDs: 5819, 81607); neural cell adhesion molecule 1 (NCAM1, CD56; NCBI Gene ID: 4684); neuropilins (e.g., NRP1 (CD304, VEGF165R), NRP2 (VEGF165R2); NCBI Gene IDs: 8828, 8829); neurotrophic receptor tyrosine kinases (e.g., NTRK1 (TRKA), NTRK2 (TRKB), NTRK3 (TRKC); NCBI Gene IDs: 4914, 4915, 4916); NFKB activating protein (NKAP; NCBI Gene ID: 79576); NIMA related kinase 9 (NEK9; NCBI Gene ID: 91754); NLR family pyrin domain containing 3 (NLRP3, NALP3; NCBI Gene ID: 114548); notch receptors (e.g., NOTCH1, NOTCH2, NOTCH3, NOTCH4; NCBI Gene IDs: 4851, 4853, 4854, 4855); NRAS proto-oncogene, GTPase (NRAS; NCBI Gene ID: 4893); nuclear factor kappa B (NFKB1, NFKB2; NCBI Gene IDs: 4790, 4791); nuclear factor, erythroid 2 like 2 (NFE2L2; NRF2; NCBI Gene ID: 4780); nuclear receptor subfamily 4 group A member 1 (NR4A1; NCBI Gene ID: 3164); nucleolin (NCL; NCBI Gene ID: 4691); nucleophosmin 1 (NPM1; NCBI Gene ID: 4869); nucleotide binding oligomerization domain containing 2 (NOD2; NCBI Gene ID: 64127); nudix hydrolase 1 (NUDT1; NCBI Gene ID: 4521); O-6-methylguanine-DNA methyltransferase (MGMT; NCBI Gene ID: 4255); opioid receptor delta 1 (OPRD1; NCBI Gene ID: 4985); ornithine decarboxylase 1 (ODC1; NCBI Gene ID: 4953); oxoglutarate dehydrogenase (OGDH; NCBI Gene ID: 4967); parathyroid hormone (PTH; NCBI Gene ID: 5741); PD-L1 (CD274; NCBI Gene ID: 29126); periostin (POSTN; NCBI Gene ID: 10631); peroxisome proliferator activated receptors (e.g., PPARA (PPAR alpha), PPARD (PPAR delta), PPARG (PPAR gamma); NCBI Gene IDs: 5465, 5467, 5468); phosphatase and tensin homolog (PTEN; NCBI Gene ID: 5728); phosphatidylinositol-4,5-bisphosphate 3-kinases (PIK3CA (PI3K alpha), PIK3CB (PI3K beta), PIK3CD (PI3K delta), PIK3CG (PI3K gamma); NCBI Gene IDs: 5290, 5291, 5293, 5294); phospholipases (e.g., PLA2G1B, PLA2G2A, PLA2G2D, PLA2G3, PLA2G4A, PLA2G5, PLA2G7, PLA2G10, PLA2G12A, PLA2G12B, PLA2G15; NCBI Gene IDs: 5319, 5320, 5321, 5322, 7941, 8399, 50487, 23659, 26279, 81579, 84647); Pim proto-oncogene, serine/threonine kinases (e.g., PIM1, PIM2, PIM3; NCBI Gene IDs: 5292, 11040, 415116); placenta growth factor (PGF; NCBI Gene ID: 5228); plasminogen activator, urokinase (PLAU, u-PA, ATF; NCBI Gene ID: 5328); platelet derived growth factor receptors (e.g., PDGFRA (CD140A, PDGFR2), FDGFRB (CD140B, PDGFR1); NCBI Gene IDs: 5156, 5159); plexin B1 (PLXNB1; NCBI Gene ID: 5364); poliovirus receptor (PVR) cell adhesion molecule (PVR, CD155; NCBI Gene ID: 5817); polo like kinase 1 (PLK1; NCBI Gene ID: 5347); poly(ADP-ribose) polymerases (e.g., PARP1, PARP2, PARP3; NCBI Gene IDs: 142, 10038, 10039); polycomb protein EED (EED; NCBI Gene ID: 8726); porcupine O-acyltransferase (PORCN; NCBI Gene ID: 64840); PRAME nuclear receptor transcriptional regulator (PRAME; NCBI Gene ID: 23532); premelanosome protein (PMEL; NCBI Gene ID: 6490); progesterone receptor (PGR; NCBI Gene ID: 5241); programmed cell death 1 (PDCD1, PD-1, CD279; NCBI Gene ID: 5133); programmed cell death 1 ligand 2 (PDCD1LG2, CD273, PD-L2; NCBI Gene ID: 80380); prominin 1 (PROM1, CD133; NCBI Gene ID: 8842); promyelocytic leukemia (PML; NCBI Gene ID: 5371); prosaposin (PSAP; NCBI Gene ID: 5660); prostaglandin E receptor 4 (PTGER4; NCBI Gene ID: 5734); prostaglandin E synthase (PTGES; NCBI Gene ID: 9536); prostaglandin-endoperoxide synthases (PTGS1 (COX1), PTGS2 (COX2); NCBI Gene ID: 5742, 5743); proteasome 20S subunit beta 9 (PSMB9; NCBI Gene ID: 5698); protein arginine methyltransferases (e.g., PRMT1, PRMT5; NCBI Gene ID: 3276, 10419); protein kinase N3 (PKN3; NCBI Gene ID: 29941); protein phosphatase 2A (PPP2CA; NCBI Gene ID: 5515); protein tyrosine kinase 7 (inactive) (PTK7; NCBI Gene ID: 5754); protein tyrosine phosphatase receptors (PTPRB (PTPB), PTPRC (CD45R); NCBI Gene ID: 5787, 5788); prothymosin alpha (PTMA; NCBI Gene ID: 5757); purine nucleoside phosphorylase (PNP; NCBI Gene ID: 4860); purinergic receptor P2X 7 (P2RX7; NCBI Gene ID: 5027); PVR related immunoglobulin domain containing (PVRIG, CD112R; NCBI Gene ID: 79037); Raf-1 proto-oncogene, serine/threonine kinase (RAF1, c-Raf; NCBI Gene ID: 5894); RAR-related orphan receptor gamma (RORC; NCBI Gene ID: 6097); ras homolog family member C (RHOC); NCBI Gene ID: 389); Ras homolog, mTORC1 binding (RHEB; NCBI Gene ID: 6009); RB transcriptional corepressor 1 (RB1; NCBI Gene ID: 5925); receptor-interacting serine/threonine protein kinase 1 (RIPK1; NCBI Gene ID: 8737); ret proto-oncogene (RET; NCBI Gene ID: 5979); retinoic acid early transcripts (e.g., RAETIE, RAETIG, RAET1L; NCBI Gene IDs: 135250, 154064, 353091); retinoic acid receptors alpha (e.g., RARA, RARG; NCBI Gene IDs: 5914, 5916); retinoid X receptors (e.g., RXRA, RXRB, RXRG; NCBI Gene IDs: 6256, 6257, 6258); Rho associated coiled-coil containing protein kinases (e.g., ROCK1, ROCK2; NCBI Gene IDs: 6093, 9475); ribosomal protein S6 kinase B1 (RPS6KB1, S6K-beta 1; NCBI Gene ID: 6198); ring finger protein 128 (RNF128, GRAIL; NCBI Gene ID: 79589); ROS proto-oncogene 1, receptor tyrosine kinase (ROS1; NCBI Gene ID: 6098); roundabout guidance receptor 4 (ROBO4; NCBI Gene ID: 54538); RUNX family transcription factor 3 (RUNX3; NCBI Gene ID: 864); S100 calcium binding protein A9 (S100A9; NCBI Gene ID: 6280); secreted frizzled related protein 2 (SFRP2; NCBI Gene ID: 6423); secreted phosphoprotein 1 (SPP1; NCBI Gene ID: 6696); secretoglobin family 1A member 1 (SCGB1A1; NCBI Gene ID: 7356); selectins (e.g., SELE, SELL (CD62L), SELP (CD62); NCBI Gene IDs: 6401, 6402, 6403); semaphorin 4D (SEMA4D; CD100; NCBI Gene ID: 10507); sialic acid binding Ig like lectins (SIGLEC7 (CD328), SIGLEC9 (CD329), SIGLEC10; NCBI Gene ID: 27036, 27180, 89790); signal regulatory protein alpha (SIRPA, CD172A; NCBI Gene ID: 140885); signal transducer and activator of transcription (e.g., STAT1, STAT3, STAT5A, STAT5B; NCBI Gene IDs: 6772, 6774, 6776, 6777); sirtuin-3 (SIRT3; NCBI Gene ID: 23410); signaling lymphocytic activation molecule (SLAM) family members (e.g., SLAMF1 (CD150), SLAMF6 (CD352), SLAMF7 (CD319), SLAMF8 (CD353), SLAMF9; NCBI Gene IDs: 56833, 57823, 89886, 114836); SLIT and NTRK like family member 6 (SLITRK6; NCBI Gene ID: 84189); smoothened, frizzled class receptor (SMO; NCBI Gene ID: 6608); soluble epoxide hydrolase 2 (EPHX2; NCBI Gene ID: 2053); solute carrier family members (e.g., SLC3A2 (CD98), SLC5A5, SLC6A2, SLC10A3, SLC34A2, SLC39A6, SLC43A2 (LAT4), SLC44A4; NCBI Gene IDs: 6520, 6528, 6530, 8273, 10568, 25800, 80736, 124935); somatostatin receptors (e.g., SSTR1, SSTR2, SSTR3, SSTR4, SSTR5; NCBI Gene IDs: 6751, 6752, 6753, 6754, 6755); sonic hedgehog signaling molecule (SHH; NCBI Gene ID: 6469); Sp1 transcription factor (SP1; NCBI Gene ID: 6667); sphingosine kinases (e.g., SPHK1, SPHK2; NCBI Gene IDs: 8877, 56848); sphingosine-1-phosphate receptor 1 (S1PR1, CD363; NCBI Gene ID: 1901); spleen associated tyrosine kinase (SYK; NCBI Gene ID: 6850); splicing factor 3B factor 1 (SF3B1; NCBI Gene ID: 23451); SRC proto-oncogene, non-receptor tyrosine kinase (SRC; NCBI Gene ID: 6714); stabilin 1 (STAB1, CLEVER-1; NCBI Gene ID: 23166); STEAP family member 1 (STEAP1; NCBI Gene ID: 26872); steroid sulfatase (STS; NCBI Gene ID: 412); stimulator of interferon response cGAMP interactor 1 (STING1; NCBI Gene ID: 340061); superoxide dismutase 1 (SOD1, ALS1; NCBI Gene ID:

6647); suppressors of cytokine signaling (SOCS1 (CISH1), SOCS3 (CISH3); NCBI Gene ID: 8651, 9021); synapsin 3 (SYN3; NCBI Gene ID: 8224); syndecan 1 (SDC1, CD138, syndecan; NCBI Gene ID: 6382); synuclein alpha (SNCA, PARK1; NCBI Gene ID: 6622); T cell immunoglobulin and mucin domain containing 4 (TIMD4, SMUCKLER; NCBI Gene ID: 91937); T cell immunoreceptor with Ig and ITIM domains (TIGIT; NCBI Gene ID: 201633); tachykinin receptors (e.g., TACR1, TACR3; NCBI Gene ID: 6869, 6870); TANK binding kinase 1 (TBK1; NCBI Gene ID: 29110); tankyrase (TNKS; NCBI Gene ID: 8658); TATA-box binding protein associated factor, RNA polymerase I subunit B (TAF1B; NCBI Gene ID: 9014); T-box transcription factor T (TBXT; NCBI Gene ID: 6862); TCDD inducible poly(ADP-ribose) polymerase (TIPARP, PAPR7; NCBI Gene ID: 25976); tec protein tyrosine kinase (TEC; NCBI Gene ID: 7006); TEK receptor tyrosine kinase (TEK, CD202B, TIE2; NCBI Gene ID: 7010); telomerase reverse transcriptase (TERT; NCBI Gene ID: 7015); tenascin C (TNC; NCBI Gene ID: 3371); three prime repair exonucleases (e.g., TREX1, TREX2; NCBI Gene ID: 11277, 11219); thrombomodulin (THBD, CD141; NCBI Gene ID: 7056); thymidine kinases (e.g., TK1, TK2; NCBI Gene IDs: 7083, 7084); thymidine phosphorylase (TYMP; NCBI Gene ID: 1890); thymidylate synthase (TYMS; NCBI Gene ID: 7298); thyroid hormone receptor (THRA, THRB; NCBI Gene IDs: 7606, 7608); thyroid stimulating hormone receptor (TSHR; NCBI Gene ID: 7253); TNF superfamily members (e.g., TNFSF4 (OX40L, CD252), TNFSF5 (CD40L), TNFSF7 (CD70), TNFSF8 (CD153, CD30L), TNFSF9 (4-1BB-L, CD137L), TNFSF10 (TRAIL, CD253, APO2L), TNFSF11 (CD254, RANKL2, TRANCE), TNFSF13 (APRIL, CD256, TRAIL2), TNFSF13b (BAFF, BLYS, CD257), TNFSF14 (CD258, LIGHT), TNFSF18 (GITRL); NCBI Gene IDs: 944, 959, 970, 7292, 8600, 8740, 8741, 8743, 8744, 8995); toll like receptors (e.g., TLR1 (CD281), TLR2 (CD282), TLR3 (CD283), TLR4 (CD284), TLR5, TLR6 (CD286), TLR7, TLR8 (CD288), TLR9 (CD289), TLR10 (CD290); NCBI Gene IDs: 7096, 7097, 7098, 7099, 10333, 51284, 51311, 54106, 81793); transferrin (TF; NCBI Gene ID: 7018); transferrin receptor (TFRC, CD71; NCBI Gene ID: 7037); transforming growth factors (e.g., TGFA, TGFB1; NCBI Gene ID: 7039, 7040); transforming growth factor receptors (e.g., TGFBR1, TGFBR2, TGFBR3; NCBI Gene ID: 7046, 7048, 7049); transforming protein E7 (E7; NCBI Gene ID: 1489079); transglutaminase 5 (TGM5; NCBI Gene ID: 9333); transient receptor potential cation channel subfamily V member 1 (TRPV1, VR1; NCBI Gene ID: 7442); transmembrane and immunoglobulin domain containing 2 (TMIGD2, CD28H, IGPR1; NCBI Gene ID: 126259); triggering receptors expressed on myeloid cells (e.g., TREM1 (CD354), TREM2; NCBI Gene ID: 54209, 54210); trophinin (TRO, MAGED3; NCBI Gene ID: 7216); trophoblast glycoprotein (TPBG; NCBI Gene ID: 7162); tryptophan 2,3-dioxygenase (TDO2; NCBI Gene ID: 6999); tryptophan hydroxylases (e.g., TPH1, TPH2; NCBI Gene ID: 7166, 121278); tumor associated calcium signal transducer 2 (TACSTD2, TROP2, EGP1; NCBI Gene ID: 4070); tumor necrosis factor (TNF; NCBI Gene ID: 7124); tumor necrosis factor (TNF) receptor superfamily members (e.g., TNFRSF1A (CD120a), TNFRSF1B (CD120b), TNFRSF4 (OX40), TNFRSF5 (CD40), TNFRSF6 (CD95, FAS receptor), TNFRSF7 (CD27), TNFRSF8 (CD30), TNFRSF9 (CD137, 4-1BB), TNFRSF10A (CD261), TNFRSF10B (TRAIL, DR5, CD262), TNFRSF10C, TNFRSF10D, TNFRSF11A, TNFRSF11B (OPG), TNFRSF12A, TNFRSF13B, TNFR13C, (CD268, BAFFR), TNFRSF14 (CD270, LIGHTR), TNFRSF16, TNFRSF17 (CD269, BCMA), TNFRSF18 (GITR, CD357), TNFRSF19, TNFRSF21, TNFRSF25; NCBI Gene IDs: 355, 608, 939, 943, 958, 3604, 4804, 4982, 7132, 7133, 7293, 8718, 8764, 8784, 8792, 8793, 8794, 8795, 8797, 23495, 27242, 51330, 55504); tumor protein p53 (TP53; NCBI Gene ID: 7157); tumor suppressor 2, mitochondrial calcium regulator (TUSC2; NCBI Gene ID: 11334); TYRO3 protein tyrosine kinase (TYRO3; BYK; NCBI Gene ID: 7301); tyrosinase (TYR; NCBI Gene ID: 7299); tyrosine hydroxylase (TH; NCBI Gene ID: 7054); tyrosine kinase with immunoglobulin like and EGF like domains 1 (e.g., TIE1, TIE1; NCBI Gene ID: 7075); tyrosine-protein phosphatase non-receptor type 11 (PTPN11, SHP2; NCBI Gene ID: 5781); ubiquitin conjugating enzyme E2 I (UBE2I, UBC9; NCBI Gene ID: 7329); ubiquitin C-terminal hydrolase L5 (UCHL5; NCBI Gene ID: 51377); ubiquitin specific peptidase 7 (USP7; NCBI Gene ID: 7874); ubiquitin-like modifier activating enzyme 1 (UBA1; NCBI Gene ID: 7317); UL16 binding proteins (e.g., ULBP1, ULBP2, ULBP3; NCBI Gene ID: 79465, 80328, 80328); valosin-containing protein (VCP, CDC48; NCBI Gene ID: 7415); vascular cell adhesion molecule 1 (VCAM1, CD106; NCBI Gene ID: 7412); vascular endothelial growth factors (e.g., VEGFA, VEGFB; NCBI Gene ID: 7422, 7423); vimentin (VIM; NCBI Gene ID: 7431); vitamin D receptor (VDR; NCBI Gene ID: 7421); V-set domain containing T cell activation inhibitor 1 (VTCN1, B7-H4; NCBI Gene ID: 79679); V-set immuno-regulatory receptor (VSIR, VISTA, B7-H5; NCBI Gene ID: 64115); WEE1 G2 checkpoint kinase (WEE1; NCBI Gene ID: 7465); WRN RecQ like helicase (WRN; RECQ3; NCBI Gene ID: 7486); WT1 transcription factor (WT1; NCBI Gene ID: 7490); WW domain containing transcription regulator 1 (WWTR1; TAZ; NCBI Gene ID: 25937); X—C motif chemokine ligand 1 (XCL1, ATAC; NCBI Gene ID: 6375); X—C motif chemokine receptor 1 (XCR1, GPR5, CCXCR1; NCBI Gene ID: 2829); Yes1 associated transcriptional regulator (YAP1; NCBI Gene ID: 10413); or zeta chain associated protein kinase 70 (ZAP70; NCBI Gene ID: 7535).

In some embodiments, the one or more additional therapeutic agents include, e.g., an agent targeting 5'-nucleotidase ecto (NT5E or CD73; NCBI Gene ID: 4907); adenosine A2A receptor (ADORA2A; NCBI Gene ID: 135); adenosine $A_{2B}$ receptor (ADORA2B; NCBI Gene ID: 136); C-C motif chemokine receptor 8 (CCR8, CDw198; NCBI Gene ID: 1237); cytokine inducible SH2 containing protein (CISH; NCBI Gene ID: 1154); diacylglycerol kinase alpha (DGKA, DAGK, DAGK1 or DGK-alpha; NCBI Gene ID: 1606); fms like tyrosine kinase 3 (FLT3, CD135; NCBI Gene ID: 2322); integrin associated protein (IAP, CD47; NCBI Gene ID: 961); interleukine-2 (IL2; NCBI Gene ID: 3558); interleukine 2 receptor (IL2RA, IL2RB, IL2RG; NCBI Gene IDs: 3559, 3560, 3561); Kirsten rat sarcoma virus (KRAS; NCBI Gene ID: 3845; including mutations, such as KRAS G12C or G12D); mitogen-activated protein kinase kinase kinase 1 (MAP4K1) (also called Hematopoietic Progenitor Kinase 1 (HPK1), NCBI Gene ID: 11184); myeloid cell leukemia sequence 1 apoptosis regulator (MCL1; NCBI Gene ID: 4170); phosphatidylinositol-4,5-bisphosphate 3-kinase, catalytic subunit delta (PIK3CD; NCBI Gene ID: 5293); programmed death-ligand 1 (PD-L1, CD274; NCBI Gene ID 29126); programmed cell death protein 1 (PD-1, CD279; NCBI Gene ID: 5133); proto-oncogen c-KIT (KIT, CD117; NCBI Gene ID: 3815); signal-regulatory protein alpha (SIRPA, CD172A; NCBI Gene ID: 140885); TCDD inducible poly(ADP-ribose) polymerase (TIPARP, PARP7;

NCBI Gene ID: 25976); T cell immunoreceptor with Ig and ITIM domains (TIGIT; NCBI Gene ID: 201633); triggering receptor expressed on myeloid cells 1 (TREM1; NCBI Gene ID: 54210); triggering receptor expressed on myeloid cells 2 (TREM2; NCBI Gene ID: 54209); tumor-associated calcium signal transducer 2 (TACSTD2, TROP2, EGP1; NCBI Gene ID: 4070); tumor necrosis factor receptor superfamily, member 4 (TNFRSF4, CD134, OX40; NCBI Gene ID: 7293); tumor necrosis factor receptor superfamily, member 9 (TNFRSF9, 4-1BB, CD137; NCBI Gene ID: 3604); tumor necrosis factor receptor superfamily, member 18 (TNFRSF18, CD357, GITR; NCBI Gene ID: 8784); WRN RecQ like helicase (WRN; NCBI Gene ID: 7486); or zinc finger protein Helios (IKZF2; NCBI Gene ID: 22807).

Illustrative Mechanisms of Action

Immune Checkpoint Modulators

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In some embodiments, the immune checkpoint proteins or receptors regulate T cell responses (e.g., reviewed in Xu, et al., *J Exp Clin Cancer Res.* (2018) 37:110). In some embodiments, the immune checkpoint proteins or receptors regulate NK cell responses (e.g., reviewed in Davis, et al., *Semin Immunol.* (2017) 31:64-75 and Chiossone, et al., *Nat Rev Immunol.* (2018) 18(11):671-688). Inhibition of regulatory T-cells (Treg) or Treg depletion can alleviate their suppression of antitumor immune responses and have anticancer effects (e.g., reviewed in Plitas and Rudensky, *Annu. Rev. Cancer Biol.* (2020) 4:459-77; Tanaka and Sakaguchi, *Eur. J. Immunol.* (2019) 49:1140-1146).

Examples of immune checkpoint proteins or receptors that can be combined with a compound provided herein, or pharmaceutically acceptable salt thereof, include CD27 (NCBI Gene ID: 939), CD70 (NCBI Gene ID: 970); CD40 (NCBI Gene ID: 958), CD40LG (NCBI Gene ID: 959); CD47 (NCBI Gene ID: 961), SIRPA (NCBI Gene ID: 140885); CD48 (SLAMF2; NCBI Gene ID: 962), transmembrane and immunoglobulin domain containing 2 (TMIGD2, CD28H; NCBI Gene ID: 126259), CD84 (LY9B, SLAMF5; NCBI Gene ID: 8832), CD96 (NCBI Gene ID: 10225), CD160 (NCBI Gene ID: 11126), MS4A1 (CD20; NCBI Gene ID: 931), CD244 (SLAMF4; NCBI Gene ID: 51744); CD276 (B7H3; NCBI Gene ID: 80381); V-set domain containing T cell activation inhibitor 1 (VTCN1, B7H4); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943), TNFSF8 (CD30L; NCBI Gene ID: 944); TNFRSF10A (CD261, DR4, TRAILR1; NCBI Gene ID: 8797), TNFRSF9 (CD137; NCBI Gene ID: 3604), TNFSF9 (CD137L; NCBI Gene ID: 8744); TNFRSF10B (CD262, DR5, TRAILR2; NCBI Gene ID: 8795), TNFRSF10 (TRAIL; NCBI Gene ID: 8743); TNFRSF14 (HVEM, CD270; NCBI Gene ID: 8764), TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608), TNFSF13B (BAFF; NCBI Gene ID: 10673); TNFRSF18 (GITR; NCBI Gene ID: 8784), TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941), CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAETIE; ULBP4; NCBI Gene ID: 135250); retinoic acid early transcript 1G (RAETIG; ULBP5; NCBI Gene ID: 353091); retinoic acid early transcript 1L (RAET1L; ULBP6; NCBI Gene ID: 154064); killer cell immunoglobulin like receptor, three Ig domains and long cytoplasmic tail 1 (KIR, CD158E1; NCBI Gene ID: 3811, e.g., lirilumab (IPH-2102, IPH-4102)); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1); killer cell lectin like receptor D1 (KLRD1; NCBI Gene ID: 3824); killer cell lectin like receptor G1 (KLRG1; CLEC15A, MAFA, 2F1; NCBI Gene ID: 10219); sialic acid binding Ig like lectin 7 (SIGLEC7;

NCBI Gene ID: 27036); and sialic acid binding Ig like lectin 9 (SIGLEC9; NCBI Gene ID: 27180).

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with one or more blockers or inhibitors of one or more T-cell inhibitory immune checkpoint proteins or receptors. Illustrative T-cell inhibitory immune checkpoint proteins or receptors include CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the compound or pharmaceutically acceptable salt thereof provided herein is administered with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res.* (2018) 37:110.

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with one or more blockers or inhibitors of one or more NK-cell inhibitory immune checkpoint proteins or receptors. Illustrative NK-cell inhibitory immune checkpoint proteins or receptors include killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); killer cell lectin like receptor D1 (KLRD1, CD94), killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments the compound or pharmaceutically acceptable salt thereof provided herein is administered with one or more agonist or activators of one or more NK-cell stimulatory immune checkpoint proteins or receptors. Illustrative NK-cell stimulatory immune checkpoint proteins or receptors include CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol.* (2017) 31:64-75; Fang, et al., *Semin Immunol.* (2017) 31:37-54; and Chiossone, et al., *Nat Rev Immunol.* (2018) 18(11):671-688.

In some embodiments the one or more immune checkpoint inhibitors comprise a proteinaceous (e.g., antibody or fragment thereof, or antibody mimetic) inhibitor of PD-L1 (CD274), PD-1 (PDCD1), CTLA4, or TIGIT. In some embodiments the one or more immune checkpoint inhibitors comprise a small organic molecule inhibitor of PD-L1 (CD274), PD-1 (PDCD1), CTLA4, or TIGIT. In some embodiments the one or more immune checkpoint inhibitors comprise a proteinaceous (e.g., antibody or fragment thereof, or antibody mimetic) inhibitor of LAG3.

Examples of inhibitors of CTLA4 that can be co-administered include ipilimumab, tremelimumab, BMS-986218, AGEN1181, zalifrelimab (AGEN1884), BMS-986249, MK-1308, REGN-4659, ADU-1604, CS-1002 (ipilimumab biosimilar), BCD-145, APL-509, JS-007, BA-3071, ONC-392, AGEN-2041, HBM-4003, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include pembrolizumab, nivolumab, cemiplimab, pidilizumab, AMP-224, MEDI0680 (AMP-514), spartalizumab, atezolizumab, avelumab, durvalumab, BMS-936559, cosibelimab (CK-301), sasanlimab (PF-06801591), tislelizumab (BGB-A317), GLS-010 (WBP-3055), AK-103 (HX-008), AK-105, CS-1003, HLX-10, retifanlimab (MGA-012), BI-754091, balstilimab (AGEN-2034), AMG-404, toripalimab (JS-001), cetrelimab (JNJ-63723283), genolimzumab (CBT-501), LZM-009, prolgolimab (BCD-100), lodapolimab (LY-3300054), SHR-1201, camrelizumab (SHR-1210), Sym-021, budigalimab (ABBV-181), PD1-PIK, BAT-1306, avelumab (MSB0010718C), CX-072, CBT-502, dostarlimab (TSR-042), MSB-2311, JTX-4014, BGB-A333, SHR-1316, CS-1001 (WBP-3155), envafolimab (KN-035), sintilimab (IBI-308), HLX-20, KL-A167, STI-A1014, STI-A1015 (IMC-001), BCD-135, FAZ-053, TQB-2450, MDX1105-01, GS-4224, GS-4416, INCB086550, MAX10181, zimberelimab (AB122), spartalizumab (PDR-001), and compounds disclosed in WO2018195321, WO2020014643, WO2019160882, or WO2018195321, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1), RO-7247669 (PD-1/LAG-3), MGD-019 (PD-1/CTLA4), KN-046 (PD-1/CTLA4), MEDI-5752 (CTLA4/PD-1), RO-7121661 (PD-1/TIM-3), RG7769 (PD-1/TIM-3), TAK-252 (PD-1/OX40L), XmAb-20717 (PD-1/CTLA4), AK-104 (CTLA4/PD-1), FS-118 (LAG-3/PD-L1), FPT-155 (CTLA4/PD-L1/CD28), GEN-1046 (PD-L1/4-1BB), bintrafusp alpha (M7824; PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments the PD-L1 inhibitor is a small molecule inhibitor, such as CA-170, GS-4224, GS-4416 and lazertinib (GNS-1480; PD-L1/EGFR).

Examples of inhibitors of TIGIT that can be co-administered include tiragolumab (RG-6058), vibostolimab, domvanalimab (AB154), AB308, BMS-986207, AGEN-1307, COM-902, or etigilimab.

Examples of inhibitors of LAG3 that can be co-administered include leramilimab (LAG525).

Inhibition of regulatory T-cell (Treg) activity or Treg depletion can alleviate their suppression of antitumor immune responses and have anticancer effects. See, e.g., Plitas and Rudensky, *Annu. Rev. Cancer Biol.* (2020) 4:459-77; Tanaka and Sakaguchi, *Eur. J. Immunol.* (2019) 49:1140-1146. In some embodiments, a compound of Formula (I), (Ia), (Ib), or (Ic) provided herein, or pharmaceutically acceptable salt thereof, provided herein is administered with one or more inhibitors of Treg activity or a Treg depleting agent. Treg inhibition or depletion can augment the effect of immune checkpoint inhibitors in cancer therapeutics.

In some embodiments compound or pharmaceutically acceptable salt thereof provided herein is administered with one or more Treg inhibitors. In some embodiments the Treg inhibitor can suppress the migration of Tregs into the tumor microenvironment. In some embodiments Treg inhibitor can reduce the immunosuppressive function of Tregs. In some embodiments, the Treg inhibitor can modulate the cellular phenotype and induce production of proinflammatory cytokines. Exemplary Treg inhibitors include, without limitation, CCR4 (NCBI Gene ID: 1233) antagonists and degraders of Ikaros zinc-finger proteins (e.g., Ikaros (IKZF1; NCBI Gene ID: 10320), Helios (IKZF2; NCBI Gene ID: 22807), Aiolos (IKZF3; NCBI Gene ID: 22806), and Eos (IKZF4; NCBI Gene ID: 64375).

Examples of Helios degraders that can be co-administered include without limitation I-57 (Novartis) and compounds disclosed in WO2019038717, WO2020012334, WO20200117759, and WO2021101919.

In some embodiments a compound or pharmaceutically acceptable salt thereof provided herein is administered with one or more Treg depleting agents. In some embodiments the Treg depleting agent is an antibody. In some embodiments the Treg depleting antibody has antibody-dependent cytotoxic (ADCC) activity. In some embodiments, the Treg depleting antibody is Fc-engineered to possess an enhanced ADCC activity. In some embodiments the Treg depleting antibody is an antibody-drug conjugate (ADC). Illustrative targets for Treg depleting agents include without limitation CD25 (IL2RA; NCBI Gene ID: 3559), CTLA4 (CD152; NCBI Gene ID: 1493); GITR (TNFRSF18; NCBI Gene ID: 8784); 4-1BB (CD137; NCBI Gene ID: 3604), OX-40 (CD134; NCBI Gene ID: 7293), LAG3 (CD223; NCBI Gene ID: 3902), TIGIT (NCBI Gene ID: 201633), CCR4 (NCBI Gene ID: 1233), and CCR8 (NCBI Gene ID: 1237).

In some embodiments the Treg inhibitor or Treg depleting agent that can be co-administered comprises an antibody or antigen-binding fragment thereof that selectively binds to a cell surface receptor selected from the group consisting of C-C motif chemokine receptor 4 (CCR4), C-C motif chemokine receptor 7 (CCR7), C-C motif chemokine receptor 8 (CCR8), C—X—C motif chemokine receptor 4 (CXCR4; CD184), TNFRSF4 (OX40), TNFRSF18 (GITR, CD357), TNFRSF9 (4-1BB, CD137), cytotoxic T-lymphocyte associated protein 4 (CTLA4, CD152), programmed cell death 1 (PDCD1, PD-1), Sialyl Lewis x (CD15s), CD27, ecto-nucleoside triphosphate diphosphohydrolase 1 (ENTPD1; CD39), protein tyrosine phosphatase receptor type C (PTPRC; CD45), neural cell adhesion molecule 1 (NCAM1; CD56), selectin L (SELL; CD62L), integrin subunit alpha E (ITGAE; CD103), interleukin 7 receptor (IL7R; CD127), CD40 ligand (CD40LG; CD154), folate receptor alpha (FOLR1), folate receptor beta (FOLR2), leucine rich repeat containing 32 (LRRC32; GARP), IKAROS family zinc finger 2 (IKZF2; HELIOS), inducible T cell costimulatory (ICOS; CD278), lymphocyte activating 3 (LAG3; CD223), transforming growth factor beta 1 (TGFB1), hepatitis A virus cellular receptor 2 (HAVCR2; CD366; TIM3), T cell immunoreceptor with Ig and ITIM domains (TIGIT), TNF receptor superfamily member 1B (CD120b; TNFR2), IL2RA (CD25) or a combination thereof.

Examples of Treg depleting anti-CCR8 antibodies that can be administered include without limitation JTX-1811 (GS-1811) (Jounce Therapeutics, Gilead Sciences), BMS-986340 (Bristol Meyers Squibb), S-531011 (Shionogi), FPA157 (Five Prime Therapeutics), SRF-114 (Surface Oncology), HBM1022 (Harbor BioMed), IO-1 (Oncurious), and antibodies disclosed in WO2021163064, WO2020138489, and WO2021152186.

Examples of Treg depleting anti-CCR4 antibodies that can be administered include mogamulizumab.

Inhibiting, depleting, or reprogramming of non-stimulatory myeloid cells in the tumor microenvironment can enhance anti-cancer immune responses (see, e.g., Binnewies et al., *Nat. Med.* (2018) 24(5): 541-550; WO2016049641). Illustrative targets for depleting or reprogramming non-stimulatory myeloid cells include triggering receptors expressed on myeloid cells, TREM-1 (CD354, NCBI Gene ID: 54210) and TREM-2 (NCBI Gene ID: 54209). In some embodiments a compound or pharmaceutically acceptable salt thereof provided herein is administered with one or more myeloid cell depleting or reprogramming agents, such as an anti-TREM-1 antibody (e.g. PY159; antibodies disclosed in WO2019032624) or an anti-TREM-2 antibody (e.g., PY314; antibodies disclosed in WO2019118513).

Cluster of Differentiation Agonists or Activators

In some embodiments, a compound of Formula (I), (Ia), (Ib), or (Ic) provided herein, or pharmaceutically acceptable salt thereof, is administered with agents targeting a cluster of differentiation (CD) marker. Exemplary CD marker targeting agents that can be co-administered include without limitation A6, AD-IL24, neratinib, tucatinib (ONT 380), mobocertinib (TAK-788), tesevatinib, trastuzumab (HERCEPTIN®), trastuzumab biosimimar (HLX-02), margetuximab, BAT-8001, pertuzumab (Perjeta), pegfilgrastim, RG6264, zanidatamab (ZW25), cavatak, AIC-100, tagraxofusp (SL-401), HLA-A2402/HLA-A0201 restricted epitope peptide vaccine, dasatinib, imatinib, nilotinib, sorafenib, lenvatinib mesylate, ofranergene obadenovec, cabozantinib malate, AL-8326, ZLJ-33, KBP-7018, sunitinib malate, pazopanib derivatives, AGX-73, rebastinib, NMS-088, lucitanib hydrochloride, midostaurin, cediranib, dovitinib, sitravatinib, tivozanib, masitinib, regorafenib, olverembatinib dimesylate (HQP-1351), cabozantinib, ponatinib, and famitinib L-malate, CX-2029 (ABBV-2029), SCB-313, CA-170, COM-701, CDX-301, GS-3583, asunercept (APG-101), APO-010, and compounds disclosed in WO2016196388, WO2016033570, WO2015157386, WO199203459, WO199221766, WO2004080462, WO2005020921, WO2006009755, WO2007078034, WO2007092403, WO2007127317, WO2008005877, WO2012154480, WO2014100620, WO2014039714, WO2015134536, WO2017167182, WO2018112136, WO2018112140, WO2019155067, WO2020076105, PCT/US2019/063091, WO19173692, WO2016179517, WO2017096179, WO2017096182, WO2017096281, WO2018089628, WO2017096179, WO2018089628, WO2018195321, WO2020014643, WO2019160882, WO2018195321, WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170, WO2020068752, Cancer Discov. 2019 Jan. 9(1):8; and Gariepy J., et al. 106th Annu Meet Am Assoc Immunologists (AAI) (May 9-13, San Diego, 2019, Abst 71.5).

In some embodiments the CD marker targeting agents that can be co-administered include small molecule inhibitors, such as PBF-1662, BLZ-945, pemigatinib (INCB-054828), rogaratinib (BAY-1163877), AZD4547, roblitinib (FGF-401), quizartinib dihydrochloride, SX-682, AZD-5069, PLX-9486, avapritinib (BLU-285), ripretinib (DCC-2618), imatinib mesylate, JSP-191, BLU-263, CD117-ADC, AZD3229, telatinib, vorolanib, GO-203-2C, AB-680, PSB-12379, PSB-12441, PSB-12425, CB-708, HM-30181A, motixafortide (BL-8040), LY2510924, burixafor (TG-0054), X4P-002, mavorixafor (X4P-001-IO), plerixafor, CTX-5861, and REGN-5678 (PSMA/CD28).

In some embodiments the CD marker targeting agent that can be co-administered include small molecule agonists, such as interleukin 2 receptor subunit gamma, eltrombopag, rintatolimod, poly-ICLC (NSC-301463), Riboxxon, Apoxxim, RIBOXXIM®, MCT-465, MCT-475, G100, PEPA-10, eftozanermin alfa (ABBV-621), E-6887, motolimod, resiquimod, selgantolimod (GS-9688), VTX-1463, NKTR-262, AST-008, CMP-001, cobitolimod, tilsotolimod, litenimod, MGN-1601, BB-006, IMO-8400, IMO-9200, agatolimod, DIMS-9054, DV-1079, lefitolimod (MGN-1703), CYT-003, and PUL-042.

In some embodiments the CD marker targeting agent that can be co-administered include antibodies, such as tafasitamab (MOR208; MorphoSys AG), Inebilizumab (MEDI-551), obinutuzumab, IGN-002, rituximab biosimilar (PF-05280586), varlilumab (CDX-1127), AFM-13 (CD16/CD30), AMG330, otlertuzumab (TRU-016), isatuximab, felzartamab (MOR-202), TAK-079, TAK573, daratumumab (DARZALEX®), TTX-030, selicrelumab (RG7876), APX-005M, ABBV-428, ABBV-927, mitazalimab (JNJ-64457107), lenziluma, alemtuzuma, emactuzumab, AMG-820, FPA-008 (cabiralizumab), PRS-343 (CD-137/Her2), AFM-13 (CD16/CD30), belantamab mafodotin (GSK-2857916), AFM26 (BCMA/CD16A), simlukafusp alfa (RG7461), urelumab, utomilumab (PF-05082566), AGEN2373, ADG-106, BT-7480, PRS-343 (CD-137/HER2), FAP-4-IBBL (4-1BB/FAP), ramucirumab, CDX-0158, CDX-0159 and FSI-174, relatlimab (ONO-4482), LAG-525, MK-4280, fianlimab (REGN-3767), INCAGN2385, encelimab (TSR-033), atipotuzumab, BrevaRex (Mab-AR-20.5), MEDI-9447 (oleclumab), CPX-006, IPH-53, BMS-986179, NZV-930, CPI-006, PAT-SC1, lirilumab (IPH-2102), lacutamab (IPH-4102), monalizumab, BAY-1834942, NEO-201 (CEACAM 5/6), Iodine (131I) apamistamab (131I-BC8 (lomab-B)), MEDI0562 (tavolixizumab), GSK-3174998, INCAGN1949, BMS-986178, GBR-8383, ABBV-368, denosumab, BION-1301, MK-4166, INCAGN-1876, TRX-518, BMS-986156, MK-1248, GWN-323, CTB-006, INBRX-109, GEN-1029, pepinemab (VX-15), vopratelimab (JTX-2011), GSK3359609, cobolimab (TSR-022), MBG-453, INCAGN-2390, and compounds disclosed in WO 2017096179, WO2017096276, WO2017096189, and WO2018089628.

In some embodiments the CD marker targeting agent that can be co-administered include cell therapies, such as CD19-ARTEMIS, TBI-1501, CTL-119 huCART-19 T cells, 1 iso-cel, lisocabtagene maraleucel (JCAR-017), axicabtagene ciloleucel (KTE-C19, Yescarta®), axicabtagene ciloleucel (KTE-X19), U.S. Pat. Nos. 7,741,465, 6,319,494, UCART-19, tabelecleucel (EBV-CTL), T tisagenlecleucel-T (CTL019), CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T, TC-110, anti-CD19 CAR T-cell therapy (B-cell acute lymphoblastic leukemia, Universiti Kebangsaan Malaysia), anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Bio-medicine Technology), MB-CART2019.1 (CD19/CD20), GC-197 (CD19/CD7), CLIC-1901, ET-019003, anti-CD19-STAR-T cells, AVA-001, BCMA/CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem, UCAR-011, ICTCAR-014, GC-007F, PTG-01, CC-97540, GC-007G, TC-310, GC-197, tisagenlecleucel-T, CART-19, tisagenlecleucel (CTL-019)), anti-CD20 CAR T-cell therapy (non-Hodgkin's lymphoma), MB-CART2019.1 (CD19/CD20), WZTL-002 dual anti-CD19/anti-CD20 CAR-T cells, ICG-132 (CD19/CD20), ACTR707 ATTCK-20, PBCAR-20A, LB-1905, CIK-CAR.CD33, CD33CART, dual anti-BCMA/anti-CD38 CAR T-cell therapy, CART-ddBCMA, MB-102, IM-23, JEZ-567, UCART-123, PD-1 knockout T cell therapy (esophageal cancer/NSCLC), ICT-CAR-052, Tn MUC-1 CAR-T, ICTCAR-053, PD-1 knockout T cell therapy (esophageal cancer/NSCLC), AUTO-2, anti-BCMA CAR T-cell therapy, Descartes-011, anti-BCMA/anti-CD38 CAR T-cell therapy, CART-ddBCMA, BCMA-CS1 cCAR, CYAD-01 (NKG2D LIGAND MODULATOR), KD-045, PD-L1 t-haNK, BCMA-CS1 cCAR, MEDI5083, anti-CD276 CART, and therapies disclosed in WO2012079000 or WO2017049166.

Cluster of Differentiation 47 (CD47) Inhibitors

In some embodiments a compound of Formula (I), (Ia), (Ib), (IIa), (IIb), (IIc), (IId), (IIe), (IIf), (IIg), (IIh), (IIi), (IIIa), (IIIb), (IIIc), (IIId), (IIIe), (IIIf), (IVa), (IVa-1), or (IVa-2), provided herein, or pharmaceutically acceptable salt thereof, is administered with an inhibitor of CD47 (IAP, MER6, OA3; NCBI Gene ID: 961). Examples of CD47 inhibitors include anti-CD47 mAbs (Vx-1004), anti-human CD47 mAbs (CNTO-7108), CC-90002, CC-90002-ST-001, humanized anti-CD47 antibody or a CD47-blocking agent, NI-1701, NI-1801, RCT-1938, ALX148, SG-404, SRF-231, and TTI-621. Additional exemplary anti-CD47 antibodies include CC-90002, magrolimab (Hu5F9-G4), AO-176 (Vx-1004), letaplimab (IBI-188) (letaplimab), lemzoparlimab (TJC-4), SHR-1603, HLX-24, LQ-001, IMC-002, ZL-1201, IMM-01, B6H12, GenSci-059, TAY-018, PT-240, 1F8-GMCSF, SY-102, KD-015, ALX-148, AK-117, TTI-621, TTI-622, or compounds disclosed in WO199727873, WO199940940, WO2002092784, WO2005044857, WO2009046541, WO2010070047, WO2011143624, WO2012170250, WO2013109752, WO2013119714, WO2014087248, WO2015191861, WO2016022971, WO2016023040, WO2016024021, WO2016081423, WO2016109415, WO2016141328, WO2016188449, WO2017027422, WO2017049251, WO2017053423, WO2017121771, WO2017194634, WO2017196793, WO2017215585, WO2018075857, WO2018075960, WO2018089508, WO2018095428, WO2018137705, WO2018233575, WO2019027903, WO2019034895, WO2019042119, WO2019042285, WO2019042470, WO2019086573, WO2019108733, WO2019138367, WO2019144895, WO2019157843, WO2019179366, WO2019184912, WO2019185717, WO2019201236, WO2019238012, WO2019241732, WO2020019135, WO2020036977, WO2020043188, and WO2020009725. In some embodiments, the CD47 inhibitor is RRx-001, DSP-107, VT-1021, IMM-02, SGN-CD47M, or SIRPa-Fc-CD40L (SL-172154). In some embodiments the CD47 inhibitor is magrolimab.

In some embodiments, the CD47 inhibitor is a bispecific antibodies targeting CD47, such as IBI-322 (CD47/PD-L1), IMM-0306 (CD47/CD20), TJ-L1C4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), HMBD-004A (CD47/CD33), TG-1801 (NI-1701), or NI-1801.

SIRPα Targeting Agents

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with a SIRPα targeting agent (NCBI Gene ID: 140885; UniProt P78324). Examples of SIRPα targeting agents that can be co-administered include SIRPα inhibitors, such as AL-008, RRx-001, and CTX-5861, and anti-SIRPα antibodies, such as FSI-189 (GS-0189), ES-004, BI-765063, ADU1805, CC-95251, Q-1801 (SIRPa/PD-L1). Additional SIRPa-targeting agents of use are described, for example, in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170 and WO2020068752.

FLT3R Agonists

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with a FLT3R agonist. In some embodiments, the compound provided herein, or pharmaceutically acceptable salt thereof, is administered with a FLT3 ligand. In some embodiments, the compound provided herein, or pharmaceutically acceptable salt thereof, is administered with a FLT3L-Fc fusion protein, e.g., as described in WO2020263830. In some embodiments the compound provided herein, or pharmaceutically acceptable salt thereof, is administered with GS-3583 or CDX-301. In some embodiments the compound provided herein, or pharmaceutically acceptable salt thereof, is administered with GS-3583.

TNF Receptor Superfamily (TNFRSF) Member Agonists or Activators

In some embodiments, a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include MEDI6469, MEDI6383, tavolixizumab (MEDI0562), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include RG7876, SEA-CD40, APX-005M, and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include urelumab, utomilumab (PF-05082566), AGEN-2373, and ADG-106.

In some embodiments the anti-TNFRSF17 (BCMA) antibody GSK-2857916 is co-administered.

Example anti-TNFRSF18 (GITR) antibodies that can be co-administered include MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi-specific antibodies targeting TNFRSF family members that can be co-administered include PRS-343 (CD-137/HER2), AFM26 (BCMA/CD16A), AFM-13 (CD16/CD30), odronextamab (REGN-1979; CD20/CD3), AMG-420 (BCMA/CD3), INHIBRX-105 (4-1BB/PDL1), FAP-4-IBBL (4-1BB/FAP), plamotamab (XmAb-13676; CD3/CD20), RG-7828 (CD20/CD3), CC-93269 (CD3/BCMA), REGN-5458 (CD3/BCMA), and IMM-0306 (CD47/CD20).

TGFβ Antagonists

In some embodiments, a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with a TGFβ antagonist. In some embodiments, the TGFβ antagonist is a TGFβ-specific antibody. TGFβ-specific antibodies can be prepared and characterized using methods known to those of skill in the art, such as those described in PCT International Application Publication No. WO 2018/129329 and in U.S. Pat. No. 9,518,112. In some embodiments, the TGFβ antagonist binds to a TGFβ latency-associated peptide (LAP), e.g., TGFβ 1-LAP. TGFβ 1-LAP-specific antibodies can be prepared and characterized using methods known to those of skill in the art, such as those described in U.S. Pat. No. 8,198,412 or U.S. Pat. No. 10,017,567. In some embodiments, the TGFβ antagonist binds to TGFβ (e.g., TGFβ 1) in a context independent manner (e.g., independent of the presentation of TGFβ in a specific tissue or organ). In some embodiments, the TGFβ antagonist binds to TGFβ (e.g., TGFβ 1) in a context-dependent manner. In some embodiments, the TGFβ antagonist blocks activation of latent TGFβ (e.g., latent TGFβ 1) that is localized in extracellular matrix, e.g., in connective tissue of the liver. In some embodiments, the TGFβ antagonist blocks activation of latent TGFβ (e.g., latent TGFβ 1) that is localized in the thymus, a lymph node, or in a tumor microenvironment (e.g., in a patient having liver cancer). In some embodiments, the TGFβ antagonist blocks activation of latent TGFβ (e.g., latent TGFβ 1) by Latent TGFβ Binding Protein (LTBP). In some embodiments, the TGFβ antagonist blocks activation of latent TGFβ (e.g., latent TGFβ 1) by Glycoprotein-A Repetitions Predominant protein (GARP), as described, e.g., in U.S. Pat. No. 10,000,572. In some embodiments, the TGFβ antagonist is ARGX-115. In some embodiments, the TGFβ antagonist is SK-181. In some embodiments, the TGFβ antagonist is an anti-latency-associated peptide (LAP) antibody that specifically binds to a LAP-TGFβ complex. In some embodiments, the anti-LAP antibody specifically binds to LAP-TGFβ complexes in extracellular matrix (ECM), e.g., of connective tissue in the liver. In some embodiments, the anti-LAP antibody specifically binds to LAP-TGFβ complexes on the surfaces of certain immunosuppressive cell types, such as regulatory T cells (Tregs), tumor-associated macrophages, or myeloid-derived suppressor cells, e.g., in a tumor microenvironment. In some embodiments, the anti-LAP antibody is a TLS-01 antibody. In some embodiments, the anti-LAP antibody specifically binds to LAP-TGFβ complexes in any context. In some embodiments, the anti-LAP antibody is a TLS-02 antibody. In some embodiments, the TGFβ antagonist comprises a TGFβ receptor. In some embodiments, the TGFβ antagonist is a TGFβ receptor-Fc fusion protein. In some embodiments, the TGFβ antagonist is an antibody comprising a TGFβ receptor. TGFβ antagonists comprising a TGFβ receptor that can be useful in connection with the compositions and methods provided herein have been described, e.g., in PCT International Publication Nos. WO 2019/113123 A1 and WO 2019/113464 A1.

Bi-Specific T-Cell Engagers

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with a bi-specific T-cell engager (e.g., not having an Fc) or an anti-CD3 bi-specific antibody (e.g., having an Fc). Illustrative anti-CD3 bi-specific antibodies or BiTEs that can be co-administered include duvortuxizumab (JNJ-64052781; CD19/CD3), AMG-211 (CEA/CD3), AMG-160 (PSMA/CD3), RG7802 (CEA/CD3), ERY-974 (CD3/GPC3), PF-06671008 (Cadherins/CD3), APV0436 (CD123/CD3), flotetuzumab (CD123/CD3), odronextamab (REGN-1979; CD20/CD3), MCLA-117 (CD3/CLEC12A), JNJ-0819 (heme/CD3), JNJ-7564 (CD3/heme), AMG-757 (DLL3-CD3), AMG-330 (CD33/CD3), AMG-420 (BCMA/CD3), AMG-427 (FLT3/CD3), AMG-562 (CD19/CD3), AMG-596 (EGFRvIII/CD3), AMG-673 (CD33/CD3), AMG-701 (BCMA/CD3), AMG-757 (DLL3/CD3), AMG-211 (CEA/CD3), blinatumomab (CD19/CD3), huGD2-BsAb (CD3/GD2), ERY974 (GPC3/CD3), GEMoab (CD3/PSCA), RG6026 (CD20/CD3), RG6194 (HER2/CD3), PF-06863135 (BCMA/CD3), SAR440234 (CD3/CDw123), JNJ-9383 (MGD-015), AMG-424 (CD38/CD3), tidutamab (XmAb-18087 (SSTR2/CD3)), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), tidutamab (XmAb-18087; SSTR2/CD3), catumaxomab (CD3/EpCAM), REGN-4018 (MUC16/CD3), mosunetuzumab (RG-7828; CD20/CD3), CC-93269 (CD3/BCMA), REGN-5458 (CD3/BCMA), GRB-1302 (CD3/Erbb2), GRB-1342 (CD38/CD3), GEM-333 (CD3/CD33). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., *Oncoimmunology*. (2017) May 17; 6(7):e1326437); PD-L1 (Horn, et al., *Oncotarget*. 2017 Aug. 3; 8(35):57964-57980); and EGFRvIII (Yang, et al., *Cancer Lett*. 2017 Sep. 10; 403: 224-230).

Bi- and Tri-Specific Natural Killer (NK)-Cell Engagers

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol*. (2016) 1441:333-346; Fang, et al., *Semin Immunol*. (2017) 31:37-54.

MCL1 Apoptosis Regulator, BCL2 Family Member (MCL1) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of MCL1 apoptosis regulator, BCL2 family member (MCL1, TM; EAT; MCL1L; MCL1S; Mcl-1; BCL2L3; MCLI-ES; bcl2-L-3; mcl1/EAT; NCBI Gene ID: 4170). Examples of MCL1 inhibitors include tapotoclax (AMG-176), AMG-397, S-64315, AZD-5991, 483-LM, A-1210477, UMI-77, JKY-5-037, PRT-1419, GS-9716, and those described in WO2018183418, WO2016033486, and WO2017147410.

SHP2 Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, and those described in WO2018172984 and WO2017211303.

Hematopoietic Progenitor Kinase 1 (HPK1) Inhibitors and Degraders

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO2020092621, WO2018183956, WO2018183964, WO2018167147, WO2018049152, WO2020092528, WO2016205942, WO2016090300, WO2018049214, WO2018049200, WO2018049191, WO2018102366, WO2018049152, and WO2016090300.

Apoptosis Signal-Regulating Kinase (ASK) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include those described in WO2011008709 (Gilead Sciences) and WO 2013112741 (Gilead Sciences).

Bruton Tyrosine Kinase (BTK) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include (S)-6-amino-9-(1-(but-2-ynoyl)pyrrolidin-3-yl)-7-(4-phenoxyphenyl)-7H-purin-8(9H)-one, acalabrutinib (ACP-196), zanubrutinib (BGB-3111), CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, PCI-32765, and TAS-5315.

Cyclin-Dependent Kinase (CDK) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of cyclin dependent kinase 1 (CDK1, CDC2; CDC28A; P34CDC2; NCBI Gene ID: 983); cyclin dependent kinase 2 (CDK2, CDKN2; p33 (CDK2); NCBI Gene ID: 1017); cyclin dependent kinase 3 (CDK3; NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; MO15; STK1; CDKN7; p39MO15; NCBI Gene ID: 1022), or cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include abemaciclib, alvocidib (HMR-1275, flavopiridol), AT-7519, dinaciclib, ibrance, FLX-925, LEE001, palbociclib, samuraciclib, ribociclib, rigosertib, selinexor, UCN-01, SY1365, CT-7001, SY-1365, G1T38, milciclib, trilaciclib, simurosertib hydrate (TAK931), and TG-02.

Discoidin Domain Receptor (DDR) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Targeted E3 Ligase Ligand Conjugates

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with a targeted E3 ligase ligand conjugate. Such conjugates have a target protein binding moiety and an E3 ligase binding moiety (e.g., an inhibitor of apoptosis protein (IAP) (e.g., XIAP, c-IAP1, c-IAP2, NIL-IAP, Bruce, and surviving) E3 ubiquitin ligase binding moiety, Von Hippel-Lindau E3 ubiquitin ligase (VHL) binding moiety, a cereblon E3 ubiquitin ligase binding moiety, mouse double minute 2 homolog (MDM2) E3 ubiquitin ligase binding moiety), and can be used to promote or increase the degradation of targeted proteins, e.g., via the ubiquitin pathway. In some embodiments the targeted E3 ligase ligand conjugates comprise a targeting or binding moiety that targets or binds a protein described herein, and an E3 ligase ligand or binding moiety. In some embodiments the targeted E3 ligase ligand conjugates comprise a targeting or binding moiety that targets or binds a protein selected from Cbl proto-oncogene B (CBLB; Cbl-b, Nbla00127, RNF56; NCBI Gene ID: 868) and hypoxia inducible factor 1 subunit alpha (HIF1A; NCBI Gene ID: 3091). In some embodiments the targeted E3 ligase ligand conjugates comprise a kinase inhibitor (e.g., a small molecule kinase inhibitor, e.g., of BTK and an E3 ligase ligand or binding moiety. See, e.g., WO2018098280. In some embodiments the targeted E3 ligase ligand conjugates comprise a binding moiety targeting or binding to Interleukin-1 (IL-1) Receptor-Associated Kinase-4 (IRAK-4); Rapidly Accelerated Fibrosarcoma (RAF, such as c-RAF, A-RAF and/or B-RAF), c-Met/p38, or a BRD protein; and an E3 ligase ligand or binding moiety. See, e.g., WO2019099926, WO2018226542, WO2018119448, WO2018223909, WO2019079701. Additional targeted E3 ligase ligand conjugates that can be co-administered are described, e.g., in WO2018237026, WO2019084026, WO2019084030, WO2019067733, WO2019043217, WO2019043208, and WO2018144649.

Histone Deacetylase (HDAC) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, and entinostat.

Indoleamine-Pyrrole-2,3-Dioxygenase (IDO1) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of indoleamine 2,3-dioxygenase 1 (IDO1; NCBI Gene ID: 3620). Examples of IDO1 inhibitors include BLV-0801, epacadostat, linrodostat (F-001287, BMS-986205), GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST, EOS-200271, KHK-2455, and LY-3381916.

Janus Kinase (JAK) Inhibitors

In some embodiments, a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, LJAK; NCBI Gene ID: 3718). Examples of JAK inhibitors include AT9283, AZD1480, baricitinib, BMS-911543, fedratinib, filgotinib (GLPG0634), gandotinib (LY2784544), INCB039110 (itacitinib), lestaurtinib, momelotinib (CYT0387), ilginatinib maleate (NS-018), pacritinib (SB1518), peficitinib (ASP015K), ruxolitinib, tofacitinib (formerly tasocitinib), INCB052793, and XL019.

Lysyl Oxidase-Like Protein (LOXL) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of a LOXL protein, e.g., LOXL1 (NCBI Gene ID: 4016), LOXL2 (NCBI Gene ID: 4017), LOXL3 (NCBI Gene ID: 84695), LOXL4 (NCBI Gene ID: 84171), and/or LOX (NCBI Gene ID: 4015). Examples of LOXL2 inhibitors include the antibodies described in WO 2009017833 (Arresto Biosciences), WO 2009035791 (Arresto Biosciences), and WO 2011097513 (Gilead Biologics).

Matrix Metalloprotease (MMP) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include marimastat (BB-2516), cipemastat (Ro 32-3555), GS-5745 (andecaliximab), and those described in WO 2012027721 (Gilead Biologics).

RAS and RAS Pathway Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of KRAS proto-oncogene, GTPase (KRAS; a.k.a., NS; NS3; CFC2; RALD; K-Ras; KRAS1; KRAS2; RASK2; KI-RAS; C—K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893) or HRAS proto-oncogene, GTPase (HRAS; a.k.a., CTLO; KRAS; HAMSV; HRAS1; KRAS2; RASH1; RASK2; Ki-Ras; p21ras; C—H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR. Illustrative K-Ras inhibitors that can be co-administered include sotorasib (AMG-510), COTI-219, ARS-3248, WDB-178, BI-3406, BI-1701963, SML-8-73-1 (G12C), adagrasib (MRTX-849), ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 and KRpep-2d. Illustrative KRAS mRNA inhibitors include anti-KRAS U1 adaptor, AZD-4785, siG12D-LODER™, and siG12D exosomes. Illustrative MEK inhibitors that can be co-administered include binimetinib, cobimetinib, PD-0325901, pimasertib, RG-7304, selumetinib, trametinib, and those described below and herein. Illustrative Raf dimer inhibitors that can be co-administered include BGB-283, HM-95573, LXH-254, LY-3009120, RG7304 and TAK-580. Illustrative ERK inhibitors that can be co-administered include LTT-462, LY-3214996, MK-8353, ravoxertinib and ulixertinib. Illustrative Ras GTPase inhibitors that can be co-administered include rigosertib. Illustrative PI3K inhibitors that can be co-administered include idelalisib (Zydelig®), alpelisib, buparlisib, pictilisib, inavolisib (RG6114), ASN-003. Illustrative AKT inhibitors that can be co-administered include capivasertib and GSK2141795. Illustrative PI3K/mTOR inhibitors that can be co-administered include dactolisib, omipalisib, voxtalisib. gedatolisib, GSK2141795, GSK-2126458, inavolisib (RG6114), sapanisertib, ME-344, sirolimus (oral nano-amorphous formulation, cancer), racemetyrosine (TYME-88 (mTOR/cytochrome P450 3A4)), temsirolimus (TORISEL®, CCI-779), CC-115, onatasertib (CC-223), SF-1126, and PQR-309 (bimiralisib). In some embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., *Cancer Biol Ther.* 2018 Feb. 1; 19(2):132-137.

Mitogen-Activated Protein Kinase (MEK) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, and refametinib.

Phosphatidylinositol 3-Kinase (PI3K) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/orphosphatidylinositol-4,5-bisphosphate 3-kinase catalytic subunit delta (PIK3CD, APDS, IMD14, P110DELTA, PI3K, p110D, NCBI Gene ID: 5293). In some embodiments the PI3K inhibitor is a pan-PI3K inhibitor. Examples of PI3K inhibitors include ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO2005113556 (ICOS), WO 2013/052699 (Gilead Calistoga), WO2013116562 (Gilead Calistoga), WO2014100765 (Gilead Calistoga), WO2014100767 (Gilead Calistoga), and WO2014201409 (Gilead Sciences).

Spleen Tyrosine Kinase (SYK) Inhibitors

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an inhibitor of spleen associated tyrosine kinase (SYK, p72-Syk, NCBI Gene ID: 6850). Examples of SYK inhibitors include 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), gusacitinib (ASN-002), and those described in U.S. Pat. No. 8,450,321 (Gilead Connecticut) and US20150175616.

Toll-Like Receptor (TLR) Agonists

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include DS-0509, GS-9620 (vesatolimod), vesatolimod analogs, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, BDB-001, DSP-0509, and the compounds disclosed in US20100143301 (Gilead Sciences), US20110098248 (Gilead Sciences), and US20090047249 (Gilead Sciences), US20140045849 (Janssen), US20140073642 (Janssen), WO2014056953 (Janssen), WO2014076221 (Janssen), WO2014128189 (Janssen), US20140350031 (Janssen), WO2014023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Tyrosine-Kinase Inhibitors (TKIs)

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, famitinib L-malate, (MAC-4), tivoanib, TH-4000, and MEDI-575 (anti-PDGFR antibody). Exemplary EGFR targeting agents include neratinib, tucatinib (ONT-380), tesevatinib, mobocertinib (TAK-788), DZD-9008, varlitinib, abivertinib (ACEA-0010), EGF816 (nazartinib), olmutinib (BI-1482694), osimertinib (AZD-9291), AMG-596 (EGFRvIII/CD3), lifirafenib (BGB-283), vectibix, lazertinib (LECLAZA®), and compounds disclosed in Booth, et al., Cancer Biol Ther. 2018 Feb. 1; 19(2):132-137. Antibodies targeting EGFR include without limitation modotuximab, cetuximab sarotalocan (RM-1929), seribantumab, necitumumab, depatuxizumab mafodotin (ABT-414), tomuzotuximab, depatuxizumab (ABT-806), and cetuximab.

Chemotherapeutic Agents

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adoz- elesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; sabizabulin (Veru-111); platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2''-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan);

FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204, enobosarm (GTX-024), darolutamide, and IONIS-AR-2.5Rx (antisense).

An example progesterone receptor antagonist includes onapristone. Additional progesterone targeting agents include TRI-CYCLEN LO (norethindrone+ethinyl estradiol), norgestimate+ethinylestradiol (Tri-Cyclen) and levonorgestrel.

Anti-Angiogenic Agents

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an anti-angiogenic agent. Anti-angiogenic agents that can be co-administered include retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2. Examples for anti-VEGFA antibodies that can be co-administered include bevacizumab, vanucizumab, faricimab, dilpacimab (ABT-165; DLL4/VEGF), ornavicixizumab (OMP-305B83; DLL4/VEGF).

Anti-Fibrotic Agents

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an anti-fibrotic agent. Anti-fibrotic agents that can be co-administered include the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 20040248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio) butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID:

768), CA10 (NCBI Gene ID: 56934), CA1 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include mofezolac, GLY-230, and TRK-700.

Examples of inhibitors of prostaglandin-endoperoxide synthase 2 (PTGS2, COX-2; NCBI Gene ID: 5743) that can be co-administered include diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, NS-398, pamicogrel, parecoxib, robenacoxib, rofecoxib, rutecarpine, tilmacoxib, and zaltoprofen. Examples of dual COX1/COX2 inhibitors that can be co-administered include HP-5000, lornoxicam, ketorolac tromethamine, bromfenac sodium, ATB-346, HP-5000. Examples of dual COX-2/carbonic anhydrase (CA) inhibitors that can be co-administered include polmacoxib and imrecoxib.

Examples of inhibitors of secreted phospholipase A2, prostaglandin E synthase (PTGES, PGES; Gene ID: 9536) that can be co-administered include LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., Cancer Lett. (2017) 389:23-32; and Liu, et al., Oncotarget. (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include meclofenamate sodium, zileuton.

Examples of inhibitors of soluble epoxide hydrolase 2 (EPHX2, SEH; NCBI Gene ID: 2053) that can be co-administered include compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include GS-4875, GS-5290, BHM-078 and those described in WO2006124944, WO2006124692, WO2014064215, WO2018005435, Teli, et al., J Enzyme Inhib Med Chem. (2012) 27(4):558-70; Gangwall, et al., Curr Top Med Chem. (2013) 13(9):1015-35; Wu, et al., Bioorg Med Chem Lett. (2009) 19(13):3485-8; Kaila, et al., Bioorg Med Chem. (2007) 15(19):6425-42; and Hu, et al., Bioorg Med Chem Lett. (2011) 21(16):4758-61.

Tumor Oxygenation Agents

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an agent that promotes or increases tumor oxygenation or reoxygenation, or prevents or reduces tumor hypoxia. Illustrative agents that can be co-administered include, e.g., Hypoxia inducible factor-1 alpha (HIF-1α) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO2007137767, WO2007139791, WO2014107171, and WO2016149562.

Immunotherapeutic Agents

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with an immunotherapeutic agent. In some embodiments the immunotherapeutic agent is an antibody. Example immunotherapeutic agents that can be co-administered include abagovomab, AB308, ABP-980, adecatumumab, afutuzumab, alemtuzumab, altumomab, amatuximab, anatumomab, arcitumomab, atezolizumab, bavituximab, bectumomab, bevacizumab, bivatuzumab, blinatumomab, brentuximab, camidanliumab, cantuzumab, catumaxomab, CC49, cetuximab, citatuzumab, cixutumumab, clivatuzumab, conatumumab, dacetuzumab, dalotuzumab, daratumumab, detumomab, dinutuximab, domvanalimab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, zimberelimab, and 3F8. Rituximab can be used for treating indolent B-cell cancers, including marginal-zone lymphoma, WM, CLL, and small lymphocytic lymphoma. A combination of rituximab and chemotherapy agents is especially effective.

The exemplified therapeutic antibodies can be further labeled or combined with a radioisotope particle such as indium-111, yttrium-90 (90Y-clivatuzumab), or iodine-131.

In some embodiments, the immunotherapeutic agent that can be co-administered is an antibody-drug conjugate (ADC). Illustrative ADCs that can be co-administered include without limitation drug-conjugated antibodies, fragments thereof, or antibody mimetics targeting the proteins or antigens listed above and herein. Example ADCs that can be co-administered include gemtuzumab, brentuximab, belantamab (e.g., belantamab mafodotin), cainidaniumab (e.g., camidanilumab tesirine), trastuzumab (e.g., trastuzumab deruxtecan; trasuzumab emtansine), inotuzumab, glembatumumab, anetumab, mirvetuximab (e.g., mirvetuximab soravtansine), depatuxizumab, vadastuximab, labetuzumab, ladiratuzumab (e.g., ladiratuzumab vedotin), loncastuximab (e.g., loncastuximab tesirine), sacituzumab (e.g., sacituzumab govitecan), datopotamab (e.g., datopotamab deruxtecan; DS-1062; Dato-DXd), patritumab (e.g., patritumab deruxtecan), lifastuzumab, indusatumab, polatuzumab (e.g., polatuzumab vedotin), pinatuzumab, coltuximab, upifitiab (e.g., upifitiamab rilsodotin), indatuximab, milatuzumab, rovalpituzumab (e.g., rovalpituzumab tesirine), enfortumab (e.g., enfortumab vedotin), tisotumab (e.g., tisotumab vedotin), tusamitamab (e.g., tusanitamab ravtansine), disitamab (e.g., disitamab vedotin), telisotuximab vedotin (ABBV-399), AGS-16C3F, ASG-22ME, AGS67E, AMG172, AMG575, BAY1129980, BAY1187982, BAY94-9343, GSK2857916, Humax-TF-ADC, IMGN289, IMGN151, IMGN529, IMGN632, IMGN853, IMGC936, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A, SYD985, DS-7300, XMT-1660, IMMU-130, and IMMU-140. ADCs that can be co-administered are described, e.g., in Lambert, et al., *Adv Ther* (2017) 34:1015-1035 and in de Goeij, *Current Opinion in Immunology* (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a vinca alkaloid, an epothilone), a pyrrolobenzodiazepine (PBD) or dimer thereof, a duocarmycin (A, B1, B2, Cl, C2, D, SA, CC-1065), and other anticancer or anti-neoplastic agents described herein. In some embodiments, the therapeutic agent conjugated to the drug-conjugated antibody is a topoisomerase I inhibitor (e.g., a camptothecin analog, such as irinotecan or its active metabolite SN38). In some embodiments, the therapeutic agents (e.g., anticancer or antineoplastic agents) that can be conjugated to the drug-conjugated antibodies, fragments thereof, or antibody mimetics include an immune checkpoint inhibitor. In some embodiments the conjugated immune checkpoint inhibitor is a conjugated small molecule inhibitor of CD274 (PDL1, PD-L1), programmed cell death 1 (PDCD1, PD1, PD-1) or CTLA4. In some embodiments the conjugated small molecule inhibitor of CD274 or PDCD1 is selected from the group consisting of GS-4224, GS-4416, INCB086550 and MAX10181. In some embodiments the conjugated small molecule inhibitor of CTLA4 comprises BPI-002.

In some embodiments the ADCs that can be co-administered include an antibody targeting tumor-associated calcium signal transducer 2 (TROP-2; TACSTD2; EGP-1; NCBI Gene ID: 4070). Illustrative anti-TROP-2 antibodies include without limitation TROP2-XPAT (Amunix), BAT-8003 (Bio-Thera Solutions), TROP-2-IR700 (Chiome Bioscience), datopotamab deruxtecan (Daiichi Sankyo, AstraZeneca), GQ-1003 (Genequantum Healthcare, Samsung BioLogics), DAC-002 (Hangzhou DAC Biotech, Shanghai Junshi Biosciences), sacituzumab govitecan (Gilead Sciences), E1-3s (Immunomedics/Gilead, IBC Pharmaceuticals), TROP2-TRACTr (Janux Therapeutics), LIV-2008 (LivTech/Chiome, Yakult Honsha, Shanghai Henlius Bio-Tech), LIV-2008b (LivTech/Chiome), anti-TROP-2a (Oncoxx), anti-TROP-2b (Oncoxx), OXG-64 (Oncoxx), OXS-55 (Oncoxx), humanized anti-Trop2-SN38 antibody conjugate (Shanghai Escugen Biotechnology, TOT Biopharma), anti-Trop2 antibody-CLB-SN-38 conjugate (Shanghai Fudan-Zhangjiang Bio-Pharmaceutical), SKB-264 (Sichuan Kelun Pharmaceutical/Klus Pharma), TROP2-Ab8 (Abmart), Trop2-IgG (Nanjing Medical University (NMU)), 90Y-DTPA-AF650 (Peking University First Hospital), hRS7-CM (SynAffix), 89Zr-DFO-AF650 (University of Wisconsin-Madison), anti-Trop2 antibody (Mediterranea Theranostic, LegoChem Biosciences), KD-065 (Nanjing KAEDI Biotech), and those described in WO2020016662 (Abmart), WO2020249063 (Bio-Thera Solutions), US20190048095 (Bio-Thera Solutions), WO2013077458 (LivTech/Chiome), EP20110783675 (Chiome), WO2015098099 (Daiichi Sankyo), WO2017002776 (Daiichi Sankyo), WO2020130125 (Daiichi Sankyo), WO2020240467 (Daiichi Sankyo), US2021093730 (Daiichi Sankyo), U.S. Pat. No. 9,850,312 (Daiichi Sankyo), CN112321715 (Biosion), US2006193865 (Immunomedics/Gilead), WO2011068845 (Immunomedics/Gilead), US2016296633 (Immunomedics/Gilead), US2017021017 (Immunomedics/Gilead), US2017209594 (Immunomedics/Gilead), US2017274093 (Immunomedics/Gilead), US2018110772 (Immunomedics/Gilead), US2018185351 (Immunomedics/Gilead), US2018271992 (Immunomedics/Gilead), WO2018217227 (Immunomedics/Gilead), US2019248917 (Immunomedics/Gilead), CN111534585 (Immunomedics/Gilead), US2021093730 (Immunomedics/Gilead), US2021069343 (Immunomedics/Gilead), U.S. Pat. No. 8,435,539 (Immunomedics/Gilead), U.S. Pat. No. 8,435,529 (Immunomedics/Gilead), U.S. Pat. No. 9,492,566 (Immunomedics/Gilead), WO2003074566 (Gilead), WO2020257648 (Gilead), US2013039861 (Gilead), WO2014163684 (Gilead), U.S. Pat. No. 9,427,464

(LivTech/Chiome), U.S. Ser. No. 10/501,555 (Abruzzo Theranostic/Oncoxx), WO2018036428 (Sichuan Kelun Pharma), WO2013068946 (Pfizer), WO2007095749 (Roche), and WO2020094670 (SynAffix). In some embodiments, the anti-Trop-2 antibody is selected from hRS7, Trop-2-XPAT, and BAT-8003. In some embodiments, the anti-Trop-2 antibody is hRS7. In some embodiments, hRS7 is as disclosed in U.S. Pat. Nos. 7,238,785; 7,517,964 and 8,084,583, which are incorporated herein by reference. In some embodiments, the antibody-drug conjugate comprises an anti-Trop-2 antibody and an anticancer agent linked by a linker. In some embodiments, the linker includes the linkers disclosed in U.S. Pat. No. 7,999,083. In some embodiments, the linker is CL2A. In some embodiments, the drug moiety of antibody-drug conjugate is a chemotherapeutic agent. In some embodiments, the chemotherapeutic agent is selected from doxorubcin (DOX), epirubicin, morpholinodoxorubicin (morpholino-DOX), cyanomorpholino-doxorubicin (cyanomorpholinoDOX), 2-pyrrolino-doxorubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In some embodiments, the chemotherapeutic moiety is SN-38. In some embodiments the antibody and/or fusion protein provided herein is administered with sacituzumab govitecan.

In some embodiments the ADCs that can be co-administered include an antibody targeting carcinoembryonic antigen-related cell adhesion molecule 1 (CEACAM1; CD66a; NCBI Gene ID: 634). In some embodiments the CEACAMI antibody is hMN-14 (e.g., as described in WO1996011013). In some embodiments the CEACAM1-ADC is as described in WO2010093395 (anti-CEACAM-1-CL2A-SN38). In some embodiments the antibody and/or fusion protein provided herein is administered with the CEACAM1-ADC IMMU-130.

In some embodiments the ADCs that can be co-administered include an antibody targeting MHC class II cell surface receptor encoded by the human leukocyte antigen complex (HLA-DR). In some embodiments the HLA-DR antibody is hL243 (e.g., as described in WO2006094192). In some embodiments the HLA-DR-ADC is as described in WO2010093395 (anti-HLA-DR-CL2A-SN38). In some embodiments the antibody and/or fusion protein provided herein is administered with the HLA-DR-ADC IMMU-140.

Cancer Gene Therapy and Cell Therapy

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with one or more cellular therapies. Illustrative cellular therapies include without limitation co-administration of one or more of a population of natural killer (NK) cells, NK-T cells, T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments the cellular therapy entails co-administering cells comprising chimeric antigen receptors (CARs). In such therapies, a population of immune effector cells engineered to express a CAR, wherein the CAR comprises a tumor antigen-binding domain. In T cell therapies, the T cell receptors (TCRs) are engineered to target tumor derived peptides presented on the surface of tumor cells.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon R1b), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CD1E (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD160, CD19, IL2R beta, IL2R gamma, IL7R, ITGA1, VLA1, CD49$^a$, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, CD29, ITGB2 (LFA-1, CD18), ITGB7, TNFR2, DNAM1 (CD226), SLAMF4 (CD244, 2B4), CD84, CD96 (TACTILE), CEACAMI, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvlll); ganglioside G2 (GD2); ganglioside GD3 (αNeuSAc(2-8)αNeuSAc(2-3)βDGaip(1-4)bDGlcp(1-1) Cer); ganglioside GM3 (αNeuSAc(2-3)βDGalp(1-4) βDGlcp(1-1)Cer); TNF receptor superfamily member 17 (TNFRSF17, BCMA); Tn antigen ((Tn Ag) or (GaINAcu-Ser/Thr)); prostate-specific membrane antigen (PSMA); receptor tyrosine kinase-like orphan receptor 1 (RORI); tumor-associated glycoprotein 72 (TAG72); CD38; CD44v6; Carcinoembryonic antigen (CEA); epithelial cell adhesion molecule (EPCAM); B7H3 (CD276); KIT (CD117); interleukin-13 receptor subunit alpha-2 (IL-13Ra2 or CD213A2); mesothelin; interleukin 11 receptor alpha (IL-11Ra); prostate stem cell antigen (PSCA); protease serine 21 (Testisin or PRSS21); vascular endothelial growth factor receptor 2 (VEGFR2); Lewis(Y)antigen; CD24; platelet-derived growth factor receptor beta (PDGFR-beta); stage-specific embryonic antigen-4 (SSEA-4); CD20; delta like 3 (DLL3); folate receptor alpha; receptor tyrosine-protein kinase, ERBB2 (Her2/neu); mucin 1, cell surface associated (MUC1); epidermal growth factor receptor (EGFR); neural cell adhesion molecule (NCAM); prostase; prostatic acid phosphatase (PAP); elongation factor 2 mutated (ELF2M); ephrin B2; fibroblast activation protein alpha (FAP); insulin-like growth factor 1 receptor (IGF-I receptor), carbonic anhydrase IX (CAIX); proteasome (Prosome, Macropain) subunit, beta type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); fucosyl GM1; sialyl Lewis adhesion molecule (sLe); transglutaminase 5 (TGS5); high molecular weight-melanomaassociatedantigen (HMW-MAA); o-acetyl-GD2 ganglioside (OAcGD2); folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CX-ORF61); CD97; CD179a; anaplastic lymphoma kinase (ALK); polysialic acid; placenta-specific 1 (PLAC1); hexa-saccharide portion of globoH glycoceramide (GloboH); mammary gland differentiation antigen (NY-BR-1); uroplakin 2 (UPK2); hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); olfactory receptor 51E2 (ORS IE2); TCR Gamma Alternate Reading Frame Protein (TARP); Wilms tumor protein (WT1); cancer/testis antigen 1 (NY-ESO-1); cancer/testis antigen 2 (LAGE-la); melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); rat sarcoma (Ras) mutant; human telomerase reverse transcriptase (hTERT); sarcoma translocation breakpoints; melanoma inhibitor of apoptosis (ML-IAP); ERG (transmembrane protease, serine 2 (TM-PRSS2) ETS fusion gene); N-Acetyl glucosaminyl-transferase V (NA17); paired box protein Pax-3 (PAX3); androgen receptor; cyclin B1; v-myc avian myelocytomatosis viral oncogene neuroblastoma derived homolog (MYCN); ras homolog family member C (RhoC); tyrosinase-related protein 2 (TRP-2); cytochrome P450 1B1(CYP IBI); CCCTC-Binding Factor (Zinc Finger Protein)-Like (BORIS or Brother of the Regulator of Imprinted Sites), squamous cell carcinoma antigen recognized by T-cells 3 (SART3); paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); receptor for advanced glycation end products (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; leukocyte-associated immunoglobulin-like receptor 1 (LAIRI); Fc fragment of IgA receptor (FCAR or CD89); leukocyte immunoglobulin-like receptor subfamily A member 2 (LILRA2); CD300 molecule-like family member f (CD300LF); C-type lectin domain family 12 member A (CLECI2A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

In some embodiments, the antigen binding domain binds to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP; CT23, OY-TES-1, SP32; NCBI Gene ID: 84519), alpha fetoprotein (AFP; AFPD, FETA, HPAFP; NCBI Gene ID: 174); A-kinase anchoring protein 4 (AKAP4; AKAP 82, AKAP-4, AKAP82, CT99, FSC1, HI, PRKA4, hAKAP82, p82; NCBI Gene ID: 8852), ATPase family AAA domain containing 2 (ATAD2; ANCCA, CT137, PRO2000; NCBI Gene ID: 29028), kinetochore scaffold 1 (KNL1; AF15Q14, CASC5, CT29, D40, MCPH4, PPP1R55, Spc7, hKNL-1, hSpci05; NCBI Gene ID: 57082), centrosomal protein 55 (CEP55; C10orf3, CT111, MARCH, URCC6; NCBI Gene ID: 55165), cancer/testis antigen 1A (CTAG1A; ESO1; CT6.1; LAGE-2; LAGE2A; NY-ESO-1; NCBI Gene ID: 246100), cancer/testis antigen 1B (CTAG1B; CT6.1, CTAG, CTAG1, ESO1, LAGE-2, LAGE2B, NY-ESO-1; NCBI Gene ID: 1485), cancer/testis antigen 2 (CTAG2; CAMEL, CT2, CT6.2, CT6.2a, CT6.2b, ESO2, LAGE-1, LAGE2B; NCBI Gene ID: 30848), CCCTC-binding factor like (CTCFL; BORIS, CT27, CTCF-T, HMGB1L1, dJ579F20.2; NCBI Gene ID: 140690), catenin alpha 2 (CTNNA2; CAP-R, CAPR, CDCBM9, CT114, CTNR; NCBI Gene ID: 1496), cancer/testis antigen 83 (CT83; CXorf61, KK-LC-1, KKLC1; NCBI Gene ID: 203413), cyclin A1 (CCNA1; CT146; NCBI Gene ID: 8900), DEAD-box helicase 43 (DDX43; CT13, HAGE; NCBI Gene ID: 55510), developmental pluripotency associated 2 (DPPA2; CT100, ECAT15-2, PESCRG1; NCBI Gene ID: 151871), fetal and adult testis expressed 1 (FATE1; CT43, FATE; NCBI Gene ID: 89885), FMR1 neighbor (FMR1NB; CT37, NY-SAR-35, NYSAR35; NCBI Gene ID: 158521), HORMA domain containing 1 (HORMAD1; CT46, NOHMA; NCBI Gene ID: 84072), insulin like growth factor 2 mRNA binding protein 3 (IGF2BP3; CT98, IMP-3, IMP3, KOC, KOC1, VICKZ3; NCBI Gene ID: 10643), leucine zipper protein 4 (LUZP4; CT-28, CT-8, CT28, HOM-TES-85; NCBI Gene ID: 51213), lymphocyte antigen 6 family member K (LY6K; CT97, HSJ001348, URLC10, 1y-6K; NCBI Gene ID: 54742), maelstrom spermatogenic transposon silencer (MAEL; CT128, SPATA35; NCBI Gene ID: 84944), MAGE family member A1 (MAGEA1; CT1.1, MAGE1; NCBI Gene ID: 4100); MAGE family member A3 (MAGEA3; CT1.3, HIP8, HYPD, MAGE3, MAGEA6; NCBI Gene ID: 4102); MAGE family member A4 (MAGEA4; CT1.4, MAGE-41, MAGE-X2, MAGE4, MAGE4A, MAGE4B; NCBI Gene ID: 4103); MAGE family member A11 (MAGEA11; CT1.11, MAGE-11, MAGE11, MAGEA-11; NCBI Gene ID: 4110); MAGE family member C1 (MAGEC1; CT7, CT7.1; NCBI Gene ID: 9947); MAGE family member C2 (MAGEC2; CT10, HCA587, MAGEE1; NCBI Gene ID: 51438); MAGE family member D1 (MAGED1; DLXIN-1, NRAGE; NCBI Gene ID: 9500); MAGE family member D2 (MAGED2; 11B6, BARTS5, BCG-1, BCG1, HCA10, MAGE-D2; NCBI Gene ID: 10916), kinesin family member 20B (KIF20B; CT90, KRMP1, MPHOSPH1, MPP-1, MPP1; NCBI Gene ID: 9585), NUF2 component of NDC80 kinetochore complex (NUF2; CDCA1, CT106, NUF2R; NCBI Gene ID: 83540), nuclear RNA export factor 2 (NXF2; CT39, TAPL-2, TCPl1X2; NCBI Gene ID: 56001), PAS domain containing repressor 1 (PASD1; CT63, CT64, OXTESi; NCBI Gene ID: 139135), PDZ binding kinase (PBK; CT84, HEL164, Nori-3, SPK, TOPK; NCBI Gene ID: 55872), piwi like RNA-mediated gene silencing 2 (PIWIL2; CT80, HILI, PIWILiL, mili; NCBI Gene ID: 55124), preferentially expressed antigen in melanoma (PRAME; CT130, MAPE, OIP-4, OIP4; NCBI Gene ID: 23532), sperm associated antigen 9 (SPAG9; CT89, HLC-6, HLC4, HLC6, JIP-4, JIP4, JLP, PHET, PIG6; NCBI Gene ID: 9043), sperm protein associated with the nucleus, X-linked, family member A1 (SPANXA1; CT11.1, CT11.3, NAP-X, SPAN-X, SPAN-Xa, SPAN-Xb, SPANX, SPANX-A; NCBI Gene ID: 30014), SPANX family member A2 (SPANXA2; CT11.1, CT11.3, SPANX, SPANX-A, SPANX-C, SPANXA, SPANXC; NCBI Gene ID: 728712), SPANX family member C (SPANXC; CT11.3, CTp11, SPANX-C, SPANX-E, SPANXE; NCBI Gene ID: 64663), SPANX family member D (SPANXD; CT11.3, CT11.4, SPANX-C, SPANX-D, SPANX-E, SPANXC, SPANXE, dJ171K16.1; NCBI Gene ID: 64648), SSX family member 1 (SSX1; CT5.1, SSRC; NCBI Gene ID: 6756), SSX family member 2 (SSX2; CT5.2, CT5.2A, HD21, HOM-MEL-40, SSX; NCBI Gene ID: 6757), synaptonemal complex protein 3 (SYCP3; COR1, RPRGL4, SCP3, SPGF4; NCBI Gene ID: 50511), testis expressed 14, intercellular bridge forming factor (TEX14; CT113, SPGF23; NCBI Gene ID: 56155), transcription factor Dp family member 3 (TFDP3; CT30, DP4, HCA661; NCBI Gene ID: 51270), serine protease 50 (PRSS50; CT20, TSP50; NCBI Gene ID: 29122), TTK protein kinase (TTK; CT96, ESK, MPH1, MPS1, MPS1L1, PYT; NCBI Gene ID: 7272) and zinc finger protein 165 (ZNF165; CT53, LD65, ZSCAN7; NCBI Gene ID: 7718). T cell receptors (TCRs) and TCR-like antibodies that bind to an epitope of a cancer testis antigen presented in a major histocompatibility complex (MHC) molecule are known in the art and can be used in the herein described heterodimers. Cancer testis antigens associated with neoplasia are summarized, e.g., in Gibbs, et al., *Trends Cancer* 2018 October; 4(10):701-712 and the CT database website at cta.lncc.br/index.php. Illustrative TCRs and TCR-like antibodies that bind to an epitope of NY-ESO-1 presented in an MHC are described, e.g., in Stewart-Jones, et al., *Proc Natd Acad Sci USA*. 2009 Apr. 7; 106(14):5784-8; WO2005113595, WO2006031221, WO2010106431, WO2016177339, WO2016210365, WO2017044661, WO2017076308, WO2017109496, WO2018132739, WO2019084538, WO2019162043, WO2020086158 and WO2020086647. Illustrative TCRs and TCR-like antibodies that bind to an epitope of PRAME presented in an MHC are described, e.g., in WO2011062634, WO2016142783, WO2016191246, WO2018172533, WO2018234319 and WO2019109821. Illustrative TCRs and TCR-like antibodies that bind to an epitope of a MAGE variant presented in an MHC are described, e.g., in WO2007032255, WO2012054825, WO2013039889, WO2013041865, WO2014118236, WO2016055785, WO2017174822, WO2017174823, WO2017174824, WO2017175006, WO2018097951, WO2018170338, WO2018225732 and WO2019204683. Illustrative TCRs and TCR-like antibodies that bind to an epitope of alpha fetoprotein (AFP) presented in an MHC are described, e.g., in WO2015011450. Illustrative TCRs and TCR-like antibodies that bind to an epitope of SSX2 presented in an MHC are described, e.g., in WO2020063488.

Illustrative TCRs and TCR-like antibodies that bind to an epitope of KK-LC-1 (CT83) presented in an MHC are described, e.g., in WO2017189254.

Examples of cell therapies include: Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CART cells, autologous 4H11-28z/fIL-12/EGFRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, and CSG-005.

In some embodiments the one or more additional co-administered therapeutic agents can be categorized by their mechanism of action, e.g., into the following groups:

agents targeting adenosine deaminase, such as pentostatin or cladribine;

agents targeting ATM, such as AZD1390;

agents targeting MET, such as savolitinib, capmatinib, tepotinib, ABT-700, AG213, JNJ-38877618 (OMO-1), merestinib, HQP-8361, BMS-817378, or TAS-115;

agents targeting mitogen-activated protein kinase, such as antroquinonol, binimetinib, cobimetinib, selumetinib, trametinib, uprosertib, mirdametinib (PD-0325901), pimasertib, refametinib, or compounds disclosed in WO2011008709, WO2013112741, WO2006124944, WO2006124692, WO2014064215, WO2018005435, Zhou, et al., Cancer Lett. 2017 Nov. 1, 408:130-137, Teli, et al., J Enzyme Inhib Med Chem. (2012) 27(4): 558-70; Gangwall, et al., Curr Top Med Chem. (2013) 13(9):1015-35; Wu, et al., Bioorg Med Chem Lett. (2009) 19(13):3485-8; Kaila, et al., Bioorg Med Chem. (2007) 15(19):6425-42, or Hu, et al., Bioorg Med Chem Lett. (2011) 21(16):4758-61;

agents targeting thymidine kinase, such as aglatimagene besadenovec (ProstAtak, PancAtak, GliAtak, GMCI, or AdV-tk);

agents targeting targeting an interleukin pathway, such as pegilodecakin (AM-0010) (pegylated IL10), CA-4948 (IRAK4 inhibitor);

agents targeting cytochrome P450 family members, such as letrozole, anastrozole, aminoglutethimide, megestrol acetate (MEGACE®), exemestane, formestane, fadrozole, vorozole (RIVISOR®), letrozole (FEMARA®), or anastrozole (ARIMIDEX®);

agents targeting interleukin-2 receptor, e.g., an IL-2 variant (IL-2v: IL-2v is aldesleukin (Proleukin), bempegaldesleukin (NKTR-214), nemvaleukin alfa (ALKS-4230), THOR-202 (SAR-444245), BNT-151, ANV-419, XTX-202, RG-6279 (RO-7284755), NL-201, STK-012, SHR-1916, or GS-4528);

agents targeting CD39, such as an anti-CD39 antibody (e.g., TTX-030);

agents targeting CD73, such as a CD73 inhibitor (e.g., quemliclustat (AB680), ORIC-533) or an anti-CD73 antibody (e.g., oleclumab, uliledlimab, mupadolimab, BMS-986179, NVZ-930, AK-199);

agents targeting DKK3, such as MTG-201;

agents targeting EEF1A2, such as plitidepsin;

agents targeting EIF4A1, such as rohinitib;

agents targeting endoglin, such as TRC105 (carotuximab);

agents targeting exportin-1, such as eltanexor;

agents targeting fatty acid amide hydrolase, such as compounds disclosed in WO2017160861;

agents targeting heat shock protein 90 beta family member 1, such as anlotinib;

agents targeting lactotransferrin, such as ruxotemitide (LTX-315);

agents targeting lysyl oxidase, such as compounds disclosed in U.S. Pat. Nos. 4,965,288, 4,997,854, 4,943,593, 5,021,456, 5,059,714, 5,120,764, 5,182,297, 5,252,608, or US20040248871;

agents targeting MAGE family members, such as KITE-718, MAGE-A10C796T, or MAGE-A10 TCR;

agents targeting MDM2, such as ALRN-6924, CMG-097, milademetan monotosylate monohydrate (DS-3032b), or AMG-232;

agents targeting MDM4, such as ALRN-6924;

agents targeting melan-A, such as MART-1 F5 TCR engineered PBMCs;

agents targeting mesothelin, such as CSG-MESO or TC-210;

agents targeting METAP2, such as M8891 or APL-1202;

agents targeting NLRP3, such as BMS-986299;

agents targeting oxoglutarate dehydrogenase, such as devimistat (CPI-613);

agents targeting placenta growth factor, such as aflibercept;

agents targeting SLC10A3, such as compounds disclosed in WO2015148954, WO2012082647, or WO2017160861;

agents targeting transforming growth factor alpha (TGFα), such as compounds disclosed in WO2019103203;

agents targeting tumor protein p53, such as kevetrin (stimulator);

agents targeting vascular endothelial growth factor A, such as aflibercept;

agents targeting vascular endothelial growth factor receptor, such as fruquintinib or MP0250;

agents targeting VISTA, such as CA-170, or HMBD-002;

agents targeting WEE1, such as adavosertib (AZD-1775);

small molecule inhibitors targeting ABL1, such as imatinib, rebastinib, asciminib, or ponatinib (ICLUSIG®);

small molecule antagonists targeting adenosine receptor, such as CPI-444, AZD-4635, preladenant, etrumadenant (AB928), taminadenant, TT-10, TT-4, M1069, or PBF-509;

small molecule inhibitors targeting arachidonate 5-lipoxygenase, such as meclofenamate sodium or zileuton;

small molecule inhibitors targeting ATR serine/threonine kinase, such as BAY-937, ceralasertib (AZD6738), AZD6783, VX-803, or VX-970 (berzosertib);

small molecule inhibitors targeting AXL receptor tyrosine kinase, such as bemcentinib (BGB-324), SLC-0211, or gilteritinib (Ax1/Flt3);

small molecule inhibitors targeting Bruton's tyrosine kinase (BTK), such as (S)-6-amino-9-(1-(but-2-ynoyl) pyrrolidin-3-yl)-7-(4-phenoxyphenyl)-7H-purin-8 (9H)-one, acalabrutinib (ACP-196), zanubrutinib (BGB-3111), CB988, poseltinib (HM71224), ibrutinib (Imbruvica), M-2951 (evobrutinib), tirabrutinib (ONO-4059), rilzabrutinib (PRN-1008), spebrutinib (CC-292), vecabrutinib, ARQ-531 (MK-1026), SHR-1459, DTRMWXHS-12, or TAS-5315;

small molecule inhibitors targeting neurotrophic receptor tyrosine kinase such as larotrectinib, entrectinib, or selitrectinib (LOXO-195);

small molecule inhibitors targeting ROS proto-oncogene 1, receptor tyrosine kinase, such as entrectinib, repotrectinib (TPX-0005), or lorlatinib;

small molecule inhibitors targeting SRC proto-oncogene, non-receptor tyrosine kinase, such as VAL-201, tirbanibulin (KX2-391), or ilginatinib maleate (NS-018);

small molecule inhibitors targeting B-cell lymphoma 2, such as navitoclax (ABT-263), venetoclax (ABT-199, RG-7601), or AT-101 (gossypol);

small molecule inhibitors targeting bromodomain and external domain (BET) bromodomain containing protein, such as ABBV-744, INCB-054329, INCB057643, AZD-5153, ABT-767, BMS-986158, CC-90010, NHWD-870, ODM-207, ZBC246, ZEN3694, CC-95775 (FT-1101), mivebresib, BI-894999, PLX-2853, PLX-51107, CPI-0610, or GS-5829;

small molecule inhibitors targeting carbohydrate sulfotransferase 15, such as STNM-01;

small molecule inhibitors targeting carbonic anhydrase, such as polmacoxib, acetazolamide, or methazolamide;

small molecule inhibitors targeting catenin beta 1, such as CWP-291, or PRI-724;

small molecule antagonists targeting a C-C motif chemokine receptor, such as CCX-872, BMS-813160 (CCR2/CCR5) or MK-7690 (vicriviroc);

small molecule antagonists targeting a C-X-C motif chemokine receptor (e.g., CXCR4), blixafortide;

small molecule inhibitors targeting cereblon, such as avadomide (CC-122), CC-92480, CC-90009, or iberdomide;

small molecule inhibitors targeting checkpoint kinase 1, such as SRA737;

small molecule inhibitors targeting a complement component, such as Imprime PGG (Biothera Pharmaceuticals);

small molecule inhibitor targeting a C-X-C motif chemokine ligand (e.g., CXCL12), such as olaptesed pegol (NOX-A12);

small molecule inhibitors targeting cytochrome P450 family, such as ODM-209, LAE-201, seviteronel (VT-464), CFG920, abiraterone, or abiraterone acetate;

small molecule inhibitors targeting DEAD-box helicase 5, such as supinoxin (RX-5902);

small molecule inhibitors targeting DGKat, e.g., such as described in WO2021130638;

small molecule inhibitors targeting diablo IAP-binding mitochondrial protein, such as BI-891065;

small molecule inhibitors targeting dihydrofolate reductase, such as pralatrexate or pemetrexed disodium;

small molecule inhibitors targeting DNA dependent protein kinase, such as MSC2490484A (nedisertib), VX-984, AsiDNA (DT-01), LXS-196, or sotrastaurin;

small molecule inhibitors targeting MARCKS, such as BIG-11006;

small molecule inhibitors targeting RIPK1, such as GSK-3145094;

small molecule inhibitors targeting Rho associated coiled-coil containing protein kinase, such as AT13148 or KD025;

small molecule inhibitors targeting DNA topoisomerase, such as irinotecan, firtecan pegol, or amrubicin;

small molecule inhibitors targeting dopamine receptor D2, such as ONC-201;

small molecule inhibitors targeting DOT1 like histone lysine methyltransferase, such as pinometostat (EPZ-5676);

small molecule inhibitors targeting EZH2, such as tazemetostat, CPI-1205, or PF-06821497;

small molecule inhibitors targeting fatty acid synthase, such as TVB-2640 (Sagimet Biosciences);

small molecule inhibitors targeting fibroblast growth factor receptor 2 (FGFR2), such as bemarituzumab (FPA144);

small molecule inhibitors targeting focal adhesion kinase (FAK, PTK2), such as VS-4718, defactinib, or GSK2256098;

small molecule inhibitors targeting folate receptor 1, such as pralatrexate;

small molecule inhibitors targeting FOXM1, such as thiostrepton;

small molecule inhibitors targeting galectin 3, such as belapectin (GR-MD-02);

small molecule antagonists targeting glucocorticoid receptor, such as relacorilant (CORT-125134);

small molecule inhibitors targeting glutaminase include without limitation CB-839 (telaglenastat), or bis-2-(5-phenylacetamido-1,3,4-thiadiazol-2-yl)ethyl sulfide (BPTES);

small molecule inhibitors targeting GNRHR, such as elagolix, relugolix, or degarelix;

small molecule inhibitors targeting EPAS1, such as belzutifan (PT-2977 (Merck & Co.));

small molecule inhibitors targeting isocitrate dehydrogenase (NADP(+)), such as limitation ivosidenib (AG-120), vorasidenib (AG-881) (IDH1 and IDH2), IDH-305, or enasidenib (AG-221);

small molecule inhibitors targeting lysine demethylase 1A, such as CC-90011;

small molecule inhibitors targeting MAPK interacting serine/threonine kinase, such as tomivosertib (eFT-508);

small molecule inhibitors targeting notch receptor, such as AL-101 (BMS-906024);

small molecule inhibitors targeting polo like kinase 1 (PLK1), such as volasertib or onvansertib;

small molecule inhibitors targeting poly(ADP-ribose) polymerase (PARP), such as olaparib (MK7339), rucaparib, veliparib, talazoparib, ABT-767, pamiparib (BGB-290), fluazolepali (SHR-3162), niraparib (JNJ-64091742), stenoparib (2X-121 (e-7499)), simmiparib, IMP-4297, SC-10914, IDX-1197, HWH-340, CEP 9722, CEP-8983, E7016, 3-aminobenzamide, or CK-102;

small molecule inhibitors targeting polycomb protein EED, such as MAK683;

small molecule inhibitors targeting porcupine O-acyltransferase, such as WNT-974;

small molecule inhibitors targeting prostaglandin-endoperoxide synthase, such as HP-5000, lornoxicam, ketorolac tromethamine, bromfenac sodium, otenaproxesul (ATB-346), mofezolac, GLY-230, TRK-700, diclofenac, meloxicam, parecoxib, etoricoxib, celecoxib, AXS-06, diclofenac potassium, reformulated celecoxib (DRGT-46), AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, pamicogrel, parecoxib, robenacoxib, rofecoxib, rutecarpine, tilmacoxib, zaltoprofen, or imrecoxib;

small molecule inhibitors targeting protein arginine N methyltransferase, such as MS203, PF-06939999, GSK3368715, or GSK3326595;

small molecule inhibitors targeting PTPN11, such as TNO155 (SHP-099), RMC-4550, JAB-3068, RMC-4630 (SAR442720), or compounds disclosed in WO2018172984 or WO2017211303;

small molecule antagonist targeting retinoic acid receptor, such as tamibarotene (SY-1425);

small molecule inhibitors targeting ribosomal protein S6 kinase B1, such as MSC2363318A;

small molecule inhibitors targeting S100 calcium binding protein A9, such as tasquinimod;

small molecule inhibitors targeting selectin E, such as uproleselan sodium (GMI-1271);

small molecule inhibitors targeting SF3B1, such as H3B-8800;

small molecule inhibitors targeting Sirtuin-3, such as YC8-02;

small molecule inhibitors targeting SMO, such as sonidegib (Odomzo®, formerly LDE-225), vismodegib (GDC-0449), glasdegib (PF-04449913), itraconazole, or patidegib, taladegib;

small molecule antagonists targeting somatostatin receptor, such as OPS-201;

small molecule inhibitors targeting sphingosine kinase 2, such as opaganib (Yeliva®, ABC294640);

small molecule inhibitors targeting STAT3, such as napabucasin (BBI-608);

small molecule inhibitors targeting tankyrase, such as G007-LK or stenoparib (2X-121 (e-7499));

small molecule inhibitors targeting TFGBR1, such as galunisertib, PF-06952229;

small molecule inhibitors targeting thymidylate synthase, such as idetrexed (ONX-0801);

small molecule inhibitors targeting tumor protein p53, such as CMG-097;

small molecule inhibitors targeting valosin-containing protein, such as CB-5083;

small molecule inhibitors targeting WT1, such as ombipepimut-S(DSP-7888);

small molecule agonists targeting adenosine receptor, such as namodenoson (CF102);

small molecule agonist(s) targeting asparaginase, such as crisantaspase (Erwinase®), GRASPA (ERY-001, ERY-ASP), calaspargase pegol, or pegaspargase;

small molecule agonists targeting CCAAT enhancer binding protein alpha, such as MTL-501;

small molecule agonists targeting cytochrome P450 family, such as mitotane;

small molecule agonists targeting DExD/H-box helicase 58, such as RGT-100;

small molecule agonists targeting GNRHR, such as leuprorelin acetate, leuprorelin acetate sustained release depot (ATRIGEL), triptorelin pamoate, or goserelin acetate;

small molecule agonists targeting GRB2, such as prexigebersen (BP1001);

small molecule agonists targeting NFE2L2, such as omaveloxolone (RTA-408);

small molecule agonists targeting NOD2, such as mifamurtide (liposomal);

small molecule agonists targeting RAR-related orphan receptor gamma, such as cintirorgon (LYC-55716);

small molecule agonists targeting retinoic acid receptor (RAR), such as tretinoin;

small molecule agonists targeting STINGI, such as ADU-S100 (MIW-815), SB-11285, MK-1454, SR-8291, AdVCA0848, GSK-532, SYN-STING, MSA-1, SR-8291, cyclic-GAMP (cGAMP), or cyclic-di-AMP;

small molecule agonists targeting thyroid hormone receptor beta, such as levothyroxine sodium;

small molecule agonists targeting tumor necrosis factor, such as tasonermin;

antisense agents targeting baculoviral IAP repeat containing 5, such as EZN-3042;

antisense agents targeting GRB2, such as prexigebersen;

antisense agents targeting heat shock protein 27, such as apatorsen;

antisense agents targeting STAT3, such as danvatirsen (IONIS-STAT3-2.5Rx);

gene therapies targeting a C-C motif chemokine receptor, such as SB-728-T;

gene therapies targeting an interleukin, such as EGENE-001, tavokinogene telseplasmid, nogapendekin alfa (ALT-803), NKTR-255, NIZ-985 (hetIL-15), SAR441000, or MDNA-55;

antibodies targeting claudin 18, such as claudiximab;

antibodies targeting clusterin, such as AB-16B5;

antibodies targeting a complement component, such as ravulizumab (ALXN-1210);

antibodies targeting a C-X-C motif chemokine ligand, such as BMS-986253 (HuMax-Inflam);

antibodies targeting delta like canonical Notch ligand 4 (DLL4), such as demcizumab, navicixizumab (DLL4/VEGF);

antibodies targeting EPH receptor A3, such as fibatuzumab (KB-004);

antibodies targeting epithelial cell adhesion molecule, such as oportuzumab monatox (VB4-845);

antibodies targeting fibroblast growth factor, such as GAL-F2, B-701 (vofatamab);

antibodies targeting hepatocyte growth factor, such as MP-0250;

antibodies targeting an interleukin, such as canakinumab (ACZ885), gevokizumab (VPM087), CJM-112, guselkumab, talacotuzumab (JNJ-56022473), siltuximab, or tocilizumab;

antibodies targeting LRRC15, such as ABBV-085 or cusatuzumab (ARGX-110);

antibodies targeting mesothelin, such as BMS-986148, SEL-403, or anti-MSLN-MMAE;

antibodies targeting myostatin, such as landogrozumab;

antibodies targeting notch receptor, such as tarextumab;

antibodies targeting TGFB1 (TGFP1), such as SAR439459, ABBV-151, NIS793, SRK-181, XOMA089, or compounds disclosed in WO2019103203;

vaccines targeting fms related receptor tyrosine kinase, such as HLA-A2402/HLA-A0201 restricted epitope peptide vaccine;

vaccines targeting heat shock protein 27, such as PSV-AML (PhosphoSynVax);

vaccines targeting PD-L1, such as IO-120+IO-103 (PD-L1/PD-L2 vaccines) or IO-103;

vaccines targeting tumor protein p53, such as MVA-p53;

vaccines targeting WT1, such as WT-1 analog peptide vaccine (WT1-CTL);

cell therapies targeting baculoviral IAP repeat containing 5, such as tumor lysate/MUC1/survivin PepTivator-loaded dendritic cell vaccine;

cell therapies targeting carbonic anhydrase, such as DC-Ad-GMCAIX;

cell therapies targeting C-C motif chemokine receptor, such as CCR5-SBC-728-HSPC;
cell therapies targeting folate hydrolase 1, such as CIK-CAR.PSMA or CART-PSMA-TGFβRDN;
cell therapies targeting GSTP1, such as CPG3-CAR (GLYCAR);
cell therapies targeting HLA-A, such as FH-MCVA2TCR or NeoTCR-P1;
cell therapies targeting an interleukin, such as CST-101;
cell therapies targeting KRAS, such as anti-KRAS G12D mTCR PBL;
cell therapies targeting MET, such as anti-cMet RNA CAR T;
cell therapies targeting MUC16, such as JCAR-020;
cell therapies targeting PD-1, such as PD-1 knockout T cell therapy (esophageal cancer/NSCLC);
cell therapies targeting PRAME, such as BPX-701;
cell therapies targeting transforming protein E7, such as KITE-439;
cell therapies targeting WT1, such as WT1-CTL, ASP-7517, or JTCR-016.

Exemplified Combination Therapies

Lymphoma or Leukemia Combination Therapy

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCl-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCI-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma (DLBCL) Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and RICE. In some embodiments therapeutic agents used to treat DLBCL include rituximab (Rituxan®), cyclophosphamide, doxorubicin hydrochloride (hydroxydaunorubicin), vincristine sulfate (Oncovin®), prednisone, bendamustine, ifosfamide, carboplatin, etoposide, ibrutinib, polatuzumab vedotin piiq, bendamustine, copanlisib, lenalidomide (Revlimid®), dexamethasone, cytarabine, cisplatin, Yescarta®, Kymriah®, Polivy® (polatuzumab vedotin), BR (bendamustine (Treanda®), gemcitabine, oxiplatin, oxaliplatin, tafasitamab, polatuzumab, cyclophosphamide, or combinations thereof. In some embodiments therapeutic agents used to treat DLBCL include R-CHOP (rituximab+cyclophosphamide+doxorubicin hydrochloride (hydroxydaunorubicin)+vincristine sulfate (Oncovin®), +prednisone), rituximab+bendamustine, R-ICE (Rituximab+Ifosfamide+Carboplatin+Etoposide), rituximab+lenalomide, R-DHAP (rituximab+dexamethasone+high-dose cytarabine (Ara C)+cisplatin), Polivy® (polatuzumab vedotin)+BR (bendamustine (Treanda®) and rituximab (Rituxan®), R-GemOx (Gemcitabine+oxaliplatin+rituximab), Tafa-Len (tafasitamab+lenalidomide), Tafasitamab+Revlimid®, polatuzumab+bendamustine, Gemcitabine+oxaliplatin, R-EPOCH (rituximab+etoposide phosphate+prednisone+vincristine sulfate (Oncovin®)+cyclophosphamide+doxorubicin hydrochloride (hydroxydaunorubicin)), or CHOP (cyclophosphamide+doxorubicin hydrochloride (hydroxydaunorubicin)+vincristine sulfate (Oncovin®)+prednisone). In some embodiments therapeutic agents used to treat DLBCL include tafasitamab, glofitamab, epcoritamab, Lonca-T (loncastuximab tesirine), Debio-1562, polatuzumab, Yescarta, JCAR017, ADCT-402, brentuximab vedotin, MT-3724, odronextamab, Auto-03, Allo-501A, or TAK-007.

Chronic Lymphocytic Leukemia Combination Therapy

Therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

High Risk Myelodysplastic Syndrome (HR MDS) Combination Therapy

Therapeutic agents used to treat HR MDS include azacitidine (Vidaza®), decitabine (Dacogen®), lenalidomide (Revlimid®), cytarabine, idarubicin, daunorubicin, and combinations thereof. In some embodiments, combinations include cytarabine+daunorubicin and cytarabine+idarubicin. In some embodiments therapeutic agents used to treat HR MDS include pevonedistat, venetoclax, sabatolimab, guadecitabine, rigosertib, ivosidenib, enasidenib, selinexor, BGB324, DSP-7888, or SNS-301.

Low Risk Myelodysplastic Syndrome (LR MDS) Combination Therapy

Therapeutic agents used to treat LR MDS include lenalidomide, azacytidine, and combinations thereof. In some embodiments therapeutic agents used to treat LR MDS include roxadustat, luspatercept, imetelstat, LB-100, or rigosertib.

Acute Myeloid Leukemia (AML) Combination Therapy

Therapautic agents used to treat AML include cytarabine, idarubicin, daunorubicin, midostaurin (Rydapt®), venetoclax, azacitidine, ivasidenib, gilteritinib, enasidenib, low-dose cytarabine (LoDAC), mitoxantrone, fludarabine, granulocyte-colony stimulating factor, idarubicin, gilteritinib (Xospata®), enasidenib (Idhifa®), ivosidenib (Tibsovo®), decitabine (Dacogen®), mitoxantrone, etoposide, Gemtuzumab ozogamicin (Mylotarg®), glasdegib (Daurismo®), and combinations thereof. In some embodiments therapeutic agents used to treat AML include FLAG-Ida (fludarabine, cytarabine (Ara-C), granulocyte-colony stimulating factor (G-CSF) and idarubicin), cytarabine+idarubicin, cytarabine+daunorubicin+midostaurin, venetoclax+azacitidine, cytarabine+daunorubicin, or MEC (mitoxantrone, etoposide, and cytarabine). In some embodiments, therapeutic agents used to treat AML include pevonedistat, venetoclax, sabatolimab, eprenetapopt, or lemzoparlimab.

Multiple Myeloma (MM) Combination Therapy

Therapeutic agents used to treat MM include lenalidomide, bortezomib, dexamethasone, daratumumab (Darzalex®), pomalidomide, Cyclophosphamide, Carfilzomib (Kyprolis®), Elotuzumab (Empliciti), and combinations thereof. In some embodiments therapeutic agents used to treat MM include RVS (lenalidomide+bortezomib+dexamethasone), RevDex (lenalidomide plus dexamethasone), CYBORD (Cyclophosphamide+Bortezomib+Dexamethasone), Vel/Dex (bortezomib plus dexamethasone), or PomDex (Pomalidomide+low-dose dexamethasone). In some embodiments therapeutic agents used to treat MM include JCARH125, TAK-573, belantamab-m, ide-cel (CAR-T).

Breast Cancer Combination Therapy

Therapeutic agents used to treat breast cancer include albumin-bound paclitaxel, anastrozole, atezolizumab, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, letrozole, methotrexate, mitoxantrone, paclitaxel, pegylated liposomal doxorubicin, pertuzumab, tamoxifen, toremifene, trastuzumab, vinorelbine, and any combinations thereof. In some embodiments therapeutic agents used to treat breast cancer (e.g., HR+/−/HER2+/−) include trastuzumab (Herceptin®), pertuzumab (Perjeta®), docetaxel, carboplatin, palbociclib (Ibrance®), letrozole, trastuzumab emtansine (Kadcyla®), fulvestrant (Faslodex®), olaparib (Lynparza®), eribulin, tucatinib, capecitabine, lapatinib, everolimus (Afinitor®), exemestane, eribulin mesylate (Halaven®), and combinations thereof. In some embodiments therapeutic agents used to treat breast cancer include trastuzumab+pertuzumab+docetaxel, trastuzumab+pertuzumab+docetaxel+carboplatin, palbociclib+letrozole, tucatinib+capecitabine, lapatinib+capecitabine, palbociclib+fulvestrant, or everolimus+exemestane. In some embodiments therapeutic agents used to treat breast cancer include trastuzumab deruxtecan (Enhertu®), datopotamab deruxtecan (DS-1062), enfortumab vedotin (Padcev®), balixafortide, elacestrant, or a combination thereof. In some embodiments therapeutic agents used to treat breast cancer include balixafortide+eribulin.

Triple Negative Breast Cancer (TNBC) Combination Therapy

Therapeutic agents used to treat TNBC include atezolizumab, cyclophosphamide, docetaxel, doxorubicin, epirubicin, fluorouracil, paclitaxel, and combinations thereof. In some embodiments therapeutic agents used to treat TNBC include olaparib (Lynparza®), atezolizumab (Tecentriq®), paclitaxel (Abraxane®), eribulin, bevacizumab (Avastin®), carboplatin, gemcitabine, eribulin mesylate (Halaven®), sacituzumab govitecan (Trodelvy®), pembrolizumab (Keytruda®), cisplatin, doxorubicin, epirubicin, or a combination thereof. In some embodiments therapeutic agents to treat TNBC include atezolizumab+paclitaxel, bevacizumab+paclitaxel, carboplatin+paclitaxel, carboplatin+gemcitabine, or paclitaxel+gemcitabine. In some embodiments therapeutic agents used to treat TNBC include eryaspase, capivasertib, alpelisib, rucaparib+nivolumab, atezolumab+paclitaxel+gemcitabine+capecitabine+carboplatin, ipatasertib+paclitaxel, ladiratuzumab vedotin+pembrolimab, durvalumab+DS-8201a, trilaciclib+gemcitabine+carboplatin. In some embodiments therapeutic agents used to treat TNBC include trastuzumab deruxtecan (Enhertu®), datopotamab deruxtecan (DS-1062), enfortumab vedotin (Padcev®), balixafortide, adagloxad simolenin, nelipepimut-s (NeuVax®), nivolumab (Opdivo®), rucaparib, toripalimab (Tuoyi®), camrelizumab, capivasertib, durvalumab (Imfinzi®), and combinations thereof. In some embodiments therapeutic agents use to treat TNBC include nivolumab+rucaparib, bevacizumab (Avastin®)+chemotherapy, toripalimab+paclitaxel, toripalimab+albumin-bound paclitaxel, camrelizumab+chemotherapy, pembrolizumab+chemotherapy, balixafortide+eribulin, durvalumab+trastuzumab deruxtecan, durvalumab+paclitaxel, or capivasertib+paclitaxel.

Bladder Cancer Combination Therapy

Therapeutic agents used to treat bladder cancer include datopotamab deruxtecan (DS-1062), trastuzumab deruxtecan (Enhertu®), erdafitinib, eganelisib, lenvatinib, bempegaldesleukin (NKTR-214), or a combination thereof. In some embodiments therapeutic agents used to treat bladder cancer include eganelisib+nivolumab, pembrolizumab (Keytruda®)+enfortumab vedotin (Padcev®), nivolumab+ipilimumab, duravalumab+tremelimumab, lenvatinib+pembrolizumab, enfortumab vedotin (Padcev®)+pembrolizumab, and bempegaldesleukin+nivolumab.

Colorectal Cancer (CRC) Combination Therapy

Therapeutic agents used to treat CRC include bevacizumab, capecitabine, cetuximab, fluorouracil, irinotecan, leucovorin, oxaliplatin, panitumumab, ziv-aflibercept, and any combinations thereof. In some embodiments therapeutic agents used to treat CRC include bevacizumab (Avastin®), leucovorin, 5-FU, oxaliplatin (FOLFOX), pembrolizumab (Keytruda®), FOLFIRI, regorafenib (Stivarga®), aflibercept (Zaltrap®), cetuximab (Erbitux®), Lonsurf (Orcantas®), XELOX, FOLFOXIRI, or a combination thereof. In some embodiments therapeutic agents used to treat CRC include bevacizumab+leucovorin+5-FU+oxaliplatin (FOLFOX), bevacizumab+FOLFIRI, bevacizumab+FOLFOX, aflibercept+FOLFIRI, cetuximab+FOLFIRI, bevacizumab+XELOX, and bevacizumab+FOLFOXIRI. In some embodiments therapeutic agents used to treat CRC include binimetinib+encorafenib+cetuximab, trametinib+dabrafenib+panitumumab, trastuzumab+pertuzumab, napabucasin+FOLFIRI+bevacizumab, nivolumab+ipilimumab.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof. In some embodiments therapeutic agents used to treat gastroesophageal junction cancer (GEJ) include herceptin, cisplatin, 5-FU, ramicurimab, or paclitaxel. In some embodiments therapeutic agents used to treat GEJ cancer include ALX-148, AO-176, or IBI-188.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Therapeutic agents used to treat head and neck squamous cell carcinoma (HNSCC) include pembrolizumab, carboplatin, 5-FU, docetaxel, cetuximab (Erbitux®), cisplatin, nivolumab (Opdivo®), and combinations thereof. In some embodiments therapeutic agents used to treat HNSCC include pembrolizumab+carboplatin+5-FU, cetuximab+cisplatin+5-FU, cetuximab+carboplatin+5-FU, cisplatin+5-FU, and carboplatin+5-FU. In some embodiments therapeutic agents used to treat HNSCC include durvalumab, durvalumab+tremelimumab, nivolumab+ipilimumab, rovaluecel, pembrolizumab, pembrolizumab+epacadostat, GSK3359609+pembrolizumab, lenvatinib+pembrolizumab, retifanlimab, retifanlimab+enobituzumab, ADU-S100+pembrolizumab, epacadostat+nivolumab+ipilimumab/lirilumab.

Non-Small Cell Lung Cancer Combination Therapy

Therapeutic agents used to treat non-small cell lung cancer (NSCLC) include afatinib, albumin-bound paclitaxel, alectinib, atezolizumab, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof. In some embodiments therapeutic agents used to treat NSCLC include alectinib (Alecensa®), dabrafenib (Tafinlar®), trametinib (Mekinist®), osimertinib (Tagrisso®), entrectinib (Tarceva®), crizotinib (Xalkori®), pembrolizumab (Keytruda®), carboplatin, pemetrexed (Alimta®), nab-paclitaxel (Abraxane®), ramucirumab (Cyramza®), docetaxel, bevacizumab (Avastin®), brigatinib, gemcitabine, cisplatin, afatinib (Gilotrif®), nivolumab (Opdivo®), gefitinib (Iressa®), and combinations thereof. In some embodiments therapeutic agents used to treat NSCLC include dabrafenib+trametinib, pembrolizumab+carboplatin+pemetrexed, pembrolizumab+carboplatin+nab-paclitaxel, ramucirumab+docetaxel, bevacizumab+carboplatin+pemetrexed, pembrolizumab+pemetrexed+carboplatin, cisplatin+pemetrexed, bevacizumab+carboplatin+nab-paclitaxel, cisplatin+gemcitabine, nivolumab+docetaxel, carboplatin+pemetrexed, carboplatin+nab-paclitaxel, or pemetrexed+cisplatin+carboplatin. In some embodiments therapeutic agents used to NSCLC include datopotamab deruxtecan (DS-1062), trastuzumab deruxtecan (Enhertu®), enfortumab vedotin (Padcev®), durvalumab, canakinumab, cemiplimab, nogapendekin alfa, avelumab, tiragolumab, domvanalimab, vibostolimab, ociperlimab, or a combination thereof. In some embodiments therapeutic agents used to treat NSCLC include datopotamab deruxtecan+pembrolizumab, datopotamab deruxtecan+durvalumab, durvalumab+tremelimumab, pembrolizumab+lenvatinib+pemetrexed, pembrolizumab+olaparib, nogapendekin alfa (N-803)+pembrolizumab, tiragolumab+atezolizumab, vibostolimab+pembrolizumab, or ociperlimab+tislelizumab.

Small Cell Lung Cancer Combination Therapy

Therapeutic agents used to treat small cell lung cancer (SCLC) include atezolizumab, bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof. In some embodiments therapeutic agents used to treat SCLC include atezolizumab, carboplatin, cisplatin, etoposide, paclitaxel, topotecan, nivolumab, durvalumab, trilaciclib, or combinations thereof. In some embodiments therapeutic agents used to treat SCLC include atezolizumab+carboplatin+etoposide, atezolizumab+carboplatin, atezolizumab+etoposide, or carboplatin+paclitaxel.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, pazopanib, pemetrexed, tamoxifen, topotecan, vinorelbine, and any combinations thereof.

Pancreatic Cancer Combination Therapies

Therapeutic agents used to treat pancreatic cancer include 5-FU, leucovorin, oxaliplatin, irinotecan, gemcitabine, nab-paclitaxel (Abraxane*), FOLFIRINOX, and combinations thereof. In some embodiments therapeutic agents used to treat pancreatic cancer include 5-FU+leucovorin+oxaliplatin+irinotecan, 5-FU+nanoliposomal irinotecan, leucovorin+nanoliposomal irinotecan, and gemcitabine+nab-paclitaxel.

Prostate Cancer Combination Therapies

Therapeutic agents used to treat prostate cancer include enzalutamide (Xtandi©), leuprolide, trifluridine, tipiracil (Lonsurf), cabazitaxel, prednisone, abiraterone (Zytiga*), docetaxel, mitoxantrone, bicalutamide, LHRH, flutamide, ADT, sabizabulin (Veru-111), and combinations thereof. In some embodiments therapeutic agents used to treat prostate cancer include enzalutamide+leuprolide, trifluridine+tipiracil (Lonsurf), cabazitaxel+prednisone, abiraterone+prednisone, docetaxel+prednisone, mitoxantrone+prednisone, bicalutamide+LHRH, flutamide+LHRH, leuprolide+flutamide, and abiraterone+prednisone+ADT.

Additional Exemplified Combination Therapies

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with one or more therapeutic agents selected from a PI3K inhibitor, a Trop-2 binding agent, CD47 antagonist, a SIRPa antagonist, a FLT3R agonist, a PD-1 antagonist, a PD-L1 antagonist, an MCL1 inhibitor, a CCR8 binding agent, an HPK1 antagonist, a DGKα inhibitor, a CISH inhibitor, a PARP-7 inhibitor, a Cbl-b inhibitor, a KRAS inhibitor (e.g., a KRAS G12C or G12D inhibitor), a KRAS degrader, a beta-catenin degrader, a helios degrader, a CD73 inhibitor, an adenosine receptor antagonist, a TIGIT antagonist, a TREM1 binding agent, a TREM2 binding agent, a CD137 agonist, a GITR binding agent, an OX40 binding agent, and a CAR-T cell therapy.

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with one or more therapeutic agents selected from a PI3KS inhibitor (e.g., idealisib), an anti-Trop-2 antibody drug conjugate (e.g., sacituzumab govitecan, datopotamab deruxtecan (DS-1062)), an anti-CD47 antibody or a CD47-blocking agent (e.g., magrolimab, DSP-107, AO-176, ALX-148, letaplimab (IBI-188), lemzoparlimab, TTI-621, TTI-622), an anti-SIRPa antibody (e.g., GS-0189), a FLT3L-Fc fusion protein (e.g., GS-3583), an anti-PD-1 antibody (pembrolizumab, nivolumab, zimberelimab), a small molecule PD-L1 inhibitor (e.g., GS-4224), an anti-PD-L1 antibody (e.g., atezolizumab, avelumab), a small molecule MCL1 inhibitor (e.g., GS-9716), a small molecule HPK1 inhibitor (e.g., GS-6451), a HPK1 degrader (PROTAC; e.g., ARV-766), a small molecule DGKα inhibitor, a small molecule CD73 inhibitor (e.g., quemliclustat (AB680)), an anti-CD73 antibody (e.g., oleclumab), a dual A2a/A2b adenosine receptor antagonist (e.g., etrumadenant (AB928)), an anti-TIGIT antibody (e.g., tiragolumab, vibostolimab, domvanalimab, AB308), an anti-TREM1 antibody (e.g., PY159), an anti-TREM2 antibody (e.g., PY314), a CD137 agonist (e.g., AGEN-2373), a GITR/OX40 binding agent (e.g., AGEN-1223), an IL-2 variant (IL-2v; e.g., aldesleukin (Proleukin), bempegaldesleukin (NKTR-214), nemvaleukin alfa (ALKS-4230), or GS-4528), and a CAR-T cell therapy (e.g., axicabtagene ciloleucel, brexucabtagene autoleucel, tisagenlecleucel).

In some embodiments a compound of Formula (I), (Ia), (Ib), (IIa), (IIb), (IIc), (IId), (IIe), (IIf), (IIg), (IIh), (IIi), (IIj), (IIk), (IIIa), (IIIa-1), (IIIa-2), (IIIa-3), (IIIb), (IIIc), (IIId), (IIIe), (IIIf), (IVa), (IVa-1), (IVa-2), (V), (Va), (VI), or (VIa), provided herein, or pharmaceutically acceptable salt thereof, is administered with one or more therapeutic agents selected from idealisib, sacituzumab govitecan, magrolimab, GS-0189, GS-3583, zimberelimab, GS-4224, GS-9716, GS-6451, GS-4528, quemliclustat (AB680), etrumadenant (AB928), domvanalimab, AB308, PY159, PY314, AGEN-1223, AGEN-2373, axicabtagene ciloleucel and brexucabtagene autoleucel.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that these examples are exemplary and not exhaustive. Many changes can be made in the specific embodiments which are disclosed and still obtain a like or similar result without departing from the spirit and scope of the disclosure.

Compounds disclosed herein can be prepared according to the procedures of the following Schemes and Examples, using appropriate materials and are further exemplified by the following specific examples. Moreover, by utilizing the procedures described herein, in conjunction with ordinary skills in the art, additional compounds of the present disclosure claimed herein can be readily prepared. The examples further illustrate details for the preparation of the compounds of the present disclosure. Those skilled in the art will readily understand that known variations of the conditions and processes of the following preparative procedures can be used to prepare these compounds. For synthesizing compounds which are embodiments described in the present disclosure, inspection of the structure of the compound to be synthesized will provide the identity of each substituent group. In some cases, the identity of the final product can render apparent the identity of the necessary starting materials by a process of inspection, given the examples herein. Compounds can be isolated in the form of their pharmaceutically acceptable salts, such as those described above. Compounds described herein are typically stable and isolatable at room temperature and pressure.

An illustration of the preparation of compounds disclosed herein is shown below. Unless otherwise indicated, variables have the same meaning as described above. The examples presented below are intended to illustrate particular embodiments of the disclosure. Suitable starting materials, building blocks and reagents employed in the synthesis as described below are commercially available from AbovChem, Acros Organics, Astatech, Combi Blocks, Oakwood Chemical, or Sigma-Aldrich, for example, or can be routinely prepared by procedures described in the literature, for example in "March's Advanced Organic Chemistry: Reactions, Mechanisms, and Structure", 5$^{th}$ Edition; John Wiley & Sons or T. Eicher, S. Hauptmann "The Chemistry of Heterocycles; Structures, Reactions, Synthesis and Application", 2$^{nd}$ edition, Wiley-VCH 2003; Fieser et al. "Fiesers' Reagents for organic Synthesis" John Wiley & Sons 2000.

General Reaction Scheme 1

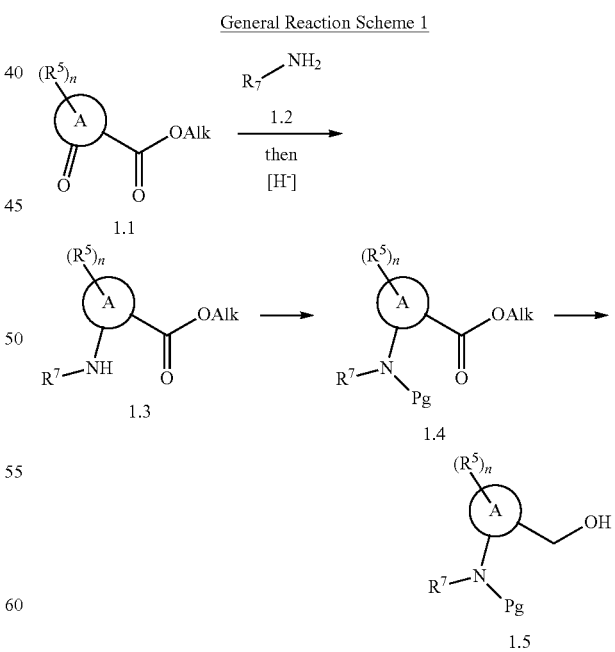

Compounds of the Formula 1.3 may be produced by reacting Intermediate 1.1 with a suitable amine of Formula 1.2 in the presence or absence of a catalyst (e.g. p-toluenesulfonic acid, Ca(OTf)$_2$, TiCl$_4$) in an inert solvent (e.g.

benzene, toluene) at elevated temperature or at ambient temperature followed treatment with a suitable reducing reagent (e.g., NaBH$_4$, Na(OAc)$_3$BH, NaBH$_3$CN). A compound of the Formula 1.3 can be protected with a suitable reagent (e.g. Boc$_2$O) in the presence or absence of a base (e.g., N,N-diisopropylethylamine, triethylamine, DMAP) to produce compounds of Formula 1.4 (e.g. Pg=Boc). Compounds of Formula 1.4 can be reacted with a suitable reducing agent (e.g. LiAlH$_4$, DIBAL-H) to generate compounds of Formula 1.5. Alternatively compounds of Formula 1.5 can be produced by hydrolysis of compounds of Formula 1.4 with a suitable base (e.g. NaOH, KOH, LiOH) followed by reduction of the carboxylic acid under suitable reducing conditions (e.g. isobutyl chloroformate followed by NaBH$_4$, BH$_3$ in THF). Ring A represents a cycloalkyl or heterocylycl (e.g., cyclohexyl, cyclohexenyl, or tetrahydropyranyl).

General Reaction Scheme 2

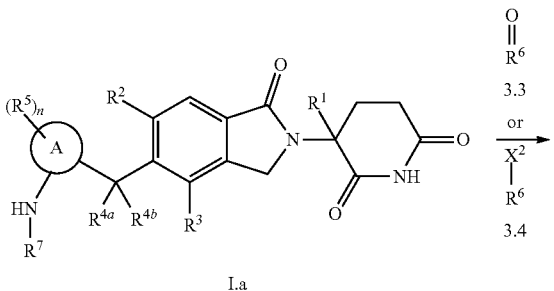

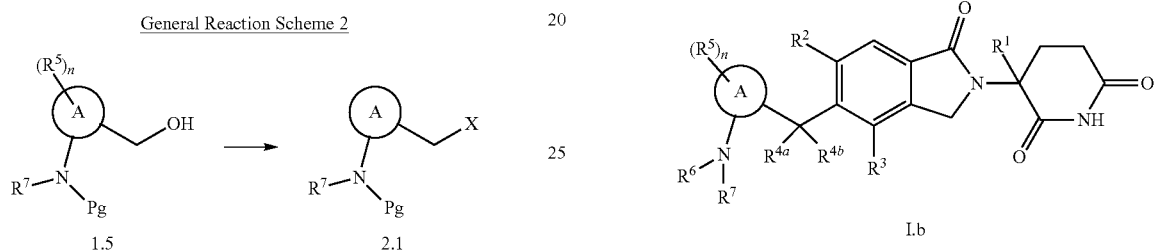

Compounds of the Formula 2.1, where X is a leaving group (e.g. Cl, Br, I, OTs, OMs), may be produced by reacting intermediate 1.5 under suitable conditions (e.g. PPh$_3$ with I$_2$, PPh$_3$ with CCl$_4$, PPh$_3$ with CBr$_4$, SOCl$_2$, TsCl, MsCl, Ms$_2$O) in an inert solvent (e.g. THF, MeCN, DCM). Ring A represents a cycloalkyl or heterocylycl (e.g., cyclohexyl, cyclohexenyl, or tetrahydropyranyl).

General Reaction Scheme 3

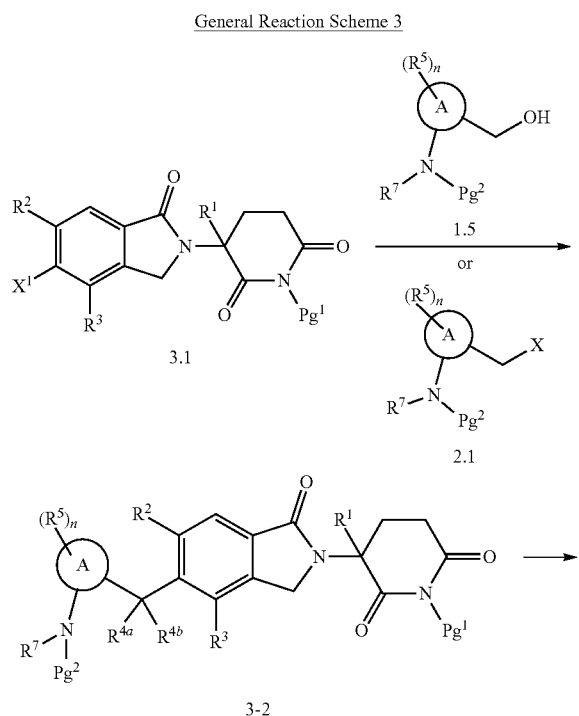

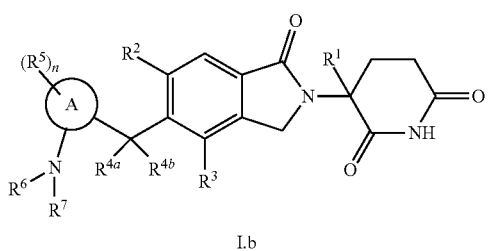

Compounds of the Formula 3.2 may be produced by reacting Intermediate 3.1 (where X$^1$=Br, I, Cl, OTf) with an compound of Formula 1.5 in the presence of a suitable metal precatalyst (e.g. NiBr$_2$(glyme), NiCl$_2$(glyme)) with an appropriate ligand (e.g. dtbbpy), photocatalyst (e.g. Ir[(dF (CF$_3$)ppy$_2$)dtbbpy]PF$_6$), and base (e.g. TMP, quinuclidine, K$_2$CO$_3$) in an inert solvent (e.g. DMF, DMA, TBME, CpOMe, 1,4-dioxane) under irradiation by blue LEDs following activation of alcohol 1.5 with a suitable N-heterocyclic carbene (e.g. 5,7-di-tert-butyl-3-phenylbenzo[d]oxazol-3-ium tetrafluoroborate). Alternatively, compounds of the Formula 3.2 may be produced by reacting Intermediate 3.1 (where X$^1$=Br, I, Cl, OTf) with a compound of Formula 2.1 (where X=Br, I, Cl, OTf) in the presence of a suitable palladium or nickel catalyst with a suitable reducing reagent (e.g. Zn, Mn, TMS silane). A compound of the Formula 3.2 (e.g. Pg$^2$=Boc, Pg$^1$=SEM) can be subsequently deprotected under suitable conditions (e.g. trifluoroacetic acid or hydrochloric acid followed by DMEDA) to reveal a compound of Formula I.a that contains a secondary amine. Compounds of Formula I.a can then be reacted with a suitable aldehyde or ketone of Formula 3.3 in the presence of a suitable reducing reagent (e.g., NaBH$_4$, Na(OAc)$_3$BH, Na(CN)$_3$BH) to produce compounds of Formula I.b. Alternatively, compounds of Formula I.b can be assembled by the combination of compounds of Formula I.a with an Intermediate 3.4, where X$^2$ is a leaving group (e.g. Cl, Br, I, OTs, OMs), in the presence or absence of a base (e.g., N,N-diisopropylethylamine, triethylamine, K$_2$CO$_3$, CsCO$_3$) in an inert solvent (e.g. DMF, acetonitrile) at r.t. or elevated temperature. Ring A represents a cycloalkyl or heterocylycl (e.g., cyclohexyl, cyclohexenyl, or tetrahydropyranyl).

General Reaction Scheme 4

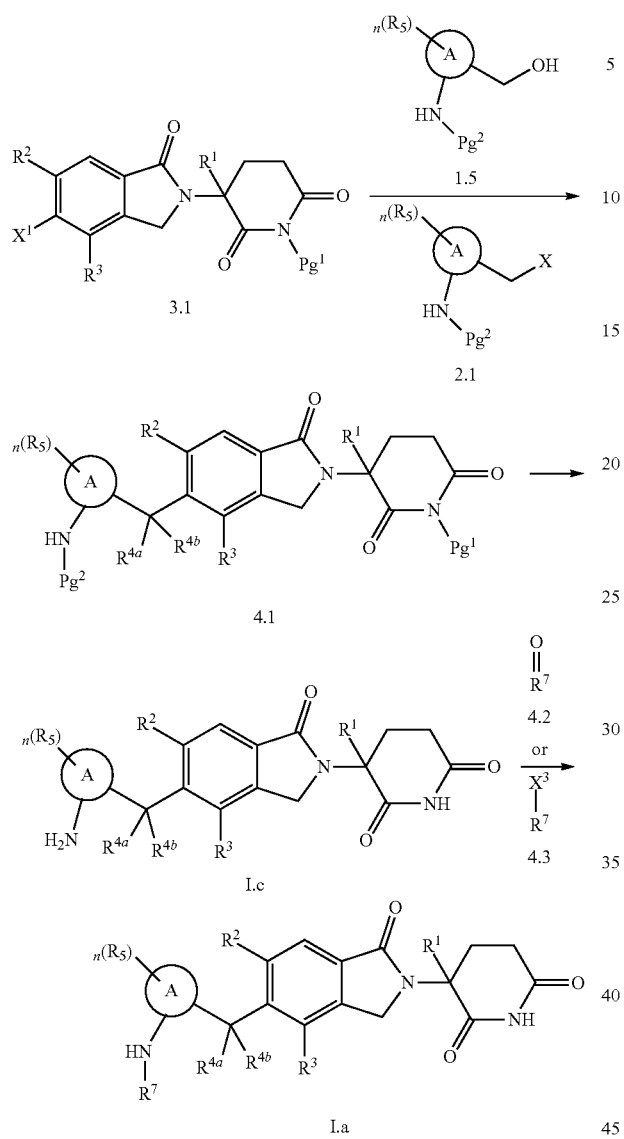

Compounds of the Formula 4.1 may be produced by reacting Intermediate 3.1 (where $X^1$=Br, I, Cl, OTf) with an compound of Formula 1.5 in the presence of a suitable metal precatalyst (e.g. NiBr$_2$(glyme), NiCl$_2$(glyme)) with an appropriate ligand (e.g. dtbbpy), photocatalyst (e.g. Ir[(dF(CF$_3$)ppy$_2$)dtbbpy]PF$_6$), and base (e.g. TMP, quinuclidine, K$_2$CO$_3$) in an inert solvent (e.g. DMF, DMA, TBME, CpOMe, 1,4-dioxane) under irradiation by blue LEDs following activation of alcohol 1.5 with a suitable N-heterocyclic carbene (e.g. 5,7-di-tert-butyl-3-phenylbenzo[d]oxazol-3-ium tetrafluoroborate). Alternatively, compounds of the Formula 4.1 may be produced by reacting Intermediate 3.1 (where $X^1$=Br, I, Cl, OTf) with a compound of Formula 2.1 (where X=Br, I, Cl, OTf) in the presence of a suitable palladium or nickel catalyst with a suitable reducing reagent (e.g. Zn, Mn, TMS silane). A compound of the Formula 4.1 (e.g. Pg$^2$=Boc, Pg$^1$=SEM) can be subsequently deprotected under suitable conditions (e.g. trifluoroacetic acid or hydrochloric acid followed by DMEDA) to reveal a compound of Formula I.c that contains a primary amine. Compounds of Formula I.c can then be reacted with a suitable aldehyde or ketone of Formula 4.2 in the presence of a suitable reducing reagent (e.g., NaBH$_4$, Na(OAc)$_3$BH, NaBH$_3$CN) to produce compounds of Formula I.a. Alternatively, compounds of Formula I.a can be assembled by the combination of compounds of Formula I.c with an Intermediate 4.3, where $X^2$ is a leaving group (e.g. Cl, Br, I, OTs, OMs), in the presence or absence of a base (e.g., N,N-diisopropylethylamine, triethylamine, K$_2$CO$_3$, CsCO3) in an inert solvent (e.g. DMF, acetonitrile) at r.t. or elevated temperature. Ring A represents a cycloalkyl or heterocylycl (e.g., cyclohexyl, cyclohexenyl, or tetrahydropyranyl).

General Reaction Scheme 5

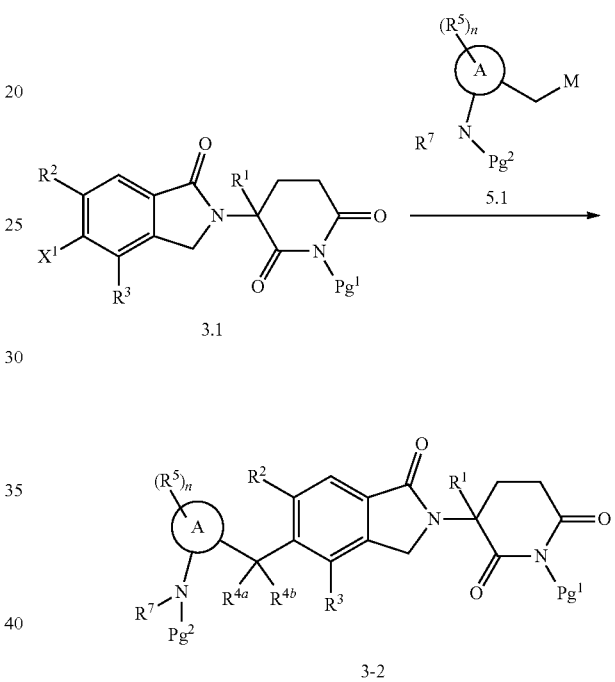

Compounds of the Formula 3.2 may be produced by reacting Intermediate 3.1 (where $X^1$=Br, I, Cl, OTf) with an suitable metallated coupling partner of Formula 5.1 (where M is —B, —Sn, —Zn, —Si, or —Mg) in the presence of a suitable palladium or nickel catalyst. Ring A represents a cycloalkyl or heterocylycl (e.g., cyclohexyl, cyclohexenyl, or tetrahydropyranyl).

General Reaction Scheme 6

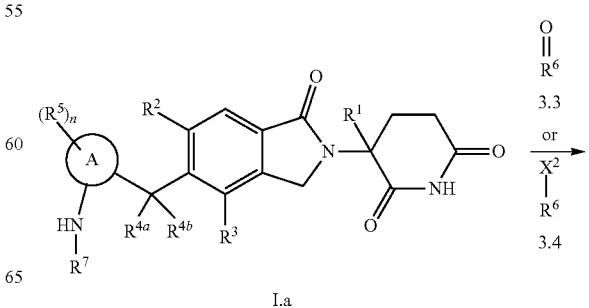

251

-continued

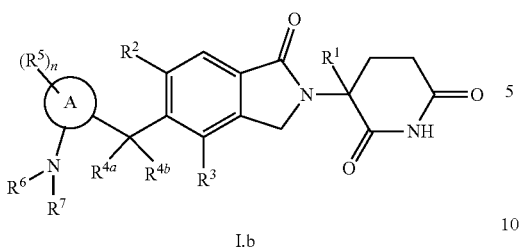

I.b

252

-continued

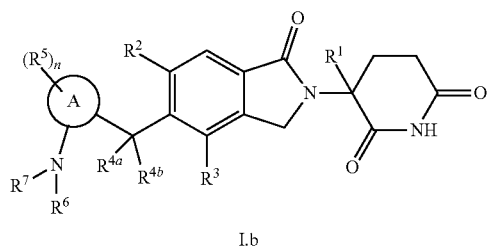

I.b

Compounds of Formula I.a can be reacted with a suitable aldehyde or ketone of Formula 3.3 in the presence of a suitable reducing reagent (e.g., NaBH$_4$, Na(OAc)$_3$BH, NaBH$_3$CN) to produce compounds of Formula I.b. Alternatively, compounds of Formula I.b can be assembled by the combination of compounds of Formula I.c with an intermediate 3.4, where $X^2$ is a leaving group (e.g. Cl, Br, I, OTs, OMs), in the presence or absence of a base (e.g., N,N-diisopropylethylamine, triethylamine, K$_2$CO$_3$, CsCO$_3$) in an inert solvent (e.g. DMF, acetonitrile) at r.t. or elevated temperature. Ring A represents a cycloalkyl or heterocylycl (e.g., cyclohexyl, cyclohexenyl, or tetrahydropyranyl).

General Reaction Scheme 7

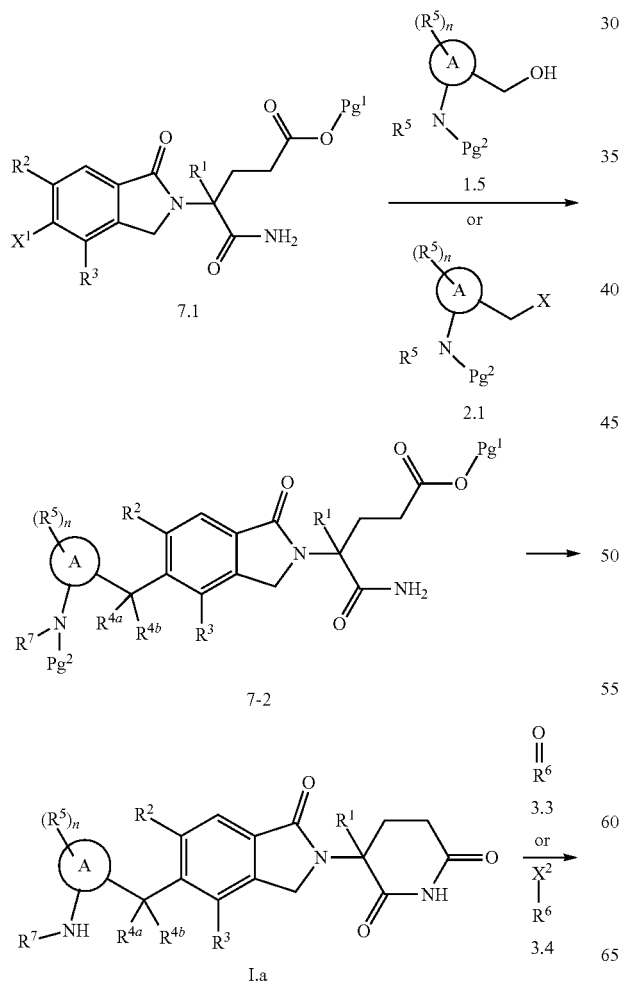

Compounds of the Formula 7.2 may be produced by reacting Intermediate 7.1 (where $X^1$=Br, I, Cl, OTf) with an compound of Formula 1.5 in the presence of a suitable metal precatalyst (e.g. NiBr$_2$(glyme), NiCl$_2$(glyme)) with an appropriate ligand (e.g. dtbbpy), photocatalyst (e.g. Ir[(dF(CF$_3$)ppy$_2$)dtbbpy]PF$_6$), and base (e.g. TMP, quinuclidine, K$_2$CO$_3$) in an inert solvent (e.g. DMF, DMA, TBME, CpOMe, 1,4-dioxane) under irradiation by blue LEDs following activation of alcohol 1.5 with a suitable N-heterocyclic carbene (e.g. 5,7-di-tert-butyl-3-phenylbenzo[d]oxazol-3-ium tetrafluoroborate). Alternatively, compounds of the Formula 7.2 may be produced by reacting Intermediate 7.1 (where $X^1$=Br, I, Cl, OTf) with a compound of Formula 2.1 (where X=Br, I, Cl, OTf) in the presence of a suitable palladium or nickel catalyst with a suitable reducing reagent (e.g. Zn, Mn, TMS silane). A compound of the Formula 7.2 (e.g. Pg$^2$=Boc, Pg$^1$=tert-butyl) can be subsequently deprotected and cyclized under suitable conditions (e.g. trifluoroacetic acid or benzene sulfonic acid) to reveal a compound of Formula I.a that contains a secondary amine. Compounds of Formula I.a can then be reacted with a suitable aldehyde or ketone of Formula 3.3 in the presence of a suitable reducing reagent (e.g., NaBH$_4$, Na(OAc)$_3$BH, NaBH$_3$CN) to produce compounds of Formula I.b. Alternatively, compounds of Formula I.b can be assembled by the combination of compounds of Formula I.a with an Intermediate 3.4, where $X^2$ is a leaving group (e.g. Cl, Br, I, OTs, OMs), in the presence or absence of a base (e.g., N,N-diisopropylethylamine, triethylamine, K$_2$CO$_3$, CsCO3) in an inert solvent (e.g. DMF, acetonitrile) at r.t. or elevated temperature. Ring A represents a cycloalkyl or heterocylycl (e.g., cyclohexyl, cyclohexenyl, or tetrahydropyranyl).

General Reaction Scheme 8

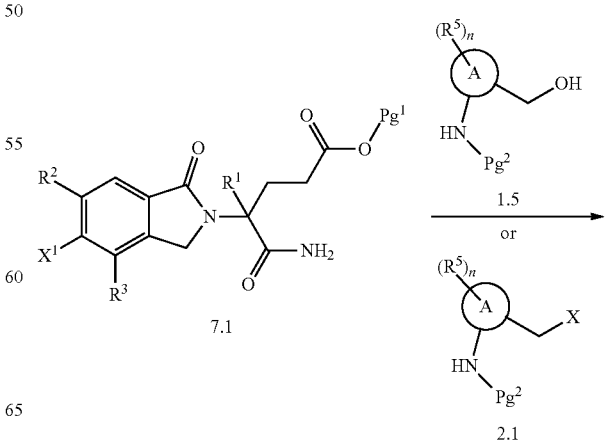

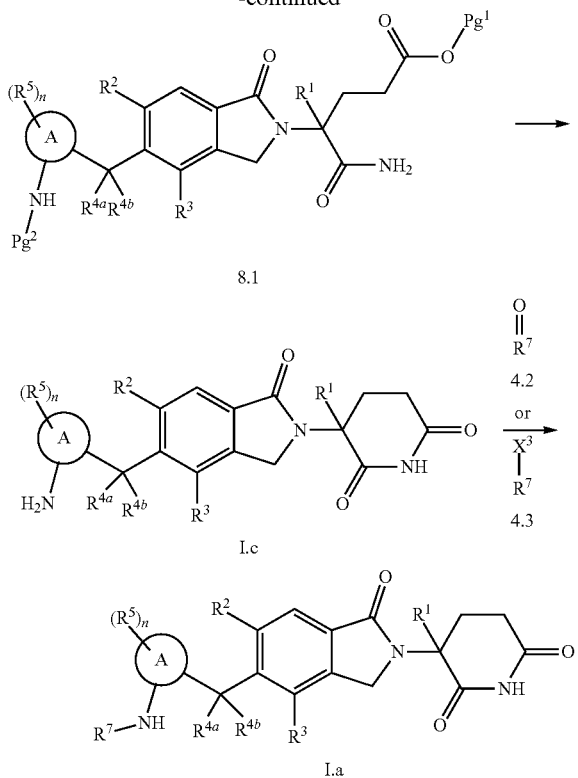

8.1

I.c

I.a

Compounds of the Formula 8.1 may be produced by reacting intermediate 7.1 (where $X^1$=Br, I, Cl, OTf) with an compound of Formula 1.5 in the presence of a suitable metal precatalyst (e.g. NiBr$_2$(glyme), NiCl$_2$(glyme)) with an appropriate ligand (e.g. dtbbpy), photocatalyst (e.g. Ir[(dF(CF$_3$)ppy$_2$)dtbbpy]PF$_6$), and base (e.g. TMP, quinuclidine, K$_2$CO$_3$) in an inert solvent (e.g. DMF, DMA, TBME, CpOMe, 1,4-dioxane) under irradiation by blue LEDs following activation of alcohol 1.5 with a suitable N-heterocyclic carbene (e.g. 5,7-di-tert-butyl-3-phenylbenzo[d]oxazol-3-ium tetrafluoroborate). Alternatively, compounds of the Formula 8.1 may be produced by reacting Intermediate 7.1 (where $X^1$=Br, I, Cl, OTf) with a compound of Formula 2.1 (where X=Br, I, Cl, OTf) in the presence of a suitable palladium or nickel catalyst with a suitable reducing reagent (e.g. Zn, Mn, TMS silane). A compound of the Formula 8.1 (e.g.

Pg$^2$=Boc, Pg$^1$=tert-butyl) can be subsequently deprotected and cyclized under suitable conditions (e.g. trifluoroacetic acid or benzene sulfonic acid) to reveal a compound of Formula I.c that contains a primary amine. Compounds of Formula I.c can then be reacted with a suitable aldehyde or ketone of Formula 4.2 in the presence of a suitable reducing reagent (e.g., NaBH$_4$, Na(OAc)$_3$BH, NaBH$_3$CN) to produce compounds of Formula L.a. Alternatively, compounds of Formula I.a can be assembled by the combination of compounds of Formula I.c with an Intermediate 4.3, where $X^2$ is a leaving group (e.g. Cl, Br, I, OTs, OMs), in the presence or absence of a base (e.g., N,N-diisopropylethylamine, triethylamine, K$_2$CO$_3$, CsCO$_3$) in an inert solvent (e.g. DMF, acetonitrile) at r.t. or elevated temperature. Ring A represents a cycloalkyl or heterocylycl (e.g., cyclohexyl, cyclohexenyl, or tetrahydropyranyl).

General Reaction Scheme 9

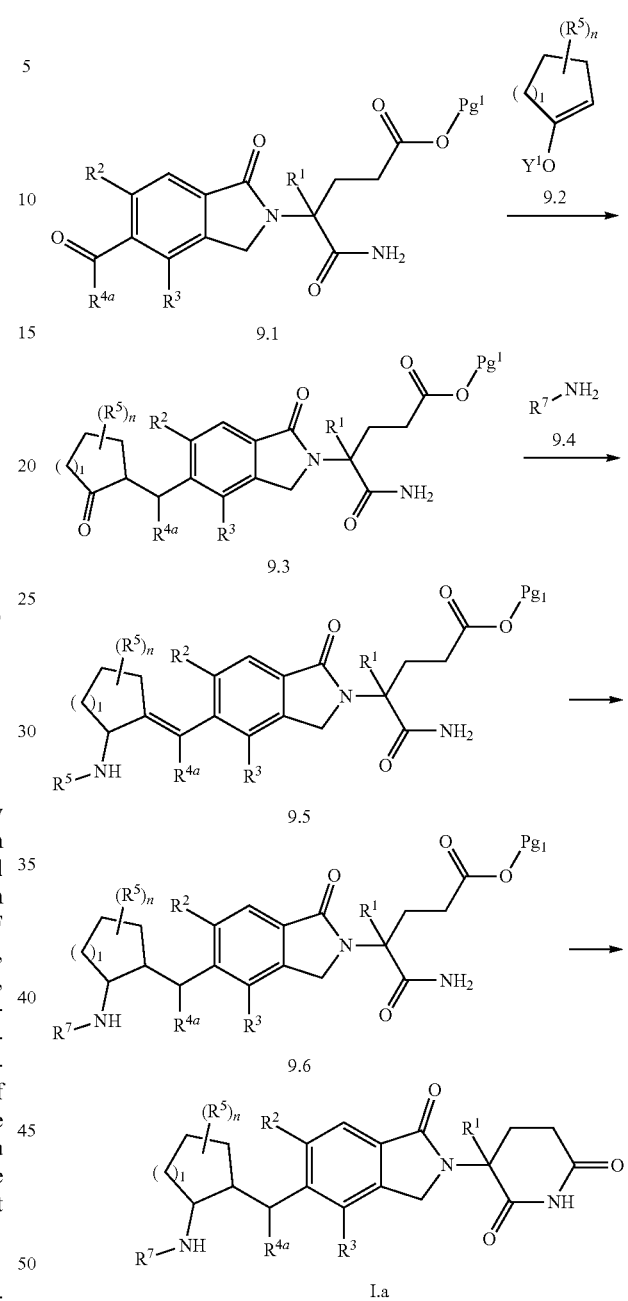

I.a

Compounds of the Formula 9.3 may be produced by reacting Intermediate 9.1 with a compound of Formula 9.1 (e.g. where $Y^1$=TMS, morpholine). Compounds of Formula 9.3 can then be reacted with amines of Formula 9.4 in the presence of a suitable reducing reagent (e.g., NaBH$_4$, Na(OAc)$_3$BH, NaBH$_3$CN) in the presence or absence of an acid catalyst (e.g. AcOH, Ti(OiPr)$_4$) to generate compounds of Formula 9.5. Compounds of Formula 9.5 can then be reduced to compounds of Formula 9.6 with a suitable metal hydride catalyst (e.g. Pd/C, Crabtree's catalyst) in the presence of hydrogen. A compound of the Formula 9.6 (e.g. Pg$^1$=tert-butyl) can be subsequently deprotected and cyclized under suitable conditions (e.g. trifluoroacetic acid or benzene sulfonic acid) to reveal a compound of Formula L.a.

General Reaction Scheme 10

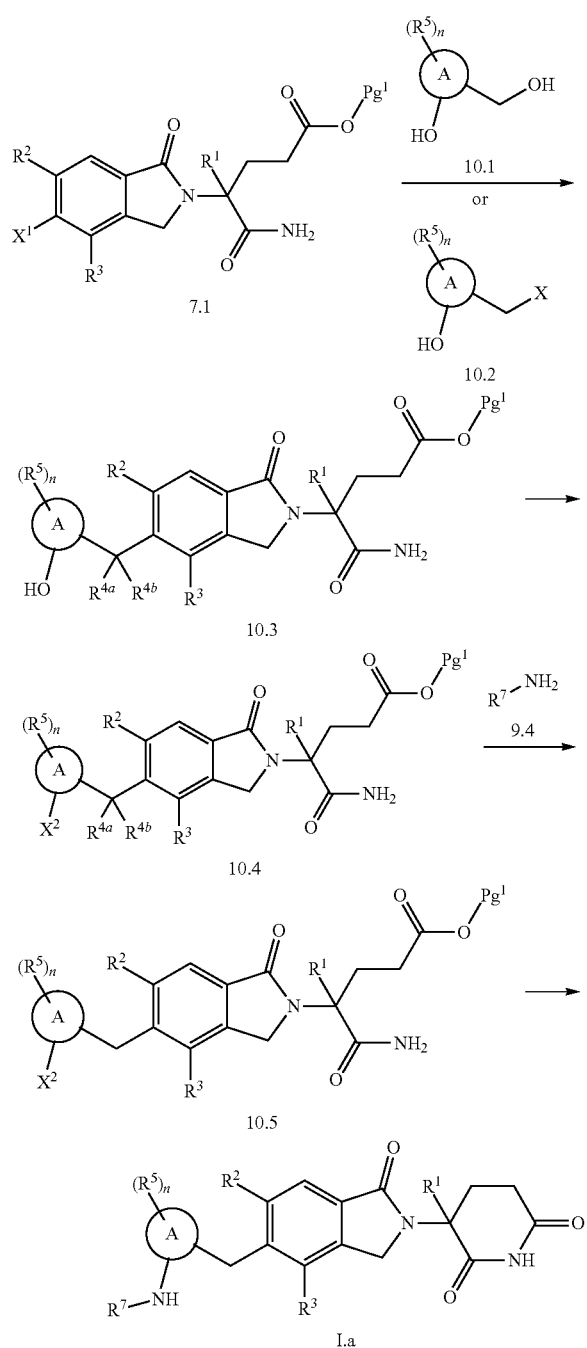

Compounds of the Formula 10.3 may be produced by reacting Intermediate 7.1 (where $X^1$=Br, I, Cl, OTf) with an compound of Formula 10.1 in the presence of a suitable metal precatalyst (e.g. NiBr$_2$(glyme), NiCl$_2$(glyme)) with an appropriate ligand (e.g. dtbbpy), photocatalyst (e.g. Ir[(dF(CF$_3$)ppy$_2$)dtbbpy]PF$_6$), and base (e.g. TMP, quinuclidine, K$_2$CO$_3$) in an inert solvent (e.g. DMF, DMA, TBME, CpOMe, 1,4-dioxane) under irradiation by blue LEDs following activation of alcohol 1.5 with a suitable N-heterocyclic carbene (e.g. 5,7-di-tert-butyl-3-phenylbenzo[d]oxazol-3-ium tetrafluoroborate). Alternatively, compounds of the Formula 10.3 may be produced by reacting Intermediate 7.1 (where $X^1$=Br, I, Cl, OTf) with a compound of Formula 10.2 (where X=Br, I, Cl, OTf) in the presence of a suitable palladium or nickel catalyst with a suitable reducing reagent (e.g., Zn, Mn, TMS silane). Compounds of the Formula 10.4, where $X^2$ is a leaving group (e.g., Cl, Br, I, OTs, OMs), may be produced by reacting Intermediate 10.3 under suitable conditions (e.g., PPh$_3$ with I$_2$, PPh$_3$ with CCl$_4$, PPh$_3$ with CBr$_4$, SOCl$_2$, TsCl, MsCl, Ms$_2$O) in an inert solvent (e.g., THF, MeCN, DCM). Compounds of Formula 10.4 can then be combined with an amine of formula 9.4 in the presence or absence of a base (e.g., N,N-diisopropylethylamine, triethylamine, K$_2$CO$_3$, CsCO$_3$) in an inert solvent (e.g., DMF, acetonitrile) at r.t. or elevated temperature. A compound of the Formula 10.5 (e.g., Pg$^1$=tert-butyl) can be subsequently deprotected and cyclized under suitable conditions (e.g., trifluoroacetic acid or benzene sulfonic acid) to reveal a compound of Formula I.a. Ring A represents a cycloalkyl or heterocylycl (e.g., cyclohexyl, cyclohexenyl, or tetrahydropyranyl).

General Reaction Scheme 11

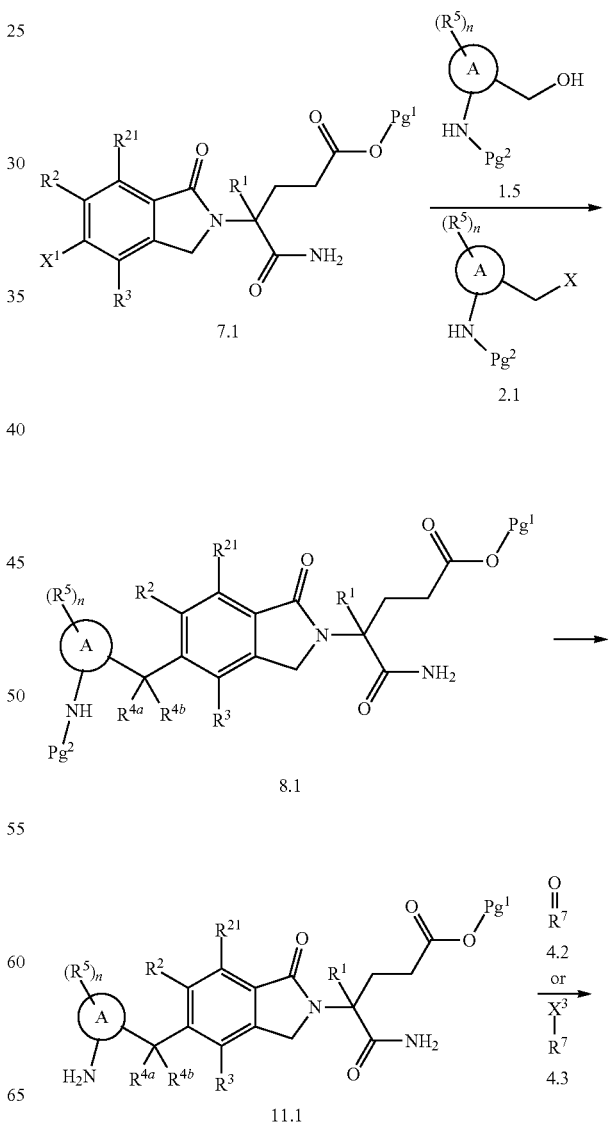

-continued
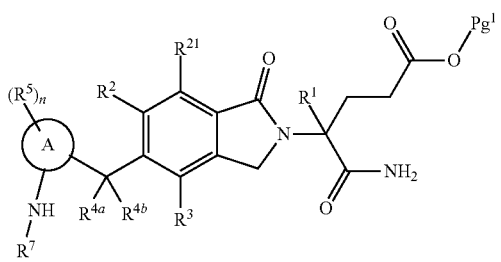
11.2
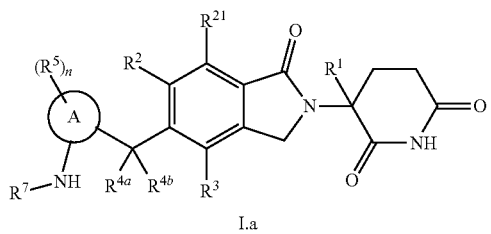
I.a
-continued
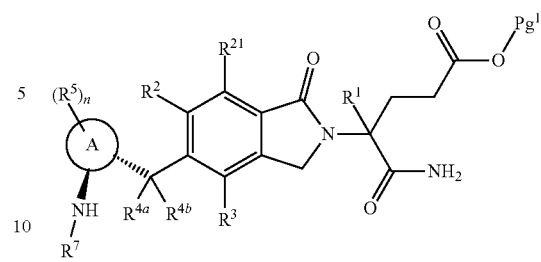
11.2a
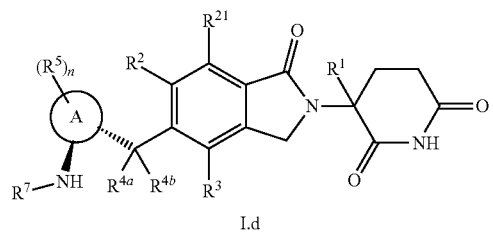
I.d
General Reaction Scheme 11a
General Reaction Scheme 11b
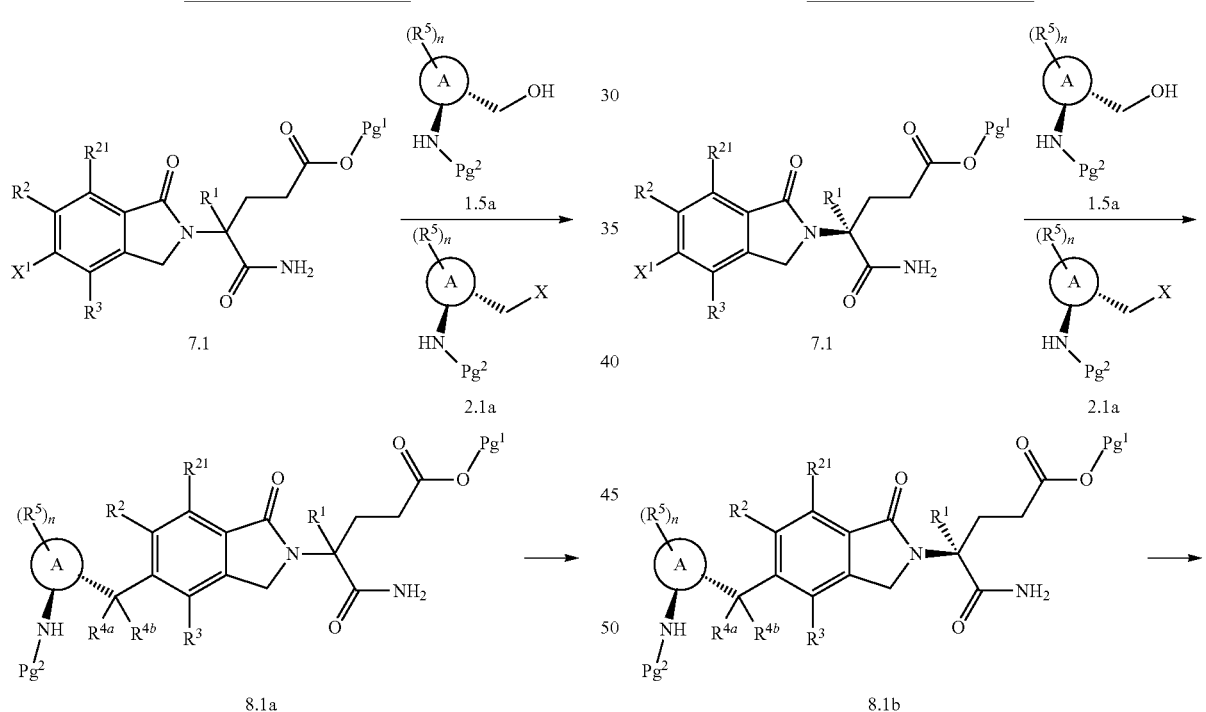

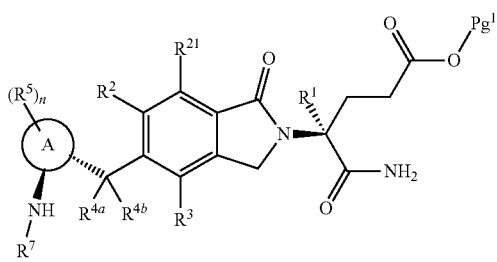

11.2b

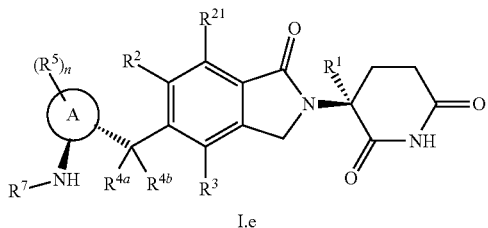

I.e

General Reaction Scheme 11c

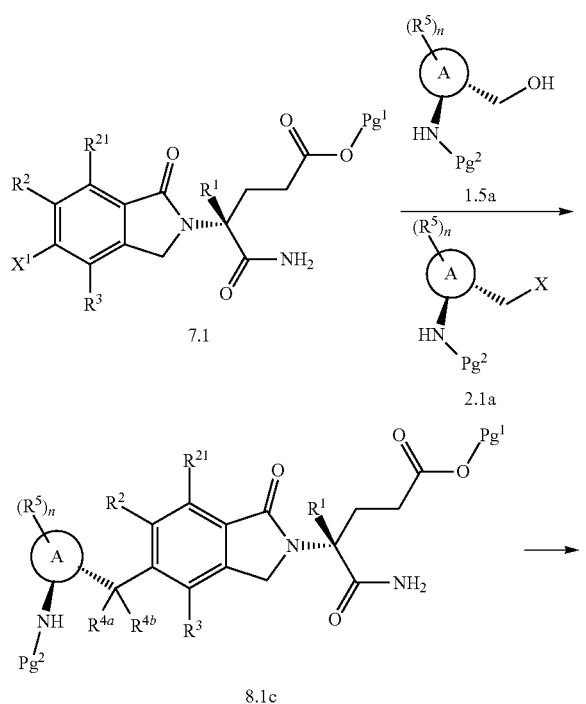

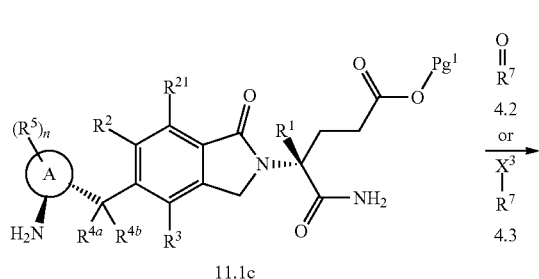

11.1c

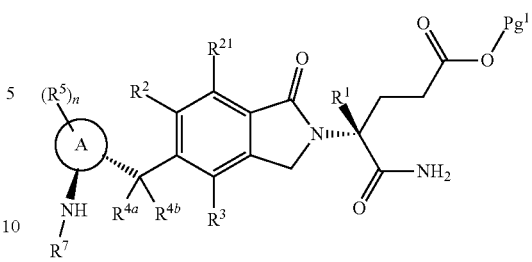

11.2c

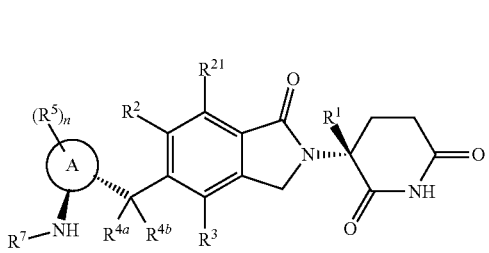

I.f

Compounds of the Formula 8.1, 8.1a, 8.1b, or 8.1c may be produced by reacting Intermediate 7.1, 7.1a, or 7.1b (where $X^1$=Br, I, Cl, OTf) with an compound of Formula 1.5 or 1.5a in the presence of a suitable metal precatalyst (e.g. $NiBr_2$(glyme), $NiCl_2$(glyme)) with an appropriate ligand (e.g. dtbbpy), photocatalyst (e.g. $Ir[(dF(CF_3)ppy_2)dtbbpy]PF_6$), and base (e.g. TMP, quinuclidine, $K_2CO_3$) in an inert solvent (e.g. DMF, DMA, TBME, CpOMe, 1,4-dioxane) under irradiation by blue LEDs following activation of alcohol 1.5 or 1.5a with a suitable N-heterocyclic carbene (e.g. 5,7-di-tert-butyl-3-phenylbenzo[d]oxazol-3-ium tetrafluoroborate). Alternatively, compounds of the Formula 8.1, 8.1a, 8.1b, or 8.1c may be produced by reacting Intermediate 7.1, 7.1a, or 7.1b (where $X^1$=Br, I, Cl, OTf) with a compound of Formula 2.1 or 2.1a (where X=Br, I, Cl, OTf) in the presence of a suitable palladium or nickel catalyst with a suitable reducing reagent (e.g. Zn, Mn, TMS silane). A compound of the Formula 8.1a, 8.1b, or 8.1c (e.g. $Pg^2$=Boc, $Pg^1$=tert-butyl) can be subsequently deprotected under suitable conditions (e.g. $ZnBr_2$, HCl in dioxane) to reveal a compound of Formula 11.1, 11.1a, 11.1b, or 11.1c that contains a primary amine. Compounds of Formula 11.1, 11.1a, 11.1b, or 11.1c can then be reacted with a suitable aldehyde or ketone of Formula 4.2 in the presence of a suitable reducing reagent (e.g., $NaBH_4$, $Na(OAc)_3BH$, $NaBH_3CN$) to produce compounds of Formula 11.2, 11.2a, 11.2b, or 11.2c. Alternatively, compounds of Formula 11.2, 11.2a, 11.2b, or 11.2c can be assembled by the combination of compounds of Formula 11.1, 11.1a, 11.1b, or 11.1c with an Intermediate 4.3, where $X^2$ is a leaving group (e.g. Cl, Br, I, OTs, OMs), in the presence or absence of a base (e.g., N,N-diisopropylethylamine, triethylamine, $K_2CO_3$, $CsCO_3$) in an inert solvent (e.g. DMF, acetonitrile) at r.t. or elevated temperature. Ring A represents a cycloalkyl or heterocylycl (e.g., cyclohexyl, cyclohexenyl, or tetrahydropyranyl). A compound of the Formula 11.2, 11.2a, 11.2b, or 11.2c (e.g. $Pg^1$=tert-butyl) can be subsequently deprotected and cyclized under suitable conditions (e.g. benzenesulfonic acid) at r.t. or elevated temperature to reveal a compound of Formula I.a, I.d, I.e, or I.f.

Preparation of Intermediate I-1

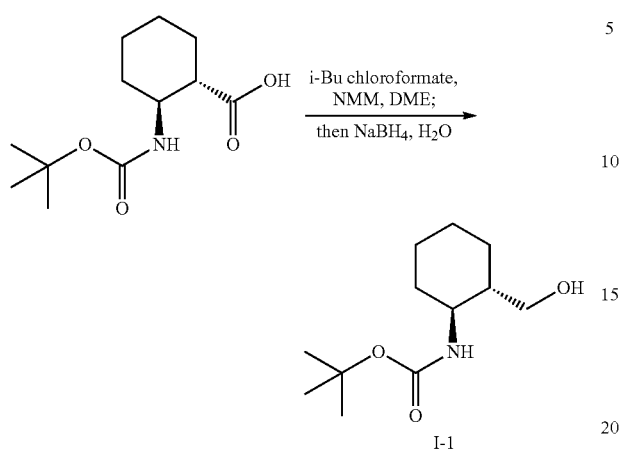

Preparation of tert-butyl N-[(1S,2S)-2-(hydroxymethyl)cyclohexyl]carbamate (I-1)

To a solution of (1S,2S)-2-(tert-butoxycarbonylamino)cyclohexanecarboxylic acid (10.0 g, 41.1 mmol) in DME (75.0 mL) was added N-methylmorpholine (5.42 mL, 49.3 mmol). The reaction was cooled to −20° C. in a crushed ice/NaCl bath and isobutyl chloroformate (6.40 mL, 0.0493 mol) was added slowly. The mixture was warmed to r.t. and stirred for 30 min then filtered to remove the precipitate. The filtrate was treated with a solution of $NaBH_4$ (3.33 g, 88.1 mmol) in water (7.50 mL) at r.t. then stirred for an additional 2 hours. Following this time, the reaction mixture was diluted with water (200 mL) and extracted with $CH_2Cl_2$ (3×200 mL). The combined organics were dried over $Na_2SO_4$, filtered, and concentrated under reduced pressure to afford I-1 which was used in subsequent reactions without further purification. ES/MS m/z: 252.2 (M+Na)⁺.

Preparation of Intermediate I-2

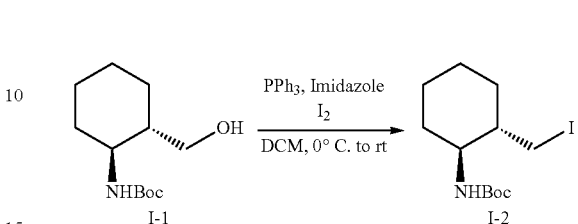

Preparation of tert-butyl ((1S,2S)-2-(iodomethyl)cyclohexyl)carbamate (I-2)

A solution of triphenylphosphine (297 mg, 1.13 mmol) and imidazole (77.2 mg, 1.13 mmol) in DCM (3.0 mL) was treated with iodine (288 mg, 1.13 mmol) as a single portion, and the resulting mixture was stirred for 5 min. The mixture was then cooled in an ice bath, and I-1 (200 mg, 0.872 mmol) was added as a solid with stirring. The reaction mixture was warmed to rt and stirred overnight. The mixture was then filtered through celite, rinsing with DCM. The resulting filtrate was washed twice with 5% aq. $NaHSO_3$, then 2M hydrochloric acid followed by brine. The organic phase was dried over $Na_2SO_4$, filtered, and concentrated under reduce pressure, and the resulting crude residue was purified by normal phase column chromatography (0→100% EtOAc in hexanes) to afford the product (I-2). ES/MS m/z: 362.1 (M+Na⁺).

Preparation of Intermediate I-3

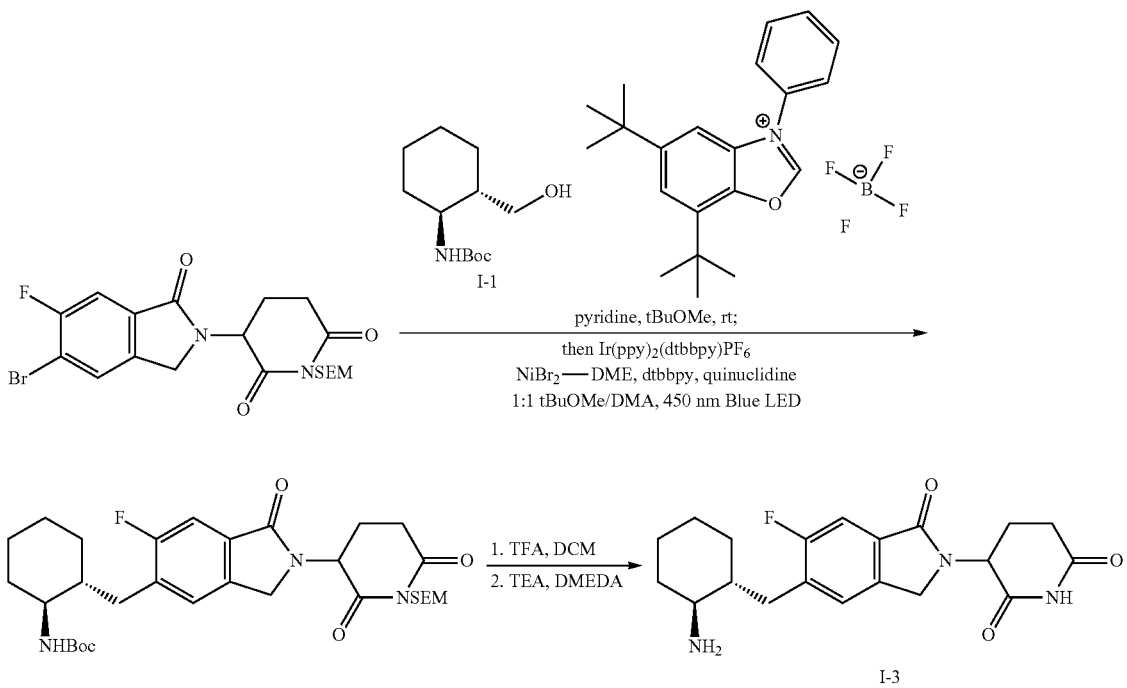

Step 1: Preparation of tert-butyl ((1S,2R)-2-((2-(2, 6-dioxo-1-((2-(trimethylsilyl)ethoxy)methyl)piperidin-3-yl)-6-fluoro-1-oxoisoindolin-5-yl)methyl)cyclohexyl)carbamate In a 40 mL vial, I-1 (255 mg, 1.11 mmol) was taken up in MTBE (8.75 mL) and 5,7-di-tert-butyl-3-phenylbenzo[d]oxazol-3-ium tetrafluoroborate (402 mg, 1.02 mmol) was added followed by pyridine (0.8 M in MTBE, 1.27 mL, 1.02 mmol). This mixture was stirred at r.t. while in a second 40 mL vial 3-(5-bromo-6-fluoro-1-oxoisoindolin-2-yl)-1-((2-(trimethylsilyl)ethoxy)methyl)piperidine-2,6-dione ([prepared according to the procedure described in WO2020/012334] 300 mg, 0.64 mmol), [Ir(ppy)$_2$(dtbbpy)]PF$_6$ (8.7 mg, 0.095 µmol), quinuclidine (124 mg, 1.11 mol), NiBr$_2$-DME (9.8 mg, 0.32 mmol), and 4,4'-Di-tert-butyl-2,2'-dipyridyl (102 mg, 0.38 mmol) were combined. The vial was purged with argon then DMA (8.75 mL) was added. The activated alcohol suspension was then transferred to a syringe fitted with a syringe filter and needle. The suspension was filtered into the solution of aryl bromide and the mixture sparged with argon for 5 min. The reaction was then stirred under irradiation by 450 nm light in the photoreactor for 2 hours. Following this time, the reaction was complete by LC/MS analysis. The mixture was diluted with EtOAc (50 mL), transferred to a separatory funnel and washed with water (100 mL). The aqueous phase was extracted with EtOAc (2×100 mL) then the combined organic extracts were dried over MgSO$_4$ and concentrated in vacuo. The crude product was purified normal-phase column chromatography (eluent: EtOAc/Hexanes gradient) to yield the product. ES/MS m/z: 626.2 (M+Na$^+$).

Step 2: Preparation of 3-(5-(((1R,2S)-2-aminocyclohexyl)methyl)-6-fluoro-1-oxoisoindolin-2-yl)piperidine-2,6-dione (I-3)

tert-butyl ((1S,2R)-2-((2-(2,6-dioxo-1-((2-(trimethylsilyl)ethoxy)methyl)piperidin-3-yl)-6-fluoro-1-oxoisoindolin-5-yl)methyl)cyclohexyl) carbamate (92 mg, 0.15 mmol) was taken up in dichloromethane (1.5 mL) and trifluoroacetic acid (267 µL, 0.15 mmol) was added. The reaction was stirred at r.t. for 1 hour then the mixture was concentrated in vacuo. The residue was re-dissolved in dichloromethane (1.5 mL) and the mixture cooled to 0° C. Triethylamine (170 µL, 1.22 mmol) was added followed by N,N'-dimethylethylenediamine (20 µL, 0.183 mmol) and then the reaction was warmed to r.t. and stirred overnight. The reaction mixture was concentrated in vacuo to afford the crude product (I-3) which was used in subsequent reactions without further purification. ES/MS m/z: 374.1 (M+H$^+$).

Preparation of Intermediate I-4

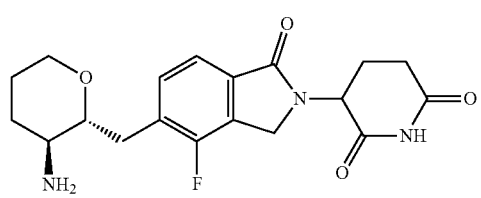

I-4

3-(5-(((1R,2S)-2-aminocyclohexyl)methyl)-4-fluoro-1-oxoisoindolin-2-yl)piperidine-2,6-dione (I-4)

3-(5-(((1R,2S)-2-aminocyclohexyl)methyl)-4-fluoro-1-oxoisoindolin-2-yl)piperidine-2,6-dione was synthesized in the same manner as I-3 substituting 3-(5-bromo-6-fluoro-1-oxoisoindolin-2-yl)-1-((2-(trimethylsilyl)ethoxy)methyl)piperidine-2,6-dione with 3-(5-bromo-4-fluoro-1-oxoisoindolin-2-yl)-1-((2 (trimethylsilyl)ethoxy)methyl) piperidine-2, 6-dione. ES/MS m/z: 374.1 (M+H$^+$).

Preparation of Intermediate I-5

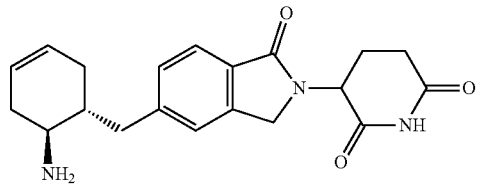

I-5

3-(5-(((1R,6S)-6-aminocyclohex-3-en-1-yl)methyl)-1-oxoisoindolin-2-yl)piperidine-2,6-dione (I-5)

3-(5-(((1R,6S)-6-aminocyclohex-3-en-1-yl)methyl)-1-oxoisoindolin-2-yl)piperidine-2,6-dione was synthesized in the same manner as I-3 substituting I-1 with ((1S,6S)-6-aminocyclohex-3-en-1-yl)methanol and 3-(5-bromo-6-fluoro-1-oxoisoindolin-2-yl)-1-((2-(trimethylsilyl)ethoxy)methyl)piperidine-2,6-dione with 3-(5-bromo-1-oxoisoindolin-2-yl)-1-((2-(trimethylsilyl)ethoxy)methyl) piperidine-2,6-dione. ES/MS m/z: 354.3 (M+H$^+$).

Preparation of Intermediate I-6

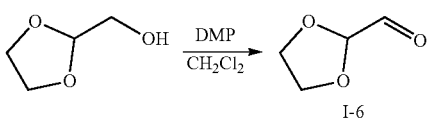

I-6

1,3-Dioxolane-2-carbaldehyde (I-6)

(1,3-dioxolan-2-yl)methanol (200 mg, 1.92 mmol) dissolved in dichloromethane (10 mL) was treated with Dess-Martin periodinane (850 mg, 2.00 mmol). The reaction mixture was stirred at room temperature for 1 hour and concentrated. The residue was suspended in ethyl acetate and washed with saturated sodium thiosulfate solution. The organic layer was dried over sodium sulfate and filtered. The filtrate was concentrated in vacuo to give 1,3-dioxolane-2-carbaldehyde (I-6) which was used without subsequent purification.

Preparation of Intermediate I-7

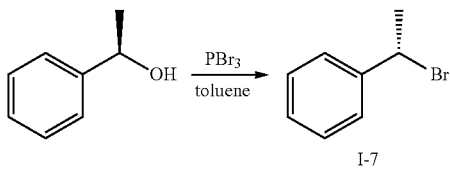

(S)-(1-Bromoethyl)benzene (I-7)

(1R)-1-phenylethanol (400 mg, 3.27 mmol) dissolved in toluene (20 mL) was cooled to 0° C. and then treated with dropwise addition of phosphorus tribromide (100 µL, 1.06 mmol). The reaction mixture was warmed to room temperature. After stirring for 3 h, the reaction mixture was cooled to 0° C. again and quenched by the addition of saturated sodium bicarbonate solution. The aqueous phase was extracted with dichloromethane and the organic layer dried over sodium sulfate and filtered. The filtrate was concentrated in vacuo to give (S)-(1-bromoethyl)benzene which was used without subsequent purification.

Preparation of Intermediate I-8

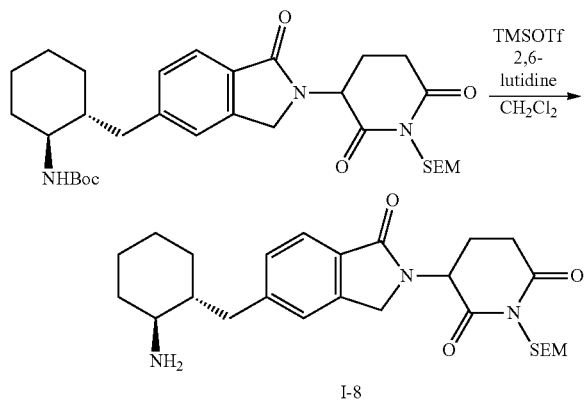

3-(5-(((1R,2S)-2-aminocyclohexyl)methyl)-1-oxoisoindolin-2-yl)-1-((2-(trimethylsilyl)ethoxy)methyl)piperidine-2,6-dione (I-8)

tert-butyl ((1S,2R)-2-((2-(2,6-dioxo-1-((2-(trimethylsilyl)ethoxy)methyl)piperidin-3-yl)-1-oxoisoindolin-5-yl)methyl)cyclohexyl) carbamate ([prepared according to the method described for I-3, step 1] 1.2 g, 2.05 mmol) was taken up in dichloromethane (20.0 mL) and 2,6-lutidine (1.19 mL, 10.2 mmol) was added followed by trimethylsilyl trifluoromethanesulfonate (1.11 mL, 6.15 mmol) slowly dropwise. The reaction was stirred at r.t. for 1 hour. Following this time, the reaction was quenched by addition of methanol and then transferred to a separatory funnel. The organic phase was washed with saturated aqueous NaHCO$_3$, water, and brine then the combined organics were dried over MgSO$_4$ and concentrated in vacuo. The title product (I-8) was isolated following silica gel column chromatography (eluent: MeOH/DCM). ES/MS m/z: 486.2 (M+H$^+$).

Preparation of Intermediate I-9

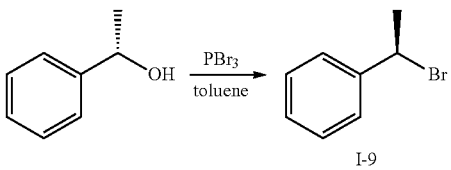

(R)-(1-bromoethyl)benzene

The title compound was prepared in the same manner as I-7 substituting (1R)-1-phenylethanol with (1S)-1-phenylethanol.

Preparation of Intermediate I-10

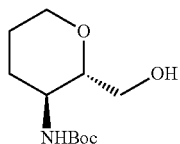

tert-butyl ((2S,3S)-2-(hydroxymethyl)tetrahydro-2H-pyran-3-yl)carbamate (I-10)

tert-butyl ((2S,3S)-2-(hydroxymethyl)tetrahydro-2H-pyran-3-yl)carbamate (I-10) was prepared according to the procedure described in Eur. J. Org. Chem. 2014, 20, p. 4295-4308 replacing (S)-2,2-dimethyl-1,3-dioxolane-4-carbaldehyde with (R)-2,2-dimethyl-1,3-dioxolane-4-carbaldehyde. ES/MS m/z: 231.7 (M+H$^+$).

Preparation of Intermediate I-11

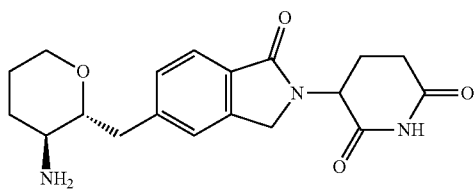

3-(5-(((2R,3S)-3-aminotetrahydro-2H-pyran-2-yl)methyl)-1-oxoisoindolin-2-yl)piperidine-2,6-dione (I-11)

3-(5-(((2R,3S)-3-aminotetrahydro-2H-pyran-2-yl)methyl)-1-oxoisoindolin-2-yl)piperidine-2,6-dione was synthesized in the same manner as I-3 substituting I-1 with I-10 and 3-(5-bromo-6-fluoro-1-oxoisoindolin-2-yl)-1-((2-(trimethylsilyl)ethoxy)methyl)piperidine-2,6-dione with 3-(5-bromo-1-oxoisoindolin-2-yl)-1-((2-(trimethylsilyl)ethoxy)methyl)piperidine-2,6-dione. ES/MS m/z: 358.1 (M+H$^+$).

Preparation of Intermediate I-12

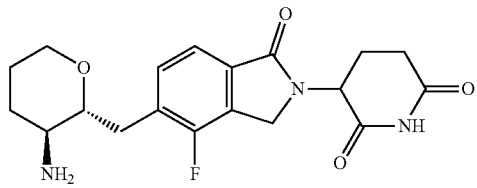

I-12

3-(5-(((2R,3S)-3-aminotetrahydro-2H-pyran-2-yl)methyl)-4-fluoro-1-oxoisoindolin-2-yl)piperidine-2,6-dione (I-12)

3-(5-(((2R,3S)-3-aminotetrahydro-2H-pyran-2-yl)methyl)-4-fluoro-1-oxoisoindolin-2-yl)piperidine-2,6-dione was synthesized in the same manner as I-3 substituting I-1 with I-10 and 3-(5-bromo-6-fluoro-1-oxoisoindolin-2-yl)-1-((2-(trimethylsilyl)ethoxy)methyl)piperidine-2,6-dione with 3-(5-bromo-4-fluoro-1-oxoisoindolin-2-yl)-1-((2 (trimethylsilyl)ethoxy)methyl)piperidine-2,6-dione. ES/MS m/z: 376.2 (M+H⁺).

Preparation of Intermediate I-13

Step 1: Preparation of tert-butyl (S)-5-amino-4-(5-(((1R,2S)-2-((tert-butoxycarbonyl)amino)cyclohexyl)methyl)-1-oxoisoindolin-2-yl)-5-oxopentanoate tert-butyl (S)-5-amino-4-(5-(((1R,2S)-2-((tert-butoxycarbonyl)amino)cyclohexyl)methyl)-1-oxoisoindolin-2-yl)-5-oxopentanoate was synthesized in the same manner as tert-butyl ((1S,2R)-2-((2-(2,6-dioxo-1-((2-(trimethylsilyl)ethoxy)methyl)piperidin-3-yl)-6-fluoro-1-oxoisoindolin-5-yl)methyl)cyclohexyl)carbamate (I-3, step 1) substituting 3-(5-bromo-6-fluoro-1-oxoisoindolin-2-yl)-1-((2-(trimethylsilyl)ethoxy)methyl)piperidine-2,6-dione with tert-butyl (S)-5-amino-4-(5-bromo-1-oxoisoindolin-2-yl)-5-oxopentanoate [prepared according to the procedure described in WO2021/101919]. ES/MS m/z: 530.2 (M+H⁺).

Step 2: Preparation of tert-butyl (S)-5-amino-4-(5-(((1R,2S)-2-aminocyclohexyl)methyl)-1-oxoisoindolin-2-yl)-5-oxopentanoate (I-13)

tert-butyl (S)-5-amino-4-(5-(((1R,2S)-2-((tert-butoxycarbonyl)amino)cyclohexyl)methyl)-1-oxoisoindolin-2-yl)-5-oxopentanoate (2.83 g, 5.34 mmol) was taken up in dichloromethane (55 mL) and the solution cooled to 0° C. A solution of HCl in 1,4-dioxane (4 M, 8.0 mL. 32.1 mmol) was then added slowly to the mixture and following complete addition the reaction was warmed to r.t. and stirred for 3 hours. At this time, the reaction was cooled to 0° C. and

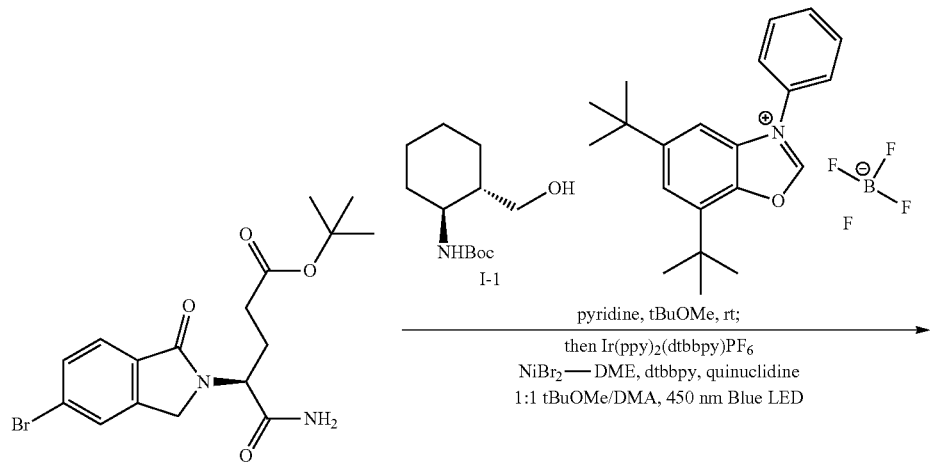

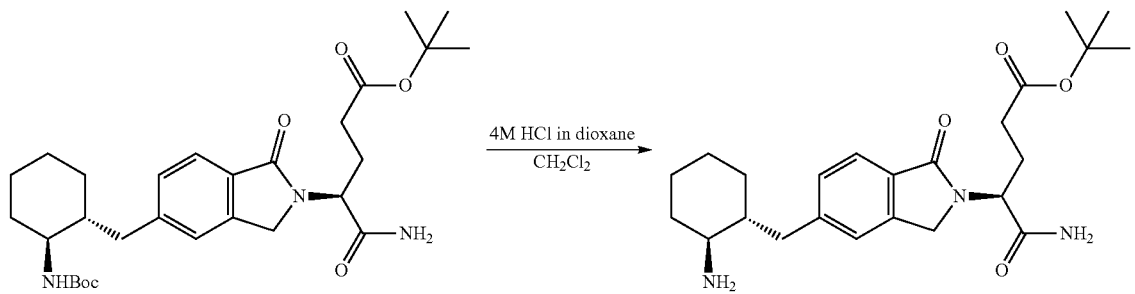

I-13 quenched by addition of triethylamine (4.5 mL, 32.1 mmol). The resulting mixture was diluted with EtOAc and the organic phase washed with ½ saturated aqueous NH₄Cl (3×). The organic phase was discarded and the aqueous phase was treated with saturated NaHCO₃ until pH ~8 then the aqueous phase was extracted with 4:1 CH$_2$Cl$_2$:IPA (3×). The combined organic extracts were dried over MgSO$_4$, concentrated in vacuo, and the product (I-13) isolated as a foam that was used without further purification. ES/MS m/z: 430.2 (M+H$^+$).

Preparation of Intermediate I-14 yl)methyl)cyclohexyl)carbamate (I-3, step 1) substituting 3-(5-bromo-6-fluoro-1-oxoisoindolin-2-yl)-1-((2-(trimethylsilyl)ethoxy)methyl)piperidine-2,6-dione with tert-butyl (S)-5-amino-4-(5-bromo-4-fluoro-1-oxoisoindolin-2-yl)-5-oxopentanoate. ES/MS m/z: 570.4 (M+Na$^+$).

Step 2: Preparation of (S)-5-Amino-4-(5-(((1R,2S)-2-aminocyclohexyl)methyl)-4-fluoro-1-oxoisoindolin-2-yl)-5-oxopentanoic acid (I-14)

tert-butyl (4S)-5-amino-4-[5-[[(1R,2S)-2-(tert-butoxycarbonylamino)cyclohexyl]methyl]-4-fluoro-1-oxo-isoindolin-2-yl]-5-oxo-pentanoate (6.50 g, 11.9 mmol) was taken up in

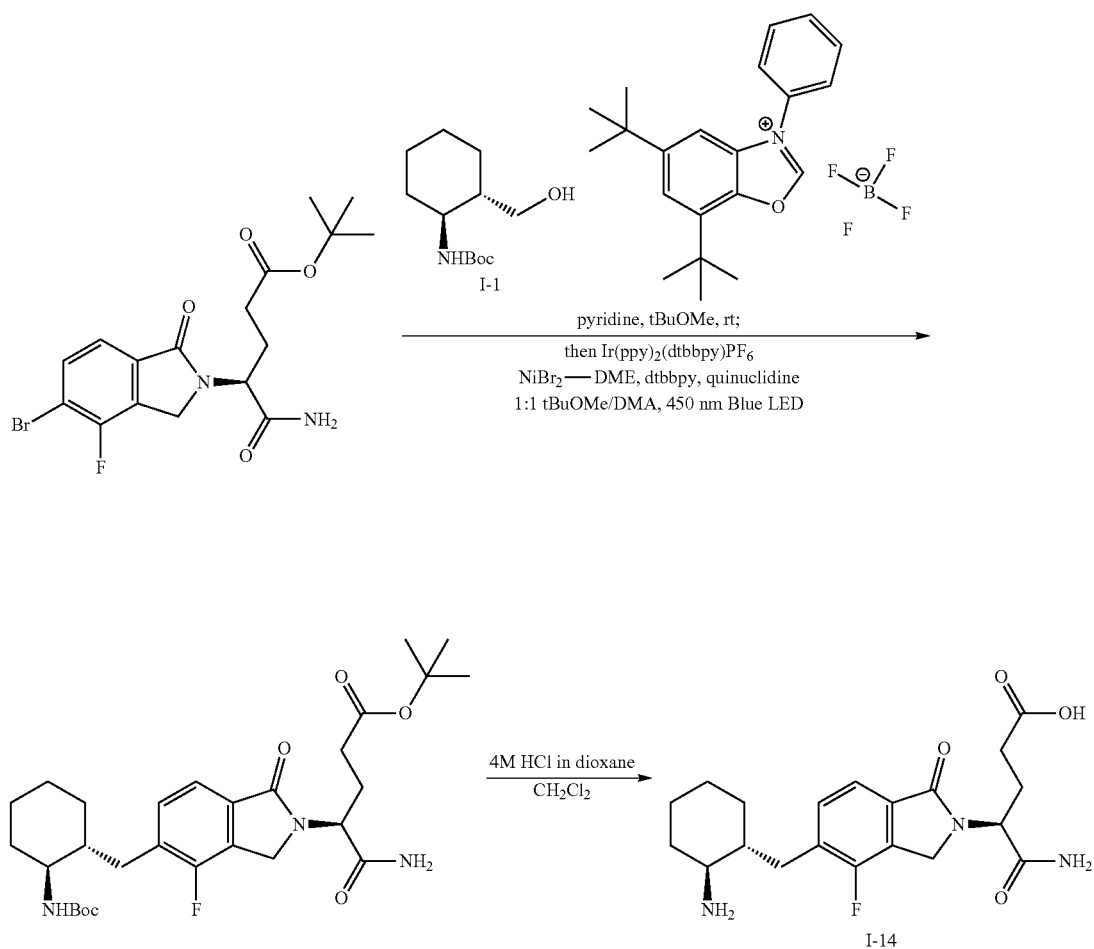

Step 1: Preparation of tert-Butyl (S)-5-amino-4-(5-(((1R,2S)-2-((tert-butoxycarbonyl)amino)cyclohexyl)methyl)-4-fluoro-1-oxoisoindolin-2-yl)-5-oxopentanoate tert-Butyl (S)-5-amino-4-(5-(((1R,2S)-2-((tert-butoxycarbonyl)amino)cyclohexyl)methyl)-4-fluoro-1-oxoisoindolin-2-yl)-5-oxopentanoate was synthesized in the same manner as tert-butyl ((1S,2R)-2-((2-(2,6-dioxo-1-((2-(trimethylsilyl)ethoxy)methyl)piperidin-3-yl)-6-fluoro-1-oxoisoindolin-5- dichloromethane (100 mL) and the solution was cooled to 0° C. A solution of 4N HCl in dioxane (17.8 mL, 71.2 mmol) was then added slowly to the mixture and, following complete addition, the reaction was warmed to r.t. and stirred for 3 hours. Following this time, acetonitrile (100 mL) was added slowly to the reaction mixture and the resulting precipitate was collected and dried in vacuo to afford I-14 as a white solid that was used without further purification. ES/MS m/z: 392.3 (M+H$^+$).

Preparation of Intermediate I-15

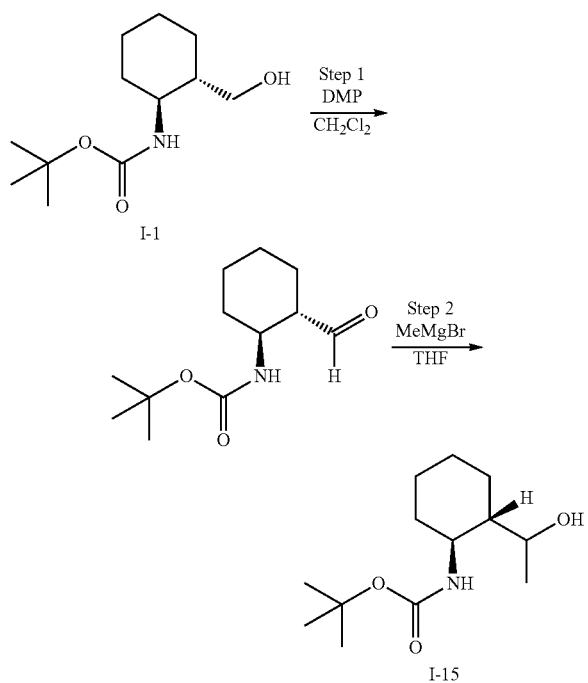

Step 1: Preparation of tert-butyl ((1S,2S)-2-formylcyclohexyl)carbamate

A vial was charged with tert-butyl ((1S,2S)-2-(hydroxymethyl)cyclohexyl)carbamate (I-1) (500 mg, 2.18 mmol) and CH$_2$Cl$_2$ (5.0 mL). The reaction was cooled to 0° C. and then Dess-Martin periodinane (1.85 g, 4.36 mmol) was added in one portion. The reaction was warmed to r.t. and stirred for 3.5 h. Following this time, the reaction was cooled to 0° C. and water and sat. NaHCO$_3$ were added to quench the reaction. The solution was transferred to a separatory funnel and back-extracted with CH$_2$Cl$_2$(3×). The combined organics were washed with brine and concentrated in vacuo. The residue was purified directly by column chromatography (eluent: EtOAc/hexanes gradient) to afford tert-butyl ((1S, 2S)-2-formylcyclohexyl)carbamate as a solid. ES/MS m/z: 228 (M+H$^+$). $^1$H NMR (400 MHz, DMSO-d$_6$) δ 9.48 (d, J=3.5 Hz, 1H), 6.97 (d, J=8.7 Hz, 1H), 3.52 (qd, J=10.4, 4.1 Hz, 1H), 2.18-2.08 (m, 1H), 1.82-1.72 (m, 1H), 1.72-1.58 (m, 3H), 1.35 (s, 9H), 1.31-1.26 (m, 1H), 1.22 (dd, J=10.9, 7.1 Hz, 2H), 1.18-1.03 (m, 1H).

Step 2: Preparation of tert-butyl ((1S,2S)-2-(1-hydroxyethyl)cyclohexyl)carbamate (I-15)

A vial was charged with tert-butyl ((1S,2S)-2-formylcyclohexyl)carbamate (311 mg, 1.37 mmol) and THF (3.11 mL). The reaction was cooled to 0° C. and then MeMgBr (3.4 M solution in 2-MeTHF, 1.21 mL, 4.10 mmol) was added slowly. The reaction was warmed to room temperature and mixed for 2 h, adding additional MeMgBr (3.4 M solution in 2-MeTHF 0.40 mL, 1.37 mmol) after 1.5 h. Following this time, the reaction was cooled to 0° C. and water was added to quench the reaction. The solution was concentrated in vacuo and was purified directly by column chromatography (eluent: EtOAc/hexanes gradient) to afford tert-butyl ((1S,2S)-2-(1-hydroxyethyl)cyclohexyl)carbamate (I-15) as an oil. ES/MS m/z: 244.1 (M+H$^+$).

Preparation of Intermediate I-16

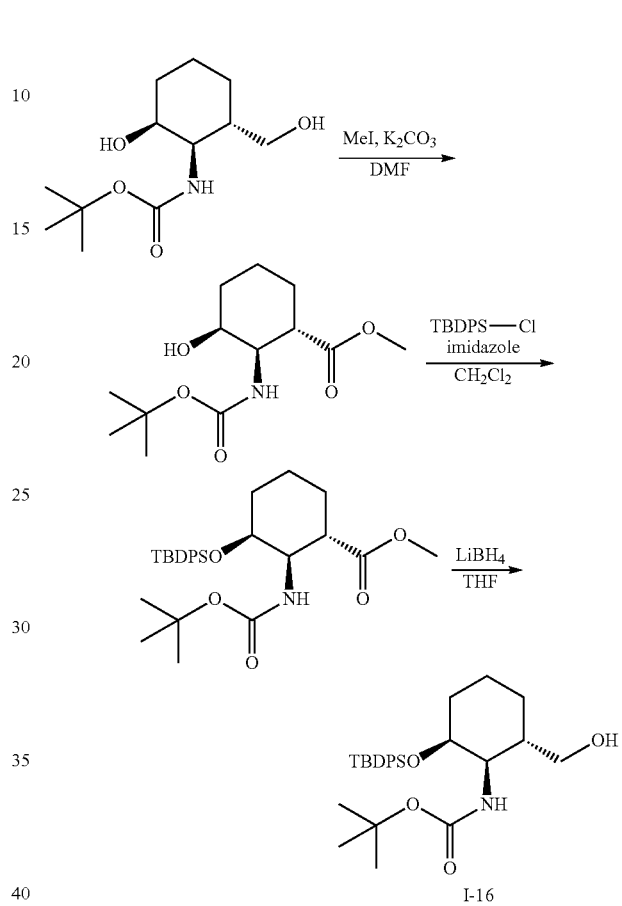

Step 1: Methyl (1S,2R,3S)-rel-2-((tert-butoxycarbonyl)amino)-3-hydroxycyclohexane-1-carboxylate (1S,2R,3S)-rel-2-((tert-butoxycarbonyl)amino)-3-hydroxycyclohexane-1-carboxylic acid ([prepared according to the procedure described in Eur. J. Org. Chem. 2009, 1619-1624.] 2.0 g, 7.71 mmol) was taken up in DMF (80 mL) and iodomethane (576 µL, 9.26 mmol) was added followed by K$_2$CO$_3$ (1.28 g, 9.26 mmol). The reaction was stirred at r.t. overnight. The reaction mixture was then diluted with EtOAc, transferred to a separatory funnel and washed with water and brine. The combined organic extracts were dried over MgSO$_4$, concentrated in vacuo, and purified by SiO$_2$ column chromatography (eluent: EtOAc/hexanes gradient) to afford methyl (1S,2R,3S)-rel-2-((tert-butoxycarbonyl)amino)-3-hydroxycyclohexane-1-carboxylate.

Step 2: Methyl (1S,2R,3S)-rel-2-((tert-butoxycarbonyl)amino)-3-((tert-butyldiphenylsilyl)oxy)cyclohexane-1-carboxylate Methyl (1S,2R,3S)-rel-2-((tert-butoxycarbonyl)amino)-3-hydroxycyclohexane-1-carboxylate (2.12 g, 7.76 mmol) was taken up in CH$_2$Cl$_2$ (50 mL) and tert-butyldiphenylchlorosilane (2.11 mL, 8.14 mmol) was added followed by imidazole (1.16 g, 17.1 mmol). The reaction was stirred at r.t. overnight. Following this time, the reaction mixture was filtered, concentrated in vacuo and purified by $SiO_2$ column chromatography (eluent: EtOAc/hexanes gradient) to afford methyl (1S,2R,3S)-rel-2-((tert-butoxycarbonyl)amino)-3-((tert-butyldiphenylsilyl)oxy)cyclohexane-1-carboxylate.

Step 3: tert-Butyl ((1R,2S,6S)-rel-2-((tert-butyldiphenylsilyl)oxy)-6-(hydroxymethyl)cyclohexyl)carbamate (I-16)

Methyl (1S,2R,3S)-rel-2-((tert-butoxycarbonyl)amino)-3-((tert-butyldiphenylsilyl)oxy)cyclohexane-1-carboxylate (3.40 g, 6.64 mmol) was taken up in THF (70 mL) and the reaction mixture cooled to 0° C. $LiBH_4$ (2.0 M in THF, 13.3 mL, 26.6 mmol) was added slowly over 5 min then the reaction was warmed to r.t. and stirred for 48 h. The reaction mixture was then diluted with EtOAc and water and the biphasic mixture was transferred to a separatory funnel. The organic extracts were collected, washed with brine, dried over $MgSO_4$ and concentrated in vacuo. The residue was then purified by $SiO_2$ column chromatography (eluent: EtOAc/hexanes) to afford tert-Butyl ((1R,2S,6S)-rel-2-((tert-butyldiphenylsilyl)oxy)-6-(hydroxymethyl)cyclohexyl)carbamate (I-16). $^1$H NMR (400 MHz, Chloroform-d) δ 7.69 (dt, J=8.1, 1.9 Hz, 4H), 7.54-7.33 (m, 6H), 4.89 (d, J=9.5 Hz, 1H), 4.15 (q, J=3.8, 3.2 Hz, 1H), 3.72 (dd, J=12.1, 3.0 Hz, 1H), 3.49-3.30 (m, 2H), 1.76 (ddt, J=28.2, 13.5, 3.3 Hz, 3H), 1.67-1.45 (m, 2H), 1.40 (s, 9H), 1.35-1.22 (m, 2H), 1.14 (s, 8H).

Preparation of Intermediate I-17

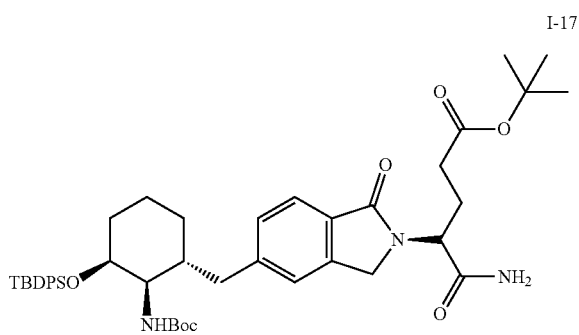

tert-Butyl (S)-5-amino-4-(5-(((1R,2R,3S)-rel-2-((tert-butoxycarbonyl)amino)-3-((tert-butyldiphenylsilyl)oxy)cyclohexyl)methyl)-1-oxoisoindolin-2-yl)-5-oxopentanoate (I-17)

tert-Butyl (S)-5-amino-4-(5-(((1R,2R,3S)-rel-2-((tert-butoxycarbonyl)amino)-3-((tert-butyldiphenylsilyl)oxy)cyclohexyl)methyl)-1-oxoisoindolin-2-yl)-5-oxopentanoate was synthesized in the same manner as I-13, step 1 substituting I-1 with I-16. $^1$H NMR (400 MHz, Chloroform-d) δ 7.79 (d, J=7.7 Hz, 1H), 7.68 (ddt, J=5.3, 3.8, 1.4 Hz, 4H), 7.53-7.33 (m, 7H), 4.98-4.80 (m, 2H), 4.61-4.32 (m, 2H), 3.33 (t, J=10.0 Hz, 1H), 3.06 (d, J=13.6 Hz, 1H), 2.52-2.12 (m, 5H), 1.64 (d, J=21.1 Hz, 6H), 1.44 (s, 9H), 1.40 (s, 9H), 1.14 (s, 9H), 1.09-0.86 (m, 1H).

Preparation of Intermediate I-18

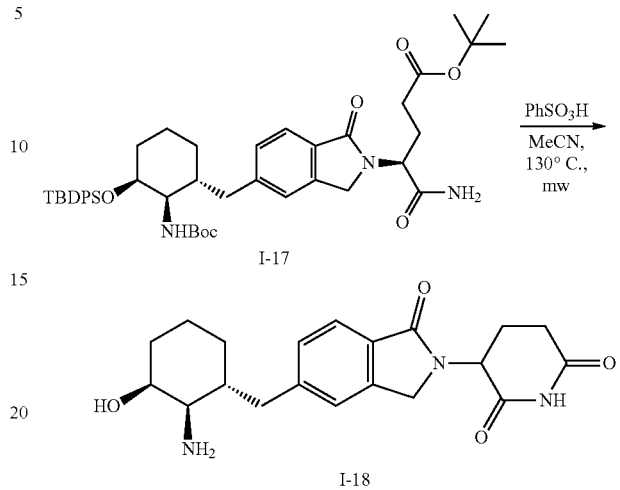

3-(5-(((1R,2R,3S)-rel-2-amino-3-hydroxycyclohexyl)methyl)-1-oxoisoindolin-2-yl)piperidine-2,6-dione (I-18)

I-17 (100 mg, 0.128 mmol) was taken up in MeCN (1.3 mL) and benzenesulfonic acid (121 mg, 0.765 mmol) was added. The reaction was heated to 130° C. under microwave irradiation for 30 min. Following this time, the resulting solid was filtered off, washed with acetonitrile and dried to afford 3-(5-(((1R,2R,3S)-rel-2-amino-3-hydroxycyclohexyl)methyl)-1-oxoisoindolin-2-yl)piperidine-2,6-dione (I-18) as the benzenesulfonic acid salt. ES/MS m/z: 372.1 $(M+H^+)$.

Preparation of Intermediate I-19

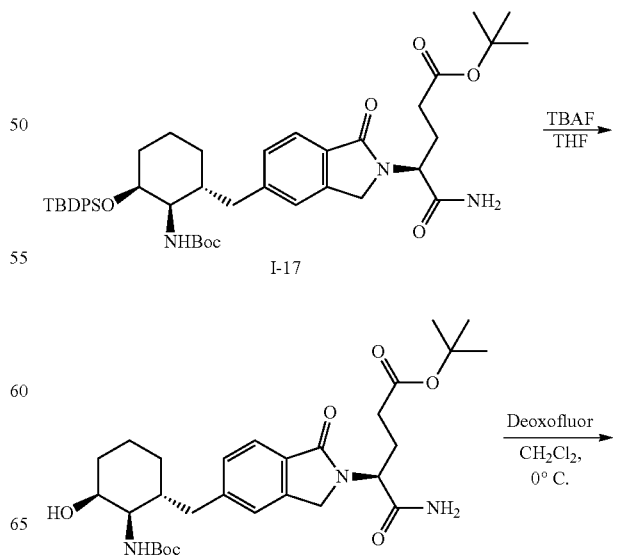

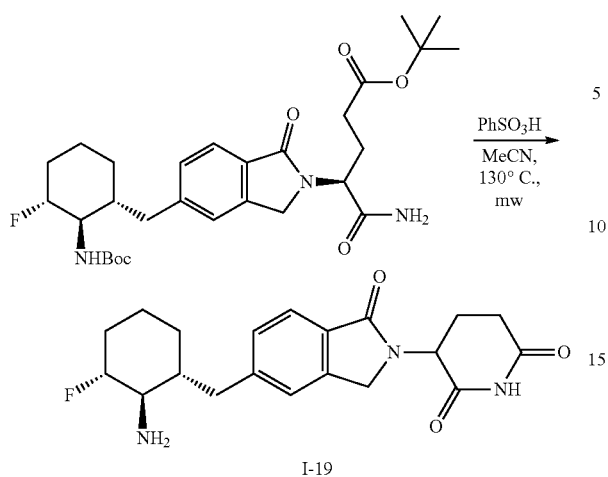

Step 1. tert-Butyl (S)-5-amino-4-(5-(((1R,2R,3S)-rel-2-((tert-butoxycarbonyl)amino)-3-hydroxycyclohexyl)methyl)-1-oxoisoindolin-2-yl)-5-oxopentanoate I-17 (390 mg, 0.497 mmol) was taken up in THF (5.0 mL) and the mixture cooled to 0° C. TBAF (1.0 M in THF, 995 µL, 0.995 mmol) was added and the reaction warmed to r.t. and stirred overnight. Following this time, the reaction mixture was concentrated in vacuo and purified directly by SiO$_2$ column chromatography (eluent: EtOAc/hexanes) to afford tert-butyl (S)-5-amino-4-(5-(((1R,2R,3S)-rel-2-((tert-butoxycarbonyl)amino)-3-hydroxycyclohexyl)methyl)-1-oxoisoindolin-2-yl)-5-oxopentanoate. ES/MS m/z: 546.2 (M+H$^+$).

Step 2. tert-Butyl (S)-5-amino-4-(5-(((1R,2R,3R)-rel-2-((tert-butoxycarbonyl)amino)-3-fluorocyclohexyl)methyl)-1-oxoisoindolin-2-yl)-5-oxopentanoate tert-Butyl (S)-5-amino-4-(5-(((1R,2R,3S)-rel-2-((tert-butoxycarbonyl)amino)-3-hydroxycyclohexyl)methyl)-1-oxoisoindolin-2-yl)-5-oxopentanoate (221 mg, 0.405 mmol) was taken up in CH$_2$Cl$_2$ (4.0 mL). The solution was cooled to 0° C. and Deoxo-Fluor® (2.7 M in toluene, 0.30 mL, 0.809 mmol) was added slowly. The reaction was warmed to r.t. and stirred for 1 h, then the reaction was quenched by addition of saturated aqueous NaHCO$_3$ at 0° C. The mixture was transferred to a separatory funnel and extracted with CH$_2$Cl$_2$ (3×). The combined organic phases were dried over MgSO$_4$ and concentrated in vacuo to yield tert-butyl (S)-5-amino-4-(5-(((1R,2R,3R)-rel-2-((tert-butoxycarbonyl)amino)-3-fluorocyclohexyl)methyl)-1-oxoisoindolin-2-yl)-5-oxopentanoate which was used without further purification in the subsequent reaction. ES/MS m/z: 548.2 (M+H$^+$).

Step 3. 3-(5-(((1R,2R,3R)-rel-2-amino-3-fluorocyclohexyl)methyl)-1-oxoisoindolin-2-yl)piperidine-2,6-dione (I-19)

tert-Butyl (S)-5-amino-4-(5-(((1R,2R,3R)-rel-2-((tert-butoxycarbonyl)amino)-3-fluorocyclohexyl)methyl)-1-oxoisoindolin-2-yl)-5-oxopentanoate (136 mg, 0.249 mmol) was taken up in acetonitrile (2.5 mL) and benzenesulfonic acid (118 mg, 0.746 mmol) was added. The reaction was heated to 130° C. under microwave irradiation for 30 minutes and then the reaction mixture was concentrated in vacuo to afford 3-(5-(((1R,2R,3R)-rel-2-amino-3-fluorocyclohexyl)methyl)-1-oxoisoindolin-2-yl)piperidine-2,6-dione as the benzenesulfonic acid salt which was used in subsequent transformations without further purification. ES/MS m/z: 374.1 (M+H$^+$).

Preparation of Intermediate I-20

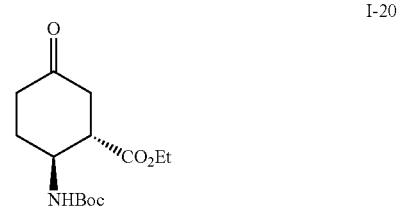 [SMILES: CCOC(=O)[C@H]1CC(=O)CC[C@@H]1NC(=O)OC(C)(C)C]

Ethyl (1S,2S)-2-((tert-butoxycarbonyl)amino)-5-oxocyclohexane-1-carboxylate (I-20)

Racemic ethyl trans-2-((tert-butoxycarbonyl)amino)-5-oxocyclohexane-1-carboxylate was prepared as described in the literature (Kiss et. al Eur. J. Org. Chem. 2011, 4993-5001.), then chiral separation was carried out by SFC using a Daicel Chiralpak AD column (250×50 mm, 10 micron) with 25% IPA (containing 0.1% NH$_4$OH as a modifier) as the mobile phase (retention time=4.2 min) to afford the title product. ES/MS m/z: 186.1 (M-C$_5$H$_8$O$_2$+H$^+$). $^1$H NMR: (400 MHz, CDCl$_3$-d) δ=4.63 (br s, 1H), 4.26-4.05 (m, 3H), 2.86-2.69 (m, 2H), 2.58-2.37 (m, 3H), 2.36-2.27 (m, 1H), 1.80-1.68 (m, 1H), 1.45 (s, 9H), 1.28 (t, J=7.2 Hz, 3H). [a]$_D^{25.0}$=+34.25° (c=1.06, CH$_2$Cl$_2$).

Preparation of Intermediate I-21 and I-22

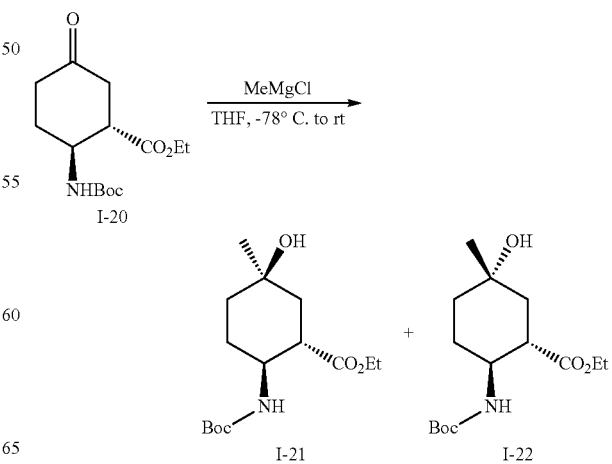

Ethyl (1S,2S,5R)-2-((tert-butoxycarbonyl)amino)-5-hydroxy-5-methylcyclohexane-1-carboxylate (I-21) and ethyl (1S,2S,5S)-2-((tert-butoxycarbonyl)amino)-5-hydroxy-5-methylcyclohexane-1-carboxylate (I-22)

A round-bottom flask equipped with stir bar was charged with ethyl (1S,2S)-2-((tert-butoxycarbonyl)amino)-5-oxo-cyclohexane-1-carboxylate (I-20, 1.00 g, 3.50 mmol), and the headspace was purged with $N_2$. THF (40 mL) was then added, and the mixture was stirred at r.t. until homogeneous, then cooled to −78° C. with stirring. Methyl magnesium bromide (3.0 M solution in THF, 11.7 mL, 35 mmol) was then added dropwise. The resulting mixture was stirred for an additional hour at −78° C., then warmed to 0° C. in an ice bath over 15 min. The reaction mixture was quenched with saturated aqueous $NH_4Cl$, then warmed to r.t., further diluted with brine (to give a final ratio of 1:1 saturated $NH_4Cl$ to brine), transferred to a separatory funnel, and extracted with EtOAc (3×). The combined organics were then dried over $Na_2SO_4$, filtered, and concentrated under vacuum. The title products were isolated following silica gel column chromatography (eluent: hexanes/EtOAc gradient). ES/MS m/z: 324.3 (M+$Na^+$, I-21) and 324.3 (M+$Na^+$, I-22).

Preparation of Intermediate I-23

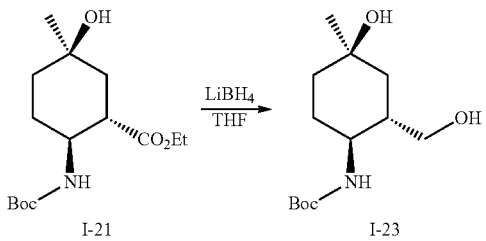

tert-butyl ((1S,2S,4R)-4-hydroxy-2-(hydroxymethyl)-4-methylcyclohexyl) carbamate (I-23)

A round-bottom flask equipped with a stir bar was charged with I-21 (708 mg, 2.35 mmol) and the headspace was purged with $N_2$. THF (23 mL) was then added, and the mixture was stirred at r.t. until homogeneous, then cooled to 0° C. with stirring. Lithium borohydride (2 M solution in THF, 4.7 mL, 9.4 mmol) was added dropwise and the reaction was then allowed to warm to r.t. The reaction mixture was stirred at r.t. for 4 d, then was cooled to 0° C. and quenched with saturated aqueous $NH_4Cl$, then warmed to r.t., further diluted with brine (to give a final ratio of 1:1 saturated $NH_4Cl$ to brine), transferred to a separatory funnel, and extracted with EtOAc (3×). The combined organics were then dried over $Na_2SO_4$, filtered, and concentrated under vacuum. The title product was isolated following silica gel column chromatography (eluent: hexanes/EtOAc gradient). ES/MS m/z: 282.2 (M+$Na^+$).

Preparation of Intermediate I-24

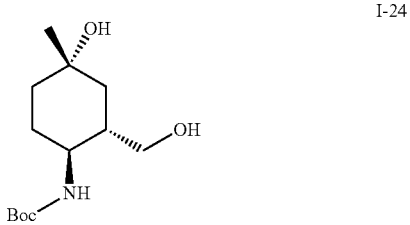 [SMILES: CC(C)(C)OC(=O)N[C@H]1CC[C@](C)(O)C[C@@H]1CO]

tert-butyl ((1S,2S,4S)-4-hydroxy-2-(hydroxymethyl)-4-methylcyclohexyl) carbamate (I-24)

tert-butyl ((1S,2S,4S)-4-hydroxy-2-(hydroxymethyl)-4-methylcyclohexyl)carbamate was synthesized in the same manner as I-23 substituting I-21 with I-22. ES/MS m/z: 282.2 (M+$Na^+$).

Preparation of Intermediate I-25

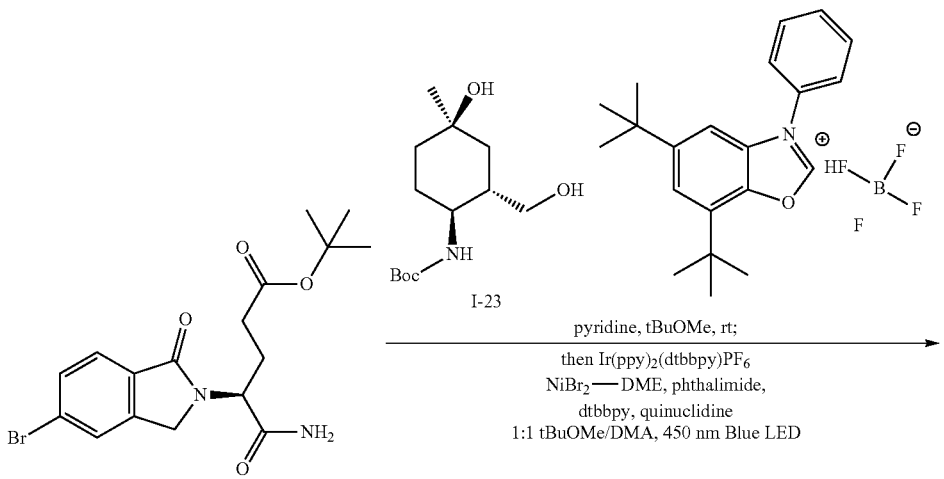

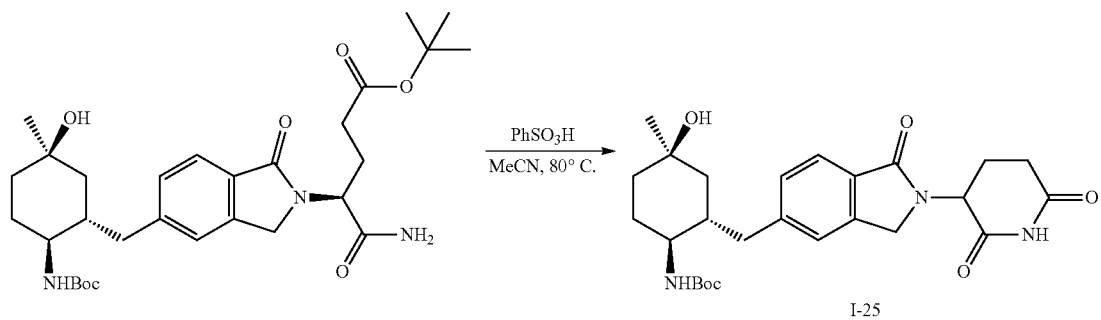

Step 1: Preparation of tert-Butyl 5-amino-4-(5-(((1S,2S,5R)-2-((tert-butoxycarbonyl)amino)-5-hydroxy-5-methylcyclohexyl)methyl)-1-oxoisoindolin-2-yl)-5-oxopentanoate In a 40 mL vial, I-23 (365 mg, 1.41 mmol) and 5,7-di-tert-butyl-3-phenylbenzo[d]oxazol-3-ium tetrafluoroborate (513 mg, 1.30 mmol) were taken up in MTBE (10 mL) and stirred for 5 min. Pyridine (105 uL, 1.30 mmol) was then added dropwise. This mixture was stirred at r.t. for 10 min. Meanwhile in a second 40 mL vial tert-butyl (S)-5-amino-4-(5-bromo-1-oxoisoindolin-2-yl)-5-oxopentanoate (430 mg, 1.08 mmol), [Ir(ppy)$_2$(dtbbpy)]PF$_6$ (14.8 mg, 0.016 mmol), quinuclidine (156 mg, 1.41 mmol), NiBr$_2$-DME (16.7 mg, 0.054 mmol), phthalimide (35.8 mg, 0.244 mmol), and 4,4'-di-tert-butyl-2,2'-dipyridyl (17.4 mg, 0.065 mmol) were combined. The vial was purged with N$_2$ then DMA (10 mL) was added. The activated alcohol suspension was then transferred to a syringe fitted with a syringe filter and needle. The suspension was filtered into the solution of aryl bromide and the mixture sparged with N$_2$ for 5 min. The reaction was then stirred under irradiation by 450 nm light overnight. Following this time, the reaction was complete by LC/MS analysis. The mixture was diluted with EtOAc, transferred to a separatory funnel and washed with water. The aqueous phase was extracted with EtOAc (2×) then the combined organic extracts were dried over Na$_2$SO$_4$, filtered, and concentrated under vacuum. The crude product was purified by normal-phase column chromatography (eluent: EtOAc/Hexanes gradient followed by MeOH/DCM) to yield the product. ES/MS m/z: 582.4 (M+Na$^+$)

Step 2: Preparation of 3-(5-(((1S,2S,5R)-2-amino-5-hydroxy-5-methylcyclohexyl)methyl)-1-oxoisoindolin-2-yl)piperidine-2,6-dione (I-25)

tert-Butyl 5-amino-4-(5-(((1S,2S,5R)-2-((tert-butoxycarbonyl)amino)-5-hydroxy-5-methylcyclohexyl)methyl)-1-oxoisoindolin-2-yl)-5-oxopentanoate (259 mg, 0.463 mmol) was treated with benzenesulfonic acid (0.3M solution in MeCN, 4.6 mL, 1.4 mmol) and the mixture was stirred at 80° C. for 15 min. The reaction mixture was then cooled to r.t., then concentrated under vacuum and the residue purified directly by RP-HPLC (eluent: MeCN/water gradient with 0.1% TFA) to yield the product. ES/MS m/z: 386.3 (M+H$^+$).

Preparation of Intermediate I-26

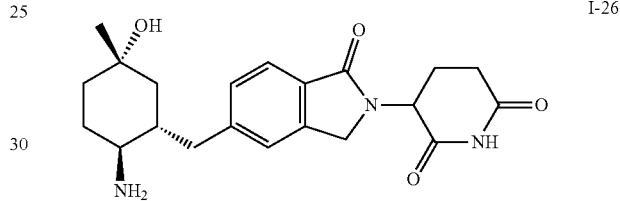

3-(5-(((1S,2S,5S)-2-amino-5-hydroxy-5-methylcyclohexyl)methyl)-1-oxoisoindolin-2-yl)piperidine-2,6-dione (I-26)

3-(5-(((1S,2S,5S)-2-amino-5-hydroxy-5-methylcyclohexyl)methyl)-1-oxoisoindolin-2-yl)piperidine-2,6-dione was synthesized in the same manner as I-25 substituting I-23 with I-24. ES/MS m/z: 386.3 (M+H$^+$).

Preparation of Intermediate I-27

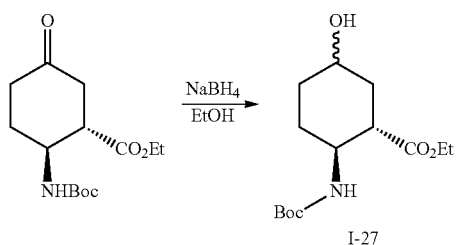

Ethyl (1S,2S)-2-((tert-butoxycarbonyl)amino)-5-hydroxycyclohexane-1-carboxylate (I-27)

Ethyl (1S,2S)-2-((tert-butoxycarbonyl)amino)-5-oxocyclohexane-1-carboxylate (500 mg, 1.75 mmol) was dissolved in ethanol (10 mL) and sodium borohydride (265 mg, 7.01 mmol) was added as a single portion with stirring. The mixture was stirred for 3 h, then quenched with saturated aqueous NH₄Cl, further diluted with brine (to give a final ratio of 1:1 saturated NH₄Cl to brine), transferred to a separatory funnel, and extracted with EtOAc (3×). The combined organics were then dried over Na₂SO₄, filtered, and concentrated under vacuum to afford the title product, which was used in subsequent reactions without further purification. ES/MS m/z: 310.2 (M+Na⁺).

Preparation of Intermediate I-28 and I-29

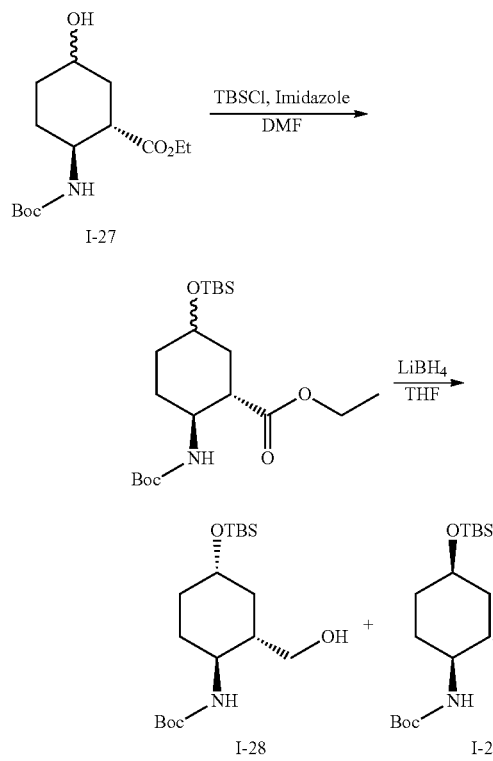

Step 1: Preparation of ethyl (1S,2S)-2-((tert-butoxycarbonyl)amino)-5-((tert-butyldimethylsilyl)oxy) cyclohexane-1-carboxylate I-27 (560 mg, 1.95 mmol) and imidazole (265 mg, 3.9 mmol) were dissolved in DMF (4 mL), then tert-butyldimethylsilyl chloride (382 mg, 2.53 mmol) was added as a single portion. The reaction mixture was stirred overnight, then diluted with EtOAc, transferred to a separatory funnel, and washed with water (3×), followed by brine. The organic layer was then dried over Na₂SO₄, filtered, and concentrated under vacuum. The resulting crude residue was further purified by normal-phase column chromatography (eluent: hexanes/EtOAc) to afford the product. ES/MS m/z: 424.3 (M+Na⁺).

Step 2: Preparation of tert-butyl ((1S,2S,4S)-4-((tert-butyldimethylsilyl)oxy)-2-(hydroxymethyl) cyclohexyl)carbamate (I-28) and tert-butyl ((1S,2S, 4R)-4-((tert-butyldimethylsilyl)oxy)-2-(hydroxymethyl)cyclohexyl)carbamate (I-29)

A round-bottom flask equipped with a stir bar was charged with ethyl (1S,2S)-2-((tert-butoxycarbonyl)amino)-5-((tert-butyldimethylsilyl)oxy)cyclohexane-1-carboxylate (658 mg, 1.64 mmol), and the headspace was purged with N₂. THF (16 mL) was then added, and the mixture was stirred at r.t. until homogeneous, then cooled to 0° C. with stirring. Lithium borohydride (2 M solution in THF, 3.3 mL, 6.6 mmol) was added dropwise and the reaction was then allowed to warm to r.t. The reaction mixture was stirred at r.t. for 2 days, then was cooled to 0° C. and quenched with saturated aqueous NH₄Cl, then warmed to r.t., further diluted with brine (to give a final ratio of 1:1 saturated NH₄Cl to brine), transferred to a separatory funnel, and extracted with EtOAc (3×). The combined organics were then dried over Na₂SO₄, filtered, and concentrated under vacuum. The title products were isolated following silica gel column chromatography (eluent: hexanes/EtOAc gradient). The second eluting product was tentatively assigned as tert-butyl ((1S,2S,4S)-4-((tert-butyldimethylsilyl)oxy)-2-(hydroxymethyl)cyclohexyl)carbamate (I-28) and the first as tert-butyl ((1S,2S,4R)-4-((tert-butyldimethylsilyl)oxy)-2-(hydroxymethyl)cyclohexyl)carbamate (I-29). ES/MS m/z: 382.3 (M+Na⁺, I-28) and 382.3 (M+Na⁺, I-29).

Preparation of Intermediate I-30

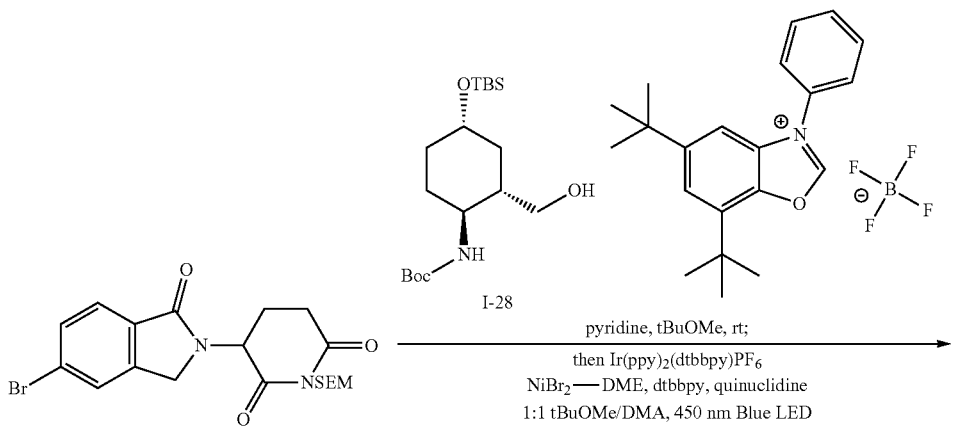

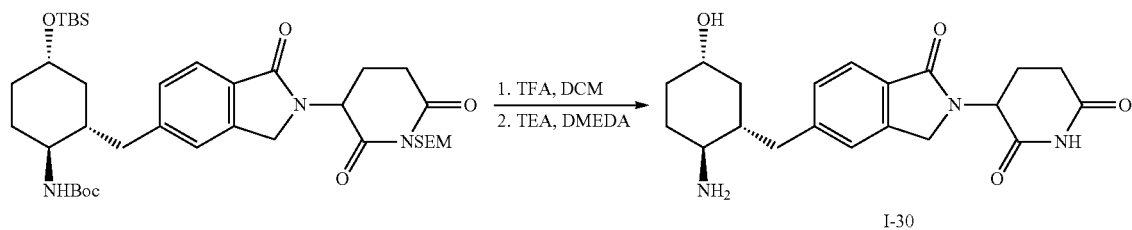

I-30

Step 1: Preparation of tert-butyl ((1S,2S,4R)-4-((tert-butyldimethylsilyl)oxy)-2-((2-(2,6-dioxo-1-((2-(trimethylsilyl)ethoxy)methyl)piperidin-3-yl)-1-oxoisoindolin-5-yl)methyl)cyclohexyl)carbamate In a 40 mL vial, I-28 (201 mg, 0.559 mmol) and 5,7-di-tert-butyl-3-phenylbenzo[d]oxazol-3-ium tetrafluoroborate (204 mg, 0.516 mmol) were taken up in MTBE (4.3 mL) and stirred for 5 min. Pyridine (0.8 M in MTBE, 645 uL, 0.516 mmol) was then added dropwise. This mixture was stirred at r.t. for 10 min. Meanwhile in a second 40 mL vial 3-(5-bromo-1-oxoisoindolin-2-yl)-1-((2-(trimethylsilyl)ethoxy)methyl)piperidine-2,6-dione (195 mg, 0.430 mmol), [Ir(ppy)$_2$(dtbbpy)]PF$_6$ (5.9 mg, 0.0065 mmol), quinuclidine (62 mg, 0.559 mmol), NiBr$_2$-DME (6.6 mg, 0.022 mmol), and 4,4'-di-tert-butyl-2,2'-dipyridyl (6.9 mg, 0.026 mmol) were combined. The vial was purged with N$_2$ then DMA (4.3 mL) was added. The activated alcohol suspension was then transferred to a syringe fitted with a syringe filter and needle. The suspension was filtered into the solution of aryl bromide and the mixture sparged with N$_2$ for 5 min. The reaction was then stirred under irradiation by 450 nm light for 2 days. The mixture was diluted with EtOAc, transferred to a separatory funnel and washed with water. The aqueous phase was extracted with EtOAc (2×) then the combined organic extracts were dried over Na$_2$SO$_4$, filtered, and concentrated under vacuum. The crude product was purified by normal-phase column chromatography (eluent: EtOAc/Hexanes gradient) to yield the product. ES/MS m/z: 738.6 (M+Na$^+$).

Step 2: Preparation of 3-(5-(((1S,2S,5R)-2-amino-5-hydroxycyclohexyl)methyl)-1-oxoisoindolin-2-yl)piperidine-2,6-dione (I-30)

Tert-butyl ((1S,2S,4R)-4-((tert-butyldimethylsilyl)oxy)-2-((2-(2,6-dioxo-1-((2-(trimethylsilyl)ethoxy)methyl)piperidin-3-yl)-1-oxoisoindolin-5-yl)methyl)cyclohexyl)carbamate (100 mg, 0.112 mmol) was dissolved in CH$_2$Cl$_2$ (1.0 mL), treated with TFA (171 μL, 2.2 mmol), and stirred at r.t. After 2 h, an additional quantity of TFA (1.0 mL, 13 mmol) was added, and the reaction was stirred at r.t. for an additional 90 min. The reaction mixture was then concentrated under vacuum. The resulting residue was take up in CH$_2$Cl$_2$ (1.0 mL), cooled to 0° C. with stirring, and treated with triethylamine (125 μL, 0.894 mmol) followed by N,N'-dimethylethylenediamine (14 μL, 0.134 mmol) and then the reaction was warmed to r.t. and stirred overnight. The mixture was then concentrated under vacuum and the residue purified directly by RP-HPLC (eluent: MeCN/water gradient with 0.1% TFA) to yield the product. ES/MS m/z: 372.3 (M+H$^+$).

Preparation of Intermediate I-31

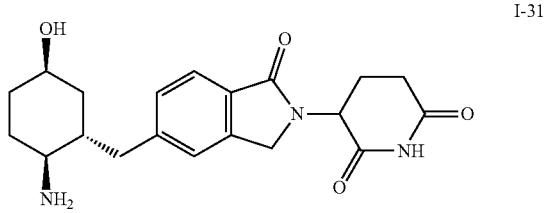 [SMILES: N[C@H]1CC[C@@H](O)C[C@@H]1Cc1ccc2c(c1)CN(C1CCC(=O)NC1=O)C2=O]

I-31

3-(5-(((1S,2S,5S)-2-amino-5-hydroxycyclohexyl)methyl)-1-oxoisoindolin-2-yl)piperidine-2,6-dione (I-31)

3-(5-(((1S,2S,5S)-2-amino-5-hydroxycyclohexyl)methyl)-1-oxoisoindolin-2-yl)piperidine-2,6-dione was synthesized in the same manner as I-30 substituting I-28 with I-29. ES/MS m/z: 372.3 (M+H$^+$).

Preparation of Intermediate I-32

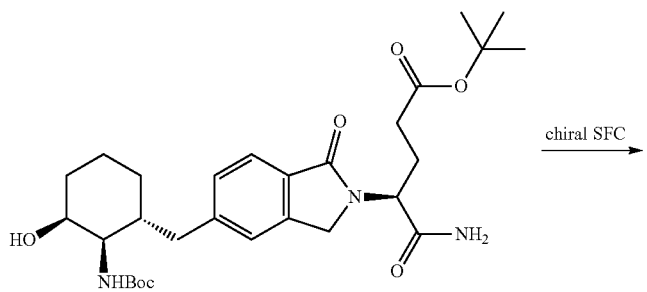

chiral SFC →

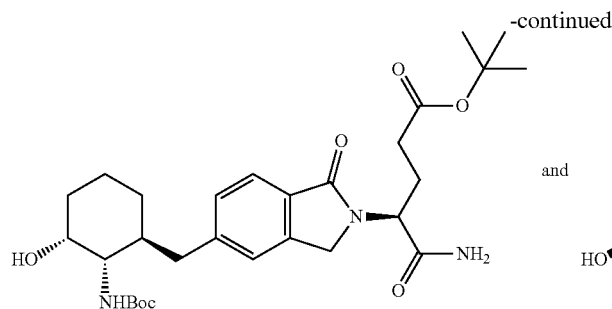

and

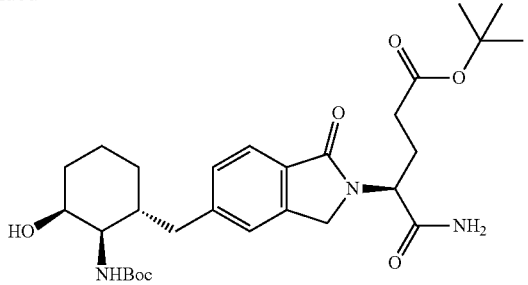

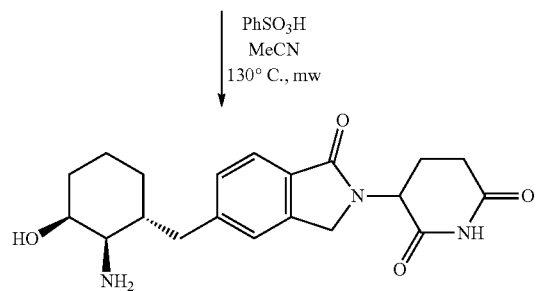

I-32

Step 1. tert-Butyl (S)-5-amino-4-(5-((((1S,2S,3R)-2-((tert-butoxycarbonyl)amino)-3-hydroxycyclohexyl)methyl)-1-oxoisoindolin-2-yl)-5-oxopentanoate (Isomer 1) and tert-Butyl (S)-5-amino-4-(5-(((1R,2R,3S)-2-((tert-butoxycarbonyl)amino)-3-hydroxycyclohexyl)methyl)-1-oxoisoindolin-2-yl)-5-oxopentanoate (Isomer 2)

tert-Butyl (S)-5-amino-4-(5-(((1R,2R,3S)-rel-2-((tert-butoxycarbonyl)amino)-3-hydroxycyclohexyl)methyl)-1-oxoisoindolin-2-yl)-5-oxopentanoate (I-14, step 1) was subjected to chiral SFC (Column: AD-H 250 mm×21 mm, 5 μm, eluent: 25% EtOH) and the resulting fractions were concentrated in vacuo to afford tert-Butyl (S)-5-amino-4-(5-(((1S,2S,3R)-2-((tert-butoxycarbonyl)amino)-3-hydroxycyclohexyl)methyl)-1-oxoisoindolin-2-yl)-5-oxopentanoate (peak 1, Isomer 1) and tert-Butyl (S)-5-amino-4-(5-(((1R,2R,3S)-2-((tert-butoxycarbonyl)amino)-3-hydroxycyclohexyl)methyl)-1-oxoisoindolin-2-yl)-5-oxopentanoate (peak 2, Isomer 2).

Step 2. 3-(5-(((1R,2R,3S)-2-amino-3-hydroxycyclohexyl)methyl)-1-oxoisoindolin-2-yl)piperidine-2,6-dione (I-32)

tert-Butyl (S)-5-amino-4-(5-(((1R,2R,3S)-2-((tert-butoxycarbonyl)amino)-3-hydroxycyclohexyl)methyl)-1-oxoisoindolin-2-yl)-5-oxopentanoate (52.6 mg, 96.4 μmol) was taken up in MeCN (1.5 mL) and benzenesulfonic acid (45.7 mg, 0.289 mmol) was added. The reaction was heated to 130° C. under microwave irradiation for 1 h. Following this time, the resulting solid was filtered off, washed with acetonitrile and dried to afford 3-(5-(((1R,2R,3S)-2-amino-3-hydroxycyclohexyl)methyl)-1-oxoisoindolin-2-yl) piperidine-2,6-dione (I-32) as the benzenesulfonic acid salt. ES/MS m/z: 372.1 (M+H⁺).

Preparation of Intermediate I-33

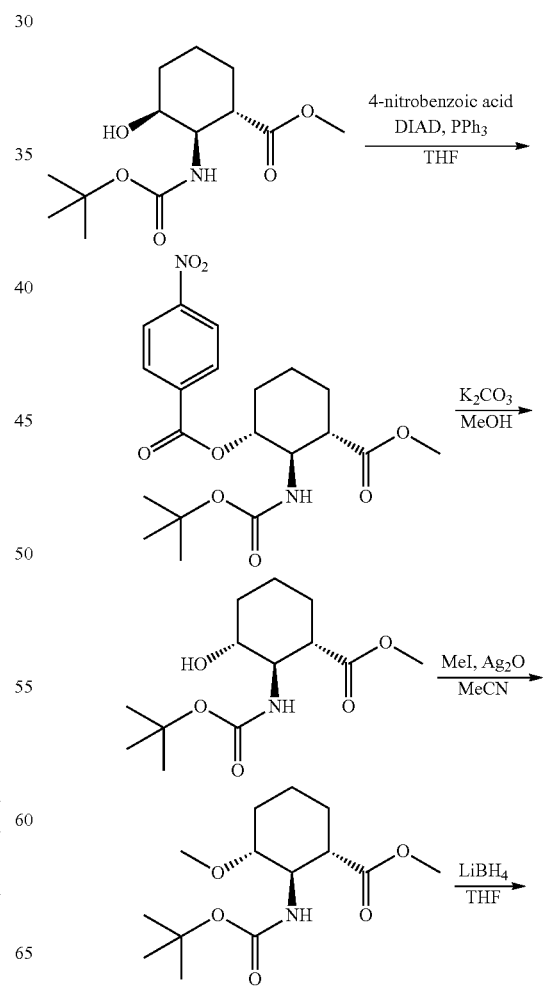

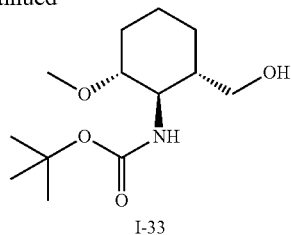

I-33

Step 1. (1R,2R,3S)-2-((tert-butoxycarbonyl)amino)-3-(methoxycarbonyl)cyclohexyl 4-nitrobenzoate To a solution of methyl (1S,2R,3S)-rel-2-((tert-butoxycarbonyl)amino)-3-hydroxycyclohexane-1-carboxylate ([prepared according to the procedure described for I-16, step 1], 270 mg, 0.988 mmol) was added diisopropyl azodicarboxylate (233 µL, 1.19 mmol) and triphenylphosphine (311 mg, 1.19 mmol). To this was added, 4-nitrobenzoic acid (198 mg, 1.19 mmol), and the reaction was stirred at r.t. overnight. Following this time, the reaction was diluted with EtOAc, transferred to a separatory funnel and washed with water. The aqueous phase was extracted with additional EtOAc (2×) and the combined organic extracts were dried over MgSO$_4$, concentrated in vacuo, and then the residue purified by SiO$_2$ column chromatography (eluent: EtOAc/hexanes) to afford (1R,2R,3S)-rel-2-((tert-butoxycarbonyl)amino)-3-(methoxycarbonyl)cyclohexyl 4-nitrobenzoate. ES/MS m/z: 431.1 (M+Na$^+$).

Step 2. Methyl (1S,2R,3R)-rel-2-((tert-butoxycarbonyl)amino)-3-hydroxycyclohexane-1-carboxylate (1R,2R,3S)-rel-2-((tert-butoxycarbonyl)amino)-3-(methoxycarbonyl)cyclohexyl 4-nitrobenzoate (296 mg, 0.701 mmol) and K$_2$CO$_3$ (291 mg, 2.10 mmol) were combined in methanol (3.5 mL) and the resulting suspension was stirred at r.t. overnight. The reaction mixture was then filtered to removed solids, concentrated in vacuo, and purified by SiO$_2$ column chromatography (eluent: EtOAc/hexanes) to afford methyl (1S,2R,3R)-rel-2-((tert-butoxycarbonyl)amino)-3-hydroxycyclohexane-1-carboxylate. ES/MS m/z: 296.1 (M+Na$^+$).

Step 3. Methyl (1S,2R,3R)-rel-2-((tert-butoxycarbonyl)amino)-3-methoxycyclohexane-1-carboxylate Methyl (1S,2R,3R)-rel-2-((tert-butoxycarbonyl)amino)-3-hydroxycyclohexane-1-carboxylate (330 mg, 1.21 mmol) was taken up in acetonitrile (6.0 mL) and iodomethane (376 µL, 6.04 mmol) was added followed by silver (I) oxide (449 mg, 3.62 mmol). The reaction was stirred at r.t. for 5 days and then the solids were filtered off and the mixture concentrated in vacuo. The resulting residue was purified by SiO$_2$ column chromatography (eluent: EtOAc/hexanes) to yield methyl (1S,2R,3R)-rel-2-((tert-butoxycarbonyl)amino)-3-methoxycyclohexane-1-carboxylate. ES/MS m/z: 310.1 (M+Na$^+$).

Step 4. tert-Butyl ((1R,2S,6R)-rel-2-(hydroxymethyl)-6-methoxycyclohexyl)carbamate (I-33)

Methyl (1S,2R,3R)-rel-2-((tert-butoxycarbonyl)amino)-3-methoxycyclohexane-1-carboxylate (118 mg, 0.412 mmol) was taken up in THF (4.2 mL) and the reaction mixture cooled to 0° C. LiBH$_4$ (2.0 M in THF, 824 µL, 1.65 mmol) was added slowly over 5 min then the reaction was warmed to r.t. and stirred for 48 h. The reaction mixture was then diluted with EtOAc and water and the biphasic mixture was transferred to a separatory funnel. The organic extracts were collected, washed with brine, dried over MgSO$_4$ and concentrated in vacuo. The residue was the purified by SiO$_2$ column chromatography (eluent: EtOAc/hexanes) to afford tert-butyl ((1R,2S,6R)-rel-2-(hydroxymethyl)-6-methoxycyclohexyl)carbamate (I-33). ES/MS m/z: 282.1 (M+Na$^+$).

Preparation of Intermediate I-34

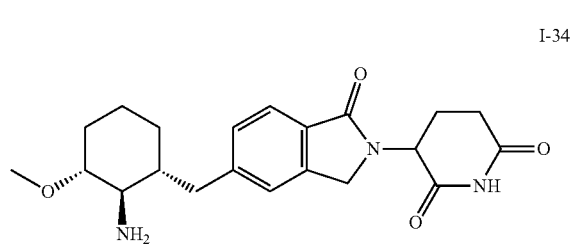 [SMILES: CO[C@@H]1CCC[C@H](Cc2ccc3c(c2)CN(C2CCC(=O)NC2=O)C3=O)[C@H]1N]

I-34

3-(5-(((1R,2R,3R)-rel-2-amino-3-methoxycyclohexyl)methyl)-1-oxoisoindolin-2-yl)piperidine-2,6-dione (I-34)

3-(5-(((1R,2R,3R)-2-amino-3-methoxycyclohexyl)methyl)-1-oxoisoindolin-2-yl)piperidine-2,6-dione was synthesized in the same manner as I-13 substituting I-1 with I-33. ES/MS m/z: 582.2 (M+Na$^+$).

Preparation of Intermediate I-35

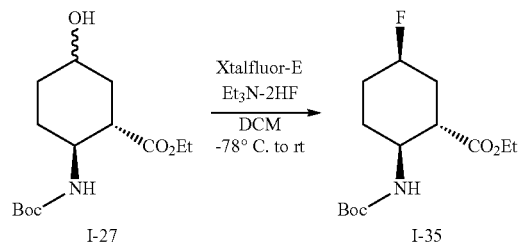

Ethyl (1S,2S,5R)-2-((tert-butoxycarbonyl)amino)-5-fluorocyclohexane-1-carboxylate (I-35)

A 100 mL PFA flask equipped with a teflon stir bar was charged with Xtalfluor-E (1.20 g, 5.22 mmol), and the headspace was purged with N$_2$. CH$_2$Cl$_2$ (10 mL) was then added, and the mixture was cooled to −78° C. with stirring. Triethylamine trishydrofluoride (1.12 mL, 6.96 mmol) was added dropwise, followed by triethylamine (485 uL, 3.48 mmol). I-27 (1.00 g, 3.48 mmol) was then added dropwise as a solution in CH$_2$Cl$_2$ (5 mL). The resulting mixture was allowed to warm to r.t. and stirred for an additional 4 h. The mixture was then carefully quenched with saturated aqueous NaHCO$_3$, then transferred to a separatory funnel. The layers were separated, and the aqueous layer was extracted with CH$_2$Cl$_2$ (2×). The combined organics were dried over Na$_2$SO$_4$, filtered, and concentrated under vacuum. The resulting crude residue was further purified by silica gel chromatography (eluent: hexanes/EtOAc) to afford the product. ES/MS m/z: 312.2 (M+Na$^+$).

Preparation of Intermediate I-36

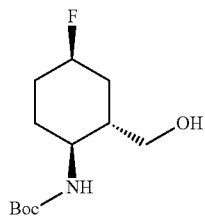

I-36 tert-Butyl ((1S,2S,4R)-4-fluoro-2-(hydroxymethyl)cyclohexyl)carbamate (I-36)

tert-Butyl ((1S,2S,4R)-4-fluoro-2-(hydroxymethyl)cyclohexyl)carbamate was synthesized in the same manner as I-23 substituting I-21 with I-27. ES/MS m/z: 270.2 (M+Na$^+$).

Preparation of Intermediate I-37

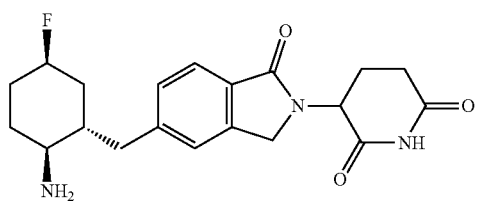

I-37

3-(5-(((1S,2S,5R)-2-amino-5-fluorocyclohexyl)methyl)-1-oxoisoindolin-2-yl)piperidine-2,6-dione (I-37)

3-(5-(((1S,2S,5R)-2-amino-5-fluorocyclohexyl)methyl)-1-oxoisoindolin-2-yl)piperidine-2,6-dione was synthesized in the same manner as Example 1 substituting I-1 with I-36

Preparation of Intermediate I-38

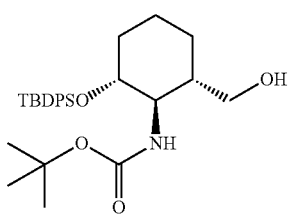

I-38 tert-Butyl ((1R,2R,6S)-rel-2-((tert-butyldiphenylsilyl)oxy)-6-(hydroxymethyl)cyclohexyl)carbamate (I-38)

tert-Butyl ((1R,2R,6S)-rel-2-((tert-butyldiphenylsilyl)oxy)-6-(hydroxymethyl)cyclohexyl)carbamate was prepared according to the procedure described for (I-16, steps 2 and 3) substituting methyl (1S,2R,3S)-rel-2-((tert-butoxycarbonyl)amino)-3-((tert-butyldiphenylsilyl)oxy)cyclohexane-1-carboxylate with methyl (1S,2R,3R)-rel-2-((tert-butoxycarbonyl)amino)-3-hydroxycyclohexane-1-carboxylate (prepared according to the procedure described for I-33, steps 1 and 2).

Preparation of Intermediate I-39

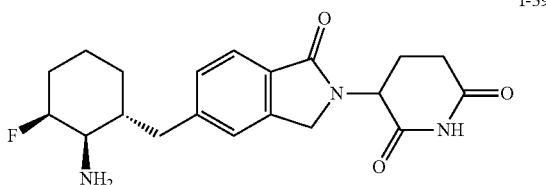

I-39

3-(5-(((1R,2R,3S)-rel-2-amino-3-fluorocyclohexyl)methyl)-1-oxoisoindolin-2-yl)piperidine-2,6-dione (I-39)

3-(5-(((1R,2R,3S)-rel-2-amino-3-fluorocyclohexyl)methyl)-1-oxoisoindolin-2-yl)piperidine-2,6-dione was synthesized in the same manner as I-19 substituting I-16 with I-38. ES/MS m/z: 374.1 (M+NH$^+$).

Preparation of Intermediate I-40

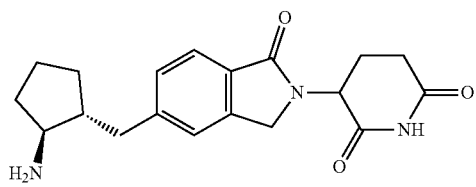

I-40

3-(5-(((1R,2S)-2-aminocyclopentyl)methyl)-1-oxoisoindolin-2-yl)piperidine-2,6-dione (I-40)

3-(5-(((1R,2S)-2-aminocyclopentyl)methyl)-1-oxoisoindolin-2-yl)piperidine-2,6-dione was synthesized in the same manner as I-24 substituting I-23 with tert-butyl ((1S,2S)-2-(hydroxymethyl)cyclopentyl)carbamate. ES/MS m/z: 342.3 (M+H⁺).

Preparation of Intermediate I-41

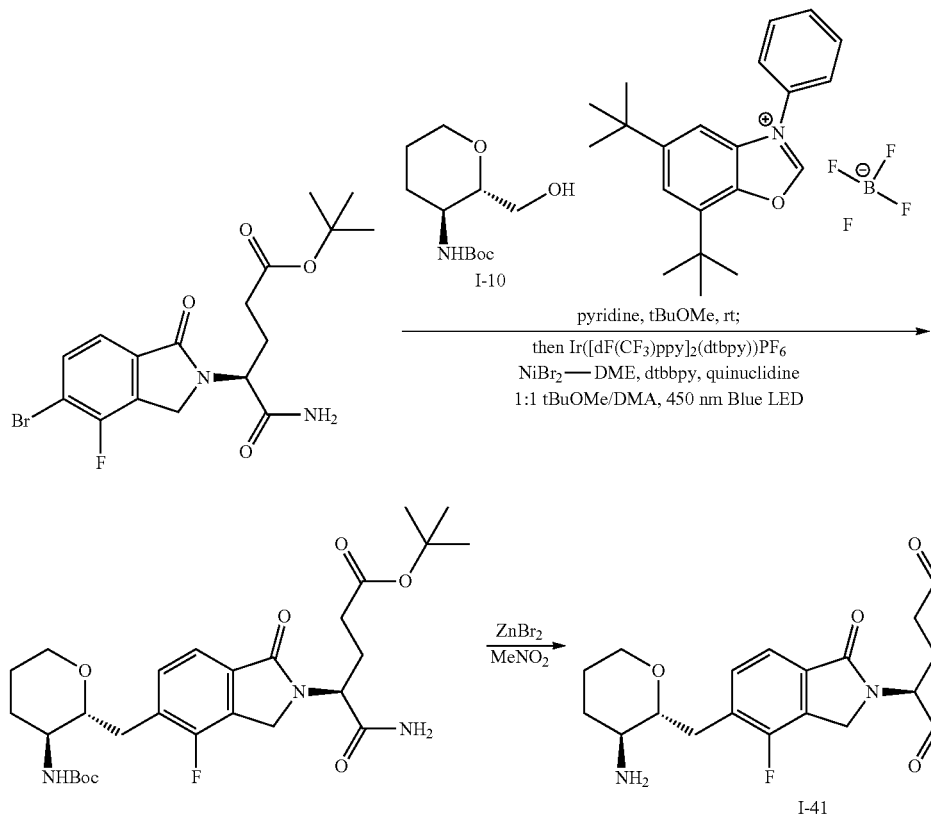

Step 1: Preparation of tert-butyl (S)-5-amino-4-(5-(((2R,3S)-3-((tert-butoxycarbonyl)amino)tetrahydro-2H-pyran-2-yl)methyl)-4-fluoro-1-oxoisoindolin-2-yl)-5-oxopentanoate The title compound was prepared in the same manner as I-13, step 1 substituting I-1 with I-10 and tert-butyl (S)-5-amino-4-(5-bromo-1-oxoisoindolin-2-yl)-5-oxopentanoate with tert-butyl (S)-5-amino-4-(5-bromo-4-fluoro-1-oxoisoindolin-2-yl)-5-oxopentanoate. ES/MS m/z: 572.2 (M+Na⁺).

Step 2: Preparation of tert-butyl (S)-5-amino-4-(5-(((2R,3S)-3-aminotetrahydro-2H-pyran-2-yl)methyl)-4-fluoro-1-oxoisoindolin-2-yl)-5-oxopentanoate (I-41)

Tert-butyl (S)-5-amino-4-(5-(((2R,3S)-3-((tert-butoxycarbonyl)amino)tetrahydro-2H-pyran-2-yl)methyl)-4-fluoro-1-oxoisoindolin-2-yl)-5-oxopentanoate (83 mg, 0.158 mmol) dissolved in nitromethane (2 mL) was treated with zinc bromide (168 mg, 0.746 mmol). The reaction mixture was stirred at room temperature for 3 h and then concentrated directly. The residue was partitioned between ethyl acetate and saturated aqueous NaHCO₃. The organic phase was collected washed with saturated aqueous NaHCO₃ and brine, then dried over sodium sulfate and concentrated in vacuo to yield tert-butyl (S)-5-amino-4-(5-(((2R,3S)-3-aminotetrahydro-2H-pyran-2-yl)methyl)-4-fluoro-1-oxoisoindolin-2-yl)-5-oxopentanoate which was used without further purification (I-41). ES/MS m/z: 450.1 (M+H⁺).

Preparation of Intermediate I-42

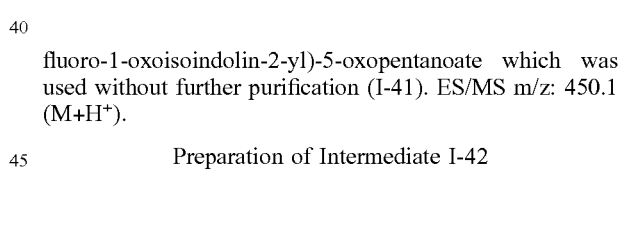

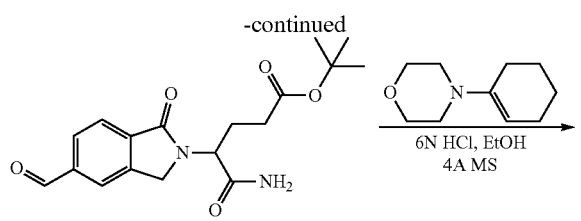

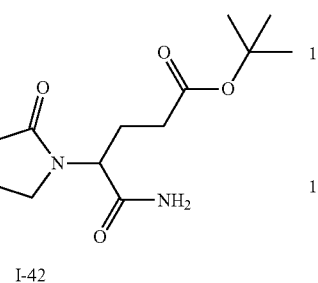

I-42

Step 1: Preparation of tert-butyl 5-amino-5-oxo-4-(1-oxo-5-vinylisoindolin-2-yl)pentanoate To tert-butyl (S)-5-amino-4-(5-bromo-1-oxoisoindolin-2-yl)-5-oxopentanoate (15 g, 38 mmol) and 4,4,5,5-tetramethyl-2-vinyl-1,3,2-dioxaborolane (8.3 mL, 49 mmol) in DME (200 mL) was added 2 M aqueous $Na_2CO_3$ (57 mL, 113 mmol) and the mixture degassed with $N_2$ for a 5 minutes. [1,1'-bis(di-tert-butylphosphino)ferrocene]dichloropalladium(II) (2.5 g, 3.8 mmol) was then added and the mixture was degassed for an additional 1 minute. The reaction was then heated at 90° C. for 3 hours and stirred at r.t. overnight. Following this time, the reaction was diluted with EtOAc and filtered through a pad of celite. The resulting phases were separated and the aqueous phase was extracted with EtOAc (2×). The combined organics were washed with water and brine then dried over $Na_2SO_4$ and concentrated in vacuo. The residue was purified by $SiO_2$ column chromatography (eluent: hexanes/EtOAc then EtOAc/MeOH) to afford the title product.

Step 2: Preparation of tert-butyl 5-amino-4-(5-formyl-1-oxoisoindolin-2-yl)-5-oxopentanoate To a flask charged with tert-butyl 5-amino-5-oxo-4-(1-oxo-5-vinylisoindolin-2-yl)pentanoate (10.8 g, 31 mmol) was added THF (100 mL) and water (100 mL). The resulting mixture was cooled to 0° C. and potassium osmate (0.25 g, 0.69 mmol) was added in one portion followed by portionwise addition of sodium periodate (20.5 g, 95.9 mmol). Following complete addition, the reaction was warmed to r.t. and stirred for 2.5 hours. Following this time, the reaction was diluted with EtOAc and water, transferred to a separatory funnel and the organic phase collected. The aqueous layer was extracted with EtOAc (2×) and then the combined organics were washed with water and brine, dried over $Na_2SO_4$, and concentrated in vacuo. The residue was purified by $SiO_2$ column chromatography (eluent: hexanes/EtOAc then EtOAc/MeOH) to afford the title product.

Step 3: Preparation of tert-butyl (E)-5-amino-5-oxo-4-(1-oxo-5-((2-oxocyclohexylidene)methyl)isoindolin-2-yl)pentanoate (I-42)

To a solution of tert-butyl 5-amino-4-(5-formyl-1-oxoisoindolin-2-yl)-5-oxopentanoate (2 g, 5.8 mmol) in EtOH (25 mL) was added 4 Å mol sieves (2 g) followed by 4-(cyclohex-1-en-1-yl)morpholine (2.9 mL, 17 mmol) and 6 N aqueous HCl (0.5 mL, 2.9 mmol). The reaction mixture was heated at 80° C. for 44 hours after which the reaction was cooled to r.t. and diluted with EtOAc. The mixture was filtered over celite, washing with EtOAc, and the filtrate concentrated in vacuo. The crude product was subjected to $SiO_2$ column chromatography (eluent: hexanes/EtOAc then EtOAc/MeOH). The resulting material was suspended in $Et_2O$ (55 mL) and the suspension sonicated before pentane (11 mL) was added and the resulting precipitate was filtered (washed with minimum $Et_2O$) and dried overnight to give title product I-42. ES/MS: 427.1 (M+H$^+$). $^1$H NMR (400 MHz, DMSO-d6) δ 7.72 (d, J=7.9 Hz, 1H), 7.69 (s, 1H), 7.60-7.52 (m, 2H), 7.39 (d, J=2.4 Hz, 1H), 7.20 (s, 1H), 4.74 (dd, J=10.4, 3.8 Hz, 1H), 4.67-4.44 (m, 2H), 2.82 (td, J=6.5, 2.2 Hz, 2H), 2.47 (d, J=6.8 Hz, 2H), 2.15 (dd, J=10.6, 2.8 Hz, 3H), 2.07-1.92 (m, 1H), 1.87 (p, J=6.5 Hz, 2H), 1.71 (p, J=6.2 Hz, 2H), 1.33 (s, 9H).

Preparation of Intermediate I-43

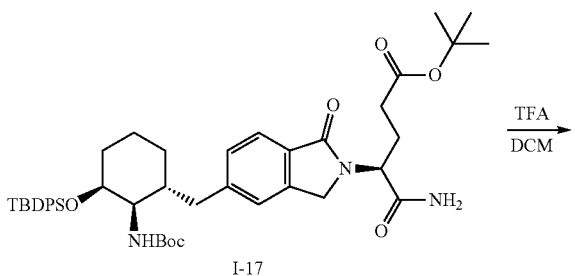

I-17

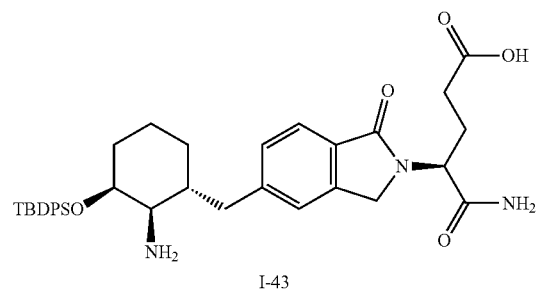

I-43

(S)-5-amino-4-(5-(((1R,2R,3S)-rel-2-amino-3-((tert-butyldiphenylsilyl)oxy) cyclohexyl)methyl)-1-oxoisoindolin-2-yl)-5-oxopentanoic acid (I-43)

I-17 (100 mg, 0.128 mmol) was taken up in $CH_2Cl_2$ (1.3 mL) and trifluoroacetic acid (98 µL, 1.28 mmol) was added. The reaction mixture was stirred at r.t. overnight then concentrated in vacuo to afford (S)-5-amino-4-(5-(((1R,2R,3S)-rel-2-amino-3-((tert-butyldiphenylsilyl)oxy)cyclohexyl)methyl)-1-oxoisoindolin-2-yl)-5-oxopentanoic acid which was used in subsequent reactions without further purification. ES/MS m/z: 628.3 (M+H$^+$).

Preparation of Intermediates I-44a and I-44b
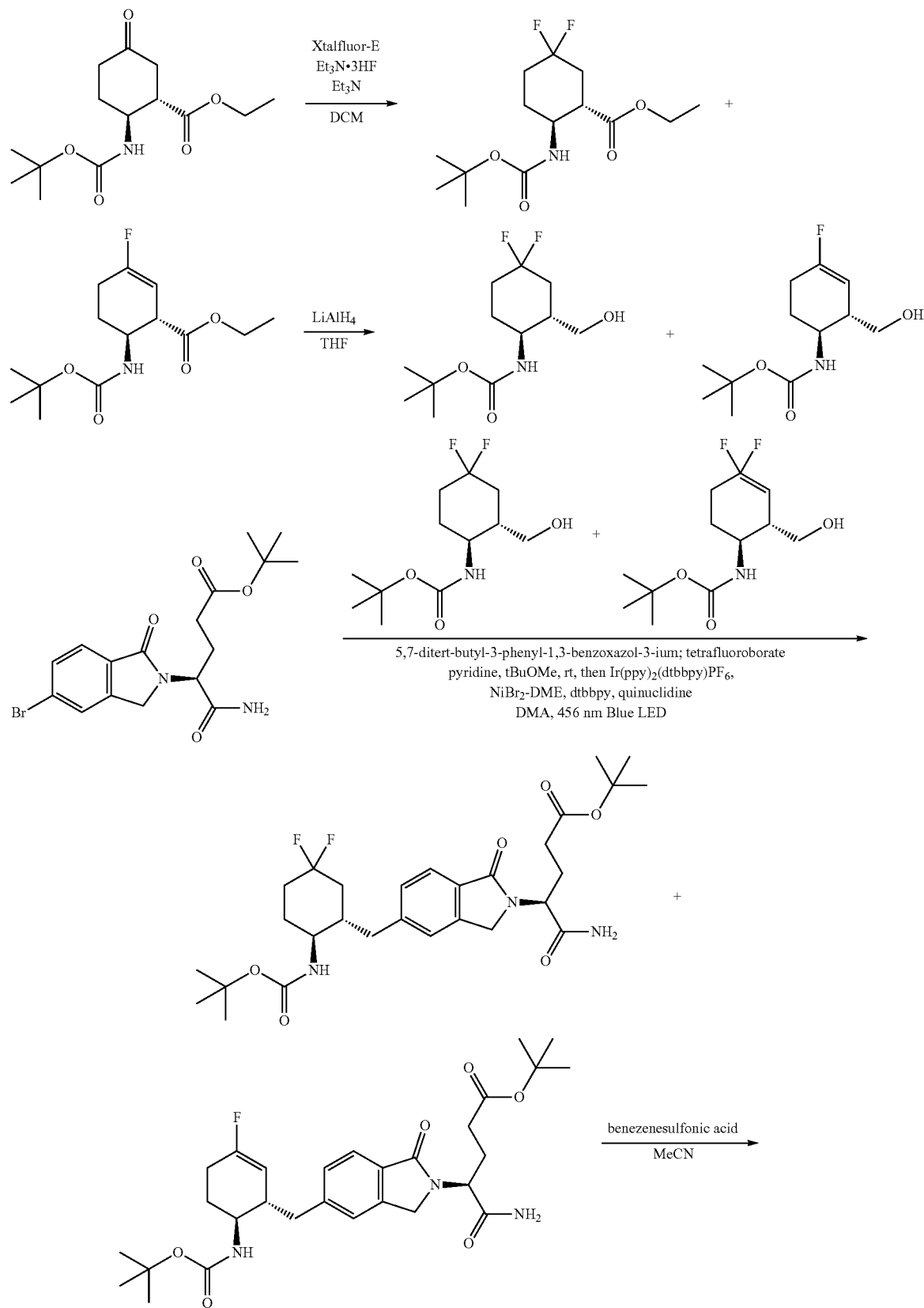

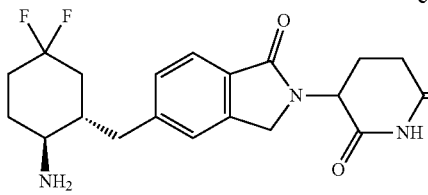 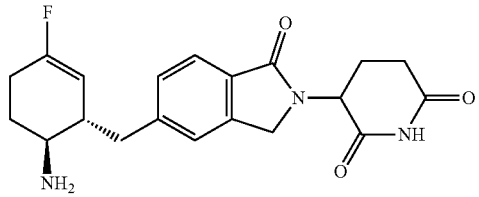

I-44a            I-44b

Step 1: Preparation of ethyl (1S,2S)-2-((tert-butoxy-carbonyl)amino)-5,5-difluorocyclohexane-1-carboxylate and ethyl (1S,6S)-6-((tert-butoxycarbonyl)amino)-3-fluorocyclohex-2-ene-1-carboxylate A PFA round-bottomed-flask was charged with XtalFluor-E (602 mg, 2.63 mmol) and CH$_2$Cl$_2$ (5 mL) and placed under an atmosphere of nitrogen. Et$_3$N·3HF (0.565 mL, 3.50 mmol) was then added slowly, followed by slow addition of Et$_3$N (0.244 mL, 1.75 mmol). A solution of ethyl (1S,2S)-2-((tert-butoxycarbonyl)amino)-5-oxocyclohexane-1-carboxylate (500 mg, 1.75 mmol) in CH$_2$Cl$_2$ (5 mL) was then added to the mixture slowly. Following complete addition, the reaction was warmed to r.t. and stirred for 23 h. Following this time, the reaction was diluted with CH$_2$Cl$_2$ and quenched by slow addition of saturated aqueous NaHCO$_3$. The mixture was transferred to a separatory funnel and extracted with CH$_2$Cl$_2$(2×). The combined organics were concentrated in vacuo and the residue purified by SiO$_2$ column chromatography (eluent: EtOAc/hexanes gradient) to afford a mixture of ethyl (1S,2S)-2-((tert-butoxycarbonyl)amino)-5,5-difluorocyclohexane-1-carboxylate and ethyl (1S,6S)-6-((tert-butoxycarbonyl)amino)-3-fluorocyclohex-2-ene-1-carboxylate (372 mg) which was carried forward without further purification. ES/MS m/z: 308.1 (M+H$^+$, difluoride) and 288.1 (M+H$^+$, vinyl fluoride).

Step 2: Preparation of tert-butyl ((1S,2S)-4,4-difluoro-2-(hydroxymethyl)cyclohexyl)carbamate and tert-butyl ((1S,2S)-4-fluoro-2-(hydroxymethyl)cyclohex-3-en-1-yl)carbamate A vial was charged with a mixture of ethyl (1S,2S)-2-((tert-butoxycarbonyl)amino)-5,5-difluorocyclohexane-1-carboxylate and ethyl (1S,6S)-6-((tert-butoxycarbonyl)amino)-3-fluorocyclohex-2-ene-1-carboxylate (416 mg, 1.35 mmol) and THF (5.20 mL) and placed under an atmosphere of nitrogen. The reaction was cooled to 0° C. and charged with lithium aluminum hydride (205 mg, 5.41 mmol) in one portion then stirring was continued for 1.5 h. Following this time, the reaction was treated with Na$_2$SO$_4$·10H$_2$O (800 mg, 2.48 mmol). The resulting slurry was stirred for 1 h, filtered (washing with CH$_2$Cl$_2$) and the filtrate concentrated in vacuo. The residue was purified by SiO$_2$ column chromatography (eluent: EtOAc/hexanes gradient) to afford a mixture of tert-butyl ((1S,2S)-4,4-difluoro-2-(hydroxymethyl)cyclohexyl)carbamate and tert-butyl ((1S,2S)-4-fluoro-2-(hydroxymethyl)cyclohex-3-en-1-yl)carbamate. ES/MS m/z: 266.1 (M+H$^+$, difluoride) and 246.1 (M+H$^+$, vinyl fluoride).

Step 3: Preparation of tert-butyl (S)-5-amino-4-(5-(((1S,2S)-2-((tert-butoxycarbonyl)amino)-5,5-difluorocyclohexyl)methyl)-1-oxoisoindolin-2-yl)-5-oxopentanoate and tert-butyl (S)-5-amino-4-(5-(((1S,6S)-6-((tert-butoxycarbonyl)amino)-3-fluorocyclohex-2-en-1-yl)methyl)-1-oxoisoindolin-2-yl)-5-oxopentanoate A vial was charged tert-butyl (S)-5-amino-4-(5-bromo-1-oxoisoindolin-2-yl)-5-oxopentanoate ([prepared according to the procedure described in WO2021/101919] 290 mg, 0.730 mmol), [Ir(dtbbpy)(ppy)$_2$]PF$_6$ (10 mg, 0.0109 mmol), NiBr$_2$-DME (11.3 mg, 0.0365 mmol), 4,4'-di-tert-butyl-2,2'-dipyridyl (11.8 mg, 0.0438 mmol), and quinuclidine (142 mg, 1.28 mmol). The headspace was purged while in a second vial, a mixture of tert-butyl ((1S,2S)-4,4-difluoro-2-(hydroxymethyl)cyclohexyl)carbamate and tert-butyl ((1S,2S)-4-fluoro-2-(hydroxymethyl)cyclohex-3-en-1-yl)carbamate (271 mg, 0.846 mmol), 5,7-ditert-butyl-3-phenyl-1,3-benzoxazol-3-ium; tetrafluoroborate (448 mg, 0.967 mmol), and pyridine (0.0945 mL, 1.17 mmol) were combined in MTBE (7.30 mL). This mixture was stirred for 10 minutes. DMA (7.30 mL) was added to the first vial and the activated alcohol suspension was then transferred to a syringe fitted with a syringe filter and needle. The suspension was filtered into the solution of aryl bromide and the mixture sparged with nitrogen for 5 min. The reaction was then stirred under irradiation by blue light irradiation (Kessil Lamp/450 nm Blue LED combined with a small fan to increase air circulation) for 91 h. Following this time, the reaction was quenched by addition of sat. aqueous NaHCO$_3$ and diluted with water and EtOAc. The reaction was transferred to a separatory funnel and the layers were separated. The aqueous layer was extracted with additional EtOAc (2×) and then the combined organics were washed with water and brine and then concentrated in vacuo. The residue was purified by SiO$_2$ column chromatography (eluent: 0-100% EtOAc/hexanes gradient) to afford a mixture of tert-butyl (S)-5-amino-4-(5-(((1S,2S)-2-((tert-butoxycarbonyl)amino)-5,5-difluorocyclohexyl)methyl)-1-oxoisoindolin-2-yl)-5-oxopentanoate and tert-butyl (S)-5-amino-4-(5-(((1S,6S)-6-((tert-butoxycarbonyl)amino)-3-fluorocyclohex-2-en-1-yl)methyl)-1-oxoisoindolin-2-yl)-5-oxopentanoate. ES/MS m/z: 566.2 (M+H$^+$, difluoride) and 546.2 (M+H$^+$, vinyl fluoride).

Step 2: Preparation of 3-(5-(((1S,2S)-2-amino-5,5-difluorocyclohexyl)methyl)-1-oxoisoindolin-2-yl)piperidine-2,6-dione (I-44a) and 3-(5-(((1S,6S)-6-amino-3-fluorocyclohex-2-en-1-yl)methyl)-1-oxoisoindolin-2-yl)piperidine-2,6-dione (I-44b)

A vial was charged with a mixture tert-butyl (S)-5-amino-4-(5-(((1S,2S)-2-((tert-butoxycarbonyl)amino)-5,5-difluorocyclohexyl)methyl)-1-oxoisoindolin-2-yl)-5-oxopentanoate and tert-butyl (S)-5-amino-4-(5-(((1S,6S)-6-((tert-butoxycarbonyl)amino)-3-fluorocyclohex-2-en-1-yl) methyl)-1-oxoisoindolin-2-yl)-5-oxopentanoate (218 mg, 0.385 mmol), MeCN (6.55 mL), and benzenesulfonic acid (183 mg, 1.16 mmol). The reaction was heated to 130° C. under microwave irradiation for 30 min. Following this time, the reaction was filtered, the solids washed with MeCN and dried under reduced pressure to yield 3-(5-(((1S,2S)-2-amino-5,5-difluorocyclohexyl)methyl)-1-oxoisoindolin-2-yl)piperidine-2,6-dione (I-44a) and 3-(5-(((1S,6S)-6-amino-3-fluorocyclohex-2-en-1-yl)methyl)-1-oxoisoindolin-2-yl) piperidine-2,6-dione (I-44b) as a mixture. ES/MS m/z: 392.1 (M+H$^+$, I-44a) and 372.1 (M+H$^+$, I-44b).

Preparation of Intermediate I-45

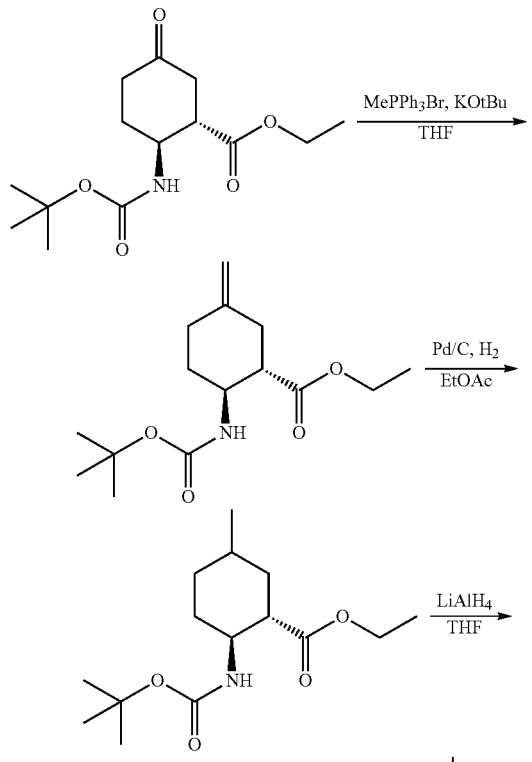

I-45

Step 1: Preparation of ethyl (1S,2S)-2-((tert-butoxycarbonyl)amino)-5-methylenecyclohexane-1-carboxylate A vial was charged with THF (5.00 mL) and KOtBu (1.0 M solution in THF, 3.50 mL, 3.50 mmol). Methyltriphenylphosphonium bromide (1.25 g, 3.50 mmol) was then added in one portion and the reaction was mixed at r.t. for 15 min. Following this time, a solution of ethyl (1S,2S)-2-((tert-butoxycarbonyl)amino)-5-oxocyclohexane-1-carboxylate (500 mg, 1.75 mmol) in THF (5.00 mL) was added dropwise. The reaction was mixed at room temperature for 2.5 h. Following this time, the reaction was quenched by addition of water and the resulting mixture filtered through Celite, washing with CH$_2$Cl$_2$. The filtrate was concentrated in vacuo and the resulting residue was purified directly by SiO$_2$ column chromatography (eluent: EtOAc/hexanes gradient) to afford ethyl (1S,2S)-2-((tert-butoxycarbonyl) amino)-5-methylenecyclohexane-1-carboxylate. ES/MS m/z: 306.2 (M+Na$^+$).

Step 2: Preparation of ethyl (1S,2S)-2-((tert-butoxycarbonyl)amino)-5-methylcyclohexane-1-carboxylate A flask was charged with ethyl (1S,2S)-2-((tert-butoxycarbonyl)amino)-5-methylenecyclohexane-1-carboxylate (370 mg, 1.31 mmol), Pd/C (278 mg, 0.261 mmol), and EtOAc (3.70 mL) and shaken on a Parr shaker under 50 psi H$_2$ for 2 h. Following this time, the reaction was filtered through Celite, washing with EtOAc. The filtrate was concentrated in vacuo and the resulting residue was purified directly by SiO$_2$ column chromatography (eluent: EtOAc/ hexanes gradient) to afford ethyl (1S,2S)-2-((tert-butoxycarbonyl)amino)-5-methylcyclohexane-1-carboxylate. ES/MS m/z: 286.1 (M+H$^+$).

Step 3: Preparation of tert-butyl ((1S,2S)-2-(hydroxymethyl)-4-methylcyclohexyl)carbamate (I-45)

A vial was charged with ethyl (1S,2S)-2-((tert-butoxycarbonyl)amino)-5-methylcyclohexane-1-carboxylate (323.4 mg, 1.13 mmol) and THF (4.04 mL) and placed under an atmosphere of nitrogen. The reaction was cooled to 0° C. and charged with lithium aluminium hydride (172 mg, 4.53 mmol) in one portion and then stirred for 1.5 h. Following this time, the reaction was treated with Na$_2$SO$_4$·10H$_2$O (650 mg, 2.02 mmol) and the resulting slurry was stirred for 0.5 h. The slurry was then filtered, washing with CH$_2$Cl$_2$ and the filtrate concentrated in vacuo. The residue was purified directly by column chromatography (eluent: EtOAc/hexanes gradient) to afford tert-butyl ((1S,2S)-2-(hydroxymethyl)-4-methylcyclohexyl)carbamate (I-45). ES/MS m/z: 244.1 (M+H$^+$).

Preparation of Intermediate I-46

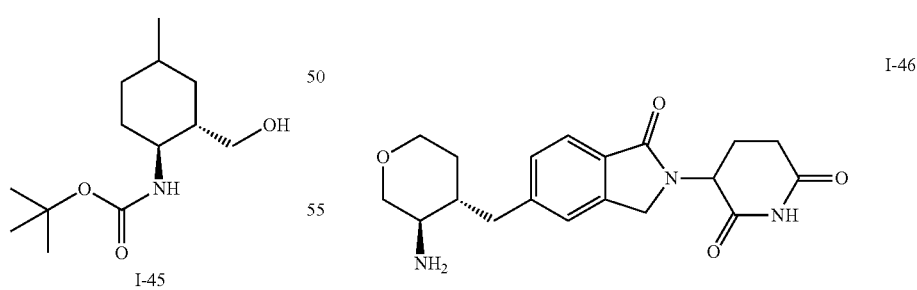

I-46

Step 3: Preparation of tert-butyl ((1S,2S)-2-(hydroxymethyl)-4-methylcyclohexyl)carbamate 3-(5-(((3R,4S)-3-aminotetrahydro-2H-pyran-4-yl) methyl)-1-oxoisoindolin-2-yl)piperidine-2,6-dione (I-46)

3-(5-(((3R,4S)-3-aminotetrahydro-2H-pyran-4-yl) methyl)-1-oxoisoindolin-2-yl)piperidine-2,6-dione was synthesized in the same manner as I-3 substituting I-1 with ((3R,4S)-3-aminotetrahydro-2H-pyran-4-yl)methanol and 3-(5-bromo-6-fluoro-1-oxoisoindolin-2-yl)-1-((2-(trimethylsilyl)ethoxy)methyl)piperidine-2,6-dione with 3-(5-bromo-1-oxoisoindolin-2-yl)-1-((2-(trimethylsilyl)ethoxy)methyl)piperidine-2,6-dione. ES/MS m/z: 358.1 (M+H$^+$).

Preparation of Intermediate I-47

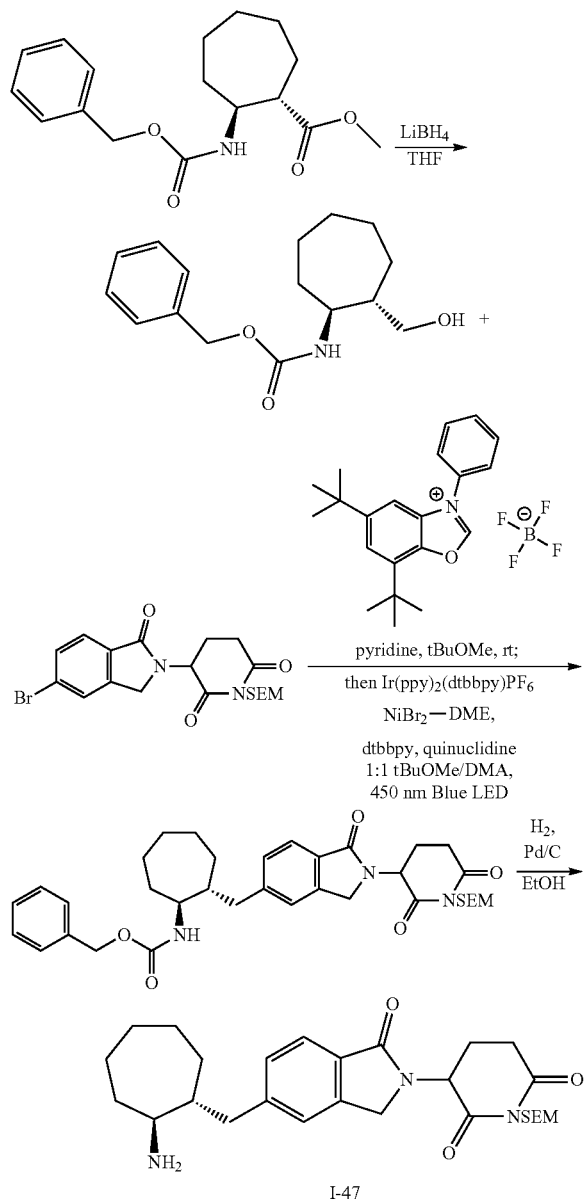

Step 1: Preparation of benzyl ((1S,2S)-2-(hydroxymethyl)cycloheptyl)carbamate Methyl (1S, 2S)-2-(((benzyloxy)carbonyl)amino)cycloheptane-1-carboxylate (200 mg, 0.655 mmol) dissolved in tetrahydrofuran (7 mL) was cooled to 0° C. and then treated with lithium borohydride solution (0.36 mL, 0.720 mmol). The reaction mixture was stirred at room temperature overnight, quenched with the addition of water, and extracted with dichloromethane. The organic layer was concentrated to give crude benzyl ((1S,2S)-2-(hydroxymethyl)cycloheptyl) carbamate. ES/MS: 278.0 (M+H$^+$).

Step 2: Preparation of benzyl ((1S,2R)-2-((2-(2,6-dioxo-1-((2-(trimethylsilyl)ethoxy)methyl)piperidin-3-yl)-1-oxoisoindolin-5-yl)methyl)cycloheptyl) carbamate The title compound was prepared in the same manner as I-13, step 1 substituting tert-butyl (S)-5-amino-4-(5-(((1R, 2S)-2-((tert-butoxycarbonyl)amino)cyclohexyl)methyl)-1-oxoisoindolin-2-yl)-5-oxopentanoate with benzyl ((1S,2S)-2-(hydroxymethyl)cycloheptyl)carbamate and 3-(5-bromo-1-oxoisoindolin-2-yl)-1-((2-(trimethylsilyl)ethoxy)methyl) piperidine-2,6-dione. ES/MS: 655.9 (M+Na$^+$).

Step 3: Preparation of 3-(5-(((1R,2S)-2-aminocycloheptyl)methyl)-1-oxoisoindolin-2-yl)-1-((2-(trimethylsilyl)ethoxy)methyl)piperidine-2,6-dione Benzyl ((1S,2R)-2-((2-(2,6-dioxo-1-((2-(trimethylsilyl)ethoxy)methyl)piperidin-3-yl)-1-oxoisoindolin-5-yl) methyl) cycloheptyl)carbamate (110 mg, 0.174 mmol) dissolved in ethanol (2 mL) was treated with 10% Pd/C (20 mg, 0.018 mmol). The reaction flask was evacuated and backfilled with hydrogen, and then stirred under an atmosphere of hydrogen at 45° C. for 1 h. After cooling to room temperature, the reaction mixture was filtered, washing with ethanol. The filtrate was concentrated to give I-47 which was used without further purification. ES/MS: 500.0 (M+H$^+$).

Preparation of Intermediate I-48

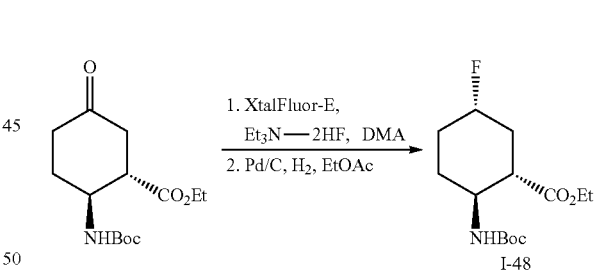

Preparation of ethyl (1S,2S,5S)-2-((tert-butoxycarbonyl)amino)-5-fluorocyclohexane-1-carboxylate A 100 mL PFA flask equipped with a teflon stir bar was charged with Xtalfluor-E (4.82 g, 21.0 mmol), and the headspace was purged with N$_2$. DMA (24 mL) was added. Triethylamine trishydrofluoride (2.26 mL, 14.0 mmol) was added dropwise and with stirring, followed by triethylamine (977 uL, 7.01 mmol). Ethyl (1S,2S)-2-((tert-butoxycarbonyl)amino)-5-oxocyclohexane-1-carboxylate (2.00 g, 7.01 mmol) was added as a solid in a single portion, then the reaction mixture was allowed to stir at r.t. overnight. The mixture was then carefully quenched with saturated aqueous NaHCO$_3$, diluted with EtOAc, then transferred to a separatory funnel. The layers were separated, and the aqueous layer was extracted with EtOAc (2×). The combined organics were dried over Na$_2$SO$_4$, filtered, and concentrated under vacuum. The resulting crude residue was further purified by silica gel chromatography (eluent: hexanes/EtOAc). The product was then dissolved in EtOAc (40 mL), transferred to a Parr shaker bottle, and treated with Pd/C (10% Pd loading, 433 mg, 0.407 mmol). The bottle was then connected to a Parr shaker apparatus and shaken under H$_2$ atmosphere (50 psi) for 2 h. An additional quantity of Pd/C (10% Pd loading, 433 mg, 0.407 mmol) was added, and the mixture was shaken under H$_2$ atmosphere (50 psi) for an additional 90 min. The reaction mixture was then sparged with N$_2$ for 5 min and filtered through celite. The filtrate was concentrated under reduced pressure to afford the I-48. ES/MS m/z: 312.2 (M+Na$^+$).

Preparation of Intermediate I-49

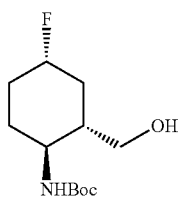

tert-butyl ((1S,2S,4S)-4-fluoro-2-(hydroxymethyl)cyclohexyl)carbamate (I-49)

tert-butyl ((1S,2S,4S)-4-fluoro-2-(hydroxymethyl)cyclohexyl)carbamate was synthesized in the same manner as I-23 substituting I-21 with I-48. ES/MS m/z: 270.2 (M+Na$^+$).

Preparation of Intermediate I-50

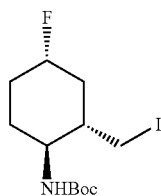

tert-butyl ((1S,2S,4S)-4-fluoro-2-(iodomethyl)cyclohexyl)carbamate (I-50)

tert-butyl ((1S,2S,4S)-4-fluoro-2-(iodomethyl)cyclohexyl)carbamate was synthesized in the same manner as I-2 substituting I-1 with I-49. ES/MS m/z: 380.1 (M+Na$^+$).

Preparation of Intermediate I-51

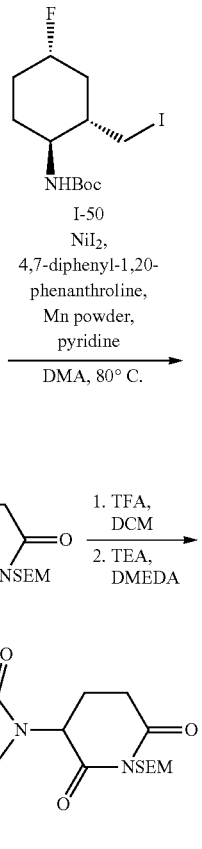

Step 1: Preparation of tert-butyl ((1S,2S,4S)-2-((2-(2,6-dioxo-1-((2-(trimethylsilyl)ethoxy)methyl)piperidin-3-yl)-1-oxoisoindolin-5-yl)methyl)-4-fluorocyclohexyl)carbamate In a 2-dram vial equipped with a magnetic stir bar and under a nitrogen atmosphere, 3-(5-bromo-1-oxo-isoindolin-2-yl)-1-(2-trimethylsilylethoxymethyl)piperidine-2,6-dione (120 mg, 0.265 mmol), I-50 (189 mg, 0.529 mmol), manganese powder (29.1 mg, 0.529 mmol), nickel(II) iodide (16.5 mg, 52.9 µmol), 4,7-Diphenyl-1,10-phenanthroline (13.2 mg, 39.7 µmol), and sodium iodide (9.9 mg, 66 µmol) were suspended in DMA (3.3 mL, previously sparged with N$_2$ for 5 min) and treated with pyridine (4.3 µL, 53 µmol). The pierced septum cap was quickly replaced with a fresh one, and the vial was sealed and the mixture stirred at 80° C. overnight. The reaction mixture was cooled to rt and combined with that of a previous reaction, carried out in an identical manner. The combined mixture was filtered through celite, and the filtrate diluted with EtOAc, washed with water (3×), dried over Na$_2$SO$_4$, filtered, and concentrated under vacuum. The resulting crude residue was purified by normal phase column chromatography (0→100% EtOAc in hexanes) to afford the product. ES/MS m/z: 626.4 (M+Na$^+$).

Step 2: Preparation of 3-(5-(((1S,2S,5S)-2-amino-5-fluorocyclohexyl)methyl)-1-oxoisoindolin-2-yl)piperidine-2,6-dione (I-51)

tert-butyl ((1S,2S,4S)-2-((2-(2,6-dioxo-1-((2-(trimethylsilyl)ethoxy)methyl)piperidin-3-yl)-1-oxoisoindolin-5-yl)methyl)-4-fluorocyclohexyl)carbamate (163 mg, 0.256 mmol) was dissolved in DCM (2.0 mL), treated with TFA (393 uL, 5.13 mmol), and stirred at r.t. After 1 h, the reaction mixture was concentrated under vacuum. The resulting residue was take up in DCM (2.0 mL), cooled to 0° C. with stirring, and treated with triethylamine (286 uL, 2.05 mmol) followed by N,N'-dimethylethylenediamine (33 μL, 0.308 mmol) and then the reaction was warmed to r.t. and stirred overnight. The mixture was then concentrated under vacuum and the residue purified directly by RP-HPLC (eluent: MeCN/water gradient with 0.1% TFA) to yield the product. ES/MS m/z: 374.3 (M+H$^+$).

Preparation of Intermediate I-52

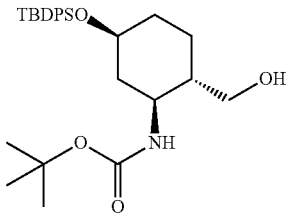

I-52 tert-Butyl ((1S,2S,5S-rel)-5-((tert-butyldiphenylsilyl)oxy)-2-(hydroxymethyl)cyclohexyl)carbamate (I-52)

tert-Butyl ((1S,2S,5S-rel)-5-((tert-butyldiphenylsilyl)oxy)-2-(hydroxymethyl)cyclohexyl)carbamate was prepared according to the procedure described for I-16 (steps 2 and 3) substituting methyl (1S,2R,3S-rel)-2-((tert-butoxycarbonyl)amino)-3-((tert-butyldiphenylsilyl)oxy)cyclohexane-1-carboxylate with ethyl (1S,2S,4S-rel)-2-((tert-butoxycarbonyl)amino)-4-hydroxycyclohexane-1-carboxylate. ES/MS m/z: 506.0 (M+Na$^+$).

Preparation of Intermediate I-53

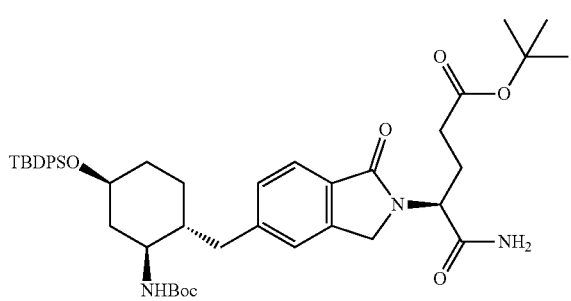

I-53 tert-Butyl (S)-5-amino-4-(5-(((1R,2S,4S)-rel-2-((tert-butoxycarbonyl)amino)-4-((tert-butyldiphenylsilyl)oxy)cyclohexyl)methyl)-1-oxoisoindolin-2-yl)-5-oxopentanoate (I-53)

tert-Butyl (S)-5-amino-4-(5-(((1R,2S,4S)-rel-2-((tert-butoxycarbonyl)amino)-4-((tert-butyldiphenylsilyl)oxy)cyclohexyl)methyl)-1-oxoisoindolin-2-yl)-5-oxopentanoate was prepared according to the procedure described for I-17 substituting I-16 with I-52.

Preparation of Intermediate I-54

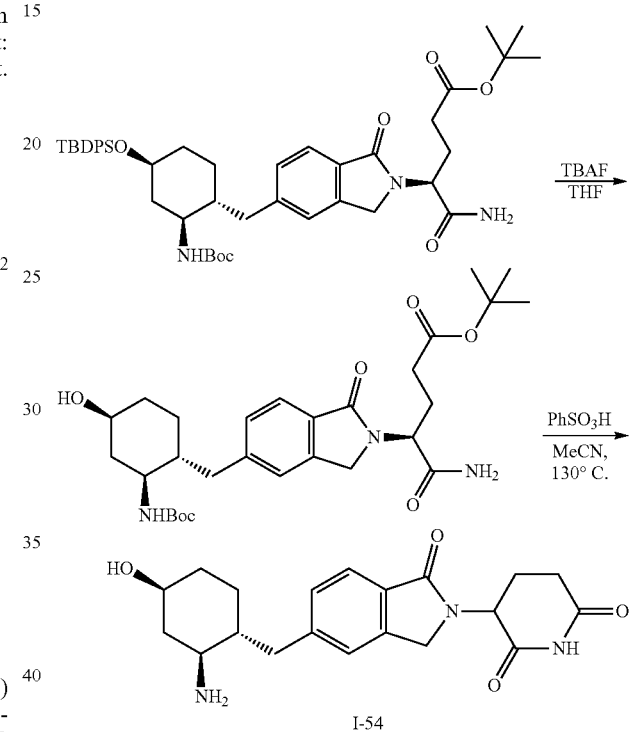

I-54

Step 1: Preparation of tert-butyl (S)-5-amino-4-(5-(((1R,2S,4S)-2-((tert-butoxycarbonyl)amino)-4-hydroxycyclohexyl)methyl)-1-oxoisoindolin-2-yl)-5-oxopentanoate I-53 (181 mg, 0.230 mmol) was taken up in THF (2.3 mL) and TBAF (1.0M in THF, 0.46 mL, 0.46 mmol) was added. The reaction was stirred at r.t. for 3 days. Following this time, the reaction mixture was concentrated in vacuo and purified directly by normal phase column chromatography (eluent: hexanes/EtOAc) to yield the title product. ES/MS m/z: 546.1 (M+H$^+$).

Step 2: Preparation of 3-(5-(((1R,2S,4S)-2-amino-4-hydroxycyclohexyl)methyl)-1-oxoisoindolin-2-yl)piperidine-2,6-dione (I-54)

tert-butyl (S)-5-amino-4-(5-(((1R,2S,4S)-2-((tert-butoxycarbonyl)amino)-4-hydroxycyclohexyl)methyl)-1-oxoisoindolin-2-yl)-5-oxopentanoate (82.1 mg, 0.150 mmol) was taken up in MeCN (1.1 mL) and benzenesulfonic acid (71.4 mg, 0.451 mmol) was added. The reaction was heated to 130° C. for 30 minutes under microwave irradiation. Following this time, the reaction was cooled to r.t. and concentrated in vacuo to afford the crude product as the benzenesulfonic acid salt which was used in subsequent reactions without further purification. ES/MS m/z: 372.0 (M+H⁺).

Preparation of Intermediate I-55

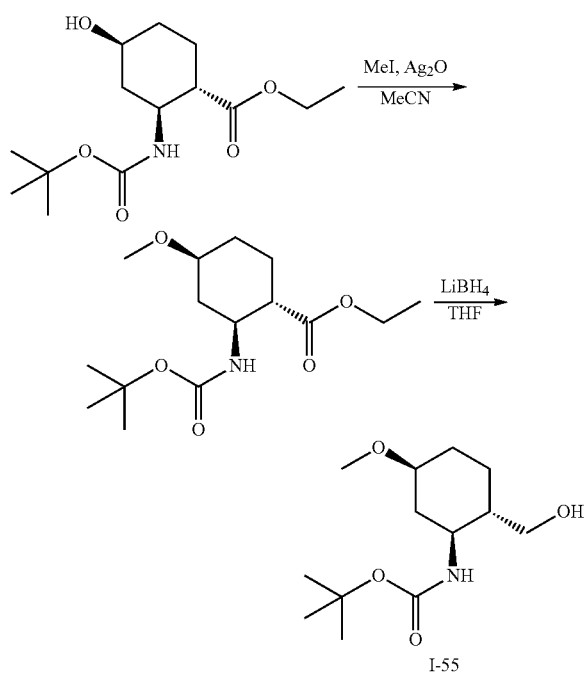

I-55

Step 1: Ethyl (1S,2S,4S-rel)-2-((tert-butoxycarbonyl)amino)-4-methoxycyclohexane-1-carboxylate Ethyl (1S,2S,4S-rel)-2-((tert-butoxycarbonyl)amino)-4-hydroxycyclohexane-1-carboxylate (500 mg, 1.74 mmol) was taken up in MeCN (9.0 mL) and silver oxide (647 mg, 5.22 mmol) was added followed by iodomethane (0.325 mL, 5.22 mmol). The reaction was stirred at r.t. for 5 days. Following this time, the reaction was filtered to remove solids and the filtered washed with additional MeCN. The filtrate was concentrated in vacuo and the residue purified by normal phase column chromatography (eluent: hexanes/EtOAc) to yield the title product. ES/MS m/z: 282.0 (M+Na⁺).

Step 2: tert-Butyl ((1S,2S,5S-rel)-2-(hydroxymethyl)-5-methoxycyclohexyl)carbamate (I-55)

Ethyl (1S,2S,4S-rel)-2-((tert-butoxycarbonyl)amino)-4-methoxycyclohexane-1-carboxylate (495 mg, 1.64 mmol) was taken up in THF (16.0 mL) and the solution cooled to 0° C. Lithium borohydride (2.0 M in THF, 3.29 mL, 6.57 mmol) was then added slowly to the mixture over 5 minutes. Following this time, the reaction was warmed to r.t. and stirred for 2 days. The reaction was then diluted with EtOAc and water and transferred to a separatory funnel. The organic phase was collected and washed with water and brine then dried over MgSO₄ and conc. in vacuo. The residue was purified by normal phase column chromatography (eluent: hexanes/EtOAc) to yield the title product. ES/MS m/z: 324.0 (M+Na⁺).

Preparation of Intermediate I-56

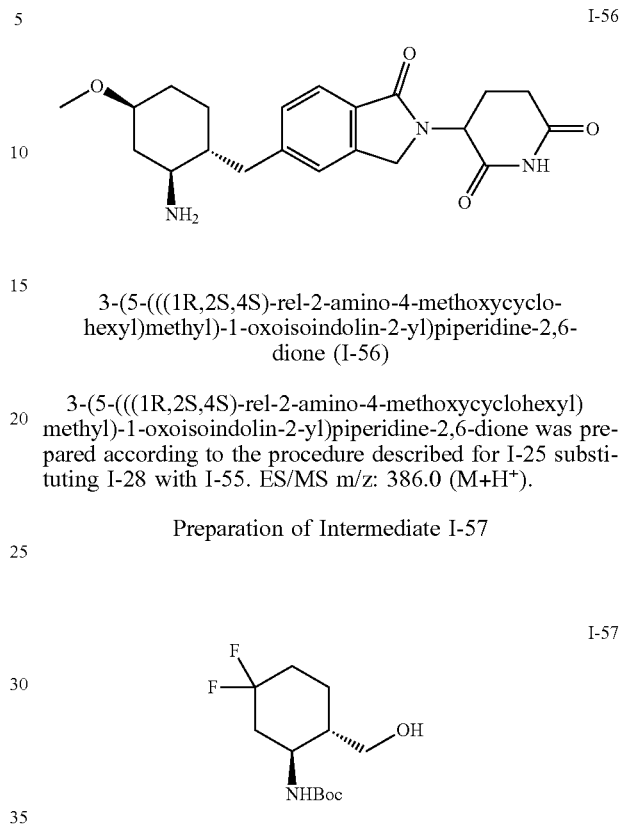

3-(5-(((1R,2S,4S)-rel-2-amino-4-methoxycyclohexyl)methyl)-1-oxoisoindolin-2-yl)piperidine-2,6-dione (I-56)

3-(5-(((1R,2S,4S)-rel-2-amino-4-methoxycyclohexyl)methyl)-1-oxoisoindolin-2-yl)piperidine-2,6-dione was prepared according to the procedure described for I-25 substituting I-28 with I-55. ES/MS m/z: 386.0 (M+H⁺).

Preparation of Intermediate I-57

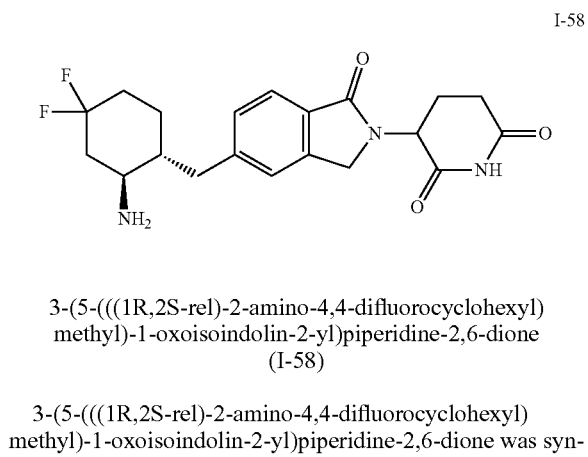

tert-butyl ((1S,2S-rel)-5,5-difluoro-2-(hydroxymethyl)cyclohexyl)carbamate (I-57)

tert-butyl ((1S,2S-rel)-5,5-difluoro-2-(hydroxymethyl)cyclohexyl)carbamate was synthesized in the same manner as I-23 substituting I-21 with ethyl (1S,2S-rel)-2-((tert-butoxycarbonyl)amino)-4,4-difluorocyclohexane-1-carboxylate (Kiss et al. *Beilstein J. Org. Chem.* 2013, 9, 1164-1169.). ES/MS m/z: 288.0 (M+Na⁺).

Preparation of Intermediate I-58

I-58

3-(5-(((1R,2S-rel)-2-amino-4,4-difluorocyclohexyl)methyl)-1-oxoisoindolin-2-yl)piperidine-2,6-dione (I-58)

3-(5-(((1R,2S-rel)-2-amino-4,4-difluorocyclohexyl)methyl)-1-oxoisoindolin-2-yl)piperidine-2,6-dione was synthesized in the same manner as I-25 substituting I-23 with I-57 and Ir(ppy)₂(dtbbpy)PF₆ with Ir([dF(CF₃)ppy]₂(dtbpy))PF₆. ES/MS m/z: 392.1 (M+H⁺).

Preparation of Intermediate I-59

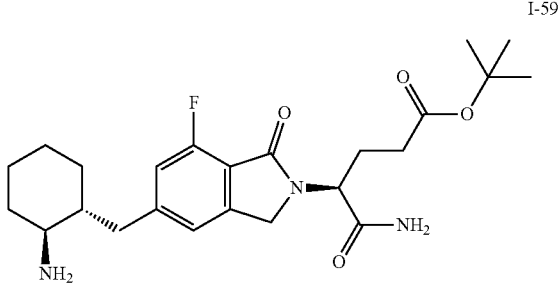 [SMILES: CC(C)(C)OC(=O)CC[C@@H](C(N)=O)N1Cc2cc(C[C@H]3CCCC[C@@H]3N)cc(F)c2C1=O]

3-(5-(((1R,2S)-2-aminocyclohexyl)methyl)-7-fluoro-1-oxoisoindolin-2-yl)piperidine-2,6-dione (I-59)

3-(5-(((1R,2S)-2-aminocyclohexyl)methyl)-7-fluoro-1-oxoisoindolin-2-yl)piperidine-2,6-dione was synthesized in the same manner as I-25 substituting I-23 with tert-butyl (S)-5-amino-4-(5-bromo-7-fluoro-1-oxoisoindolin-2-yl)-5-oxopentanoate [prepared according to the procedure described in WO2021/101919 for tert-butyl (S)-5-amino-4-(5-bromo-1-oxoisoindolin-2-yl)-5-oxopentanoate] and I-23 with I-2. ES/MS m/z: 448.1 (M+H⁺).

Preparation of Intermediate I-60

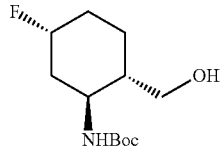

tert-butyl ((1S,2S,5R-rel)-5-fluoro-2-(hydroxymethyl)cyclohexyl)carbamate (I-60)

tert-butyl ((1S,2S,5R-rel)-5-fluoro-2-(hydroxymethyl)cyclohexyl)carbamate was synthesized in the same manner as I-23 substituting I-21 with ethyl (1S,2S,4R-rel)-2-((tert-butoxycarbonyl)amino)-4-fluorocyclohexane-1-carboxylate (Kiss et al. *Beilstein J. Org. Chem.* 2013, 9, 1164-1169.). ES/MS m/z: 270.0 (M+Na⁺).

Preparation of Intermediate I-61

3-(5-(((1R,2S,4R-rel)-2-amino-4-fluorocyclohexyl)methyl)-1-oxoisoindolin-2-yl)piperidine-2,6-dione (I-61)

3-(5-(((1R,2S,4R-rel)-2-amino-4-fluorocyclohexyl)methyl)-1-oxoisoindolin-2-yl)piperidine-2,6-dione was synthesized in the same manner as I-25 substituting I-23 with I-59. ES/MS m/z: 374.1 (M+H⁺).

Preparation of Intermediate I-62

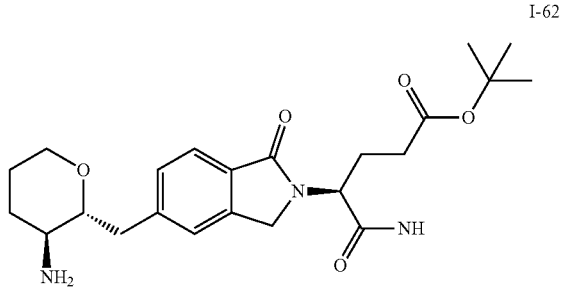 [SMILES: CC(C)(C)OC(=O)CC[C@@H](C(N)=O)N1Cc2cc(C[C@H]3OCCC[C@@H]3N)ccc2C1=O]

tert-butyl (S)-5-amino-4-(5-(((2R,3S)-3-aminotetrahydro-2H-pyran-2-yl)methyl)-1-oxoisoindolin-2-yl)-5-oxopentanoate (I-62)

tert-butyl (S)-5-amino-4-(5-(((2R,3S)-3-aminotetrahydro-2H-pyran-2-yl)methyl)-1-oxoisoindolin-2-yl)-5-oxopentanoate was synthesized in the same manner as I-41 substituting tert-butyl (S)-5-amino-4-(5-bromo-4-fluoro-1-oxoisoindolin-2-yl)-5-oxopentanoate with tert-butyl (S)-5-amino-4-(5-bromo-1-oxoisoindolin-2-yl)-5-oxopentanoate and Ir([dF(CF₃)ppy]₂(dtbpy))PF₆ with Ir(ppy)₂(dtbbpy)PF₆. ES/MS m/z: 432.3 (M+H⁺).

Preparation of Intermediate I-63

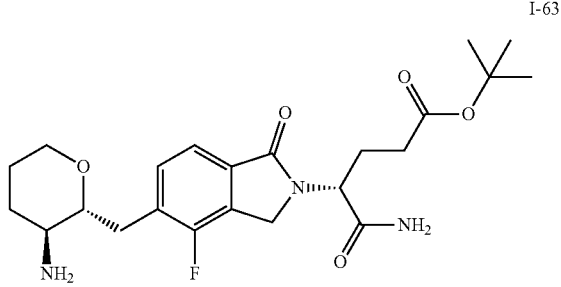 [SMILES: CC(C)(C)OC(=O)CC[C@H](C(N)=O)N1Cc2c(ccc(C[C@H]3OCCC[C@@H]3N)c2F)C1=O]

tert-Butyl (R)-5-amino-4-(5-(((2R,3S)-3-aminotetrahydro-2H-pyran-2-yl)methyl)-4-fluoro-1-oxoisoindolin-2-yl)-5-oxopentanoate (I-63). tert-Butyl (R)-5-amino-4-(5-(((2R,3S)-3-aminotetrahydro-2H-pyran-2-yl)methyl)-4-fluoro-1-oxoisoindolin-2-yl)-5-oxopentanoate was synthesized in the same manner as I-41 substituting tert-butyl (S)-5-amino-4-(5-bromo-4-fluoro-1-oxoisoindolin-2-yl)-5-oxopentanoate with tert-butyl (R)-5-amino-4-(5-bromo-4-fluoro-1-oxoisoindolin-2-yl)-5-oxopentanoate. ES/MS m/z: 450.1 (M+H⁺).

Preparation of Intermediate I-64

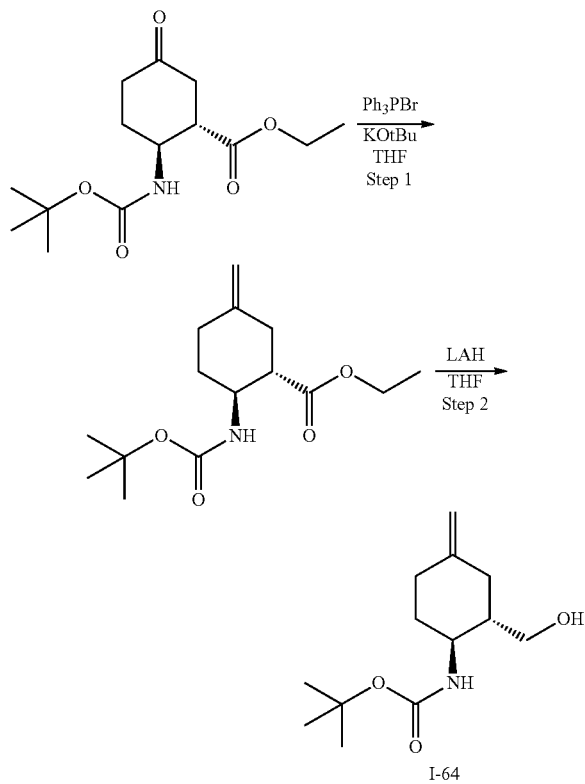

Step 1: Preparation of ethyl (1S,2S)-2-((tert-butoxycarbonyl)amino)-5-methylenecyclohexane-1-carboxylate To a mixture of potassium tert-butoxide (0.78 g, 7.01 mmol) and THF (5 mL), methyltriphenylphosphonium bromide (2.5 g, 7.01 mmol) was added and the reaction mixture stirred at room temperature for 15 minutes. Ethyl (1S,2S)-2-((tert-butoxycarbonyl)amino)-5-oxocyclohexane-1-carboxylate (1.0 g, 3.5 mmol) was then added as a solution in THF (5 mL) and the mixture was stirred at r.t. for two hours. The reaction was quenched by addition of water (0.13 mL) and the mixture was filtered through celite, washing with methylene chloride. The filtrate was concentrated and purified by silica gel chromatography (eluent: hexanes/EtOAc then EtOAc/MeOH) Desired fractions were combined and concentrated to give the title compound as a white solid. ES/MS m/z: 306.3 (M+Na$^+$). $^1$H NMR (400 MHz, DMSO-d$_6$) δ 6.82 (d, J=9.1 Hz, 1H), 4.69 (d, J=1.8 Hz, 2H), 4.13-3.93 (m, 2H), 3.64 (tq, J=10.6, 4.1 Hz, 1H), 2.43-2.27 (m, 2H), 2.20 (q, J=12.9, 12.0 Hz, 2H), 2.13-1.99 (m, 1H), 1.79 (dt, J=12.8, 4.1 Hz, 1H), 1.35 (s, 9H), 1.31-1.21 (m, 1H), 1.16 (t, J=7.1 Hz, 3H).

Step 2: Preparation of tert-butyl ((1S,2S)-2-(hydroxymethyl)-4-methylenecyclohexyl)carbamate (I-64)

A reaction vial was charged with ethyl (1S,2S)-2-((tert-butoxycarbonyl)amino)-5-methylenecyclohexane-1-carboxylate (0.41 g, 1.3 mmol) and THF (2 mL). The mixture was cooled to 0° C. and lithium aluminum hydride (2.0 M in THF, 1.32 mL) was added in a slow stream. After 40 minutes of stirring, the reaction was quenched using the Fieser method while still at 0° C. It was first diluted with ether (8 mL) and water (0.1 mL) was added slowly. This was followed by addition of 15% aqueous sodium hydroxide (0.1 mL) and water (0.3 mL) again. The reaction mix was allowed to warm to r.t. and stirred for 15 minutes. Anhydrous magnesium sulfate was added and stirred another 15 minutes. The mixture was then filtered to remove salts. The filtrate was concentrated and purified by silica gel chromatography (ELSD detector, eluent: hexanes/EtOAc) Desired fractions were combined and concentrated to give the title compound as a white solid. ES/MS m/z: 242.1 (M+H$^+$).

Preparation of Intermediate I-65

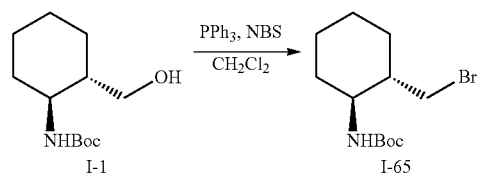

tert-butyl ((1S,2S)-2-(bromomethyl)cyclohexyl)carbamate (I-65)

I-1 (1.0 g, 4.36 mmol) and triphenylphosphine (1.72 g, 6.54 mmol) were combined in CH$_2$Cl$_2$ (20 mL) and the solution cooled to −15° C. in a NaCl/brine/ice bath. N-bromosuccinimide (1.01 g, 5.67 mmol) was then added portionwise while maintaining the temperature below 5° C. The reaction was allowed to warm to r.t. and stirred overnight. The mixture was then concentrated in vacuo and purified directly by silica gel chromatography (eluent: hexanes/EtOAc) to afford the title product. $^1$H NMR (400 MHz, Chloroform-d) δ 4.36 (s, 1H), 3.68-3.60 (m, 1H), 3.29 (t, J=10.7 Hz, 2H), 2.15 (d, J=13.0 Hz, 1H), 2.04-1.94 (m, 1H), 1.80-1.71 (m, 2H), 1.47 (s, 9H), 1.38-1.06 (m, 3H).

Preparation of Intermediate I-66

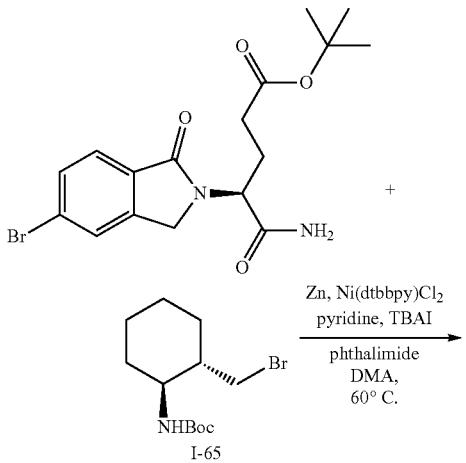

313

-continued

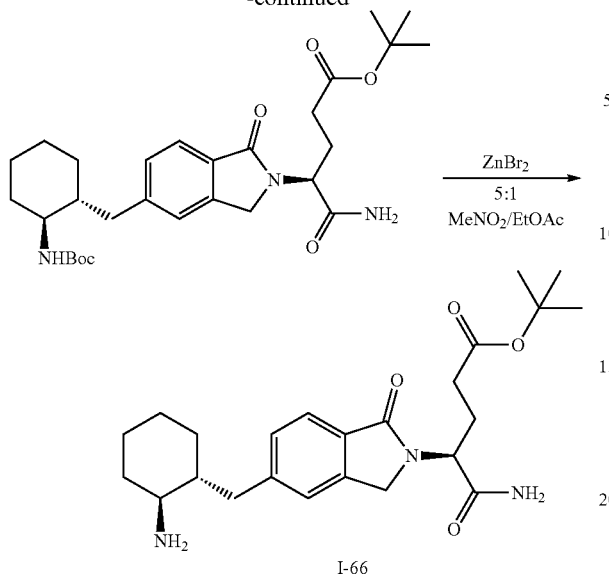

Step 1: tert-butyl (S)-5-amino-4-(5-(((1R,2S)-2-((tert-butoxycarbonyl)amino)cyclohexyl)methyl)-1-oxoisoindolin-2-yl)-5-oxopentanoate tert-butyl (4S)-5-amino-4-(5-bromo-1-oxo-isoindolin-2-yl)-5-oxo-pentanoate (2.0 g, 5.03 mmol), I-65 (1.91 g, 6.54 mmol), [4,4'-Bis(1,1-dimethylethyl)-2,2'-bipyridine] nickel (II) dichloride (200 mg, 0.503 mmol), zinc (1.32 g, 20.1 mmol), TBAI (1.85 g, 5.03 mmol), and phthalimide (0.370 g, 2.52 mmol) were taken up in DMA (50.0 mL) and the reaction mixture sparged with argon while sonicating for 5 min. Pyridine (41 µL, 0.503 mmol) was then added and sparging was continued for 5 min before the reaction was set up under argon atmosphere and heated to 60° C. overnight. The reaction was then cooled to r.t. and filtered through celite (washed with 5 mL of DMA) to remove the inorganics salts. The solution was then transferred to an additional funnel and added dropwise to water (200 mL) while stirring vigorously. The resulting solid was collected by filtration and then taken up in $CH_2Cl_2$ and purified directly by silica gel chromatography (eluent: hexanes/EtOAc) to afford tert-butyl (S)-5-amino-4-(5-(((1R,2S)-2-((tert-butoxycarbonyl)amino)cyclohexyl)methyl)-1-oxoisoindolin-2-yl)-5-oxopentanoate. ES/MS m/z: 530.0 (M+H$^+$).

Step 2: tert-butyl (S)-5-amino-4-(5-(((1R,2S)-2-aminocyclohexyl)methyl)-1-oxoisoindolin-2-yl)-5-oxopentanoate (I-66)

tert-butyl (S)-5-amino-4-(5-(((1R,2S)-2-((tert-butoxycarbonyl)amino)cyclohexyl)methyl)-1-oxoisoindolin-2-yl)-5-oxopentanoate (1.5 g, 2.44 mmol) was taken up in 5:1 nitromethane/EtOAc (30 mL) and the solution cooled to 0° C. Zinc (II) bromide (2.74 g, 12.2 mmol) was then added portionwise. Following complete addition, the reaction was allowed to warm to r.t. and stirred for 24 hours. The mixture was diluted with 4:1 $CH_2Cl_2$/iPrOH (100 mL) and poured into a stirring saturated aqueous NaHCO$_3$ solution (100 mL). The mixture was stirred vigorously for 15 min then filtered to remove solids. The organic phase was collected and the aqueous phase was extracted with addition 4:1 4:1 $CH_2Cl_2$/iPrOH (2×150 mL). The combined organics were dried over

314

$MgSO_4$ and concentrated in vacuo to afford the product (I-66) which was used without additional purification. ES/MS m/z: 430.1 (M+H$^+$).

Example Procedures

Procedure 1, Example 1

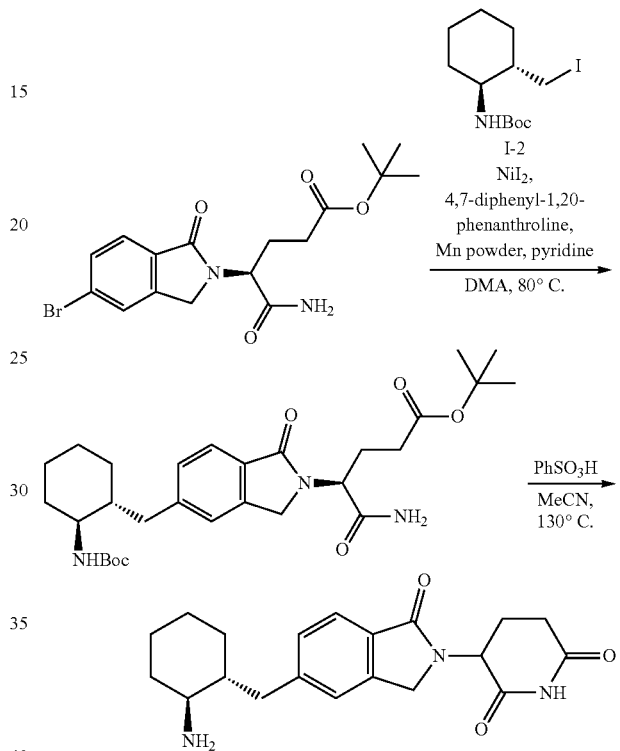

Example 1

Step 1: Preparation of tert-butyl 5-amino-4-(5-(((1R,2S)-2-((tert-butoxycarbonyl)amino)cyclohexyl)methyl)-1-oxoisoindolin-2-yl)-5-oxopentanoate In a 2-dram vial equipped with a magnetic stir bar and under a nitrogen atmosphere, tert-butyl (S)-5-amino-4-(5-bromo-1-oxoisoindolin-2-yl)-5-oxopentanoate ([prepared according to the procedure described in WO2021/101919] 50 mg, 0.126 mmol), I-2 (85.4 mg, 0.252 mmol), manganese powder (13.8 mg, 0.252 mmol), nickel(II) iodide (7.9 mg, 25 umol), and 4,7-Diphenyl-1,10-phenanthroline (6.3 mg, 19 umol) were suspended in DMA (1.6 mL, previously sparged with $N_2$ for 5 min) and treated with pyridine (2 uL, 25 umol). The pierced septum cap was quickly replaced with a fresh one, and the vial was sealed and the mixture stirred at 80° C. for 30 min. The reaction mixture was cooled to r.t. and combined with that of a previous reaction, carried out in an identical manner. The combined mixture was filtered through celite, and the filtrate concentrated under reduced pressure. The resulting crude residue was purified by normal phase column chromatography (0→100% EtOAc in hexanes) to afford the product. ES/MS m/z: 552.4 (M+Na$^+$).

Step 2: Preparation of 3-(5-(((1R,2S)-2-aminocyclohexyl)methyl)-1-oxoisoindolin-2-yl)piperidine-2,6-dione (Example 1)

tert-butyl 5-amino-4-(5-(((1R,2S)-2-((tert-butoxycarbonyl)amino)cyclohexyl)methyl)-1-oxoisoindolin-2-yl)-5-oxopentanoate (96 mg, 0.181 mmol) was taken up in MeCN (1.8 mL) and treated with benzenesulfonic acid (86 mg, 0.544 mmol). The mixture was stirred at 130° C. under microwave irradiation for 30 min, then cooled to rt and concentrated under reduced pressure. The resulting crude residue was purified by normal phase column chromatography (0→30% MeOH w/0.5% Et$_3$N in DCM), and product-containing fractions were combined, concentrated under reduced pressure, and further purified by RP-HPLC (eluent: MeCN/water gradient with 0.1% TFA) to afford the product (Example 1) as the trifluoroacetate salt. ES/MS m/z: 356.3 (M+H$^+$). $^1$H NMR (400 MHz, DMSO-d6) δ 10.99 (s, 1H), 7.92 (s, 3H), 7.69 (d, J=7.8 Hz, 1H), 7.41 (s, 1H), 7.35-7.31 (m, 1H), 5.11 (dd, J=13.3, 5.1 Hz, 1H), 4.45 (dd, J=17.4, 4.5 Hz, 1H), 4.31 (dd, J=17.3, 5.2 Hz, 1H), 3.17 (dd, J=13.3, 3.2 Hz, 1H), 2.97-2.85 (m, 2H), 2.64-2.56 (m, 1H), 2.45-2.28 (m, 2H), 2.04-1.95 (m, 2H), 1.73-1.63 (m, 2H), 1.58-1.43 (m, 2H), 1.36-1.21 (m, 2H), 1.07-0.90 (m, 2H).

Procedure 2, Example 1 while in a second flask, I-1 (4.43 g, 19.3 mmol) and 5,7-di-tert-butyl-3-phenylbenzo[d]oxazol-3-ium tetrafluoroborate (6.97 g, 17.6 mmol) were combined in MTBE (150 mL). This mixture was stirred for 5 minutes, then a solution of pyridine in MTBE (22.1 mL, 0.8 M) was added slowly over 5 minutes. The suspension was sonicated to loosen solids, then stirred at r.t. for 30 minutes. DMA (150 mL) was added to the first flask and the activated alcohol suspension was then transferred to a syringe fitted with a syringe filter and needle. The suspension was filtered into the solution of aryl bromide and the mixture sparged with argon for 5 min. The reaction was then stirred under irradiation by blue light irradiation (Kessil Lamp/450 nm Blue LED combined with a small fan to increase air circulation). The reaction mixture was diluted with ~1:1 0.05 M KH$_2$PO$_4$/Na$_2$HPO$_4$ buffer/water and extracted 3x with EtOAc. The combined organics were washed with water then brine, dried over Na$_2$SO$_4$, filtered, and concentrated. The material was purified by SiO$_2$ column chromatography (eluent: 0-100% EtOAc in dichloromethane) to afford the title product. ES/MS m/z: 608.4 (M+Na$^+$).

Step 2: Preparation of 3-(5-(((1R,2S)-2-aminocyclohexyl)methyl)-1-oxoisoindolin-2-yl)piperidine-2,6-dione (Example 1)

tert-butyl ((1S,2R)-2-((2-(2,6-dioxo-1-((2-(trimethylsilyl)ethoxy) methyl) piperidin-3-yl)-1-oxoisoindolin-5-yl)

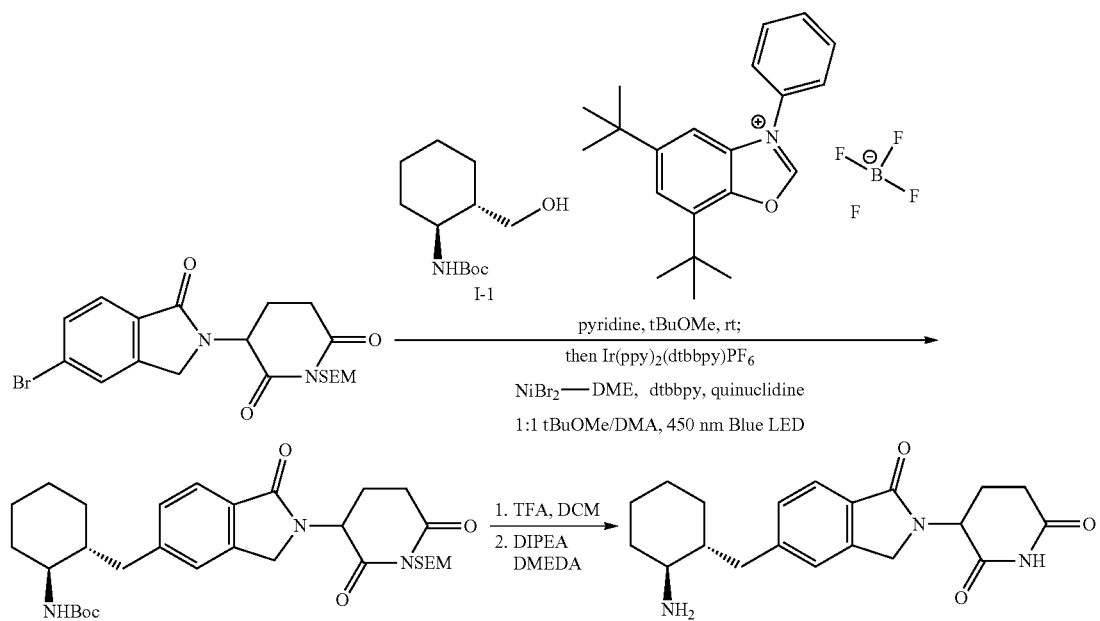

Step 1: Preparation of tert-butyl ((1S,2R)-2-((2-(2,6-dioxo-1-((2-(trimethylsilyl)ethoxy)methyl)piperidin-3-yl)-1-oxoisoindolin-5-yl)methyl) cyclohexyl) carbamate A flask was charged with 3-(5-bromo-1-oxo-isoindolin-2-yl)-1-(2-trimethylsilylethoxymethyl)piperidine-2,6-dione ([prepared according to the procedure described in 2020/012334] 5.0 g, 11 mmol), [Ir(dtbbpy)(ppy)$_2$]PF$_6$ (151 mg, 0.165 mmol), NiBr$_2$-DME (170 mg, 0.551 mmol), 4,4'-Di-tert-butyl-2,2'-dipyridyl (178 mg, 0.662 mmol), and quinuclidine (2.15 g, 19.3 mmol). The headspace was purged methyl)cyclohexyl) carbamate (8.20 g, 14.0 mmol) was taken up in dichloromethane (60 mL) and trifluoroacetic acid (24.6 mL, 322 mmol) was added. The reaction was stirred at r.t. for 16 hours then the reaction mixture was concentrated to an oil under reduced pressure. The residue was re-dissolved in dichloromethane (60 mL) and the mixture cooled to 0° C. DIPEA (20.1 mL, 112 mmol) was added followed by N,N'-dimethylethylenediamine (1.23 g, 0.0140 mol) and then the reaction was warmed to r.t. and stirred for 16 hours then concentrated to an oil. The residue was taken up in CH$_2$Cl$_2$ and washed with saturated sodium bicarbonate solution. The aqueous phase was back extracted with CH₂Cl₂:IPA (4:1) twice. The combined organics were dried over Na₂SO₄ and concentrated to an oil under reduced pressure. The material was taken up in a minimal volume of CH₂Cl₂ and toluene (100 mL) and THF (200 mL) were added. The resulting solution was concentrated to almost dryness and the resulting solid was collected and washed with ether to afford Example 1 which was used in subsequent reactions without further purification. ES/MS m/z: 356.2 (M+H⁺).

Procedure 3, Example 2

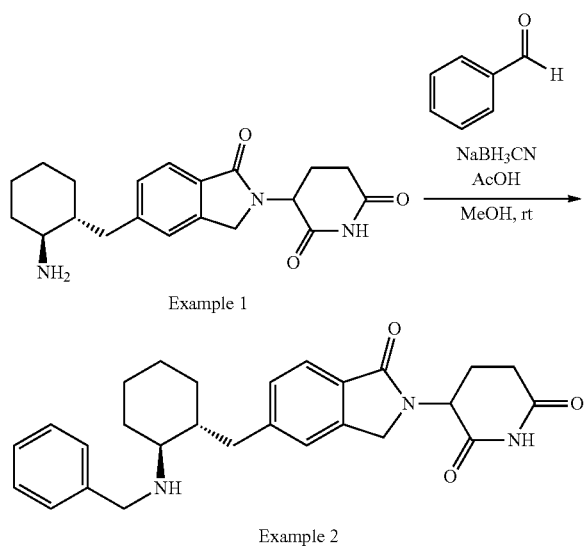

Example 1

Example 2

3-(5-(((1R,2S)-2-(benzylamino)cyclohexyl)methyl)-1-oxoisoindolin-2-yl)piperidine-2,6-dione (Example 2) Example 1

(24.0 mg, 51.1 μmol) was taken up in MeOH (0.5 mL) and treated with benzaldehyde (7.8 μL, 77 μmol) followed by acetic acid (2.9 μL, 51 μmol) and sodium cyanoborohydride (9.6 mg, 0.15 mmol). The reaction mixture was stirred at rt for 45 min, then treated with an additional quantity of benzaldehyde (7.8 μL, 77 μmol). The reaction mixture was stirred for an additional 30 min, then diluted with DMSO, filtered through a syringe filter, and purified by RP-HPLC (eluent: MeCN/water gradient with 0.1% TFA). Product-containing fractions were combined, lyophilized, and subjected to a second purification by RP-HPLC to afford the product (Example 2) as the trifluoroacetate salt. ES/MS: 446.3. ¹H NMR (400 MHz, DMSO-d6) δ 10.99 (s, 1H), 9.01-8.91 (m, 1H), 8.76-8.67 (m, 1H), 7.66 (d, J=7.7 Hz, 1H), 7.56-7.51 (m, 2H), 7.48-7.42 (m, 3H), 7.41 (s, 1H), 7.35-7.31 (m, 1H), 5.11 (dd, J=13.3, 5.1 Hz, 1H), 4.42 (dd, J=17.3, 4.5 Hz, 1H), 4.37-4.19 (m, 3H), 3.20 (dd, J=13.2, 4.1 Hz, 1H), 2.98-2.86 (m, 2H), 2.65-2.56 (m, 1H), 2.47-2.31 (m, 2H), 2.19-2.09 (m, 1H), 2.04-1.90 (m, 2H), 1.78-1.66 (m, 1H), 1.62-1.48 (m, 3H), 1.34-1.22 (m, 1H), 1.16-0.98 (m, 2H).

The following Examples were made using the general route described in Procedure 3 and are shown below in Table 1. To prepare the below Examples, different reagents/starting materials were used than some of those described in Procedure 3 and are noted in the last column of Table 1—"Changes to Procedure 3: Different Reagents/Starting Materials". A person of ordinary skill in the art will readily recognize which reagents/starting materials of Procedure 3

TABLE 1

| Example | Structure | ES/MS m/z | ¹H-NMR | Changes to Procedure 3: Different Reagents/Starting Materials |
|---|---|---|---|---|
| 3 | 3-(5-(((1R,2S)-2-((2-chlorobenzyl)amino)cyclohexyl)methyl)-1-oxoisoindolin-2-yl)piperidine-2,6-dione | 480.3 | ¹H NMR (400 MHz, DMSO-d6) δ 10.99 (s, 1H), 9.05-8.92 (m, 1H), 8.80-8.67 (m, 1H), 7.75-7.70 (m, 1H), 7.68 (d, J = 7.7 Hz, 1H), 7.62-7.57 (m, 1H), 7.52-7.46 (m, 2H), 7.45 (s, 1H), 7.37 (d, J = 7.5 Hz, 1H), 5.11 (dd, J = 13.3, 5.1 Hz, 1H), 4.50-4.40 (m, 2H), 4.40-4.27 (m, 2H), 3.31 (dd, J = 13.3, 3.8 Hz, 1H), 3.14-3.04 (m, 1H), 2.92 (ddd, J = 17.2, 13.6, 5.4 Hz, 1H), 2.65-2.56 (m, 1H), 2.47-2.34 (m, 2H), 2.21-2.11 (m, 1H), 2.06-1.95 (m, 2H), 1.80-1.72 (m, 1H), 1.71-1.59 (m, 1H), 1.59-1.47 (m, 2H), 1.39-1.27 (m, 1H), 1.17-0.99 (m, 2H). | 2-chlorobenzaldehyde |
| 4 | 3-(5-(((1R,2S)-2-(benzylamino)cyclohexyl)methyl)-6-fluoro-1-oxoisoindolin-2-yl)piperidine-2,6-dione | 464.1 | ¹H NMR (400 MHz, Methanol-d4) δ 7.67-7.35 (m, 7H), 5.18 (ddd, J = 13.3, 5.2, 1.9 Hz, 1H), 4.58-4.41 (m, 2H), 4.34 (q, J = 13.2 Hz, 2H), 3.16-3.04 (m, 1H), 3.04-2.86 (m, 2H), 2.81 (ddd, J = 17.6, 4.7, 2.4 Hz, 1H), 2.71-2.45 (m, 2H), 2.35-2.03 (m, 4H), 1.94-1.61 (m, 4H), 1.50 (d, J = 12.5 Hz, 1H), 1.28 (q, J = 10.2, 9.6 Hz, 2H). | I-3 |

TABLE 1-continued

| Example | Structure | ES/MS m/z | ¹H-NMR | Changes to Procedure 3: Different Reagents/Starting Materials |
|---|---|---|---|---|
| 5 | 3-(5-(((1R,2S)-2-(dibenzylamino)cyclohexyl)methyl)-4-fluoro-1-oxoisoindolin-2-yl)piperidine-2,6-dione | 554.2 | ¹H NMR (400 MHz, Methanol-d4) δ 7.85-7.16 (m, 12H), 5.17 (ddd, J = 13.4, 5.2, 2.3 Hz, 1H), 4.69-4.28 (m, 2H), 3.49 (d, J = 13.1 Hz, 1H), 2.92 (ddd, J = 17.7, 13.4, 5.4 Hz, 1H), 2.80 (ddd, J = 17.6, 4.7, 2.4 Hz, 1H), 2.65-2.42 (m, 1H), 2.42-2.04 (m, 2H), 1.97-1.70 (m, 3H), 1.65-1.42 (m, 3H), 1.09 (p, J = 13.7, 12.7 Hz, 2H), 0.90 (s, 1H). | I-4 |
| 6 | 3-(1-oxo-5-(((1R,2S)-2-((thiazol-5-ylmethyl)amino)cyclohexyl)methyl)isoindolin-2-yl)piperidine-2,6-dione | 453.3 | ¹H NMR (400 MHz, DMSO-d6) δ 10.99 (s, 1H), 9.21-9.19 (m, 1H), 9.17-9.05 (m, 1H), 8.85-8.74 (m, 1H), 8.10 (d, J = 2.5 Hz, 1H), 7.67 (d, J = 7.8 Hz, 1H), 7.41 (s, 1H), 7.34 (d, J = 8.1 Hz, 1H), 5.11 (dd, J = 13.3, 5.1 Hz, 1H), 4.70-4.55 (m, 2H), 4.43 (dd, J = 17.4, 4.3 Hz, 1H), 4.30 (dd, J = 17.3, 4.4 Hz, 1H), 3.19 (dd, J = 13.5, 4.0 Hz, 1H), 3.01-2.86 (m, 2H), 2.65-2.56 (m, 1H), 2.46-2.34 (m, 2H), 2.21-2.11 (m, 1H), 2.05-1.96 (m, 1H), 1.96-1.86 (m, 1H), 1.77-1.68 (m, 1H), 1.60-1.46 (m, 3H), 1.35-1.23 (m, 1H), 1.16-0.98 (m, 2H). | thiazole-5-carbaldehyde |
| 7 | 3-(5-(((1R,2S)-2-(isopropylamino)cyclohexyl)methyl)-1-oxoisoindolin-2-yl)piperidine-2,6-dione | 398.3 | ¹H NMR (400 MHz, DMSO-d6) δ 10.99 (s, 1H), 8.39 (s, 1H), 8.05 (s, 1H), 7.69 (d, J = 7.8 Hz, 1H), 7.45 (s, 1H), 7.36 (dd, J = 7.8, 1.3 Hz, 1H), 5.11 (dd, J = 13.3, 5.1 Hz, 1H), 4.50-4.27 (m, 2H), 3.50 (qt, J = 9.9, 5.0 Hz, 1H), 3.29 (dd, J = 13.2, 3.4 Hz, 1H), 3.03 (d, J = 8.4 Hz, 1H), 2.92 (ddd, J = 17.3, 13.6, 5.4 Hz, 1H), 2.65-2.56 (m, 1H), 2.40 (dqt, J = 17.8, 9.3, 4.4 Hz, 1H), 2.12-1.95 (m, 2H), 1.83 (d, J = 9.5 Hz, 1H), 1.72 (d, J = 12.5 Hz, 1H), 1.51 (dt, J = 20.2, 4.5 Hz, 2H), 1.42-1.34 (m, 2H), 1.30 (dd, J = 18.8, 6.4 Hz, 6H), 1.03 (dd, J = 10.9, 7.1 Hz, 2H). | acetone |
| 8 | 3-(5-(((1R,2S)-2-((cyclopropylmethyl)amino)cyclohexyl)methyl)-1-oxoisoindolin-2-yl)piperidine-2,6-dione | 410.3 | ¹H NMR (400 MHz, DMSO-d6) δ 10.99 (s, 1H), 8.60 (s, 1H), 8.40 (s, 1H), 7.69 (d, J = 7.8 Hz, 1H), 7.48 (d, J = 14.6 Hz, 1H), 7.43-7.29 (m, 1H), 5.11 (dd, J = 13.3, 5.1 Hz, 1H), 4.50-4.27 (m, 2H), 3.43-3.30 (m, 1H), 3.22 (ddd, J = 21.7, 13.3, 6.9 Hz, 1H), 3.03 (p, J = 6.4, 5.7 Hz, 1H), 2.98-2.78 (m, 2H), 2.65-2.56 (m, 1H), 2.47-2.31 (m, 2H), 2.12-1.95 (m, 2H), 1.94-1.64 (m, 2H), 1.46 (dt, J = 35.2, 11.6 Hz, 3H), 1.35-1.21 (m, 1H), 1.20-0.95 (m, 3H), 0.74-0.49 (m, 2H), 0.39 (dt, J = 6.1, 3.0 Hz, 2H). | |

TABLE 1-continued

| Example | Structure | ES/MS m/z | ¹H-NMR | Changes to Procedure 3: Different Reagents/ Starting Materials |
|---|---|---|---|---|
| 9 | 3-(5-(((1R,2S)-2-((naphthalen-2-ylmethyl)amino)cyclohexyl)methyl)-1-oxoisoindolin-2-yl)piperidine-2,6-dione | 496.4 | ¹H NMR (400 MHz, DMSO-d6) δ 11.00 (s, 1H), 9.10 (d, J = 11.4 Hz, 1H), 8.81 (s, 1H), 8.16-8.10 (m, 1H), 8.02 (dd, J = 8.5, 2.7 Hz, 1H), 7.97 (tt, J = 6.5, 2.6 Hz, 2H), 7.65 (ddd, J = 18.8, 8.2, 2.1 Hz, 2H), 7.61-7.56 (m, 2H), 7.36 (d, J = 8.6 Hz, 1H), 7.32 (dt, J = 7.8, 1.7 Hz, 1H), 5.10 (dd, J = 13.3, 5.1 Hz, 1H), 4.57-4.41 (m, 2H), 4.37 (dd, J = 17.3, 7.2 Hz, 1H), 4.23 (t, J = 18.1 Hz, 1H), 3.23 (dt, J = 13.4, 4.6 Hz, 1H), 3.01 (s, 1H), 2.92 (ddd, J = 17.3, 13.7, 5.5 Hz, 1H), 2.65-2.56 (m, 1H), 2.48-2.32 (m, 2H), 2.20 (dt, J = 13.1, 4.4 Hz, 1H), 1.99 (h, J = 5.1 Hz, 2H), 1.79-1.71 (m, 1H), 1.63 (dd, J = 13.7, 10.5 Hz, 1H), 1.54 (d, J = 8.9 Hz, 2H), 1.27 (dd, J = 21.2, 9.7 Hz, 1H), 1.07 (ddt, J = 32.0, 21.5, 11.6 Hz, 2H). | naphthalene-2-carbaldehyde |
| 10 | 3-(5-(((1R,2S)-2-(((4,4-difluorocyclohexyl)methyl)amino)cyclohexyl)methyl)-1-oxoisoindolin-2-yl)piperidine-2,6-dione | 488.4 | ¹H NMR (400 MHz, DMSO-d6) δ 10.99 (s, 1H), 8.40 (s, 1H), 8.18 (s, 1H), 7.69 (d, J = 7.8 Hz, 1H), 7.45 (s, 1H), 7.43-7.33 (m, 1H), 5.11 (dd, J = 13.3, 5.1 Hz, 1H), 4.45 (dd, J = 17.4, 2.9 Hz, 1H), 4.32 (dd, J = 17.3, 3.6 Hz, 1H), 3.21 (dd, J = 13.4, 3.6 Hz, 2H), 3.06-2.83 (m, 4H), 2.64-2.57 (m, 1H), 2.39 (tdt, J = 13.0, 9.7, 4.1 Hz, 2H), 2.13-1.98 (m, 3H), 1.96-1.78 (m, 5H), 1.73 (d, J = 13.7 Hz, 2H), 1.48 (ddd, J = 23.3, 18.1, 8.9 Hz, 3H), 1.36-1.20 (m, 3H), 1.03 (q, J = 10.7 Hz, 2H). | 4,4-difluoro-cyclohexane-carbaldehyde |
| 11 | 3-(5-(((1R,2S)-2-(benzylamino)cyclohexyl)methyl)-4-fluoro-1-oxoisoindolin-2-yl)piperidine-2,6-dione | 464.2 | ¹H NMR (400 MHz, DMSO-d6) δ 11.01 (s, 1H), 7.60-7.23 (m, 7H), 5.13 (dd, J = 13.3, 5.1 Hz, 1H), 4.55 (dd, J = 17.4, 8.7 Hz, 1H), 4.45-4.10 (m, 3H), 3.19 (d, J = 13.5 Hz, 1H), 3.07-2.80 (m, 3H), 2.80-2.55 (m, 2H), 2.14 (d, J = 14.4 Hz, 1H), 2.01 (dtd, J = 11.9, 6.8, 6.2, 3.4 Hz, 2H), 1.74 (d, J = 17.2 Hz, 1H), 1.59 (d, J = 27.3 Hz, 3H), 1.32 (d, J = 11.1 Hz, 1H), 1.22-0.94 (m, 3H). | I-4 |
| 12 | 3-(5-(((1R,2S)-2-((4-(methylsulfonyl)benzyl)amino)cyclohexyl)methyl)-1-oxoisoindolin-2-yl)piperidine-2,6-dione | 524.2 | ¹H NMR (400 MHz, DMSO-d6) δ 10.99 (s, 1H), 8.12-7.98 (m, 2H), 7.87-7.74 (m, 2H), 7.68 (d, J = 7.7 Hz, 1H), 7.44 (s, 1H), 7.42-7.27 (m, 1H), 5.12 (dd, J = 13.3, 5.1 Hz, 1H), 4.55-4.16 (m, 4H), 3.26 (s, 3H), 3.05 (s, 1H), 2.99-2.81 (m, 2H), 2.75-2.52 (m, 2H), 2.43-2.30 (m, 2H), 2.17 (d, J = 12.6 Hz, 1H), 2.08-1.83 (m, 2H), 1.75 (d, J = 11.2 Hz, 1H), 1.56 (d, J = 10.3 Hz, 1H), 1.32 (d, J = 11.8 Hz, 1H), 1.20-0.96 (m, 3H). | 4-methyl-sulfonyl-benzaldehyde |
| 13 | 3-(5-(((1R,2S)-2-((3,5-dichlorobenzyl)amino)cyclohexyl)methyl)-1-oxoisoindolin-2-yl)piperidine-2,6-dione | 514.1 | ¹H NMR (400 MHz, DMSO-d6) δ 10.99 (s, 1H), 7.83-7.55 (m, 4H), 7.44 (s, 1H), 7.37 (dd, J = 7.8, 1.4 Hz, 1H), 5.12 (dd, J = 13.3, 5.1 Hz, 1H), 4.49-4.08 (m, 4H), 3.25 (d, J = 13.2, 4.1 Hz, 1H), 3.05 (s, 1H), 3.00-2.81 (m, 1H), 2.75-2.54 (m, 1H), 2.45-2.29 (m, 1H), 2.29-2.06 (m, 1H), 2.06-1.85 (m, 2H), 1.74 (d, J = 13.3 Hz, 1H), 1.56 (d, J = 10.8 Hz, 4H), 1.33 (d, J = 11.6 Hz, 1H), 1.10 (q, J = 10.8 Hz, 2H). | 3,5-dichloro-benzaldehyde |

TABLE 1-continued

| Example | Structure | ES/MS m/z | ¹H-NMR | Changes to Procedure 3: Different Reagents/ Starting Materials |
|---|---|---|---|---|
| 14 | 3-(5-(((1R,2S)-2-((4-methoxybenzyl)amino)cyclohexyl)methyl)-1-oxoisoindolin-2-yl)piperidine-2,6-dione | 476.2 | ¹H NMR (400 MHz, Methanol-d4) δ 7.82-7.70 (m, 1H), 7.44-7.29 (m, 4H), 7.08-6.94 (m, 2H), 5.18 (ddd, J = 13.3, 5.2, 1.9 Hz, 1H), 4.57-4.39 (m, 2H), 4.27 (q, J = 13.2 Hz, 2H), 3.84 (d, J = 1.8 Hz, 3H), 3.24-3.10 (m, 1H), 3.10-2.72 (m, 3H), 2.66-2.40 (m, 2H), 2.21 (q, J = 7.2 Hz, 2H), 2.15-1.99 (m,1H), 1.82 (s, 1H), 1.68 (d, J = 11.0 Hz, 4H), 1.47 (d, J = 11.7 Hz, 1H), 1.38-1.10 (m, 2H). | 4-methoxy-benzaldehyde |
| 15 | 3-(5-(((1R,2S)-2-((3,5-difluorobenzyl)amino)cyclohexyl)methyl)-1-oxoisoindolin-2-yl)piperidine-2,6-dione | 482.1 | ¹H NMR (400 MHz, Methanol-d4) δ 7.77 (d, J = 7.8 Hz, 1H), 7.51-7.25 (m, 2H), 7.25-7.00 (m, 3H), 5.18 (dd, J = 13.3, 5.1 Hz, 1H), 4.53-4.47 (m, 2H), 4.43 (d, J = 13.2 Hz, 1H), 4.33 (dd, J = 13.4, 2.2 Hz, 1H), 3.20-3.07 (m, 1H), 3.04-2.70 (m, 2H), 2.63-2.38 (m, 2H), 2.36-2.13 (m, 2H), 2.07 (s, 1H), 1.83 (s, 1H), 1.68 (d, J = 11.9 Hz, 3H), 1.51 (d, J = 12.1 Hz, 1H), 1.41-1.10 (m, 3H). | 3,5-difluoro-benzaldehyde |
| 16 | 3-(1-oxo-5-(((1R,2S)-2-((4-(trifluoromethyl)benzyl)amino)cyclohexyl)methyl)isoindolin-2-yl)piperidine-2,6-dione | 514.1 | ¹H NMR (400 MHz, Methanol-d4) δ 7.88-7.68 (m, 5H), 7.46 (s, 1H), 7.40 (d, J = 7.9 Hz, 1H), 5.24-5.09 (m, 1H), 4.56-4.31 (m, 4H), 3.30-3.08 (m, 1H), 3.05-2.75 (m, 2H), 2.67-2.45 (m, 2H), 2.41-2.17 (m, 2H), 2.17-1.99 (m, 1H), 1.86 (s, 1H), 1.71 (d, J = 15.1 Hz, 3H), 1.58-1.03 (m, 3H), 0.99-0.86 (m, 1H), 0.62 (d, J = 13.4 Hz, 1H), 0.20-0.05 (m, 1H). | 4-(trifluoro-methyl)benzaldehyde |
| 17 | 4-((((1S,2R)-2-((2-(2,6-dioxopiperidin-3-yl)-1-oxoisoindolin-5-yl)methyl)cyclohexyl)amino)methyl)-3-fluorobenzonitrile | 489.1 | ¹H NMR (400 MHz, DMSO-d6) δ 10.97 (s, 1H), 7.95-7.64 (m, 3H), 7.61 (d, J = 7.7 Hz, 1H), 7.35 (s, 1H), 7.28 (dd, J = 7.8, 1.3 Hz, 2H), 5.21-5.00 (m, 1H), 4.41 (dd, J = 17.3, 3.0 Hz, 1H), 4.28 (d, J = 17.1 Hz, 1H), 3.97 (d, J = 15.0 Hz, 1H), 3.79 (d, J = 14.8 Hz, 1H), 3.39-3.32 (m, 1H), 2.92 (ddd, J = 17.5, 13.5, 5.4 Hz, 1H), 2.76-2.55 (m, 1H), 2.44-2.24 (m, 1H), 2.24-1.87 (m, 4H), 1.65 (s, 1H), 1.53 (d, J = 11.5 Hz, 4H), 1.29-0.95 (m, 3H), 0.95-0.71 (m, 1H). | 3-fluoro-4-formyl-benzonitrile |
| 18 | 3-(5-(((1R,2S)-2-((2,6-difluorobenzyl)amino)cyclohexyl)methyl)-1-oxoisoindolin-2-yl)piperidine-2,6-dione | 482.1 | ¹H NMR (400 MHz, DMSO-d6) δ 10.97 (s, 1H), 7.57 (d, J = 7.7 Hz, 1H), 7.47-7.14 (m, 3H), 7.15-6.95 (m, 3H), 5.10 (ddd, J = 13.3, 5.1, 1.6 Hz, 1H), 4.39 (d, J = 17.2 Hz, 1H), 4.26 (d, J = 17.1 Hz, 1H), 3.92 (d, J = 12.6 Hz, 1H), 3.74 (d, J = 12.7 Hz, 1H), 3.19 (d, J = 13.5 Hz, 1H), 2.91 (ddd, J = 17.3, 13.6, 5.4 Hz, 1H), 2.74-2.52 (m, 1H), 2.44-2.22 (m, 1H), 2.21-1.88 (m, 3H), 1.73 (d, J = 51.8 Hz, 2H), 1.50 (t, J = 16.6 Hz, 4H), 1.09 (p, J = 13.7, 12.8 Hz, 3H), 0.87 (d, J = 11.0 Hz, 1H). | 2,6-difluoro-benzaldehyde |

TABLE 1-continued

| Example | Structure | ES/MS m/z | ¹H-NMR | Changes to Procedure 3: Different Reagents/ Starting Materials |
|---|---|---|---|---|
| 19 | 3-(5-(((1R,2S)-2-((2,4-difluorobenzyl)amino)cyclohexyl)methyl)-1-oxoisoindolin-2-yl)piperidine-2,6-dione | 482.1 | ¹H NMR (400 MHz, DMSO-d6) δ 10.97 (s, 1H), 7.66-7.41 (m, 2H), 7.35 (s, 1H), 7.28 (d, J = 1.3 Hz, 1H), 7.26 (m, 1H), 7.12-7.01 (m, 1H), 5.10 (ddd, J = 13.3, 5.1, 1.3 Hz, 1H), 4.41 (dd, J = 17.3, 2.5 Hz, 1H), 4.28 (d, J = 17.1 Hz, 1H), 3.87 (d, J = 13.8 Hz, 1H), 3.69 (d, J = 13.8 Hz, 1H), 2.92 (ddd, J = 17.3, 13.6, 5.4 Hz, 1H), 2.63 (tdd, J = 17.3, 4.2, 2.1 Hz, 1H), 2.43-2.26 (m, 2H), 2.25-1.80 (m, 2H), 1.66 (d, J = 11.4 Hz, 1H), 1.53 (d, J = 12.0 Hz, 4H), 1.32-0.98 (m, 3H), 0.98-0.74 (m, 1H). | 2,4-difluoro-benzaldehyde |
| 20 | 4-((((1S,2R)-2-((2-(2,6-dioxopiperidin-3-yl)-1-oxoisoindolin-5-yl)methyl)cyclohexyl)amino)methyl)benzonitrile | 471.1 | ¹H NMR (400 MHz, DMSO-d6) δ 10.97 (s, 1H), 7.78 (dq, J = 8.4, 1.8 Hz, 2H), 7.69-7.46 (m, 3H), 7.46-7.18 (m, 2H), 5.10 (ddd, J = 13.3, 5.2, 1.6 Hz, 1H), 4.51-4.14 (m, 2H), 3.96 (dd, J = 14.8, 1.9 Hz, 1H), 3.78 (d, J = 14.7 Hz, 1H), 3.42 (dt, J = 13.2, 4.0 Hz, 1H), 2.92 (ddd, J = 17.2, 13.6, 5.4 Hz, 1H), 2.77-2.53 (m, 1H), 2.45-2.23 (m, 2H), 2.18-1.90 (m, 2H), 1.65 (s, 1H), 1.60-1.34 (m, 4H), 1.10 (dd, J = 22.7, 12.3 Hz, 3H), 0.95-0.75 (m, 1H). | 4-formyl-benzo-nitrile |
| 21 | 3-(5-(((1R,2S)-2-(benzyl(methyl)amino)cyclohexyl)methyl)-1-oxoisoindolin-2-yl)piperidine-2,6-dione | 460.2 | ¹H NMR (400 MHz, DMSO-d6) δ 10.99 (d, J = 2.7 Hz, 1H), 7.84-7.47 (m, 6H), 7.42 (d, J = 8.8 Hz, 1H), 7.32 (d, J = 7.8 Hz, 1H), 5.11 (dt, J = 13.0, 6.0 Hz, 1H), 4.59-4.22 (m, 3H), 3.33 (d, J = 12.9 Hz, 1H), 3.09-2.71 (m, 4H), 2.71-2.57 (m, 1H), 2.53-2.32 (m, 5H), 2.32-1.96 (m, 2H), 1.96-1.71 (m, 1H), 1.71-1.24 (m, 3H), 1.04 (d, J = 11.3 Hz, 2H), 0.95-0.70 (m, 1H). | Example 2 paraformal-dehyde |
| 22 | 3-(5-(((1R,2S)-2-((2,5-difluorobenzyl)amino)cyclohexyl)methyl)-1-oxoisoindolin-2-yl)piperidine-2,6-dione | 482.1 | ¹H NMR (400 MHz, DMSO-d6) δ 10.99 (s, 1H), 7.69 (d, J = 7.8 Hz, 1H), 7.56 (ddd, J = 8.9, 5.8, 2.9 Hz, 1H), 7.50-7.23 (m, 4H), 5.12 (dd, J = 13.2, 5.1 Hz, 1H), 4.48-4.21 (m, 3H), 3.26 (dd, J = 13.3, 3.9 Hz, 1H), 3.08 (s, 1H), 3.00-2.81 (m, 2H), 2.72-2.55 (m, 1H), 2.41 (qd, J = 13.0, 3.3 Hz, 2H), 2.15 (d, J = 12.7 Hz, 1H), 2.07-1.83 (m, 2H), 1.76 (d, J = 10.7 Hz, 1H), 1.67-1.43 (m, 3H), 1.33 (d, J = 12.0 Hz, 1H), 1.07 (p, J = 11.6 Hz, 2H). | 2,5-difluoro-benzal-dehyde |
| 23 | 3-(1-oxo-5-(((1R,2S)-2-(pentan-3-ylamino)cyclohexyl)methyl)isoindolin-2-yl)piperidine-2,6-dione | 426.4 | ¹H NMR (400 MHz, DMSO-d6) δ 10.99 (s, 1H), 8.08 (s, 1H), 7.81 (s, 1H), 7.70 (d, J = 7.8 Hz, 1H), 7.45 (s, 1H), 7.37 (d, J = 7.8 Hz, 1H), 5.11 (dd, J = 13.3, 5.1 Hz, 1H), 4.45 (dd, J = 17.3, 2.9 Hz, 1H), 4.32 (dd, J = 17.4, 3.1 Hz, 1H), 3.31 (dd, J = 12.8, 3.4 Hz, 1H), 3.15 (s, 1H), 3.03 (s, 1H), 2.92 (ddd, J = 17.1, 13.6, 5.4 Hz, 1H), 2.66-2.56 (m, 1H), 2.39 (qd, J = 13.3, 12.8, 3.9 Hz, 2H), 2.14-1.94 (m, 2H), 1.87 (d, J = 9.8 Hz, 1H), 1.70 (tdd, J = 15.0, 8.2, 5.1 Hz, 5H), 1.59-1.24 (m, 4H), 1.04 (t, J = 9.3 Hz, 2H), 0.95 (dt, J = 9.5, 7.4 Hz, 6H). | pentan-3-one |

TABLE 1-continued

| Example | Structure | ES/MS m/z | ¹H-NMR | Changes to Procedure 3: Different Reagents/Starting Materials |
|---|---|---|---|---|
| 24 | 3-(5-(((1R,2S)-2-(((3,3-difluorocyclobutyl)methyl)amino)cyclohexyl)methyl)-1-oxoisoindolin-2-yl)piperidine-2,6-dione | 460.3 | ¹H NMR (400 MHz, DMSO-d6) δ 10.99 (s, 1H), 8.55 (s, 1H), 8.28 s, 1H), 7.69 (d, J = 7.8 Hz, 1H), 7.45 (s, 1H), 7.37 (dd, J = 7.8, 1.3 Hz, 1H), 5.11 (dd, J = 13.3, 5.1 Hz, 1H), 4.49-4.26 (m, 2H), 3.21 (dd, J = 13.8, 4.4 Hz, 3H), 3.02 (s, 1H), 2.92 (ddd, J = 17.4, 13.7, 5.5 Hz, 1H), 2.76 (ddq, J = 14.8, 10.8, 4.8 Hz, 2H), 2.66-2.57 (m, 1H), 2.46-2.31 (m, 1H), 2.11-1.95 (m, 2H), 1.86 (d, J = 9.9 Hz, 1H), 1.72 (d, J = 12.8 Hz, 1H), 1.48 (dd, J = 25.0, 13.6 Hz, 3H), 1.30 (d, J = 11.5 Hz, 1H), 1.04 (q, J = 11.0 Hz, 2H). | 3,3-cyclobutanecarbaldehyde |
| 25 | 3-(1-oxo-5-(((1R,2S)-2-(((phenyl-d$_5$)methyl)amino)cyclohexyl)methyl)isoindolin-2-yl)piperidine-2,6-dione | 451.4 | ¹H NMR (400 MHz, DMSO-d6) δ 10.99 (s, 1H), 8.93 (s, 1H), 8.70 (s, 1H), 7.66 (dd, J = 7.8, 1.5 Hz, 1H), 7.40 (s, 1H), 7.33 (dt, J = 7.9, 1.6 Hz, 1H), 5.11 (dd, J = 13.3, 5.1 Hz, 1H), 4.46-4.17 (m, 4H), 3.20 (dd, J = 13.4, 4.1 Hz, 1H), 2.92 (ddd, J = 17.3, 13.6, 5.4 Hz, 1H), 2.63 (t, J = 17.0 Hz, 1H), 2.46-2.32 (m, 2H), 2.14 (d, J = 12.5 Hz, 1H), 2.05-1.88 (m, 2H), 1.72 (d, J = 12.6 Hz, 1H), 1.55 (t, J = 12.2 Hz, 4H), 1.29 (d, J = 11.4 Hz, 1H), 1.16-0.96 (m, 2H). | benzaldehyde-2,3,4,5,6-d$_5$ |
| 26 | 3-(5-(((1R,2S)-2-(bis((phenyl-d$_5$)methyl)amino)cyclohexyl)methyl)-1-oxoisoindolin-2-yl)piperidine-2,6-dione | 546.5 | ¹H NMR (400 MHz, DMSO-d6) δ 10.97 (s, 1H), 7.56 (d, J = 7.7 Hz, 1H), 7.23-7.09 (m, 2H), 5.08 (dd, J = 13.3, 5.1 Hz, 1H), 4.44-4.15 (m, 2H), 3.78 (d, J = 12.8 Hz, 4H), 2.90 (ddd, J = 18.2, 13.5, 5.5 Hz, 2H), 2.59 (d, J = 17.2 Hz, 2H), 2.44-2.30 (m, 1H), 2.20 (t, J = 11.4 Hz, 1H), 2.10 (d, J = 11.7 Hz, 1H), 2.02-1.94 (m, 1H), 1.87-1.71 (m, 2H), 1.44 (d, J = 12.8 Hz, 2H), 1.28 (d, J = 12.1 Hz, 1H), 1.00 (q, J = 11.7 Hz, 2H), 0.68 (d, J = 12.0 Hz, 1H). | benzaldehyde-2,3,4,5,6-d$_5$ |
| 27 | 3-(5-(((1R,2S)-2-((4,4-dimethylcyclohexyl)amino)cyclohexyl)methyl)-1-oxoisoindolin-2-yl)piperidine-2,6-dione | 466.2 | ¹H NMR (400 MHz, DMSO-d6) δ 10.99 (s, 1H), 7.70 (d, J = 7.8 Hz, 1H), 7.45 (s, 1H), 7.37 (d, J = 7.9 Hz, 1H), 5.12 (dd, J = 13.3, 5.1 Hz, 1H), 4.60-4.38 (m, 1H), 4.33 (dd, J = 17.1, 1.7 Hz, 1H), 3.27 (d, J = 13.4 Hz, 1H), 3.12 (d, J = 28.1 Hz, 2H), 2.99-2.81 (m, 2H), 2.70-2.54 (m, 1H), 2.45-2.21 (m, 1H), 2.18-1.95 (m, 2H), 1.95-1.61 (m, 5H), 1.61-1.14 (m, 8H), 1.04 (s, 2H), 0.93 (d, J = 4.1 Hz, 7H). | 4,4-dimethylcyclohexanone |

TABLE 1-continued

| Example | Structure | ES/MS m/z | ¹H-NMR | Changes to Procedure 3: Different Reagents/ Starting Materials |
|---|---|---|---|---|
| 28 | 3-(1-oxo-5-(((1R,2S)-2-(spiro[2.5]octan-6-ylamino)cyclohexyl)methyl)isoindolin-2-yl)piperidine-2,6-dione | 464.2 | ¹H NMR (400 MHz, DMSO-d6) δ 10.99 (s, 1H), 7.71 (d, J = 7.8 Hz, 1H), 7.45 (s, 1H), 7.37 (d, J = 7.9 Hz, 1H), 5.12 (dd, J = 13.3, 5.1 Hz, 1H), 4.46 (dd, J = 17.4, 2.5 Hz, 1H), 4.41-4.21 (m, 1H), 3.10 (s, 1H), 3.03-2.84 (m, 2H), 2.83-2.55 (m, 2H), 2.45-2.20 (m, 1H), 2.18-1.88 (m, 3H), 1.88-1.22 (m, 10H), 1.20-0.78 (m, 5H), 0.36 (dd, J = 8.5, 5.7 Hz, 2H), 0.25 (t, J = 7.4 Hz, 2H). | spiro[2.5]octan-6-one |
| 29 | 3-(5-(((1R,2S)-2-(bicyclo[3.1.1]heptan-3-ylamino)cyclohexyl)methyl)-1-oxoisoindolin-2-yl)piperidine-2,6-dione | 450.2 | ¹H NMR (400 MHz, DMSO-d6) δ 10.99 (s, 1H), 7.71 (d, J = 7.8 Hz, 1H), 7.46 (s, 1H), 7.38 (d, J = 7.8 Hz, 1H), 5.12 (dd, J = 13.3, 5.2 Hz, 1H), 4.46 (d, J = 17.2 Hz, 1H), 4.33 (d, J = 17.2 Hz,1H), 3.94 (s, 1H), 2.90 (s, 3H), 2.72-2.57 (m, 2H), 2.43-2.24 (m, 3H), 2.15 (s, 1H), 1.95-1.63 (m, 7H), 1.63-1.19 (m, 5H), 1.07 (d, J = 8.7 Hz, 2H). | norpinan-3-one |
| 79 | 3-(1-oxo-5-(((1R,2S)-2-(spiro[2.3]hexan-5-ylamino)cyclohexyl)methyl)isoindolin-2-yl)piperidine-2,6-dione | 436.3 | ¹H NMR (400 MHz, DMSO-d6) δ 10.99 (s, 1H), 8.78 (s, 1H), 8.60 (s, 1H), 7.69 (d, J = 7.8 Hz, 1H), 7.45 (s, 1H), 7.37 (d, J = 7.9 Hz, 1H), 5.11 (dd, J = 13.2, 5.1 Hz, 1H), 4.52-4.21 (m, 2H), 4.19-4.00 (m, 1H), 3.29-3.19 (m, 1H), 2.92 (ddd, J = 18.6, 12.0, 3.9 Hz, 2H), 2.59 (t, J = 10.8 Hz, 2H), 2.49-2.31 (m, 2H), 2.30-2.17 (m, 2H), 2.14-2.07 (m, 1H), 2.00 (d, J = 10.0 Hz, 2H), 1.87 (s, 1H), 1.66 (s, 1H), 1.52 (s, 2H), 1.35 (dd, J = 42.7, 11.0 Hz, 2H), 1.07 (q, J = 11.2 Hz, 2H), 0.60-0.43 (m, 4H). | spiro[2.3]hexan-5-one |
| 80 | 3-(5-(((1R,2S)-2-((2-oxaspiro[3.3]heptan-6-yl)amino)cyclohexyl)methyl)-1-oxoisoindolin-2-yl)piperidine-2,6-dione | 452.3 | ¹H NMR (400 MHz, DMSO-d6) δ 10.99 (s, 1H), 8.63 (s, 1H), 8.41 (s, 1H), 7.70 (d, J = 7.8 Hz, 1H), 7.43 (s, 1H), 7.35 (d, J = 7.8 Hz, 1H), 5.11 (dd, J = 13.3, 5.1 Hz, 1H), 4.57 (d, J = 36.7 Hz, 4H), 4.51-4.25 (m, 2H), 3.78 (d, J = 7.2 Hz, 1H), 3.19 (d, J = 12.9 Hz, 2H), 2.92 (ddd, J = 18.0, 13.4, 5.5 Hz, 2H), 2.66-2.56 (m, 2H), 2.47-2.28 (m, 3H), 2.00 (d, J = 13.4 Hz, 2H), 1.83 (s, 1H), 1.67 (s, 1H), 1.50 (d, J = 14.6 Hz, 2H), 1.33 (dt, J = 20.8, 11.6 Hz, 2H), 1.18-0.94 (m, 2H) | 2-oxaspiro[3.3]heptan-6-one |

TABLE 1-continued

| Example | Structure | ES/MS m/z | ¹H-NMR | Changes to Procedure 3: Different Reagents/Starting Materials |
|---|---|---|---|---|
| 81 | 3-(5-(((1R,2S)-2-(((3,3-difluorocyclobutyl)methyl)amino)cyclohexyl)methyl)-4-fluoro-1-oxoisoindolin-2-yl)piperidine-2,6-dione | 478.3 | ¹H NMR (400 MHz, DMSO-d6) δ 11.01 (s, 1H), 8.68 (s, 1H), 8.37 (s, 1H), 7.58 (d, J = 7.7 Hz, 1H), 7.49 (t, J = 7.0 Hz, 1H), 5.12 (dd, J = 13.3, 5.1 Hz, 1H), 4.48 (ddd, J = 69.5, 17.4, 4.9 Hz, 2H), 3.29-3.02 (m, 5H), 2.92 (ddd, J = 17.3, 13.6, 5.4 Hz, 1H), 2.85-2.68 (m, 2H), 2.63-2.56 (m, 2H), 2.50-2.35 (m, 2H), 2.02 (tdd, J = 10.5, 7.2, 3.6 Hz, 2H), 1.95-1.81 (m, 1H), 1.77-1.62 (m, 1H), 1.48 (qd, J = 15.3, 13.6, 8.0 Hz, 3H), 1.41-1.23 (m, 1H), 1.06 (t, J = 9.5 Hz, 2H). | I-4, 3,3-difluoro-cyclo-butane-carbal-dehyde |
| 82 | 3-(5-(((1R,2S)-2-((3,3-dimethylcyclobutyl)amino)cyclohexyl)methyl)-1-oxoisoindolin-2-yl)piperidine-2,6-dione | 438.4 | ¹H NMR (400 MHz, DMSO-d6) δ 10.99 (s, 1H), 8.81-8.67 (m, 1H), 8.56 (s, 1H), 7.69 (d, J = 7.8 Hz, 1H), 7.45 (s, 1H), 7.36 (dd, J = 7.8, 1.4 Hz, 1H), 5.11 (dd, J = 13.3, 5.1 Hz, 1H), 4.51-4.24 (m, 2H), 3.89 (p, J = 7.6 Hz, 1H), 3.23 (dd, J = 13.4, 4.0 Hz, 1H), 2.98-2.83 (m, 2H), 2.61 (dt, J = 15.6, 2.8 Hz, 1H), 2.49-2.31 (m, 2H), 2.14-1.94 (m, 6H), 1.88 (s, 1H), 1.66 (s, 1H), 1.51 (dt, J = 11.9, 7.4 Hz, 2H), 1.45-1.21 (m, 2H), 1.14 (d, J = 10.2 Hz, 6H), 1.10-0.91 (m, 2H). | 3,3-dimethyl-cyclo-butanone |
| 83 | 3-(5-(((1R,2S)-2-((bicyclo[2.2.2]octan-1-ylmethyl)amino)cyclohexyl)methyl)-1-oxoisoindolin-2-yl)piperidine-2,6-dione | 478.4 | ¹H NMR (400 MHz, DMSO-d6) δ 10.99 (s, 1H), 8.02 (d, J = 23.6 Hz, 2H), 7.69 (d, J = 7.7 Hz, 1H), 7.45 (s, 1H), 7.36 (d, J = 7.8 Hz, 1H), 5.11 (dd, J = 13.3, 5.1 Hz, 1H), 4.45 (dd, J = 17.3, 6.2 Hz, 1H), 4.31 (dd, J = 17.3, 6.2 Hz, 1H), 3.13-3.05 (m, 1H), 3.01 (s, 1H), 2.92 (dd, J = 17.3, 13.7, 5.5 Hz, 2H), 2.86-2.73 (m, 2H), 2.65-2.57 (m, 1H), 2.43-2.30 (m, 2H), 2.04-1.90 (m, 3H), 1.73 (d, J = 13.1 Hz, 1H), 1.65-1.40 (m, 14H), 1.35-1.22 (m, 2H), 1.01 (d, J = 7.3 Hz, 2H). | bicyclo[2.2.2]octane-1-carbal-dehyde |
| 84 | 3-(5-(((1R,2S)-2-((4,4-difluorocyclohexyl)amino)cyclohexyl)methyl)-4-fluoro-1-oxoisoindolin-2-yl)piperidine-2,6-dione | 492.1 | ¹H NMR (400 MHz, DMSO-d6) δ 11.01 (s, 1H), 8.62 (s, 1H), 8.12 (d, J = 11.4 Hz, 1H), 7.60 (d, J = 7.6 Hz, 1H), 7.49 (t, J = 7.0 Hz, 1H), 5.12 (dd, J = 13.3, 5.1 Hz, 1H), 4.57 (dd, J = 17.4, 4.6 Hz, 1H), 4.40 (dd, J = 17.4, 4.3 Hz, 1H), 3.28-3.10 (m, 2H), 3.04-2.82 (m, 2H), 2.73-2.56 (m, 2H), 2.42 (td, J = 13.2, 4.5 Hz, 1H), 2.23-1.95 (m, 6H), 1.95-1.62 (m, 5H), 1.62-1.24 (m, 4H), 1.07 (t, J = 9.6 Hz, 2H). | I-4, 4,4-difluoro-cyclo-hexanone |

TABLE 1-continued

| Example | Structure | ES/MS m/z | 1H-NMR | Changes to Procedure 3: Different Reagents/ Starting Materials |
|---|---|---|---|---|
| 85 | 3-(4-fluoro-5-(((1R,2S)-2-(isopropylamino)cyclohexyl)methyl)-1-oxoisoindolin-2-yl)piperidine-2,6-dione | 416.2 | $^1$H NMR (400 MHz, DMSO-d6) δ 11.01 (s, 1H), 8.27 (s, 1H), 7.92 (d, J = 28.5 Hz, 1H), 7.60 (d, J = 7.7 Hz, 1H), 7.49 (t, J = 7.0 Hz, 1H), 5.12 (dd, J = 13.3, 5.1 Hz, 1H), 4.57 (dd, J = 17.4, 3.9 Hz, 1H), 4.40 (dd, J = 17.4, 3.7 Hz, 1H), 3.52 (s, 1H), 3.13 (s, 2H), 2.92 (dt, J = 17.8, 7.4 Hz, 1H), 2.79-2.55 (m, 3H), 2.20-1.93 (m, 2H), 1.93-1.62 (m, 3H), 1.62-1.40 (m, 2H), 1.30 (dd, J = 20.4, 6.4 Hz, 7H), 1.08 (t, J = 9.3 Hz, 2H). | I-4, acetone |
| 86 | 3-(5-(((1R,2S)-2-((2-oxaspiro[3.5]nonan-7-yl)amino)cyclohexyl)methyl)-1-oxoisoindolin-2-yl)piperidine-2,6-dione | 480.2 | $^1$H NMR (400 MHz, DMSO-d6) δ 10.99 (s, 1H), 7.70 (d, J = 7.8 Hz, 1H), 7.44 (s, 1H), 7.36 (dd, J = 7.7, 1.3 Hz, 1H), 5.12 (dd, J = 13.3, 5.1 Hz, 1H), 4.45 (dd, J = 17.5, 2.3 Hz, 1H), 4.34 (s, 3H), 4.23 (s, 2H), 3.29-3.00 (m, 3H), 2.92 (ddd, J = 17.3, 13.6, 5.4 Hz, 1H), 2.68-2.54 (m, 1H), 2.38 (ddd, J = 18.6, 10.8, 4.8 Hz, 2H), 2.05 (ddd, J = 56.6, 21.6, 15.7 Hz, 6H), 1.75 (dd, J = 26.9, 13.5 Hz, 2H), 1.59-1.17 (m, 8H), 1.03 (s, 2H). | 2-oxaspiro[3.5]nonan-7-one |

Procedure 4, Example 30

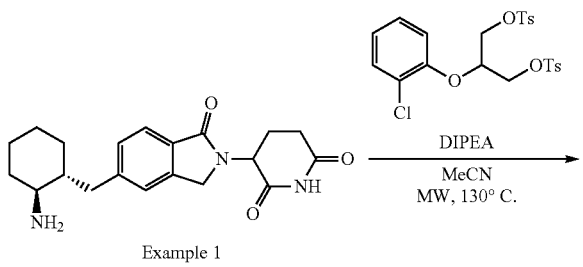

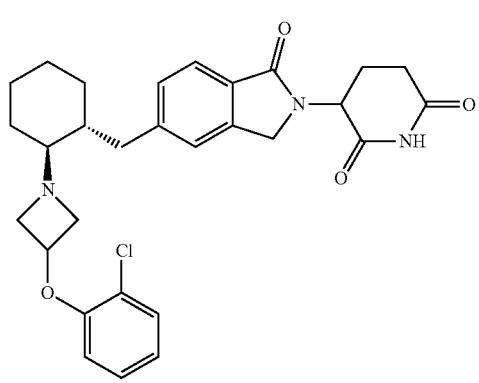 [SMILES: O=C1CCC(N2Cc3cc(C[C@H]4CCCC[C@@H]4N4CC(Oc5ccccc5)C4)ccc3C2=O)C(=O)N1]

Example 30

3-(5-(((1R,2S)-2-(3-(2-chlorophenoxy)azetidin-1-yl)cyclohexyl)methyl)-1-oxoisoindolin-2-yl)piperidine-2,6-dione (Example 30) Example 1

(50.0 mg, 141 umol) and 2-(2-chlorophenoxy)propane-1,3-diyl bis(4-methylbenzenesulfonate) (prepared as described in WO2020/012334) (216 mg, 422 umol) were taken up in MeCN (1.4 mL) and treated with N,N-diisopropylethylamine (147 uL, 844 umol). The mixture was stirred under microwave irradiation at 130° C. for 4 h, then cooled to rt, diluted with DMSO, filtered through a syringe filter, and purified by RP-HPLC (eluent: MeCN/water gradient with 0.1% TFA). Product-containing fractions were combined, lyophilized, taken up in DCM, treated with triethylamine (500 uL), and further purified by normal-phase column chromatography (04100% EtOAc in hexanes followed by 0430% MeOH in DCM). Product-containing fractions were combined, concentrated under vacuum, and subjected to a final purification by RP-HPLC to afford the product (Example 30) as the trifluoroacetate salt. ES/MS m/z: 522.3 (M+H$^+$). $^1$H NMR (400 MHz, DMSO-d6; mixture of two diastereomeric protonation states, * denotes major, #denotes minor) δ 10.99 (s, 1H*, 1H #), 10.56-10.43 (m, 1H #), 10.19-10.08 (m, 1H*), 7.68 (dd, J=7.8, 3.4 Hz, 1H*, 1H #), 7.51 (ddd, J=7.8, 5.9, 1.6 Hz, 1H*, 1H #), 7.48-7.43 (m, 1H*, 1H #), 7.40-7.30 (m, 2H*, 2H #), 7.07 (tt, J=7.7, 1.6 Hz, 1H*, 1H #), 6.99 (dd, J=8.3, 1.3 Hz, 1H*), 6.89 (dd, J=8.3, 1.3 Hz, 1H #), 5.15-5.04 (m, 2H*, 2H #), 4.93-4.83 (m, 1H*), 4.81-4.68 (m, 1H*, 2H #), 4.59-4.51 (m, 1H #), 4.49-4.27 (m, 4H*, 3H #), 3.38-3.21 (m, 1H*, 1H #), 3.08-2.85 (m, 2H*, 2H #), 2.71-2.53 (m, 2H*, 2H #), 2.40 (qd, J=13.2, 4.5 Hz, 1H*, 1H #), 2.08-1.88 (m, 3H*, 3H #), 1.72-1.29 (m, 5H*, 5H #), 1.25-1.00 (m, 2H*, 2H #).

The following Examples were made using the general route described in Procedure 4 and are shown below in Table 2. To prepare the below Examples, different reagents/starting materials were used than some of those described in Procedure 4 and are noted in the last column of Table 2—"Changes to Procedure 4: Different Reagents/Starting Materials". A person of ordinary skill in the art will readily recognize which reagents/starting materials of Procedure 4 were replaced with the different reagents/starting materials noted below.

TABLE 2

| Example | Structure | ES/MS m/z | ¹H-NMR | Changes to Procedure 4: Different Reagents/Starting Materials |
|---|---|---|---|---|
| 31 | 3-(5-(((1R,2S)-2-(3-ethoxyazetidin-1-yl)cyclohexyl)methyl)-1-oxoisoindolin-2-yl)piperidine-2,6-dione | 440.3 | ¹H NMR (400 MHz, DMSO-d6; mixture of two diastereomeric protonation states, *denotes major, #denotes minor) δ 10.99 (s, 1H*, 1H#), 10.29-10.18 (m, 1H#), 9.73-9.62 (m, 1H*), 7.68 (d, J = 7.7 Hz, 1H*, 1H#), 7.45 (d, J = 9.7 Hz, 1H*, 1H#), 7.36 (t, J = 8.2 Hz, 1H*, 1H#), 5.11 (dd, J = 13.3, 5.1 Hz, 1H*, 1H#), 4.56-4.01 (m, 7H*, 7H#), 3.52-3.42 (m, 2H*, 2H#), 3.25-3.11 (m, 1H*, 1H#), 3.03-2.86 (m, 2H*, 2H#), 2.69-2.52 (m, 2H*, 2H#), 2.40 (qd, J = 13.2, 4.5 Hz, 1H*, 1H#), 2.04-1.84 (m, 3H*, 3H#), 1.70-1.27 (m, 5H*, 5H#), 1.24-0.96 (m, 5H*, 5H#). | 1,3-dibromo-2-ethoxypropane |
| 32 | 3-(1-oxo-5-(((1R,2S)-2-(3-phenoxyazetidin-1-yl)cyclohexyl)methyl)isoindolin-2-yl)piperidine-2,6-dione | 488.3 | ¹H NMR (400 MHz, DMSO-d6) δ 10.99 (s, 1H), 10.35 (s, 0H), 9.86 (s, 1H), 7.68 (d, J = 7.7 Hz, 1H), 7.46 (d, J = 6.1 Hz, 1H), 7.40-7.29 (m, 3H), 7.05 (t, J = 7.3 Hz, 1H), 6.94-6.83 (m, 2H), 5.11 (dd, J = 13.3, 5.1 Hz, 1H), 5.07-4.97 (m, 1H), 4.83 (s, 1H), 4.68 (d, J = 9.0 Hz, 1H), 4.52-4.22 (m, 4H), 3.28 (d, J = 32.0 Hz, 1H), 3.07-2.83 (m, 2H), 2.70-2.55 (m, 1H), 2.45-2.27 (m, 1H), 2.07-1.85 (m, 3H), 1.48 (d, J = 63.2 Hz, 6H), 1.13 (d, J = 57.6 Hz, 2H). | 2-phenoxypropane-1,3-diyl bis(4-methylbenzenesulfonate) |
| 33 | 3-(5-(((1R,2S)-2-(3-(benzyloxy)azetidin-1-yl)cyclohexyl)methyl)-1-oxoisoindolin-2-yl)piperidine-2,6-dione | 502.4 | ¹H NMR (400 MHz, DMSO-d6) δ 10.99 (s, 1H), 9.56 (s, 1H), 7.69 (d, J = 7.8 Hz, 1H), 7.44 (d, J = 7.9 Hz, 1H), 7.43-7.20 (m, 6H), 5.11 (dd, J = 13.3, 5.1 Hz, 1H), 4.54 (s, 1H), 4.51 (s, 1H), 4.46 (d, J = 6.8 Hz, 1H), 4.42 (q, J = 4.2 Hz, 1H), 4.39-4.31 (m, 1H), 4.31-4.26 (m, 1H), 4.14 (dt, J = 16.6, 5.5 Hz, 1H), 3.19 (d, J = 28.4 Hz, 1H), 3.04-2.83 (m, 2H), 2.65-2.56 (m, 1H), 2.47-2.34 (m, 1H), 2.07-1.81 (m, 4H), 1.65 (s, 1H), 1.53 (d, J = 8.7 Hz, 2H), 1.47-1.27 (m, 3H), 1.26-1.14 (m, 1H), 1.14-0.87 (m, 2H). | 2-(benzyloxy)propane-1,3-diyl bis(4-methylbenzenesulfonate) |

Procedure 5, Example 34

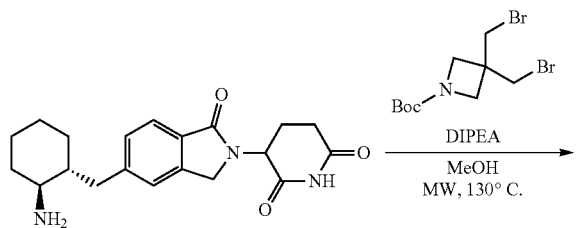

Example 1

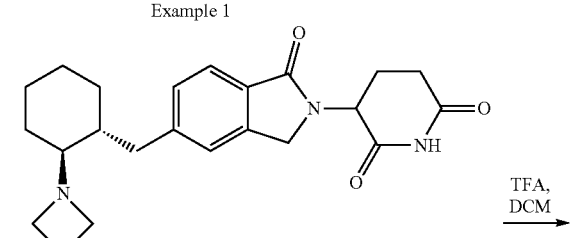

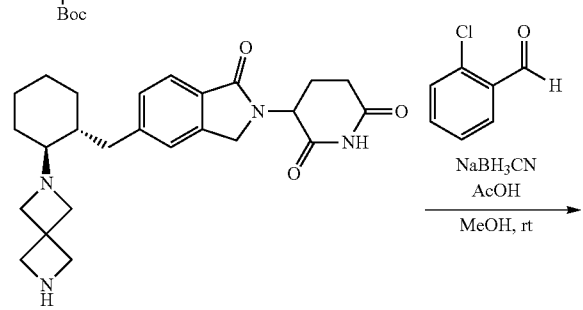

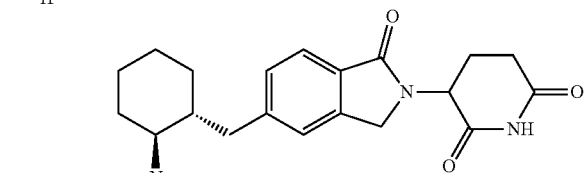

Example 34

Step 1: Preparation of tert-butyl 6-((1S,2R)-2-((2-(2,6-dioxopiperidin-3-yl)-1-oxoisoindolin-5-yl)methyl)cyclohexyl)-2,6-diazaspiro[3.3]heptane-2-carboxylate. Example 1

(100 mg, 0.281 mmo) was taken up in MeCN (2.8 mL) and tert-butyl 3,3-bis(bromomethyl)azetidine-1-carboxylate (291 mg, 0.844 mmol) was added followed by N,N-diisopropylethylamine (294 uL, 1.69 mmol). The mixture was stirred at 130° C. for 4 h under microwave irradiation. The mixture was then cooled to r.t., concentrated under reduced pressure, and purified by normal phase column chromatography (0→100% EtOAc in hexanes, then 0→30% MeOH in DCM) to afford the product. ES/MS m/z: 537.4 (M+H$^+$).

Step 2: Preparation of 3-(5-(((1R,2S)-2-(2,6-diazaspiro[3.3]heptan-2-yl)cyclohexyl)methyl)-1-oxoisoindolin-2-yl)piperidine-2,6-dione tert-butyl 6-((1S,2R)-2-((2-(2,6-dioxopiperidin-3-yl)-1-oxoisoindolin-5-yl)methyl)cyclohexyl)-2,6-diazaspiro[3.3]heptane-2-carboxylate (151 mg, 0.281 mmol) was taken up in DCM (2.0 mL) and treated with TFA (2.0 mL). The mixture was stirred at rt for 1 h, then was concentrated under reduced pressure to afford the product, which was used in subsequent reactions without further purification. ES/MS m/z: 437.4 (M+H$^+$).

Step 3: Preparation of 3-(5-(((1R,2S)-2-(6-(2-chlorobenzyl)-2,6-diazaspiro[3.3]heptan-2-yl)cyclohexyl)methyl)-1-oxoisoindolin-2-yl)piperidine-2,6-dione (Example 34)

3-(5-(((1R,2S)-2-(2,6-diazaspiro[3.3]heptan-2-yl)cyclohexyl)methyl)-1-oxoisoindolin-2-yl)piperidine-2,6-dione (61 mg, 0.14 mmol) was taken up in MeOH (1.4 mL) and treated with 2-chlorobenzaldehyde (47 uL, 0.419 mmol) followed by acetic acid (8.0 uL, 0.14 mmol) and sodium cyanoborohydride (26.3 mg, 0.419 mmol). The mixture was stirred at r.t. for 90 min, then diluted with DMSO, filtered through a syringe filter, and purified by RP-HPLC (eluent: MeCN/water gradient with 0.1% TFA). Product-containing fractions were combined, lyophilized, and subjected to a second purification by RP-HPLC to afford the product (Example 34) as the trifluoroacetate salt. ES/MS m/z: 561.4 (M+H$^+$). $^1$H NMR (400 MHz, DMSO-d6) δ 10.99 (s, 1H), 10.56 (s, 1H), 7.68 (d, J=7.7 Hz, 1H), 7.61-7.57 (m, 1H), 7.55-7.43 (m, 4H), 7.39-7.34 (m, 1H), 5.11 (dd, J=13.3, 5.1 Hz, 1H), 4.53 (s, 2H), 4.50-4.19 (m, 10H), 3.13 (s, 1H), 2.98-2.84 (m, 2H), 2.69-2.56 (m, 2H), 2.40 (qd, J=13.1, 4.5 Hz, 1H), 2.04-1.86 (m, 3H), 1.60-1.31 (m, 5H), 1.25-1.05 (m, 2H).

Procedure 6, Example 35

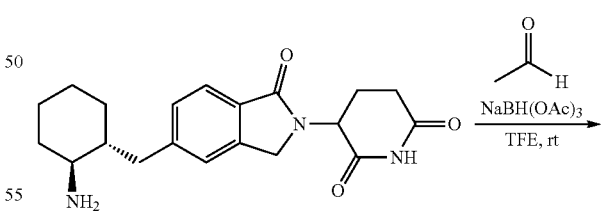

Example 1

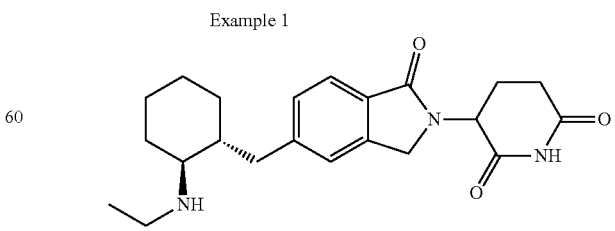

Example 35

3-(5-(((1R,2S)-2-(ethylamino)cyclohexyl)methyl)-1-oxoisoindolin-2-yl)piperidine-2,6-dione (Example 35). Example 1 (30.0 mg, 84.4 μmol) was taken up in TFE (1.0 mL) and treated with acetaldehyde (14.2 μL, 253 umol). The mixture was stirred for 30 min at rt, then treated with NaHB(OAc)$_3$ (53.7 mg, 253 μmol). The reaction mixture was stirred for an additional 3 hour at r.t., then diluted with DMSO, filtered through a syringe filter, and purified by RP-HPLC (eluent: MeCN/water gradient with 0.1% TFA). Product-containing fractions were combined, lyophilized, taken up in DCM, treated with triethylamine (500 μL), and further purified by normal-phase column chromatography (0→100% EtOAc in hexanes followed by 0→30% MeOH in DCM). Product-containing fractions were combined, concentrated under vacuum, and subjected to a final purification by RP-HPLC to afford the product (Example 35) as the trifluoroacetate salt. ES/MS m/z: 384.3 (M+H$^+$). $^1$H NMR (400 MHz, DMSO-d6) δ 10.99 (s, 1H), 8.43-8.32 (m, 1H), 8.23-8.13 (m, 1H), 7.69 (d, J=7.7 Hz, 1H), 7.45 (s, 1H), 7.36 (dd, J=7.9, 1.4 Hz, 1H), 5.11 (dd, J=13.3, 5.1 Hz, 1H), 4.45 (dd, J=17.4, 3.5 Hz, 1H), 4.31 (dd, J=17.3, 4.1 Hz, 1H), 3.21 (dd, J=13.4, 3.8 Hz, 1H), 3.17-3.08 (m, 1H), 3.06-2.94 (m, 2H), 2.94-2.86 (m, 1H), 2.65-2.56 (m, 1H), 2.46-2.33 (m, 2H), 2.09-1.96 (m, 2H), 1.88-1.78 (m, 1H), 1.75-1.66 (m, 1H), 1.58-1.21 (m, 7H), 1.13-0.97 (m, 2H).

The following Examples were made using the general route described in Procedure 6 and are shown below in Table 3. To prepare the below Examples, different reagents/starting materials were used than some of those described in Procedure 6 and are noted in the last column of Table 3—"Changes to Procedure 6: Different Reagents/Starting Materials". A person of ordinary skill in the art will readily recognize which reagents/starting materials of Procedure 6 were replaced with the different reagents/starting materials noted below.

TABLE 3

| Example | Structure | ES/MS m/z | $^1$H-NMR | Changes to Procedure 6: Different Reagents/Starting Materials |
|---|---|---|---|---|
| 36 | 3-(1-oxo-5-(((1R,2S)-2-((thiazol-4-ylmethyl)amino)cyclohexyl)methyl)isoindolin-2-yl)piperidine-2,6-dione | 453.3 | $^1$H NMR (400 MHz, DMSO-d6) δ 10.99 (s, 1H), 9.25 (d, J = 1.9 Hz, 1H), 9.20-9.09 (m, 1H), 8.98-8.88 (m, 1H), 7.93 (dd, J = 3.3, 2.0 Hz, 1H), 7.66 (dd, J = 7.8, 1.3 Hz, 1H), 7.41 (s, 1H), 7.33 (dd, J = 7.8, 1.6 Hz, 1H), 5.11 (dd, J = 13.3, 5.1 Hz, 1H), 4.50-4.38 (m, 3H), 4.30 (dd, J = 17.3, 4.3 Hz, 1H), 3.19 (dd, J = 13.3, 3.9 Hz, 1H), 2.97-2.86 (m, 2H), 2.65-2.56 (m, 1H), 2.46-2.34 (m, 2H), 2.18-2.10 (m, 1H), 2.04-1.88 (m, 2H), 1.76-1.67 (m, 1H), 1.57-1.45 (m, 3H), 1.31-1.19 (m, 1H), 1.13-0.95 (m, 2H). | thiazole-4-carbaldehyde |
| 37 | 3-(1-oxo-5-(((1R,2S)-2-((thiazol-2-ylmethyl)amino)cyclohexyl)methyl)isoindolin-2-yl)piperidine-2,6-dione | 453.3 | $^1$H NMR (400 MHz, DMSO-d6) δ 10.99 (s, 1H), 9.46-9.30 (m, 1H), 9.22-9.07 (m, 1H), 7.96 (dd, J = 3.2, 2.0 Hz, 1H), 7.89 (dd, J = 3.3, 1.8 Hz, 1H), 7.67 (dd, J = 7.8, 1.4 Hz, 1H), 7.43 (s, 1H), 7.38-7.32 (m, 1H), 5.11 (dd, J = 13.3, 5.1 Hz, 1H), 4.80-4.67 (m, 2H), 4.44 (dd, J = 17.4, 3.1 Hz, 1H), 4.31 (dd, J = 17.3, 4.7 Hz, 1H), 3.22 (dd, J = 13.3, 3.9 Hz, 1H), 3.10-3.00 (m, 1H), 2.92 (ddd, J = 17.2, 13.6, 5.4 Hz, 1H), 2.65-2.57 (m, 1H), 2.46-2.34 (m, 2H), 2.19-2.11 (m, 1H), 2.04-1.90 (m, 2H), 1.77-1.68 (m, 1H), 1.58-1.45 (m, 3H), 1.33-1.20 (m, 1H), 1.14-0.97 (m, 2H). | thiazole-2-carbaldehyde |
| 38 | 3-(5-(((1R,2S)-2-(((1-methyl-1H-pyrazol-3-yl)methyl)amino)cyclohexyl)methyl)-1-oxoisoindolin-2-yl)piperidine-2,6-dione | 450.3 | $^1$H NMR (400 MHz, DMSO-d6) δ 10.99 (s, 1H), 9.03-8.92 (m, 1H), 8.84-8.72 (m, 1H), 7.76 (d, J = 2.1 Hz, 1H), 7.66 (d, J = 7.7 Hz, 1H), 7.40 (s, 1H), 7.32 (dt, J = 7.8, 1.6 Hz, 1H), 6.39 (d, J = 2.2 Hz, 1H), 5.11 (dd, J = 13.2, 5.1 Hz, 1H), 4.43 (dd, J = 17.5, 2.0 Hz, 1H), 4.34-4.14 (m, 3H), 3.85 (s, 3H), 3.16 (dd, J = 13.5, 4.1 Hz, 1H), 2.98-2.86 (m, 2H), 2.65-2.56 (m, 1H), 2.46-2.34 (m, 2H), 2.16-2.08 (m, 1H), 2.04-1.87 (m, 2H), 1.75-1.66 (m, 1H), 1.58-1.43 (m, 3H), 1.32-1.19 (m, 1H), 1.15-0.96 (m, 2H). | 1-methyl-pyrazole-3-carbaldehyde |

TABLE 3-continued

| Example | Structure | ES/MS m/z | ¹H-NMR | Changes to Procedure 6: Different Reagents/Starting Materials |
|---|---|---|---|---|
| 39 | 3-(5-(((1R,2S)-2-(((1-methyl-1H-pyrazol-5-yl)methyl)amino)cyclohexyl)methyl)-1-oxoisoindolin-2-yl)piperidine-2,6-dione | 450.3 | ¹H NMR (400 MHz, DMSO-d6) δ 10.99 (s, 1H), 9.06-8.94 (m, 1H), 8.84-8.72 (m, 1H), 7.68 (d, J = 7.8 Hz, 1H), 7.47 (d, J = 1.9 Hz, 1H), 7.45 (s, 1H), 7.37 (dd, J = 8.0, 1.3 Hz, 1H), 6.50-6.48 (m, 1H), 5.11 (dd, J = 13.3, 5.1 Hz, 1H), 4.51-4.35 (m, 3H), 4.31 (dd, J = 17.3, 5.0 Hz, 1H), 3.89 (s, 3H), 3.23 (dd, J = 13.3, 3.9 Hz, 1H), 3.14-3.04 (m, 1H), 2.92 (ddd, J = 17.7, 13.6, 5.4 Hz, 1H), 2.65-2.56 (m, 1H), 2.47-2.34 (m, 2H), 2.20-2.10 (m, 1H), 2.04-1.91 (m, 2H), 1.79-1.70 (m, 1H), 1.64-1.47 (m, 3H), 1.39-1.25 (m, 1H), 1.16-0.99 (m, 2H). | 2-methyl-pyrazole-3-carbaldehyde |
| 40 | 3-(1-oxo-5-(((1R,2S)-2-((pyridin-4-ylmethyl)amino)cyclohexyl)methyl)isoindolin-2-yl)piperidine-2,6-dione | 447.3 | ¹H NMR (400 MHz, DMSO-d6) δ 10.99 (s, 1H), 9.17-9.05 (m, 1H), 8.93-8.80 (m, 1H), 8.72-8.66 (m, 2H), 7.67 (d, J = 7.7 Hz, 1H), 7.63-7.58 (m, 2H), 7.43 (s, 1H), 7.35 (d, J = 7.8 Hz, 1H), 5.11 (dd, J = 13.2, 5.1 Hz, 1H), 4.48-4.38 (m, 2H), 4.35-4.25 (m, 2H), 3.28-3.20 (m, 1H), 3.08-2.98 (m, 1H), 2.92 (ddd, J = 17.7, 13.5, 5.4 Hz, 1H), 2.65-2.56 (m, 1H), 2.46-2.34 (m, 2H), 2.18-2.09 (m, 1H), 2.05-1.90 (m, 2H), 1.78-1.68 (m, 1H), 1.62-1.47 (m, 3H), 1.37-1.23 (m, 1H), 1.16-0.98 (m, 2H). | pyridine-4-carbaldehyde |
| 41 | 3-(1-oxo-5-(((1R,2S)-2-((pyridin-3-ylmethyl)amino)cyclohexyl)methyl)isoindolin-2-yl)piperidine-2,6-dione | 447.3 | ¹H NMR (400 MHz, DMSO-d6) δ 10.98 (s, 1H), 8.60 (s, 1H), 8.47 (s, 1H), 7.81 (s, 1H), 7.61 (d, J = 7.8 Hz, 1H), 7.42-7.33 (m, 2H), 7.29 (d, J = 7.8 Hz, 1H), 5.10 (dd, J = 13.3, 5.1 Hz, 1H), 4.41 (dd, J = 17.2, 4.2 Hz, 1H), 4.28 (dd, J = 17.2, 3.3 Hz, 1H), 4.06-3.62 (m, 2H), 3.41-3.27 (m, 1H), 2.91 (ddd, J = 17.7, 13.5, 5.4 Hz, 1H), 2.64-2.56 (m, 1H), 2.45-2.30 (m, 2H), 2.16-2.06 (m, 1H), 2.04-1.95 (m, 1H), 1.73-1.63 (m, 1H), 1.58-1.47 (m, 3H), 1.27-0.81 (m, 6H). | pyridine-4-carbaldehyde |
| 42 | 3-(5-(((1R,2S)-2-(((1-methyl-1H-pyrazol-4-yl)methyl)amino)cyclohexyl)methyl)-1-oxoisoindolin-2-yl)piperidine-2,6-dione | 450.3 | ¹H NMR (400 MHz, DMSO-d6) δ 10.99 (s, 1H), 8.85-8.73 (m, 1H), 8.58-8.47 (m, 1H), 7.80 (d, J = 4.9 Hz, 1H), 7.66 (d, J = 7.7 Hz, 1H), 7.57 (d, J = 1.5 Hz, 1H), 7.40 (s, 1H), 7.32 (d, J = 8.1 Hz, 1H), 5.11 (ddd, J = 13.3, 5.1, 1.4 Hz, 1H), 4.43 (dd, J = 17.5, 2.4 Hz, 1H), 4.30 (dd, J = 17.5, 2.1 Hz, 1H), 4.21-4.06 (m, 2H), 3.84 (s, 3H), 3.17 (dd, J = 13.4, 3.6 Hz, 1H), 2.97-2.83 (m, 2H), 2.64-2.56 (m, 1H), 2.46-2.32 (m, 2H), 2.17-2.09 (m, 1H), 2.04-1.96 (m, 1H), 1.94-1.84 (m, 1H), 1.75-1.66 (m, 1H), 1.59-1.42 (m, 3H), 1.34-1.22 (m, 1H), 1.14-0.96 (m, 2H). | 1-methyl-pyrazole-4-carbaldehyde |
| 43 | 3-(5-(((1R,2S)-2-(((3,5-difluoropyridin-4-yl)methyl)amino)cyclohexyl)methyl)-1-oxoisoindolin-2-yl)piperidine-2,6-dione | 483.3 | ¹H NMR (400 MHz, DMSO-d6) δ 10.98 (s, 1H), 8.51 (s, 2H), 7.57 (d, J = 7.1 Hz, 1H), 7.31 (s, 1H), 7.23 (d, J = 4.4 Hz, 1H), 5.10 (dd, J = 13.3, 5.1 Hz, 1H), 4.40 (d, J = 17.1 Hz, 1H), 4.27 (d, J = 17.1 Hz, 1H), 3.97 (d, J = 11.4 Hz, 1H), 3.79 (d, J = 11.2 Hz, 1H), 3.25-3.15 (m, 1H), 2.91 (ddd, J = 17.2, 13.6, 5.4 Hz, 1H), 2.64-2.55 (m, 1H), 2.44-2.27 (m, 2H), 2.16-1.95 (m, 3H), 1.73-1.62 (m, 1H), 1.57-1.39 (m, 3H), 1.20-0.98 (m, 3H), 0.95-0.80 (m, 1H). | 3,5-difluoro-pyridine-4-carbaldehyde |

TABLE 3-continued

| Example | Structure | ES/MS m/z | ¹H-NMR | Changes to Procedure 6: Different Reagents/Starting Materials |
|---|---|---|---|---|
| 44 | ![structure] 3-(5-(((1R,2S)-2-(((3,5-difluoropyridin-2-yl)methyl)amino)cyclohexyl)methyl)-1-oxoisoindolin-2-yl)piperidine-2,6-dione | 483.3 | ¹H NMR (400 MHz, DMSO-d6) δ 10.98 (s, 1H), 8.53 (s, 1H), 8.03-7.92 (m, 1H), 7.61 (d, J = 7.7 Hz, 1H), 7.38 (s, 1H), 7.29 (d, J = 7.8 Hz, 1H), 5.10 (ddd, J = 13.2, 5.2, 1.6 Hz, 1H), 4.41 (d, J = 17.0 Hz, 1H), 4.28 (d, J = 17.2 Hz, 1H), 4.22-3.88 (m, 2H), 3.35-3.19 (m, 2H), 2.91 (ddd, J = 17.2, 13.6, 5.4 Hz, 1H), 2.64-2.56 (m, 1H), 2.45-2.32 (m, 2H), 2.12-1.95 (m, 2H), 1.75-1.58 (m, 2H), 1.58-1.46 (m, 2H), 1.29-0.85 (m, 4H). | 3,5-difluoropyridine-2-carbaldehyde |
| 45 | ![structure] 3-(1-oxo-5-(((1R,2S)-2-((pyridin-2-ylmethyl)amino)cyclohexyl)methyl)isoindolin-2-yl)piperidine-2,6-dione | 447.3 | ¹H NMR (400 MHz, DMSO-d6) δ 10.99 (s, 1H), 8.61-8.56 (m, 1H), 7.88-7.81 (m, 1H), 7.64 (dd, J = 7.9, 1.9 Hz, 1H), 7.53 (d, J = 7.9 Hz, 1H), 7.43-7.30 (m, 3H), 5.11 (dd, J = 13.2, 5.1 Hz, 1H), 4.47-4.07 (m, 4H), 3.35-3.26 (m, 2H), 2.92 (ddd, J = 17.2, 13.6, 5.4 Hz, 1H), 2.64-2.57 (m, 1H), 2.45-2.33 (m, 2H), 2.12-2.05 (m, 1H), 2.03-1.96 (m, 1H), 1.89-1.74 (m, 1H), 1.74-1.65 (m, 1H), 1.57-1.49 (m, 2H), 1.42-1.27 (m, 1H), 1.27-1.14 (m, 1H), 1.12-0.91 (m, 2H). | pyridine-2-carbaldehyde |

Procedure 7, Example 46

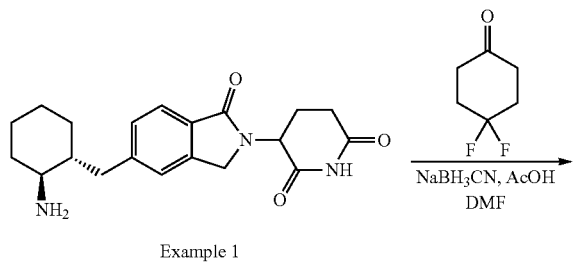

Example 1

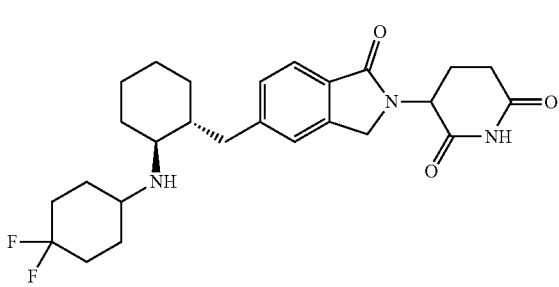 [SMILES: O=C1CCC(N2Cc3cc(C[C@H]4CCCC[C@@H]4NC4CCS(=O)(=O)CC4)ccc3C2=O)C(=O)N1]

Example 46

3-(5-(((1R,2S)-2-((4,4-difluorocyclohexyl)amino)cyclohexyl)methyl)-1-oxoisoindolin-2-yl)piperidine-2,6-dione (Example 46)

A vial was charged with Example 1 (40.0 mg, 0.113 mmol), 4,4-difluorocyclohexan-1-one (22.7 µL, 0.563 mmol), sodium cyanoborohydride (21.2 mg, 0.338 mmol), N,N-dimethylformamide (0.40 mL), and acetic acid (6.5 µL, 0.113 mmol). The reaction was then mixed at room temperature 18 h. Following this time, the reaction mixture was concentrated in vacuo. The residue was taken up in DMSO and purified directly by RP-HPLC (eluent: 0-100% MeCN/water gradient with 0.1% TFA) to afford the product (Example 46) as the trifluoroacetate salt. ES/MS: 474.3 (M+H⁺). ¹H NMR (400 MHz, DMSO-d6) δ 10.99 (s, 1H), 8.56 (s, 1H), 8.16 (s, 1H), 7.70 (d, J=7.7 Hz, 1H), 7.44 (s, 1H), 7.39-7.30 (m, 1H), 5.11 (dd, J=13.3, 5.1 Hz, 1H), 4.45 (dd, J=17.5, 3.0 Hz, 1H), 4.32 (dd, J=17.4, 2.9 Hz, 1H), 3.46 (s, 1H), 3.28 (dd, J=13.0, 3.4 Hz, 1H), 3.11 (s, 1H), 2.92 (ddd, J=17.3, 13.6, 5.4 Hz, 1H), 2.65-2.56 (m, 1H), 2.40 (dqt, J=13.3, 9.5, 4.6 Hz, 2H), 2.20-2.05 (m, 5H), 2.05-1.87 (m, 3H), 1.72 (ddd, J=41.4, 20.5, 11.1 Hz, 4H), 1.59-1.43 (m, 2H), 1.41-1.22 (m, 2H), 1.11-0.94 (m, 2H).

The following Examples were made using the general route described in Procedure 7 and are shown below in Table 4. To prepare the below Examples, different reagents/starting materials were used than some of those described in Procedure 7 and are noted in the last column of Table 4—"Changes to Procedure 7: Different Reagents/Starting Materials". A person of ordinary skill in the art will readily recognize which reagents/starting materials of Procedure 7

TABLE 4

| Example | Structure | ES/MS m/z | 1H-NMR | Changes to Procedure 7: Different Reagents/Starting Materials |
|---|---|---|---|---|
| 47 | 3-(5-(((1R,2S)-2-(cyclopropylamino)cyclohexyl)methyl)-1-oxoisoindolin-2-yl)piperidine-2,6-dione | 396.3 | 1H NMR (400 MHz, DMSO-d6) δ 10.99 (s, 1H), 8.58 (s, 2H), 7.69 (d, J = 7.8 Hz, 1H), 7.43 (s, 1H), 7.35 (dd, J = 7.8, 1.4 Hz, 1H), 5.11 (dd, J = 13.3, 5.1 Hz, 1H), 4.45 (dd, J = 17.3, 4.6 Hz, 1H), 4.31 (dd, J = 17.3, 4.8 Hz, 1H), 3.22 (dd, J = 13.4, 3.7 Hz, 1H), 3.14 (s, 1H), 2.92 (ddd, J = 17.2, 13.6, 5.4 Hz, 1H), 2.79 (d, J = 7.3 Hz, 1H), 2.65-2.56 (m, 1H), 2.47-2.32 (m, 2H), 2.24-2.11 (m, 1H), 2.06-1.95 (m, 1H), 1.90 (d, J = 9.5 Hz, 1H), 1.72 (d, J = 12.2 Hz, 1H), 1.61-1.43 (m, 3H), 1.32 (d, J = 10.9 Hz, 1H), 1.06 (q, J = 10.5 Hz, 2H), 0.97-0.77 (m, 4H). | (1-Ethoxycyclopropoxy)trimethylsilane |

Procedure 8, Example 48

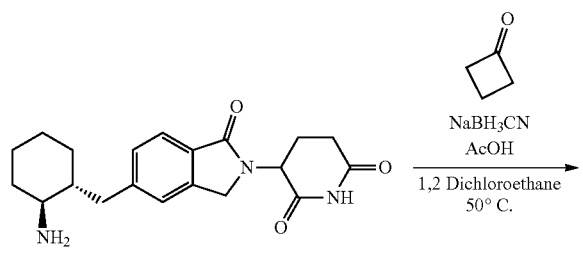

Example 1

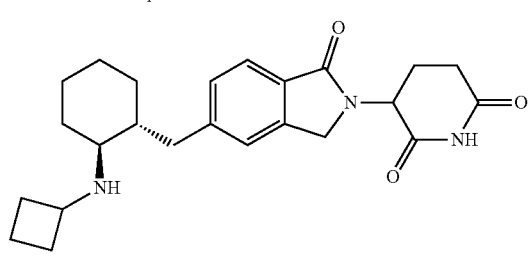

Example 48

3-(5-(((1R,2S)-2-(cyclobutylamino)cyclohexyl)methyl)-1-oxoisoindolin-2-yl)piperidine-2,6-dione (Example 48)

Example 1 (42 mg, 11.8 μmol) was taken up in 1,2-dichloroethane (0.5 mL) and treated with cyclobutanenone (12.4 mg, 17.7 μmol) followed by acetic acid (33.8 μL, 59 μmol) and sodium cyanoborohydride (22.3 mg, 35.4 μmol). The reaction mixture was stirred at 50° C. overnight. The mixture was then diluted with DMSO (3 mL), filtered through a syringe filter, and purified by RP-HPLC (eluent: MeCN/water gradient with 0.1% TFA). Product-containing fractions were combined, lyophilized to afford the above title product (Example 48) as a trifluoroacetate salt. ES/MS m/z: 410.30 (M+H$^+$). 1H NMR (400 MHz, DMSO-d6) δ 10.99 (s, 1H), 8.81 (s, 1H), 8.59 (s, 1H), 8.00-7.88 (m, 1H), 7.69 (d, J=7.8 Hz, 1H), 7.50 (t, J=7.7 Hz, 1H), 7.45 (s, 1H), 7.37 (d, J=7.8 Hz, 1H), 5.11 (dd, J=13.3, 5.2 Hz, 1H), 4.49-4.28 (m, 2H), 3.97-3.80 (m, 1H), 3.54-3.39 (m, 2H), 3.12 (s, 1H), 3.00-2.84 (m, 1H), 2.60 (d, J=16.8 Hz, 1H), 2.49-2.28 (m, 2H), 2.22 (q, J=8.5, 7.9 Hz, 3H), 2.05-1.93 (m, 2H), 1.93-1.74 (m, 2H), 1.45 (d, J=47.0 Hz, 2H).

The following Examples were made using the general route described in Procedure 8 and are shown below in Table 5. To prepare the below Examples, different reagents/starting materials were used than some of those described in Procedure 8 and are noted in the last column of Table 5—"Changes to Procedure 8: Different Reagents/Starting Materials". A person of ordinary skill in the art will readily recognize which reagents/starting materials of Procedure 8

TABLE 5

| Example | Structure | ES/MS m/z | 1H-NMR | Changes to Procedure 8: Different Reagents/Starting Materials |
|---|---|---|---|---|
| 49 | 3-(5-(((1R,2S)-2-(((5-fluoropyridin-2-yl)methyl)amino)cyclohexyl)methyl)-1-oxoisoindolin-2-yl)piperidine-2,6-dione | 465.2 | 1H NMR (400 MHz, DMSO-d6) δ 10.99 (s, 1H), 9.02 (d, J = 61.5 Hz, 2H), 8.69 (t, J = 2.9 Hz, 1H), 7.88 (tt, J = 8.8, 2.7 Hz, 1H), 7.67 (dt, J = 8.8, 3.0 Hz, 2H), 7.44 (s, 1H), 7.36 (dt, J = 7.8, 1.6 Hz, 1H), 5.12 (ddd, J = 13.3, 5.2, 2.2 Hz, 1H), 4.48-4.36 (m, 3H), 4.31 (dd, J = 17.3, 3.7 Hz, 1H), 3.38-3.17 (m, 1H), 2.92 (ddd, J = 17.4, 13.7, 5.5 Hz, 1H), 2.67-2.56 (m, 1H), 2.38 (qd, J = 12.7, 11.5, 8.5 Hz, 2H), 2.11 (d, J = 12.3 Hz, 1H), 2.06-1.88 (m, 2H), 1.72 (d, J = 13.1 Hz, 1H), 1.51 (t, J = 10.4 Hz, 3H), 1.26 (d, J = 12.0 Hz, 1H), 1.05 (d, J = 10.0 Hz, 2H). | 5-fluoropyridine-2-carbaldehyde |

TABLE 5-continued

| Example | Structure | ES/MS m/z | ¹H-NMR | Changes to Procedure 8: Different Reagents/ Starting Materials |
|---|---|---|---|---|
| 50 | 3-(5-(((1R,2S)-2-(((3-fluoropyridin-2-yl)methyl)amino)cyclohexyl)methyl)-1-oxoisoindolin-2-yl)piperidine-2,6-dione | 465.3 | ¹H NMR (400 MHz, DMSO-d6) δ 10.98 (s, 1H), 8.53 (s, 1H), 8.03-7.92 (m, 1H), 7.61 (d, J = 7.7 Hz, 1H), 7.38 (s, 1H), 7.29 (d, J = 7.8 Hz, 1H), 7.26 (dd, J = 7.8, 3.6 Hz, 1H), 5.10 (ddd, J = 13.2, 5.2, 1.6 Hz, 1H), 4.41 (d, J = 17.0 Hz, 1H), 4.28 (d, J = 17.2 Hz, 1H), 4.22-3.88 (m, 2H), 3.35 3.19 (m, 2H), 2.91 (ddd, J = 17.2, 13.6, 5.4 Hz, 1H), 2.64-2.56 (m, 1H), 2.45-2.32 (m, 2H), 2.12-1.95 (m, 2H), 1.75-1.58 (m, 2H), 1.58-1.46 (m, 2H), 1.29-0.85 (m, 4H). | 3-fluoro-pyridine-2-carbal-dehyde |
| 51 | 3-(5-(((1R,2S)-2-(((5-fluoropyridin-3-yl)methyl)amino)cyclohexyl)methyl)-1-oxoisoindolin-2-yl)piperidine-2,6-dione | 465.3 | ¹H NMR (400 MHz, DMSO-d6) δ 10.99 (s, 1H), 8.98 (s, 1H), 8.71 (s, 1H), 8.67 (d, J = 2.8 Hz, 1H), 8.64 (s, 1H), 7.96 (d, J = 9.6 Hz, 1H), 7.68 (d, J = 7.7 Hz, 1H), 7.44 (s, 1H), 7.39-7.30 (m, 1H), 5.76 (s, 1H), 5.11 (dd, J = 13.3, 5.1 Hz, 1H), 4.44 (dd, J = 17.3, 5.3 Hz, 1H), 4.31 (dd, J = 17.2, 5.0 Hz, 1H), 3.25 (dd, J = 13.5, 4.0 Hz, 1H), 3.07 (s, 1H), 2.92 (ddd, J = 18.1, 13.6, 5.4 Hz, 1H), 2.63 (t, J = 17.3 Hz, 1H), 2.46-2.34 (m, 1H), 2.16 (d, J = 12.7 Hz, 1H), 1.99 (dd, J = 12.4, 6.0 Hz, 1H), 1.74 (d, J = 12.4 Hz, 1H), 1.65-1.46 (m, 3H), 1.42-1.00 (m, 3H). | 5-fluoro-pyridine-3-carbal-dehyde |
| 52 | 3-(5-(((1R,2S)-2-(cyclopentylamino)cyclohexyl)methyl)-1-oxoisoindolin-2-yl)piperidine-2,6-dione | 424.3 | ¹H NMR (400 MHz, DMSO-d6) δ 10.99 (s, 1H), 8.52 (s, 1H), 8.12 (s, 1H), 7.70 (d, J = 7.7 Hz, 1H), 7.45 (s, 1H), 7.39-7.31 (m, 1H), 5.11 (dd, J = 13.3, 5.1 Hz, 1H), 4.51-4.27 (m, 2H), 3.69 (s, 1H), 3.26 (d, J = 13.0 Hz, 1H), 2.92 (ddd, J = 17.9, 14.1, 5.9 Hz, 2H), 2.70-2.56 (m, 1H), 2.47-2.31 (m, 2H), 2.17-1.92 (m, 4H), 1.88 (d, J = 19.1 Hz, 1H), 1.78-1.64 (m, 0H), 1.64-1.20 (m, 7H), 1.07 (q, J = 10.1 Hz, 2H). | cyclo-pentanone |
| 53 | 3-(5-(((1R,2S)-2-(cyclohexylamino)cyclohexyl)methyl)-1-oxoisoindolin-2-yl)piperidine-2,6-dione | 410.3 | ¹H NMR (400 MHz, DMSO-d6) δ 10.99 (s, 1H), 8.21 (s, 1H), 7.91 (s, 1H), 7.70 (d, J = 7.8 Hz, 1H), 7.44 (s, 1H), 7.36 (d, J = 8.0 Hz, 1H), 5.76 (s, 1H), 5.11 (dd, J = 13.2, 5.1 Hz, 1H), 4.67-4.18 (m, 2H), 3.42-3.03 (m, 3H), 2.92 (ddd, J = 18.2, 13.6, 5.2 Hz, 1H), 2.72-2.56 (m, 1H), 2.45-2.21 (m, 1H), 2.25-1.91 (m, 4H), 1.76 (dd, J = 72.3, 42.1 Hz, 4H), 1.59-0.87 (m, 12H). | cyclo-hexanone |
| 54 | 3-(5-(((1R,6S)-6-(isopropylamino)cyclohex-3-en-1-yl)methyl)-1-oxoisoindolin-2-yl)piperidine-2,6-dione | 396.3 | ¹H NMR (400 MHz, DMSO-d6) δ 10.99 (s, 1H), 8.24 (s, 1H), 7.99 (s, 1H), 7.70 (d, J = 7.8 Hz, 1H), 7.47 (s, 1H), 7.39 (d, J = 7.8 Hz, 1H), 5.66 (q, J = 11.1 Hz, 2H), 5.11 (dd, J = 13.3, 5.1 Hz, 1H), 4.57-4.25 (m, 2H), 3.57-3.40 (m, 1H), 3.32 (s, 1H), 3.03 (dd, J = 13.2, 5.0 Hz, 1H), 2.92 (ddd, J = 18.1, 13.6, 5.4 Hz, 1H), 2.65-2.55 (m, 1H), 2.47-2.32 (m, 1H), 2.32-2.22 (m, 1H), 2.17 (d, J = 18.7 Hz, 1H), 2.00 (d, J = 15.6 Hz, 2H), 1.84 (d, J = 18.2 Hz, 1H), 1.25 (dd, J = 6.6, 2.2 Hz, 6H). | I-5, acetone |

TABLE 5-continued

| Example | Structure | ES/MS m/z | ¹H-NMR | Changes to Procedure 8: Different Reagents/ Starting Materials |
|---|---|---|---|---|
| 87 | 3-(5-(((1R,2S)-2-(cyclopentylamino)cyclohexyl)methyl)-4-fluoro-1-oxoisoindolin-2-yl)piperidine-2,6-dione | 442.3 | ¹H NMR (400 MHz, DMSO-d6) δ 11.01 (s, 1H), 8.54 (s, 1H), 8.08 (s, 1H), 7.59 (d, J = 7.6 Hz, 1H), 7.49 (t, J = 7.0 Hz, 1H), 5.12 (dd, J = 13.3, 5.1 Hz, 1H), 4.62-4.32 (m, 2H), 3.68 (s, 12H), 3.20 (d, J = 13.4 Hz, 1H), 3.05 (s, 1H), 2.92 (ddd, J = 18.1, 13.5, 5.4 Hz, 1H), 2.75-2.57 (m, 2H), 2.47-2.29 (m, 1H), 2.20-1.96 (m, 1H), 1.89 (s, 1H), 1.72 (s, 3H), 1.64-1.25 (m, 6H), 1.10 (s, 2H). | I-4; cyclopentanone |
| 88 | 3-(5-(((1R,2S)-2-(cyclohexylamino)cyclohexyl)methyl)-4-fluoro-1-oxoisoindolin-2-yl)piperidine-2,6-dione | 456.4 | ¹H NMR (400 MHz, DMSO-d6) δ 11.01 (s, 1H), 8.44 (s, 1H), 8.04 (t, J = 9.7 Hz, 1H), 7.59 (d, J = 7.7 Hz, 1H), 7.50 (t, J = 6.9 Hz, 1H), 5.12 (dd, J = 13.3, 5.1 Hz, 1H), 4.57 (dd, J = 17.4, 3.7 Hz, 1H), 4.39 (dd, J = 17.4, 3.3 Hz, 1H), 3.29-3.07 (m, 3H), 2.92 (ddd, J = 17.2, 13.6, 5.4 Hz, 1H), 2.60 (ddd, J = 13.2, 10.7, 4.7 Hz, 2H), 2.49-2.36 (m, 1H), 2.25 (t, J = 6.6 Hz, 1H), 2.16-2.06 (m, 2H), 2.00 (ddq, J = 10.5, 5.2, 2.6 Hz, 2H), 1.96-1.83 (m, 1H), 1.83-1.60 (m, 5H), 1.60-1.22 (m, 8H), 1.10 (dt, J = 19.5, 11.0 Hz, 3H). | I-4; cyclohexanone |

Procedure 9, Example 55

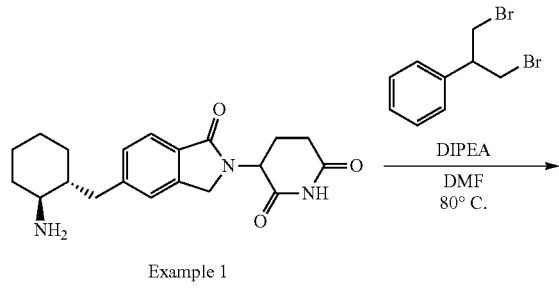

3-(1-oxo-5-(((1R,2S)-2-(3-phenylazetidin-1-yl)cyclohexyl)methyl)isoindolin-2-yl)piperidine-2,6-dione (Example 55)

Example 1 (30.0 mg, 84.4 μmmol) was taken up in DMF (1.0 mL) and (1,3-dibromopropan-2-yl)benzene (70.4 mg, 0.25 mmol) was added followed by N,N-diisopropylethylamine (88 μL, 0.51 mmol). The reaction was heated to 80° C. for 1 hour. Following this time, the reaction was complete and the reaction mixture was filtered through a syringe filter (washed with DMF) and purified directly by RP-HPLC (eluent: MeCN/water gradient with 0.1% TFA) to yield the product (Example 55) as the trifluoracetate salt. ES/MS: 472.2 (M+H⁺). ¹H NMR (400 MHz, DMSO-d6) δ 10.99 (s, 1H), 7.68 (d, J=7.8 Hz, 1H), 7.61-7.51 (m, 2H), 7.51-7.22 (m, 5H), 5.77 (s, 1H), 5.63 (s, 1H), 5.12 (dd, J=13.2, 5.1 Hz, 1H), 4.44 (dd, J=17.3, 2.8 Hz, 1H), 4.31 (dd, J=17.4, 4.2 Hz, 1H), 4.24-4.11 (m, 1H), 3.20-2.79 (m, 3H), 2.71-2.56 (m, 1H), 2.50-2.24 (m, 2H), 2.19-1.87 (m, 3H), 1.82-1.63 (m, 1H), 1.53 (q, J=14.2, 12.3 Hz, 3H), 1.28 (d, J=14.6 Hz, 1H), 1.04 (dq, J=22.0, 11.1 Hz, 2H).

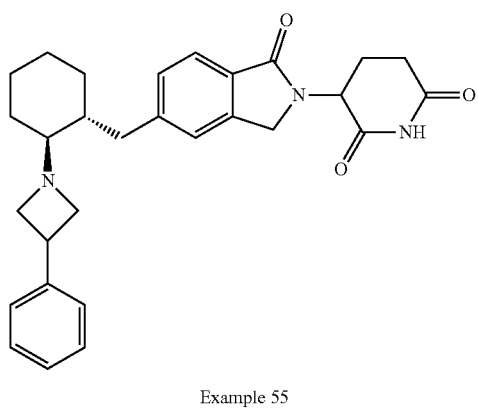

Example 55

Procedure 10, Example 56

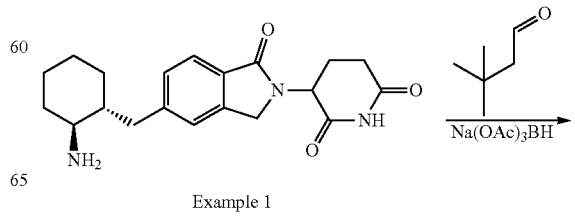

Example 1

-continued

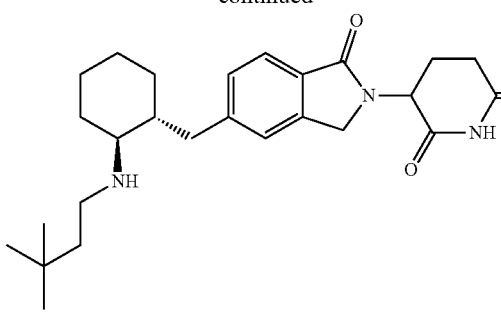

Example 56

3-(5-(((1R,2S)-2-((3,3-dimethylbutyl)amino)cyclohexyl)methyl)-1-oxoisoindolin-2-yl)piperidine-2,6-dione (Example 56)

3,3-dimethylbutanal (17 mg, 0.169 mmol), glacial acetic acid (0.024 ml, 0.422 mmol), and Na(OAc)₃BH (89 mg, 0.422 mmol) were added to a stirring solution of Example 1 (50 mg, 0.141 mmol) in dichloroethane (5 mL). The resulting mixture was stirred o/n at r.t. then diluted with $CH_2Cl_2$.

The organic layer was washed with saturated aqueous $NaHCO_3$ and brine, then dried over $Na_2SO_4$ and concentrated to give the crude product. Purification by RP-HPLC chromatography (eluent: MeCN/water gradient with 0.1% TFA) afforded the title compound (Example 56). ES/MS: 440.4 (M+H⁺). ¹H NMR (400 MHz, DMSO-d) δ 10.99 (s, 1H), 8.45 (s, 1H), 8.21 (s, 1H), 7.69 (d, J=7.7 Hz, 1H), 7.44 (s, 1H), 7.36 (dd, J=7.8, 1.4 Hz, 1H), 5.11 (dd, J=13.3, 5.1 Hz, 1H), 4.44 (dd, J=17.4, 3.4 Hz, 1H), 4.31 (dd, J=17.3, 4.0 Hz, 1H), 3.22 (dd, J=13.4, 3.7 Hz, 1H), 3.03-2.85 (m, 4H), 2.60 (d, J=17.5 Hz, 1H), 2.47-2.31 (m, 2H), 2.09 (d, J=11.2 Hz, 1H), 2.03-1.95 (m, 1H), 1.89-1.84 (m, 1H), 1.76-1.23 (m, 6H), 1.14-0.99 (m, 2H), 0.93 (s, 9H).

The following Examples were made using the general route described in Procedure 10 and are shown below in Table 6. To prepare the below Examples, different reagents/starting materials were used than some of those described in Procedure 10 and are noted in the last column of Table 6—"Changes to Procedure 10: Different Reagents/Starting Materials". A person of ordinary skill in the art will readily recognize which reagents/starting materials of Procedure 10 were replaced with the different reagents/starting materials noted below.

TABLE 6

| Example | Structure | ES/MS m/z | ¹H-NMR | Changes to Procedure 10: Different Reagents/Starting Materials |
|---|---|---|---|---|
| 57 | 3-(5-(((1R,2S)-2-(neopentylamino)cyclohexyl)methyl)-1-oxoisoindolin-2-yl)piperidine-2,6-dione | 426.4 | ¹H NMR (400 MHz, DMSO-d6) δ 10.99 (s, 1H), 8.22 (s, 1H), 8.06 (s, 1H), 7.69 (d, J = 7.7 Hz, 1H), 7.46 (s, 1H), 7.37 (dd, J = 7.8, 1.4 Hz, 1H), 5.11 (dd, J = 13.3, 5.1 Hz, 1H), 4.45 (dd, J = 17.3, 5.4 Hz, 1H), 4.31 (dd, J = 17.3, 5.4 Hz, 1H), 3.13 (dd, J = 13.4, 3.3 Hz, 1H), 3.11-2.98 (m, 1H), 3.02-2.85 (m, 3H), 2.60 (d, J = 17.1 Hz, 1H), 2.48-2.32 (m, 2H), 2.04-1.95 (m, 2H), 1.75 (d, J = 13.0 Hz, 1H), 1.53 (t, J = 22.4 Hz, 4H), 1.35-1.26 (m, 1H), 1.05 (s, 9H), 1.03-0.97 (m, 1H). | 2,2-dimethyl-propanal |
| 89 | 3-(5-(((1R,2S)-2-((3,3-dimethylbutyl)amino)cyclohexyl)methyl)-4-fluoro-1-oxoisoindolin-2-yl)piperidine-2,6-dione | 458.4 | ¹H NMR (400 MHz, DMSO-d6) δ 11.01 (s, 1H), 8.54 (s, 1H), 8.28 (s, 1H), 7.58 (d, J = 7.6 Hz, 1H), 7.47 (t, J = 7.0 Hz, 1H), 5.11 (dd, J = 13.3, 5.1 Hz, 1H), 4.56 (dd, J = 17.4, 4.6 Hz, 1H), 4.38 (dd, J = 17.3, 5.3 Hz, 1H), 3.22-3.14 (m, 1H), 3.11-2.85 (m, 3H), 2.65-2.50 (m, 2H), 2.50-2.35 (m, 1H), 2.11-1.94 (m, 2H), 1.93-1.82 (m, 1H), 1.75-1.43 (m, 5H), 1.31 (d, J = 10.8 Hz, 2H), 1.11-1.06 (m, 2H), 0.94 (s, 9H). | I-4 |

TABLE 6-continued

| Example | Structure | ES/MS m/z | ¹H-NMR | Changes to Procedure 10: Different Reagents/Starting Materials |
|---|---|---|---|---|
| 90 | 3-(5-(((1R,2S)-2-(bis(3,3-dimethylbutyl)amino)cyclohexyl)methyl)-4-fluoro-1-oxoisoindolin-2-yl)piperidine-2,6-dione | 542.5 | ¹H NMR (400 MHz, DMSO-d6) δ 11.00 (s, 1H), 8.34 (s, 1H), 7.58 (d, J = 7.6 Hz, 1H), 7.42 (t, J = 7.0 Hz, 1H), 5.12 (dd, J = 13.3, 5.1 Hz, 1H), 4.56 (dd, J = 17.4, 11.5 Hz, 1H), 4.38 (dd, J = 17.4, 11.0 Hz, 1H), 3.39-3.10 (m, 4H), 3.04-2.85 (m, 2H), 2.65-2.55 (m, 1H), 2.48-2.36 (m, 2H), 2.18 (d, J = 9.5 Hz, 1H), 2.05-1.76 (m, 4H), 1.71-1.50 (m, 5H), 1.46-1.30 (m, 2H), 1.14 (t, J = 10.4 Hz, 2H), 0.98 (d, J = 7.4 Hz, 18H). | I-4 |
| 91 | 3-(5-(((1R,2S)-2-((1,1-dioxidotetrahydro-2H-thiopyran-4-yl)amino)cyclohexyl)methyl)-1-oxoisoindolin-2-yl)piperidine-2,6-dione | 488.1 | ¹H NMR (400 MHz, DMSO-d6) δ 10.99 (s, 1H), 7.71 (d, J = 7.8 Hz, 1H), 7.44 (s, 1H), 7.36 (d, J = 7.8 Hz, 1H), 5.12 (dd, J = 13.2, 5.1 Hz, 1H), 4.46 (dd, J = 17.3, 3.9 Hz, 1H), 4.33 (dd, J = 17.3, 4.2 Hz, 1H), 3.38-3.02 (m, 4H), 3.02-2.82 (m, 2H), 2.70-2.53 (m, 1H), 2.47-2.17 (m, 8H), 2.17-1.90 (m, 3H), 1.90-1.68 (m, 2H), 1.53 (d, J = 16.4 Hz, 2H), 1.45-1.18 (m, 2H), 1.18-0.87 (m, 2H). | 1,1-dioxothian-4-one |

Procedure 11, Example 58

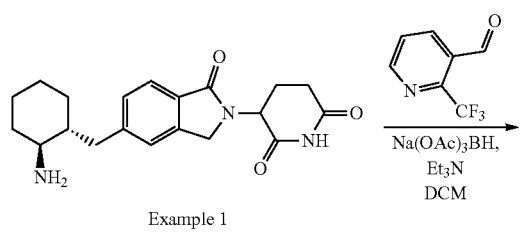

Example 1

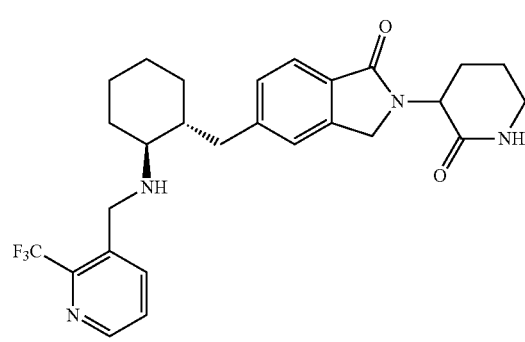

Example 58

Preparation of 3-(1-oxo-5-(((1R,2S)-2-(((2-(trifluoromethyl)pyridin-3-yl)methyl)amino)cyclohexyl)methyl)isoindolin-2-yl)piperidine-2,6-dione Example 1

(30 mg, 0.084 mmol) dissolved in dichloromethane (1 mL) was treated with 2-(trifluoromethyl)nicotinaldehyde (30 mg, 0.171 mmol), followed by triethylamine (30 μL, 0.215 mmol). The reaction mixture was stirred at room temperature for 30 min before sodium triacetoxyborohydride (60 mg, 0.283 mmol) was added and the reaction continued overnight. The reaction mixture was quenched with trifluoroacetic acid (300 μL, 3.92 mmol) and concentrated. The residue was purified by RP-HPLC to give 3-(1-oxo-5-(((1R,2S)-2-(((2-(trifluoromethyl)pyridin-3-yl)methyl)amino)cyclohexyl)methyl)isoindolin-2-yl)piperidine-2,6-dione (Example 58). ES/MS: 515.3 (M+H⁺). ¹H NMR (400 MHz, Methanol-d4) δ 8.55 (dd, J=4.7, 1.5 Hz, 1H), 8.24-8.15 (m, 1H), 7.70 (dd, J=7.8, 1.6 Hz, 1H), 7.64 (dd, J=8.0, 4.7 Hz, 1H), 7.41-7.28 (m, 2H), 5.16 (dd, J=13.3, 5.1 Hz, 1H), 4.51-4.36 (m, 2H), 4.18-4.06 (m, 1H), 3.94 (d, J=14.6 Hz, 1H), 3.49-3.39 (m, 1H), 2.96-2.86 (m, 1H), 2.80 (ddd, J=17.7, 4.7, 2.5 Hz, 1H), 2.56-2.36 (m, 2H), 2.30 (td, J=9.4, 7.3, 3.3 Hz, 1H), 2.19 (dtd, J=12.9, 5.3, 2.5 Hz, 2H), 1.78 (d, J=12.7 Hz, 1H), 1.65 (d, J=10.7 Hz, 3H), 1.36-1.11 (m, 4H), 1.03 (q, J=11.4 Hz, 1H).

The following Examples were made using the general route described in Procedure 11 and are shown below in Table 7. To prepare the below Examples, different reagents/starting materials were used than some of those described in Procedure 11 and are noted in the last column of Table 7—"Changes to Procedure 11: Different Reagents/Starting Materials". A person of ordinary skill in the art will readily recognize which reagents/starting materials of Procedure 11

TABLE 7

| Example | Structure | ES/MS m/z | 1H-NMR | Changes to Procedure 11: Different Reagents/Starting Materials |
|---|---|---|---|---|
| 59 | 3-(1-oxo-5-(((1R,2S)-2-((pyrazin-2-ylmethyl)amino)cyclohexyl)methyl)isoindolin-2-yl)piperidine-2,6-dione | 448.3 | $^1$H NMR (400 MHz, Methanol-d4) δ 8.75 (dd, J = 3.0, 1.1 Hz, 1H), 8.67 (t, J = 1.4 Hz, 2H), 7.76 (d, J = 7.8 Hz, 1H), 7.47 (s, 1H), 7.44-7.32 (m, 1H), 5.18 (ddd, J = 13.4, 5.2, 3.9 Hz, 1H), 4.66-4.54 (m, 2H), 4.53-4.43 (m, 2H), 3.19 (dq, J = 9.6, 5.2 Hz, 2H), 2.97-2.87 (m, 1H), 2.81 (ddd, J = 17.6, 4.7, 2.5 Hz, 1H), 2.62 (ddd, J = 13.5, 9.7, 3.9 Hz, 1H), 2.50 (tdd, J = 13.4, 4.8, 2.4 Hz, 1H), 2.32-2.18 (m, 2H), 2.15 (d, J = 24.1 Hz, 1H), 1.87 (d, J = 12.6 Hz, 1H), 1.79-1.59 (m, 3H), 1.48 (q, J = 11.5 Hz, 1H), 1.27 (dq, J = 18.8, 9.8 Hz, 2H). | pyrazine-2-carbaldehyde |
| 60 | 3-(5-(((1R,2S)-2-(((1,3-dioxolan-2-yl)methyl)amino)cyclohexyl)methyl)-1-oxoisoindolin-2-yl)piperidine-2,6-dione | 442.3 | $^1$H NMR (400 MHz, Methanol-d4) δ 7.78 (t, J = 6.9 Hz, 1H), 7.51-7.37 (m, 2H), 5.19 (d, J = 5.5 Hz, 1H), 4.50 (t, J = 6.2 Hz, 2H), 4.17-3.93 (m, 4H), 3.53-3.39 (m, 2H), 3.25-3.13 (m, 2H), 2.92 (tt, J = 12.1, 5.9 Hz, 1H), 2.80 (d, J = 17.3 Hz, 1H), 2.50 (q, J = 14.1, 13.1 Hz, 2H), 2.26-2.08 (m, 2H), 1.93 (d, J = 60.2 Hz, 2H), 1.64 (d, J = 22.7 Hz, 3H), 1.44 (d, J = 12.1 Hz, 1H), 1.15 (s, 2H). | I-6 |
| 92 | 3-(5-(((2R,3S)-3-((4,4-difluorocyclohexyl)amino)tetrahydro-2H-pyran-2-yl)methyl)-1-oxoisoindolin-2-yl)piperidine-2,6-dione | 476.3 | $^1$H NMR (400 MHz, Methanol-d4) δ 7.78 (d, J = 7.8 Hz, 1H), 7.54 (s, 1H), 7.51-7.44 (m, 1H), 5.18 (dd, J = 13.3, 5.2 Hz, 1H), 4.56-4.44 (m, 2H), 3.94 (d, J = 11.6 Hz, 1H), 3.82 (dt, J = 6.7, 3.4 Hz, 1H), 3.56-3.40 (m, 2H), 3.24 (d, J = 14.1 Hz, 1H), 3.09 (dd, J = 14.2, 9.8 Hz, 1H), 2.91 (dd, J = 13.3, 5.3 Hz, 1H), 2.81 (ddd, J = 17.5, 4.7, 2.4 Hz, 1H), 2.56-2.48 (m, 1H), 2.40 (d, J = 12.4 Hz, 1H), 2.30-2.12 (m, 5H), 2.08-1.68 (m, 8H). | I-11; 4,4-difluoro-cyclohexanone |
| 93 | 3-(1-oxo-5-(((1R,2S)-2-(phenethylamino)cyclohexyl)methyl)isoindolin-2-yl)piperidine-2,6-dione | 515.3 | $^1$H NMR (400 MHz, Methanol-d4) δ 8.55 (dd, J = 4.7, 1.5 Hz, 1H), 8.24-8.15 (m, 1H), 7.70 (dd, J = 7.8, 1.6 Hz, 1H), 7.64 (dd, J = 8.0, 4.7 Hz, 1H), 7.41-7.28 (m, 2H), 5.16 (dd, J = 13.3, 5.1 Hz, 1H), 4.51-4.36 (m, 2H), 4.18-4.06 (m, 1H), 3.94 (d, J = 14.6 Hz, 1H), 3.49-3.39 (m, 1H), 2.96-2.86 (m, 1H), 2.80 (ddd, J = 17.7, 4.7, 2.5 Hz, 1H), 2.56-2.36 (m, 2H), 2.30 (td, J = 9.4, 7.3, 3.3 Hz, 1H), 2.19 (dtd, J = 12.9, 5.3, 2.5 Hz, 2H), 1.78 (d, J = 12.7 Hz, 1H), 1.65 (d, J = 10.7 Hz, 3H), 1.36-1.11 (m, 4H), 1.03 (q, J = 11.4 Hz, 1H). | 2-phenyl-acetaldehyde |
| 94 | 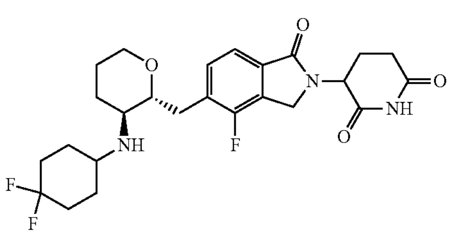 [SMILES: O=C1CCC(N2Cc3cc(C[C@H]4OCCC[C@@H]4NC4CCC(F)(F)CC4)ccc3C2=O)C(=O)N1] | 494.3 | $^1$H NMR (400 MHz, Methanol-d4) δ 7.62 (d, J = 7.7 Hz, 1H), 7.58-7.50 (m, 1H), 5.18 (ddd, J = 13.4, 5.2, 2.4 Hz, 1H), 4.64-4.49 (m, 2H), 3.96-3.82 (m, 2H), 3.55 (d, J = 12.2 Hz, 1H), 3.46-3.36 (m, 2H), 3.18-3.10 (m, 1H), 2.96-2.87 (m, 1H), 2.81 (ddd, J = 17.5, 4.6, 2.4 Hz, 1H), 2.52 (dt, J = 13.0, 7.0 Hz, 1H), 2.39 (s, 1H), 2.32-2.10 (m, 5H), 2.10-1.63 (m, 9H). | I-12; 4,4-difluoro-cyclohexanone |

TABLE 7-continued

| Example | Structure | ES/MS m/z | ¹H-NMR | Changes to Procedure 11: Different Reagents/Starting Materials |
|---|---|---|---|---|
| 95 | 3-(5-(((2R,3S)-3-((4,4-difluorocyclohexyl)amino)tetrahydro-2H-pyran-2-yl)methyl)-4-fluoro-1-oxoisoindolin-2-yl)piperidine-2,6-dione<br><br>3-(5-(((2R,3S)-3-(cyclohexylamino)tetrahydro-2H-pyran-2-yl)methyl)-1-oxoisoindolin-2-yl)piperidine-2,6-dione | 440.3 | ¹H NMR (400 MHz, Methanol-d4) δ 7.77 (d, J = 7.8 Hz, 1H), 7.54 (s, 1H), 7.48 (dd, J = 7.9, 1.4 Hz, 1H), 5.17 (dd, J = 13.3, 5.2 Hz, 1H), 4.54-4.42 (m, 2H), 3.92 (d, J = 11.9 Hz, 1H), 3.80 (ddt, J = 9.6, 6.1, 3.0 Hz, 1H), 3.46-3.38 (m, 1H), 3.10-3.02 (m, 1H), 2.96-2.88 (m, 1H), 2.80 (ddd, J = 17.6, 4.7, 2.4 Hz, 1H), 2.51 (dd, J = 13.2, 4.8 Hz, 1H), 2.41-2.30 (m, 1H), 2.25-2.04 (m, 3H), 1.96-1.61 (m, 8H), 1.55-1.19 (m, 7H). | I-11; cyclohexanone |

Procedure 12, Example 61

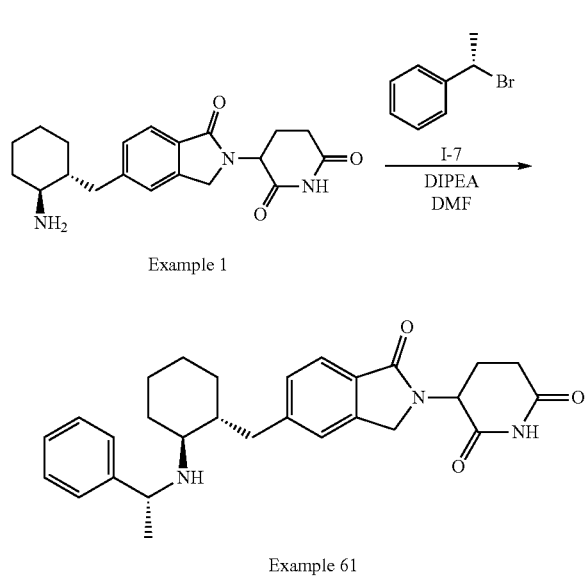

Example 1

Example 61

3-(1-oxo-5-(((1R,2S)-2-(((R)-1-phenylethyl)amino)cyclohexyl)methyl)isoindolin-2-yl)piperidine-2,6-dione (Example 61). Example 1 (30 mg, 0.084 mmol) dissolved in dimethylformamide (1 mL) was treated with I-7 (18 mg, 0.097 mmol) followed by N,N-diisopropylethylamine (30 μL, 0.172 mmol). The reaction mixture was heated at 80° C. for 4 h. After cooling to room temperature, the reaction mixture was concentrated. The residue was purified by RP-HPLC to give 3-(1-oxo-5-(((1R,2S)-2-(((R)-1-phenylethyl)amino) cyclohexyl)methyl)isoindolin-2-yl)piperidine-2,6-dione (Example 61). ES/MS: 460.2 (M+H⁺). ¹H NMR (400 MHz, Methanol-d4) δ 7.72 (td, J=14.2, 7.6 Hz, 1H), 7.55 (d, J=6.9 Hz, 1H), 7.49-7.21 (m, 6H), 5.19 (dt, J=13.3, 5.0 Hz, 1H), 4.60-4.50 (m, 1H), 4.51-4.38 (m, 2H), 3.22-3.07 (m, 2H), 2.95 (ddd, J=18.1, 13.8, 6.3 Hz, 2H), 2.81 (d, J=16.2 Hz, 1H), 2.68-2.42 (m, 2H), 2.21 (s, 1H), 2.08 (s, 1H), 2.01-1.91 (m, 1H), 1.85-1.52 (m, 6H), 1.52-1.24 (m, 4H).

The following Examples were made using the general route described in Procedure 12 and are shown below in Table 8. To prepare the below Examples, different reagents/starting materials were used than some of those described in Procedure 12 and are noted in the last column of Table 8—"Changes to Procedure 12: Different Reagents/Starting Materials". A person of ordinary skill in the art will readily recognize which reagents/starting materials of Procedure 12

TABLE 8

| Example | Structure | | ES/MS m/z | ¹H-NMR | Changes to Procedure 12: Different Reagents/ Starting Materials |
|---|---|---|---|---|---|
| 62 | 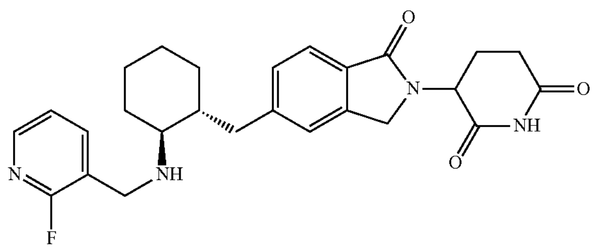 | 3-(5-(((1R,2S)-2-(((2-fluoropyridin-3-yl)methyl)amino)cyclohexyl)methyl)-1-oxoisoindolin-2-yl)piperidine-2,6-dione | 465.3 | ¹H NMR (400 MHz, Methanol-d4) δ 8.39-8.30 (m, 1H), 8.15-8.04 (m, 1H), 7.82-7.72 (m, 1H), 7.53-7.35 (m, 3H), 5.24-5.11 (m, 1H), 4.58-4.34 (m, 4H), 3.25-3.14 (m, 2H), 2.97-2.87 (m, 1H), 2.81 (ddd, J = 17.6, 4.6, 2.4 Hz, 1H), 2.62-2.45 (m, 2H), 2.33-2.17 (m, 2H), 2.11 (s, 1H), 1.87 (s, 1H), 1.80-1.61 (m, 3H), 1.51 (d, J = 9.8 Hz, 1H), 1.34-1.13 (m, 2H). | 3-(bromomethyl)-2-fluoropyridine |
| 63 | 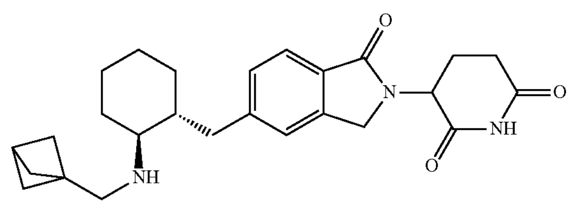 | 3-(5-(((1R,2S)-2-((bicyclo[1.1.1]pentan-1-yl)methyl)amino)cyclohexyl)methyl)-1-oxoisoindolin-2-yl)piperidine-2,6-dione | 436.4 | ¹H NMR (400 MHz, DMSO-d6) δ 10.99 (s, 1H), 8.47 (s, 1H), 8.33 (s, 1H), 7.69 (d, J = 7.8 Hz, 1H), 7.45 (s, 1H), 7.36 (dd, J = 7.8, 1.4 Hz, 1H), 5.11 (dd, J = 13.3, 5.1 Hz, 1H), 4.51-4.24 (m, 2H), 3.14 (q, J = 6.7, 5.4 Hz, 3H), 3.07-2.85 (m, 2H), 2.66-2.57 (m, 1H), 2.39 (qd, J = 13.3, 12.8, 6.8 Hz, 2H), 2.08-1.95 (m, 2H), 1.86 (d, J = 1.0 Hz, 6H), 1.72 (d, J = 12.4 Hz, 1H), 1.63 (s, 2H), 1.57-1.21 (m, 4H), 1.06 (d, J = 9.3 Hz, 2H). | 1-(bromomethyl)bicyclo[1.1.1] pentane |

TABLE 8-continued

| Example | Structure | ES/MS m/z | ¹H-NMR | Changes to Procedure 12: Different Reagents/ Starting Materials |
|---|---|---|---|---|
| 64 | 3-(5-(((1R,2S)-2-((2-methoxyethyl)amino)cyclohexyl)methyl)-1-oxoisoindolin-2-yl)piperidine-2,6-dione | 428.3 | ¹H NMR (400 MHz, DMSO-d6) δ 10.99 (s, 1H), 8.52 (s, 1H), 8.31 (s, 1H), 7.69 (d, J = 7.7 Hz, 1H), 7.45 (s, 1H), 7.37 (dd, J = 7.8, 1.3 Hz, 1H), 5.11 (dd, J = 13.2, 5.1 Hz, 1H), 4.50-4.23 (m, 2H), 3.70-3.62 (m, 2H), 3.52 (q, J = 7.0 Hz, 2H), 3.23 (dd, J = 14.9, 11.7 Hz, 2H), 3.01 (s, 1H), 2.97-2.81 (m, 1H), 2.65-2.55 (m, 1H), 2.46-2.28 (m, 2H), 2.12-1.94 (m, 2H), 1.88 (d, J = 10.0 Hz, 1H), 1.72 (d, J = 12.8 Hz, 1H), 1.46 (td, J = 22.4, 20.2, 9.7 Hz, 3H), 1.28 (d, J = 11.7 Hz, 1H), 1.15 (t, J = 7.0 Hz, 3H), 1.03 (q, J = 10.3 Hz, 2H). | 1-bromo-2-ethoxy-ethane |
| 65 | 3-(5-(((1R,2S)-2-((2-(2-chlorophenoxy)ethyl)amino)cyclohexyl)methyl)-1-oxoisoindolin-2-yl)piperidine-2,6-dione | 510.3 | ¹H NMR (400 MHz, DMSO-d6) δ 10.99 (s, 1H), 8.80 (s, 1H), 8.61 (d, J = 10.9 Hz, 1H), 7.67 (d, J = 7.8 Hz, 1H), 7.46 (dd, J = 7.9, 1.6 Hz, 1H), 7.43 (s, 1H), 7.36 (ddd, J = 7.8, 4.7, 1.8 Hz, 2H), 7.22 (dd, J = 8.4, 1.3 Hz, 1H), 7.03 (td, J = 7.7, 1.3 Hz, 1H), 5.11 (dd, J = 13.3, 5.1 Hz, 1H), 4.51-4.22 (m, 4H), 3.56 (d, J = 8.4 Hz, 2H), 3.30 (dd, J = 13.3, 3.5 Hz, 1H), 3.17 (s, 1H), 3.01-2.83 (m, 1H), 2.63 (td, J = 16.0, 14.4, 2.8 Hz, 1H), 2.40 (dtd, J = 26.4, 13.3, 12.2, 6.6 Hz, 2H), 2.22-2.09 (m, 1H), 2.06-1.85 (m, 2H), 1.75 (d, J = 13.0 Hz, 1H), 1.51 (dq, J = 21.1, 11.2 Hz, 3H), 1.30 (dd, J = 14.2, 10.1 Hz, 1H), 1.05 (q, J = 11.4, 10.1 Hz, 2H). | 1-(2-bromoethoxy)-2-chlorobenzene |

TABLE 8-continued

| Example | Structure | ES/MS m/z | ¹H-NMR | Changes to Procedure 12: Different Reagents/ Starting Materials |
|---|---|---|---|---|
| 96 | 3-(5-(((1R,2S)-2-((bicyclo[1.1.1]pentan-1-ylmethyl)amino)cyclohexyl)methyl)-4-fluoro-1-oxoisoindolin-2-yl)piperidine-2,6-dione | 454.3 | ¹H NMR (400 MHz, DMSO-d6) δ 11.01 (s, 1H), 8.53 (s, 1H), 8.39 (s, 1H), 7.58 (d, J = 7.6 Hz, 1H), 7.49 (t, J = 7.0 Hz, 1H), 5.12 (dd, J = 13.3, 5.1 Hz, 1H), 4.47 (ddd, J = 69.9, 17.4, 5.8Hz, 2H), 3.10 (t, J = 10.9 Hz, 4H), 2.92 (ddd, J = 18.0, 13.5, 5.5 Hz, 1H), 2.66-2.56 (m, 1H), 2.43 (dd, J = 13.2, 4.5 Hz, 1H), 2.06-1.95 (m, 2H), 1.87 (s, 7H), 1.72 (d, J = 12.9 Hz, 1H), 1.61-1.39 (m, 3H), 1.31 (d, J = 11.7 Hz, 1H), 1.08 (d, J = 8.5 Hz, 2H). | I-4; 1-(bromomethyl)bicyclo[1.1.1]pentane |
| 97 | 3-(1-oxo-5-(((1R,2S)-2-((phenylmethyl-d₂)amino)cyclohexyl)methyl)isoindolin-2-yl)piperidine-2,6-dione | 448.3 | ¹H NMR (400 MHz, DMSO-d6) δ 10.99 (s, 1H), 8.91 (dd, J = 12.4, 6.0 Hz, 1H), 8.67 (d, J = 12.6 Hz, 1H), 7.66 (dd, J = 7.7, 1.4 Hz, 1H), 7.61-7.50 (m, 3H), 7.50-7.38 (m, 3H), 7.37-7.29 (m, 1H), 5.11 (dd, J = 13.3, 5.1 Hz, 1H), 4.50-4.25 (m, 2H), 3.20 (dd, J = 13.4, 4.1 Hz, 1H), 3.01-2.83 (m, 2H), 2.69-2.54 (m, 1H), 2.47-2.31 (m, 2H), 2.14 (d, J = 12.8 Hz, 1H), 2.05-1.87 (m, 2H), 1.72 (d, J = 12.6 Hz, 1H), 1.56 (d, J = 17.2 Hz, 3H), 1.36-1.19 (m, 1H), 1.07 (dt, J = 18.6, 11.4 Hz, 2H). | I-4; 1-(bromomethyl-d₂)benzene |

TABLE 8-continued

| Example | Structure | ES/MS m/z | ¹H-NMR | Changes to Procedure 12: Different Reagents/ Starting Materials |
|---|---|---|---|---|
| 98 | 3-(1-oxo-5-((((1R,2S)-2-(((phenyl-d5)methyl-d2)amino)cyclohexyl)methyl)isoindolin-2-yl)piperidine-2,6-dione | 453.4 | ¹H NMR (400 MHz, DMSO-d6) δ 10.99 (s, 1H), 8.89 (d, J = 11.2 Hz, 1H), 8.65 (d, J = 12.5 Hz, 1H), 7.66 (dd, J = 7.9, 1.4 Hz, 1H), 7.41 (s, 1H), 7.33 (d, J = 7.8 Hz, 1H), 5.11 (dd, J = 13.3, 5.1 Hz, 1H), 4.48-4.24 (m, 2H), 3.20 (dd, J = 13.3, 4.1 Hz, 1H), 2.99-2.86 (m, 2H), 2.63 (t, J = 16.2 Hz, 1H), 2.46-2.31 (m, 1H), 2.14 (d, J = 12.7 Hz, 1H), 2.07-1.89 (m, 2H), 1.71 (s, 1H), 1.56 (d, J = 16.8 Hz, 3H), 1.35-1.20 (m, 2H), 1.20-0.92 (m, 2H). | 1-(bromomethyl-d2)benzene-2,3,4,5,6-d5 |
| 99 | 3-(5-(((1R,2S)-2-(((4,4-difluorocyclohexyl)methyl)amino)cyclohexyl)methyl)-4-fluoro-1-oxoisoindolin-2-yl)piperidine-2,6-dione | 506.1 | ¹H NMR (400 MHz, DMSO-d6) δ 11.01 (s, 1H), 7.59 (d, J = 7.6 Hz, 1H), 7.51 (q, J = 7.7, 7.1 Hz, 1H), 5.12 (dd, J = 13.2, 5.1 Hz, 1H), 4.56 (dt, J = 17.4, 5.4 Hz, 1H), 4.39 (dt, J = 17.1, 5.8 Hz, 1H), 3.21-2.74 (m, 4H), 2.76-2.52 (m, 2H), 2.45-2.21 (m, 1H), 2.21-1.62 (m, 7H), 1.42 (ddd, J = 54.1, 29.5, 16.6 Hz, 9H), 1.07 (t, J = 9.4 Hz, 2H). | I-4; 4-(bromomethyl)-1,1-difluoro-cyclohexane |

Procedure 13, Example 66

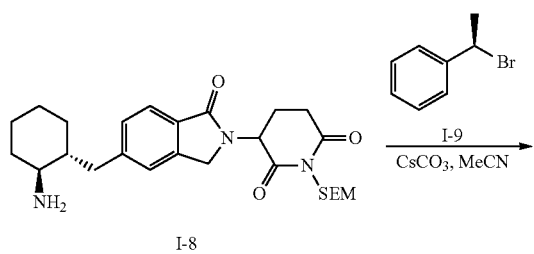

I-8

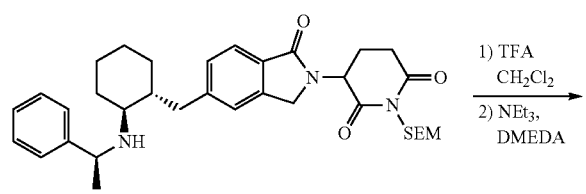

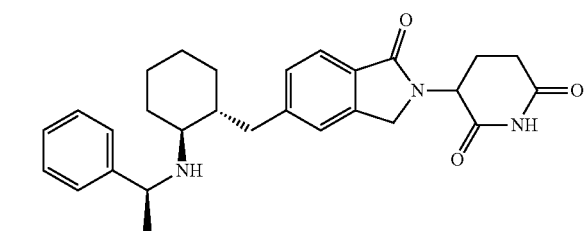

Example 66

Step 1: Preparation of 3-(1-oxo-5-((((1R,2S)-2-(((S)-1-phenylethyl)amino) cyclohexyl)methyl)isoindolin-2-yl)-1-((2-(trimethylsilyl)ethoxy)methyl)piperidine-2,6-dione I-8

(40 mg, 0.082 mmol) dissolved in acetonitrile (1 mL) was treated with I-9 (20 mg, 0.108 mmol) followed by cesium carbonate (80 mg, 0.246 mmol). The reaction mixture was heated at 50° C. overnight. After cooling to room temperature, the reaction mixture was diluted with ethyl acetate and washed with water. The organic layer was dried over sodium sulfate and filtered. The filtrate was concentrated in vacuo and the residue was purified by column chromatography to give 3-(1-oxo-5-((((1R,2S)-2-(((S)-1-phenylethyl)amino)cyclohexyl)methyl)isoindolin-2-yl)-1-((2-(trimethylsilyl)ethoxy)methyl)piperidine-2,6-dione.

Step 2: Preparation of 3-(1-oxo-5-((((1R,2S)-2-(((S)-1-phenylethyl)amino) cyclohexyl)methyl)isoindolin-2-yl)piperidine-2,6-dione (Example 66)

3-(1-oxo-5-((((1R,2S)-2-(((S)-1-phenylethyl)amino)cyclohexyl)methyl)isoindolin-2-yl)-1-((2-(trimethylsilyl)ethoxy)methyl)piperidine-2,6-dione (15 mg, 0.025 mmol) dissolved in dichloromethane (1 mL) was treated with trifluoroacetic acid (100 μL, 1.31 mmol). The reaction mixture was stirred at room temperature for 1 h and then concentrated in vacuo. The residue was then dissolved in dichloromethane, cooled to 0° C., and treated with triethylamine (20 μL, 0.142 mmol) followed by N,N'-dimethylethylenediamine (10 μL, 0.093 mmol). The reaction mixture was warmed to room temperature and stirred for 1 hour. The reaction mixture was concentrated in vacuo and purified by RP-HPLC to give 3-(1-oxo-5-((((1R,2S)-2-(((S)-1-phenylethyl)amino) cyclohexyl)methyl)isoindolin-2-yl)piperidine-2,6-dione (Example 66) as the trifluoroacetate salt. ES/MS: 460.2 (M+H$^+$). $^1$H NMR (400 MHz, Methanol-d4) δ 7.74 (dd, J=14.5, 7.8 Hz, 1H), 7.48-7.22 (m, 8H), 5.19 (dt, J=13.3, 4.8 Hz, 1H), 4.60-4.37 (m, 4H), 3.12 (d, J=6.3 Hz, 2H), 3.03-2.88 (m, 2H), 2.85-2.78 (m, 1H), 2.66-2.49 (m, 2H), 2.22 (d, J=6.3 Hz, 1H), 2.05 (d, J=17.6 Hz, 2H), 1.79-1.55 (m, 8H), 1.33 (s, 3H).

Procedure 14, Example 67

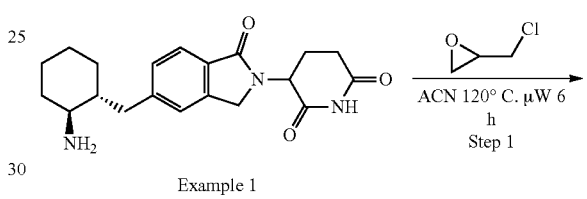

Example 1

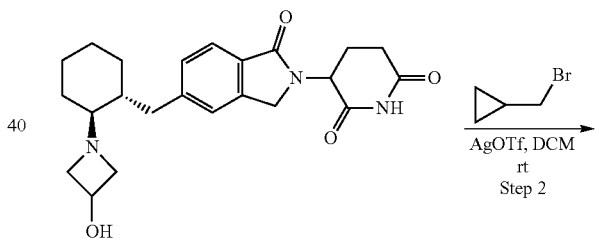

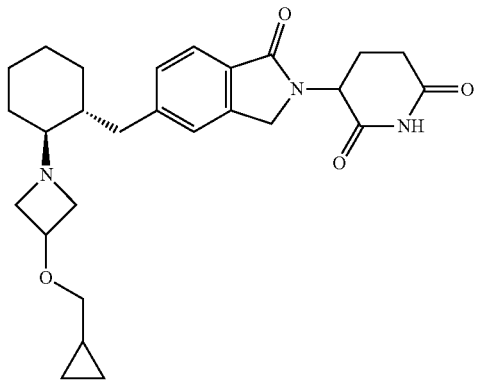

Example 67

Step 1: Preparation of 3-(5-(((1R,2S)-2-(3-hydroxyazetidin-1-yl)cyclohexyl)methyl)-1-oxoisoindolin-2-yl)piperidine-2,6-dione To a solution of Example 1 (200 mg, 0.563 mmol) in acetonitrile (4.0 mL) was added epichlorohydrin (0.521 g, 0.563 mmol) the resulting mixture was stirred at 120° C. under microwave irradiation for 6 h. The residue was taken up in DMSO and purified directly by RP-HPLC (eluent: MeCN/water gradient with 0.1% TFA) to yield the product 3-(5-(((1R,2S)-2-(3-hydroxyazetidin-1-yl)cyclohexyl)methyl)-1-oxoisoindolin-2-yl)piperidine-2,6-dione as the trifluoracetate salt. ES/MS m/z: 412.3 (M+H$^+$).

Step 2: Preparation of 3-(5-(((1R,2S)-2-(3-(cyclopropylmethoxy)azetidin-1-yl)cyclohexyl)methyl)-1-oxo-isoindolin-2-yl)piperidine-2,6-dione (Example 67)

To 3-(5-(((1R,2S)-2-(3-hydroxyazetidin-1-yl)cyclohexyl)methyl)-1-oxoisoindolin-2-yl)piperidine-2,6-dione (70.0 mg, 0.170 mmol) (mixed with silica in a 1:1 ratio) in dichloromethane (1.00 mL) was added silver trifluoromethanesulfonate (43.7 mg, 0.170 mmol), and the resulting mixture was stirred at r.t. for 12 h. The reaction mixture was then diluted with dichloromethane, filtered, and concentrated to dryness. The material was taken up in DMSO and TFA was added then the sample was purified directly by RP-HPLC (eluent: MeCN/water gradient with 0.1% TFA) to yield (Example 67) as the trifluoroacetate salt. ES/MS m/z: 466.4 (M+H$^+$). $^1$H NMR (400 MHz, DMSO-d6) δ 10.99 (s, 1H), 9.89 (d, J=242.8 Hz, 1H), 7.69 (d, J=7.7 Hz, 1H), 7.44 (d, J=9.2 Hz, 1H), 7.36 (t, J=8.2 Hz, 1H), 5.11 (dd, J=13.3, 5.1 Hz, 1H), 4.56-4.15 (m, 5H), 4.10 (q, J=7.9 Hz, 1H), 4.06-3.93 (m, 1H), 3.37 (ddt, J=13.2, 7.7, 4.4 Hz, 1H), 3.27-3.07 (m, 1H), 3.04-2.89 (m, 2H), 2.71-2.56 (m, 2H), 2.47-2.31 (m, 1H), 2.22-2.06 (m, 2H), 2.04-1.77 (m, 4H), 1.66 (dq, J=12.4, 9.5, 8.8 Hz, 2H), 1.58-1.25 (m, 5H), 1.24-0.92 (m, 2H).

Procedure 15, Example 68

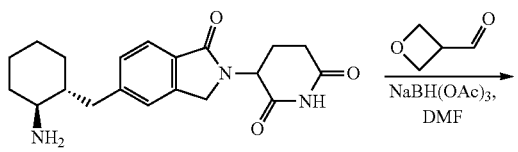

Example 1

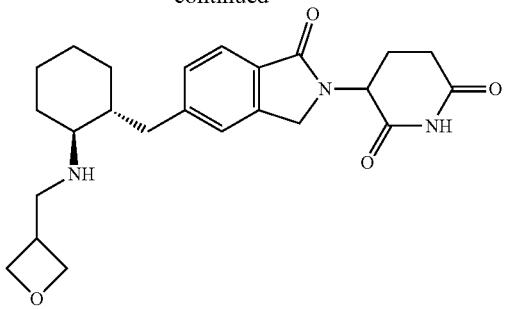

Example 68

3-(5-(((1R,2S)-2-((oxetan-3-ylmethyl)amino)cyclohexyl)methyl)-1-oxoisoindolin-2-yl)piperidine-2,6-dione To a solution of Example 1 (50.0 mg, 0.141 mmol) in DMF (1.0 mL) was added oxetane-3-carbaldehyde (0.0121 g, 0.141 mmol) and the resulting solution was stirred for 30 min. Following this time, sodium triacetoxyborohydride (89.4 mg, 0.422 mmol) was added and the reaction stirred overnight at r.t. The reaction mixture was diluted with DMSO and TFA and purified directly by RP-HPLC (eluent: MeCN/water gradient with 0.1% TFA) to yield (Example 68) as the trifluoroacetate salt. ES/MS: 426.3 (M+H$^+$). $^1$H NMR (400 MHz, DMSO-d6) δ 10.99 (s, 1H), 8.31 (d, J=87.9 Hz, 2H), 7.70 (d, J=7.7 Hz, 1H), 7.44 (d, J=5.9 Hz, 1H), 7.43-7.29 (m, 1H), 5.11 (dd, J=13.3, 5.1 Hz, 1H), 4.69 (dd, J=7.4, 6.2 Hz, 2H), 4.52-4.16 (m, 4H), 3.41-327 (m, 3H), 3.24-3.13 (m, 1H), 3.00 (s, 1H), 2.92 (ddd, J=17.4, 13.7, 5.5 Hz, 1H), 2.71-2.56 (m, 1H), 2.47-2.34 (m, 2H), 2.03 (td, J=15.3, 12.5, 5.3 Hz, 2H), 1.94-1.80 (m, 1H), 1.71 (d, J=12.3 Hz, 1H), 1.61-1.39 (m, 3H), 1.30 (d, J=11.7 Hz, 1H), 1.05 (dt, J=21.9, 12.0 Hz, 2H).

The following Examples were made using the general route described in Procedure 15 and are shown below in Table 9. To prepare the below Examples, different reagents/starting materials were used than some of those described in Procedure 15 and are noted in the last column of Table 9—"Changes to Procedure 15: Different Reagents/Starting Materials". A person of ordinary skill in the art will readily recognize which reagents/starting materials of Procedure 15 were replaced with the different reagents/starting materials noted below.

TABLE 9

| Example | Structure | ES/MS m/z | ¹H-NMR | Changes to Procedure 15; Different Reagents/Starting Materials |
|---|---|---|---|---|
| 69 | 3-(1-oxo-5-((((1R,2S)-2-(((tetrahydrofuran-3-yl)methyl)amino)cyclohexyl)methyl)isoindolin-2-yl)piperidine-2,6-dione | 440.3 | 1H NMR (400 MHz, DMSO-d6) δ 10.99 (s, 1H), 8.44 (s, 1H), 8.19 (s, 1H), 7.70 (d, J = 7.7 Hz, 1H), 7.45 (s, 1H), 7.37 (d, J = 7.7 Hz, 1H), 5.11 (dd, J = 13.3, 5.1 Hz, 1H), 4.53-4.23 (m, 2H), 3.79 (tdt, J = 8.2, 5.3, 2.5 Hz, 2H), 3.71-3.59 (m, 1H), 3.55-3.42 (m, 1H), 3.22 (d, J = 13.5 Hz, 1H), 3.15-2.98 (m, 4H), 2.92 (ddd, J = 17.9, 13.5, 5.5 Hz, 1H), 2.58 (dd, J = 20.1, 14.5 Hz, 2H), 2.40 (td, J = 13.3, 8.6 Hz, 1H), 2.16-1.95 (m, 3H), 1.88 (s, 1H), 1.78-1.58 (m, 2H), 1.48 (p, J = 11.4 Hz, 2H), 1.30 (d, J = 11.6 Hz, 1H), 1.04 (q, J = 11.2 Hz, 2H). | tetrahydrofuran-3-carbaldehyde |
| 70 | 3-(5-(((1R,2S)-2-(bis((tetrahydro-2H-pyran-4-yl)methyl)amino)cyclohexyl)methyl)-1-oxoisoindolin-2-yl)piperidine-2,6-dione | 552.5 | 1H NMR (400 MHz, DMSO-d6) δ 10.99 (s, 1H), 8.37 (s, 1H), 8.15 (s, 1H), 7.69 (d, J = 7.7 Hz, 1H), 7.45 (s, 1H), 7.37 (dd, J = 7.8, 1.4 Hz, 1H), 5.11 (dd, J = 13.3, 5.1 Hz, 1H), 4.49-4.25 (m, 2H), 3.89 (d, J = 11.5 Hz, 2H), 3.36-3.25 (m, 2H), 3.21 (dd, J = 13.4, 3.7 Hz, 1H), 3.09-2.81 (m, 3H), 2.65-2.56 (m, 1H), 2.47-2.29 (m, 2H), 2.15-1.82 (m, 4H), 1.80-1.60 (m, 3H), 1.60-1.38 (m, 3H), 1.38-1.18 (m, 3H), 1.15-0.91 (m, 2H); 1H NMR (400 MHz, DMSO-d6) δ 11.07-10.92 (m, 1H), 7.82 (s, 1H), 7.67 (dd, J = 31.3, 7.7 Hz, 1H), 7.52-7.15 (m, 2H), 5.11 (dt, J = 13.2, 6.2 Hz, 1H), 4.57-4.20 (m, 2H), 3.87 (t, J = 12.7 Hz, 4H), 3.66 (d, J = 13.3 Hz, 1H), 3.48-3.13 (m, 8H), 3.03-2.78 (m, 2H), 2.60 (d, J = 17.2 Hz, 1H), 2.47-2.35 (m, 1H), 2.31 (d, J = 14.2 Hz, 1H), 2.21 (d, J = 9.8 Hz, 1H), 2.15-1.92 (m, 3H), 1.83 (dd, J = 27.0, 12.4 Hz, 1H), 1.76-1.57 (m, 3H), 1.57-1.24 (m, 6H), 1.24-1.01 (m, 4H), 0.92 (dq, J = 22.9, 12.9, 12.4 Hz, 1H). | tetrahydropyran-4-carbaldehyde |

TABLE 9-continued

| Example | Structure | ES/MS m/z | ¹H-NMR | Changes to Procedure 15; Different Reagents/Starting Materials |
|---|---|---|---|---|
| 71 | 3-(1-oxo-5-(((1R,2S)-2-(((tetrahydro-2H-pyran-4-yl)methyl)amino)cyclohexyl)methyl)isoindolin-2-yl)piperidine-2,6-dione | 454.4 | 1H NMR (400 MHz, DMSO-d6) δ 10.99 (s, 1H), 8.37 (s, 1H), 8.15 (s, 1H), 7.69 (d, J = 7.7 Hz, 1H), 7.45 (s, 1H), 7.37 (dd, J = 7.8, 1.4 Hz, 1H), 5.11 (dd, J = 13.3, 5.1 Hz, 1H), 4.49-4.25 (m, 2H), 3.89 (d, J = 11.5 Hz, 2H), 3.36-3.25 (m, 2H), 3.21 (dd, J = 13.4, 3.7 Hz, 1H), 3.09-2.81 (m, 3H), 2.65-2.56 (m, 1H), 2.47-2.29 (m, 2H), 2.15-1.82 (m, 4H), 1.80-1.60 (m, 3H), 1.60-1.38 (m, 3H), 1.38-1.18 (m, 3H), 1.15-0.91 (m, 2H); 1H NMR (400 MHz, DMSO-d6) δ 11.07-10.92 (m, 1H), 7.82 (s, 1H), 7.67 (dd, J = 31.3, 7.7 Hz, 1H), 7.52-7.15 (m, 2H), 5.11 (dt, J = 13.2, 6.2 Hz, 1H), 4.57-4.20 (m, 2H), 3.87 (t, J = 12.7 Hz, 4H), 3.66 (d, J = 13.3 Hz, 1H), 3.48-3.13 (m, 8H), 3.03-2.78 (m, 2H), 2.60 (d, J = 17.2 Hz, 1H), 2.47-2.35 (m, 1H), 2.31 (d, J = 14.2 Hz, 1H), 2.21 (d, J = 9.8 Hz, 1H), 2.15-1.92 (m, 3H), 1.83 (dd, J = 27.0, 12.4 Hz, 1H), 1.76-1.57 (m, 3H), 1.57-1.24 (m, 6H), 1.24-1.01 (m, 4H), 0.92 (dq, J = 22.9, 12.9, 12.4 Hz, 1H). | tetrahydropyran-4-carbaldehyde |
| 72 | 3-(5-(((1R,2S)-2-(oxetan-3-ylamino)cyclohexyl)methyl)-1-oxoisoindolin-2-yl)piperidine-2,6-dione | 412.3 | 1H NMR (400 MHz, DMSO-d6) δ 10.99 (s, 1H), 9.34 (s, 1H), 9.03 (d, J = 11.9 Hz, 1H), 7.70 (d, J = 7.7 Hz, 1H), 7.44 (s, 1H), 7.42-7.23 (m, 1H), 5.11 (dd, J = 13.2, 5.1 Hz, 1mH), 4.78 (q, J = 7.4 Hz, 2H), 4.71 (dt, J = 10.5, 6.9 Hz, 1H), 4.65-4.52 (m, 1H), 4.50-4.26 (m, 2H), 3.24 (dd, J = 13.3, 3.5 Hz, 1H), 3.09-2.77 (m, 3H), 2.61 (d, J = 17.4 Hz, 1H), 2.47-2.29 (m, 2H), 2.08-1.91 (m, 1H), 1.82 (d, J = 4.8 Hz, 1H), 1.67 (s, 1H), 1.58-1.37 (m, 2H), 1.27 (t, J = 9.1 Hz, 2H), 1.14-0.89 (m, 2H). | 3-oxetanone |

TABLE 9-continued

| Example | Structure | ES/MS m/z | ¹H-NMR | Changes to Procedure 15; Different Reagents/Starting Materials |
|---|---|---|---|---|
| 73 | 3-(1-oxo-5-(((1R,2S)-2-(((tetrahydrofuran-3-yl)amino)cyclohexyl)methyl)isoindolin-2-yl)piperidine-2,6-dione | 426.3 | 1H NMR (400 MHz, DMSO-d6) δ 10.99 (s, 1H), 8.68 (d, J = 30.5 Hz, 1H), 8.36 (d, J = 53.0 Hz, 1H), 7.70 (d, J = 7.7 Hz, 1H), 7.45 (s, 1H), 7.37 (d, J = 7.8 Hz, 1H), 5.11 (dd, J = 13.3, 5.1 Hz, 1H), 4.57-4.21 (m, 2H), 4.06 (s, 1H), 3.95 (td, J = 8.3, 5.0 Hz, 1H), 3.89-3.80 (m, 2H), 3.67 (q, J = 7.5 Hz, 1H), 3.31-3.19 (m, 1H), 3.04 (s, 1H), 2.92 (ddd, J = 18.0, 13.6, 5.4 Hz, 1H), 2.61 (d, J = 16.9 Hz, 1H), 2.41 (td, J = 13.5, 5.0 Hz, 2H), 2.36-2.22 (m, 1H), 2.09 (d, J = 9.1 Hz, 1H), 2.05-1.93 (m, 1H), 1.87 (s, 1H), 1.69 (s, 1H), 1.59-1.39 (m, 3H), 1.33 (d, J = 10.9 Hz, 1H), 1.07 (q, J = 11.0 Hz, 2H). | tetrahydrofuran-3-one |
| 74 | 3-(1-oxo-5-(((1R,2S)-2-(((tetrahydro-2H-pyran-4-yl)amino)cyclohexyl)methyl)isoindolin-2-yl)piperidine-2,6-dione | 440.4 | 1H NMR (400 MHz, DMSO-d6) δ 10.99 (s, 1H), 8.44 (s, 1H), 8.09 (s, 1H), 7.70 (d, J = 7.7 Hz, 1H), 7.45 (s, 1H), 7.42-7.25 (m, 1H), 5.11 (dd, J = 13.3, 5.1 Hz, 1H), 4.58-4.21 (m, 2H), 3.94 (d, J = 11.4 Hz, 2H), 3.51 (s, 1H), 3.36 (t, J = 11.9 Hz, 2H), 3.27 (d, J = 13.2 Hz, 1H), 3.11 (s, 1H), 2.92 (ddd, J = 17.3, 13.6, 5.5 Hz, 1H), 2.61 (d, J = 9.8 Hz, 1H), 2.47-2.36 (m, 2H), 2.10 (t, J = 9.8 Hz, 1H), 2.05-1.96 (m, 2H), 1.96-1.80 (m, 1H), 1.80-1.66 (m, 1H), 1.65-1.20 (m, 6H), 1.05 (q, J = 10.5 Hz, 2H). | tetrahydropyran-4-one |

TABLE 9-continued

| Example | Structure | ES/MS m/z | ¹H-NMR | Changes to Procedure 15; Different Reagents/Starting Materials |
|---|---|---|---|---|
| 75 | 3-(5-(((1R,2S)-2-((3-ethoxycyclobutyl)amino)cyclohexyl)methyl)-1-oxoisoindolin-2-yl)piperidine-2,6-dione | 454.4 | 1H NMR (400 MHz, DMSO-d6) δ 10.99 (s, 1H), 8.76 (s, 1H), 8.54 (s, 1H), 7.69 (d, J = 7.7 Hz, 1H), 7.44 (s, 1H), 7.36 (dd, J = 7.8, 1.5 Hz, 1H), 5.11 (dd, J = 13.3, 5.1 Hz, 1H), 4.52-4.22 (m, 2H), 3.75 (h, J = 8.0, 7.5 Hz, 1H), 3.52 (q, J = 7.3 Hz, 1H), 3.37 (q, J = 6.9 Hz, 2H), 3.26-3.16 (m, 1H), 3.00-2.90 (m, 1H), 2.69-2.56 (m, 2H), 2.48-2.36 (m, 2H), 2.36-2.24 (m, 1H), 2.19 (q, J = 8.5 Hz, 1H), 2.13-2.04 (m, 1H), 2.04-1.91 (m, 2H), 1.84 (s, 1H), 1.66 (s, 1H), 1.49 (d, J = 15.1 Hz, 2H), 1.44-1.19 (m, 2H), 1.12 (q, J = 6.9 Hz, 5H). | 3-ethoxycyclobutanone |
| 76 | 3-(5-(((1R,2S)-2-((2-methoxyphenethyl)amino)cyclohexyl)methyl)-1-oxoisoindolin-2-yl)piperidine-2,6-dione | 490.4 | 1H NMR (400 MHz, DMSO-d6) δ 10.99 (s, 1H), 8.61 (s, 1H), 8.44 (s, 1H), 7.70 (d, J = 7.8 Hz, 1H), 7.44 (s, 1H), 7.36 (dd, J = 7.8, 1.3 Hz, 1H), 7.31-7.20 (m, 2H), 7.03 (dd, J = 8.3, 1.0 Hz, 1H), 6.94 (td, J = 7.4, 1.1 Hz, 1H), 5.11 (dd, J = 13.3, 5.1 Hz, 1H), 4.56-4.21 (m, 2H), 3.82 (s, 3H), 3.29-3.12 (m, 2H), 3.12-2.82 (m, 4H), 2.65-2.56 (m, 1H), 2.47-2.31 (m, 2H), 2.08 (dd, J = 8.9, 4.3 Hz, 1H), 1.72 (d, J = 12.8 Hz, 1H), 1.58-1.38 (m, 3H), 1.30 (d, J = 11.5 Hz, 1H), 1.03 (p, J = 11.7, 11.2 Hz, 2H). | 2-(2-methoxyphenyl)acetaldehyde |

TABLE 9-continued

| Example | Structure | ES/MS m/z | ¹H-NMR | Changes to Procedure 15; Different Reagents/Starting Materials |
|---|---|---|---|---|
| 77 | 3-(1-oxo-5-(((1R,2S)-2-((1-phenoxypropan-2-yl)amino)cyclohexyl)methyl)isoindolin-2-yl)piperidine-2,6-dione | 490.4 | 1H NMR (400 MHz, DMSO-d6) δ 10.99 (s, 1H), 8.36 (d, J = 29.6 Hz, 1H), 7.67 (t, J = 8.1 Hz, 1H), 7.42 (s, 1H), 7.35 (ddt, J = 8.9, 7.2, 3.0 Hz, 3H), 7.11-6.92 (m, 3H), 5.11 (ddd, J = 13.2, 5.2, 2.3 Hz, 1H), 4.50-4.35 (m, 1H), 4.35-4.26 (m, 1H), 4.26-4.08 (m, 2H), 3.96-3.72 (m, 1H), 3.33 (ddd, J = 21.6, 13.2 Hz, 1H), 3.18 (s, 1H), 2.92 (ddd, J = 17.2, 13.6, 5.5 Hz, 1H), 2.65-2.55 (m, 1H), 2.47-2.29 (m, 2H), 2.23-2.06 (m, 1H), 2.06-1.90 (m, 2H), 1.88 (d, J = 9.4 Hz, 1H), 1.73 (d, J = 12.5 Hz, 1H), 1.62-1.47 (m, 2H), 1.45 (d, J = 6.7 Hz, 1H), 1.40 (d, J = 6.6 Hz, 2H), 1.29 (dd, J = 36.1, 7.6 Hz, 1H), 1.18-0.89 (m, 2H). | 1-phenoxypropan-2-one |
| 78 | 3-(5-(((1R,2S)-2-((1-ethoxypropan-2-yl)amino)cyclohexyl)methyl)-1-oxoisoindolin-2-yl)piperidine-2,6-dione | 442.3 | 1H NMR (400 MHz, DMSO-d6) δ 10.99 (s, 1H), 8.10 (s, 1H), 7.70 (d, J = 7.7 Hz, 1H), 7.45 (s, 1H), 7.37 (d, J = 7.8 Hz, 1H), 5.11 (dd, J = 13.3, 5.1 Hz, 1H), 4.55-4.18 (m, 2H), 3.66-3.57 (m, 1H), 3.55 (d, J = 2.5 Hz, 1H), 3.51 (tq, J = 7.8, 2.6 Hz, 2H), 3.40-3.21 (m, 1H), 3.07 (s, 1H), 2.92 (ddd, J = 17.9, 13.6, 5.4 Hz, 1H), 2.66-2.56 (m, 1H), 2.39 (pd, J = 12.5, 11.9, 6.3 Hz, 1H), 2.19-2.04 (m, 1H), 2.04-1.88 (m, 1H), 1.81 (s, 1H), 1.72 (d, J = 12.5 Hz, 1H), 1.63-1.35 (m, 3H), 1.31 (d, J = 6.5 Hz, 1H), 1.26 (d, J = 6.1 Hz, 2H), 1.20-1.10 (m, 3H), 1.04 (d, J = 6.5 Hz, 2H). | 1-ethoxypropan-2-one |

TABLE 9-continued

| Example | Structure | ES/MS m/z | ¹H-NMR | Changes to Procedure 15; Different Reagents/Starting Materials |
|---|---|---|---|---|
| 100 | 3-(5-(((1R,2S)-2-((6,6-dimethylspiro[3.3]heptan-2-yl)amino)cyclohexyl)methyl)-1-oxoisoindolin-2-yl)piperidine-2,6-dione | 478.3 | 1H NMR (400 MHz, DMSO-d6) δ 10.99 (s, 1H), 8.61 (d, J = 10.4 Hz, 1H), 8.41 (s, 1H), 7.69 (d, J = 7.8 Hz, 1H), 7.43 (s, 1H), 7.35 (dd, J = 7.8, 1.3 Hz, 1H), 5.11 (dd, J = 13.3, 5.1 Hz, 1H), 4.55-4.21 (m, 2H), 3.82-3.69 (m, H), 3.19 (dd, J = 13.2, 4.0 Hz, 1H), 2.92 (ddd, J = 18.0, 13.5, 5.6 Hz, 2H), 2.62 (dd, J = 17.6, 14.0 Hz, 1H), 2.47-2.27 (m, 5H), 2.22 (dd, J = 12.0, 8.7 Hz, 1H), 2.05-1.95 (m, 1H), 1.92 (s, 2H), 1.91-1.72 (m, 4H), 1.65 (s, 1H), 1.48 (d, J = 15.3 Hz, 1H), 1.31 (dt, J = 33.2, 9.0 Hz, 1H), 1.05 (s, 9H). | 2,3-dimethylspiro[3.4]heptan-6-one |
| 101 | 3-(5-(((1R,2S)-2-((6,6-difluorospiro[3.3]heptan-2-yl)amino)cyclohexyl)methyl)-1-oxoisoindolin-2-yl)piperidine-2,6-dione | 486.3 | 1H NMR (400 MHz, DMSO-d6) δ 10.99 (s, 1H), 8.81-8.69 (m, 1H), 8.54 (s, 1H), 7.69 (d, J = 7.7 Hz, 1H), 7.44 (s, 1H), 7.36 (dd, J = 7.8, 1.4 Hz, 1H), 5.11 (dd, J = 13.3, 5.1 Hz, 1H), 4.45 (dd, J = 17.5, 2.5 Hz, 1H), 4.31 (dd, J = 17.4, 3.4 Hz, 1H), 3.94-3.80 (m, 3H), 3.20 (dd, J = 13.3, 4.0 Hz, 1H), 3.00-2.85 (m, 2H), 2.77-2.56 (m, 6H), 2.48-2.28 (m, 4H), 2.06-1.94 (m, 2H), 1.90=1.76 (m, 1H), 1.73-1.61 (m, 1H), 1.60-1.44 (m, 2H), 1.44-1.20 (m, 2H), 1.06 (q, J = 12.1, 11.0 Hz, 2H). | 2,3-difluorospiro[3.3]heptan-6-one |

TABLE 9-continued

| Example | Structure | ES/MS m/z | ¹H-NMR | Changes to Procedure 15; Different Reagents/Starting Materials |
|---|---|---|---|---|
| 102 | 3-(5-(((1R,2S)-2-((1-cyclopropylethyl)amino)cyclohexyl)methyl)-1-oxoisoindolin-2-yl)piperidine-2,6-dione | 424.3 | 1H NMR (400 MHz, DMSO-d6) δ 10.99 (s, 1H), 8.35 (d, J = 46.7 Hz, 1H), 8.11 (s, 1H), 7.70 (dd, J = 7.8, 1.6 Hz, 1H), 7.45 (d, J = 4.0 Hz, 1H), 7.37 (dt, J = 7.9, 1.7 Hz, 1H), 5.11 (dd, J = 13.3, 5.1 Hz, 1H), 4.46 (dd, J = 17.4, 2.9 Hz, 1H), 4.32 (dd, J = 17.3, 3.2 Hz, 1H), 3.38-3.25 (m, 1H), 3.21-3.01 (m, 2H), 2.99-2.81 (m, 2H), 2.75-2.66 (m, 1H), 2.66-2.56 (m, 1H), 2.48-2.30 (m, 2H), 2.17-1.95 (m, 2H), 1.94-1.80 (m, 1H), 1.71 (d, J = 12.5 Hz, 1H), 1.61-1.45 (m, 2H), 1.46-1.21 (m, 4H), 1.19-0.94 (m, 2H), 0.74-0.55 (m, 1H), 0.55-0.43 (m, 1H), 0.40-0.25 (m, 1H). | 1-cyclopropylethanone |
| 103 | 3-(5-(((1R,2S)-2-((1-cyclobutylethyl)amino)cyclohexyl)methyl)-1-oxoisoindolin-2-yl)piperidine-2,6-dione | 438.3 | 1H NMR (400 MHz, DMSO-d6) δ 10.99 (s, 1H), 8.35-7.75 (m, 2H), 7.70 (d, J = 7.8 Hz, 1H), 7.44 (d, J = 6.4 Hz, 1H), 7.41-7.32 (m, 1H), 5.11 (dd, J = 13.3, 5.1 Hz, 1H), 4.45 (dd, J = 17.4, 3.5 Hz, 1H), 4.32 (dd, J = 17.3, 4.0 Hz, 1H), 3.50-3.20 (m, 1H), 3.06-2.80 (m, 1H), 2.65-2.54 (m, 2H), 2.47-2.29 (m, 2H), 2.21-1.64 (m, 11H), 1.62-1.25 (m, 4H), 1.21 (d, J = 6.5 Hz, 1H), 1.16 (d, J = 6.4 Hz, 2H), 1.11-0.95 (m, 2H). | 1-cyclobutylethanone |

TABLE 9-continued

| Example | Structure | ES/MS m/z | ¹H-NMR | Changes to Procedure 15; Different Reagents/Starting Materials |
|---|---|---|---|---|
| 104 | 3-(1-oxo-5-(((1R,2S)-2-((3,3,3-trifluoropropyl)amino)cyclohexyl)methyl)isoindolin-2-yl)piperidine-2,6-dione | 452.3 | 1H NMR (400 MHz, DMSO-d6) δ 10.99 (s, 1H), 8.77 (s, 1H), 8.43 (s, 1H), 7.70 (d, J = 7.8 Hz, 1H), 7.45 (s, 1H), 7.36 (dd, J = 7.7, 1.3 Hz, 1H), 5.11 (dd, J = 13.3, 5.1 Hz, 1H), 4.45 (dd, J = 17.3, 3.9 Hz, 1H), 4.32 (dd, J = 17.3, 4.4 Hz, 1H), 3.36-3.15 (m, 3H), 3.09 (s, 1H), 2.99-2.67 (m, 2H), 2.60 (dd, J = 17.3, 3.4 Hz, 1H), 2.47-2.37 (m, 2H), 2.17-2.07 (m, 1H), 2.07-1.94 (m, 1H), 1.88 (d, J = 9.8 Hz, 1H), 1.71 (d, J = 13.1 Hz, 1H), 1.61-1.37 (m, 3H), 1.37-1.21 (m, 1H), 1.16-0.93 (m, 2H). | 3,3,3-trifluoropropanal |
| 105 | 3-(5-(((1R,2S)-2-(((2S)-2-fluorocyclohexyl)amino)cyclohexyl)methyl)-1-oxoisoindolin-2-yl)piperidine-2,6-dione (isomer 1) | 456.4 | 1H NMR (400 MHz, DMSO-d6) δ 10.99 (s, 1H), 8.86-7.86 (m, 2H), 7.69 (dd, J = 7.8, 3.7 Hz, 1H), 7.46 (d, J = 8.8 Hz, 1H), 7.38 (dd, J = 8.0, 4.5 Hz, 1H), 5.35-5.16 (m, 1H), 5.11 (dd, J = 13.3, 5.2 Hz, 1H), 4.45 (d, J = 17.3 Hz, 1H), 4.31 (d, J = 17.3 Hz, 1H), 3.65-3.29 (m, 1H), 3.28-3.09 (m, 2H), 2.99-2.85 (m, 1H), 2.66-2.56 (m, 1H), 2.48-2.30 (m, 2H), 2.20-1.84 (m, 4H), 1.84-1.62 (m, 3H), 1.61-1.20 (m, 8H), 1.15-0.93 (m, 2H). | (2S)-2-fluorocyclohexanone |

TABLE 9-continued

| Example | Structure | ES/MS m/z | ¹H-NMR | Changes to Procedure 15; Different Reagents/Starting Materials |
|---|---|---|---|---|
| 106 | 3-(5-(((1R,2S)-2-(((2S)-2-fluorocyclohexyl)amino)cyclohexyl)methyl)-1-oxoisoindolin-2-yl)piperidine-2,6-dione (isomer 2) | 456.4 | 1H NMR (400 MHz, DMSO-d6) δ 10.99 (s, 1H), 8.86-7.94 (m, 2H), 7.76-7.64 (m, 1H), 7.49-7.40 (m, 1H), 7.40-7.31 (m, 1H), 5.17-5.04 (m, 1H), 4.90-4.63 (m, 1H), 4.50-4.41 (m, 1H), 4.36-4.27 (m, 1H), 3.56-3.40 (m, 1H), 3.31 (d, J = 12.5 Hz, 1H), 3.20-3.07 (m, 1H), 2.98-2.82 (m, 1H), 2.65-2.56 (m, 1H), 2.47-2.27 (m, 2H), 2.26-2.06 (m, 2H), 2.06-1.85 (m, 2H), 1.83-1.63 (m, 3H), 1.63-1.14 (m, 8H), 1.13-0.89 (m, 2H). | (2S)-2-fluorocyclohexanone |
| 107 | 3-(5-(((1R,2S)-2-(((2R)-2-fluorocyclohexyl)amino)cyclohexyl)methyl)-1-oxoisoindolin-2-yl)piperidine-2,6-dione (isomer 2) | 456.4 | 1H NMR (400 MHz, DMSO-d6) δ 10.99 (s, 1H), 8.76-7.95 (m, 2H), 7.72-7.62 (m, 1H), 7.51-7.41 (m, 1H), 7.41-7.30 (m, 1H), 5.35-5.16 (m, 1H), 5.15-5.03 (m, 2H), 4.45 (d, J = 17.2 Hz, 1H), 4.31 (d, J = 17.3 Hz, 1H), 3.59-3.29 (m, 2H), 3.29-3.19 (m, 1H), 3.15 (s, 1H), 3.03-2.81 (m, 1H), 2.66-2.57 (m, 1H), 2.48-2.27 (m, 2H), 2.19-1.84 (m, 3H), 1.83-1.60 (m, 3H), 1.60-1.15 (m, 7H), 1.05 (q, J = 12.9 Hz, 2H). | (2R)-2-fluorocyclohexanone |

TABLE 9-continued

| Example | Structure | ES/MS m/z | ¹H-NMR | Changes to Procedure 15; Different Reagents/Starting Materials |
|---|---|---|---|---|
| 108 | 3-(5-(((1R,2S)-2-((1-acetylpiperidin-4-yl)amino)cyclohexyl)methyl)-1-oxoisoindolin-2-yl)piperidine-2,6-dione | 481.4 | 1H NMR (400 MHz, DMSO-d6) δ 10.99 (s, 1H), 8.46 (s, 1H), 8.06 (s, 1H), 7.70 (d, J = 7.8 Hz, 1H), 7.44 (s, 1H), 7.36 (d, J = 7.8 Hz, 1H), 5.11 (dd, J = 13.3, 5.1 Hz, 1H), 4.55-4.39 (m, 2H), 4.32 (dd, J = 17.3, 3.1 Hz, 1H), 3.97-3.88 (m, 1H), 3.53 (s, 1H), 3.26 (d, J = 13.2 Hz, 2H), 3.17-3.01 (m, 2H), 2.92 (ddd, J = 17.3, 13.6, 5.4 Hz, 1H), 2.65-2.54 (m, 1H), 2.46-2.29 (m, 2H), 2.17-1.91 (m, 7H), 1.89-1.77 (m, 1H), 1.72 (d, J = 12.3 Hz, 1H), 1.66-1.44 (m, 3H), 1.44-1.24 (m, 2H), 1.16-0.93 (m, 2H). | 1-acetylpiperidin-4-one |
| 109 | 3-(5-(((1R,2S)-2-((2,2-dimethyltetrahydro-2H-pyran-4-yl)amino)cyclohexyl)methyl)-1-oxoisoindolin-2-yl)piperidine-2,6-dione (Isomer 1) | 468.4 | 1H NMR (400 MHz, DMSO-d6) δ 10.99 (s, 1H), 8.32 (s, 1H), 8.00 (s, 1H), 7.70 (d, J = 7.8 Hz, 1H), 7.45 (s, 1H), 7.37 (d, J = 7.8 Hz, 1H), 5.11 (dd, J = 13.3, 5.1 Hz, 1H), 4.45 (d, J = 17.3 Hz, 1H), 4.32 (d, J = 17.2 Hz, 1H), 3.77-3.69 (m, 1H), 3.65-3.56 (m, 2H), 3.26 (dd, J = 13.1, 3.9 Hz, 1H), 3.08 (s, 1H), 2.92 (ddd, J = 17.6, 13.5, 5.4 Hz, 1H), 2.61 (d, 1H), 2.47-2.30 (m, 2H), 2.22-2.08 (m, 1H), 2.05-1.91 (m, 2H), 1.82 (d, J = 11.6 Hz, 2H), 1.69 (d, 1H), 1.61-1.24 (m, 5H), 1.18 (d, J = 3.3 Hz, 6H), 1.14-1.00 (m, 2H). | 2,2-dimethyltetrahydropyran-4-one |

TABLE 9-continued

| Example | Structure | ES/MS m/z | ¹H-NMR | Changes to Procedure 15; Different Reagents/Starting Materials |
|---|---|---|---|---|
| 110 | 3-(5-(((1R,2S)-2-((2,2-dimethyltetrahydro-2H-pyran-4-yl)amino)cyclohexyl)methyl)-1-oxoisoindolin-2-yl)piperidine-2,6-dione (Isomer 2) | 468.4 | 1H NMR (400 MHz, DMSO-d6) δ 10.99 (s, 1H), 8.46 (s, 1H), 7.97 (s, 1H), 7.70 (d, J = 7.7 Hz, 1H), 7.45 (s, 1H), 7.36 (d, J = 7.8 Hz, 1H), 5.11 (dd, J =13.3, 5.1 Hz, 1H), 4.45 (d, J = 17.4 Hz, 1H), 4.32 (d, J = 17.2 Hz, 1H), 3.76-3.69 (m, 1H), 3.67-3.56 (m, 1H), 3.25 (dd, 1H), 3.17-3.02 (m, 1H), 2.92 (ddd, J = 18.0, 13.6, 5.5 Hz, 1H), 2.66-2.56 (m, 1H), 2.47-2.30 (m, 2H), 2.14-1.94 (m, 3H), 1.94-1.77 (m, 2H), 1.77-1.66 (m, 1H), 1.63 (dd, J = 11.9, 4.8 Hz, 1H), 1.59-1.45 (m, 2H), 1.45-1.24 (m, 3H), 1.19 (s, 6H), 1.15-0.98 (m, 2H). | 2,2-dimethyltetrahydropyran-4-one |
| 111 | 3-(5-(((1R,2S)-2-((2,2-difluorocyclohexyl)amino)cyclohexyl)methyl)-1-oxoisoindolin-2-yl)piperidine-2,6-dione | 474.4 | 1H NMR (400 MHz, DMSO-d6) δ 10.99 (s, 1H), 8.84 (s, 1H), 8.55 (s, 1H), 7.69 (d, J = 7.7 Hz, 1H), 7.44 (s, 1H), 7.36 (d, J = 7.8 Hz, 1H), 5.11 (dd, J = 13.3, 5.1 Hz, 1H), 4.45 (dd, J = 17.3, 4.5 Hz, 1H), 4.32 (dd, J = 17.3, 4.1 Hz, 1H), 3.92 (s, 1H), 3.70-3.57 (m, 2H), 3.44-3.34 (m, 2H), 3.14-3.08 (m, 1H), 2.92 (ddd, J = 17.2, 13.6, 5.4 Hz, 1H), 2.61 (dt, J = 17.4, 3.3 Hz, 1H), 2.46-2.29 (m, 2H), 2.29-2.15 (m, 1H), 2.15-2.06 (m, 1H), 2.29 (m, 2H), 2.29-2.15 (m, 1H), 2.15-2.06 (m, 1H), 2.06-1.85 (m, 2H), 1.84-1.63 (m, 3H), 1.63-1.38 (m, 3H), 1.38-1.17 (m, 2H), 1.10-0.91 (m, 2H). | 2,2-difluorocyclohexanone |

TABLE 9-continued

| Example | Structure | ES/MS m/z | ¹H-NMR | Changes to Procedure 15; Different Reagents/Starting Materials |
|---|---|---|---|---|
| 112 | 3-(5-(((1R,2S)-2-((2,2-difluorocyclohexyl)amino)cyclohexyl)methyl)-1-oxoisoindolin-2-yl)piperidine-2,6-dione (Isomer 1) | 466.4 | 1H NMR (400 MHz, DMSO-d6) δ 10.99 (s, 1H), 8.44 (s, 1H), 7.99 (s, 1H), 7.69 (d, J = 7.7 Hz, 1H), 7.44 (s, 1H), 7.35 (dd, J = 7.8, 1.4 Hz, 1H), 5.11 (dd, J = 13.3, 5.1 Hz, 1H), 4.50-4.37 (m, 3H), 4.32 (dd, J = 17.4, 2.0 Hz, 1H), 3.41-3.28 (m, 2H), 3.24 (dd, J = 13.2, 3.5 Hz, 1H), 3.01 (s, 1H), 2.98-2.84 (m, 1H), 2.65-2.56 (m, 1H), 2.46-2.30 (m, 2H), 2.12-1.95 (m, 2H), 1.94-1.86 (m, 2H), 1.86-1.76 (m, 1H), 1.76-1.60 (m, 4H), 1.60-1.41 (m, 3H), 1.41-1.23 (m, 3H), 1.12-0.89 (m, 2H). | 8-oxabicyclo[3.2.1]octan-3-one |
| 113 | 3-(5-(((1R,2S)-2-((2,2-difluorocyclohexyl)amino)cyclohexyl)methyl)-1-oxoisoindolin-2-yl)piperidine-2,6-dione (Isomer 2) | 440.4 | 1H NMR (400 MHz, DMSO-d6) δ 10.99 (s, 1H), 8.43-7.87 (m, 2H), 7.69 (d, J = 7.7 Hz, 1H), 7.47-7.40 (m, 1H), 7.36 (dd, J = 7.8, 1.5 Hz, 1H), 5.11 (dd, J = 13.3, 5.1 Hz, 1H), 4.45 (dd, J = 17.4, 2.0 Hz, 1H), 4.32 (dd, J = 17.4, 2.9 Hz, 1H), 3.42-3.20 (m, 2H), 3.04 (s, 1H), 2.92 (ddd, J = 17.3, 13.6,5.4 Hz, 1H), 2.61 (dt, J = 15.3, 2.8 Hz, 1H), 2.47-2.30 (m, 2H), 2.18-1.94 (m, 2H), 1.85 (s, 1H), 1.78-1.62 (m, 2H), 1.61-1.45 (m, 4H), 1.45-1.33 (m, 1H), 1.30 (d, J = 6.3 Hz, 1H), 1.25 (d, J = 6.3 Hz, 2H), 1.12-1.00 (m, 2H), 0.98-0.91 (m, 3H), 0.91-0.81 (m, 3H). | 8-oxabicyclo[3.2.1]octan-3-one |

TABLE 9-continued

| Example | Structure | ES/MS m/z | ¹H-NMR | Changes to Procedure 15; Different Reagents/Starting Materials |
|---|---|---|---|---|
| 114 | 3-(4-fluoro-5-(((1R,2S)-2-(((oxetan-3-yl)methyl)amino)cyclohexyl)methyl)-1-oxoisoindolin-2-yl)piperidine-2,6-dione | 444.3 | 1H NMR (400 MHz, DMSO-d6) δ 11.01 (s, 1H), 8.59 (s, 1H), 8.32 (s, 1H), 7.66-7.55 (m, 1H), 7.55-7.43 (m, 1H), 5.12 (dd, J = 13.3, 5.1 Hz,1H), 4.69 (t, J = 6.7 Hz, 1H), 4.61-4.50 (m, 1H), 4.44-4.32 (m, 3H), 3.64-3.53 (m, 2H), 3.50-3.39 (m, 1H), 3.39-3.28 (m, 1H), 3.21-3.01 (m, 2H), 2.92 (ddd, J = 17.3, 13.6, 5.5 Hz, 1H), 2.64-2.56 (m, 2H), 2.46-2.35 (m, 1H), 2.10-1.96 (m, 1H), 1.95-1.82 (m, 1H), 1.79-1.64 (m, 1H), 1.62-1.38 (m, 3H), 1.38-1.23 (m, 1H), 1.16-0.98 (m, 2H). | I-4; oxetane-3-carbaldehyde |
| 115 | 3-(4-fluoro-1-oxo-5-(((1R,2S)-2-(((tetrahydro-2H-pyran-4-yl)methyl)amino)cyclohexyl)methyl)isoindolin-2-yl)piperidine-2,6-dione | 472.3 | 1H NMR (400 MHz, DMSO-d6) δ 11.01 (s, 1H), 8.54 (d, J = 1.0 Hz, 1H), 8.29 (s, 1H), 7.58 (d, J = 7.7 Hz, 1H), 7.49 (t, J = 7.0 Hz, 1H), 5.12 (dd, J = 13.3, 5.1 Hz, 1H), 4.56 (dd, J = 17.4, 4.9 Hz, 1H), 4.39 (dd, J = 17.4, 5.5 Hz, 1H), 3.95-3.79 (m, 2H), 3.30 (tt, J = 11.7, 2.7 Hz, 2H), 3.20-3.00 (m, 2H), 3.00-2.81 (m, 3H), 2.66-2.53 (m, 1H), 2.48-2.36 (m, 1H), 2.10-1.84 (m, 4H), 1.80-1.63 (m, 3H), 1.62-1.41 (m, 3H), 1.39-1.20 (m, 3H), 1.08 (q, J = 10.5, 9.6 Hz, 2H). | I-4; tetrahydropyran-4-carbaldehyde |

TABLE 9-continued

| Example | Structure | ES/MS m/z | ¹H-NMR | Changes to Procedure 15; Different Reagents/Starting Materials |
|---|---|---|---|---|
| 116 | 3-(4-fluoro-1-oxo-5-(((1R,2S)-2-((tetrahydro-2H-pyran-4-yl)amino)cyclohexyl)methyl)isoindolin-2-yl)piperidine-2,6-dione | 458.4 | 1H NMR (400 MHz, DMSO-d6) δ 11.01 (s, 1H), 8.58 (s, 1H), 8.13 (s, 1H), 7.59 (d, J = 7.7 Hz, 1H), 7.50 (t, J = 7.0 Hz, 1H), 5.12 (dd, J = 13.3, 5.1 Hz, 1H), 4.56 (dd, J = 17.4, 4.0 Hz, 1H), 4.39 (dd, J = 17.4, 3.4 Hz, 1H), 4.00-3.88 (m, 2H), 3.53 (s, 1H), 3.36 (t, J = 11.8 Hz, 2H), 3.27-3.10 (m, 2H), 3.00-2.84 (m, 1H), 2.67-2.56 (m, 2H), 2.48-2.37 (m, 1H), 2.18-2.07 (m, 1H), 2.06-1.96 (m, 2H), 1.96-1.83 (m, 2H), 1.83-1.24 (m, 6H), 1.16-1.00 (m, 2H). | I-4; tetrahydropyran-4-one |
| 117 | 3-(4-fluoro-1-oxo-5-(((1R,2S)-2-((tetrahydrofuran-3-yl)amino)cyclohexyl)methyl)isoindolin-2-yl)piperidin-2,6-dione (Isomer 1) | 444.3 | 1H NMR (400 MHz, DMSO-d6) δ 11.01 (s, 1H), 8.96-8.70 (m, 1H), 8.61-8.27 (m, 1H), 7.59 (d, J = 7.7 Hz, 1H), 7.49 (t, J = 7.0 Hz, 1H), 5.12 (dd, J = 13.3, 5.1 Hz, 1H), 4.64-4.48 (m, 1H), 4.46-4.32 (m, 1H), 4.06 (s, 1H), 3.99-3.90 (m, 1H), 3.89-3.83 (m, 2H), 3.67 (q, J = 7.7 Hz, 1H), 3.20 (d, J = 13.6, 1H), 3.12 (s, 1H), 2.92 (ddd, J = 17.2, 13.6, 5.4 Hz, 1H), 2.71-2.57 (m, 2H), 2.48-2.37 (m, 1H), 2.35-2.22 (m, 1H), 2.16-1.85 (m, 3H), 1.77-1.62 (m, 1H), 1.62-1.40 (m, 3H), 1.39-1.25 (m, 1H), 1.10 (q, J = 9.7 Hz, 2H). | I-4; tetrahydrofuran-3-one |

TABLE 9-continued

| Example | Structure | ES/MS m/z | ¹H-NMR | Changes to Procedure 15; Different Reagents/Starting Materials |
|---|---|---|---|---|
| 118 | 3-(4-fluoro-1-oxo-5-(((1R,2S)-2-((tetrahydrofuran-3-yl)amino)cyclohexyl)methyl)isoindolin-2-yl)piperidin-2,6-dione (Isomer 2) | 444.3 | 1H NMR (400 MHz, DMSO-d6) δ 11.01 (s, 1H), 8.73 (d, J = 32.3 Hz, 1H), 8.37 (d, J = 46.1 Hz, 1H), 7.60 (d, J = 7.7 Hz, 1H), 7.49 (t, J = 7.0 Hz, 1H), 5.12 (dd, J = 13.3, 5.1 Hz, 1H), 4.65-4.49 (m, 1H), 4.45-4.30 (m, 1H), 4.07 (s, 1H), 3.95 (ddd, J = 8.4, 5.7, 3.4 Hz, 1H), 3.92-3.78 (m, 2H), 3.67 (q, J = 7.8 Hz, 1H), 3.18 (d, J = 13.3 Hz, 1H), 3.11 (s, 1H), 2.92 (ddd, J = 17.2, 13.6, 5.4 Hz, 1H), 2.72-2.56 (m, 2H), 2.47-2.36 (m, 1H), 2.35-2.22 (m, 1H), 2.16-1.82 (m, 4H), 1.68 (s, 1H), 1.61-1.40 (m, 2H), 1.33 (dd, J = 10.9 Hz, 1H), 1.10 (q, J = 9.6 Hz, 2H). | I-4; tetrahydrofuran-3-one |

Procedure 16, Example 119

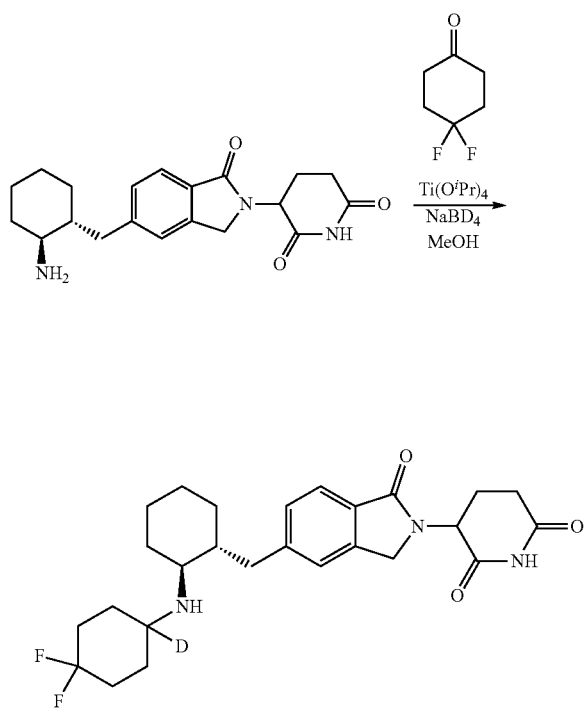

Example 119

Example 1 (38 mg, 0.28 mmol) was taken up in methanol (0.5 mL). Titanium (IV) isopropoxide (0.13 mL, 0.42 mmol) was then added at room temperature drop wise. A precipitate was seen. The reaction mixture was stirred for 15 minutes after which it was cooled to 0° C. and sodium borodeuteride (11.8 mg, 0.28 mmol) was added. After a few minutes, LC/MS indicated full conversion to product. The reaction mix was diluted with DMSO and a few drops of water and TFA were added. It was purified directly by RP-HPLC (eluent: MeCN/water gradient with 0.1% TFA) to yield the product (Example 119) as the trifluoracetate salt. ES/MS: 475.3 (M+H$^+$). $^1$H NMR (400 MHz, DMSO-d6) δ 10.99 (s, 1H), 8.54 (s, 1H), 8.15 (d, J=12.6 Hz, 1H), 7.70 (d, J=7.8 Hz, 1H), 7.44 (s, 1H), 7.36 (d, J=7.8 Hz, 1H), 5.11 (dd, J=13.3, 5.1 Hz, 1H), 4.38 (ddd, J=53.6, 17.4, 3.0 Hz, 2H), 3.34-3.21 (m, 1H), 3.10 (s, 1H), 2.92 (ddd, J=17.2, 13.6, 5.4 Hz, 1H), 2.66-2.55 (m, 1H), 2.46-2.24 (m, 3H), 2.23-2.04 (m, 4H), 2.04-1.88 (m, 3H), 1.89-1.60 (m, 4H), 1.60-1.45 (m, 2H), 1.37 (td, J=21.7, 19.6, 11.7 Hz, 2H), 1.15-0.92 (m, 2H).

The following Examples were made using the general route described in Procedure 16 and are shown below in Table 10. To prepare the below Examples, different reagents/starting materials were used than some of those described in Procedure 16 and are noted in the last column of Table 10—"Changes to Procedure 16: Different Reagents/Starting Materials". A person of ordinary skill in the art will readily recognize which reagents/starting materials of Procedure 16 were replaced with the different reagents/starting materials noted below.

TABLE 10

| Example | Structure | ES/MS m/z | $^1$H-NMR | Changes to Procedure 16: Different Reagents/Starting Materials |
|---|---|---|---|---|
| 120 | 3-(1-oxo-5-(((1R,2S)-2-(((phenyl-d$_5$)methyl-d)amino)cyclohexyl)methyl)isoindolin-2-yl)piperidine-2,6-dione | 452.4 | $^1$H NMR (400 MHz, DMSO-d6) δ 10.99 (s, 1H), 8.90 (d, J = 8.6 Hz, 1H), 8.68 (s, 1H), 7.66 (dd, J = 7.8, 1.4 Hz, 1H), 7.41 (s, 1H), 7.33 (d, J = 7.9 Hz, 1H), 5.11 (dd, J = 13.3, 5.1 Hz, 1H), 4.52-4.17 (m, 3H), 3.20 (dd, J = 13.2, 4.1 Hz, 1H), 2.92 (ddd, J = 17.2, 13.5, 5.3 Hz, 1H), 2.65-2.57 (m, 1H), 2.40 (ddt, J = 17.6, 13.0, 6.0 Hz, 2H), 2.14 (d, J = 12.7 Hz, 1H), 2.07-1.90 (m, 3H), 1.72 (d, J = 12.8 Hz, 1H), 1.56 (d, J = 16.9 Hz, 3H), 1.29 (d, J = 11.7 Hz, 1H), 1.07 (dd, J = 22.9, 13.6 Hz, 2H). | benzaldehyde-2,3,4,5,6-d$_5$ |

Procedure 17, Examples 121 and 122

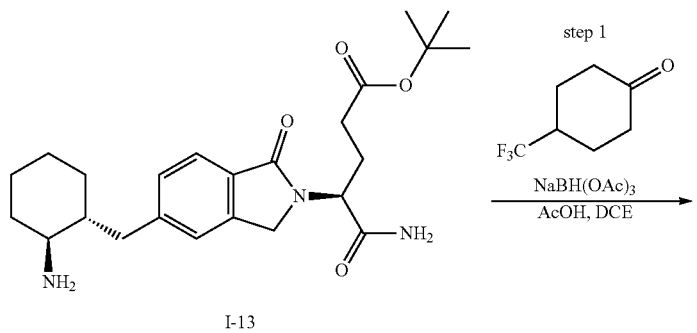

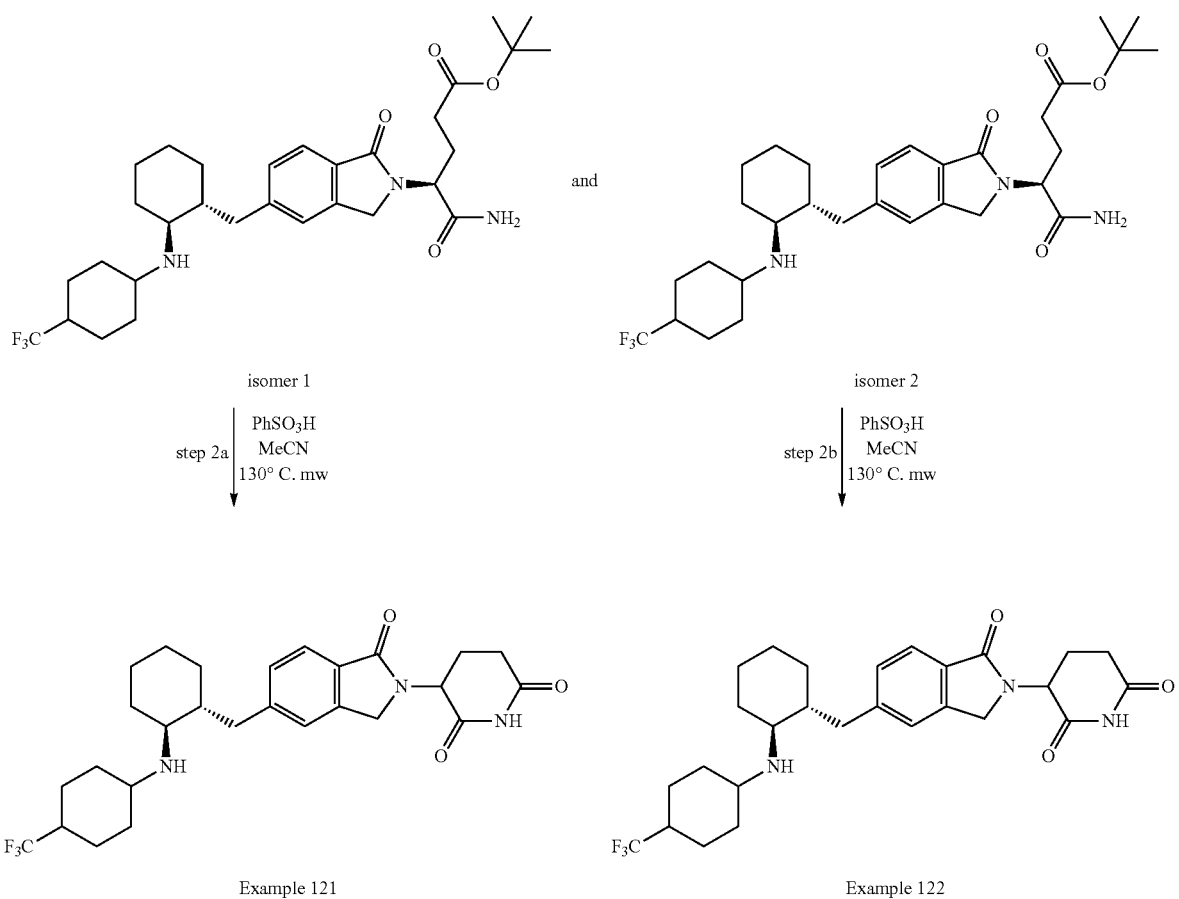

Step 1: Preparation of tert-butyl (S)-5-amino-5-oxo-4-(1-oxo-5-(((1R,2S)-2-((4-(trifluoromethyl)cyclohexyl)amino)cyclohexyl)methyl)isoindolin-2-yl)pentanoate (Isomer 1) and tert-butyl (S)-5-amino-5-oxo-4-(1-oxo-5-(((1R,2S)-2-((4-(trifluoromethyl)cyclohexyl)amino)cyclohexyl)methyl)isoindolin-2-yl)pentanoate (Isomer 2). I-13

(100 mg, 0.13 mmol) was taken up in 1,2-dichloroethane (2.5 mL) and acetic acid (0.186 mL, 3.26 mmol) was added followed by 4-(trifluoromethyl)cyclohexanone (433 mg, 2.61 mmol). The mixture was stirred at r.t. for 3 hours and then NaBH(OAc)$_3$ (138 mg, 0.652 mmol) was added and the reaction stirred overnight a r.t. Following this time, the reaction was concentrated in vacuo and subjected to purification by SiO$_2$ column chromatography (eluent: CH$_2$Cl$_2$/MeOH) to afford tert-butyl (S)-5-amino-5-oxo-4-(1-oxo-5-(((1R,2S)-2-((4-(trifluoromethyl) cyclohexyl) amino) cyclohexyl)methyl)isoindolin-2-yl)pentanoate (Isomer 1) and tert-butyl (S)-5-amino-5-oxo-4-(1-oxo-5-(((1R,2S)-2-((4-(trifluoromethyl)cyclohexyl) amino)cyclohexyl)methyl) isoindolin-2-yl)pentanoate (Isomer 2). ES/MS: 580.2 (M+H$^+$, Isomer 1) and 580.2 (M+H$^+$, Isomer 2).

Step 2a: Preparation of 3-(1-oxo-5-(((1R,2S)-2-((4-(trifluoromethyl) cyclohexyl)amino)cyclohexyl) methyl)isoindolin-2-yl)piperidine-2,6-dione (Example 121)

tert-Butyl (S)-5-amino-5-oxo-4-(1-oxo-5-(((1R,2S)-2-((4-(trifluoromethyl)cyclohexyl) amino)cyclohexyl)methyl) isoindolin-2-yl)pentanoate (Isomer 1) (48.3 mg, 83.3 μmol) was taken up in MeCN (1.0 mL) and benzenesulfonic acid (32.9 mg, 0.208 mmol) was added. The reaction was heated to 130° C. under microwave irradiation for 30 minutes and then the reaction mixture was concentrated in vacuo and the residue purified directly by RP-HPLC (eluent: MeCN/water gradient with 0.1% TFA) to yield the product (Example 121) as the trifluoracetate salt. ES/MS: 506.2 (M+H$^+$). $^1$H NMR (400 MHz, DMSO-d6) δ 10.99 (s, 1H), 7.70 (d, J=7.7 Hz, 1H), 7.46 (s, 1H), 7.38 (d, J=7.8 Hz, 1H), 5.12 (dd, J=13.3, 5.1 Hz, 1H), 4.45 (d, J=17.2 Hz, 1H), 4.32 (d, J=17.2 Hz, 1H), 3.39 (s, 1H), 3.26 (dd, J=13.2, 3.5 Hz, 1H), 3.09 (s, 1H), 2.99-2.78 (m, 1H), 2.69-2.54 (m, 1H), 2.48-2.29 (m, 1H), 2.17-1.63 (m, 13H), 1.63-1.37 (m, 3H), 1.37 (s, 1H), 1.05 (q, J=10.6 Hz, 2H).

Step 2b: Preparation of 3-(1-oxo-5-(((1R,2S)-2-((4-(trifluoromethyl)cyclohexyl)amino)cyclohexyl) methyl)isoindolin-2-yl)piperidine-2,6-dione (Example 122)

tert-Butyl (S)-5-amino-5-oxo-4-(1-oxo-5-(((1R,2S)-2-((4-(trifluoromethyl)cyclohexyl)amino)cyclohexyl)methyl) isoindolin-2-yl)pentanoate (Isomer 2) (15.3 mg, 26.4 μmol) was taken up in MeCN (0.5 mL) and benzenesulfonic acid (10.4 mg, 0.208 mmol) was added. The reaction was heated to 130° C. under microwave irradiation for 30 minutes and then the reaction mixture was concentrated in vacuo and the residue purified directly by RP-HPLC (eluent: MeCN/water gradient with 0.1% TFA) to yield the product (Example 122) as the trifluoracetate salt. ES/MS: 506.2 (M+H$^+$). $^1$H NMR (400 MHz, DMSO-d6) δ 10.99 (s, 1H), 7.71 (d, J=7.8 Hz, 1H), 7.45 (s, 1H), 7.41-7.21 (m, 1H), 5.12 (dd, J=13.3, 5.1 Hz, 1H), 4.45 (d, J=17.3 Hz, 1H), 4.33 (d, J=17.3 Hz, 1H), 3.34-3.18 (m, 2H), 3.09 (s, 2H), 3.01-2.82 (m, 2H), 2.70-2.52 (m, 1H), 2.46-2.22 (m, 1H), 2.22-1.91 (m, 6H), 1.88-1.64 (m, 2H), 1.64-1.19 (m, 6H), 1.04 (d, J=9.2 Hz, 3H).

Procedure 18, Example 123

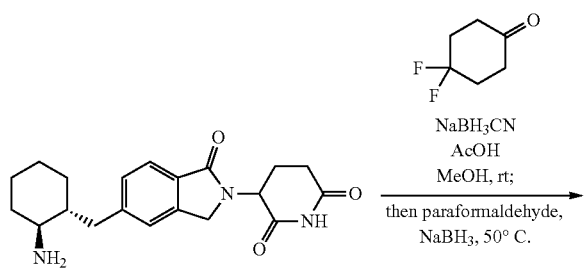

Example 1

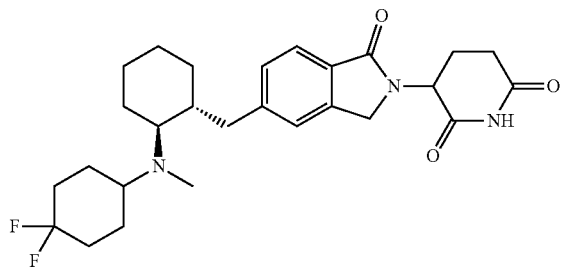

Example 123

3-(5-(((1R,2S)-2-((4,4-difluorocyclohexyl)(methyl) amino)cyclohexyl)methyl)-1-oxoisoindolin-2-yl) piperidine-2,6-dione (Example 123) Example 1

(30.0 mg, 84 μmol) was taken up in MeOH (1.0 mL) and treated with 4,4-difluorocyclohexan-1-one (56.6 mg, 422 μmol) followed by acetic acid (4.8 μL, 84 umol) and sodium cyanoborohydride (15.9 mg, 253 μmol). The reaction mixture was stirred at r.t. for 2 h, then treated with paraformaldehyde (12.7 mg, 422 μmol) followed by additional sodium cyanoborohydride (15.9 mg, 253 μmol). The reaction mixture was stirred at 50° C. for 1 h, then cooled to rt, diluted with DMSO, filtered through a syringe filter, and purified by RP-HPLC (eluent: MeCN/water gradient with 0.1% TFA). Product-containing fractions were combined, lyophilized, taken up DCM, treated with triethylamine (300 μL), and further purified by normal-phase column chromatography (04100% EtOAc in hexanes followed by 0430% MeOH in DCM) to afford the product (Example 123). ES/MS m/z: 488.4 (M+H$^+$). $^1$H NMR (400 MHz, DMSO-d6) δ 10.98 (s, 1H), 7.62 (d, J=7.8 Hz, 1H), 7.36 (s, 1H), 7.27 (d, J=7.6 Hz, 1H), 5.10 (dd, J=13.2, 5.1 Hz, 1H), 4.42 (dd, J=17.2, 3.1 Hz, 1H), 4.29 (dd, J=17.2, 4.2 Hz, 1H), 3.41-3.35 (m, 1H), 2.91 (ddd, J=17.7, 13.5, 5.4 Hz, 1H), 2.71-2.56 (m, 2H), 2.45-2.26 (m, 2H), 2.25 (s, 3H), 2.18-2.09 (m, 1H), 2.09-1.49 (m, 14H), 1.29-1.12 (m, 2H), 1.04-0.83 (m, 2H).

The following Examples were made using the general route described in Procedure 18 and are shown below in Table 11. To prepare the below Examples, different reagents/starting materials were used than some of those described in Procedure 18 and are noted in the last column of Table 11—"Changes to Procedure 18: Different Reagents/Starting Materials". A person of ordinary skill in the art will readily recognize which reagents/starting materials of Procedure 18 were replaced with the different reagents/starting materials noted below.

The following Examples were made using the general routes described in Procedures 3, 9, 10, 11, 12, 15, 16, or 17 (as indicated) and are shown below in Table 12. To prepare the below Examples, different reagents/starting materials were used than some of those described in indicated Procedures and are noted in the last column of Table 12—"Changes to Procedures: Different Reagents/Starting Materials". A person of ordinary skill in the art will readily recognize which reagents/starting materials of indicated Procedures were replaced with the different reagents/starting materials noted below.

TABLE 11

| Example | Structure | ES/MS m/z | ¹H-NMR | Changes to Procedure 18: Different Reagents/Starting Materials |
|---|---|---|---|---|
| 124 | 3-(5-(((1R,2S)-2-((4,4-difluorocyclohexyl)(methyl)amino)cyclohexyl)methyl)-4-fluoro-1-oxoisoindolin-2-yl)piperidine-2,6-dione | 506.4 | ¹H NMR (400 MHz, DMSO-d6) δ 11.00 (s, 1H), 7.50 (d, J = 7.6 Hz, 1H), 7.38 (t, J = 7.0 Hz, 1H), 5.10 (dd, J = 13.2, 5.1 Hz, 1H), 4.53 (d, J = 17.3 Hz, 1H), 4.36 (dd, J = 17.2, 4.0 Hz, 1H), 3.45 (d, J = 12.8 Hz, 1H), 2.97-2.81 (m, 1H), 2.70-2.56 (m, 2H), 2.47-2.29 (m, 2H), 2.26-2.20 (m, 3H), 2.20-2.10 (m, 1H), 2.10-1.45 (m, 14H), 1.30-1.13 (m, 2H), 1.04-0.91 (m, 2H). | I-4 |

The following Examples were made using the general routes described in Procedures 3, 9, 10, 11, 12, 15, 16, or 17 (as indicated) and are shown below in Table 12. To prepare the below Examples, different reagents/starting materials were used than some of those described in indicated Procedures and are noted in the last column of Table 12—"Changes to Procedures: Different Reagents/Starting Materials". A person of ordinary skill in the art will readily recognize which reagents/starting materials of indicated Procedures were replaced with the different reagents/starting materials noted below.

TABLE 12

| Example | Structure | ES/MS m/z: | 1H NMR | Procedure | Changes to Procedure: Different Reagents/ Starting Materials |
|---------|-----------|------------|--------|-----------|-------------------------------------------------------------|
| 125 | 3-(5-(((1R,2S)-2-((7-oxaspiro[3.5]nonan-2-yl)amino)cyclohexyl)methyl)-1-oxoisoindolin-2-yl)piperidine-2,6-dione | 480.3 | ¹H NMR (400 MHz, DMSO-d6) δ 10.99 (s, 1H), 8.91-8.63 (m, 1H), 8.56 (s, 1H), 7.70 (d, J = 7.8 Hz, 1H), 7.45 (s, 1H), 7.37 (dd, J = 7.8, 1.4 Hz, 1H), 5.12 (dd, J = 13.3, 5.1 Hz, 1H), 4.45 (d, J = 17.2 Hz, 1H), 4.32 (dd, J = 17.4, 2.1 Hz, 1H), 3.96-3.84 (m, 2H), 3.61-3.35 (m, 4H), 3.23 (dd, J = 13.3, 4.1 Hz, 1H), 2.92 (ddd, J = 13.2, 9.5, 6.6 Hz, 2H), 2.63 (tt, J = 17.1, 2.2 Hz, 1H), 2.46-2.31 (m, 1H), 2.22 (tq, J = 8.3, 4.2 Hz, 2H), 2.13-1.77 (m ,5H), 1.77-1.18 (m, 7H), 1.08 (q, J = 12.2, 11.0 Hz, 2H). | 3 | 7-oxaspiro[3.5]nonan-2-one |
| 126 | 3-(5-(((3R,4S)-3-((4,4-difluorocyclohexyl)amino)tetrahydro-2H-pyran-4-yl)methyl)-1-oxoisoindolin-2-yl)piperidine-2,6-dione | 476.4 | ¹H NMR (400 MHz, DMSO-d6) δ 10.99 (s, 1H), 8.75 (s, 1H), 8.64-8.46 (m, 1H), 7.70 (d, J = 7.8 Hz, 1H), 7.50 (d, J = 2.3 Hz, 1H), 7.41 (d, J = 7.8 Hz, 1H), 5.19-5.03 (m, 1H), 4.51-4.25 (m, 2H), 4.04 (dd, J = 12.6, 2.9 Hz, 1H), 3.78 (dddt, J = 11.5, 8.0, 3.3 Hz, 1H), 3.69 (dddt, J = 7.4, 5.5, 3.7, 1.7 Hz, 1H), 3.67-3.55 (m, 1H), 3.55-3.28 (m, 2H), 3.25-3.11 (m, 2H), 2.92 (ddd, J = 17.3, 13.6, 5.4 Hz, 1H), 2.79 (ddd, J = 13.4, 9.8, 3.3 Hz, 1H), 2.61 (dt, J = 15.4, 2.5 Hz, 1H), 2.40 (qd, J = 13.2, 4.5 Hz, 1H), 2.28-2.05 (m, 2H), 2.05-1.90 (m, 2H), 1.90-1.74 (m, 2H), 1.73-1.64 (m, 12H), 1.64-1.45 (m, 2H), 1.33-1.21 (m, 1H). | 3 | I-46; 4,4-difluorocyclohexanone |

TABLE 12-continued

| Example | Structure | ES/MS m/z: | 1H NMR | Procedure | Changes to Procedure: Different Reagents/ Starting Materials |
|---|---|---|---|---|---|
| 127 | 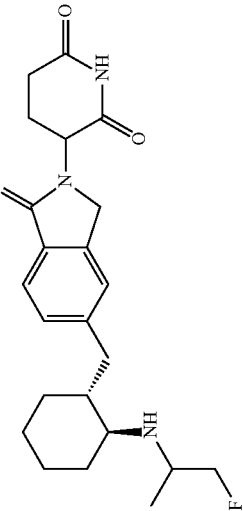<br>3-(5-(((1R,2S)-2-((1-fluoropropan-2-yl)amino)cyclohexyl)methyl)-1-oxoisoindolin-2-yl)piperidine-2,6-dione | 416.3 | ¹H NMR (400 MHz, DMSO-d6) δ 10.98 (s, 1H), 7.62 (d, J = 7.8 Hz, 1H), 7.40 (s, 1H), 7.31 (d, J = 7.8 Hz, 1H), 5.10 (dd, J = 13.3, 5.1 Hz, 1H), 4.42 (d, J = 17.2 Hz, 1H), 4.36-4.08 (m, 3H), 3.51-3.36 (m, 1H), 3.14-2.97 (m, 1H), 2.91 (ddd, J = 17.2, 13.6, 5.4 Hz, 1H), 2.64-2.55 (m, 1H), 2.38 (qd, J = 13.2, 4.5 Hz, 1H), 1.65 (d, J = 12.6 Hz, 1H), 1.95 (m, 2H), 1.56-1.45 (m, 2H), 1.42-1.28 (m, 1H), 1.25-1.11 (m, 1H), 1.08-0.84 (m, 6H). | 3 | 1-fluoropropan-2-one |
| 128 | 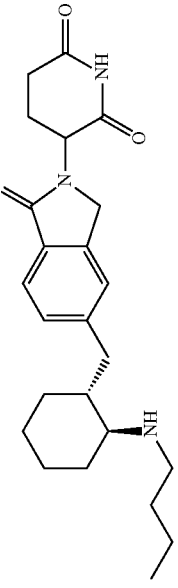<br>3-(5-(((1R,2S)-2-(butylamino)cyclohexyl)methyl)-1-oxoisoindolin-2-yl)piperidine-2,6-dione | 412.3 | ¹H NMR (400 MHz, DMSO-d6) δ 10.99 (s, 1H), 8.49 (s, 1H), 8.28 (s, 1H), 7.69 (d, J = 7.8 Hz, 1H), 7.45 (s, 1H), 7.36 (dd, J = 7.8, 1.4 Hz, 1H), 5.11 (dd, J = 13.3, 5.1 Hz, 1H), 4.45 (dd, J = 17.4, 3.1 Hz, 1H), 4.31 (dd, J = 17.3, 3.8 Hz, 1H), 3.22 (dd, J = 13.3, 3.7 Hz, 1H), 3.08-2.84 (m, 4H), 2.65-2.56 (m, 1H), 2.50 (qd, J = 13.7, 4.7 Hz, 2H), 2.03 (ddd, J = 20.1, 10.2, 5.1 Hz, 2H), 1.92-1.81 (m, 1H), 1.76-1.58 (m, 2H), 1.58-1.41 (m, 2H), 1.41-1.18 (m, 3H), 1.04 (q, J = 10.3 Hz, 2H), 0.92 (t, J = 7.4 Hz, 3H), 0.90-0.83 (m, 2H). | 3 | Butanal |

TABLE 12-continued

| Example | Structure | ES/MS m/z: | 1H NMR | Procedure | Changes to Procedure: Different Reagents/ Starting Materials |
|---|---|---|---|---|---|
| 129 | 3-(5-(((1R,2S)-2-(isopentylamino)cyclohexyl)methyl)-1-oxoisoindolin-2-yl)piperidine-2,6-dione | 426.4 | $^{1}$H NMR (400 MHz, DMSO-d6) δ 10.99 (s, 1H), 8.48 (s, 1H), 8.26 (s, 1H), 7.69 (d, J = 7.8 Hz, 1H), 7.45 (s, 1H), 7.36 (dd, J = 7.8, 1.4 Hz, 1H), 5.11 (dd, J = 13.3, 5.1 Hz, 1H), 4.54-4.40 (m, 1H), 4.31 (dd, J = 17.3, 3.9 Hz, 1H), 3.22 (dd, J = 13.3, 3.8 Hz, 1H), 3.08-2.84 (m, 4H), 2.67-2.55 (m, 1H), 2.47-2.31 (m, 2H), 2.12-2.04 (m, 1H), 1.99 (dd, J = 9.2, 4.1 Hz, 1H), 1.87 (d, J = 9.8 Hz, 1H), 1.77-1.60 (m, 2H), 1.59-1.38 (m, 5H), 1.30 (d, J = 12.0 Hz, 1H), 1.05 (q, J = 10.7 Hz, 2H), 0.91 (dd, J = 7.9, 7.2, 1.9 Hz, 6H). | 3 | 3-methylbutanal |
| 130 | 3-(5-(((1R,2S)-2-((1,1-difluoropropan-2-yl)amino)cyclohexyl)methyl)-1-oxoisoindolin-2-yl)piperidine-2,6-dione | 434.3 | $^{1}$H NMR (400 MHz, DMSO-d6) δ 10.98 (s, 1H), 7.62 (d, J = 7.7 Hz, 1H), 7.45-7.26 (m, 2H), 5.98-5.62 (m, 1H), 5.10 (dd, J = 13.3, 5.1 Hz, 1H), 4.42 (d, J = 17.1 Hz, 1H), 4.29 (d, J = 17.2 Hz, 1H), 3.11-2.97 (m, 1H), 2.91 (ddd, J = 18.1, 13.5, 5.4 Hz, 1H), 2.65-2.55 (m, 1H), 2.46-2.12 (m, 3H), 2.03-1.89 (m, 2H), 1.77-0.78 (m, 12H). | 3 | 1,1-difluoropropan-2-one |

TABLE 12-continued

| Example | Structure | ES/MS m/z: | 1H NMR | Procedure | Changes to Procedure: Different Reagents/ Starting Materials |
|---|---|---|---|---|---|
| 131 | 3-(5-(((1R,2S)-2-((2,3-dihydro-1H-inden-1-yl)amino)cyclohexyl)methyl)-1-oxoisoindolin-2-yl)piperidine-2,6-dione | 472.4 | 1H NMR (400 MHz, DMSO-d6) δ 10.99 (s, 1H), 8.75 (s, 1H), 8.60 (s, 1H), 7.69 (d, J = 7.7 Hz, 1H), 7.60 (t, J = 6.4 Hz, 1H), 7.45-7.21 (m, 4H), 5.36-4.78 (m, 2H), 4.50-4.12 (m, 2H), 3.34 (d, J = 14.9 Hz, 1H), 3.14 (ddd, J = 30.2, 9.7, 6.0 Hz, 1H), 2.98-2.80 (m, 2H), 2.70-2.56 (m, 1H), 2.45-2.31 (m, 1H), 2.31-2.09 (m, 1H), 2.08-1.93 (m, 1H), 1.54 (d, J = 15.8 Hz, 2H), 1.01-1.14 (m). | 3 | indan-1-one |
| 132 | 3-(5-(((1R,2S)-2-(bicyclo[3.2.0]heptan-3-ylamino)cyclohexyl)methyl)-1-oxoisoindolin-2-yl)piperidine-2,6-dione | 450.4 | 1H NMR (400 MHz, DMSO-d6) δ 10.99 (s, 1H), 8.67 (s, 1H), 8.28 (s, 1H), 7.70 (d, J = 7.8 Hz, 1H), 7.45 (s, 1H), 7.37 (d, J = 7.9 Hz, 1H), 5.11 (dd, J = 13.3, 5.1 Hz, 1H), 4.53 (ddd, J = 9.1, 7.5, 4.6 Hz, 1H), 4.49-4.24 (m, 2H), 3.57 (s, 2H), 3.29 (d, J = 13.8 Hz, 1H), 3.10-2.86 (m, 2H), 2.73-2.56 (m, 5H), 2.46-2.31 (m, 1H), 2.22 (p, J = 5.7 Hz, 1H), 2.17-2.05 (m, 2H), 2.05-1.95 (m, 1H), 1.68 (dd, J = 12.5, 5.8 Hz, 3H), 1.50-1.29 (m, 3H), 1.19-0.97 (m, 2H). | 3 | Bicyclo[3.2.0]heptan-3-one |

TABLE 12-continued

| Example | Structure | ES/MS m/z: | 1H NMR | Procedure | Changes to Procedure: Different Reagents/ Starting Materials |
|---|---|---|---|---|---|
| 133 | 4-(((1S,2R)-2-((2-(2,6-dioxopiperidin-3-yl)-1-oxoisoindolin-5-yl)methyl)cyclohexyl)amino)-2,2-dimethylbutanenitrile | 451.4 | 1H NMR (400 MHz, DMSO-d6) δ 10.99 (s, 1H), 8.75 (s, 1H), 8.46 (s, 1H), 7.69 (d, J = 7.8 Hz, 1H), 7.45 (s, 1H), 7.36 (dd, J = 7.8, 1.4 Hz, 1H), 5.11 (dd, J = 13.3, 5.1 Hz, 1H), 4.50-4.38 (m, 1H), 4.31 (dd, J = 17.3, 3.9 Hz, 1H), 3.24 (dd, J = 13.4, 3.6 Hz, 1H), 3.20-3.00 (m, 2H), 2.92 (ddd, J = 17.2, 13.6, 5.4 Hz, 1H), 2.60 (dd, J = 16.9, 3.3 Hz, 1H), 2.40 (qd, J = 13.0, 4.3 Hz, 2H), 2.12 (dt, J = 12.3, 3.4 Hz, 1H), 2.08-1.96 (m, 2H), 1.90 (td, J = 12.3, 4.9 Hz, 2H), 1.72 (d, J = 12.3 Hz, 1H), 1.61-1.51 (m, 2H), 1.48-1.42 (m, 1H), 1.38 (d, J = 2.2 Hz, 6H), 1.32-1.20 (m, 2H), 1.04 (p, J = 11.8, 11.3 Hz, 2H). | 3 | 2,2-dimethyl-4-oxo-butanenitrile |
| 134 | 3-(5-(((1R,2S)-2-((3-methoxy-3-methylbutyl)amino)cyclohexyl)methyl)-1-oxoisoindolin-2-yl)piperidine-2,6-dione | 456.4 | 1H NMR (400 MHz, DMSO-d6) δ 10.99 (s, 1H), 8.38 (s, 1H), 8.14 (s, 1H), 7.69 (d, J = 7.8 Hz, 1H), 7.44 (s, 1H), 7.36 (dd, J = 7.8, 1.4 Hz, 1H), 5.11 (dd, J = 13.3, 5.1 Hz, 1H), 4.45 (dd, J = 17.4, 3.8 Hz, 1H), 4.31 (dd, J = 17.3, 4.3 Hz, 1H), 3.20 (dd, J = 13.3, 3.7 Hz, 1H), 3.12 (s, 3H), 2.99 (d, J = 18.4 Hz, 3H), 2.96-2.84 (m, 1H), 2.65-2.56 (m, 1H), 2.46-2.35 (m, 2H), 2.09-1.96 (m, 2H), 1.92-1.65 (m, 4H), 1.50 (d, J = 15.8 Hz, 2H), 1.45-1.36 (m, 1H), 1.30 (d, J = 11.7 Hz, 1H), 1.16 (s, 6H), 1.03 (p, J = 11.5 Hz, 2H). | 3 | 3-methoxy-3-methyl-butanal |

TABLE 12-continued

| Example | Structure | ES/MS m/z: | 1H NMR | Procedure | Changes to Procedure: Different Reagents/ Starting Materials |
|---|---|---|---|---|---|
| 135 | 3-(5-(((1R,2S)-2-((4,4-difluorobutyl)amino)cyclohexyl)methyl)-1-oxoisoindolin-2-yl)piperidine-2,6-dione | 448.3 | ¹H NMR (400 MHz, DMSO-d6) δ 10.99 (s, 1H), 8.52 (s, 1H), 8.30 (s, 1H), 7.69 (d, J = 7.8 Hz, 1H), 7.45 (s, 1H), 7.37 (dd, J = 7.8, 1.4 Hz, 1H), 6.17 (tt, J = 56.5, 4.1 Hz, 1H), 5.11 (dd, J = 13.3, 5.1 Hz, 1H), 4.45 (dd, J = 17.5, 3.2 Hz, 1H), 4.31 (dd, J = 17.3, 4.1 Hz, 1H), 3.23 (dd, J = 13.5, 3.7 Hz, 1H), 3.12 (s, 1H), 3.02 (s, 2H), 2.92 (ddd, J = 17.4, 13.6, 5.4 Hz, 1H), 2.65-2.56 (m, 1H), 2.45-2.36 (m, 2H), 2.11-1.90 (m, 4H), 1.90-1.66 (m, 4H), 1.60-1.39 (m, 3H), 1.30 (d, J = 11.5 Hz, 1H), 1.05 (q, J = 10.3 Hz, 2H). | 3 | 4,4-difluorobutanal |
| 136 | 3-(5-(((1R,2S)-2-((1-(3,3-difluorocyclobutyl)ethyl)amino)cyclohexyl)methyl)-1-oxoisoindolin-2-yl)piperidine-2,6-dione (isomer 1) | 474.3 | ¹H NMR (400 MHz, DMSO-d6) δ 10.99 (s, 1H), 8.37 (s, 1H), 8.00 (s, 1H), 7.71 (dd, J = 7.8, 2.9 Hz, 1H), 7.44 (d, J = 8.1 Hz, 1H), 7.36 (d, J = 7.8 Hz, 1H), 5.11 (dd, J = 13.3, 5.1 Hz, 1H), 4.39 (ddd, J = 53.1, 17.3, 4.3 Hz, 2H), 3.55 (q, J = 6.3 Hz, 2H), 3.23 (d, J = 12.5 Hz, 1H), 3.02 (s, 1H), 2.92 (ddd, J = 18.1, 13.6, 5.4 Hz, 1H), 2.75 (dd, J = 13.7, 8.3 Hz, 0H), 2.63 (t, J = 17.2 Hz, 3H), 2.47-2.29 (m, 5H), 2.10 (d, J = 8.7 Hz, 1H), 2.05-1.95 (m, 2H), 1.78 (d, J = 53.2 Hz, 1H), 1.64-1.30 (m, 3H), 1.27 (d, J = 6.5 Hz, 3H), 1.03 (d, J = 9.2 Hz, 2H). | 3 | 1-(3,3-difluorocyclobutyl)ethanone |

TABLE 12-continued

| Example | Structure | ES/MS m/z: | 1H NMR | Procedure | Changes to Procedure: Different Reagents/ Starting Materials |
|---|---|---|---|---|---|
| 137 | 3-(5-(((1R,2S)-2-((1-(3,3-difluorocyclobutyl)amino)cyclohexyl)methyl)-1-oxoisoindolin-2-yl)piperidine-2,6-dione (isomer 2) | 474.3 | 1H NMR (400 MHz, DMSO-d6) δ 10.99 (s, 1H), 8.14 (s, 1H), 7.91 (s, 1H), 7.71 (d, J = 7.8 Hz, 1H), 7.43 (s, 1H), 7.35 (d, J = 7.9 Hz, 1H), 5.11 (dd, J = 13.3, 5.1 Hz, 1H), 4.39 (ddd, J = 53.7, 17.3, 4.7 Hz, 2H), 3.31 (d, J = 13.0 Hz, 2H), 3.06 (s, 1H), 2.92 (ddd, J = 18.0, 13.6, 5.4 Hz, 1H), 2.80-2.65 (m, 2H), 2.65-2.56 (m, 2H), 2.47-2.31 (m, 3H), 2.12 (d, J = 11.2 Hz, 1H), 2.06-1.94 (m, 1H), 1.84 (s, 1H), 1.74 (d, J = 12.4 Hz, 1H), 1.61-1.45 (m, 2H), 1.45-1.25 (m, 2H), 1.23 (d, J = 6.4 Hz, 3H), 1.10-0.95 (m, 2H). | 3 | 1-(3,3-difluorocyclobutyl)ethanone |
| 138 | 3-(5-(((1R,2S)-2-((1-(bicyclo[1.1.1]pentan-1-yl)ethyl)amino)cyclohexyl)methyl)-1-oxoisoindolin-2-yl)piperidine-2,6-dione | 450.4 | 1H NMR (400 MHz, DMSO-d6) δ 10.99 (s, 1H), 8.11 (s, 1H), 8.00 (s, 1H), 7.70 (dd, J = 7.8, 2.3 Hz, 1H), 7.46 (d, J = 4.5 Hz, 1H), 7.37 (dd, J = 7.9, 4.9 Hz, 1H), 5.11 (dd, J = 13.3, 5.1 Hz, 1H), 4.51-4.27 (m, 2H), 3.50 (q, J = 6.5, 5.5 Hz, 1H), 3.40 (q, J = 5.9 Hz, 1H), 3.26 (td, J = 15.2, 13.2, 3.6 Hz, 1H), 2.99-2.84 (m, 2H), 2.66-2.56 (m, 1H), 2.47-2.30 (m, 2H), 2.08 (dd, J = 8.8, 4.6 Hz, 0H), 2.05-1.91 (m, 2H), 1.90-1.79 (m, 6H), 1.79-1.67 (m, 1H), 1.62-1.38 (m, 3H), 1.31 (t, J = 12.1 Hz, 1H), 1.23 (t, J = 6.9 Hz, 3H), 1.13-0.98 (m, 3H). | 3 | 1-(1-bicyclo[1.1.1]pentanyl)ethanone |

TABLE 12-continued

| Example | Structure | ES/MS m/z: | 1H NMR | Procedure | Changes to Procedure: Different Reagents/ Starting Materials |
|---|---|---|---|---|---|
| 139 | 3-(5-(((1R,2S)-2-(bicyclo[3.1.0]hexan-3-ylamino)cyclohexyl)methyl)-1-oxoisoindolin-2-yl)piperidine-2,6-dione | 454.3 | ¹H NMR (400 MHz, DMSO-d6) δ 11.01 (s, 1H), 8.49 (s, 1H), 8.05 (s, 1H), 7.59 (d, J = 7.6 Hz, 1H), 7.47 (t, J = 7.0 Hz, 1H), 5.12 (dd, J = 13.3, 5.1 Hz, 1H), 4.47 (ddd, J = 69.9, 17.4, 3.4 Hz, 2H), 4.02 (s, 1H), 3.15 (d, J = 13.8 Hz, 1H), 3.01-2.78 (m, 2H), 2.75-2.52 (m, 3H), 2.42 (dt, J = 13.4, 7.2 Hz, 1H), 2.15-1.95 (m, 2H), 1.86 (s, 1H), 1.67 (s, 1H), 1.63-1.23 (m, 6H), 1.08 (s, 2H), 0.87 (dd, J = 9.3, 7.4, 3.3 Hz, 1H), 0.51-0.28 (m, 1H). | 3 | bicyclo[3.1.0]hexan-3-one |
| 140 | 3-(5-(((1R,2S)-2-((6,6-dimethylbicyclo[3.1.0]hexan-3-yl)amino)cyclohexyl)methyl)-1-oxoisoindolin-2-yl)piperidine-2,6-dione | 482.3 | ¹H NMR (400 MHz, DMSO-d6) δ 11.01 (s, 1H), 8.56 (s, 1H), 8.18 (s, 1H), 7.59 (d, J = 7.7 Hz, 1H), 7.49 (t, J = 7.0 Hz, 1H), 5.12 (dd, J = 13.3, 5.1 Hz, 1H), 4.47 (ddd, J = 69.6, 17.4, 2.2 Hz, 2H), 3.21-3.06 (m, 1H), 3.06-2.82 (m, 2H), 2.72-2.55 (m, 2H), 2.41 (td, J = 13.2, 4.5 Hz, 1H), 2.33-2.13 (m, 1H), 2.13-1.97 (m, 2H), 1.91 (s, 1H), 1.70 (d, J = 21.8 Hz, 1H), 1.51 (dd, J = 29.8, 9.9 Hz, 2H), 1.31 (dt, J = 51.4, 12.1 Hz, 2H), 1.12 (dd, J = 17.9, 2.3 Hz, 5H), 0.99 (s, 3H). | 3 | 6,6-dimethylbicyclo[3.1.0]hexan-3-one |

TABLE 12-continued

| Example | Structure | ES/MS m/z: | 1H NMR | Procedure | Changes to Procedure: Different Reagents/ Starting Materials |
|---|---|---|---|---|---|
| 141 | 3-(4-fluoro-5-(((1R,2S)-2-((octahydropentalen-2-yl)amino)cyclohexyl)methyl)-1-oxoisoindolin-2-yl)piperidine-2,6-dione | 482.3 | $^1$H NMR (400 MHz, DMSO-d6) δ 11.01 (s, 1H), 8.55 (d, J = 32.9 Hz, 1H), 8.06 (s, 1H), 7.59 (d, J = 7.6 Hz, 1H), 7.49 (t, J = 6.9 Hz, 1H), 5.12 (dd, J = 13.3, 5.1 Hz, 1H), 4.62-4.28 (m, 2H), 3.19 (d, J = 10.8 Hz, 1H), 3.03 (s, 1H), 2.92 (ddd, J = 18.0, 13.6, 5.3 Hz, 1H), 2.63 (t, J = 17.5 Hz, 2H), 2.46-2.36 (m, 2H), 2.27 (dd, J = 29.4, 17.2 Hz, 1H), 2.08 (d, J = 4.5 Hz, 1H), 1.96-1.63 (m, 2H), 1.63-1.29 (m, 5H), 1.29-0.95 (m, 3H). | 3 | I-4; hexahydropentalen-2(1H)-one |
| 142 | 3-(5-(((1R,2S)-2-((7,7-difluorospiro[3.5]nonan-2-yl)amino)cyclohexyl)methyl)-1-oxoisoindolin-2-yl)piperidine-2,6-dione | 514.4 | $^1$H NMR (400 MHz, DMSO-d6) δ 10.99 (s, 1H), 8.84 (dt, J = 12.9, 6.5 Hz, 1H), 8.71-8.47 (m, 1H), 7.69 (d, J = 7.8 Hz, 1H), 7.45 (s, 1H), 7.37 (d, J = 7.8 Hz, 1H), 5.11 (dd, J = 13.3, 5.1 Hz, 1H), 4.45 (d, J = 17.2 Hz, 1H), 4.31 (dd, J = 17.4, 2.4 Hz, 1H), 3.23 (dd, J = 13.4, 4.0 Hz, 1H), 2.91 (dq, J = 17.2, 6.7, 5.3 Hz, 2H), 2.61 (dt, J = 17.5, 3.2 Hz, 1H), 2.48-2.31 (m, 2H), 2.20 (tt, J = 9.2, 4.6 Hz, 2H), 2.08 (dd, J = 12.3, 8.4 Hz, 1H), 2.00 (ddd, J = 10.0 ,6.1, 3.1 Hz, 3H), 1.84 (dtd, J = 26.4, 13.2, 6.6 Hz, 6H), 1.67 (dt, J = 23.9, 6.3 Hz, 5H), 1.51 (tq, J = 11.9, 6.4, 5.2 Hz, 2H), 1.44-1.35 (m, 1H), 1.34-1.21 (m, 1H), 1.06 (hept, J = 9.8, 8.5 Hz, 2H). | 3 | 7,7-difluorospiro[3.5]nonan-2-one |

TABLE 12-continued

| Example | Structure | ES/MS m/z: | 1H NMR | Procedure | Changes to Procedure: Different Reagents/ Starting Materials |
|---|---|---|---|---|---|
| 143 | 3-(5-(((1R,2S)-2-(chroman-3-ylamino)cyclohexyl)methyl)-1-oxoisoindolin-2-yl)piperidine-2,6-dione | 488.3 | ¹H NMR (400 MHz, DMSO-d6) δ 10.99 (s, 1H), 8.80 (s, 1H), 8.30 (s, 1H), 7.70 (d, J = 7.8 Hz, 1H), 7.46 (s, 1H), 7.38 (d, J = 7.7 Hz, 1H), 7.16 (t, J = 7.6 Hz, 3H), 6.96 (td, J = 7.4, 1.3 Hz, 1H), 6.88 (d, J = 8.0 Hz, 1H), 5.12 (dd, J = 13.3, 5.1 Hz, 1H), 4.52-4.32 (m, 3H), 4.32-4.20 (m, 1H), 3.99 (s, 2H), 3.31-3.16 (m, 3H), 3.03 (d, J = 6.5 Hz, 1H), 3.00-2.83 (m, 1H), 2.69-2.56 (m, 1H), 2.45-2.31 (m, 1H), 2.15 (d, J = 12.1 Hz, 1H), 2.06-1.87 (m, 2H), 1.71 (s, 1H), 1.54 (s, 4H), 1.36 (d, J = 11.3 Hz, 1H), 1.18-0.99 (m, 3H). | 3 | chroman-3-one |
| 144 | 3-(1-oxo-5-(((1R,2S)-2-((3,3,5,5-tetramethylcyclohexyl)amino)cyclohexyl)methyl)isoindolin-2-yl)piperidine-2,6-dione | 494.4 | ¹H NMR (400 MHz, DMSO-d6) δ 10.99 (s, 1H), 8.39 (s, 1H), 7.97 (s, 1H), 7.69 (d, J = 7.7 Hz, 1H), 7.45 (s, 1H), 7.37 (d, J = 7.8 Hz, 1H), 5.11 (dd, J = 13.3, 5.1 Hz, 1H), 4.45 (d, J = 17.3 Hz, 1H), 4.32 (d, J = 17.2 Hz, 1H), 3.47-3.34 (m, 1H), 3.25 (dd, J = 13.2, 4.0 Hz, 1H), 3.10 (d, J = 7.7 Hz, 1H), 2.92 (ddd, J = 18.0, 13.6, 5.4 Hz, 1H), 2.78 (d, J = 12.3 Hz, 1H), 2.65-2.56 (m, 1H), 2.48-2.33 (m, 2H), 2.14-2.04 (m, 1H), 1.99 (ddq, J = 10.6, 5.6, 3.5, 2.9 Hz, 1H), 1.88-1.78 (m, 2H), 1.78-1.60 (m, 2H), 1.60-1.49 (m, 2H), 1.50-1.34 (m, 2H), 1.34 (s, 2H), 1.17 (t, J = 12.3 Hz, 1H), 1.08 (q, J = 5.9, 5.4 Hz, 2H), 1.05-0.99 (m, 6H), 0.98-0.89 (m, 6H). | 3 | 3,3,5,5-tetramethylcyclohexanone |

TABLE 12-continued

| Example | Structure | ES/MS m/z: | 1H NMR | Procedure | Changes to Procedure: Different Reagents/ Starting Materials |
|---|---|---|---|---|---|
| 145 | 3-(1-oxo-5-(((1R,2S)-2-((4-(trifluoromethoxy)cyclohexyl)amino)cyclohexyl)methyl)isoindolin-2-yl)piperidine-2,6-dione (Isomer 1) | 522.4 | $^1$H NMR (400 MHz, DMSO-d6) δ 10.99 (s, 1H), 8.38 (s, 1H), 8.06 (s, 1H), 7.70 (d, J = 7.7 Hz, 1H), 7.44 (s, 1H), 7.42-7.28 (m, 1H), 5.11 (dd, J = 13.3, 5.1 Hz, 1H), 4.53-4.18 (m, 3H), 3.25 (d, J = 14.1 Hz, 2H), 3.07 (s, 1H), 2.92 (ddd, J = 18.9, 13.9, 5.8 Hz, 2H), 2.61 (d, J = 17.1 Hz, 1H), 2.46-2.30 (m, 2H), 2.11 (d, J = 15.9 Hz, 4H), 2.04-1.93 (m, 1H), 1.81 (s, 1H), 1.76-1.44 (m, 4H), 1.35 (dt, J = 21.7, 11.6 Hz, 1H), 1.18-0.90 (m, 2H). | 3 | 4-(trifluoromethoxy)cyclohexanone |
| 146 | 3-(1-oxo-5-(((1R,2S)-2-((4-(trifluoromethoxy)cyclohexyl)amino)cyclohexyl)methyl)isoindolin-2-yl)piperidine-2,6-dione (Isomer 2) | 522.4 | $^1$H NMR (400 MHz, DMSO-d6) δ 10.99 (s, 1H), 8.39 (s, 1H), 8.06 (s, 1H), 7.70 (d, J = 7.8 Hz, 1H), 7.44 (s, 1H), 7.36 (d, J = 7.8 Hz, 1H), 5.11 (dd, J = 13.3, 5.1 Hz, 1H), 4.72 (s, 1H), 4.52-4.26 (m, 2H), 3.37 (s, 2H), 3.28 (d, J = 12.9 Hz, 1H), 3.08 (s, 2H), 2.98-2.85 (m, 1H), 2.71 (s, 1H), 2.61 (d, J = 16.7 Hz, 1H), 2.47-2.27 (m, 2H), 2.25-2.06 (m, 1H), 1.99 (d, J = 10.0 Hz, 3H), 1.73 (qt, J = 27.2, 12.8 Hz, 5H), 1.52 (d, J = 15.3 Hz, 1H), 1.44-1.20 (m, 1H), 1.03 (s, 2H). | 3 | 4-(trifluoromethoxy)cyclohexanone |

| Example | Structure | ES/MS m/z: | 1H NMR | Procedure | Changes to Procedure: Different Reagents/ Starting Materials |
|---|---|---|---|---|---|
| 147 | 3-(5-(1-((1R,2S)-2-((4,4-difluorocyclohexyl)amino)cyclohexyl)ethyl)-1-oxoisoindolin-2-yl)piperidine-2,6-dione | 488.4 | $^1$H NMR (400 MHz, DMSO-d6) δ 10.99 (s, 1H), 8.59 (s, 1H), 7.98 (d, J = 10.9 Hz, 1H), 7.72 (d, J = 7.9 Hz, 1H), 7.55 (s, 1H), 7.46 (d, J = 7.9 Hz, 1H), 6.78 (s, 2H), 5.11 (dt, J = 13.6, 4.0 Hz, 1H), 4.45 (d, J = 17.3 Hz, 1H), 4.31 (d, J = 17.3 Hz, 1H), 3.43 (d, J = 17.4 Hz, 2H), 3.36 (q, J = 6.5 Hz, 2H), 3.08 (s, 1H), 2.92 (ddd, J = 17.2, 13.6, 5.4 Hz, 1H), 2.65-2.57 (m, 1H), 2.41 (qd, J = 13.5, 4.7 Hz, 1H), 2.34-2.22 (m, 1H), 2.10 (qd, J = 8.7, 5.6, 3.9 Hz, 5H), 2.07-2.03 (m, 2H), 2.03-1.92 (m, 12H), 1.92-1.80 (m, 5H), 1.70 (d, J = 13.6 Hz, 2H), 1.56 (dd, J = 13.2, 8.8 Hz, 3H), 1.37 (hept, J = 6.6, 5.5 Hz, 4H), 1.23 (d, J = 6.8 Hz, 3H), 1.09 (s, 1H). | 3 | I-15; 4,4-difluorocyclohexanone |
| 148 | 3-(5-(((2R,3S)-3-(cyclopentylamino)tetrahydro-2H-pyran-2-yl)methyl)-4-fluoro-1-oxoisoindolin-2-yl)piperidine-2,6-dione | 444.3 | $^1$H NMR (400 MHz, Methanol-d4) δ 7.62 (d, J = 7.7 Hz, 1H), 7.56 (t, J = 6.9 Hz, 1H), 5.18 (ddd, J = 13.3, 5.2, 2.2 Hz, 1H), 4.67-4.50 (m, 2H), 3.92 (q, J = 10.4, 8.1 Hz, 2H), 3.80 (q, J = 7.7 Hz, 1H), 3.51-3.44 (m, 1H), 3.28 (s, 2H), 2.98-2.88 (m, 1H), 2.81 (ddd, J = 17.6, 4.8, 2.4 Hz, 1H), 2.58-2.48 (m, 1H), 2.44-2.35 (m, 1H), 2.24-2.14 (m, 3H), 2.04 (dq, J = 11.8, 7.9, 7.1 Hz, 3H), 1.93-1.79 (m, 7H), 1.72 (s, 5H). | 3 | I-12; cyclopentanone |

TABLE 12-continued

| Example | Structure | ES/MS m/z: | 1H NMR | Procedure | Changes to Procedure: Different Reagents/ Starting Materials |
|---|---|---|---|---|---|
| 149 | 3-(5-(((2R,3S)-3-(((4,4-difluorocyclohexyl)methyl)amino)tetrahydro-2H-pyran-2-yl)methyl)-4-fluoro-1-oxoisoindolin-2-yl)piperidine-2,6-dione | 508.4 | $^1$H NMR (400 MHz, DMSO-d6) δ 11.01 (s, 1H), 8.83-8.68 (m, 1H), 8.39 (s, 1H), 7.57 (d, J = 7.7 Hz, 1H), 7.52 (dd, J = 7.6, 6.1 Hz, 1H), 5.12 (dd, J = 13.3, 5.1 Hz, 1H), 4.55 (d, J = 17.3 Hz, 1H), 4.45-4.27 (m, 1H), 3.79 (dddd, J = 17.2, 11.6, 7.7, 3.4 Hz, 2H), 3.33-3.20 (m, 2H), 3.16 (s, 1H), 2.98 (dq, J = 8.5, 5.2 Hz, 3H), 2.95-2.86 (m, 1H), 2.61 (dt, J = 17.5, 3.1 Hz, 1H), 2.43 (tt, J = 13.3, 6.8 Hz, 1H), 2.27-2.16 (m, 1H), 2.12-1.98 (m, 3H), 1.98-1.80 (m, 4H), 1.80-1.65 (m, 3H), 1.62-1.50 (m, 1H), 1.29 (dq, J = 21.6, 11.8, 10.3 Hz, 2H). | 3 | I-12; 4,4-difluorocyclohexanecarbaldehyde |
| 150 | 3-(5-(((2R,3S)-3-(((3,3-difluorocyclobutyl)methyl)amino)tetrahydro-2H-pyran-2-yl)methyl)-4-fluoro-1-oxoisoindolin-2-yl)piperidine-2,6-dione | 480.3 | $^1$H NMR (400 MHz, DMSO-d6) δ 11.01 (s, 1H), 8.89 (d, J = 10.8 Hz, 1H), 8.51 (s, 1H), 7.57 (d, J = 7.7 Hz, 1H), 7.55-7.49 (m, 1H), 5.12 (dd, J = 13.3, 5.1 Hz, 1H), 4.56 (dd, J = 17.4, 5.6 Hz, 1H), 4.40 (td, J = 18.4, 17.3, 5.3 Hz, 2H), 3.85-3.74 (m, 2H), 3.44-3.39 (m, 1H), 3.32-3.12 (m, 5H), 3.05-2.86 (m, 2H), 2.86-2.67 (m, 3H), 2.65-2.56 (m, 2H), 2.54 (td, J = 6.0, 3.3 Hz, 1H), 2.48-2.40 (m, 2H), 2.39-2.26 (m, 1H), 2.22 (ddd, J = 13.6, 10.0, 6.3 Hz, 2H), 2.01 (ddq, J = 10.5, 5.5, 3.2, 2.8 Hz, 1H), 1.71 (ttd, J = 13.3, 9.3, 8.9, 3.9 Hz, 2H), 1.56 (ddt, J = 14.8, 9.3, 4.9 Hz, 1H). | 3 | I-12; 4,4-difluorocyclobutanecarbaldehyde |

TABLE 12-continued

| Example | Structure | ES/MS m/z: | 1H NMR | Procedure | Changes to Procedure: Different Reagents/ Starting Materials |
|---|---|---|---|---|---|
| 151 | 3-(5-(((1R,2R,3S)-rel-2-((4,4-difluorocyclohexyl)amino)-3-hydroxy-cyclohexyl)methyl)-1-oxoisoindolin-2-yl)piperidine-2,6-dione | 490.2 | 1H NMR (400 MHz, DMSO-d6) δ 10.99 (s, 1H), 8.36 (s, 1H), 8.19 (s, 1H), 7.71 (d, J = 7.8 Hz, 1H), 7.45 (s, 2H), 7.38 (dd, J = 7.8, 1.3 Hz, 1H), 5.12 (dd, J = 13.2, 5.2 Hz, 1H), 4.46 (d, J = 17.0 Hz, 1H), 4.33 (d, J = 17.2 Hz, 1H), 3.44 (s, 2H), 3.26-3.05 (m, 3H), 2.93 (ddd, J = 17.3, 13.6, 5.4 Hz, 1H), 2.73-2.52 (m, 1H), 2.37 (ddd, J = 27.1, 13.5, 3.7 Hz, 2H), 2.24-1.62 (m, 9H), 1.62-1.23 (m, 6H), 1.16-0.85 (m, 1H). | 3 | I-18; 4,4-difluorocyclohexanone |
| 152 | 3-(5-(((1R,3S)-3-((cyclobutylmethyl)amino)tetra-hydro-2H-pyran-2-yl)methyl)-4-fluoro-1-oxoisoindolin-2-yl)piperidine-2,6-dione | 444.3 | 1H NMR (400 MHz, DMSO-d6) δ 11.01 (s, 1H), 8.67 (s, 1H), 8.35 (s, 1H), 7.57 (d, J = 7.7 Hz, 1H), 7.54 (s, 1H), 5.12 (dd, J = 13.3, 5.1 Hz, 1H), 4.56 (dd, J = 17.4, 5.4 Hz, 1H), 4.43-4.33 (m, 1H), 3.78 (ddt, J = 14.8, 7.5, 3.5 Hz, 2H), 3.25 (dt, J = 14.8, 3.2 Hz, 2H), 3.09 (h, J = 5.7, 4.5 Hz, 3H), 3.01-2.85 (m, 2H), 2.64 (ddd, J = 17.7, 15.0, 5.7 Hz, 2H), 2.40 (dtd, J = 28.5, 14.5, 14.0, 8.0 Hz, 1H), 2.20 (dt, J = 12.7, 4.4 Hz, 1H), 2.15-2.04 (m, 2H), 2.01 (ddq, J = 10.7, 5.3, 2.4, 2.0 Hz, 1H), 1.95-1.75 (m, 4H), 1.75-1.62 (m, 2H), 1.61-1.46 (m, 1H). | 3 | I-12; cyclobutanecarbaldehyde |

TABLE 12-continued

| Example | Structure | ES/MS m/z: | 1H NMR | Procedure | Changes to Procedure: Different Reagents/ Starting Materials |
|---|---|---|---|---|---|
| 153 | 3-(5-(((1R,2R,3R)-rel-2-(cyclohexylamino)-3-fluorocyclohexyl)methyl)-1-oxoisoindolin-2-yl)piperidine-2,6-dione | 456.2 | $^1$H NMR (400 MHz, DMSO-d6) δ 10.99 (s, 1H), 7.70 (d, J = 7.8 Hz, 1H), 7.48 (t, J = 3.9 Hz, 1H), 7.39 (dt, J = 8.0, 1.8 Hz, 1H), 5.21-5.00 (m, 1H), 4.46 (dd, J = 17.3, 4.6 Hz, 1H), 4.33 (dd, J = 17.3, 4.0 Hz, 1H), 3.24-2.98 (m, 2H), 2.92 (ddd, J = 17.8, 13.4, 5.3 Hz, 1H), 2.3 (td, J = 17.2, 3.0 Hz, 1H), 2.41-2.23 (m, 1H), 2.17 (d, J = 10.3 Hz, 1H), 2.07-1.74 (m, 7H), 1.74-0.93 (m, 12H). | 3 | I-19; cyclohexanone |
| 154 | 3-(5-(((1S,2S,5R)-2-((4,4-difluorocyclohexyl)amino)-5-hydroxy-5-methylcyclohexyl)methyl)-1-oxoisoindolin-2-yl)piperidine-2,6-dione | 504.4 | $^1$H NMR (400 MHz, DMSO-d6) δ 11.00 (s, 1H), 8.64-8.51 (m, 1H), 8.15-8.02 (m, 1H), 7.71 (d, J = 7.8 Hz, 1H), 7.42 (s, 1H), 7.34 (d, J = 7.9 Hz, 1H), 5.11 (dd, J = 13.3, 5.1 Hz, 1H), 4.44 (d, J = 17.4 Hz, 1H), 4.34 (d, J = 17.3 Hz, 1H), 4.16 (s, 1H), 3.54-3.42 (m, 1H), 3.32 (d, J = 12.4 Hz, 1H), 3.11-3.00 (m, 1H), 2.92 (ddd, J = 17.3, 13.6, 5.4 Hz, 1H), 2.66-2.56 (m, 1H), 2.40 (qd, J = 13.2, 4.4 Hz, 1H), 2.32-2.07 (m, 7H), 2.06-1.47 (m, 6H), 1.42-1.31 (m, 2H), 1.10-0.97 (m, 4H). | 3 | I-25; 4,4-difluorocyclohexanone |

TABLE 12-continued

| Example | Structure | ES/MS m/z: | 1H NMR | Procedure | Changes to Procedure: Different Reagents/ Starting Materials |
|---|---|---|---|---|---|
| 155 | 3-(5-(((1S,2S,5S)-2-((4,4-difluorocyclohexyl)amino)-5-hydroxy-5-methylcyclohexyl)methyl)-1-oxoisoindolin-2-yl)piperidine-2,6-dione | 504.4 | 1H NMR (400 MHz, Methanol-d4) δ 7.78 (d, J = 7.8 Hz, 1H), 7.45 (s, 1H), 7.40 (dd, J = 7.9, 1.7 Hz, 1H), 5.17 (dd, J = 13.3, 5.1 Hz, 1H), 4.53 (d, J = 17.2 Hz, 1H), 4.46 (d, J = 17.1 Hz, 1H), 3.53-3.44 (m, 1H), 3.36-3.29 (m, 1H, obscured by residual solvent peak), 3.25-3.18 (m, 1H), 2.92 (ddd, J = 18.4, 13.5, 5.4 Hz, 1H), 2.79 (dddd, J = 17.6, 4.7, 2.4 Hz, 1H), 2.60 (dd, J = 13.2, 10.3 Hz, 1H), 2.49 (qd, J = 13.3, 4.7 Hz, 1H), 2.31-2.13 (m, 5H), 2.13-1.49 (m, 10H), 1.40-1.27 (m, 1H), 1.14 (s, 3H). | 3 | I-26; 4,4-difluorocyclohexanone |
| 156 | 3-(4-fluoro-5-(((2R,3S)-3-((4-methoxycyclohexyl)amino)tetrahydro-2H-pyran-2-yl)methyl)-1-oxoisoindolin-2-yl)piperidine-2,6-dione (Isomer 1) | 488.4 | 1H NMR (400 MHz, DMSO-d6) δ 11.01 (s, 1H), 8.52 (s, 1H), 8.17 (s, 1H), 7.57 (d, J = 7.7 Hz, 1H), 7.51 (t, J = 6.9 Hz, 1H), 5.11 (dd, J = 13.3, 5.1 Hz, 1H), 4.62-4.27 (m, 2H), 3.81-3.70 (m, 1H), 3.43 (d, J = 3.3 Hz, 1H), 3.35-3.24 (m, 1H), 3.04-2.83 (m, 2H), 2.61 (d, J = 16.9 Hz, 1H), 2.42 (td, J = 13.2, 4.5 Hz, 1H), 2.23 (d, J = 10.1 Hz, 1H), 2.06-1.90 (m, 1H), 1.90-1.66 (m, 3H), 1.61 (t, J = 10.2 Hz, 2H), 1.44 (t, J = 13.5 Hz, 2H), 1.23 (s, 3H). | 3 | I-12; 4-methoxycyclohexanone |

TABLE 12-continued

| Example | Structure | | ES/MS m/z: | 1H NMR | Procedure | Changes to Procedure: Different Reagents/ Starting Materials |
|---|---|---|---|---|---|---|
| 157 | 3-(4-fluoro-1-oxo-5-(((2R,3S)-3-(spiro[3.3]heptan-2-ylamino)tetrahydro-2H-pyran-2-yl)methyl)isoindolin-2-yl)piperidine-2,6-dione | | 470.4 | ¹H NMR (400 MHz, DMSO-d6) δ 11.01 (s, 1H), 8.99 (dt, J = 13.5, 6.8 Hz, 1H), 8.79-8.63 (m, 1H), 7.56 (d, J = 7.7 Hz, 1H), 7.54-7.47 (m, 1H), 5.11 (dd, J = 13.3, 5.1 Hz, 1H), 4.56 (dd, J = 17.4, 3.5 Hz, 1H), 4.38 (dd, J = 17.4, 1.9 Hz, 1H), 3.80-3.70 (m, 3H), 3.25 (ddd, J = 14.0, 11.5, 5.9 Hz, 2H), 3.06 (s, 1H), 3.04-2.86 (m, 2H), 2.61 (dt, J = 17.4, 3.0 Hz, 1H), 2.44 (dd, J = 13.2, 4.6 Hz, 1H), 2.40-2.22 (m, 3H), 2.17 (dd, J = 12.1, 8.7 Hz, 2H), 2.03 (q, J = 6.6, 5.7 Hz, 3H), 1.94 (dd, J = 8.6, 6.2 Hz, 2H), 1.85-1.75 (m, 2H), 1.69 (td, J = 8.8, 8.0, 4.2 Hz, 1H), 1.65-1.45 (m, 2H). | 3 | I-12; spiro[3.3]heptan-2-one |
| 158 | 3-(4-fluoro-1-oxo-5-(((2R,3S)-3-(spiro[3.5]nonan-2-ylamino)tetrahydro-2H-pyran-2-yl)methyl)isoindolin-2-yl)piperidine-2,6-dione | | 498.4 | ¹H NMR (400 MHz, DMSO-d6) δ 11.01 (s, 1H), 9.04 (dt, J = 12.7, 6.6 Hz, 1H), 8.77 (dd, J = 11.9, 5.7 Hz, 1H), 7.57 (d, J = 7.7 Hz, 1H), 7.55-7.49 (m, 1H), 5.12 (dd, J = 13.3, 5.1 Hz, 1H), 4.56 (dd, J = 17.4, 3.2 Hz, 1H), 4.38 (d, J = 16.8 Hz, 1H), 3.93-3.71 (m, 3H), 3.26 (ddd, J = 14.2, 11.6, 5.8 Hz, 2H), 3.14-3.06 (m, 1H), 3.05-2.86 (m, 2H), 2.61 (dt, J = 17.6, 3.2 Hz, 1H), 2.43 (tt, J = 13.3, 6.8 Hz, 1H), 2.13 (dtd, J = 20.5, 8.8, 8.3, 3.9 Hz, 3H), 2.05-1.94 (m, 2H), 1.89 (dd, J = 12.1, 8.5 Hz, 1H), 1.68 (ddp, J = 18.2, 13.6, 5.3, 4.8 Hz, 2H), 1.46 (qd, J = 18.0, 15.6, 9.6 Hz, 7H), 1.32 (bs, 4H). | 3 | I-12; spiro[3.5]nonan-2-one |

TABLE 12-continued

| Example | Structure | ES/MS m/z: | 1H NMR | Procedure | Changes to Procedure: Different Reagents/ Starting Materials |
|---|---|---|---|---|---|
| 159 | 3-(4-fluoro-5-(((2R,3S)-3-((4-methoxycyclohexyl)amino)tetrahydro-2H-pyran-2-yl)methyl)-1-oxoisoindolin-2-yl)piperidine-2,6-dione (Isomer 2) | 488.3 | ¹H NMR (400 MHz, DMSO-d6) δ 11.01 (s, 1H), 8.61 (s, 1H), 8.22 (s, 1H), 7.57 (d, J = 7.7 Hz, 1H), 7.55-7.48 (m, 1H), 5.11 (dd, J = 13.3, 5.1 Hz, 1H), 4.62-4.29 (m, 2H), 3.81-3.66 (m, 4H), 3.18-3.05 (m, 1H), 3.05-2.95 (m, 1H), 2.95-2.83 (m, 1H), 2.67-2.56 (m, 1H), 2.54 (s, 1H), 2.42 (td, J = 13.3, 4.5 Hz, 1H), 2.17-1.92 (m, 5H), 1.81-1.32 (m, 5H), 1.30-1.08 (m, 3H), 1.23 (s, 3H). | 3 | I-12; 4-methoxycyclohexanone |
| 160 | 3-(5-(((1S,2S,5S)-2-((4,4-difluorocyclohexyl)amino)-5-hydroxycyclohexyl)methyl)-1-oxoisoindolin-2-yl)piperidine-2,6-dione | 490.3 | ¹H NMR (400 MHz, DMSO-d6) δ 10.99 (s, 1H), 8.57-8.47 (m, 1H), 8.17-8.07 (m, 1H), 7.70 (d, J = 7.8 Hz, 1H), 7.43 (s, 1H), 7.35 (dt, J = 7.9, 1.7 Hz, 1H), 5.11 (dd, J = 13.3, 5.1 Hz, 1H), 4.45 (dd, J = 17.3, 6.4 Hz, 1H), 4.31 (dd, J = 17.3, 5.0 Hz, 1H), 3.80-3.73 (m, 1H), 3.50-3.40 (m, 1H), 3.26 (dt, J = 13.3, 3.7 Hz, 1H), 3.16-3.05 (m, 1H), 2.92 (ddd, J = 17.2, 13.6, 5.4 Hz, 1H), 2.65-2.56 (m, 1H), 2.40 (qd, J = 13.0, 4.3 Hz, 2H), 2.27-1.83 (m, 10H), 1.83-1.70 (m, 2H), 1.70-1.57 (m, 2H), 1.57-1.43 (m, 2H), 1.26-1.15 (m, 1H). | 3 | I-31; 4,4-difluorocyclohexanone |

TABLE 12-continued

| Example | Structure | ES/MS m/z: | 1H NMR | Procedure | Changes to Procedure: Different Reagents/ Starting Materials |
|---|---|---|---|---|---|
| 161 | 3-(5-(((1R,2S)-2-((2,2-dimethyl-1,3-dioxan-5-yl)amino)cyclohexyl)methyl)-1-oxoisoindolin-2-yl)piperidine-2,6-dione | 470.4 | ¹H NMR (400 MHz, DMSO-d6) δ 10.99 (s, 1H), 8.68 (s, 1H), 8.14 (s, 1H), 7.69 (d, J = 7.8 Hz, 1H), 7.49 (s, 1H), 7.39 (d, J = 7.8 Hz, 1H), 7.04 (s, 1H), 5.11 (dd, J = 13.3, 5.1 Hz, 1H), 4.49-4.25 (m, 2H), 4.17 (ddd, J = 13.3, 10.3, 3.1 Hz, 2H), 4.05-3.89 (m, 4H), 3.78-3.67 (m, 2H), 3.54-3.39 (m, 1H), 3.35-3.25 (m, 1H), 3.14 (s, 1H), 2.92 (ddd, J = 17.2, 13.6, 5.4 Hz, 1H), 2.72-2.56 (m, 1H), 2.54 (s, 1H), 2.48-2.29 (m, 1H), 2.08 (d, J = 8.1 Hz, 1H), 2.03-1.95 (m, 1H), 1.91 (d, J = 9.7 Hz, 1H), 1.71 (d, J = 12.9 Hz, 1H), 1.52 (d, J = 11.0 Hz, 2H), 1.43 (s, 3H), 1.40 (d, J = 5.7 Hz, 6H), 1.34 (s, 3H), 1.05 (q, J = 11.9, 11.5 Hz, 2H). | 3 | 2,2-dimethyl-1,3-dioxan-5-one |
| 162 | 3-(5-(((1S,2S,5R)-2-((4,4-difluorocyclohexyl)amino)-5-hydroxycyclohexyl)methyl)-1-oxoisoindolin-2-yl)piperidine-2,6-dione | 490.4 | ¹H NMR (400 MHz, DMSO-d6) δ 10.99 (s, 1H), 8.57 (m, 1H), 8.22-8.11 (m, 1H), 7.71 (d, J = 7.8 Hz, 1H), 7.44 (s, 1H), 7.35 (d, J = 7.8 Hz, 1H), 5.11 (dd, J = 13.3, 5.1 Hz, 1H), 4.46 (dd, J = 17.4, 4.0 Hz, 1H), 4.32 (dd, J = 17.4, 2.5 Hz, 1H), 3.50-3.38 (m, 1H), 3.36-3.21 (m, 2H), 3.13-3.02 (m, 1H), 2.92 (ddd, J = 17.3, 13.6, 5.4 Hz, 1H), 2.66-2.55 (m, 11H), 2.46-2.30 (m, 2H), 2.23-1.73 (m, 11H), 1.71-1.59 (m, 1H), 1.59-1.49 (m, 1H), 1.48-1.35 (m, 1H), 1.29-1.17 (m, 1H), 1.01-0.90 (m, 1H). | 3 | I-30; 4,4-difluorocyclohexanone |

TABLE 12-continued

| Example | Structure | ES/MS m/z: | 1H NMR | Procedure | Changes to Procedure: Different Reagents/ Starting Materials |
|---|---|---|---|---|---|
| 163 | 3-(5-(((1R,2R,3S)-2-((4,4-difluorocyclohexyl)amino)-3-hydroxycyclohexyl)methyl)-1-oxoisoindolin-2-yl)piperidine-2,6-dione | 490.2 | 1H NMR (400 MHz, DMSO-d6) δ 10.99 (s, 1H), 7.71 (d, J = 7.8 Hz, 1H), 7.45 (s, 1H), 7.38 (d, J = 7.8 Hz, 1H), 5.12 (dd, J = 13.3, 5.1 Hz, 1H), 4.47 (d, J = 17.2 Hz, 1H), 4.33 (d, J = 17.2 Hz, 1H), 4.13 (d, J = 4.0 Hz, 1H), 3.45 (s, 1H), 3.26-3.09 (m, 2H), 3.02-2.88 (m, 1H), 2.73-2.56 (m, 1H), 2.48-2.29 (m, 2H), 2.29-1.62 (m, 11H), 1.62-1.24 (m, 5H), 1.00 (dd, J = 16.9, 7.4 Hz, 1H). | 3 | I-32; 4,4-difluorocyclohexanone |
| 164 | 3-(5-(((1R,2R,3R)-rel-2-((4,4-difluorocyclohexyl)amino)-3-methoxycyclohexyl)methyl)-1-oxoisoindolin-2-yl)piperidine-2,6-dione | 504.2 | 1H NMR (400 MHz, DMSO-d6) δ 11.00 (s, 1H), 7.70 (d, J = 7.8 Hz, 1H), 7.48 (d, J = 3.1 Hz, 1H), 7.39 (dt, J = 7.9, 1.7 Hz, 1H), 5.20-4.97 (m, 1H), 4.46 (dd, J = 17.4, 2.6 Hz, 1H), 4.33 (dd, J = 17.4, 2.1 Hz, 1H), 3.35 (s, 3H), 3.18 (d, J = 11.6 Hz, 2H), 3.11-2.82 (m, 2H), 2.79-2.57 (m, 1H), 2.49-2.31 (m, 2H), 2.31-1.51 (m, 8H), 1.40-1.20 (m, 1H), 1.04 (dd, J = 24.0, 11.1 Hz, 3H). | 3 | I-34; 4,4-difluorocyclohexanone |

TABLE 12-continued

| Example | Structure | ES/MS m/z: | 1H NMR | Procedure | Changes to Procedure: Different Reagents/ Starting Materials |
|---|---|---|---|---|---|
| 165 | 3-(1-oxo-5-((((1R,2S)-2-((4,5,6,7-tetrahydro-1H-indazol-6-yl)amino)cyclohexyl)methyl)isoindolin-2-yl)piperidine-2,6-dione | 476.4 | ¹H NMR (400 MHz, DMSO-d6) δ 10.99 (s, 1H), 8.59 (s, 1H), 8.26 (s, 1H), 7.70 (d, J = 7.8 Hz, 1H), 7.46 (s, 1H), 7.38 (d, J = 9.4 Hz, 2H), 5.12 (dd, J = 13.2, 5.1 Hz, 1H), 4.51-4.27 (m, 2H), 3.36-3.11 (m, 2H), 2.92 (ddd, J = 18.1, 13.7, 5.4 Hz, 1H), 2.85-2.56 (m, 4H), 2.48-2.32 (m, 2H), 2.32-2.07 (m, 3H), 2.06-1.96 (m, 1H), 1.89 (d, J = 11.6 Hz, 1H), 1.73 (d, J = 6.1 Hz, 1H), 1.62-1.28 (m, 5H), 1.07 (s, 3H). | 3 | 1,4,5,7-tetrahydro-6H-indazol-6-one |
| 166 | 3-(5-(((1R,2S)-2-(heptan-4-ylamino)cyclohexyl)methyl)-1-oxoisoindolin-2-yl)piperidine-2,6-dione | 454.4 | ¹H NMR (400 MHz, DMSO-d6) δ 10.99 (s, 1H), 7.96 (s, 1H), 7.69 (s, 1H), 7.39 (d, J = 32.7 Hz, 2H), 6.65 (d, J = 9.2 Hz, 1H), 5.11 (dd, J = 13.3, 5.1 Hz, 1H), 4.63-4.16 (m, 2H), 3.57 (s, 4H), 3.49 (q, J = 5.3, 4.8 Hz, 2H), 3.42 (t, J = 5.2 Hz, 1H), 2.92 (ddd, J = 18.2, 13.8, 5.5 Hz, 1H), 2.74-2.56 (m, 1H), 2.39 (qd, J = 14.6, 13.9, 5.1 Hz, 1H), 2.07 (d, J = 11.7 Hz, 2H), 2.04-1.91 (m, 1H), 1.73 (d, J = 14.2 Hz, 3H), 1.09 (ddq, J = 17.5, 9.3, 4.7, 3.8 Hz, 3H), 0.92 (d, J = 12.9 Hz, 16H). | 3 | heptan-4-one |

TABLE 12-continued

| Example | Structure | ES/MS m/z: | 1H NMR | Procedure | Changes to Procedure: Different Reagents/ Starting Materials |
|---|---|---|---|---|---|
| 167 | 3-(5-(((1R,2S)-2-((4-isopropoxycyclohexyl)amino)cyclohexyl)methyl)-1-oxoisoindolin-2-yl)piperidine-2,6-dione (Isomer 1) | 496.4 | $^1$H NMR (400 MHz, DMSO-d6) δ 10.99 (s, 1H), 8.27 (s, 1H), 7.94 (s, 1H), 7.70 (d, J = 7.8 Hz, 1H), 7.52-7.28 (m, 2H), 5.11 (dd, J = 13.2, 5.1 Hz, 1H), 4.52-4.18 (m, 2H), 3.69 (p, J = 6.1 Hz, 1H), 3.25 (d, J = 11.6 Hz, 1H), 3.06 (s, 2H), 2.99-2.82 (m, 1H), 2.69-2.57 (m, 1H), 2.38 (q, J = 15.7, 14.4 Hz, 1H), 2.08 (d, J = 12.0 Hz, 2H), 1.99 (s, 5H), 1.80 (s, 1H), 1.72 (s, 1H), 1.53 (d, J = 10.2 Hz, 2H), 1.37 (dt, J = 18.2, 10.4 Hz, 1H), 1.22 (q, J = 12.2 Hz, 2H), 1.06 (d, J = 6.1 Hz, 7H). | 3 | 4-isopropoxycyclohexanone |
| 168 | 3-(5-(((1R,2S)-2-((4-isopropoxycyclohexyl)amino)cyclohexyl)methyl)-1-oxoisoindolin-2-yl)piperidine-2,6-dione (Isomer 2) | 496.4 | $^1$H NMR (400 MHz, DMSO-d6) δ 10.99 (s, 1H), 8.22 (s, 1H), 7.99 (s, 2H), 7.84-7.61 (m, 1H), 7.61-7.18 (m, 2H), 5.11 (dd, J = 13.3, 5.1 Hz, 1H), 4.52-4.19 (m, 2H), 3.83-3.49 (m, 2H), 3.27 (d, J = 14.4 Hz, 1H), 3.07 (s, 1H), 2.91 (ddt, J = 23.0, 14.7, 7.4 Hz, 1H), 2.74-2.57 (m, 1H), 2.43-2.30 (m, 1H), 2.07 (s, 1H), 2.05-1.92 (m, 1H), 1.91-1.67 (m, 4H), 1.58-1.33 (m, 4H), 1.09 (d, J = 6.1 Hz, 6H), 1.04-1.07 (m, 1H). | 3 | 4-isopropoxycyclohexanone |

TABLE 12-continued

| Example | Structure | ES/MS m/z: | 1H NMR | Procedure | Changes to Procedure: Different Reagents/ Starting Materials |
|---|---|---|---|---|---|
| 169 | 3-(5-(((1S,2S,5R)-2-((4,4-difluorocyclohexyl)amino)-5-fluorocyclohexyl)methyl)-1-oxoisoindolin-2-yl)piperidine-2,6-dione | 492.3 | 1H NMR (400 MHz, DMSO-d6) δ 10.99 (s, 1H), 8.71-8.60 (m, 1H), 8.29-8.18 (m, 1H), 7.72 (d, J = 7.7 Hz, 1H), 7.44 (s, 1H), 7.36 (d, J = 7.8 Hz, 1H), 5.16-5.07 (m, 1H), 4.89-4.71 (m, 1H), 4.46 (dd, J = 17.4, 3.1 Hz, 1H), 4.33 (d, J = 17.3 Hz, 1H), 3.56-3.43 (m, 1H), 3.32 (dd, J = 13.7, 3.4 Hz, 1H), 3.28-3.18 (m, 1H), 2.92 (ddd, J = 17.9, 13.5, 5.4 Hz, 1H), 2.65-2.56 (m, 1H), 2.46-2.36 (m, 3H), 2.36-2.25 (m, 1H), 2.23-1.47 (m, 13H), 1.46-1.26 (m, 1H). | 3 | I-37; 4,4-difluorocyclohexanone |
| 170 | 3-(5-(((1R,2R,3S)-rel-2-(cyclohexylamino)-3-fluorocyclohexyl)methyl)-1-oxoisoindolin-2-yl)piperidine-2,6-dione | 374.1 | 1H NMR (400 MHz, DMSO-d6) δ 11.00 (s, 1H), 7.81-7.61 (m, 1H), 7.47 (s, 1H), 7.39 (d, J = 7.9 Hz, 1H), 5.19-5.02 (m, 1H), 4.47 (d, J = 17.3 Hz, 1H), 4.33 (d, J = 17.3 Hz, 1H), 3.48 (d, J = 30.0 Hz, 0H), 3.20 (d, J = 13.1 Hz, 2H), 2.93 (ddd, J = 17.9, 13.5, 5.6 Hz, 1H), 2.74-2.54 (m, 1H), 2.48-2.25 (m, 2H), 2.25-1.91 (m, 5H), 1.91-0.87 (m, 12H). | 3 | I-39 |

TABLE 12-continued

| Example | Structure | ES/MS m/z: | 1H NMR | Procedure | Changes to Procedure: Different Reagents/ Starting Materials |
|---|---|---|---|---|---|
| 171 | 3-(5-(((1R,2S)-2-((1-oxaspiro[3.5]nonan-7-yl)amino)cyclohexyl)methyl)-1-oxoisoindolin-2-yl)piperidine-2,6-dione (Isomer 1) | 480.4 | ¹H NMR (400 MHz, DMSO-d6) δ 10.99 (s, 1H), 8.33 (s, 1H), 7.93 (s, 1H), 7.70 (d, J = 7.8 Hz, 1H), 7.44 (s, 1H), 7.35 (d, J = 7.7 Hz, 1H), 5.11 (dd, J = 13.3, 5.1 Hz, 1H), 4.50-4.23 (m, 3H), 3.26 (d, J = 13.0 Hz, 1H), 3.06 (s, 1H), 2.92 (ddd, J = 18.0, 13.6, 5.4 Hz, 1H), 2.61 (d, J = 17.2 Hz, 1H), 2.46-2.29 (m, 3H), 2.21-1.90 (m, 5H), 1.76 (d, J = 33.4 Hz, 2H), 1.49 (dd, J = 14.5, 11.3 Hz, 2H), 1.37 (dd, J = 24.5, 11.4 Hz, 1H), 1.05 (q, J = 6.8 Hz, 3H). | 3 | 1-oxaspiro[3.5]nonan-7-one |
| 172 | 3-(5-(((1R,2S)-2-((1-oxaspiro[3.5]nonan-7-yl)amino)cyclohexyl)methyl)-1-oxoisoindolin-2-yl)piperidine-2,6-dione (Isomer 2) | 480.4 | ¹H NMR (400 MHz, DMSO-d6) δ 10.99 (s, 1H), 8.32 (d, J = 53.2 Hz, 1H), 7.98 (s, 1H), 7.70 (dd, J = 7.7, 2.2 Hz, 1H), 7.44 (d, J = 4.9 Hz, 1H), 7.36 (t, J = 6.7 Hz, 1H), 5.11 (dd, J = 13.3, 5.1 Hz, 1H), 4.51-4.23 (m, 4H), 3.49-3.41 (m, 1H), 3.26 (d, J = 17.6 Hz, 9H), 3.07 (s, 1H), 2.92 (ddd, J = 18.1, 13.6, 5.4 Hz, 1H), 2.76-2.54 (m, 1H), 2.47-2.24 (m, 2H), 2.19-2.02 (m, 3H), 2.02-1.76 (m, 1H), 1.70 (d, J = 10.9 Hz, 1H), 1.64-1.42 (m, 1H), 1.06 (t, J = 7.0 Hz, 3H). | 3 | 1-oxaspiro[3.5]nonan-7-one |

TABLE 12-continued

| Example | Structure | ES/MS m/z: | 1H NMR | Procedure | Changes to Procedure: Different Reagents/ Starting Materials |
|---|---|---|---|---|---|
| 173 | 3-(4-fluoro-5-(((2R,3S)-3-(oxepan-4-ylamino)tetrahydro-2H-pyran-2-yl)methyl)-1-oxoisoindolin-2-yl)piperidine-2,6-dione | 474.4 | 1H NMR (400 MHz, DMSO-d6) δ 11.01 (s, 1H), 8.49 (s, 1H), 8.28 (s, 1H), 7.58 (d, J = 7.7 Hz, 1H), 7.52 (td, J = 7.7, 6.9, 3.1 Hz, 1H), 5.11 (dd, J = 13.3, 5.1 Hz, 1H), 4.59-4.34 (m, 2H), 3.82-3.65 (m, 2H), 3.62-3.52 (m, 2H), 3.30-3.18 (m, 3H), 2.96 (dddd, J = 31.4, 18.2, 13.2, 6.4 Hz, 3H), 2.70-2.56 (m, 2H), 2.47-2.32 (m, 1H), 2.28-2.06 (m, 3H), 2.07-1.95 (m, 1H), 1.91-1.50 (m, 8H). | 3 | I-12; oxepan-4-one |
| 174 | 3-(5-(((1R,2S)-2-(((2,2-difluoro-3-phenylbicyclo[1.1.1]pentan-1-yl)methyl)amino)cyclohexyl)methyl)-1-oxoisoindolin-2-yl)piperidine-2,6-dione | 548.4 | 1H NMR (400 MHz, DMSO-d6) δ 10.99 (s, 1H), 8.85 (s, 1H), 8.60 (s, 1H), 7.71 (d, J = 7.7 Hz, 1H), 7.47 (s, 1H), 7.45-7.35 (m, 4H), 7.30 (dt, J = 7.8, 1.4 Hz, 2H), 5.12 (dd, J = 13.3, 5.1 Hz, 1H), 4.50-4.27 (m, 2H), 3.21 (d, J = 12.4 Hz, 1H), 3.07 (s, 1H), 2.92 (ddd, J = 17.5, 13.5, 5.5 Hz, 1H), 2.60 (d, J = 17.3 Hz, 2H), 2.47-2.30 (m, 3H), 2.10 (dd, J = 17.4, 4.5 Hz, 3H), 1.98 (d, J = 12.4 Hz, 2H), 1.75 (d, J = 12.5 Hz, 1H), 1.51 (dd, J = 23.2, 12.7 Hz, 3H), 1.41-1.19 (m, 1H), 1.08 (s, 2H). | 9 | 1-(bromomethyl)-2,2-difluoro-3-phenylbicyclo[1.1.1]pentane |

TABLE 12-continued

| Example | Structure | ES/MS m/z: | 1H NMR | Procedure | Changes to Procedure: Different Reagents/ Starting Materials |
|---|---|---|---|---|---|
| 175 | 3-(5-(((1R,2S)-2-(chroman-4-ylamino)cyclohexyl)methyl)-1-oxoisoindolin-2-yl)piperidine-2,6-dione | 488.4 | ¹H NMR (400 MHz, DMSO-d6) δ 10.99 (s, 2H), 8.66 (s, 1H), 8.38 (s, 1H), 7.70 (d, J = 7.7 Hz, 1H), 7.46 (t, J = 6.6 Hz, 1H), 7.41 (s, 1H), 7.38-7.25 (m, 3H), 7.02 (t, J = 7.8 Hz, 1H), 6.91 (dd, J = 8.4, 1.2 Hz, 1H), 5.11 (dd, J = 13.2, 5.2 Hz, 2H), 4.77 (s, 1H), 4.49-4.23 (m, 4H), 3.37 (d, J = 13.7 Hz, 1H), 2.92 (t, J = 13.0 Hz, 2H), 2.77-2.54 (m, 2H), 2.46-2.20 (m, 2H), 2.05-1.84 (m, 1H), 2.56 (d, J = 11.9 Hz, 4H), 1.06 (s, 3H). | 10 | chroman-4-one |
| 176 | 3-(5-(((1R,2S)-2-(sec-butylamino)cyclohexyl)methyl)-1-oxoisoindolin-2-yl)piperidine-2,6-dione | 412.4 | ¹H NMR (400 MHz, DMSO-d6) δ 10.99 (s, 1H), 8.23 (d, J = 50.2 Hz, 1H), 7.96 (s, 1H), 7.69 (d, J = 7.7 Hz, 1H), 7.44 (s, 1H), 7.36 (d, J = 7.8 Hz, 1H), 5.11 (dd, J = 13.3, 5.1 Hz, 1H), 4.45 (dd, J = 17.4, 2.7 Hz, 1H), 4.31 (dd, J = 17.4, 2.9 Hz, 1H), 3.33-3.22 (m, 3H), 3.05 (s, 1H), 2.99-2.85 (m, 1H), 2.65-2.56 (m, 1H), 2.46-2.34 (m, 1H), 2.14-1.96 (m, 2H), 1.89-1.66 (m, 3H), 1.63-1.32 (m, 4H), 1.27 (dd, J = 15.6, 6.4 Hz, 3H), 1.03 (t, J = 9.4 Hz, 2H), 0.99-0.89 (m, 3H). | 10 | butan-2-one |

| Example | Structure | ES/MS m/z: | 1H NMR | Procedure | Changes to Procedure: Different Reagents/ Starting Materials |
|---|---|---|---|---|---|
| 177 | 3-(5-(((1R,2S)-2-((2,3-dihydro-1H-inden-2-yl)amino)cyclohexyl)methyl)-1-oxoisoindolin-2-yl)piperidine-2,6-dione | 472.4 | 1H NMR (400 MHz, DMSO-d6) δ 10.99 (s, 1H), 8.86 (s, 1H), 8.53 (s, 1H), 7.70 (d, J = 7.8 Hz, 1H), 7.46 (s, 1H), 7.37 (d, J = 7.8 Hz, 1H), 7.33-7.18 (m, 4H), 5.11 (dd, J = 13.3, 5.1 Hz, 1H), 4.45 (m, 1H), 4.37-4.27 (m, 1H), 3.43-3.24 (m, 3H), 3.23-3.06 (m, 3H), 2.99-2.85 (m, 1H), 2.60 (d, J = 17.5 Hz, 1H), 2.47-2.32 (m, 1H), 2.23-2.15 (m, 1H), 2.04-1.96 (m, 1H), 1.93-1.88 (m, 1H), 101.74 (d, J = 12.0 Hz, 1H), 1.62-1.30 (m, 5H), 1.13-1.04 (m, 2H). | 10 | indan-2-one |
| 178 | 3-(5-(((1R,2S)-2-((4,4-difluorocyclohexyl)amino)cyclopentyl)methyl)-1-oxoisoindolin-2-yl)piperidine-2,6-dione | 460.3 | 1H NMR (400 MHz, DMSO-d6) δ 10.99 (s, 1H), 8.61 (s, 1H), 8.50 (s, 1H), 7.69 (d, J = 7.8 Hz, 1H), 7.48 (s, 1H), 7.40 (d, J = 7.8 Hz, 1H), 5.11 (dd, J = 13.3, 5.1 Hz, 1H), 4.44 (dd, J = 17.3, 3.0 Hz, 1H), 4.31 (dd, J = 17.3, 4.4 Hz, 1H), 3.39 (s, 1H), 3.21 (s, 1H), 3.14-3.03 (m, 1H), 2.99-2.85 (m, 1H), 2.64-2.53 (m, 2H), 2.48-2.32 (m, 1H), 2.30-1.76 (m, 7H), 1.71-1.50 (m, 6H), 1.34 (d, J = 6.2 Hz, 2H). | 10 | I-40; 4,4-difluorocyclohexanone |

TABLE 12-continued

| Example | Structure | ES/MS m/z: | 1H NMR | Procedure | Changes to Procedure: Different Reagents/ Starting Materials |
|---|---|---|---|---|---|
| 179 | 3-(5-(((2R,3S)-3-(cyclohexylamino)tetrahydro-2H-pyran-2-yl)methyl)-1-oxoisoindolin-2-yl)piperidine-2,6-dione | 440.3 | ¹H NMR (400 MHz, Methanol-d4) δ 7.77 (d, J = 7.8 Hz, 1H), 7.54 (s, 1H), 7.48 (dd, J = 7.9, 1.4 Hz, 1H), 5.17 (dd, J = 13.3, 5.2 Hz, 1H), 4.54-4.42 (m, 2H), 3.92 (d, J = 11.9 Hz, 1H), 3.80 (ddt, J = 9.6, 6.1, 3.0 Hz, 1H), 3.46-3.38 (m, 1H), 3.10-3.02 (m, 1H), 2.96-2.88 (m, 1H), 2.80 (ddd, J = 17.6, 4.7, 2.4 Hz, 1H), 2.51 (dd, J = 13.2, 4.8 Hz, 1H), 2.41-2.30 (m, 1H), 2.25-2.04 (m, 3H), 1.96-1.61 (m, 8H), 1.55-1.19 (m, 7H). | 11 | I-11; cyclohexanone |
| 180 | 3-(5-(((2R,3S)-3-(isopropylamino)methyl)-1-oxoisoindolin-2-yl)piperidine-2,6-dione | 400.2 | ¹H NMR (400 MHz, Methanol-d4) δ 7.76 (d, J = 7.8 Hz, 1H), 7.54 (s, 1H), 7.47 (d, J = 7.8 Hz, 1H), 5.17 (dd, J = 13.3, 5.1 Hz, 1H), 4.92 (t, J = 2.5 Hz, 1H), 4.56-4.45 (m, 2H), 4.18 (ddd, J = 12.2, 9.0, 3.7 Hz, 1H), 3.96-3.87 (m, 1H), 3.80-3.74 (m, 1H), 3.73-3.69 (m, 2H), 3.66-3.54 (m, 2H), 3.44-3.36 (m, 1H), 3.25 (td, J = 13.0, 11.8, 4.5 Hz, 2H), 3.06-2.97 (m, 1H), 2.97-2.87 (m, 1H), 2.80 (ddd, J = 17.6, 4.7, 2.4 Hz, 1H), 2.51 (qd, J = 13.2, 4.6 Hz, 1H), 2.35 (q, J = 6.3, 5.1 Hz, 1H), 2.20 (ddq, J = 10.8, 5.4, 2.7 Hz, 1H), 1.88-1.68 (m, 3H), 1.38 (dd, J = 14.7, 6.5 Hz, 6H). | 11 | I-11; acetone |

TABLE 12-continued

| Example | Structure | ES/MS m/z: | 1H NMR | Procedure | Changes to Procedure: Different Reagents/ Starting Materials |
|---|---|---|---|---|---|
| 181 | 3-(5-(((2R,3S)-3-(cyclohexylamino)tetrahydro-2H-pyran-2-yl)methyl)-4-fluoro-1-oxoisoindolin-2-yl)piperidine-2,6-dione | 458.3 | ¹H NMR (400 MHz, Methanol-d4) δ 7.61 (d, J = 7.7 Hz, 1H), 7.58-7.52 (m, 1H), 5.17 (ddd, J = 13.4, 5.2, 1.6 Hz, 1H), 4.65-4.49 (m, 2H), 3.93-3.81 (m, 2H), 3.42 (ddd, J = 11.6, 8.1, 3.2 Hz, 1H), 3.27 (s, 1H), 3.18-3.09 (m, 1H), 2.97-2.89 (m, 1H), 2.81 (ddd, J = 17.6, 4.8, 2.4 Hz, 1H), 2.53 (qd, J = 13.2, 4.7 Hz, 1H), 2.37 (d, J = 13.1 Hz, 1H), 2.24-2.05 (m, 3H), 1.98-1.71 (m, 6H), 1.55-1.19 (m, 5H). | 11 | I-12; cyclohexanone |
| 182 | 3-(1-oxo-5-(((1R,2S)-2-((4,4,4-trifluoro-3,3-dimethylbutyl)amino)cyclohexyl)methyl)isoindolin-2-yl)piperidine-2,6-dione | 494.4 | ¹H NMR (400 MHz, DMSO-d6) δ 10.99 (s, 1H), 8.49 (s, 1H), 8.19 (s, 1H), 7.70 (d, J = 7.8 Hz, 1H), 7.44 (s, 1H), 7.36 (dd, J = 7.9, 1.4 Hz, 1H), 5.11 (dd, J = 13.3, 5.1 Hz, 1H), 4.45 (dd, J = 17.4, 4.0 Hz, 1H), 4.31 (dd, J = 17.3, 4.3 Hz, 1H), 3.28-3.20 (m, 1H), 3.16-3.01 (m, 4H), 2.99-2.85 (m, 1H), 2.60 (d, J = 17.1 Hz, 1H), 2.47-2.32 (m, 2H), 2.14-2.06 (m, 1H), 2.04-1.89 (m, 2H), 1.86-1.67 (m, 2H), 1.59-1.37 (m, 3H), 1.34-1.24 (m, 1H), 1.15 (d, J = 3.0 Hz, 6H), 1.10-0.96 (m, 2H). | 12 | 4-bromo-1,1,1-trifluoro-2,2-dimethylbutane |

TABLE 12-continued

| Example | Structure | ES/MS m/z: | 1H NMR | Procedure | Changes to Procedure: Different Reagents/ Starting Materials |
|---|---|---|---|---|---|
| 183 | 3-(5-(((1R,2S)-2-((2,2-difluorocyclohexyl)amino)cyclohexyl)methyl)-1-oxoisoindolin-2-yl)piperidine-2,6-dione | 474.4 | 1H NMR (400 MHz, DMSO-d6) δ 10.99 (s, 1H), 8.84 (s, 1H), 8.71 (s, 1H), 8.55 (s, 1H), 7.69 (d, J = 7.8 Hz, 1H), 7.44 (s, 1H), 7.36 (d, J = 7.8 Hz, 1H), 5.34 (s, 2H), 5.11 (dd, J = 13.3, 5.1 Hz, 1H), 4.45 (dd, J = 17.3, 4.5 Hz, 1H), 4.32 (dd, J = 17.3, 4.1 Hz, 1H), 3.92 (s, 1H), 3.70-3.58 (m, 2H), 3.43-3.34 (m, 1H), 3.14-3.08 (m, 1H), 2.92 (ddd, J = 17.2, 13.6, 5.4 Hz, 1H), 2.61 (dt, J = 17.4, 3.3 Hz, 1H), 2.46-2.28 (m, 2H), 2.21 (s, 1H), 2.11 (dd, J = 12.7, 3.9 Hz, 1H), 2.05-1.85 (m, 2H), 1.84-1.63 (m, 2H), 1.63-1.38 (m, 2H), 1.37-1.18 (m, 2H), 1.13-0.91 (m, 2H). | 15 | 2,2-difluorocyclohexanone |
| 184 | 3-(5-(((1R,2S)-2-((8-oxabicyclo[3.2.1]octan-3-yl)amino)cyclohexyl)methyl)-1-oxoisoindolin-2-yl)piperidine-2,6-dione | 466.4 | 1H NMR (400 MHz, DMSO-d6) δ 10.99 (s, 1H), 8.44 (s, 1H), 7.99 (s, 1H), 7.69 (d, J = 7.7 Hz, 1H), 7.44 (s, 1H), 7.35 (dd, J = 7.7, 1.4 Hz, 1H), 5.11 (dd, J = 13.3, 5.1 Hz, 1H), 4.50-4.37 (m, 3H), 4.32 (dd, J = 17.4, 2.0 Hz, 1H), 3.32 (d, J = 9.6 Hz, 1H), 3.24 (dd, J = 13.2, 3.5 Hz, 1H), 3.01 (s, 1H), 2.92 (ddd, J = 17.3, 13.6, 5.4 Hz, 1H), 2.66-2.52 (m, 1H), 2.47-2.31 (m, 2H), 2.11-1.94 (m, 4H), 1.94-1.86 (m, 1H), 1.81 (d, J = 10.5 Hz, 1H), 1.69 (t, J = 6.6 Hz, 4H), 1.55-1.26 (m, 6H), 1.09-0.97 (m, 2H). | 15 | 8-oxabicyclo[3.2.1]octan-3-one |

TABLE 12-continued

| Example | Structure | ES/MS m/z: | 1H NMR | Procedure | Changes to Procedure: Different Reagents/ Starting Materials |
|---|---|---|---|---|---|
| 185 | 3-(5-(((1R,2S)-2-((4-methylpentan-2-yl)amino)cyclohexyl)methyl)-1-oxoisoindolin-2-yl)piperidine-2,6-dione | 440.4 | 1H NMR (400 MHz, DMSO-d6) δ 10.99 (s, 1H), 8.18 (s, 1H), 7.97 (s, 1H), 7.69 (d, J = 7.7 Hz, 1H), 7.45 (d, J = 3.6 Hz, 1H), 7.36 (dt, J = 7.8, 1.6 Hz, 1H), 5.11 (dd, J = 13.3, 5.1 Hz, 1H), 4.45 (dd, J = 17.4, 2.9 Hz, 1H), 4.32 (dd, J = 17.4, 2.9 Hz, 1H), 3.29 (dtd, J = 26.3, 13.6, 13.1, 5.1 Hz, 2H), 3.04 (s, 1H), 2.92 (ddd, J = 17.3, 13.6, 5.4 Hz, 1H), 2.61 (dt, J = 15.3, 2.8 Hz, 1H), 2.47-2.30 (m, 2H), 2.19-1.94 (m, 2H), 1.85 (s, 1H), 1.70 (td, J = 13.4, 6.6 Hz, 2H), 1.60-1.32 (m, 5H), 1.30 (d, J = 6.4 Hz, 1H), 1.25 (d, J = 6.3 Hz, 2H), 1.13-0.97 (m, 2H), 0.96-0.82 (m, 6H). | 15 | 4-methylpentan-2-one |
| 186 | 3-(4-fluoro-5-(((1R,2S)-2-((oxetan-3-yl)methyl)amino)cyclohexyl)methyl)-1-oxoisoindolin-2-yl)piperidine-2,6-dione | 444.3 | 1H NMR (400 MHz, DMSO-d6) δ 11.01 (s, 1H), 8.59 (s, 1H), 8.32 (s, 1H), 7.64-7.54 (m, 1H), 7.54-7.35 (m, 1H), 5.12 (dd, J = 13.3, 5.1 Hz, 1H), 4.69 (t, J = 6.8 Hz, 1H), 4.63-4.50 (m, 1H), 4.49-4.31 (m, 3H), 3.64-3.56 (m, 3H), 3.50-3.39 (m, 1H), 3.36 (td, J = 9.5, 8.5, 5.8 Hz, 1H), 3.10 (dd, J = 30.2, 10.7 Hz, 2H), 2.92 (ddd, J = 17.3, 13.6, 5.5 Hz, 1H), 2.66-2.54 (m, 2H), 2.42 (td, J = 13.2, 4.5 Hz, 1H), 2.14-1.96 (m, 1H), 1.90 (d, J = 10.1 Hz, 1H), 1.71 (d, J = 11.9 Hz, 1H), 1.62-1.39 (m, 3H), 1.39-1.24 (m, 1H), 1.05 (dd, J = 14.0, 5.5 Hz, 2H). | 15 | I-4; oxetane-3-carbaldehyde |

TABLE 12-continued

| Example | Structure | ES/MS m/z: | 1H NMR | Procedure | Changes to Procedure: Different Reagents/ Starting Materials |
|---|---|---|---|---|---|
| 187 | 3-(4-fluoro-1-oxo-5-(((1R,2S)-2-(((tetrahydro-2H-pyran-4-yl)methyl)amino)cyclohexyl)meth-yl)isoindolin-2-yl)piperidine-2,6-dione | 472.3 | ¹H NMR (400 MHz, DMSO-d6) δ 11.01 (s, 1H), 8.54 (d, J = 9.1 Hz, 1H), 8.29 (s, 1H), 7.58 (d, J = 7.7 Hz, 1H), 7.49 (t, J = 7.0 Hz, 1H), 5.12 (dd, J = 13.3, 5.1 Hz, 1H), 4.56 (dd, J = 17.4, 4.9 Hz, 1H), 4.39 (dd, J = 17.4, 5.5 Hz, 1H), 3.94-3.83 (m, 2H), 3.30 (tt, J = 11.7, 2.7 Hz, 2H), 3.21-3.12 (m, 1H), 3.08 (s, 1H), 2.99-2.85 (m, 3H), 2.76 (s, 1H), 2.66-2.51 (m, 2H), 2.43 (qd, J = 13.1, 4.4 Hz, 1H), 2.10-1.88 (m, 3H), 1.80-1.63 (m, 3H), 1.58-1.40 (m, 3H), 1.38-1.19 (m, 3H), 1.08 (q, J = 10.6, 9.6 Hz, 2H). | 15 | I-4; tetrahydropyran-4-carbaldehyde |
| 188 | 3-(4-fluoro-1-oxo-5-(((1R,2S)-2-((tetrahydro-2H-pyran-4-yl)amino)cyclohexyl)methyl)iso-indolin-2-yl)piperidine-2,6-dione | 458.4 | ¹H NMR (400 MHz, DMSO-d6) δ 11.01 (s, 1H), 8.58 (s, 1H), 8.13 (s, 1H), 7.59 (d, J = 7.7 Hz, 1H), 7.50 (t, J = 7.0 Hz, 1H), 5.12 (dd, J = 13.3, 5.1 Hz, 1H), 4.56 (dd, J = 17.4, 4.0 Hz, 1H), 4.39 (dd, J = 17.4, 3.4 Hz, 1H), 3.98-3.89 (m, 2H), 3.53 (m, 1H), 3.36 (t, J = 11.8 Hz, 2H), 3.27-3.14 (m, 2H), 2.99-2.85 (m, 1H), 2.68-2.52 (m, 2H), 2.42 (tt, J = 13.2, 6.6 Hz, 1H), 2.16-2.07 (m, 1H), 2.01 (dtd, J = 12.6, 5.1, 2.2 Hz, 2H), 1.90 (s, 2H), 1.83-1.68 (m, 2H), 1.67-1.53 (m, 1H), 1.45 (dt, J = 23.4, 8.6 Hz, 2H), 1.34 (t, J = 11.3 Hz, 1H), 1.14-1.00 (m, 2H). | 15 | I-4; tetrahydropyran-4-one |

TABLE 12-continued

| Example | Structure | ES/MS m/z: | 1H NMR | Procedure | Changes to Procedure: Different Reagents/ Starting Materials |
|---|---|---|---|---|---|
| 189 | 3-(4-fluoro-1-oxo-5-(((1R,2S)-2-(((tetrahydrofuran-3-yl)amino)cyclohexyl)methyl)iso-indolin-2-yl)piperidine-2,6-dione (Isomer 1) | 444.3 | ¹H NMR (400 MHz, DMSO-d6) δ 11.01 (s, 1H), 8.81 (d, J = 31.2 Hz, 1H), 8.44 (d, J = 44.6 Hz, 1H), 7.59 (d, J = 7.7 Hz, 1H), 7.49 (t, J = 7.0 Hz, 1H), 5.12 (dd, J = 13.3, 5.1 Hz, 1H), 4.56 (dd, J = 17.4, 4.4 Hz, 1H), 4.39 (dd, J = 17.4, 4.2 Hz, 1H), 4.06 (s, 2H), 3.94 (dddd, J = 9.5, 6.7, 4.3, 1.7 Hz, 1H), 3.91-3.82 (m, 2H), 3.67 (q, J = 7.7 Hz, 1H), 3.27-3.01 (m, 2H), 2.92 (ddd, J = 17.2, 13.6, 5.4 Hz, 1H), 2.71-2.55 (m, 2H), 2.41 (td, J = 13.2, 4.5 Hz, 1H), 2.35-2.22 (m, 1H), 2.16-1.83 (m, 3H), 1.69 (s, 1H), 1.60-1.40 (m, 3H), 1.33 (d, J = 11.0 Hz, 1H), 1.10 (q, J = 9.9 Hz, 2H). | 15 | I-4; tetrahydrofuran-3-one |
| 190 | 3-(4-fluoro-1-oxo-5-(((1R,2S)-2-(((tetrahydrofuran-3-yl)amino)cyclohexyl)methyl)iso-indolin-2-yl)piperidine-2,6-dione (Isomer 2) | 444.3 | ¹H NMR (400 MHz, DMSO-d6) δ 11.01 (s, 1H), 8.81 (d, J = 31.2 Hz, 1H), 8.44 (d, J = 44.6 Hz, 1H), 7.59 (d, J = 7.7 Hz, 1H), 7.49 (t, J = 7.0 Hz, 1H), 5.12 (dd, J = 13.3, 5.1 Hz, 1H), 4.56 (dd, J = 17.4, 4.4 Hz, 1H), 4.39 (dd, J = 17.4, 4.2 Hz, 1H), 4.06 (s, 2H), 3.94 (dddd, J = 9.5, 6.7, 4.3, 1.7 Hz, 1H), 3.91-3.82 (m, 2H), 3.67 (q, J = 7.7 Hz, 1H), 3.27-3.01 (m, 2H), 2.92 (ddd, J = 17.2, 13.5, 5.4 Hz, 1H), 2.71-2.55 (m, 2H), 2.41 (td, J = 13.2, 4.5 Hz, 1H), 2.35-2.22 (m, 1H), 2.16-1.83 (m, 3H), 1.69 (s, 1H), 1.60-1.40 (m, 3H), 1.33 (d, J = 11.0 Hz, 1H), 1.10 (q, J = 9.9 Hz, 2H). | 15 | I-4; tetrahydrofuran-3-one |

TABLE 12-continued

| Example | Structure | ES/MS m/z: | 1H NMR | Procedure | Changes to Procedure: Different Reagents/ Starting Materials |
|---|---|---|---|---|---|
| 191 | 3-(5-(((1R,2S)-2-(bicyclo[3.2.1]octan-3-ylamino)cyclohexyl)methyl)-1-oxoisoindolin-2-yl)piperidine-2,6-dione | 464.3 | ¹H NMR (400 MHz, DMSO-d6) δ 10.99 (s, 1H), 8.22 (s, 1H), 7.72 (t, J = 10.4 Hz, 2H), 7.44 (s, 1H), 7.36 (d, J = 7.8 Hz, 1H), 5.12 (dd, J = 13.3, 5.1 Hz, 1H), 4.46 (dd, J = 17.4, 2.1 Hz, 1H), 4.32 (dd, J = 17.4, 2.2 Hz, 1H), 3.46-3.08 (m, 4H), 3.08-2.82 (m, 2H), 2.82-2.58 (m, 1H), 2.45-2.16 (m, 5H), 2.16-1.89 (m, 2H), 1.89-1.13 (m, 12H), 1.00 (d, J = 12.4 Hz, 4H). | 15 | bicyclo[3.2.1]octan-3-one |
| 192 | 3-(5-(((1R,2S)-2-((3,3-dimethyltetrahydro-2H-pyran-4-yl)amino)cyclohexyl)methyl)-1-oxoisoindolin-2-yl)piperidine-2,6-dione | 468.4 | ¹H NMR (400 MHz, DMSO-d6) δ 10.99 (s, 1H), 7.71 (d, J = 7.8 Hz, 1H), 7.67 (s, 1H), 7.50 (s, 1H), 7.43 (s, 1H), 7.36 (d, J = 7.8 Hz, 1H), 5.11 (ddd, J = 13.3, 5.1, 1.5 Hz, 1H), 4.58-4.24 (m, 2H), 4.04-3.93 (m, 1H), 3.55-3.23 (m, 5H), 3.13 (d, J = 11.5 Hz, 1H), 3.04 (d, J = 9.9 Hz, 1H), 2.92 (ddd, J = 17.1, 13.6, 5.4 Hz, 1H), 2.66-2.56 (m, 1H), 2.43-2.30 (m, 2H), 2.19 (d, J = 12.1 Hz, 1H), 2.06-1.81 (m, 4H), 1.76 (d, J = 13.2 Hz, 1H), 1.53 (d, J = 14.6 Hz, 3H), 1.25 (q, J = 12.0 Hz, 1H), 1.08 (s, 3H), 1.01 (s, 3H). | 15 | 3,3-dimethyltetrahydropyran-4-one |

TABLE 12-continued

| Example | Structure | ES/MS m/z: | 1H NMR | Procedure | Changes to Procedure: Different Reagents/ Starting Materials |
|---|---|---|---|---|---|
| 193 | 3-(5-(((1R,2S)-2-((7-oxabicyclo[2.2.1]heptan-2-yl)amino)cyclohexyl)methyl)-1-oxoisoindolin-2-yl)piperidine-2,6-dione | 452.3 | ¹H NMR (400 MHz, DMSO-d6) δ 10.99 (s, 1H), 9.09-8.07 (m, 2H), 7.69 (dd, J = 7.8, 3.1 Hz, 1H), 7.47 (d, J = 16.7 Hz, 1H), 7.38 (ddd, J = 12.2, 7.8, 1.4 Hz, 1H), 5.11 (dd, J = 13.3, 5.1 Hz, 1H), 4.78-4.52 (m, 2H), 4.49-4.25 (m, 2H), 3.70-3.54 (m, 1H), 3.39-3.25 (m, 1H), 3.19-2.80 (m, 3H), 2.60 (dd, J = 18.4, 4.2 Hz, 1H), 2.47-2.29 (m, 2H), 2.22-1.76 (m, 4H), 1.75-1.22 (m, 8H), 1.10 (dq, J = 29.9, 11.5, 10.2 Hz, 2H). | 15 | 7-oxabicyclo[2.2.1]heptan-2-one |
| 194 | 3-(5-(((1R,2S)-2-((3-oxabicyclo[3.2.1]octan-8-yl)amino)cyclohexyl)methyl)-1-oxoisoindolin-2-yl)piperidine-2,6-dione | 466.4 | ¹H NMR (400 MHz, DMSO-d6) δ 10.99 (s, 1H), 8.53 (d, J = 34.7 Hz, 2H), 7.70 (d, J = 7.8 Hz, 1H), 7.48 (s, 1H), 7.39 (d, J = 7.8 Hz, 1H), 5.11 (dd, J = 13.3, 5.1 Hz, 1H), 4.51-4.24 (m, 2H), 3.95 (t, J = 11.7 Hz, 2H), 3.50-3.35 (m, 3H), 3.21 (dd, J = 14.1, 4.7 Hz, 2H), 2.92 (ddd, J = 17.2, 13.6, 5.5 Hz, 1H), 2.65-2.56 (m, 1H), 2.40 (qd, J = 13.2, 4.5 Hz, 1H), 2.26 (d, J = 16.9 Hz, 2H), 2.13-1.94 (m, 4H), 1.89-1.61 (m, 6H), 1.52 (d, J = 10.4 Hz, 1H), 1.35 (d, J = 11.9 Hz, 1H), 1.20-1.00 (m, 2H). | 15 | 3-oxabicyclo[3.2.1]octan-8-one |

TABLE 12-continued

| Example | Structure | ES/MS m/z: | 1H NMR | Procedure | Changes to Procedure: Different Reagents/ Starting Materials |
|---|---|---|---|---|---|
| 195 | 3-(5-(((1R,2S)-2-((6,8-dioxabicyclo[3.2.1]octan-4-yl)amino)cyclohexyl)methyl)-1-oxoisoindolin-2-yl)piperidine-2,6-dione | 468.4 | 1H NMR (400 MHz, DMSO-d6) δ 10.99 (s, 1H), 8.38 (d, J = 27.5 Hz, 2H), 7.71-7.64 (m, 1H), 7.47 (s, 1H), 7.38 (dd, J = 7.8, 1.4 Hz, 1H), 5.69 (s, 1H), 5.11 (dd, J = 13.2, 5.1 Hz, 1H), 4.64 (d, J = 4.8 Hz, 1H), 4.52-4.27 (m, 2H), 4.02-3.95 (m, 2H), 3.81-3.73 (m, 1H), 3.37 (d, J = 7.7 Hz, 1H), 3.21 (dd, J = 13.1, 3.7 Hz, 1H), 3.12 (s, 1H), 2.99-2.84 (m, 1H), 2.65-2.56 (m, 1H), 2.48-2.32 (m, 2H), 2.12-1.95 (m, 2H), 1.94-1.60 (m, 4H), 1.60-1.43 (m, 3H), 1.40-1.18 (m, 1H), 1.03 (dt, J = 21.5, 12.8 Hz, 2H). | 15 | 6,8-dioxabicyclo[3.2.1]octan-4-one |
| 196 | 3-(5-(((1R,2S)-2-(cycloheptylamino)cyclohexyl)methyl)-1-oxoisoindolin-2-yl)piperidine-2,6-dione | 452.4 | 1H NMR (400 MHz, DMSO-d6) δ 10.99 (s, 1H), 8.20 (s, 1H), 7.98 (d, J = 13.5 Hz, 1H), 7.69 (d, J = 7.8 Hz, 1H), 7.44 (s, 1H), 7.41-7.29 (m, 1H), 5.11 (dd, J = 13.3, 5.1 Hz, 1H), 4.51-4.25 (m, 2H), 3.39-3.21 (m, 2H), 3.04 (s, 1H), 2.99-2.80 (m, 1H), 2.60 (dd, J = 17.1, 3.4 Hz, 1H), 2.46-2.34 (m, 2H), 2.13-1.94 (m, 4H), 1.88-1.63 (m, 4H), 1.63-1.18 (m, 11H), 1.03 (t, J = 9.4 Hz, 2H). | 15 | cycloheptanone |

TABLE 12-continued

| Example | Structure | ES/MS m/z: | 1H NMR | Procedure | Changes to Procedure: Different Reagents/ Starting Materials |
|---|---|---|---|---|---|
| 197 | 3-(5-(((1R,2S)-2-(oxepan-4-yl)amino)cyclohexyl)methyl)-1-oxoisoindolin-2-yl)piperidine-2,6-dione | 454.4 | $^1$H NMR (400 MHz, DMSO-d6) δ 10.99 (s, 1H), 8.36 (s, 1H), 8.13 (s, 1H), 7.69 (d, J = 7.7 Hz, 1H), 7.45 (s, 1H), 7.36 (dd, J = 7.8, 1.6 Hz, 1H), 5.11 (dd, J = 13.3, 5.1 Hz, 1H), 4.45 (dd, J = 17.4, 2.3 Hz, 1H), 4.32 (dd, J = 17.4, 2.3 Hz, 1H), 3.72 (dddd, J = 20.5, 8.1, 6.5, 4.0 Hz, 2H), 3.57 (ddt, J = 12.6, 9.4, 3.6 Hz, 2H), 3.41 (s, 1H), 3.27 (d, J = 13.0 Hz, 1H), 3.07 (s, 1H), 2.99-2.85 (m, 1H), 2.65-2.52 (m, 1H), 2.40 (tt, J = 13.5, 6.7 Hz, 2H), 2.14 (dd, J = 14.1, 10.5 Hz, 1H), 2.11 (s, 2H), 2.11-2.00 (m, 1H), 2.04-1.95 (m, 1H), 1.90-1.77 (m, 2H), 1.74 (dq, J = 18.6, 8.7, 6.2 Hz, 3H), 1.56-1.45 (m, 2H), 1.36 (dt, J = 22.6, 11.5 Hz, 2H), 1.03 (s, 2H). | 15 | oxepan-4-one |
| 198 | 3-(5-(((1R,2S)-2-(((3aR,6aS)-hexahydro-1H-cyclopenta[c]furan-5-yl)amino)cyclohexyl)methyl)-1-oxoisoindolin-2-yl)piperidine-2,6-dione | 466.4 | $^1$H NMR (400 MHz, DMSO-d6) δ 10.99 (s, 1H), 8.62 (s, 1H), 8.16 (s, 1H), 7.69 (d, J = 7.8 Hz, 1H), 7.44 (s, 1H), 7.36 (dd, J = 7.8, 1.3 Hz, 1H), 5.11 (dd, J = 13.3, 5.1 Hz, 1H), 4.45 (dd, J = 17.5, 2.5 Hz, 1H), 4.31 (dd, J = 17.5, 2.2 Hz, 1H), 3.75-3.56 (d, J = 9.6 Hz, 3H), 3.47 (dd, J = 9.0, 5.5 Hz, 2H), 3.30-3.22 (m, 1H), 3.04-2.85 (m, 2H), 2.85-2.71 (m, 1H), 2.72-2.52 (m, 3H), 2.47-2.31 (m, 3H), 2.14-2.05 (m, 1H), 2.05-1.95 (m, 3H), 1.82 (s, 1H), 1.69 (d, J = 11.5 Hz, 1H), 1.57-1.45 (m, 3H), 1.41 (d, J = 11.0 Hz, 1H), 1.40-1.27 (m, 1H), 1.05 (q, J = 11.9, 11.2 Hz, 2H). | 15 | (3aR,6aS)-tetrahydro-1H-cyclopenta[c]furan-5(3H)-one |

TABLE 12-continued

| Example | Structure | ES/MS m/z: | 1H NMR | Procedure | Changes to Procedure: Different Reagents/ Starting Materials |
|---|---|---|---|---|---|
| 199 | 3-(5-(((1R,2S)-2-(bicyclo[3.2.1]octan-ylamino)cyclohexyl)methyl)-1-oxoisoindolin-2-yl)piperidine-2,6-dione | 464.2 | ¹H NMR (400 MHz, DMSO-d6) δ 10.99 (s, 1H), 8.27 (s, 1H), 8.16 (s, 1H), 7.70 (d, J = 7.8 Hz, 1H), 7.49 (s, 1H), 7.40 (d, J = 7.8 Hz, 1H), 5.12 (dd, J = 13.2, 5.1 Hz, 1H), 4.45 (d, J = 17.3 Hz, 1H), 4.32 (d, J = 17.2 Hz, 1H), 3.40-3.04 (m, 4H), 3.04-2.81 (m, 2H), 2.70-2.55 (m, 2H), 2.46-2.22 (m, 3H), 2.21-1.92 (m, 3H), 1.88-1.48 (m, 10H), 1.48-1.23 (m, 3H), 1.12 (dd, J = 27.4, 11.6 Hz, 2H). | 15 | bicyclo[3.2.1]octan-8-one |
| 200 | 3-(1-oxo-5-(((1R,2S)-2-((1-(tetrahydro-2H-pyran-4-yl)ethyl)amino)cyclohexyl)methyl)isoindolin-2-yl)piperidine-2,6-dione | 468.4 | ¹H NMR (400 MHz, DMSO-d6) δ 10.99 (s, 1H), 7.84 (s, 2H), 7.70 (dd, J = 7.8, 2.6 Hz, 1H), 7.45 (s, 1H), 7.37 (d, J = 7.8 Hz, 1H), 5.11 (dd, J = 13.3, 5.1 Hz, 1H), 4.45 (d, J = 17.3 Hz, 1H), 4.32 (d, J = 17.2 Hz, 1H), 3.97-3.87 (m, 2H), 3.37-3.20 (m, 4H), 3.07 (s, 1H), 2.92 (ddd, J = 17.2, 13.6, 5.6 Hz, 1H), 2.66-2.52 (m, 1H), 2.48-2.31 (m, 2H), 2.16-2.06 (m, 1H), 2.00 (ddt, J = 10.4, 7.0, 4.3 Hz, 1H), 1.91 (s, 2H), 1.84 (dp, J = 8.6, 2.9 Hz, 1H), 1.76-1.58 (m, 2H), 1.57-1.26 (m, 5H), 1.30-1.20 (m, 3H), 1.06 (q, J = 9.1, 7.1 Hz, 2H). | 15 | 1-tetrahydropyran-4-ylethanone |

TABLE 12-continued

| Example | Structure | ES/MS m/z: | 1H NMR | Procedure | Changes to Procedure: Different Reagents/ Starting Materials |
|---|---|---|---|---|---|
| 201 | 3-(5-(((1R,2S)-2-(((1-cyclopentylethyl)amino)cyclohexyl)methyl)-1-oxoisoindolin-2-yl)piperidine-2,6-dione (Isomer 1) | 452.4 | 1H NMR (400 MHz, DMSO-d6) δ 10.99 (s, 1H), 7.84 (s, 1H), 7.70 (dd, J = 7.8, 3.1 Hz, 1H), 7.62 (d, J = 13.2 Hz, 1H), 7.44 (s, 1H), 7.36 (d, J = 7.8 Hz, 1H), 5.11 (dd, J = 13.3, 5.1 Hz, 1H), 4.53-4.13 (m, 2H), 3.26 (d, J = 7.6 Hz, 2H), 3.05 (s, 1H), 2.92 (ddd, J = 17.2, 13.6, 5.4 Hz, 1H), 2.65-2.56 (m, 1H), 2.46-2.27 (m, 2H), 2.21-1.81 (m, 5H), 1.81-1.46 (m, 7H), 1.44-1.14 (m, 7H), 1.14-0.94 (m, 2H). | 15 | 1-cyclopentylethanone |
| 202 | 3-(5-(((1R,2S)-2-(((1-cyclopentylethyl)amino)cyclohexyl)methyl)-1-oxoisoindolin-2-yl)piperidine-2,6-dione (Isomer 2) | 452.4 | 1H NMR (400 MHz, DMSO-d6) δ 10.99 (s, 1H), 8.28 (d, J = 12.9 Hz, 1H), 7.70 (d, J = 7.7 Hz, 1H), 7.63 (d, J = 13.8 Hz, 1H), 7.45 (s, 1H), 7.37 (d, J = 7.8 Hz, 1H), 5.11 (dd, J = 13.3, 5.1 Hz, 1H), 4.60-4.18 (m, 2H), 3.26 (dd, J = 13.1, 3.6 Hz, 1H), 3.07 (s, 1H), 2.92 (ddd, J = 17.1, 13.6, 5.5 Hz, 1H), 2.60 (dd, J = 16.9, 3.4 Hz, 1H), 2.47-2.35 (m, 2H), 2.24-2.13 (m, 1H), 2.13-2.05 (m, 1H), 2.00 (ddq, J = 10.6, 5.3, 2.8, 2.2 Hz, 1H), 1.94-1.79 (m, 2H), 1.78-1.39 (m, 8H), 1.39-1.15 (m, 7H), 1.04 (t, J = 9.4 Hz, 2H). | 15 | 1-cyclopentylethanone |

| Example | Structure | ES/MS m/z: | 1H NMR | Procedure | Changes to Procedure: Different Reagents/ Starting Materials |
|---|---|---|---|---|---|
| 203 | 3-(5-(((1R,2S)-2-(((1-cyclohexylethyl)amino)cyclohexyl)methyl)-1-oxoisoindolin-2-yl)piperidine-2,6-dione | 466.4 | 1H NMR (400 MHz, DMSO-d6) δ 10.99 (s, 1H), 7.92-7.60 (m, 3H), 7.46 (d, J = 6.0 Hz, 1H), 7.37 (d, J = 7.9 Hz, 1H), 5.11 (dd, J = 13.3, 5.1 Hz, 1H), 4.55-4.22 (m, 2H), 3.29 (td, J = 15.6, 14.4, 3.9 Hz, 1H), 3.24-3.15 (m, 1H), 3.03 (s, 1H), 2.92 (ddd, J = 17.3, 13.6, 5.5 Hz, 1H), 2.61 (dt, J = 17.2, 3.3 Hz, 1H), 2.47-2.28 (m, 2H), 2.16-1.82 (m, 3H), 1.80-1.39 (m, 11H), 1.37-0.91 (m, 9H). | 15 | 1-cyclohexylethanone |
| 204 | 3-(5-(((1R,2S)-2-(((1-cyclopropylpropan-2-yl)amino)cyclohexyl)methyl)-1-oxoisoindolin-2-yl)piperidine-2,6-dione | 438.4 | 1H NMR (400 MHz, DMSO-d6) δ 10.99 (s, 1H), 8.12 (dd, J = 76.4, 54.6 Hz, 2H), 7.70 (d, J = 7.7 Hz, 1H), 7.44 (s, 1H), 7.36 (d, J = 7.9 Hz, 1H), 5.11 (dd, J = 13.3, 5.1 Hz, 1H), 4.56-4.16 (m, 2H), 3.26 (dd, J = 13.2, 3.8 Hz, 1H), 3.06 (s, 1H), 2.92 (ddd, J = 17.3, 13.6, 5.4 Hz, 1H), 2.61 (dt, J = 16.4, 3.0 Hz, 1H), 2.47-2.36 (m, 3H), 2.18-1.91 (m, 2H), 1.90-1.66 (m, 2H), 1.67-1.42 (m, 4H), 1.36 (dd, J = 18.4, 6.3 Hz, 4H), 1.15-0.95 (m, 2H), 0.78 (qt, J = 7.3, 2.8 Hz, 1H), 0.61-0.39 (m, 2H), 0.2-0.05 (m, 2H). | 15 | 1-cyclopropylpropan-2-one |

TABLE 12-continued

| Example | Structure | ES/MS m/z: | 1H NMR | Procedure | Changes to Procedure: Different Reagents/ Starting Materials |
|---|---|---|---|---|---|
| 205 | 3-(5-(((1R,2S)-2-((4,4-dimethylpentan-2-yl)amino)cyclohexyl)methyl)-1-oxoisoindolin-2-yl)piperidine-2,6-dione | 454.4 | ¹H NMR (400 MHz, DMSO-d6) δ 10.99 (s, 1H), 8.30-7.86 (m, 2H), 7.70 (d, J = 7.8 Hz, 1H), 7.44 (d, J = 3.3 Hz, 1H), 7.36 (d, J = 7.8 Hz, 1H), 5.11 (dd, J = 13.3, 5.1 Hz, 1H), 4.45 (dd, J = 17.3, 4.1 Hz, 1H), 4.32 (dd, J = 17.4, 4.4 Hz, 1H), 3.69 (s, 1H), 3.43-3.22 (m, 2H), 2.99-2.85 (m, 1H), 2.65-2.55 (m, 1H), 2.46-2.32 (m, 1H), 2.22-1.95 (m, 4H), 1.90-1.40 (m, 6H), 1.34 (dd, J = 19.6, 6.3 Hz, 3H), 1.14-1.01 (m, 2H), 0.94 (d, J = 10.9 Hz, 9H). | 15 | 4,4-dimethylpentan-2-one |
| 206 | 3-(5-(((1R,2S)-2-((1-(1-methylcyclobutyl)ethyl)amino)cyclohexyl)methyl)-1-oxoisoindolin-2-yl)piperidine-2,6-dione (Isomer 1) | 452.4 | ¹H NMR (400 MHz, DMSO-d6) δ 10.99 (s, 1H), 7.71 (d, J = 7.7 Hz, 1H), 7.56 (s, 1H), 7.45 (d, J = 10.3 Hz, 1H), 7.37 (d, J = 7.8 Hz, 1H), 5.11 (dd, J = 13.3, 5.1 Hz, 1H), 4.46 (dd, J = 17.4, 2.4 Hz, 1H), 4.32 (dd, J = 17.5, 2.8 Hz, 1H), 3.51-3.40 (m, 2H), 3.05-2.82 (m, 1H), 2.65-2.56 (m, 2H), 2.47-2.32 (m, 2H), 2.21 (d, J = 12.0 Hz, 1H), 2.06-1.86 (m, 4H), 1.87-1.70 (m, 3H), 1.68-1.43 (m, 4H), 1.36-1.24 (m, 1H), 1.24-1.06 (m, 7H), 1.08-0.95 (m, 2H). | 15 | 1-(1-methylcyclobutyl)ethanone |

TABLE 12-continued

| Example | Structure | ES/MS m/z: | 1H NMR | Procedure | Changes to Procedure: Different Reagents/ Starting Materials |
|---|---|---|---|---|---|
| 207 | 3-(5-(((1R,2S)-2-((1-(1-methylcyclobutyl)ethyl)amino)cyclohexyl)methyl)-1-oxoisoindolin-2-yl)piperidine-2,6-dione (Isomer 2) | 452.4 | $^1$H NMR (400 MHz, DMSO-d6) δ 10.99 (s, 1H), 8.29-8.04 (m, 1H), 7.70 (d, J = 7.7 Hz, 1H), 7.58-7.22 (m, 3H), 5.11 (dd, J = 13.3, 5.1 Hz, 1H), 4.59-4.11 (m, 2H), 3.60-3.44 (m, 4H), 3.31 (dd, J = 13.2, 4.0 Hz, 1 H), 3.05-2.83 (m, 1H), 2.66-2.55 (m, 1H), 2.47-2.31 (m, 1H), 2.19-1.87 (m, 3H), 1.87-1.64 (m, 2H), 1.64-1.41 (m, 2H), 1.40-1.21 (m, 1H), 1.20-1.11 (m, 9H), 1.11-0.95 (m, 3H). | 15 | 1-(1-methylcyclobutyl)ethanone |
| 208 | 3-(1-oxo-5-(((1R,2S)-2-((2,2,6,6-tetramethyltetrahydro-2H-pyran-4-yl)amino)cyclohexyl)methyl)isoindolin-2-yl)piperidine-2,6-dione | 496.4 | $^1$H NMR (400 MHz, DMSO-d6) δ 10.99 (s, 1H), 8.55 (d, J = 11.1 Hz, 1H), 8.03 (s, 1H), 7.70 (d, J = 7.7 Hz, 1H), 7.45 (s, 1H), 7.37 (dd, J = 7.8, 1.3 Hz, 1H), 5.11 (dd, J = 13.3, 5.1 Hz, 1H), 4.52-4.25 (m, 2H), 3.77-3.62 (m, 1H), 3.26 (dd, J = 13.2, 4.0 Hz, 1H), 3.19-3.06 (m, 1H), 2.92 (ddd, J = 17.4, 13.6, 5.5 Hz, 1H), 2.66-2.54 (m, 1H), 2.49-2.30 (m, 2H), 2.19-2.06 (m, 1H), 2.06-1.93 (m, 2H), 1.93-1.79 (m, 2H), 1.72 (d, J = 13.0 Hz, 1H), 1.61-1.42 (m, 4H), 1.35 (t, J = 12.2 Hz, 1H), 1.30-0.97 (m, 14H). | 15 | 2,2,6,6-tetramethyltetrahydropyran-4-one |

TABLE 12-continued

| Example | Structure | ES/MS m/z: | 1H NMR | Procedure | Changes to Procedure: Different Reagents/ Starting Materials |
|---|---|---|---|---|---|
| 209 | 3-(5-(((1R,2S)-2-((4,4-difluorocyclohexyl)amino)cyclohexyl)methyl)-4-fluoro-1-oxoisoindolin-2-yl)piperidine-2,6-dione | 493.4 | 1H NMR (400 MHz, DMSO-d6) δ 11.01 (s, 1H), 8.56 (s, 1H), 8.09 (d, J = 12.4 Hz, 1H), 7.60 (d, J = 7.7 Hz, 1H), 7.48 (t, J = 7.0 Hz, 1H), 5.12 (dd, J = 13.3, 5.1 Hz, 1H), 4.48 (ddd, J = 69.8, 17.3, 4.5 Hz, 2H), 3.21 (d, J = 14.2 Hz, 3H), 2.92 (ddd, J = 17.3, 13.6, 5.4 Hz, 1H), 2.65-2.56 (m, 2H), 2.43 (dd, J = 13.2, 4.6 Hz, 1H), 2.12 (q, J = 15.0, 12.0 Hz, 6H), 2.00 (dp, J = 10.5, 3.3 Hz, 2H), 1.94-1.59 (m, 2H), 1.51 (d, J = 34.1 Hz, 2H), 1.36 (q, J = 16.4, 14.3 Hz, 2H), 1.06 (t, J = 9.7 Hz, 2H). | 16 | I-4; 4,4-difluorocyclohexanone |
| 210 | 3-(4-fluoro-1-oxo-5-(((1R,2S)-2-((spiro[2.5]octan-6-yl-6-d)amino)cyclohexyl)methyl)isoindolin-2-yl)piperidine-2,6-dione | 483.4 | 1H NMR (400 MHz, DMSO-d6) δ 11.01 (s, 1H), 8.38 (d, J = 12.2 Hz, 1H), 7.96 (d, J = 12.6 Hz, 1H), 7.60 (d, J = 7.7 Hz, 1H), 7.49 (t, J = 7.0 Hz, 1H), 5.12 (dd, J = 13.3, 5.1 Hz, 1H), 4.48 (ddd, J = 69.9, 17.4, 3.7 Hz, 2H), 3.28-3.11 (m, 3H), 2.92 (ddd, J = 17.3, 13.6, 5.3 Hz, 1H), 2.65-2.54 (m, 2H), 2.47-2.32 (m, 1H), 2.16-1.92 (m, 3H), 1.81 (t, J = 13.2 Hz, 3H), 1.68 (q, J = 13.5, 12.3 Hz, 2H), 1.61-1.24 (m, 5H), 1.07 (t, J = 9.3 Hz, 2H), 0.94 (d, J = 13.2 Hz, 2H), 0.35 (dd, J = 8.6, 5.7 Hz, 2H), 0.24 (dd, J = 8.8, 5.8 Hz, 2H). | 16 | I-4; spiro[2.5]octan-6-one |

TABLE 12-continued

| Example | Structure | ES/MS m/z: | 1H NMR | Procedure | Changes to Procedure: Different Reagents/ Starting Materials |
|---|---|---|---|---|---|
| 211 | 3-(5-(((1R,2S)-2-((cyclohexyl-1-d)amino)cyclohexyl)methyl)-4-fluoro-1-oxoisoindolin-2-yl)piperidine-2,6-dione | 457.4 | $^1$H NMR (400 MHz, DMSO-d6) δ 11.01 (s, 1H), 8.32 (s, 1H), 7.94 (d, J = 12.6 Hz, 1H), 7.59 (d, J = 7.7 Hz, 1H), 7.49 (t, J = 7.0 Hz, 1H), 5.12 (dd, J = 13.3, 5.1 Hz, 1H), 4.48 (ddd, J = 70.0, 17.4, 3.6 Hz, 2H), 3.20 (q, J = 15.9 Hz, 2H), 2.92 (ddd, J = 17.2, 13.6, 5.4 Hz, 1H), 2.66-2.55 (m, 2H), 2.41 (td, J = 13.2, 4.5 Hz, 1H), 2.14-1.94 (m, 4H), 1.93-1.61 (m, 5H), 1.60-1.22 (m, 6H), 1.23-0.97 (m, 5H). | 16 | I-4; cyclohexanone |
| 212 | 3-(5-(((1R,2S)-2-((cyclopentyl-1-d)amino)cyclohexyl)methyl)-4-fluoro-1-oxoisoindolin-2-yl)piperidine-2,6-dione | 443.4 | $^1$H NMR (400 MHz, DMSO-d6) δ 11.01 (s, 1H), 8.54 (s, 1H), 8.08 (d, J = 12.6 Hz, 1H), 7.64-7.53 (m, 1H), 7.49 (t, J = 7.0 Hz, 1H), 5.12 (dd, J = 13.3, 5.1 Hz, 1H), 4.47 (ddd, J = 69.9, 17.3, 3.2 Hz, 2H), 3.20 (d, J = 13.5 Hz, 1H), 3.05 (s, 1H), 2.92 (dd, J = 18.0, 13.5, 5.4 Hz, 1H), 2.69-2.55 (m, 2H), 2.46-2.37 (m, 1H), 2.17-1.96 (m, 4H), 1.89 (s, 1H), 1.70 (q, J = 13.2, 10.7 Hz, 4H), 1.56 (s, 4H), 1.53-1.21 (m, 2H), 1.10 (s, 3H). | 16 | I-4; cyclopentanone |

TABLE 12-continued

| Example | Structure | ES/MS m/z: | 1H NMR | Procedure | Changes to Procedure: Different Reagents/ Starting Materials |
|---|---|---|---|---|---|
| 213 | 3-(4-fluoro-1-oxo-5-(((1R,2S)-2-((spiro[2.3]hexan-5-yl-5-d)amino)cyclohexyl)methyl)iso-indolin-2-yl)piperidine-2,6-dione | 455.3 | 1H NMR (400 MHz, DMSO-d6) δ 11.01 (s, 1H), 8.95 (dd, J = 12.3, 7.0 Hz, 1H), 8.70 (d, J = 12.0 Hz, 1H), 7.58 (d, J = 7.7 Hz, 1H), 7.49 (t, J = 7.0 Hz, 1H), 5.12 (dd, J = 13.3, 5.1 Hz, 1H), 4.48 (ddd, J = 69.6, 17.4, 2.4 Hz, 2H), 3.19 (dd, J = 13.4, 3.6 Hz, 1H), 3.03 (d, J = 9.2 Hz, 1H), 2.92 (ddd, J = 17.3, 13.7, 5.5 Hz, 1H), 2.62 (ddd, J = 13.8, 6.2, 3.5 Hz, 3H), 2.42 (td, J = 13.1, 4.5 Hz, 1H), 2.27-2.17 (m, 2H), 2.01 (dtt, J = 12.4, 5.1, 3.0 Hz, 2H), 1.91 (s, 1H), 1.67 (d, J = 10.7 Hz, 1H), 1.61-1.23 (m, 5H), 1.11 (p, J = 9.7 Hz, 2H), 0.57-0.40 (m, 4H). | 16 | I-4; spiro[2.3]hexan-5-one |
| 214 | 3-(5-(((1R,2S)-2-((3,3-dimethylcyclobutyl)amino)cyclohexyl)methyl)-1-oxoisoindolin-2-yl)piperidine-2,6-dione | 439.4 | 1H NMR (400 MHz, DMSO-d6) δ 10.99 (s, 1H), 8.63 (s, 1H), 8.42 (d, J = 12.3 Hz, 1H), 7.69 (d, J = 7.8 Hz, 1H), 7.45 (s, 1H), 7.36 (dd, J = 7.8, 1.4 Hz, 1H), 5.11 (dd, J = 13.3, 5.1 Hz, 1H), 4.51-4.26 (m, 2H), 3.21 (dd, J = 13.1, 4.0 Hz, 1H), 2.98-2.83 (m, 2H), 2.61 (d, J = 17.3 Hz, 1H), 2.41 (td, J = 13.3, 3.9 Hz, 2H), 2.11-1.93 (m, 7H), 1.86 (s, 1H), 1.65 (s, 1H), 1.62-1.44 (m, 3H), 1.43-1.20 (m, 1H), 1.14 (d, J = 8.6 Hz, 6H). | 16 | 3,3-dimethylcyclobutanone |

TABLE 12-continued

| Example | Structure | ES/MS m/z: | 1H NMR | Procedure | Changes to Procedure: Different Reagents/ Starting Materials |
|---|---|---|---|---|---|
| 215 | 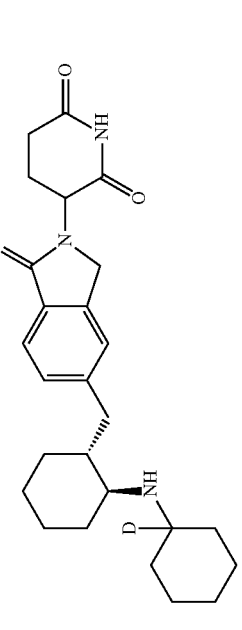<br>3-(5-(((1R,2S)-2-((cyclohexyl-1-d)amino)cyclohexyl)methyl)-1-oxoisoindolin-2-yl)piperidine-2,6-dione | 439.4 | ¹H NMR (400 MHz, DMSO-d6) δ 10.99 (s, 1H), 8.25 (s, 1H), 7.94 (d, J = 12.8 Hz, 1H), 7.70 (d, J = 7.8 Hz, 1H), 7.44 (s, 1H), 7.36 (d, J = 7.9 Hz, 1H), 5.11 (dd, J = 13.3, 5.1 Hz, 1H), 4.50-4.27 (m, 2H), 3.26 (d, J = 13.0 Hz, 1H), 3.08 (s, 1H), 2.92 (ddd, J = 17.9, 13.6, 5.4 Hz, 1H), 2.67-2.56 (m, 1H), 2.39 (qd, J = 13.7, 4.8 Hz, 2H), 2.04 (dd, J = 25.4, 7.1 Hz, 3H), 1.78 (d, J = 8.8 Hz, 2H), 1.75-1.67 (m, 2H), 1.64 (dt, J = 10.3, 2.3 Hz, 1H), 1.59-1.23 (m, 7H), 1.22-0.94 (m, 4H). | 16 | cyclohexanone |
| 216 | 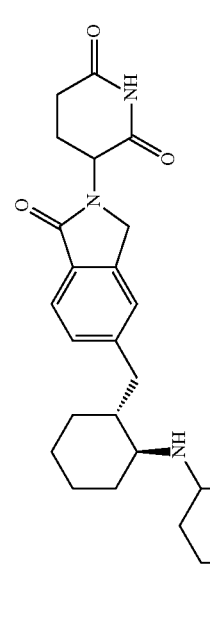<br>3-(5-(((1R,2S)-2-((4-(difluoromethyl)cyclohexyl)amino)cyclohexyl)methyl)-1-oxoisoindolin-2-yl)piperidine-2,6-dione (Isomer 1) | 488.2 | ¹H NMR (400 MHz, DMSO-d6) δ 10.99 (s, 1H), 8.34 (s, 1H), 8.06 (d, J = 11.2 Hz, 1H), 7.70 (d, J = 7.8 Hz, 1H), 7.46 (s, 1H), 7.37 (dd, J = 7.8, 1.3 Hz, 1H), 6.09 (td, J = 56.7, 5.3 Hz, 1H), 5.12 (dd, J = 13.3, 5.1 Hz, 1H), 4.45 (d, J = 17.3 Hz, 1H), 4.32 (d, J = 17.2 Hz, 1H), 3.49-3.14 (m, 2H), 3.14-2.79 (m, 2H), 2.77-2.58 (m, 1H), 2.40 (qd, J = 13.5, 12.4, 3.5 Hz, 2H), 2.19-1.18 (m, 13H), 1.18-0.86 (m, 3H)." | 17 | 4-(difluoromethyl)cyclohexanone |

TABLE 12-continued

| Example | Structure | ES/MS m/z: | 1H NMR | Procedure | Changes to Procedure: Different Reagents/ Starting Materials |
|---|---|---|---|---|---|
| 217 | 3-(5-(((1R,2S)-2-((4-(difluoromethyl)cyclohexyl)amino)cyclohexyl)methyl)-1-oxoisoindolin-2-yl)piperidine-2,6-dione (Isomer 2) | 488.2 | ¹H NMR (400 MHz, DMSO-d6) δ 10.99 (s, 1H), 8.39 (s, 1H), 8.06 (s, 1H), 7.70 (d, J = 7.8 Hz, 1H), 7.45 (s, 1H), 7.37 (dd, J = 7.8, 1.3 Hz, 1H), 6.20-5.68 (m, 2H), 5.12 (dd, J = 13.3, 5.1 Hz, 1H), 4.45 (d, J = 17.2 Hz, 1H), 4.33 (d, J = 17.2 Hz, 1H), 3.40-3.01 (m, 3H), 2.92 (ddd, J = 17.2, 13.5, 5.3 Hz, 1H), 2.70-2.53 (m, 1H), 2.46-2.25 (m, 2H), 2.25-1.91 (m, 4H), 1.91-1.62 (m, 5H), 1.62-1.14 (m, 8H), 1.14-0.85 (m, 3H). | 17 | 4-(difluoromethyl)cyclohexanone |
| 218 | 3-(5-(((1R,2S)-2-((1-cyclobutylethyl)amino)cyclohexyl)methyl)-1-oxoisoindolin-2-yl)piperidine-2,6-dione (Isomer 1) | 438.4 | ¹H NMR (400 MHz, DMSO-d6) δ 10.99 (s, 1H), 7.86 (d, J = 43.4 Hz, 2H), 7.70 (d, J = 7.8 Hz, 1H), 7.43 (s, 1H), 7.36 (d, J = 7.8 Hz, 1H), 4.56-4.22 (m, 2H), 3.42-3.20 (m, 2H), 3.08-2.79 (m, 2H), 2.67-2.53 (m, 2H), 2.47-2.29 (m, 2H), 2.20-1.94 (m, 5H), 1.94-1.65 (m, 5H), 1.61-1.22 (m, 4H), 1.16 (d, J = 6.4 Hz, 3H), 1.10-0.94 (m, 2H). | 17 | 1-cyclobutylethanone |

TABLE 12-continued

| Example | Structure | ES/MS m/z: | 1H NMR | Procedure | Changes to Procedure: Different Reagents/ Starting Materials |
|---|---|---|---|---|---|
| 219 | 3-(5-(((1R,2S)-2-((1-cyclobutylethyl)amino)cyclohexyl)methyl)-1-oxoisoindolin-2-yl)piperidine-2,6-dione (Isomer 2) | 438.4 | ¹H NMR (400 MHz, DMSO-d6) δ 10.99 (s, 1H), 8.37-8.18 (m, 1H), 7.95-7.75 (m, 1H), 7.70 (d, J = 7.7 Hz, 1H), 7.45 (s, 1H), 7.36 (d, J = 7.8 Hz, 1H), 5.11 (dd, J = 13.3, 5.1 Hz, 1H), 4.53-4.24 (m, 2H), 3.40 (q, J = 6.7, 5.7 Hz, 1H), 3.27 (dd, J = 13.2, 3.5 Hz, 1H), 3.03-2.82 (m, 2H), 2.66-2.53 (m, 2H), 2.47-2.32 (m, 2H), 2.17-1.78 (m, 7H), 1.78-1.61 (m, 2H), 1.61-1.25 (m, 3H), 1.21 (d, J = 6.5 Hz, 4H), 1.03 (t, J = 9.1 Hz, 2H). | 17 | 1-cyclobutylethanone |
| 220 | 3-(5-(((1R,2S)-2-((4,4-dimethylpentan-2-yl)amino)cyclohexyl)methyl)-1-oxoisoindolin-2-yl)piperidine-2,6-dione (Isomer 1) | 454.7 | ¹H NMR (400 MHz, DMSO-d6) δ 10.99 (s, 1H), 8.37-8.26 (m, 1H), 8.15-8.00 (m, 1H), 7.69 (d, J = 7.8 Hz, 1H), 7.45 (d, J = 4.1 Hz, 1H), 7.36 (dd, J = 7.8, 1.5 Hz, 1H), 5.11 (dd, J = 13.3, 5.1 Hz, 1H), 4.45 (dd, J = 17.4, 3.5 Hz, 1H), 4.31 (dd, J = 17.4, 4.0 Hz, 1H), 3.41-3.23 (m, 2H), 2.99-2.85 (m, 2H), 2.66-2.55 (m, 1H), 2.49-2.32 (m, 2H), 2.22-2.07 (m, 2H), 2.05-1.95 (m, 1H), 1.84 (s, 1H), 1.76-1.60 (m, 2H), 1.58-1.40 (m, 3H), 1.39-1.28 (m, 3H), 1.11-0.98 (m, 2H), 0.94 (d, J = 9.7 Hz, 9H). | 17 | 4,4-dimethylpentan-2-one |

TABLE 12-continued

| Example | Structure | ES/MS m/z: | 1H NMR | Procedure | Changes to Procedure: Different Reagents/ Starting Materials |
|---|---|---|---|---|---|
| 221 | 3-(5-(((1R,2S)-2-((4,4-dimethylpentan-2-yl)amino)cyclohexyl)methyl)-1-oxoisoindolin-2-yl)piperidine-2,6-dione (Isomer 1) | 454.7 | ¹H NMR (400 MHz, DMSO-d6) δ 10.99 (s, 1H), 8.31-8.17 (m, 1H), 8.02 (d, J = 36.0 Hz, 1H), 7.69 (d, J = 7.8 Hz, 1H), 7.45 (d, J = 3.7 Hz, 1H), 7.36 (d, J = 7.8 Hz, 1H), 5.11 (dd, J = 13.3, 5.1 Hz, 1H), 4.45 (dd, J = 17.3, 3.8 Hz, 1H), 4.32 (dd, J = 17.3, 4.0 Hz, 1H), 3.40-3.22 (m, 2H), 2.99-2.86 (m, 2H), 2.65-2.51 (m, 1H), 2.48-2.31 (m, 2H), 2.22-2.07 (m, 2H), 2.04-1.95 (m, 1H), 1.84 (s, 1H), 1.76-1.60 (m, 2H), 1.58-1.41 (m, 3H), 1.34 (dd, J = 19.9, 6.3 Hz, 3H), 1.11-0.98 (m, 2H), 0.94 (d, J = 10.1 Hz, 9H). | 17 | 4,4-dimethylpentan-2-one |
| 222 | 3-(5-(((2R,3S)-3-((2,2-dimethyltetrahydro-2H-pyran-4-yl)amino)tetrahydro-2H-pyran-2-yl)methyl)-4-fluoro-2-oxoisoindolin-2-yl)piperidine-2,6-dione (Isomer 1) | 488.4 | ¹H NMR (400 MHz, DMSO-d6) δ 11.01 (s, 1H), 8.76 (s, 1H), 8.25 (s, 1H), 7.61-7.48 (m, 2H), 5.12 (dd, J = 13.3, 5.1 Hz, 1H), 4.56 (dd, J = 17.4, 4.4 Hz, 1H), 4.38 (dd, J = 17.4, 2.5 Hz, 1H), 3.84-3.68 (m, 3H), 3.66-3.55 (m, 1H), 3.30-3.19 (m, 3H), 3.04 (dd, J = 14.4, 10.3 Hz, 1H), 2.92 (dd, J = 17.3, 13.6, 5.4 Hz, 1H), 2.58 (d, J = 35.2 Hz, 1H), 2.50-2.35 (m, 1H), 2.18 (s, 1H), 2.05-1.96 (m, 2H), 1.91 (d, J = 12.1 Hz, 1H), 1.74 (s, 1H), 1.71-1.55 (m, 1H), 1.38 (t, J = 12.3 Hz, 1H), 1.21 (d, J = 15.1 Hz, 8H). | 17 | I-41; 2,2-dimethyltetrahydropyran-4-one |

TABLE 12-continued

| Example | Structure | ES/MS m/z: | 1H NMR | Procedure | Changes to Procedure: Different Reagents/ Starting Materials |
|---|---|---|---|---|---|
| 223 | 3-(5-(((2R,3S)-3-((2,2-dimethyltetrahydro-2H-pyran-4-yl)amino)tetrahydro-2H-pyran-2-yl)methyl)-4-fluoro-2-oxoisoindolin-2-yl)piperidine-2,6-dione (Isomer 2) | 488.4 | 1H NMR (400 MHz, DMSO-d6) δ 11.01 (s, 1H), 8.61 (s, 1H), 8.26 (s, 1H), 7.62-7.48 (m, 2H), 5.11 (dd, J = 13.3, 5.1 Hz, 1H), 4.56 (dd, J = 17.4, 4.2 Hz, 1H), 4.38 (dd, J = 17.4, 2.9 Hz, 1H), 3.83-3.67 (m, 3H), 3.66-3.58 (m, 1H), 3.34-3.23 (m, 3H), 3.07-2.85 (m, 2H), 2.59 (d, J = 35.5 Hz, 2H), 2.43 (tt, J = 13.3, 6.6 Hz, 1H), 2.30 (dd, J = 11.3, 6.2 Hz, 1H), 2.00 (ddd, J = 18.9, 8.9, 6.2 Hz, 2H), 1.88 (dd, J = 11.8, 3.4 Hz, 1H), 1.76-1.65 (m, 1H), 1.64-1.54 (m, 1H), 1.53-1.40 (m, 2H), 1.18 (s, 6H). | 17 | I-41; 2,2-dimethyltetrahydropyran-4-one |
| 224 | 3-(5-(((1R,2S)-2-((1-(1-fluorocyclopropyl)ethyl)amino)cyclohexyl)methyl)-1-oxoisoindolin-2-yl)piperidine-2,6-dione (Isomer 1) | 442.3 | 1H NMR (400 MHz, DMSO-d6) δ 10.99 (s, 1H), 8.66 (s, 1H), 8.52 (s, 1H), 7.70 (d, J = 7.8 Hz, 1H), 7.46 (s, 1H), 7.42-7.34 (m, 1H), 5.11 (dd, J = 13.3, 5.1 Hz, 1H), 4.45 (dd, J = 17.3, 2.9 Hz, 1H), 4.32 (dd, J = 17.5, 3.0 Hz, 1H), 3.49 (dd, J = 25.7, 5.4 Hz, 1H), 3.32 (dd, J = 13.2, 3.4 Hz, 1H), 3.17 (s, 1H), 2.92 (ddd, J = 17.2, 13.6, 5.4 Hz, 1H), 2.65-2.52 (m, 1H), 2.49-2.31 (m, 2H), 2.09 (dd, J = 8.8, 4.4 Hz, 1H), 2.04-1.89 (m, 1H), 1.71 (s, 1H), 1.57-1.42 (m, 6H), 1.30 (tt, J = 11.3, 6.8 Hz, 2H), 1.27-1.02 (m, 2H), 1.04 (s, 3H), 1.05-0.87 (m, 1H). | 17 | 1-(1-fluorocyclopropyl)ethanone |

TABLE 12-continued

| Example | Structure | ES/MS m/z: | 1H NMR | Procedure | Changes to Procedure: Different Reagents/ Starting Materials |
|---|---|---|---|---|---|
| 225 | 3-(5-(((1R,2S)-2-((1-(1-fluorocyclopropyl)ethyl)amino)cyclohexyl)methyl)-1-oxoisoindolin-2-yl)piperidine-2,6-dione (Isomer 2) | 442.3 | 1H NMR (400 MHz, DMSO-d6) δ 10.99 (s, 1H), 8.66 (s, 1H), 8.52 (s, 1H), 7.70 (d, J = 7.8 Hz, 1H), 7.46 (s, 1H), 7.42-7.34 (m, 1H), 5.11 (dd, J = 13.3, 5.1 Hz, 1H), 4.45 (dd, J = 17.3, 2.9 Hz, 1H), 4.32 (dd, J = 17.5, 3.0 Hz, 1H), 3.32 (dd, J = 13.2, 3.4 Hz, 1H), 3.17 (s, 1H), 2.92 (ddd, J = 17.2, 13.6, 5.4 Hz, 1H), 2.65-2.52 (m, 1H), 2.49-2.31 (m, 2H), 2.09 (dd, J = 8.8, 4.4 Hz, 1H), 2.04-1.89 (m, 2H), 1.71 (s, 1H), 1.57-1.42 (m, 6H), 1.30 (tt, J = 11.3, 6.8 Hz, 2H), 1.27-1.02 (m, 1H), 1.04 (s, 3H), 1.05-0.87 (m, 1H). | 17 | 1-(1-fluorocyclopropyl)ethanone |
| 226 | 33-(5-(((1R,2S)-2-((3-fluoro-3-methylbutan-2-yl)amino)cyclohexyl)methyl)-1-oxoisoindolin-2-yl)piperidine-2,6-dione (Isomer 1) | 444.3 | 1H NMR (400 MHz, DMSO-d6) δ 10.99 (s, 1H), 8.00 (s, 2H), 7.70 (d, J = 7.7 Hz, 1H), 7.44 (s, 1H), 7.36 (d, J = 7.8 Hz, 1H), 5.11 (dd, J = 13.3, 5.1 Hz, 1H), 4.51-4.41 (m, 1H), 4.32 (dd, J = 17.4, 3.5 Hz, 1H), 3.47 (dd, J = 13.3, 3.1 Hz, 1H), 3.10-3.03 (m, 1H), 2.92 (ddd, J = 17.2, 13.6, 5.4 Hz, 1H), 2.65-2.52 (m, 1H), 2.47-2.30 (m, 2H), 2.21-2.11 (m, 1H), 2.06-1.94 (m, 3H), 1.75 (d, J = 13.4 Hz, 1H), 1.48 (dt, J = 22.0, 9.3 Hz, 9H), 1.31 (d, J = 6.7 Hz, 3H), 1.08-0.96 (m, 2H). | 17 | 3-fluoro-3-methyl-butan-2-one |

TABLE 12-continued

| Example | Structure | ES/MS m/z: | 1H NMR | Procedure | Changes to Procedure: Different Reagents/ Starting Materials |
|---|---|---|---|---|---|
| 227 | 33-(5-(((1R,2S)-2-((3-fluoro-3-methylbutan-2-yl)amino)cyclohexyl)methyl)-1-oxoisoindolin-2-yl)piperidine-2,6-dione (Isomer 1) | 444.3 | ¹H NMR (400 MHz, DMSO-d6) δ 10.99 (s, 1H), 8.39 (s, 1H), 8.02 (d, J = 13.5 Hz, 1H), 7.70 (d, J = 7.8 Hz, 1H), 7.45 (s, 1H), 7.37 (d, J = 7.7 Hz, 1H), 5.11 (dd, J = 13.3, 5.1 Hz, 1H), 4.45 (d, J = 17.2 Hz, 1H), 4.32 (d, J = 17.3, Hz, 1H), 3.67-3.58 (m, 1H), 3.25 (d, J = 12.4 Hz, 1H), 3.11 (s, 1H), 2.92 (ddd, J = 17.8, 13.6, 5.4 Hz, 1H), 2.58 (d, J = 34.5 Hz, 2H), 2.48-2.34 (m, 2H), 2.13-1.94 (m, 3H), 1.75 (d, J = 12.9 Hz, 1H), 1.53 (s, 2H), 1.45 (d, J = 22.3 Hz, 6H), 1.31 (d, J = 6.7 Hz, 3H), 1.01 (q, J = 10.9 Hz, 2H). | 17 | 3-fluoro-3-methyl-butan-2-one |
| 228 | 3-(1-oxo-5-(((1R,2S)-2-((spiro[2.5]octan-4-yl)amino)cyclohexyl)methyl)isoindolin-2-yl)piperidine-2,6-dione (Isomer 1) | 464.4 | ¹H NMR (400 MHz, DMSO-d6) δ 10.99 (s, 1H), 8.06 (d, J = 11.9 Hz, 1H), 7.71 (d, J = 7.7 Hz, 1H), 7.49-7.44 (m, 2H), 7.39 (dd, J = 7.8, 1.3 Hz, 1H), 5.11 (dd, J = 13.2, 5.1 Hz, 1H), 4.46 (d, J = 17.3 Hz, 1H), 4.32 (d, J = 17.3 Hz, 1H), 3.34 (dd, J = 12.9, 3.4 Hz, 1H), 2.99-2.85 (m, 3H), 2.78 (s, 1H), 2.65-2.52 (m, 1H), 2.47-2.31 (m, 2H), 2.12-1.95 (m, 3H), 1.89 (d, J = 10.4 Hz, 1H), 1.79-1.33 (m, 8H), 1.24 (d, J = 12.0 Hz, 1H), 1.02 (q, J = 10.8 Hz, 2H), 0.77 (d, J = 13.8 Hz, 1H), 0.67 (dd, J = 9.8, 4.4 Hz, 1H), 0.58-0.47 (m, 2H), 0.44-0.35 (m, 1H). | 17 | spiro[2.5]octan-8-one |

TABLE 12-continued

| Example | Structure | ES/MS m/z: | 1H NMR | Procedure | Changes to Procedure: Different Reagents/ Starting Materials |
|---|---|---|---|---|---|
| 229 | 3-(1-oxo-5-(((1R,2S)-2-(spiro[2.5]octan-4-yl)amino)cyclohexyl)methyl)isoindolin-2-yl)piperidine-2,6-dione (Isomer 2) | 464.4 | 1H NMR (400 MHz, DMSO-d6) δ 10.99 (s, 1H), 7.96 (s, 1H), 7.88 (d, J = 13.7 Hz, 1H), 7.70 (d, J = 7.8 Hz, 1H), 7.49 (s, 1H), 7.40 (dd, J = 7.8, 1.3 Hz, 1H), 5.11 (dd, J = 13.3, 5.1 Hz, 1H), 4.45 (d, J = 17.2 Hz, 1H), 4.32 (d, J = 17.2 Hz, 1H), 3.24-3.15 (m, 1H), 3.01 (s, 2H), 2.92 (ddd, J = 17.2, 13.6, 5.4 Hz, 1H), 2.81 (s, 1H), 2.58 (d, J = 34.8 Hz, 1H), 2.48-2.31 (m, 2H), 2.06-1.93 (m, 5H), 1.71 (dt, J = 25.1, 12.7 Hz, 1H), 1.64-1.38 (m, 2H), 1.38-1.27 (m, 1H), 1.03 (q, J = 11.0 Hz, 2H), 0.76 (d, J = 13.8 Hz, 1H), 0.69 (dd, J = 9.4, 4.2 Hz, 1H), 0.51 (td, J = 10.6, 9.9, 4.8 Hz, 2H), 0.38 (dd, J = 9.5, 4.2 Hz, 1H). | 17 | spiro[2.5]octan-8-one |
| 230 | 3-(5-(((1R,2S)-2-((1-cyclopropyl)propan-2-yl)amino)cyclohexyl)methyl)-1-oxoisoindolin-2-yl)piperidine-2,6-dione (Isomer 1) | 438.4 | 1H NMR (400 MHz, DMSO-d6) δ 10.99 (s, 1H), 8.14 (s, 1H), 7.97 (s, 1H), 7.70 (d, J = 7.8 Hz, 1H), 7.44 (s, 1H), 7.36 (dd, J = 7.8, 1.3 Hz, 1H), 5.11 (dd, J = 13.3, 5.1 Hz, 1H), 4.45 (d, J = 17.2 Hz, 1H), 4.37-4.27 (m, 1H), 3.38 (s, 1H), 3.26 (dd, J = 13.2, 3.6 Hz, 1H), 3.06 (s, 1H), 2.92 (ddd, J = 17.2, 13.6, 5.4 Hz, 1H), 2.65-2.52 (m, 1H), 2.39 (qd, J = 13.6, 4.2 Hz, 2H), 2.10 (d, J = 11.9 Hz, 1H), 2.00 (dp, J = 10.6, 3.3 Hz, 1H), 1.83 (s, 1H), 1.71 (d, J = 12.1 Hz, 1H), 1.65-1.43 (m, 3H), 1.42-1.25 (m, 4H), 1.06 (q, J = 10.8, 9.2 Hz, 2H), 0.84-0.70 (m, 1H), 0.60-0.41 (m, 2H), 0.19-0.07 (m, 2H). | 17 | 1-cyclopropylpropan-2-one |

TABLE 12-continued

| Example | Structure | ES/MS m/z: | 1H NMR | Procedure | Changes to Procedure: Different Reagents/ Starting Materials |
|---|---|---|---|---|---|
| 231 | 3-(5-(((1R,2S)-2-((1-cyclopropylpropan-2-yl)amino)cyclohexyl)methyl)-1-oxoisoindolin-2-yl)piperidine-2,6-dione (Isomer 2) | 438.4 | $^1$H NMR (400 MHz, DMSO-d6) δ 10.99 (s, 1H), 8.26 (s, 1H), 7.92 (d, J = 9.0 Hz, 1H), 7.70 (d, J = 7.7 Hz, 1H), 7.44 (s, 1H), 7.36 (d, J = 7.8 Hz, 1H), 5.11 (dd, J = 13.3, 5.1 Hz, 1H), 4.45 (d, J = 17.3 Hz, 1H), 4.32 (d, J = 17.3, Hz, 1H), 3.42 (s, 2H), 3.29-3.21 (m, 1H), 3.06 (s, 1H), 2.92 (ddd, J = 17.8, 13.5, 5.4 Hz, 1H), 2.58 (d, J = 34.7 Hz, 1H), 2.46-2.35 (m, 2H), 2.10-1.96 (m, 1H), 1.84-1.79 (m, 1H), 1.71 (d, J = 11.3 Hz, 1H), 1.65-1.57 (m, 1H), 1.57-1.24 (m, 6H), 1.06-1.01 (m, 2H), 0.79-0.73 (m, 1H), 0.48 (tdd, J = 13.0, 6.6, 4.1 Hz, 2H), 0.21-0.04 (m, 2H). | 17 | 1-cyclopropylpropan-2-one |
| 232 | 3-(5-(((1R,2S)-2-((1-cyclopropylpropyl)amino)cyclohexyl)methyl)-1-oxoisoindolin-2-yl)piperidine-2,6-dione (Isomer 1) | 438.4 | $^1$H NMR (400 MHz, DMSO-d6) δ 10.99 (s, 1H), 8.12 (s, 1H), 8.01 (s, 1H), 7.70 (d, J = 7.8 Hz, 1H), 7.46 (s, 1H), 7.38 (d, J = 7.6 Hz, 1H), 5.11 (dd, J = 13.3, 5.1 Hz, 1H), 4.45 (d, J = 17.2 Hz, 1H), 4.32 (d, J = 17.2 Hz, 1H), 3.30 (dd, J = 13.4, 3.6 Hz, 1H), 3.13 (s, 1H), 2.92 (ddd, J = 17.3, 13.6, 5.4 Hz, 1H), 2.65-2.52 (m, 3H), 2.50-2.31 (m, 2H), 2.14-2.06 (m, 1H), 2.04-1.96 (m, 1H), 1.90-1.67 (m, 2H), 1.61-1.18 (m, 4H), 1.04 (t, J = 7.4 Hz, 4H), 1.00-0.87 (m, 1H), 0.74-0.59 (m, 2H), 0.44 (ddd, J = 19.6, 9.5, 4.7 Hz, 2H). | 17 | 1-cyclopropylpropan-1-one |

TABLE 12-continued

| Example | Structure | ES/MS m/z: | 1H NMR | Procedure | Changes to Procedure: Different Reagents/ Starting Materials |
|---|---|---|---|---|---|
| 233 | 3-(5-(((1R,2S)-2-((1-cyclopropylpropyl)amino)cyclohexyl)methyl)-1-oxoisoindolin-2-yl)piperidine-2,6-dione (Isomer 2) | 438.4 | ¹H NMR (400 MHz, DMSO-d6) δ 10.99 (s, 1H), 8.12 (s, 1H), 7.97 (s, 1H), 7.71 (d, J = 7.7 Hz, 1H), 7.44 (s, 1H), 7.40-7.33 (m, 1H), 5.11 (dd, J = 13.3, 5.1 Hz, 1H), 4.45 (d, J = 17.2 Hz, 1H), 4.33 (d, J = 17.3 Hz, 1H), 3.34 (d, J = 11.7 Hz, 1H), 3.05 (s, 1H), 2.92 (ddd, J = 17.8, 13.5, 5.4 Hz, 1H), 2.58 (d, J = 35.3 Hz, 2H), 2.47-2.31 (m, 2H), 2.11-1.96 (m, 1H), 1.94-1.81 (m, 3H), 1.80-1.64 (m, 3H), 1.56-1.46 (m, 2H), 1.34 (dq, J = 25.4, 12.3 Hz, 2H), 1.08-0.99 (m, 4H), 0.79-0.67 (m, 1H), 0.67-0.56 (m, 1H), 0.43 (ddt, J = 18.9, 9.5, 4.7 Hz, 2H). | 17 | 1-cyclopropylpropan-1-one |
| 234 | 3-(5-(((1R,2S)-2-((1-methylcyclopropyl)ethyl)amino)cyclohexyl)methyl)-1-oxoisoindolin-2-yl)piperidine-2,6-dione (Isomer 1) | 438.4 | ¹H NMR (400 MHz, DMSO-d6) δ 10.99 (s, 1H), 8.47 (d, J = 28.9 Hz, 1H), 7.86-7.62 (m, 2H), 7.46 (s, 1H), 7.38 (d, J = 7.8 Hz, 1H), 5.11 (dd, J = 13.3, 5.1 Hz, 1H), 4.45 (d, J = 17.2 Hz, 1H), 4.32 (d, J = 17.1 Hz, 1H), 3.38 (d, J = 12.9 Hz, 1H), 3.12 (s, 1H), 2.90 (ddd, J = 29.1, 16.5, 6.2 Hz, 2H), 2.58 (d, J = 34.7 Hz, 2H), 2.48-2.32 (m, 1H), 2.13-1.96 (m, 2H), 1.90 (s, 1H), 1.74-1.69 (m, 1H), 1.62-1.41 (m, 2H), 1.40-1.27 (m, 4H), 1.15-1.07 (m, 2H), 1.03-0.96 (m, 3H), 0.62 (q, J = 4.9 Hz, 1H), 0.51 (dd, J = 9.3, 4.4 Hz, 1H), 0.48-0.35 (m, 1H), 0.38-0.32 (m, 1H). | 17 | 1-(1-methylcyclopropyl)ethanone |

TABLE 12-continued

| Example | Structure | ES/MS m/z: | 1H NMR | Procedure | Changes to Procedure: Different Reagents/ Starting Materials |
|---|---|---|---|---|---|
| 235 | 3-(5-(((1R,2S)-2-((1-(1-methylcyclopropyl)ethyl)amino)cyclohexyl)methyl)-1-oxoisoindolin-2-yl)piperidine-2,6-dione (Isomer 2) | 438.4 | 1H NMR (400 MHz, DMSO-d6) δ 10.99 (s, 1H), 8.06 (s, 1H), 7.88 (s, 1H), 7.71 (d, J = 7.8 Hz, 1H), 7.45 (s, 1H), 7.42-7.34 (m, 1H), 5.11 (dd, J = 13.3, 5.1 Hz, 1H), 4.45 (d, J = 17.2 Hz, 1H), 4.37-4.27 (m, 1H), 3.33 (dd, J = 13.5, 3.5 Hz, 1H), 3.04 (s, 1H), 2.92 (ddd, J = 17.3, 13.6, 5.4 Hz, 1H), 2.77-2.68 (m, 1H), 2.65-2.52 (m, 1H), 2.49-2.29 (m, 2H), 2.11-1.96 (m, 2H), 1.92 (d, J = 9.4 Hz, 1H), 1.70 (d, J = 12.3 Hz, 1H), 1.57-1.42 (m, 3H), 1.38-1.26 (m, 4H), 1.13-0.96 (m, 5H), 0.65-0.48 (m, 2H), 0.44-0.35 (m, 1H). | 17 | 1-(1-methylcyclopropyl)ethanone |
| 236 | 3-(5-(((1R,2S)-2-(((3S)-3-methylcyclohexyl)amino)cyclohexyl)methyl)-1-oxoisoindolin-2-yl)piperidine-2,6-dione (Isomer 1) | 452.4 | 1H NMR (400 MHz, DMSO-d6) δ 10.99 (s, 1H), 8.22 (d, J = 9.2 Hz, 1H), 7.90 (s, 1H), 7.69 (d, J = 7.8 Hz, 1H), 7.45 (s, 1H), 7.37 (dd, J = 7.8, 1.3 Hz, 1H), 5.11 (dd, J = 13.3, 5.1 Hz, 1H), 4.45 (d, J = 17.3 Hz, 1H), 4.32 (d, J = 17.2 Hz, 1H), 3.39 (s, 1H), 3.26 (dd, J = 13.2, 3.7 Hz, 1H), 3.04 (s, 1H), 2.92 (ddd, J = 17.3, 13.6, 5.4 Hz, 1H), 2.65-2.52 (m, 1H), 2.47-2.31 (m, 2H), 2.14-1.91 (m, 4H), 1.88-1.81 (m, 1H), 1.77-1.6 (m, 3H), 1.63-1.38 (m, 6H), 1.37-1.25 (m, 2H), 1.10-1.00 (m, 2H), 0.97 (d, J = 7.1 Hz, 3H). | 17 | (S)-3-methylcyclohexanone |

TABLE 12-continued

| Example | Structure | ES/MS m/z: | 1H NMR | Procedure | Changes to Procedure: Different Reagents/ Starting Materials |
|---|---|---|---|---|---|
| 237 | 3-(5-(((1R,2S)-2-(((3S)-3-methylcyclohexyl)amino)cyclohexyl)methyl)-1-oxoisoindolin-2-yl)piperidine-2,6-dione (Isomer 2) | 452.4 | ¹H NMR (400 MHz, DMSO-d6) δ 10.99 (s, 1H), 8.27 (s, 1H), 7.70 (d, J = 7.7 Hz, 1H), 7.44 (s, 1H), 7.40-7.32 (m, 1H), 5.11 (dd, J = 13.3, 5.1 Hz, 1H), 4.45 (d, J = 17.2 Hz, 1H), 4.37-4.27 (m, 1H), 3.26 (dd, J = 13.3, 3.6 Hz, 2H), 3.09 (s, 1H), 2.92 (ddd, J = 17.2, 13.6, 5.4 Hz, 1H), 2.58 (d, J = 34.9 Hz, 1H), 2.47-2.31 (m, 2H), 2.12-1.94 (m, 4H), 1.83-1.75 (m, 2H), 1.67 (dd, J = 26.6, 12.2 Hz, 2H), 1.56-1.46 (m, 4H), 1.43-1.28 (m, 4H), 1.08-0.94 (m, 4H), 0.93 (d, J = 6.5 Hz, 3H), 0.82 (q, J = 12.8, 10.9 Hz, 1H). | 17 | (S)-3-methylcyclohexanone |
| 311 | 3-(5-(((1R,2S)-2-((1-(1-(difluoromethyl)cyclopropyl)ethyl)amino)cyclohexyl)methyl)-1-oxoisoindolin-2-yl)piperidine-2,6-dione (Isomer 1) | 474.4 | ¹H NMR (400 MHz, DMSO-d6) δ 10.99 (s, 1H), 8.34 (s, 1H), 7.95 (s, 1H), 7.71 (d, J = 7.8 Hz, 1H), 7.45 (s, 1H), 7.41-7.34 (m, 1H), 6.21 (t, J = 55.9 Hz, 1H), 5.11 (dd, J = 13.3, 5.1 Hz, 1H), 4.45 (d, J = 172 Hz, 1H), 4.37-4.27 (m, 1H), 3.37-3.24 (m, 2H), 3.08 (s, 1H), 2.92 (ddd, J = 17.2, 13.6, 5.4 Hz, 1H), 2.59 (d, J = 35.3 Hz, 1H), 2.48-2.31 (m, 2H), 2.16-2.06 (m, 1H), 2.05-1.86 (m, 2H), 1.72 (d, J = 12.6 Hz, 1H), 1.61-1.20 (m, 7H), 1.16-0.90 (m, 4H), 0.90-0.83 (m, 1H). | 17 | 1-[1-(difluoromethyl)cyclopropyl]ethanone |

TABLE 12-continued

| Example | Structure | ES/MS m/z: | 1H NMR | Procedure | Changes to Procedure: Different Reagents/ Starting Materials |
|---|---|---|---|---|---|
| 312 | 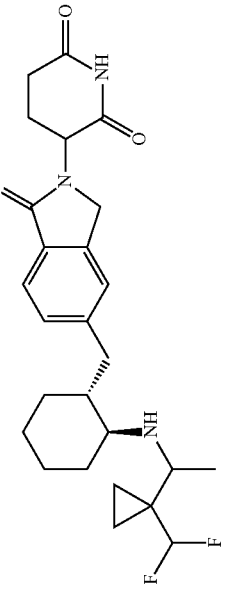<br>3-(5-(((1R,2S)-2-((1-(1-(difluoromethyl)cyclopropyl)ethyl)amino)cyclohexyl)methyl)-1-oxoisoindolin-2-1)piperidine-2,6-dione (Isomer 2) | 474.4 | $^1$H NMR (400 MHz, DMSO-d6) δ 10.99 (s, 1H), 8.71 (s, 1H), 7.81 (s, 1H), 7.71 (d, J = 7.8 Hz, 1H), 7.44 (s, 1H), 7.40-7.33 (m, 1H), 6.05 (t, J = 55.4 Hz, 1H), 5.11 (dd, J = 13.3, 5.1 Hz, 1H), 4.45 (dd, J = 17.3, 4.7 Hz, 1H), 4.32 (dd, J = 17.3, 5.2 Hz, 1H), 3.43-3.35 (m, 2H), 3.17 (s, 1H), 2.92 (ddd, J = 17.1, 13.6, 5.4 Hz, 1H), 2.58 (d, J = 35.2 Hz, 1H), 2.39 (qd, J = 13.4, 4.1 Hz, 2H), 2.15-2.07 (m, 1H), 2.04-1.96 (m, 1H), 1.86 (s, 1H), 1.74 (d, J = 12.8 Hz, 1H), 1.57-1.35 (m, 3H), 1.31 (d, J = 11.1 Hz, 1H), 1.11-1.01 (m, 4H), 0.94-0.83 (m, 4H). | 17 | 1-[1-(difluoromethyl)cyclopropyl]ethanone |

Procedure 22, Examples 247 and 248

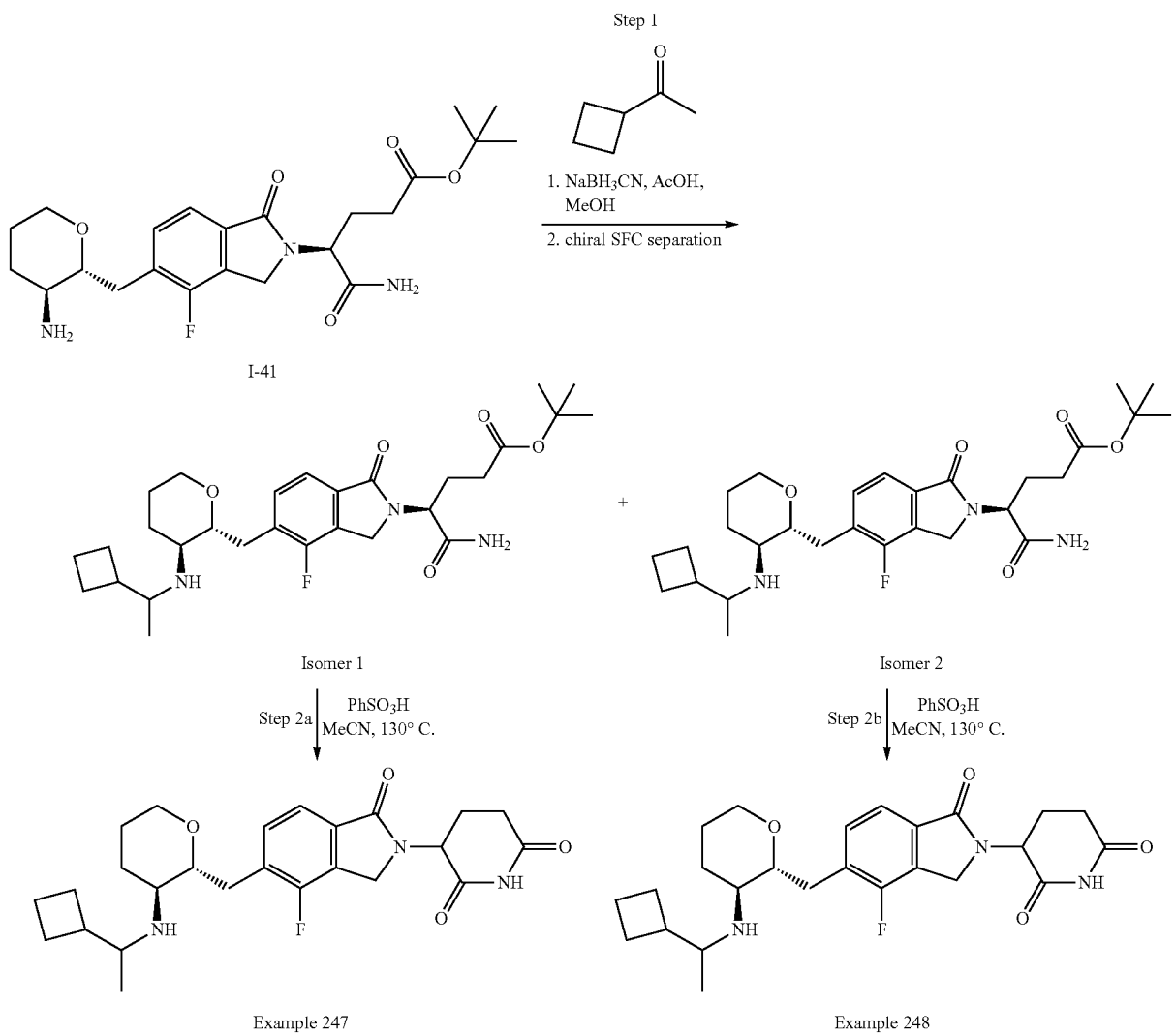

Step 1: Preparation of tert-butyl (4S)-5-amino-4-(5-(((2R,3S)-3-((1-cyclobutylethyl)amino)tetrahydro-2H-pyran-2-yl)methyl)-4-fluoro-1-oxoisoindolin-2-yl)-5-oxopentanoate (Isomer 1) and tert-butyl (4S)-5-amino-4-(5-(((2R,3S)-3-((1-cyclobutylethyl)amino)tetrahydro-2H-pyran-2-yl)methyl)-4-fluoro-1-oxoisoindolin-2-yl)-5-oxopentanoate (Isomer 2)

I-41 (182 mg, 0.405 mmol) was dissolved in MeOH (4 mL), then 1-cyclobutylethan-1-one (199 mg, 2.02 mmol) was added, followed by acetic acid (23 µL, 0.405 mmol). The mixture was stirred at r.t., and sodium cyanoborohydride (76.3 mg, 1.21 mmol) was added in a single portion. The reaction mixture was stirred for 3 h, then an additional quantity of cyclobutylethan-1-one (199 mg, 2.02 mmol) was added, and stirring continued overnight. The reaction mixture was then adsorbed onto silica gel under vacuum and purified by normal phase column chromatography (eluent: CH₂Cl₂/MeOH). Chiral separation was carried out by SFC using a Phenomenex Lux Cellulose-2 column (250×21.2 mm, 5 micron) at 40° C. using 30% MeOH (containing 0.1% diethylamine as a modifier) as the mobile phase to afford tert-butyl (4S)-5-amino-4-(5-(((2R,3S)-3-((1-cyclobutylethyl)amino)tetrahydro-2H-pyran-2-yl)methyl)-4-fluoro-1-oxoisoindolin-2-yl)-5-oxopentanoate (Isomer 1) and tert-butyl (4S)-5-amino-4-(5-(((2R,3S)-3-((1-cyclobutylethyl)amino)tetrahydro-2H-pyran-2-yl)methyl)-4-fluoro-1-oxoisoindolin-2-yl)-5-oxopentanoate (Isomer 2). ES/MS: 532.4 (M+H⁺, Isomer 1) and 532.5 (M+H⁺, Isomer 2).

Step 2a: Preparation of 3-(5-(((2R,3S)-3-((1-cyclobutylethyl)amino)tetrahydro-2H-pyran-2-yl)methyl)-4-fluoro-1-oxoisoindolin-2-yl)piperidine-2,6-dione (Example 247)

tert-butyl (4S)-5-amino-4-(5-(((2R,3S)-3-((1-cyclobutylethyl)amino)tetrahydro-2H-pyran-2-yl)methyl)-4-fluoro-1-oxoisoindolin-2-yl)-5-oxopentanoate (Isomer 1, 42 mg, 0.079 mmol) was treated with benzenesulfonic acid (0.3M solution in MeCN, 0.79 mL, 0.24 mmol) and the mixture was stirred at 130° C. under microwave irradiation for 1 h. The reaction mixture was then cooled to r.t., then concentrated under vacuum and the residue purified directly by RP-HPLC (eluent: MeCN/water gradient with 0.1% TFA) to yield the product. ES/MS m/z: 458.3 (M+H⁺). ¹H NMR (400 MHz, DMSO-d6) δ 11.01 (s, 1H), 8.15-8.04 (m, 1H), 8.03-7.93 (m, 1H), 7.58 (d, J=7.7 Hz, 1H), 7.53-7.47 (m, 1H), 5.11 (dd, J=13.3, 5.1 Hz, 1H), 4.59-4.51 (m, 1H), 4.42-4.34 (m, 1H), 3.84-3.73 (m, 2H), 3.43-3.12 (m, 4H), 2.99-2.86 (m, 2H), 2.65-2.37 (m, 3H), 2.29-2.19 (m, 1H), 2.11-1.94 (m, 3H), 1.91-1.53 (m, 7H), 1.16 (d, J=6.5 Hz, 3H).

Step 2b: Preparation of 3-(5-(((2R,3S)-3-((1-cyclobutylethyl)amino)tetrahydro-2H-pyran-2-yl)methyl)-4-fluoro-1-oxoisoindolin-2-yl)piperidine-2,6-dione (Example 248)

tert-butyl (4S)-5-amino-4-(5-(((2R,3S)-3-((1-cyclobutylethyl)amino)tetrahydro-2H-pyran-2-yl)methyl)-4-fluoro-1-oxoisoindolin-2-yl)-5-oxopentanoate (Isomer 2, 22 mg, 0.041 mmol) was treated with benzenesulfonic acid (0.3M solution in MeCN, 0.41 mL, 0.12 mmol) and the mixture was stirred at 130° C. under microwave irradiation for 1 h. The reaction mixture was then cooled to r.t., then concentrated under vacuum and the residue purified directly by RP-HPLC (eluent: MeCN/water gradient with 0.1% TFA) to yield the product. ES/MS m/z: 458.3 (M+H⁺). ¹H NMR (400 MHz, DMSO-d6) δ 11.01 (s, 1H), 8.55-8.45 (m, 1H), 8.05-7.95 (m, 1H), 7.58 (d, J=7.7 Hz, 1H), 7.55-7.50 (m, 1H), 5.11 (dd, J=13.3, 5.1 Hz, 1H), 4.60-4.52 (m, 1H), 4.42-4.33 (m, 1H), 3.81-3.70 (m, 2H), 3.48-3.40 (m, 1H), 3.30-3.20 (m, 2H), 3.14-2.86 (m, 3H), 2.65-2.37 (m, 3H), 2.30-2.21 (m, 1H), 2.13-1.51 (m, 10H), 1.20 (d, J=6.5 Hz, 3H).

The following Examples were made using the general route described in Procedure 22 and are shown below in Table 13. To prepare the below Examples, different reagents/starting materials were used than some of those described in Procedure 22 and are noted in the last column of Table 13—"Changes to Procedure 22: Different Reagents/Starting Materials". A person of ordinary skill in the art will readily recognize which reagents/starting materials of Procedure 22 were replaced with the different reagents/starting materials noted below.

TABLE 13

| Example | Structure | ES/MS m/z | ¹H-NMR | Changes to Procedure 22: Different Reagents/Starting Materials |
|---|---|---|---|---|
| 249 | 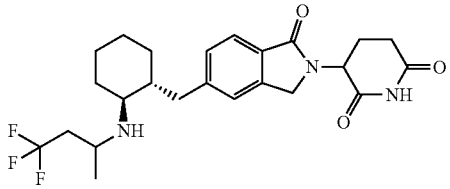 [SMILES: CC(CC(F)(F)F)N[C@H]1CCCC[C@@H]1Cc1ccc2c(c1)CN(C1CCC(=O)NC1=O)C2=O]<br>3-(1-oxo-5-(((1R,2S)-2-((4,4,4-trifluorobutan-2-yl)amino)cyclohexyl)methyl)isoindolin-2-yl)piperidine-2,6-dione (Isomer 1) | 466.3 | ¹H NMR (400 MHz, DMSO-d6) δ 10.99 (s, 1H), 8.86-8.74 (m, 1H), 8.45-8.34 (m, 1H), 7.69 (d, J = 7.8 Hz, 1H), 7.44 (s, 1H), 7.36 (d, J = 7.9 Hz, 1H), 5.11 (dd, J = 13.3, 5.1 Hz, 1H), 4.45 (d, J = 17.1 Hz, 1H), 4.32 (d, J = 17.3 Hz, 1H), 3.80-3.70 (m, 1H), 3.34-3.15 (m, 2H), 3.11-2.86 (m, 2H), 2.71-2.55 (m, 2H), 2.45-2.32 (m, 2H), 2.11-1.80 (m, 3H), 1.76-1.68 (m, 1H), 1.59-1.23 (m, 7H), 1.10-0.94 (m, 2H). | Step 1: I-13, 4,4,4-trifluorobutan-2-one Chiral SFC conditions: AD-H 5 μm-21 × 250 mm, co-solvent: EtOH—NH₃ (20%) [peak 1] |
| 250 | 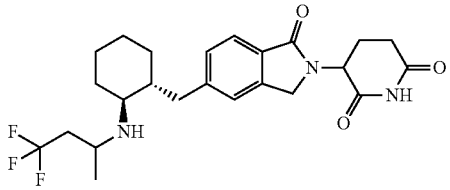 [SMILES: CC(CC(F)(F)F)N[C@H]1CCCC[C@@H]1Cc1ccc2c(c1)CN(C1CCC(=O)NC1=O)C2=O]<br>3-(1-oxo-5-(((1R,2S)-2-((4,4,4-trifluorobutan-2-yl)amino)cyclohexyl)methyl)isoindolin-2-yl)piperidine-2,6-dione (Isomer 2) | 466.3 | ¹H NMR (400 MHz, DMSO-d6) δ 10.99 (s, 1H), 8.80-8.69 (m, 1H), 8.51-8.41 (m, 1H), 7.69 (d, J = 7.8 Hz, 1H), 7.44 (s, 1H), 7.36 (d, J = 7.8 Hz, 1H), 5.11 (dd, J = 13.3, 5.1 Hz, 1H), 4.49-4.40 (m, 1H), 4.31 (dd, J = 17.4, 3.4 Hz, 1H), 3.75-3.63 (m, 1H), 3.28 (dd, J = 13.1, 3.4 Hz, 1H), 3.19-3.09 (m, 1H), 2.98-2.82 (m, 2H), 2.80-2.65 (m, 1H), 2.65-2.55 (m, 1H), 2.46-2.31 (m, 2H), 2.18-2.09 (m, 1H), 2.04-1.95 (m, 1H), 1.90-1.79 (m, 1H), 1.76-1.66 (m, 1H), 1.59-1.45 (m, 2H), 1.45-1.26 (m, 5H), 1.11-0.96 (m, 2H). | Step 1: I-13, 4,4,4-trifluorobutan-2-one Chiral SFC conditions: AD-H 5 μm-21 × 250 mm, co-solvent: EtOH—NH₃ (20%) [peak 2] |
| 251 | 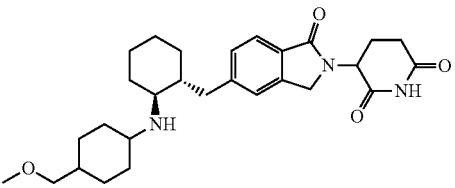 [SMILES: COCC1CCC(N[C@H]2CCCC[C@@H]2Cc2ccc3c(c2)CN(C2CCC(=O)NC2=O)C3=O)CC1]<br>3-(5-(((1R,2S)-2-((4-(methoxymethyl)cyclohexyl)amino)cyclohexyl)methyl)-1-oxoisoindolin-2-yl)piperidine-2,6-dione (Isomer 1) | 482.4 | ¹H NMR (400 MHz, DMSO-d6) δ 10.99 (s, 1H), 8.36 (s, 1H), 8.02 (s, 1H), 7.69 (d, J = 7.8 Hz, 1H), 7.45 (s, 1H), 7.37 (dd, J = 7.8, 1.3 Hz, 1H), 5.11 (dd, J = 13.3, 5.1 Hz, 1H), 4.45 (d, J = 17.2 Hz, 1H), 4.32 (d, J = 17.2 Hz, 1H), 3.33 (d, J = 7.6 Hz, 2H), 3.26 (s, 5H), 3.07 (d, J = 6.9 Hz, 1H), 2.92 (ddd, J = 17.2, 13.6, 5.4 Hz, 1H), 2.65-2.56 (m, 1H), 2.40 (dtt, J = 15.5, 8.1, 4.6 Hz, 2H), 2.13-2.04 (m, 1H), 2.00 (ddd, J = 9.4, 5.4, 2.7 Hz, 1H), 1.93-1.80 (m, 3H), 1.80-1.62 (m, 5H), 1.52 (dtd, J = 19.8, 10.8, 9.5, 4.2 Hz, 5H), 1.41 (d, J = 11.9 Hz, 1H), 1.33 (dd, J = 21.1, 8.8 Hz, 1H), 1.03 (s, 2H). | Step 1: I-13, 4-(methoxymethyl)cyclohexanone Chiral SFC conditions: AD-H 5 μm-21 × 250 mm, co-solvent: iPrOH—NH₃ (30%) [peak 1] |

TABLE 13-continued

| Example | Structure | ES/MS m/z | ¹H-NMR | Changes to Procedure 22: Different Reagents/Starting Materials |
|---|---|---|---|---|
| 252 | 3-(5-(((1R,2S)-2-((4-(methoxymethyl)cyclohexyl)amino)cyclohexyl)methyl)-1-oxoisoindolin-2-yl)piperidine-2,6-dione (Isomer 2) | 482.4 | ¹H NMR (400 MHz, DMSO-d6) δ 10.99 (s, 1H), 8.34 (s, 1H), 8.02 (s, 1H), 7.69 (d, J = 7.8 Hz, 1H), 7.44 (s, 1H), 7.36 (dd, J = 7.8, 1.3 Hz, 1H), 5.11 (dd, J = 13.3, 5.1 Hz, 1H), 4.45 (d, J = 17.5 Hz, 1H), 4.32 (d, J = 17.2 Hz, 1H), 3.30-3.24 (m, 1H), 3.23 (s, 3H), 3.15 (d, J = 6.2 Hz, 3H), 3.06 (d, J = 10.0 Hz, 1H), 2.92 (ddd, J = 17.2, 13.6, 5.4 Hz, 1H), 2.65-2.56 (m, 1H), 2.47-2.30 (m, 2H), 2.14-1.95 (m, 4H), 1.81 (d, J = 12.7 Hz, 3H), 1.71 (d, J = 12.6 Hz, 1H), 1.58-1.43 (m, 4H), 1.43-1.25 (m, 3H), 1.13-0.94 (m, 4H). | Step 1: I-13, 4-(methoxymethyl)cyclohexanone Chiral SFC conditions: AD-H 5 μm-21 × 250 mm, co-solvent: iPrOH—NH₃ (30%) [peak 2] |
| 253 | 3-(1-oxo-5-(((1R,2S)-2-((1-(tetrahydrofuran-2-yl)ethyl)amino)cyclohexyl)methyl)isoindolin-2-yl)piperidine-2,6-dione (Isomer 1) | 454.4 | ¹H NMR (400 MHz, DMSO-d6) δ 10.99 (s, 1H), 8.50-8.40 (m, 1H), 7.85-7.75 (m, 1H), 7.71-7.67 (m, 1H), 7.46 (s, 1H), 7.40-7.36 (m, 1H), 5.11 (dd, J = 13.3, 5.1 Hz, 1H), 4.45 (dd, J = 17.3, 3.2 Hz, 1H), 4.31 (dd, J = 17.3, 3.9 Hz, 1H), 4.18 (td, J = 7.5, 2.5 Hz, 1H), 3.95-3.70 (m, 2H), 3.63-3.55 (m, 1H), 3.37-3.26 (m, 1H), 3.14-3.04 (m, 1H), 2.92 (ddd, J = 17.2, 13.6, 5.4 Hz, 1H), 2.65-2.56 (m, 1H), 2.47-2.31 (m, 2H), 2.15-2.05 (m, 1H), 2.05-1.94 (m, 2H), 1.94-1.78 (m, 3H), 1.76-1.62 (m, 2H), 1.58-1.37 (m, 3H), 1.37-1.19 (m, 4H), 1.10-0.95 (m, 2H). | Step 1: I-13, 1-(tetrahydrofuran-2-yl)ethan-1-one Chiral SFC conditions: AD-H 5 μm-21 × 250 mm, co-solvent: EtOH—NH₃ (30%) [peak 1] |
| 254 | 3-(1-oxo-5-(((1R,2S)-2-((1-(tetrahydrofuran-2-yl)ethyl)amino)cyclohexyl)methyl)isoindolin-2-yl)piperidine-2,6-dione (Isomer 2) | 454.4 | ¹H NMR (400 MHz, DMSO-d6) δ 10.99 (s, 1H), 8.12-8.00 (m, 2H), 7.69 (d, J = 7.8 Hz, 1H), 7.44 (s, 1H), 7.36 (d, J = 7.9 Hz, 1H), 5.11 (dd, J = 13.3, 5.1 Hz, 1H), 4.49-4.41 (m, 1H), 4.32 (dd, J = 17.4, 3.6 Hz, 1H), 3.94 (dt, J = 9.5, 7.1 Hz, 1H), 3.87-3.76 (m, 2H), 3.39-3.23 (m, 2H), 3.12-3.01 (m, 1H), 2.92 (ddd, J = 17.2, 13.6, 5.4 Hz, 1H), 2.65-2.56 (m, 1H), 2.46-2.28 (m, 2H), 2.16-1.82 (m, 6H), 1.77-1.18 (m, 9H), 1.07-0.91 (m, 2H). | Step 1: I-13, 1-(tetrahydrofuran-2-yl)ethan-1-one Chiral SFC conditions: AD-H 5 μm-21 × 250 mm, co-solvent: EtOH—NH₃ (30%) [peak 2] |
| 255 | 1-(1-(((1S,2R)-2-((2-(2,6-dioxopiperidin-3-yl)-1-oxoisoindolin-5-yl)methyl)cyclohexyl)amino)ethyl)cyclopropane-1-carbonitrile (Isomer 1) | 449.3 | ¹H NMR (400 MHz, Methanol-d4) δ 7.80 (d, J = 7.8 Hz, 1H), 7.55-7.38 (m, 2H), 5.18 (dd, J = 13.3, 5.2 Hz, 1H), 4.57-4.40 (m, 2H), 3.22 (dd, J = 9.0, 4.1 Hz, 1H), 3.05 (q, J = 6.7 Hz, 1H), 2.96-2.86 (m, 1H), 2.87-2.75 (m, 1H), 2.66-2.43 (m, 2H), 2.30-2.14 (m, 2H), 2.09-1.95 (m, 1H), 1.82 (s, 1H), 1.78-1.41 (m, 9H), 1.36-1.13 (m, 4H).; 1H NMR (400 MHz, Methanol-d4) δ 7.80 (d, J = 7.8 Hz, 1H), 7.56-7.39 (m, 2H), 5.18 (dd, J = 13.3, 5.2 Hz, 1H), 4.51 (d, J = 5.4 Hz, 2H), 3.51-3.39 (m, 1H), 3.22 (d, J = 6.8 Hz, 1H), 2.97-2.87 (m, 1H), 2.81 (d, J = 16.0 Hz, 1H), 2.64 (dd, J = 13.3, 10.4 Hz, 1H), 2.57-2.46 (m, 1H), 2.21 (d, J = 6.1 Hz, 2H), 1.99 (d, J = 28.4 Hz, 1H), 1.83 (s, 1H), 1.74-1.44 (m, 6H), 1.40-1.13 (m, 4H).; 1H NMR (400 MHz, Methanol-d4) δ 7.80 (d, J = 7.8 Hz, 1H), 7.55-7.38 (m, 2H), 5.18 (dd, J = 13.3, 5.2 Hz, 1H), 4.57-4.40 (m, 2H), 3.22 (dd, J = 9.0, 4.1 Hz, 1H), 3.05 (q, J = 6.7 Hz, 1H), 2.96-2.86 (m, 1H), 2.87-2.75 (m, 1H), 2.66-2.43 (m, 2H), 2.30-2.14 (m, 2H), 2.09-1.95 (m, 1H), 1.82 (s, 1H), 1.78-1.41 (m, 9H), 1.36-1.13 (m, 4H). | Step 1: I-13; 1-acetyl-cyclopropanecarbonitrile Chiral SFC conditions: CELL-2 5 μm-21 × 250 mm, co-solvent: EtOH (40%) [peak 1] |

TABLE 13-continued

| Example | Structure | ES/MS m/z | ¹H-NMR | Changes to Procedure 22: Different Reagents/Starting Materials |
|---|---|---|---|---|
| 256 | 1-(1-(((1S,2R)-2-((2-(2,6-dioxopiperidin-3-yl)-1-oxoisoindolin-5-yl)methyl)cyclohexyl)amino)ethyl)cyclopropane-1-carbonitrile (Isomer 2) | 449.2 | ¹H NMR (400 MHz, Methanol-d4) δ 7.80 (d, J = 7.8 Hz, 1H), 7.56-7.39 (m, 2H), 5.18 (dd, J = 13.3, 5.2 Hz, 1H), 4.51 (d, J = 5.4 Hz, 2H), 3.51-3.39 (m, 1H), 3.22 (d, J = 6.8 Hz, 1H), 2.97-2.87 (m, 1H), 2.81 (d, J = 16.0 Hz, 1H), 2.64 (dd, J = 13.3, 10.4 Hz, 1H), 2.57-2.46 (m, 1H), 2.21 (d, J = 6.1 Hz, 2H), 1.99 (d, J = 28.4 Hz, 1H), 1.83 (s, 1H), 1.74-1.44 (m, 6H), 1.40-1.13 (m, 4H).; 1H NMR (400 MHz, Methanol-d4) δ 7.80 (d, J = 7.8 Hz, 1H), 7.56-7.39 (m, 2H), 5.18 (dd, J = 13.3, 5.2 Hz, 1H), 4.51 (d, J = 5.4 Hz, 2H), 3.51-3.39 (m, 1H), 3.22 (d, J = 6.8 Hz, 1H), 2.97-2.87 (m, 1H), 2.81 (d, J = 16.0 Hz, 1H), 2.64 (dd, J = 13.3, 10.4 Hz, 1H), 2.57-2.46 (m, 1H), 2.21 (d, J = 6.1 Hz, 2H), 1.99 (d, J = 28.4 Hz, 1H), 1.83 (s, 1H), 1.74-1.44 (m, 6H), 1.40-1.13 (m, 4H).; 1H NMR (400 MHz, Methanol-d4) δ 7.80 (d, J = 7.8 Hz, 1H), 7.55-7.38 (m, 2H), 5.18 (dd, J = 13.3, 5.2 Hz, 1H), 4.57-4.40 (m, 2H), 3.22 (dd, J = 9.0, 4.1 Hz, 1H), 3.05 (q, J = 6.7 Hz, 1H), 2.96-2.86 (m, 1H), 2.87-2.75 (m, 1H), 2.66-2.43 (m, 2H), 2.30-2.14 (m, 2H), 2.09-1.95 (m, 1H), 1.82 (s, 1H), 1.78-1.41 (m, 9H), 1.36-1.13 (m, 4H). | Step 1: I-13; 1-acetyl-cyclopropanecarbonitrile Chiral SFC conditions: CELL-2 5 μm-21 × 250 mm, co-solvent: EtOH (40%) [peak 2] |
| 257 | 3-(1-oxo-5-(((1R,2S)-2-((4-(trifluoromethyl)cyclohexyl)amino)cyclohexyl)methyl)isoindolin-2-yl)piperidine-2,6-dione (Isomer 2) | 526.2 | ¹H NMR (400 MHz, Methanol-d4) δ 7.62 (d, J = 7.7 Hz, 1H), 7.55 (t, J = 7.0 Hz, 1H), 5.17 (dd, J = 13.3, 5.2 Hz, 1H), 4.65-4.47 (m, 2H), 3.96-3.82 (m, 2H), 3.48-3.34 (m, 3H), 3.15 (dd, J = 14.2, 9.9 Hz, 1H), 2.97-2.86 (m, 1H), 2.81 (ddd, J = 17.7, 4.8, 2.5 Hz, 1H), 2.59-2.48 (m, 1H), 2.43-2.03 (m, 8H), 1.89-1.71 (m, 3H), 1.54 (dq, J = 27.6, 9.8, 9.3 Hz, 4H). | Step 1: 4-(trifluoromethyl)cyclohexan-1-one Chiral SFC conditions: AD-H 5 μm-21 × 250 mm, co-solvent: EtOH (25%) [peak 2] |
| 258 | 3-(5-(((2R,3S)-3-((3,3-dimethylcyclopentyl)amino)tetrahydro-2H-pyran-2-yl)methyl)-4-fluoro-1-oxoisoindolin-2-yl)piperidine-2,6-dione (Isomer 2) | 472.3 | 1H NMR (400 MHz, Methanol-d4) δ 7.64-7.59 (m, 1H), 7.59-7.52 (m, 1H), 5.18 (dd, J = 13.3, 5.2 Hz, 1H), 4.58 (q, J = 17.2 Hz, 2H), 3.91 (tt, J = 9.3, 4.8 Hz, 3H), 3.46 (ddd, J = 11.2, 7.3, 3.4 Hz, 1H), 3.21 (d, J = 9.8 Hz, 2H), 2.97-2.88 (m, 1H), 2.81 (ddd, J = 17.6, 4.8, 2.4 Hz, 1H), 2.58-2.49 (m, 1H), 2.39 (t, J = 7.9 Hz, 1H), 2.32-2.17 (m, 2H), 2.01 (dd, J = 12.6, 7.5 Hz, 1H), 1.87-1.66 (m, 5H), 1.58 (dd, J = 13.2, 6.9 Hz, 1H), 1.50 (dd, J = 12.6, 9.7 Hz, 1H), 1.17 (d, J = 5.4 Hz, 3H), 1.06 (d, J = 2.6 Hz, 3H). | Step 1: 3,3-dimethylcyclopentanone Chiral SFC conditions: AD-H 5 μm-21 × 250 mm, co-solvent: iPrOH—NH₃ (15%) [peak 2] |
| 259 | 3-(5-(((2R,3S)-3-((3,3-dimethylcyclopentyl)amino)tetrahydro-2H-pyran-2-yl)methyl)-4-fluoro-1-oxoisoindolin-2-yl)piperidine-2,6-dione (Isomer 1) | 472.3 | ¹H NMR (400 MHz, Methanol-d4) δ 7.62 (d, J = 7.7 Hz, 1H), 7.59-7.51 (m, 1H), 5.17 (dd, J = 13.3, 5.2 Hz, 1H), 4.58 (q, J = 17.2 Hz, 2H), 3.98-3.82 (m, 2H), 3.47 (dq, J = 7.6, 3.7 Hz, 1H), 3.23 (ddd, J = 23.8, 16.1, 6.8 Hz, 3H), 2.93 (ddd, J = 17.7, 13.5, 5.4 Hz, 1H), 2.81 (ddd, J = 17.6, 4.7, 2.4 Hz, 1H), 2.55 (td, J = 13.1, 4.7 Hz, 1H), 2.39 (q, J = 7.1, 5.2 Hz, 2H), 2.33-2.17 (m, 2H), 1.93 (dd, J = 12.6, 7.5 Hz, 1H), 1.89-1.78 (m, 3H), 1.71 (ddd, J = 12.8, 9.4, 6.0 Hz, 2H), 1.57 (dt, J = 12.5, 8.4 Hz, 2H), 1.17 (s, 3H), 1.05 (s, 3H). | Step 1: 3,3-dimethylcyclopentanone Chiral SFC conditions: AD-H 5 μm-21 × 250 mm, co-solvent: iPrOH—NH₃ (15%) [peak 1] |

TABLE 13-continued

| Example | Structure | ES/MS m/z | ¹H-NMR | Changes to Procedure 22: Different Reagents/ Starting Materials |
|---|---|---|---|---|
| 260 | 3-(1-oxo-5-(((1R,2S)-2-((tetrahydro-2H-pyran-3-yl)amino)cyclohexyl)methyl)isoindolin-2-yl)piperidine-2,6-dione (Isomer 1) | 440.3 | ¹H NMR (400 MHz, DMSO-d6) δ 10.99 (s, 1H), 8.50 (d, J = 10.9 Hz, 1H), 8.18 (s, 1H), 7.69 (d, J = 7.8 Hz, 1H), 7.45 (s, 1H), 7.44-7.33 (m, 2H), 5.11 (dd, J = 13.3, 5.1 Hz, 1H), 4.51-4.25 (m, 2H), 4.05-3.92 (m, 1H), 3.43-3.30 (m, 2H), 3.26 (dd, J = 13.0, 3.5 Hz, 1H), 3.11 (s, 1H), 2.92 (ddd, J = 17.2, 13.6, 5.4 Hz, 1H), 2.67-2.54 (m, 1H), 2.40 (qd, J = 13.1, 4.2 Hz, 2H), 2.20-1.96 (m, 1H), 1.74 (s, 2H), 1.65-1.40 (m, 1H), 1.23 (s, 4H), 1.04 (d, J = 6.7 Hz, 2H). | Step 1: I-13; tetrahydro-pyran-3-one Chiral SFC conditions: IA 5 μm-21 × 250 mm, co-solvent: EtOH (35%) [peak 1] |
| 261 | 3-(1-oxo-5-(((1R,2S)-2-((tetrahydro-2H-pyran-3-yl)amino)cyclohexyl)methyl)isoindolin-2-yl)piperidine-2,6-dione (Isomer 2) | 440.3 | ¹H NMR (400 MHz, DMSO-d6) δ 10.99 (s, 1H), 8.50 (d, J = 10.9 Hz, 1H), 8.18 (s, 1H), 7.69 (d, J = 7.8 Hz, 1H), 7.45 (s, 1H), 7.44-7.33 (m, 2H), 5.11 (dd, J = 13.3, 5.1 Hz, 1H), 4.51-4.25 (m, 2H), 4.05-3.92 (m, 1H), 3.43-3.30 (m, 2H), 3.26 (dd, J = 13.0, 3.5 Hz, 1H), 3.11 (s, 1H), 2.92 (ddd, J = 17.2, 13.6, 5.4 Hz, 1H), 2.67-2.54 (m, 1H), 2.40 (qd, J = 13.1, 4.2 Hz, 2H), 2.20-1.96 (m, 1H), 1.74 (s, 2H), 1.65-1.40 (m, 1H), 1.23 (s, 4H), 1.04 (d, J = 6.7 Hz, 2H). | Step 1: I-13; tetrahydro-pyran-3-one Chiral SFC conditions: IA 5 μm-21 × 250 mm, co-solvent: EtOH (35%) [peak 2] |
| 262 | 3-(4-fluoro-1-oxo-5-(((2R,3S)-3-((tetrahydro-2H-pyran-3-yl)amino)tetrahydro-2H-pyran-2-yl)methyl)isoindolin-2-yl)piperidine-2,6-dione (Isomer 1) | 460.3 | ¹H NMR (400 MHz, DMSO-d6) δ 11.01 (s, 1H), 8.74 (s, 1H), 8.40 (s, 1H), 7.71-7.36 (m, 2H), 5.11 (dd, J = 13.3, 5.1 Hz, 1H), 4.61-4.34 (m, 2H), 3.98 (ddd, J = 11.1, 3.9, 1.6 Hz, 1H), 3.79 (ddt, J = 25.7, 10.9, 3.2 Hz, 3H), 3.52 (dd, J = 11.2, 8.5 Hz, 1H), 3.45-3.34 (m, 2H), 3.34-3.16 (m, 2H), 3.05 (ddd, J = 14.6, 10.4, 4.2 Hz, 1H), 2.92 (ddd, J = 17.3, 13.6, 5.4 Hz, 1H), 2.66-2.57 (m, 1H), 2.54 (s, 1H), 2.42 (td, J = 13.2, 4.5 Hz, 1H), 2.27-2.17 (m, 1H), 2.12 (d, J = 5.2 Hz, 1H), 2.01 (dtd, J = 10.8, 5.4, 2.9 Hz, 1H), 1.81-1.49 (m, 3H). | Step 1: tetra-hydropyran-3-one Chiral SFC conditions: CELL-2 5 μm-21 × 250 mm, co-solvent: iPrOH—NH₃ (30%) [peak 1] |
| 263 | 3-(4-fluoro-1-oxo-5-(((2R,3S)-3-((tetrahydro-2H-pyran-3-yl)amino)tetrahydro-2H-pyran-2-yl)methyl)isoindolin-2-yl)piperidine-2,6-dione (Isomer 2) | 460.3 | ¹H NMR (400 MHz, DMSO-d6) δ 11.01 (s, 1H), 8.74 (s, 1H), 8.40 (s, 1H), 7.71-7.36 (m, 2H), 5.11 (dd, J = 13.3, 5.1 Hz, 1H), 4.61-4.34 (m, 2H), 3.98 (ddd, J = 11.1, 3.9, 1.6 Hz, 1H), 3.79 (ddt, J = 25.7, 10.9, 3.2 Hz, 3H), 3.52 (dd, J = 11.2, 8.5 Hz, 1H), 3.45-3.34 (m, 2H), 3.34-3.16 (m, 2H), 3.05 (ddd, J = 14.6, 10.4, 4.2 Hz, 1H), 2.92 (ddd, J = 17.3, 13.6, 5.4 Hz, 1H), 2.66-2.57 (m, 1H), 2.54 (s, 1H), 2.42 (td, J = 13.2, 4.5 Hz, 1H), 2.27-2.17 (m, 1H), 2.12 (d, J = 5.2 Hz, 1H), 2.01 (dtd, J = 10.8, 5.4, 2.9 Hz, 1H), 1.81-1.49 (m, 3H). | Step 1: tetra-hydropyran-3-one Chiral SFC conditions: CELL-2 5 μm-21 × 250 mm, co-solvent: iPrOH—NH₃ (30%) [peak 2] |

TABLE 13-continued

| Example | Structure | ES/MS m/z | ¹H-NMR | Changes to Procedure 22: Different Reagents/ Starting Materials |
|---|---|---|---|---|
| 264 | 3-(4-fluoro-5-(((2R,3S)-3-((4-(methoxymethyl)cyclohexyl)amino)tetrahydro-2H-pyran-2-yl)methyl)-1-oxoisoindolin-2-yl)piperidine-2,6-dione (Isomer 1) | 502.4 | ¹H NMR (400 MHz, DMSO-d6) δ 11.01 (s, 1H), 8.57 (s, 1H), 8.19 (s, 1H), 7.60-7.50 (m, 2H), 5.11 (dd, J = 13.3, 5.1 Hz, 1H), 4.55 (d, J = 17.4 Hz, 1H), 4.38 (d, J = 17.4 Hz, 1H), 3.87-3.72 (m, 2H), 3.33 (d, J = 7.6 Hz, 2H), 3.26 (s, 4H), 3.23 (d, J = 4.0 Hz, 3H), 3.05-2.94 (m, 1H), 2.95-2.86 (m, 1H), 2.65-2.56 (m, 1H), 2.42 (td, J = 13.2, 4.5 Hz, 1H), 2.26-2.15 (m, 1H), 2.01 (dtd, J = 12.5, 5.2, 2.2 Hz, 1H), 1.95-1.82 (m, 2H), 1.78 (d, J = 12.0 Hz, 1H), 1.75-1.56 (m, 6H), 1.51 (dq, J = 7.9, 4.3, 3.8 Hz, 3H). | Step 1: 4-(methoxymethyl)cyclohexanone Chiral SFC conditions: IA 5 μm-21 × 250 mm, co-solvent: iPrOH-DEA (20%) [peak 1] |
| 265 | 3-(4-fluoro-5-(((2R,3S)-3-((4-(methoxymethyl)cyclohexyl)amino)tetrahydro-2H-pyran-2-yl)methyl)-1-oxoisoindolin-2-yl)piperidine-2,6-dione (Isomer 2) | 502.4 | ¹H NMR (400 MHz, DMSO-d6) δ 11.01 (s, 1H), 8.58 (s, 1H), 8.22 (s, 1H), 7.60-7.47 (m, 2H), 5.11 (dd, J = 13.3, 5.1 Hz, 1H), 4.56 (dd, J = 17.4, 4.9 Hz, 1H), 4.37 (dd, J = 17.4, 2.9 Hz, 1H), 3.76 (ddd, J = 10.3, 7.3, 4.3 Hz, 2H), 3.30-3.18 (m, 7H), 3.15 (d, J = 6.2 Hz, 2H), 3.04-2.94 (m, 1H), 2.94-2.86 (m, 1H), 2.66-2.55 (m, 1H), 2.42 (td, J = 13.2, 4.5 Hz, 1H), 2.26-2.17 (m, 1H), 2.11 (d, J = 11.9 Hz, 1H), 2.08-1.96 (m, 2H), 1.80 (d, J = 12.9 Hz, 2H), 1.75-1.64 (m, 1H), 1.61 (d, J = 9.5 Hz, 2H), 1.55-1.45 (m, 2H), 1.45-1.30 (m, 1H), 1.12-0.98 (m, 2H). | Step 1: 4-(methoxymethyl)cyclohexanone Chiral SFC conditions: IA 5 μm-21 × 250 mm, co-solvent: iPrOH-DEA (20%) [peak 2] |
| 266 | 3-(5-(((1R,2S)-2-(bicyclo[3.1.0]hexan-3-ylamino)cyclohexyl)methyl)-1-oxoisoindolin-2-yl)piperidine-2,6-dione (Isomer 2) | 436.3 | ¹H NMR (400 MHz, DMSO-d6) δ 10.99 (s, 1H), 8.40 (s, 1H), 8.01 (s, 1H), 7.69 (d, J = 7.8 Hz, 1H), 7.44 (d, J = 6.6 Hz, 1H), 7.41-7.31 (m, 1H), 5.11 (dd, J = 13.3, 5.1 Hz, 1H), 4.54-4.27 (m, 2H), 4.02 (s, 1H), 3.09-2.74 (m, 2H), 2.61 (d, J = 17.0 Hz, 1H), 2.41 (td, J = 13.3, 5.2 Hz, 3H), 2.17-1.95 (m, 2H), 1.69 (s, 1H), 1.62-1.21 (m, 5H), 1.18-0.76 (m, 3H). | Step 1: bicyclo[3.1.0]hexan-3-one Chiral SFC conditions: IG 5 μm-21 × 250 mm, co-solvent: EtOH-TFA (30%) [peak 2] |

Procedure 23, Examples 267 and 268

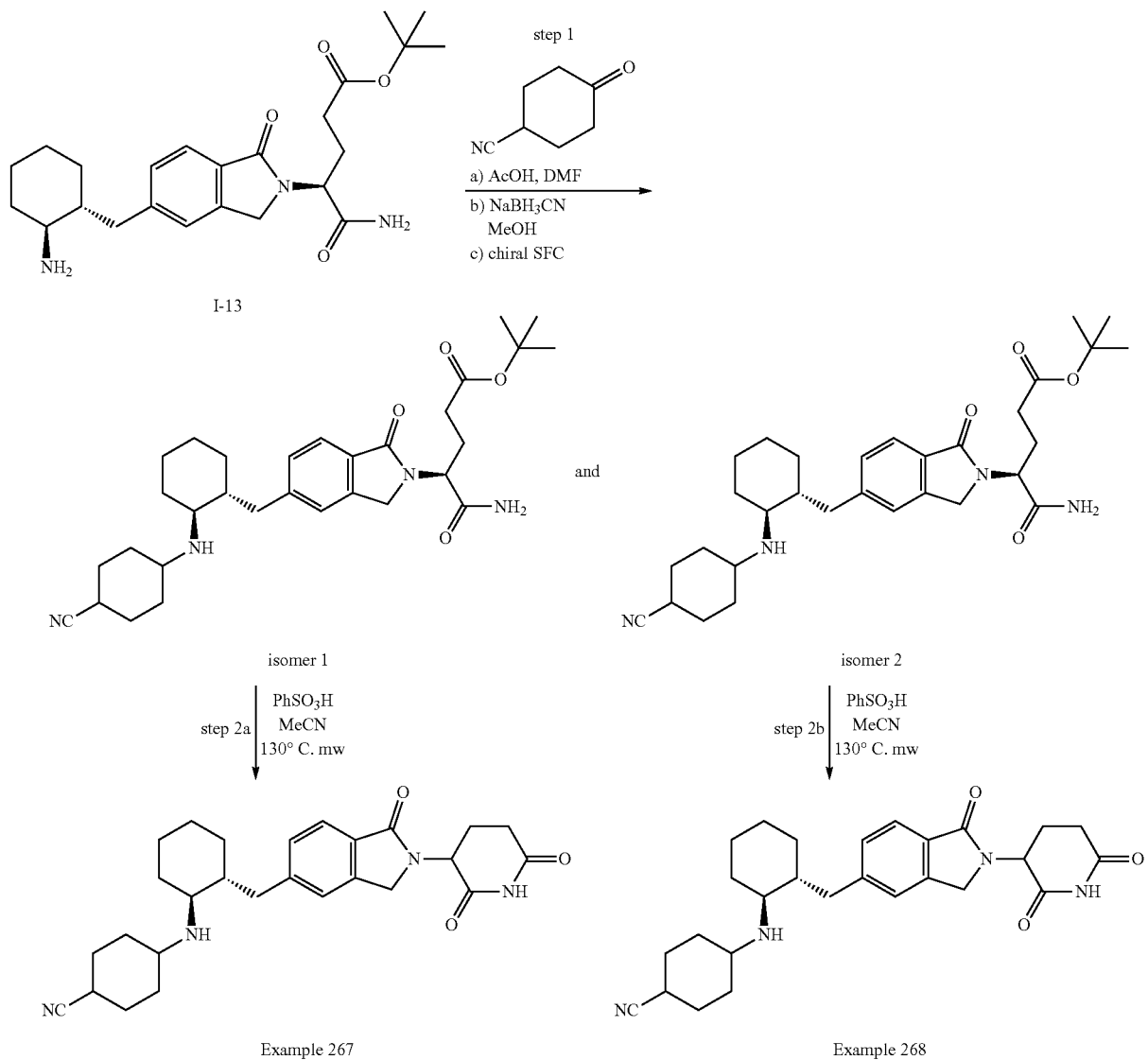

Step 1: Preparation of tert-butyl (S)-5-amino-4-(5-(((1R,2S)-2-((4-cyanocyclohexyl)amino)cyclohexyl)methyl)-1-oxoisoindolin-2-yl)-5-oxopentanoate (Isomer 1) and butyl (S)-5-amino-4-(5-(((1R,2S)-2-((4-cyanocyclohexyl)amino)cyclohexyl)methyl)-1-oxoisoindolin-2-yl)-5-oxopentanoate (Isomer 2). I-13

(75 mg, 0.175 mmol) was taken up in DMF (1.5 mL) and 4-oxocyclohexane-1-carbonitrile (215 mg, 1.75 mmol) was added followed by acetic acid (100 μL, 1.75 mmol). The reaction was stirred at r.t. overnight then concentrated in vacuo to remove the solvent. The residue was taken up in methanol (1.5 mL) and NaBH$_3$CN (54.9 mg, 0.873 mmol) was added. The reaction was stirred at r.t. for 2 hours then the mixture was concentrated in vacuo and subjected to purification by SiO$_2$ column chromatography (eluent: CH$_2$Cl$_2$/MeOH) to yield mixture of stereoisomeric products. The mixture was then further purified by chiral SFC chromatography (Column: AD-H 250 mm×21.2 mm, 5 μm, eluent: 30% IPA-NH$_3$) to afford 4-(((1S,2R)-2-((2-(2,6-dioxopiperidin-3-yl)-1-oxoisoindolin-5-yl)methyl)cyclohexyl)amino)cyclohexane-1-carbonitrile (Isomer 1) and 4-(((1S,2R)-2-((2-(2,6-dioxopiperidin-3-yl)-1-oxoisoindolin-5-yl)methyl)cyclohexyl)amino)cyclohexane-1-carbonitrile (Isomer 2). ES/MS: 537.2 (M+H$^+$, Isomer 1) and 537.2 (M+H$^+$, Isomer 2).

Step 2a: Preparation of 4-(((1S,2R)-2-((2-(2,6-dioxopiperidin-3-yl)-1-oxoisoindolin-5-yl)methyl)cyclohexyl)amino)cyclohexane-1-carbonitrile (Example 267)

4-(((1S,2R)-2-((2-(2,6-dioxopiperidin-3-yl)-1-oxoisoindolin-5-yl)methyl)cyclohexyl)amino)cyclohexane-1-carbonitrile (Isomer 1) (37.0 mg, 68.9 μmol) was taken up in MeCN (2.0 mL) and benzenesulfonic acid (27.3 mg, 0.172 mmol) was added. The reaction was heated to 130° C. under microwave irradiation for 30 minutes and then the reaction mixture was concentrated in vacuo and the residue purified directly by RP-HPLC (eluent: MeCN/water gradient with 0.1% TFA) to yield the product (Example 267) as the trifluoracetate salt. ES/MS: 463.2 (M+H$^+$). $^1$H NMR (400 MHz, DMSO-d6) δ 10.99 (s, 1H), 8.38 (s, 1H), 8.09 (s, 1H), 7.71 (d, J=7.8 Hz, 1H), 7.45 (s, 1H), 7.37 (d, J=7.9 Hz, 1H), 5.12 (dd, J=13.3, 5.1 Hz, 1H), 4.46 (d, J=17.4 Hz, 1H), 4.33 (d, J=17.3 Hz, 1H), 3.16 (d, J=40.1 Hz, 3H), 2.93 (ddd, J=17.3, 13.5, 5.4 Hz, 1H), 2.75-2.57 (m, 1H), 2.45-2.18 (m, 1H), 2.18-1.88 (m, 8H), 1.91-1.21 (m, 7H), 1.04 (s, 3H).

Step 2$^a$: Preparation of 4-(((1S,2R)-2-((2-(2,6-dioxopiperidin-3-yl)-1-oxoisoindolin-5-yl)methyl) cyclohexyl)amino)cyclohexane-1-carbonitrile (Example 268)

4-(((1S,2R)-2-((2-(2,6-dioxopiperidin-3-yl)-1-oxoisoindolin-5-yl)methyl)cyclohexyl)amino)cyclohexane-1-carbonitrile (Isomer 2) (60.9 mg, 0.113 mmol) was taken up in MeCN (2.0 mL) and benzenesulfonic acid (44.9 mg, 0.284 mmol) was added. The reaction was heated to 130° C. under microwave irradiation for 30 minutes and then the reaction mixture was concentrated in vacuo and the residue purified directly by RP-HPLC (eluent: MeCN/water gradient with 0.1% TFA) to yield the product (Example 268) as the trifluoracetate salt. ES/MS: 463.2 (M+H$^+$). $^1$H NMR (400 MHz, DMSO-d6) δ 10.99 (s, 1H), 8.36 (s, 1H), 8.03 (s, 1H), 7.70 (d, J=7.7 Hz, 1H), 7.44 (s, 1H), 7.36 (dd, J=7.8, 1.3 Hz, 1H), 5.12 (dd, J=13.3, 5.1 Hz, 1H), 4.45 (d, J=17.3 Hz, 1H), 4.33 (d, J=17.3 Hz, 1H), 3.25 (dd, J=13.2, 3.5 Hz, 1H), 3.16-2.80 (m, 3H), 2.80-2.59 (m, 3H), 2.43-2.22 (m, 1H), 2.22-1.90 (m, 7H), 1.90-1.21 (m, 10H), 1.08 (dt, J=42.8, 8.7 Hz, 2H).

The following Examples were made using the general route described in Procedure 23 and are shown below in Table 14. To prepare the below Examples, different reagents/starting materials were used than some of those described in Procedure 23 and are noted in the last column of Table 14—"Changes to Procedure 23: Different Reagents/Starting Materials". A person of ordinary skill in the art will readily recognize which reagents/starting materials of Procedure 23 were replaced with the different reagents/starting materials noted below.

TABLE 14

| Example | Structure | ES/MS m/z | $^1$H-NMR | Changes to Procedure 23: Different Reagents/ Starting Materials |
|---|---|---|---|---|
| 269 | 2-(4-(((1S,2R)-2-((2-(2,6-dioxopiperidin-3-yl)-1-oxoisoindolin-5-yl)methyl) cyclohexyl)amino)cyclohexyl) acetonitrile (Isomer 1) | 477.2 | $^1$H NMR (400 MHz, DMSO-d6) δ 10.99 (s, 1H), 8.24 (s, 1H), 7.86 (s, 1H), 7.71 (d, J = 7.8 Hz, 1H), 7.45 (s, 1H), 7.37 (d, J = 7.8 Hz, 1H), 5.12 (dd, J = 13.3, 5.1 Hz, 1H), 4.46 (d, J = 17.2 Hz, 1H), 4.33 (d, J = 17.3 Hz, 1H), 3.31-3.16 (m, 1H), 3.10 (s, 1H), 3.04-2.84 (m, 2H), 2.84-2.56 (m, 4H), 2.47-2.24 (m, 2H), 2.20-1.95 (m, 3H), 1.95-1.27 (m, 13H), 1.05 (d, J = 8.2 Hz, 2H). | Step 1: 2-(4-oxocyclohexyl) acetonitrile Chiral SFC conditions: AD-H 5 μm-21 × 250 mm, co-solvent: IPA-NH$_3$ (30%) [peak 1] |
| 270 | 2-(4-(((1S,2R)-2-((2-(2,6-dioxopiperidin-3-yl)-1-oxoisoindolin-5-yl)methyl) cyclohexyl)amino)cyclohexyl) acetonitrile (Isomer 2) | 477.3 | $^1$H NMR (400 MHz, DMSO-d6) δ 10.99 (s, 1H), 8.28 (s, 1H), 7.96 (s, 0H), 7.70 (d, J = 7.8 Hz, 1H), 7.45 (s, 1H), 7.37 (d, J = 7.8 Hz, 1H), 5.12 (dd, J = 13.3, 5.1 Hz, 1H), 4.46 (d, J = 17.3 Hz, 1H), 4.33 (d, J = 17.2 Hz, 1H), 3.30-3.02 (m, 2H), 2.99-2.84 (m, 2H), 2.72-2.56 (m, 2H), 2.49-2.30 (m, 4H), 2.25-1.95 (m, 4H), 1.95-0.91 (m, 11H)." | Step 1: 2-(4-oxocyclohexyl) acetonitrile Chiral SFC conditions: AD-H 5 μm-21 × 250 mm, co-solvent: IPA-NH$_3$ (30%) [peak 2] |

TABLE 14-continued

| Example | Structure | ES/MS m/z | ¹H-NMR | Changes to Procedure 23: Different Reagents/ Starting Materials |
|---|---|---|---|---|
| 271 | 3-(5-(((1R,2S)-2-((1,1-difluorospiro[2.5]octan-6-yl)amino)cyclohexyl)methyl)-1-oxoisoindolin-2-yl)piperidine-2,6-dione (Isomer 1) | 500.2 | ¹H NMR (400 MHz, DMSO-d6) δ 10.99 (s, 1H), 8.50 (s, 1H), 8.05 (s, 1H), 7.70 (d, J = 7.8 Hz, 1H), 7.45 (s, 1H), 7.40 (s, 1H), 5.12 (dd, J = 13.2, 5.1 Hz, 1H), 4.46 (dd, J = 17.4, 2.6 Hz, 1H), 4.32 (dd, J = 17.4, 2.2 Hz, 1H), 3.52-3.20 (m, 2H), 3.20-2.99 (m, 1H), 2.92 (ddd, J = 17.3, 13.6, 5.4 Hz, 1H), 2.61 (dt, J = 17.4, 3.1 Hz, 1H), 2.39 (ddd, J = 13.8, 9.9, 4.1 Hz, 1H), 2.25-1.90 (m, 4H), 1.90-1.66 (m, 5H), 1.66-1.17 (m, 10H), 1.17-0.77 (m, 2H). | Step 1: 2,2-difluorospiro[2.5]octan-6-one Chiral SFC conditions: IA 5 μm-21 × 250 mm, co-solvent: IPA-NH₃ (30%) [peak 1] |
| 272 | 3-(5-(((1R,2S)-2-((1,1-difluorospiro[2.5]octan-6-yl)amino)cyclohexyl)methyl)-1-oxoisoindolin-2-yl)piperidine-2,6-dione (Isomer 2) | 500.2 | ¹H NMR (400 MHz, DMSO-d6) δ 10.99 (s, 1H), 8.50 (s, 1H), 8.12 (s, 1H), 7.70 (d, J = 7.8 Hz, 1H), 7.45 (s, 1H), 7.42 (s, 1H), 5.12 (dd, J = 13.3, 5.1 Hz, 1H), 4.46 (dd, J = 17.5, 2.1 Hz, 1H), 4.32 (dd, J = 17.4, 2.7 Hz, 1H), 3.31 (dd, J = 13.3, 3.7 Hz, 2H), 3.12 (s, 1H), 2.92 (ddd, J = 17.2, 13.6, 5.4 Hz, 1H), 2.75-2.57 (m, 1H), 2.44-2.25 (m, 2H), 2.23-1.90 (m, 4H), 1.96-1.13 (m, 14H), 1.18-0.94 (m, 2H)." | Step 1: 2,2-difluorospiro[2.5]octan-6-one Chiral SFC conditions: IA 5 μm-21 × 250 mm, co-solvent: IPA-NH₃ (30%) [peak 2] |
| 273 | 3-(5-(((1R,2S)-2-((2,2-dimethyltetrahydrofuran-3-yl)amino)cyclohexyl)methyl)-1-oxoisoindolin-2-yl)piperidine-2,6-dione (Isomer 1) | 454.2 | ¹H NMR (400 MHz, DMSO-d6) δ 10.99 (s, 1H), 7.71 (d, J = 7.8 Hz, 1H), 7.47 (s, 1H), 7.38 (d, J = 7.8 Hz, 1H), 5.12 (dd, J = 13.3, 5.1 Hz, 1H), 4.46 (dd, J = 17.2, 4.7 Hz, 1H), 4.37-4.24 (m, 1H), 3.87 (td, J = 8.7, 4.2 Hz, 1H), 3.76 (q, J = 8.0 Hz, 1H), 3.65 (s, 1H), 3.32-3.03 (m, 3H), 2.93 (ddd, J = 18.2, 13.6, 5.4 Hz, 1H), 2.63 (dd, J = 19.2, 15.4 Hz, 1H), 2.46-2.30 (m, 2H), 2.30-1.88 (m, 4H), 1.75 (d, J = 9.3 Hz, 1H), 1.65-1.44 (m, 3H), 1.29 (d, J = 19.0 Hz, 7H), 1.08 (t, J = 9.4 Hz, 2H). | Step 1: 2,2-dimethyl-tetrahydrofuran-3-one Chiral SFC conditions: IA 5 μm-21 × 250 mm, co-solvent: EtOH (25%) [peak 1] |
| 274 | 3-(5-(((1R,2S)-2-((2,2-dimethyltetrahydrofuran-3-yl)amino)cyclohexyl)methyl)-1-oxoisoindolin-2-yl)piperidine-2,6-dione (Isomer 2) | 454.2 | ¹H NMR (400 MHz, DMSO-d6) δ 10.99 (s, 1H), 7.70 (d, J = 7.7 Hz, 1H), 7.47 (s, 1H), 7.38 (d, J = 7.8 Hz, 1H), 5.12 (dd, J = 13.3, 5.1 Hz, 1H), 4.46 (dd, J = 17.3, 6.0 Hz, 1H), 4.32 (dd, J = 17.3, 5.4 Hz, 1H), 3.89 (td, J = 8.8, 4.3 Hz, 1H), 3.77 (q, J = 8.0 Hz, 1H), 3.24 (dd, J = 13.3, 3.4 Hz, 1H), 3.11 (s, 1H), 2.92 (ddd, J = 18.0, 13.6, 5.4 Hz, 1H), 2.69-2.55 (m, 1H), 2.49-2.30 (m, 3H), 2.30-1.87 (m, 5H), 1.84-1.64 (m, 1H), 1.54 (t, J = 10.6 Hz, 4H), 1.31 (d, J = 3.8 Hz, 7H), 1.09-0.93 (m, 2H). | Step 1: 2,2-dimethyl-tetrahydrofuran-3-one Chiral SFC conditions: IA 5 μm-21 × 250 mm, co-solvent: EtOH (25%) [peak 1] |

Procedure 24, Examples 275 and 276

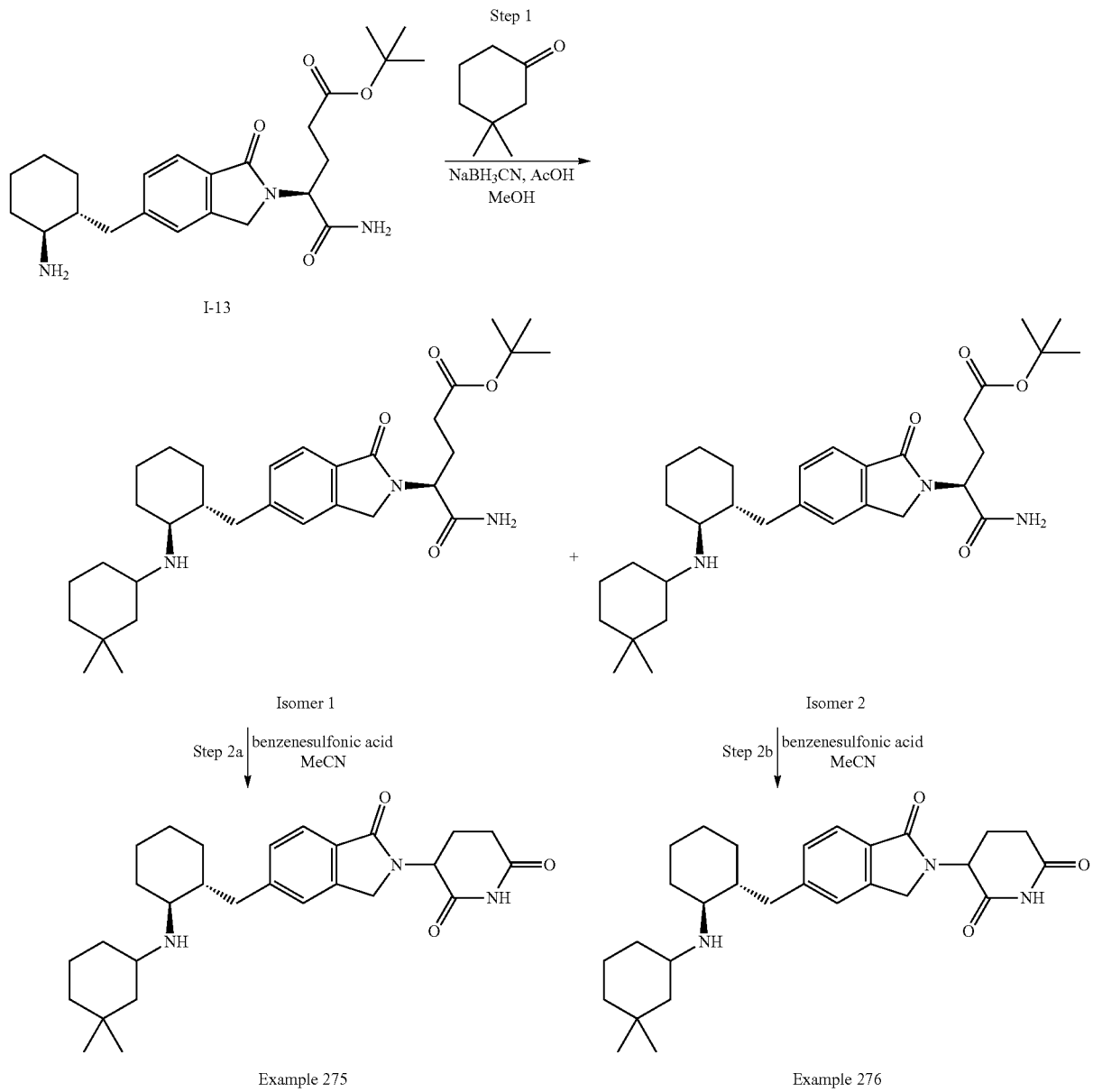

Step 1: Preparation tert-butyl (4S)-5-amino-4-(5-(((1R,2S)-2-((3,3-dimethylcyclohexyl)amino)cyclohexyl)methyl)-1-oxoisoindolin-2-yl)-5-oxopentanoate (Isomer 1) and tert-butyl (4S)-5-amino-4-(5-(((1R,2S)-2-((3,3-dimethylcyclohexyl)amino)cyclohexyl)methyl)-1-oxoisoindolin-2-yl)-5-oxopentanoate (Isomer 2)

A vial was charged with tert-butyl (S)-5-amino-4-(5-(((1R,2S)-2-aminocyclohexyl)methyl)-1-oxoisoindolin-2-yl)-5-oxopentanoate (I-13) (100 mg, 0.233 mmol), 3,3-dimethylcyclohexanone (294 mg, 2.33 mmol), sodium cyanoborohydride (43.9 mg, 0.698 mmol), MeOH (1.00 mL), and acetic acid (0.0133 mL, 0.233 mmol). The reaction was mixed at room temperature for 1.5 h, adding additional 3,3-dimethylcyclohexanone as needed to reach full conversion. Upon completion, the mixture was concentrated in vacuo and purified directly by column chromatography (eluent: 0-20% MeOH/DCM gradient) to tert-butyl (4S)-5-amino-4-(5-(((1R,2S)-2-((3,3-dimethylcyclohexyl)amino)cyclohexyl)methyl)-1-oxoisoindolin-2-yl)-5-oxopentanoate (Isomer 1) as a solid (37.3 mg) and tert-butyl (4S)-5-amino-4-(5-(((1R,2S)-2-((3,3-dimethylcyclohexyl)amino)cyclohexyl)methyl)-1-oxoisoindolin-2-yl)-5-oxopentanoate (Isomer 2). ES/MS: 540.5 (M+H$^+$, Isomer 1) and 540.3 (M+H$^+$, Isomer 2).

Step 2a: Preparation of 3-(5-(((1R,2S)-2-((3,3-dimethylcyclohexyl)amino)cyclohexyl)methyl)-1-oxoisoindolin-2-yl)piperidine-2,6-dione (Example 275)

A vial was charged with tert-butyl (4S)-5-amino-4-(5-(((1R,2S)-2-((3,3-dimethylcyclohexyl)amino)cyclohexyl)

methyl)-1-oxoisoindolin-2-yl)-5-oxopentanoate (37.3 mg, 69.1 μmol), MeCN (1.11 mL), and benzenesulfonic acid (32.8 mg, 0.106 mmol). The reaction was heated to 130° C. under microwave irradiation for 30 min. Following this time, the reaction was concentrated in vacuo. The residue was then taken up in DMSO and purified directly by RP-HPLC (eluent: 0-100% MeCN/water gradient with 0.1% TFA) to yield the product (Example 275) as the trifluoroacetate salt. ES/MS: 466.4 (M+H$^+$). $^1$H NMR (400 MHz, DMSO-d$_6$) δ 10.99 (s, 1H), 8.34 (d, J=35.7 Hz, 1H), 7.96 (s, 1H), 7.69 (d, J=7.7 Hz, 1H), 7.45 (s, 1H), 7.36 (dd, J=7.8, 1.3 Hz, 1H), 5.11 (dd, J=13.3, 5.1 Hz, 1H), 4.45 (d, J=17.3 Hz, 1H), 4.32 (d, J=17.2 Hz, 1H), 3.26 (ddd, J=12.9, 9.3, 3.7 Hz, 2H), 3.06 (s, 1H), 2.92 (ddd, J=17.2, 13.6, 5.4 Hz, 1H), 2.61 (dt, J=16.9, 3.2 Hz, 1H), 2.40 (qd, J=13.7, 13.3, 4.7 Hz, 2H), 2.08 (d, J=13.5 Hz, 1H), 1.99 (dtd, J=12.4, 5.2, 2.3 Hz, 2H), 1.88-1.68 (m, 2H), 1.68-1.46 (m, 5H), 1.45-1.15 (m, 5H), 1.07 (qd, J=12.9, 11.0, 7.1 Hz, 3H), 0.99-0.85 (m, 6H).

Step 2b: Preparation of 3-(5-(((1R,2S)-2-((3,3-dimethylcyclohexyl) amino)cyclohexyl)methyl)-1-oxoisoindolin-2-yl)piperidine-2,6-dione (Example 276)

A vial was charged with tert-butyl (4S)-5-amino-4-(5-(((1R,2S)-2-((3,3-dimethyl cyclohexyl)amino)cyclohexyl) methyl)-1-oxoisoindolin-2-yl)-5-oxopentanoate (17.9 mg, 33.2 μmol), MeCN (0.533 mL), and benzenesulfonic acid (15.7 mg, 0.224 mmol). The reaction was heated to 130° C. under microwave irradiation for 30 min. Following this time, the reaction was concentrated in vacuo. The residue was then taken up in DMSO and purified directly by RP-HPLC (eluent: 0-100% MeCN/water gradient with 0.1% TFA) to yield the product (Example 276) as the trifluoroacetate salt. ES/MS: 466.4 (M+H$^+$). $^1$H NMR (400 MHz, DMSO-d$_6$) δ 10.99 (s, 1H), 8.30 (d, J=35.7 Hz, 1H), 7.93 (s, 1H), 7.69 (d, J=7.7 Hz, 1H), 7.45 (s, 1H), 7.36 (dd, J=7.8, 1.3 Hz, 1H), 5.11 (dd, J=13.3, 5.1 Hz, 1H), 4.45 (d, J=17.3 Hz, 1H), 4.32 (d, J=17.2 Hz, 1H), 3.37-3.20 (m, 2H), 3.06 (s, 1H), 2.92 (ddd, J=17.3, 13.6, 5.4 Hz, 1H), 2.65-2.56 (m, 1H), 2.39 (qd, J=13.3, 4.3 Hz, 2H), 2.09 (t, J=13.8 Hz, 1H), 2.04-1.95 (m, 2H), 1.88-1.68 (m, 2H), 1.68-1.46 (m, 5H), 1.45-1.15 (m, 5H), 1.14-0.99 (m, 3H), 0.99-0.86 (m, 6H).

The following Examples were made using the general route described in Procedure 24 and are shown below in Table 15. To prepare the below Examples, different reagents/starting materials were used than some of those described in Procedure 24 and are noted in the last column of Table 15—"Changes to Procedure 24: Different Reagents/Starting Materials". A person of ordinary skill in the art will readily recognize which reagents/starting materials of Procedure 24 were replaced with the different reagents/starting materials noted below.

TABLE 15

| Example | Structure | ES/MS m/z | $^1$H-NMR | Changes to Procedure 24: Different Reagents/Starting Materials |
|---|---|---|---|---|
| 277 | 3-(5-(((1R,2S)-2-((4-methoxycyclohexyl)amino)cyclohexyl)methyl)-1-oxoisoindolin-2-yl)piperidine-2,6-dione (Isomer 1) | 468.4 | $^1$H NMR (400 MHz, Methanol-d4) δ 7.79 (d, J = 7.7 Hz, 1H), 7.52-7.35 (m, 2H), 5.18 (dd, J = 13.3, 5.2 Hz, 1H), 4.59-4.44 (m, 2H), 3.38 (s, 3H), 3.28-3.14 (m, 4H), 2.96-2.87 (m, 1H), 2.81 (ddd, J = 17.6, 4.7, 2.4 Hz, 1H), 2.60-2.46 (m, 2H), 2.28-2.07 (m, 6H), 1.89 (dd, J = 41.8, 11.4 Hz, 2H), 1.72-1.41 (m, 6H), 1.34 (dd, J = 16.7, 9.2 Hz, 2H), 1.19 (q, J = 12.6 Hz, 2H).; 1H NMR (400 MHz, Methanol-d4) δ 7.79 (d, J = 7.8 Hz, 1H), 7.50-7.34 (m, 2H), 5.18 (dd, J = 13.3, 5.2 Hz, 1H), 4.56-4.40 (m, 2H), 3.53 (d, J = 10.1 Hz, 1H), 3.38 (d, J = 3.8 Hz, 1H), 3.30-3.13 (m, 4H), 2.94 (ddd, J = 18.4, 13.4, 5.4 Hz, 1H), 2.85-2.76 (m, 1H), 2.60-2.41 (m, 2H), 2.28-2.04 (m, 4H), 1.98-1.77 (m, 5H), 1.77-1.39 (m, 7H), 1.19 (q, J = 12.2 Hz, 2H).; 1H NMR (400 MHz, Methanol-d4) δ 7.79 (d, J = 7.7 Hz, 1H), 7.52-7.35 (m, 2H), 5.18 (dd, J = 13.3, 5.2 Hz, 1H), 4.59-4.44 (m, 2H), 3.38 (s, 3H), 3.28-3.14 (m, 4H), 2.96-2.87 (m, 1H), 2.81 (ddd, J = 17.6, 4.7, 2.4 Hz, 1H), 2.60-2.46 (m, 2H), 2.28-2.07 (m, 6H), 1.89 (dd, J = 41.8, 11.4 Hz, 2H), 1.72-1.41 (m, 6H), 1.34 (dd, J = 16.7, 9.2 Hz, 2H), 1.19 (q, J = 12.6 Hz, 2H). | 4-methoxycyclohexanone |
| 278 | 3-(5-(((1R,2S)-2-((4-methoxycyclohexyl)amino)cyclohexyl)methyl)-1-oxoisoindolin-2-yl)piperidine-2,6-dione (Isomer 2) | 468.4 | $^1$H NMR (400 MHz, Methanol-d4) δ 7.79 (d, J = 7.8 Hz, 1H), 7.50-7.34 (m, 2H), 5.18 (dd, J = 13.3, 5.2 Hz, 1H), 4.56-4.40 (m, 2H), 3.53 (d, J = 10.1 Hz, 1H), 3.38 (d, J = 3.8 Hz, 1H), 3.30-3.13 (m, 4H), 2.94 (ddd, J = 18.4, 13.4, 5.4 Hz, 1H), 2.85-2.76 (m, 1H), 2.60-2.41 (m, 2H), 2.28-2.04 (m, 4H), 1.98-1.77 (m, 5H), 1.77-1.39 (m, 7H), 1.19 (q, J = 12.2 Hz, 2H).; 1H NMR (400 MHz, Methanol-d4) δ 7.79 (d, J = 7.8 Hz, 1H), 7.50-7.34 (m, 2H), 5.18 (dd, J = 13.3, 5.2 Hz, 1H), 4.56-4.40 (m, 2H), 3.53 (d, J = 10.1 Hz, 1H), 3.38 (d, J = 3.8 Hz, 1H), 3.30-3.13 (m, 4H), 2.94 (ddd, J = 18.4, 13.4, 5.4 Hz, 1H), 2.85-2.76 (m, 1H), 2.60-2.41 (m, 2H), 2.28-2.04 (m, 4H), 1.98-1.77 (m, 5H), 1.77-1.39 (m, 7H), 1.19 (q, J = 12.2 Hz, 2H).; 1H NMR (400 MHz, Methanol-d4) δ 7.79 (d, J = 7.7 Hz, 1H), 7.52-7.35 (m, 2H), 5.18 (dd, J = 13.3, 5.2 Hz, 1H), 4.59-4.44 (m, 2H), 3.38 (s, 3H), 3.28-3.14 (m, 4H), 2.96-2.87 (m, 1H), 2.81 (ddd, J = 17.6, 4.7, 2.4 Hz, 1H), 2.60-2.46 (m, 2H), 2.28-2.07 (m, 6H), 1.89 (dd, J = 41.8, 11.4 | 4-methoxycyclohexanone |

TABLE 15-continued

| Example | Structure | ES/MS m/z | ¹H-NMR | Changes to Procedure 24: Different Reagents/ Starting Materials |
|---|---|---|---|---|
| | | | Hz, 2H), 1.72-1.41 (m, 6H), 1.34 (dd, J = 16.7, 9.2 Hz, 2H), 1.19 (q, J = 12.6 Hz, 2H). | |
| 279 | 3-(5-(((1R,2S)-2-((4-methylcyclohexyl)amino)cyclohexyl)methyl)-1-oxoisoindolin-2-yl)piperidine-2,6-dione (Isomer 1) | 452.4 | ¹H NMR (400 MHz, DMSO-d6) δ 10.99 (s, 1H), 8.27 (d, J = 12.9 Hz, 1H), 7.96 (s, 1H), 7.69 (dd, J = 7.7, 1.5 Hz, 1H), 7.45 (d, J = 4.3 Hz, 1H), 7.40-7.30 (m, 1H), 5.11 (dd, J = 13.3, 5.1 Hz, 1H), 4.45 (d, J = 17.3 Hz, 1H), 4.32 (d, J = 17.2 Hz, 1H), 3.27 (dd, J = 13.2, 3.5 Hz, 1H), 3.21 (s, 1H), 3.07 (s, 1H), 2.92 (ddd, J = 17.2, 13.6, 5.4 Hz, 1H), 2.65-2.55 (m, 1H), 2.39 (td, J = 13.2, 8.9 Hz, 2H), 2.13-2.04 (m, 1H), 2.00 (ddd, J = 10.5, 5.4, 2.8 Hz, 1H), 1.90-1.78 (m, 2H), 1.78-1.66 (m, 3H), 1.54 (q, J = 13.3 Hz, 6H), 1.37 (dp, J = 20.6, 10.5, 9.9 Hz, 3H), 1.11-0.99 (m, 2H), 0.97 (d, J = 7.0 Hz, 3H), 0.88 (d, J = 6.5 Hz, 1H). | 4-methyl-cyclo-hexanone |
| 280 | 3-(5-(((1R,2S)-2-((4-methylcyclohexyl)amino)cyclohexyl)methyl)-1-oxoisoindolin-2-yl)piperidine-2,6-dione (Isomer 2) | 452.4 | ¹H NMR (400 MHz, DMSO-d6) δ 10.99 (s, 1H), 8.27 (s, 1H), 7.96 (s, 1H), 7.70 (d, J = 7.8 Hz, 1H), 7.45 (d, J = 4.4 Hz, 1H), 7.37 (d, J = 7.7 Hz, 1H), 5.11 (dd, J = 13.3, 5.1 Hz, 1H), 4.45 (d, J = 17.2 Hz, 1H), 4.32 (d, J = 17.2 Hz, 1H), 3.27 (dd, J = 13.3, 3.4 Hz, 1H), 3.21 (s, 1H), 3.07 (s, 1H), 2.92 (ddd, J = 17.2, 13.6, 5.4 Hz, 1H), 2.65-2.56 (m, 1H), 2.39 (qd, J = 13.5, 4.4 Hz, 2H), 2.13-2.04 (m, 1H), 2.00 (ddd, J = 10.5, 5.6, 2.9 Hz, 1H), 1.92-1.78 (m, 2H), 1.74 (q, J = 4.7, 3.9 Hz, 3H), 1.66-1.45 (m, 6H), 1.36 (dt, J = 28.6, 11.4 Hz, 3H), 1.10-0.99 (m, 2H), 0.97 (d, J = 7.0 Hz, 3H), 0.88 (d, J = 6.4 Hz, 1H). | 4-methyl-cyclo-hexanone |
| 281 | 3-(1-oxo-5-(((1R,2S)-2-(spiro[2.4]heptan-5-ylamino)cyclohexyl)methyl)isoindolin-2-yl)piperidine-2,6-dione (Isomer 1) | 450.3 | ¹H NMR (400 MHz, Methanol-d4) δ 7.79 (d, J = 7.8 Hz, 1H), 7.52-7.32 (m, 2H), 5.18 (dd, J = 13.3, 5.2 Hz, 1H), 4.60-4.41 (m, 2H), 3.97 (p, J = 7.8 Hz, 1H), 3.10 (d, J = 10.4 Hz, 1H), 2.97-2.77 (m, 2H), 2.62-2.46 (m, 2H), 2.37-2.13 (m, 3H), 2.03-1.75 (m, 6H), 1.76-1.42 (m, 6H), 1.22 (q, J = 10.5, 9.9 Hz, 2H), 0.68-0.43 (m, 4H). | spiro[2.4]heptan-6-one |
| 282 | 3-(5-(((2R,3S)-3-((4-(difluoromethyl)cyclohexyl)amino)tetrahydro-2H-pyran-2-yl)methyl)-4-fluoro-1-oxoisoindolin-2-yl)piperidine-2,6-dione (Isomer 1) | 508.3 | ¹H NMR (400 MHz, Methanol-d4) δ 7.67-7.51 (m, 2H), 5.98 (d, J = 4.6 Hz, 1H), 5.17 (dd, J = 13.4, 5.2 Hz, 1H), 4.66-4.50 (m, 2H), 3.97-3.86 (m, 2H), 3.51-3.39 (m, 2H), 3.18 (d, J = 4.6 Hz, 1H), 2.97-2.87 (m, 1H), 2.88-2.78 (m, 1H), 2.59-2.48 (m, 1H), 2.40-2.31 (m, 1H), 2.25-2.14 (m, 1H), 2.02 (q, J = 22.9, 19.5 Hz, 4H), 1.91-1.61 (m, 7H). | I-41; 4-(difluoro-methyl)cyclo-hexanone |

TABLE 15-continued

| Example | Structure | ES/MS m/z | ¹H-NMR | Changes to Procedure 24: Different Reagents/ Starting Materials |
|---|---|---|---|---|
| 283 | 3-(5-(((2R,3S)-3-((4-(difluoromethyl)cyclohexyl)amino)tetrahydro-2H-pyran-2-yl)methyl)-4-fluoro-1-oxoisoindolin-2-yl)piperidine-2,6-dione (Isomer 2) | 508.3 | 1H NMR (400 MHz, Methanol-d4) δ 7.65-7.45 (m, 2H), 5.72 (d, J = 4.1 Hz, 1H), 5.17 (dd, J = 13.3, 5.1 Hz, 1H), 4.64-4.48 (m, 2H), 3.96-3.82 (m, 2H), 3.21-3.08 (m, 2H), 2.93 (ddd, J = 18.4, 13.4, 5.3 Hz, 1H), 2.87-2.76 (m, 1H), 2.53 (qd, J = 13.3, 4.8 Hz, 1H), 2.44-2.13 (m, 4H), 2.02 (d, J = 13.2 Hz, 2H), 1.91-1.64 (m, 4H), 1.57 (q, J = 13.6, 12.8 Hz, 1H), 1.40 (p, J = 13.3, 12.8 Hz, 3H). | I-41; 4-(difluoromethyl)cyclohexanone |
| 284 | 3-(4-fluoro-5-(((2R,3S)-3-((4-isopropoxycyclohexyl)amino)tetrahydro-2H-pyran-2-yl)methyl)-1-oxoisoindolin-2-yl)piperidine-2,6-dione (Isomer 1) | 516.4 | 1H NMR (400 MHz, DMSO-d6) δ 11.01 (s, 1H), 8.60 (s, 1H), 8.22 (s, 1H), 7.57 (d, J = 7.7 Hz, 1H), 7.53 (d, J = 6.5 Hz, 1H), 5.11 (dd, J = 13.3, 5.1 Hz, 1H), 4.63-4.29 (m, 2H), 3.84-3.73 (m, 2H), 3.68 (h, J = 6.1 Hz, 1H), 3.31-3.12 (m, 5H), 3.06-2.80 (m, 2H), 2.70-2.56 (m, 1H), 2.48-2.35 (m, 1H), 2.21 (dd, J = 9.3, 5.6 Hz, 1H), 1.80-1.47 (m, 3H), 1.47-1.33 (m, 1H), 1.32-1.15 (m, 2H), 1.06 (d, J = 6.1 Hz, 6H). | I-41; 4-isopropoxycyclohexanone |
| 285 | 3-(4-fluoro-5-(((2R,3S)-3-((4-isopropoxycyclohexyl)amino)tetrahydro-2H-pyran-2-yl)methyl)-1-oxoisoindolin-2-yl)piperidine-2,6-dione (Isomer 1) | 516.4 | 1H NMR (400 MHz, DMSO-d6) δ 11.01 (s, 1H), 8.48 (s, 1H), 8.17 (s, 1H), 7.58 (d, J = 7.7 Hz, 1H), 7.52 (t, J = 7.0 Hz, 1H), 5.11 (dd, J = 13.3, 5.1 Hz, 1H), 4.60-4.32 (m, 2H), 3.75 (q, J = 10.7, 8.3 Hz, 3H), 3.69-3.58 (m, 2H), 3.26 (d, J = 12.5 Hz, 5H), 3.07-2.85 (m, 2H), 2.61 (d, J = 16.7 Hz, 1H), 2.43 (dd, J = 13.1, 4.6 Hz, 1H), 2.22 (d, J = 10.7 Hz, 1H), 2.07-1.95 (m, 1H), 1.79 (q, J = 13.1, 12.1 Hz, 4H), 1.62 (t, J = 11.0 Hz, 2H), 1.53-1.36 (m, 2H), 1.09 (d, J = 6.0 Hz, 6H). | I-41; 4-isopropoxycyclohexanone |

Procedure 25, Examples 286
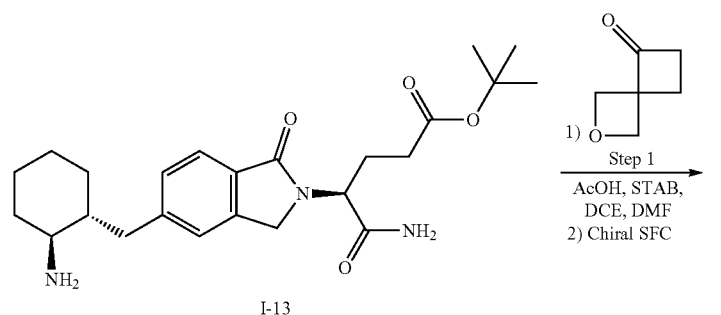
I-13
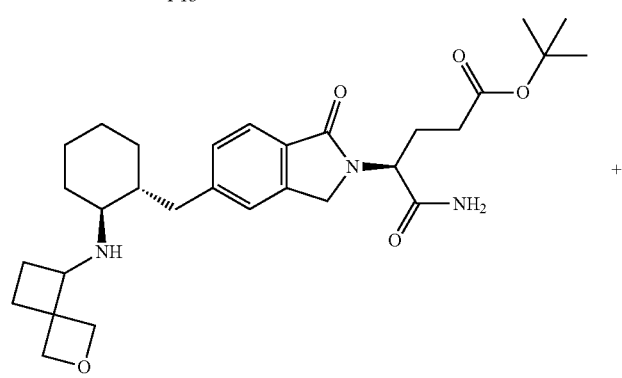
Isomer 1 +
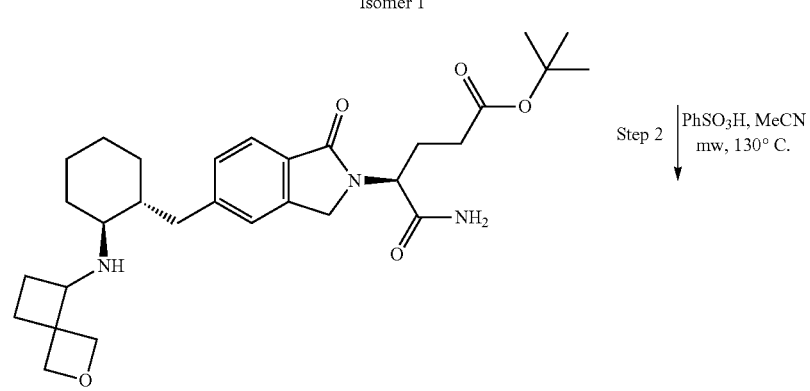
Isomer 2
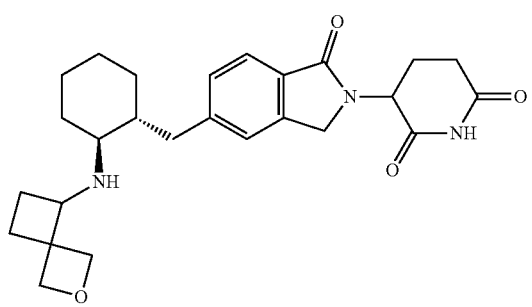
Example 286

Step 1: Preparation of tert-butyl (4S)-4-(5-(((1R, 2S)-2-((2-oxaspiro[3.3]heptan-5-yl)amino)cyclohexyl)methyl)-1-oxoisoindolin-2-yl)-5-amino-5-oxopentanoate (Isomer 1) and tert-butyl (4S)-4-(5-(((1R,2S)-2-((2-oxaspiro[3.3]heptan-5-yl)amino)cyclohexyl)methyl)-1-oxoisoindolin-2-yl)-5-amino-5-oxopentanoate (Isomer 2)

To tert-butyl (S)-5-amino-4-(5-(((1R,2S)-2-aminocyclohexyl)methyl)-1-oxoisoindolin-2-yl)-5-oxopentanoate (I-13) (86 mg, 0.20 mmol) in DCE (2.5 mL) and DMF (1.5 mL) was added 2-oxaspiro[3.3]heptan-5-one (29 mg, 0.26 mmol) followed by acetic acid (34 µL, 0.60 mmol). The reaction was stirred at room temperature for 2 minutes after which sodium triacetoxyborohydride (127 mg, 0.60 mmol) was added in one portion. The reaction was stirred at room temperature overnight. Following this time, additional 2-oxaspiro[3.3]heptan-5-one (100 mg, 0.69 mmol) was added and the reaction continued overnight. The reaction was then quenched with sat. aqueous NaHCO$_3$ and extracted with CH$_2$Cl$_2$(×2). The combined organics were washed with water and brine, dried over Na$_2$SO$_4$ and concentrated to give the crude product which was purified by SiO$_2$ column chromatography (eluent: hexanes/EtOAc then EtOAc MeOH*10% NH$_4$OH). The material was subjected to further purification by chiral SFC chromatography (column: CELL-2 250×21.2 mm, 5 µm, eluent: 45% MeOH-DEA) to obtain tert-butyl (4S)-4-(5-(((1R,2S)-2-((2-oxaspiro[3.3]heptan-5-yl)amino)cyclohexyl)methyl)-1-oxoisoindolin-2-yl)-5-amino-5-oxopentanoate (Isomer 1) and tert-butyl (4S)-4-(5-(((1R,2S)-2-((2-oxaspiro[3.3]heptan-5-yl)amino)cyclohexyl)methyl)-1-oxoisoindolin-2-yl)-5-amino-5-oxopentanoate (Isomer 2). Isomer 1 was carried forward into the next step.

Step 2a: Preparation of 3-(5-(((1R,2S)-2-((2-oxaspiro[3.3]heptan-5-yl)amino)cyclohexyl)methyl)-1-oxoisoindolin-2-yl)piperidine-2,6-dione (Example 286)

To a solution of tert-butyl (4S)-4-(5-(((1R,2S)-2-((2-oxaspiro[3.3]heptan-5-yl)amino) cyclohexyl)methyl)-1-oxoisoindolin-2-yl)-5-amino-5-oxopentanoate (Isomer 1, 21 mg, 0.04 mmol) in MeCN (1 mL) was added benzene sulfonic acid (19 mg, 0.12 mmol). The reaction was then heated under microwave irradiation at 130° C. for 10 minutes. Following this time, the reaction mixture was diluted with DMSO and purified by RP-HPLC (eluent: MeCN/water gradient with 0.1% TFA) to afford the title product. ES/MS: 452.3 (M+H$^+$). $^1$H NMR (400 MHz, Methanol-d4) δ 7.76 (d, J=7.8 Hz, 1H), 7.46 (s, 1H), 7.41 (d, J=7.9 Hz, 1H), 6.08 (s, 1H), 5.15 (dd, J=13.3, 5.2 Hz, 1H), 4.61 (d, J=7.9 Hz, 1H), 4.51-4.37 (m, 4H), 3.26 (d, J=4.8 Hz, 1H), 3.23-3.13 (m, 1H), 2.98-2.86 (m, 1H), 2.78 (ddd, J=17.5, 4.6, 2.4 Hz, 1H), 2.60 (dd, J=13.3, 10.2 Hz, 2H), 2.47 (td, J=13.4, 4.8 Hz, 4H), 2.30-2.13 (m, 2H), 2.13-1.92 (m, 2H), 1.86-1.37 (m, 5H), 1.37-1.08 (m, 2H).

The following Examples were made using the general route described in Procedure 25 and are shown below in Table 16. To prepare the below Examples, different reagents/starting materials were used than some of those described in Procedure 25 and are noted in the last column of Table 16—"Changes to Procedure 25: Different Reagents/Starting Materials". A person of ordinary skill in the art will readily recognize which reagents/starting materials of Procedure 25 were replaced with the different reagents/starting materials noted below.

TABLE 16

| Example | Structure | ES/MS m/z | $^1$H-NMR | Changes to Procedure 25: Different Reagents/ Starting Materials |
|---|---|---|---|---|
| 287 | 3-(4-fluoro-1-oxo-5-(((1R,2S)-2-((1-(tetrahydro-2H-pyran-4-yl)ethyl)amino)cyclohexyl)methyl)isoindolin-2-yl)piperidine-2,6-dione (Isomer 1) | 486.4 | $^1$H NMR (400 MHz, DMSO-d6) δ 11.01 (s, 1H), 7.83 (s, 2H), 7.60 (d, J = 7.7 Hz, 1H), 7.48 (t, J = 6.9 Hz, 1H), 5.12 (dd, J = 13.3, 5.1 Hz, 1H), 4.56 (d, J = 17.4 Hz, 1H), 4.39 (d, J = 17.4 Hz, 1H), 3.97-3.88 (m, 2H), 3.27 (tt, J = 11.6, 2.5 Hz, 4H), 3.13 (s, 1H), 2.92 (ddd, J = 17.3, 13.6, 5.4 Hz, 1H), 2.67-2.52 (m, 2H), 2.50-2.35 (m, 1H), 2.11 (d, J = 11.2 Hz, 1H), 2.05-1.79 (m, 3H), 1.77-1.41 (m, 5H), 1.41-1.28(m, 3H), 1.24 (d, J = 6.6 Hz, 3H), 1.10 (q, J = 9.9, 9.2 Hz, 2H). | Step 1: I-14; 1-tetrahydropyran-4-ylethanone Chiral SFC conditions: AD-H 5 µm-21 × 250 mm, co-solvent: IPA-NH$_3$ (30%) [peak 1] |

TABLE 16-continued

| Example | Structure | ES/MS m/z | ¹H-NMR | Changes to Procedure 25: Different Reagents/Starting Materials |
|---|---|---|---|---|
| 288 | 3-(4-fluoro-1-oxo-5-(((1R,2S)-2-((1-(tetrahydro-2H-pyran-4-yl)ethyl)amino)cyclohexyl)methyl)isoindolin-2-yl)piperidine-2,6-dione (Isomer 1) | 486.4 | ¹H NMR (400 MHz, DMSO-d6) δ 11.01 (s, 1H), 8.38-8.30 (m, 1H), 7.76 (d, J = 13.3 Hz, 1H), 7.60 (d, J = 7.6 Hz, 1H), 7.51 (t, J = 7.0 Hz, 1H), 5.12 (dd, J = 13.3, 5.1 Hz, 1H), 4.56 (d, J = 17.4 Hz, 1H), 4.39 (d, J = 17.4 Hz, 1H), 3.91 (ddd, J = 14.8, 11.1, 4.0 Hz, 2H), 3.32 (dddd, J = 18.2, 11.6, 8.3, 3.9 Hz, 3H), 3.18 (dt, J = 12.9, 6.2 Hz, 2H), 2.92 (ddd, J = 17.3, 13.6, 5.4 Hz, 1H), 2.71-2.52 (m, 3H), 2.50-2.35 (m, 1H), 2.13 1.91 (m, 4H), 1.72 (d, J = 12.9 Hz, 1H), 1.57 (s, 1H), 1.56-1.38 (m, 4H), 1.36 (dt, J = 12.2, 6.0 Hz, 2H), 1.25 (d, J = 6.6 Hz, 3H), 1.09 (t, J = 9.1 Hz, 2H). | Step 1: I-14; 1-tetrahydropyran-4-ylethanone Chiral SFC conditions: AD-H 5 μm-21 × 250 mm, co-solvent: IPA—NH₃ (30%) [peak 2] |
| 289 | 3-(4-fluoro-5-(((2R,3S)-3-((4-fluorocyclohexyl)amino)tetrahydro-2H-pyran-2-yl)methyl)-1-oxoisoindolin-2-yl)piperidine-2,6-dione (Isomer 1) | 476.4 | ¹H NMR (400 MHz, DMSO-d6) δ 11.01 (s, 1H), 8.61 (s, 1H), 8.21 (s, 1H), 7.61-7.48 (m, 2H), 5.11 (dd, J = 13.3, 5.1 Hz, 1H), 4.70-4.28 (m, 3H), 3.87-3.66 (m, 2H), 3.25 (t, J = 14.4 Hz, 3H), 3.06-2.85 (m, 2H), 2.65-2.52 (m, 2H), 2.50-2.35 (m, 1H), 2.29-1.91 (m, 4H), 1.77-1.31 (m, 7H), 1.23 (s, 1H). | Step 1: I-41; 4-fluorocyclohexanone Chiral SFC conditions: AD-H 5 μm-21 × 250 mm, co-solvent: MeOH (25%) [peak 1] |
| 290 | 3-(4-fluoro-5-(((2R,3S)-3-((4-fluorocyclohexyl)amino)tetrahydro-2H-pyran-2-yl)methyl)-1-oxoisoindolin-2-yl)piperidine-2,6-dione (Isomer 2) | 476.4 | ¹H NMR (400 MHz, DMSO-d6) δ 11.01 (s, 1H), 8.63 (s, 1H), 8.25 (s, 1H), 7.61-7.48 (m, 2H), 7.40 (s, 1H), 5.11 (dd, J = 13.3, 5.1 Hz, 1H), 4.93 (s, 1H), 4.81 (s, 1H), 4.61-4.50 (m, 1H), 4.38 (dd, J = 17.4, 3.5 Hz, 1H), 3.76 (qd, J = 9.4, 7.7, 5.1 Hz, 2H), 3.36 (s, 1H), 3.31-3.20 (m, 3H), 3.05-2.85 (m, 2H), 2.65-2.56 (m, 1H), 2.50-2.35 (m, 1H), 2.24 (d, J = 10.0 Hz, 1H), 2.12-1.83 (m, 2H), 1.82-1.49 (m, 5H), 1.23 (s, 2H). | Step 1: I-41; 4-fluorocyclohexanone Chiral SFC conditions: AD-H 5 μm-21 × 250 mm, co-solvent: MeOH (25%) [peak 2] |
| 291 | 3-(4-fluoro-1-oxo-5-(((2R,3S)-3-((1-(tetrahydro-2H-pyran-4-yl)ethyl)amino)tetrahydro-2H-pyran-2-yl)methyl)isoindolin-2-yl)piperidine-2,6-dione (Isomer 1) | 488.4 | ¹H NMR (400 MHz, DMSO-d6) δ 11.01 (s, 1H), 8.08 (s, 2H), 7.63-7.47 (m, 2H), 5.11 (dd, J = 13.3, 5.1 Hz, 1H), 4.61-4.51 (m, 1H), 4.43-4.33 (m, 1H), 4.00-3.74 (m, 3H), 3.35-3.20 (m, 5H), 3.07-2.85 (m, 2H), 2.59 (d, J = 35.6 Hz, 1H), 2.50-2.35 (m, 1H), 2.24 (d, J = 11.9 Hz, 1H), 2.06-1.95 (m, 1H), 1.95-1.85 (m, 1H), 1.79-1.48 (m, 5H), 1.43-1.29 (m, 2H), 1.23 (d, J = 6.5 Hz, 3H). | Step 1: I-41; 1-tetrahydropyran-4-ylethanone Chiral SFC conditions: IG 5 μm-21 × 250 mm, co-solvent: IPA-NH₃ (30%) [peak 1] |

TABLE 16-continued

| Example | Structure | ES/MS m/z | ¹H-NMR | Changes to Procedure 25: Different Reagents/Starting Materials |
|---|---|---|---|---|
| 292 | 3-(5-(((2R,3S)-3-(sec-butylamino)tetrahydro-2H-pyran-2-yl)methyl)-4-fluoro-1-oxoisoindolin-2-yl)piperidine-2,6-dione (Isomer 1) | 432.3 | ¹H NMR (400 MHz, DMSO-d6) δ 11.01 (s, 1H), 8.47 (s, 1H), 8.23 (s, 1H), 7.60-7.47 (m, 2H), 7.41 (s, 1H), 5.11 (dd, J = 13.3, 5.1 Hz, 1H), 4.56 (dd, J = 17.4, 5.2 Hz, 1H), 4.37 (dd, J = 17.4, 3.1 Hz, 1H), 3.82-3.72 (m, 2H), 3.33-3.18 (m, 3H), 3.03-2.85 (m, 2H), 2.65-2.56 (m, 1H), 2.50-2.35 (m, 1H), 2.26-1.96 (m, 1H), 1.86-1.71 (m, 2H), 1.68-1.46 (m, 2H), 1.28-1.20 (m, 5H), 0.95 (t, J = 7.4 Hz, 3H). | Step 1: I-41; 2-butanone Chiral SFC conditions: Cell-2 5 µm-21 × 250 mm, co-solvent: EtOH (20%) [peak 1] |
| 293 | 3-(5-(((2R,3S)-3-(sec-butylamino)tetrahydro-2H-pyran-2-yl)methyl)-4-fluoro-1-oxoisoindolin-2-yl)piperidine-2,6-dione (Isomer 2) | 432.3 | ¹H NMR (400 MHz, DMSO-d6) δ 11.01 (s, 1H), 8.56 (s, 1H), 8.21 (s, 1H), 7.61-7.47 (m, 2H), 7.41 (s, 1H), 5.11 (dd, J = 13.3, 5.1 Hz, 1H), 4.56 (dd, J = 17.4, 5.4 Hz, 1H), 4.37 (dd, J = 17.3, 3.2 Hz, 1H), 3.82-3.74 (m, 2H), 3.36-3.18 (m, 2H), 3.05-2.85 (m, 2H), 2.61 (d, J = 17.8 Hz, 1H), 2.50-2.35 (m, 1H), 2.23-1.95 (m, 1H), 1.90-1.68 (m, 2H), 1.65-1.53 (m, 2H), 1.52-1.34 (m, 1H), 1.32-1.20 (m, 5H), 0.99-0.88 (m, 3H). | Step 1: I-41; 2-butanone Chiral SFC conditions: Cell-2 5 µm-21 × 250 mm, co-solvent: EtOH (20%) [peak 2] |
| 294 | 3-(5-(((1R,2S)-2-(sec-butylamino)cyclohexyl)methyl)-4-fluoro-1-oxoisoindolin-2-yl)piperidine-2,6-dione (Isomer 1) | 430.3 | ¹H NMR (400 MHz, DMSO-d6) δ 11.01 (s, 1H), 8.35-8.12 (m, 1H), 7.89 (s, 1H), 7.60 (d, J = 7.7 Hz, 1H), 7.53-7.44 (m, 1H), 5.11 (dd, J = 13.2, 5.1 Hz, 1H), 4.56 (dd, J = 17.3, 3.8 Hz, 1H), 4.39 (d, J = 17.3 Hz, 1H), 3.22 (dd, J = 38.1, 25.6 Hz, 3H), 2.99-2.85 (m, 1H), 2.61 (d, J = 15.3 Hz, 2H), 2.48-2.36 (m, 1H), 2.11-2.06 (m, 1H), 2.04-1.96 (m, 1H), 1.88-1.67 (m, 4H), 1.59-1.32 (m, 4H), 1.27 (dd, J = 16.8, 6.4 Hz, 3H), 1.07 (t, J = 9.5 Hz, 2H), 1.00-0.89 (m, 3H). | Step 1: I-14; 2-butanone Chiral SFC conditions: IA 5 µm-21 × 250 mm, co-solvent: IPA-NH₃ (30%) [peak 1] |
| 295 | 3-(5-(((1R,2S)-2-(sec-butylamino)cyclohexyl)methyl)-4-fluoro-1-oxoisoindolin-2-yl)piperidine-2,6-dione (Isomer 2) | 430.3 | ¹H NMR (400 MHz, DMSO-d6) δ 11.01 (s, 1H), 8.48-8.28 (m, 1H), 8.02 (s, 1H), 7.58 (d, J = 7.6 Hz, 1H), 7.49 (td, J = 6.9, 3.4 Hz, 1H), 5.11 (dd, J = 13.3, 5.1 Hz, 1H), 4.56 (dd, J = 17.4, 3.7 Hz, 1H), 4.39 (dd, J = 17.4, 3.5 Hz, 1H), 3.31-3.17 (m, 2H), 3.13 (s, 1H), 2.99-2.85 (m, 1H), 2.66-2.53 (m, 2H), 2.51-2.35 (m, 1H), 2.13-1.95 (m, 2H), 1.93-1.68 (m, 4H), 1.64-1.32 (m, 4H), 1.27 (dd, J = 17.1, 6.4 Hz, 3H), 1.15-1.02 (m, 2H), 1.04-0.89 (m, 3H). | Step 1: I-14; 2-butanone Chiral SFC conditions: IA 5 µm-21 × 250 mm, co-solvent: IPA-NH₃ (30%) [peak 1] |

TABLE 16-continued

| Example | Structure | ES/MS m/z | ¹H-NMR | Changes to Procedure 25: Different Reagents/Starting Materials |
|---|---|---|---|---|
| 296 | 3-(4-fluoro-1-oxo-5-(((2R,3S)-3-((tetrahydrofuran-3-yl)amino)tetrahydro-2H-pyran-2-yl)methyl)isoindolin-2-yl)piperidine-2,6-dione (Isomer 1) | 446.3 | ¹H NMR (400 MHz, DMSO-d6) δ 11.01 (s, 1H), 8.99 (s, 1H), 8.60 (s, 1H), 7.61-7.49 (m, 2H), 5.12 (dd, J = 13.3, 5.1 Hz, 1H), 4.55 (d, J = 17.4 Hz, 1H), 4.43-4.33 (m, 1H), 3.99-3.74 (m, 4H), 3.66 (q, J = 7.8 Hz, 1H), 3.31 (t, J = 8.8 Hz, 1H), 3.23 (d, J = 12.9 Hz, 2H), 3.09 (dd, J = 14.3, 10.3 Hz, 1H), 2.92 (ddd, J = 17.3, 13.6, 5.4 Hz, 1H), 2.59 (d, J = 35.5 Hz, 2H), 2.50-2.35 (m, 1H), 2.29 (tdd, J = 16.3, 10.7, 6.6 Hz, 2H), 2.07-1.94 (m, 2H), 1.75-1.68 (m, 3H), 1.59-1.51 (m, 1H). | Step 1: I-41; tetrahydrofuran-3-one Chiral SFC conditions: AD-H 5 μm-21 × 250 mm, co-solvent: EtOH—NH₃ (20%) [peak 1] |
| 297 | 3-(4-fluoro-1-oxo-5-(((2R,3S)-3-((tetrahydrofuran-3-yl)amino)tetrahydro-2H-pyran-2-yl)methyl)isoindolin-2-yl)piperidine-2,6-dione (Isomer 2) | 446.3 | ¹H NMR (400 MHz, DMSO-d6) δ 11.01 (s, 1H), 8.94 (s, 1H), 8.70 (s, 1H), 7.61-7.48 (m, 2H), 5.11 (dd, J = 13.3, 5.1 Hz, 1H), 4.55 (d, J = 17.3 Hz, 1H), 4.38 (d, J = 17.3 Hz, 1H), 4.05 (s, 1H), 3.94 (td, J = 8.3, 5.0 Hz, 1H), 3.88-3.73 (m, 4H), 3.72-3.61 (m, 1H), 3.36-3.19 (m, 3H), 3.09 (dd, J = 14.3, 10.3 Hz, 1H), 2.92 (ddd, J = 17.2, 13.6, 5.4 Hz, 1H), 2.65-2.52 (m, 1H), 2.50-2.35 (m, 1H), 2.33-2.17 (m, 2H), 2.10-1.95 (m, 2H), 1.77-1.65 (m, 2H), 1.60-1.51 (m, 1H). | Step 1: I-41; tetrahydrofuran-3-one Chiral SFC conditions: AD-H 5 μm-21 × 250 mm, co-solvent: EtOH—NH₃ (20%) [peak 2] |
| 298 | 3-(4-fluoro-1-oxo-5-(((2R,3S)-3-((1-(tetrahydro-2H-pyran-4-yl)ethyl)amino)tetrahydro-2H-pyran-2-yl)methyl)isoindolin-2-yl)piperidine-2,6-dione (Isomer 2) | 488.4 | ¹H NMR (400 MHz, DMSO-d6) δ 11.01 (s, 1H), 8.55 (d, J = 8.7 Hz, 1H), 7.94 (d, J = 12.6 Hz, 1H), 7.62-7.50 (m, 2H), 5.11 (dd, J = 13.3, 5.1 Hz, 1H), 4.55 (d, J = 17.4 Hz, 1H), 4.38 (d, J = 17.4 Hz, 1H), 3.97-3.75 (m, 4H), 3.38-3.18 (m, 5H), 3.08 (dd, J = 14.2, 10.3 Hz, 1H), 2.92 (ddd, J = 17.3, 13.6, 5.4 Hz, 1H), 2.58 (d, J = 35.6 Hz, 1H), 2.50-2.35 (m, 1H), 2.21 (d, J = 9.9 Hz, 1H), 2.05-1.96 (m, 2H), 1.82-1.46 (m, 5H), 1.43-1.32 (m, 2H), 1.24 (d, J = 6.6 Hz, 3H). | Step 1: I-41; 1-tetrahydropyran-4-ylethanone Chiral SFC conditions: IG 5 μm-21 × 250 mm, co-solvent: IPA-NH₃ (30%) [peak 2] |
| 299 | 3-(5-(((1R,2S)-2-(sec-butylamino)cyclohexyl)methyl)-1-oxoisoindolin-2-yl)piperidine-2,6-dione (Isomer 1) | 412.4 | ¹H NMR (400 MHz, DMSO-d6) δ 10.99 (s, 1H), 8.20 (s, 1H), 7.99 (s, 1H), 7.69 (d, J = 7.7 Hz, 1H), 7.44 (s, 1H), 7.36 (dd, J = 7.8, 1.4 Hz, 1H), 5.11 (dd, J = 13.3, 5.1 Hz, 1H), 4.45 (d, J = 17.2 Hz, 1H), 4.32 (d, J = 17.3 Hz, 1H), 3.34-3.25 (m, 1H), 3.05 (s, 1H), 2.99, 2.85 (m, 1H), 2.65-2.56 (m, 1H), 2.47-2.31 (m, 2H), 2.09 (d, J = 11.0 Hz, 1H), 2.00 (ddd, J = 9.6, 5.4, 2.6 Hz, 1H), 1.91-1.68 (m, 3H), 1.63-1.47 (m, 3H), 1.43-1.25 (m, 2H), 1.25 (d, J = 6.4 Hz, 3H), 1.11-0.98 (m, 2H), 0.95 (t, J = 7.4 Hz, 3H). | Step 1: 2-butanone Chiral SFC conditions: Cell-2 5 μm-21 × 250 mm, co-solvent: EtOH—NH₃ (30%) [peak 1] |

TABLE 16-continued

| Example | Structure | ES/MS m/z | ¹H-NMR | Changes to Procedure 25: Different Reagents/Starting Materials |
|---|---|---|---|---|
| 300 | 3-(5-(((1R,2S)-2-(sec-butylamino)cyclohexyl)methyl)-1-oxoisoindolin-2-yl)piperidine-2,6-dione (Isomer 2) | 412.4 | ¹H NMR (400 MHz, DMSO-d6) δ 10.99 (s, 1H), 8.30 (s, 1H), 7.96 (s, 1H), 7.69 (d, J = 7.7 Hz, 1H), 7.45 (s, 1H), 7.36 (dd, J = 7.8, 1.4 Hz, 1H), 5.11 (dd, J = 13.3, 5.1 Hz, 1H), 4.45 (d, J = 17.3 Hz, 1H), 4.32 (d, J = 17.3 Hz, 1H), 3.31-3.22 (m, 2H), 3.06 (s, 1H), 2.99-2.85 (m, 1H), 2.65-2.56 (m, 1H), 2.47-2.31 (m, 2H), 2.11-1.96 (m, 2H), 1.89-1.77 (m, 2H), 1.72 (d, J = 12.5 Hz, 1H), 1.58-1.32 (m, 4H), 1.29 (d, J = 6.4 Hz, 3H), 1.08-0.98 (m, 2H), 0.93 (t, J = 7.4 Hz, 3H). | Step 1: 2-butanone Chiral SFC conditions: Cell-2 5 μm-21 × 250 mm, co-solvent: EtOH—NH₃ (30%) [peak 2] |

Procedure 26, Examples 301

3-(5-(((2R,3S)-3-((4,4-difluorocyclohexyl-1-d)amino)tetrahydro-2H-pyran-2-yl)methyl)-4-fluoro-1-oxoisoindolin-2-yl)piperidine-2,6-dione (Example 301)

3-(5-(((2R,3S)-3-aminotetrahydro-2H-pyran-2-yl)methyl)-4-fluoro-1-oxoisoindolin-2-yl)piperidine-2,6-dione (I-12) (30 mg, 0.06 mmol) and 4,4-difluorocyclohexan-1-one (75 mg, 0.56 mmol) were taken up in DMF (0.5 mL) and acetic acid (32 μL, 0.56 mmol) was added. The mixture was stirred at room temperature overnight. Following this time, the reaction was cooled to 0° C. and MeOH (0.5 mL) was added followed by sodium borodeuteride (12 mg, 0.28 mmol). After 5 minutes, the reaction was diluted with DMSO and subjected to RP-HPLC (eluent: MeCN/water gradient with 0.1% TFA). Product containing fractions were frozen and lyophilized to give the title product. ES/MS: 495.3 (M+H⁺). ¹H NMR (400 MHz, DMSO-d6) δ 11.01 (s, 1H), 8.70 (d, J=10.4 Hz, 1H), 8.30 (d, J=12.2 Hz, 1H), 7.58 (d, J=7.7 Hz, 1H), 7.55-7.49 (m, 1H), 5.11 (dd, J=13.3, 5.1 Hz, 1H), 4.59-4.34 (m, 2H), 3.83-3.71 (m, 1H), 3.24 (d, J=13.7 Hz, 1H), 3.07-2.84 (m, 2H), 2.63 (t, J=17.2 Hz, 1H), 2.42 (td, J=13.2, 4.5 Hz, 1H), 2.31-2.06 (m, 3H), 1.98 (dddd, J=20.1, 12.7, 7.6, 4.1 Hz, 3H), 1.80 (ddd, J=18.7, 8.9, 4.6 Hz, 2H), 1.69 (ddd, J=12.9, 8.1, 4.7 Hz, 3H), 1.61 (d, J=6.9 Hz, 1H), 1.52 (ddd, J=13.2, 8.5, 4.6 Hz, 4H).

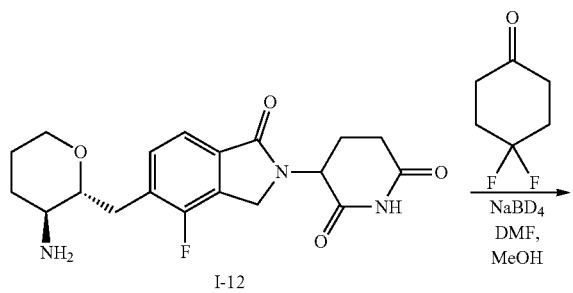

I-12

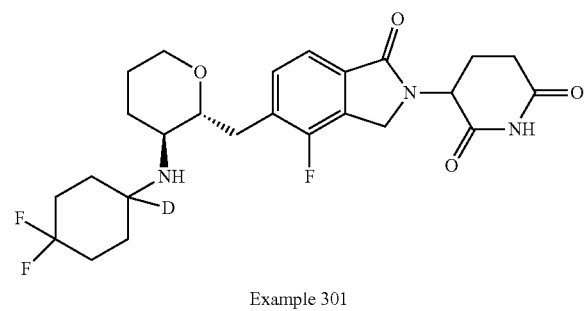

Example 301

Procedure 27, Examples 302

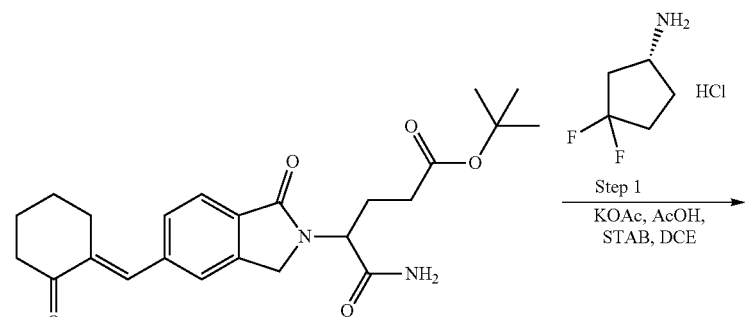

I-42

-continued
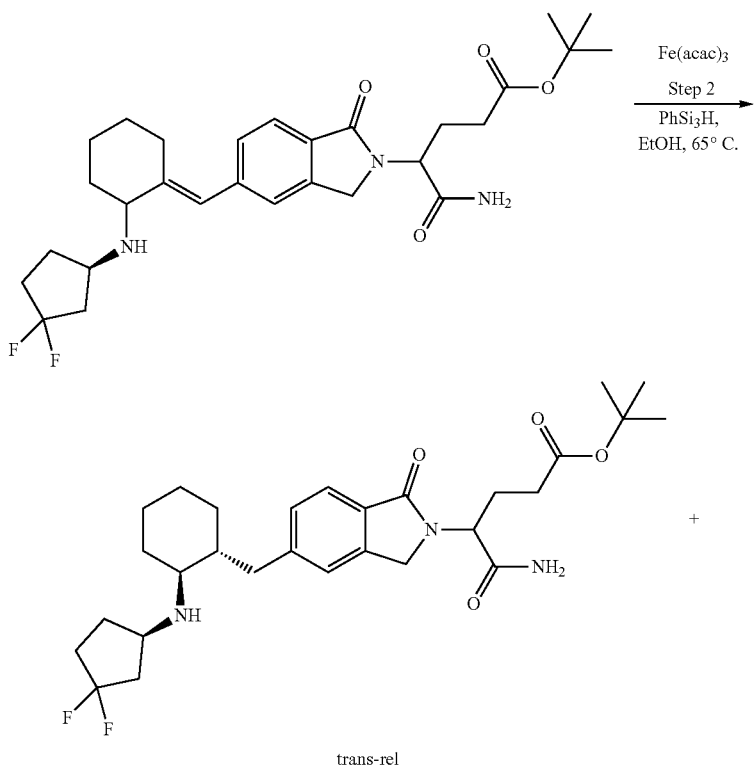
trans-rel
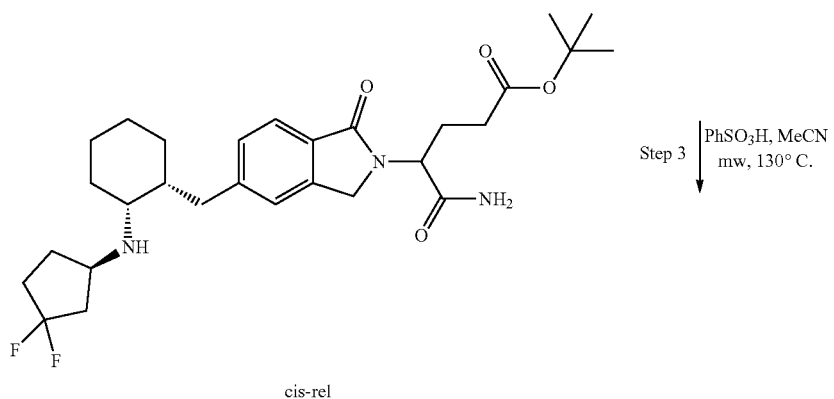
cis-rel
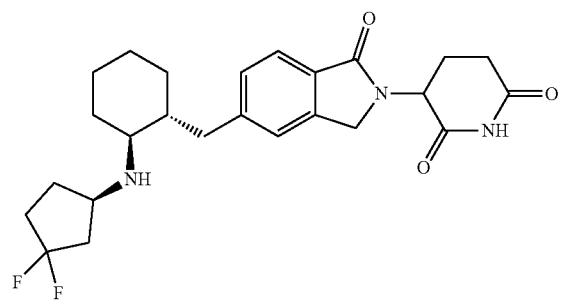
Example 302

Step 1: Preparation of tert-butyl 5-amino-4-(5-((E)-(2-(((R)-3,3-difluorocyclopentyl)amino)cyclohexylidene)methyl)-1-oxoisoindolin-2-yl)-5-oxopentanoate To a mixture of I-42 (75 mg, 0.18 mmol) and (1R)-3,3-difluorocyclopentanamine hydrochloride (55 mg, 0.35 mmol) and potassium acetate (35 mg, 0.35 mmol) was added DCE (2 mL) followed by AcOH (40 µL, 0.7 mmol). The mixture was sonicated to dissolve solids and then stirred at r.t for 10 minutes. Sodium triacetoxybotohydride (75 mg, 0.35 mmol) was then added and the reaction stirred overnight. Following this time, the reaction was then quenched with sat. aqueous NaHCO₃ and extracted with CH₂Cl₂(×2). The combined organics were washed with water and brine, dried over Na₂SO₄ and concentrated in vacuo. The crude product was purified by SiO₂ column chromatography (eluent: hexanes/EtOAc then EtOAc/MeOH). Desired fractions were combined and concentrated to give the title product.

Step 2: Preparation of tert-butyl 5-amino-4-(5-(((1R,2S)-rel-2-(((R)-3,3-difluorocyclopentyl)amino)cyclohexyl)methyl)-1-oxoisoindolin-2-yl)-5-oxopentanoate tert-Butyl 5-amino-4-(5-((E)-(2-(((R)-3,3-difluorocyclopentyl) amino) cyclohexylidene)methyl)-1-oxoisoindolin-2-yl)-5-oxopentanoate (59 mg, 0.1 mmol) was taken up in acetonitrile (1 mL) was added benzenesulfonic acid (16 mg, 0.1 mmol). The reaction was then heated to 130° C. under microwave irradiation for 20 minutes. Following this time, the reaction mixture was diluted with DMSO and purified by RP-HPLC (eluent: MeCN/water gradient with 0.1% TFA) to afford the title product. ES/MS: 460.3 (M+H⁺). ¹H NMR (400 MHz, Methanol-d4) δ 7.77 (d, J=7.8 Hz, 1H), 7.45 (s, 1H), 7.40 (d, J=7.9 Hz, 1H), 5.16 (dd, J=13.3, 5.1 Hz, 1H), 4.56-4.41 (m, 2H), 4.05 (dd, J=15.0, 7.5 Hz, 1H), 3.19-3.05 (m, 2H), 2.91 (ddd, J=18.8, 13.4, 5.0 Hz, 2H), 2.78 (ddd, J=17.6, 4.7, 2.5 Hz, 2H), 2.65-2.28 (m, 4H), 2.29-2.11 (m, 3H), 1.97 (dd, J=29.0, 17.0 Hz, 2H), 1.80 (d, J=11.6 Hz, 2H), 1.63 (t, J=11.9 Hz, 2H), 1.56-1.36 (m, 2H), 1.36-1.10 (m, 1H).

The following Examples were made using the general route described in Procedure 27 and are shown below in Table 17. To prepare the below Examples, different reagents/starting materials were used than some of those described in Procedure 27 and are noted in the last column of Table 17—"Changes to Procedure 27: Different Reagents/Starting Materials". A person of ordinary skill in the art will readily recognize which reagents/starting materials of Procedure 27 were replaced with the different reagents/starting materials noted below.

TABLE 17

| Example | Structure | ES/MS m/z | ¹H-NMR | Changes to Procedure 27: Different Reagents/Starting Materials |
|---|---|---|---|---|
| 303 | 3-(5-(((1R,2S)-rel-2-(((1R,2R)-2-methylcyclohexyl)amino)cyclohexyl)methyl)-1-oxoisoindolin-2-yl)piperidine-2,6-dione | 452.4 | ¹H NMR (400 MHz, Methanol-d4) δ 7.77 (d, J = 7.9 Hz, 1H), 7.49 (s, 1H), 7.44 (d, J = 7.8 Hz, 1H), 5.15 (dd, J = 13.3, 5.2 Hz, 1H), 4.54-4.42 (m, 2H), 3.55 (d, J = 15.6 Hz, 1H), 3.05-2.83 (m, 4H), 2.84-2.73 (m, 1H), 2.60-2.40 (m, 3H), 2.25-2.10 (m, 4H), 1.91 (s, 3H), 1.84-1.33 (m, 8H), 1.15 (dd, J = 8.5, 6.4 Hz, 5H). | (1R,2R)-2-methylcyclohexan-1-amine |

EtOH (1 mL) and iron(III) acetylacetonate (47 mg, 0.13 mmol) was added. N₂ was bubbled through the reaction for 5 minutes then the reaction was heated at 65° C. for 1 minute before addition of phenyl silane (41 µL, 0.3 mmol). The reaction was heated at 65° C. for an additional 1.5 hours after which another portion of phenyl silane (41 µL, 0.3 mmol) was added. Heating was continued for an additional 4 hours and then the reaction was stirred at r.t. overnight. The reaction was diluted with DMSO and subjected to reverse phase HPLC purification (eluent: MeCN/water gradient with 0.1% TFA). Desired fractions were frozen and lyophilized to give the title product.

Step 3: Preparation of 3-(5-(((1R,2S)-rel-2-(((R)-3,3-difluorocyclopentyl) amino)cyclohexyl)methyl)-1-oxoisoindolin-2-yl)piperidine-2,6-dione (Example 302)

To a solution of tert-butyl 5-amino-4-(5-(((1R,2S)-rel-2-(((R)-3,3-difluorocyclopentyl) amino) cyclohexyl)methyl)-

Procedure 28, Examples 304

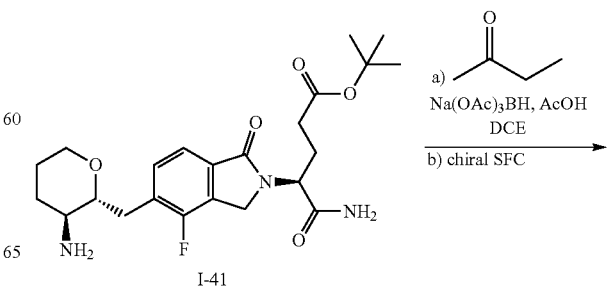

-continued

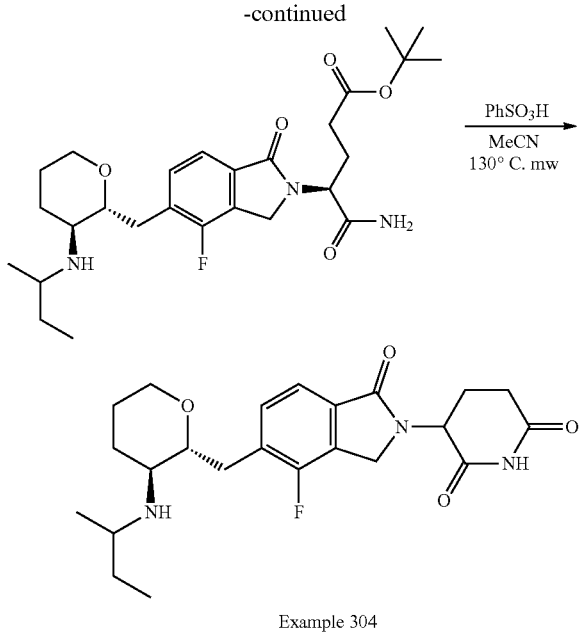

Example 304

Step 1: tert-Butyl (4S)-5-amino-4-(5-(((2R,3S)-3-(sec-butylamino)tetrahydro-2H-pyran-2-yl)methyl)-4-fluoro-1-oxoisoindolin-2-yl)-5-oxopentanoate 2-Butanone (64 mg, 0.89 mmol), acetic acid (31 µL, 0.534 mmol) and sodium triacetoxyborohydride (283 mg, 1.33 mmol) were added to a stirring solution of I-41 (200 mg, 0.445 mmol) in DCE (10 mL). The resulting mixture was stirred at r.t. overnight. Upon completion of the reaction, the mixture was diluted with CH$_2$Cl$_2$. The organic phase was transferred to a separatory funnel and washed with sat. aqueous NaHCO$_3$ and brine, dried over Na$_2$SO$_4$, and concentrated in vacuo. The crude residue was purified by SiO$_2$ column chromatography (eluent: hexanes/EtOAc) to afford the title compound.

Step 2: 3-(5-(((2R,3S)-3-(sec-butylamino)tetrahydro-2H-pyran-2-yl)methyl)-4-fluoro-1-oxoisoindolin-2-yl)piperidine-2,6-dione (Example 304)

Benzenesulfonic acid (38 mg, 0.267 mmol) was added to a solution of tert-butyl (4S)-5-amino-4-(5-(((2R,3S)-3-(sec-butylamino)tetrahydro-2H-pyran-2-yl)methyl)-4-fluoro-1-oxoisoindolin-2-yl)-5-oxopentanoate (45 mg, 0.089 mmol) in MeCN (3.0 mL). The resulting mixture was heated to 130° C. under microwave irradiation for 30 min. The reaction mixture was then concentrated and purified by RP-HPLC (eluent: MeCN/water gradient with 0.1% TFA) to give the title compound. $^1$H NMR (400 MHz, DMSO-d$_6$) δ 11.01 (s, 1H), 8.59-8.40 (m, 1H), 8.21 (s, 1H), 7.63-7.47 (m, 2H), 5.11 (dd, J=13.3, 5.1 Hz, 1H), 4.56 (dd, J=17.4, 5.3 Hz, 1H), 4.37 (dd, J=17.4, 3.2 Hz, 1H), 3.82-3.71 (m, 2H), 3.32-3.18 (m, 4H), 3.05-2.85 (m, 2H), 2.65-2.56 (m, 1H), 2.50-2.35 (m, 1H), 2.24-2.18 (m, 1H), 2.06-1.95 (m, 1H), 1.87-1.37 (m, 4H), 1.32-1.20 (m, 4H), 0.99-0.88 (m, 3H). ES/MS: 432.6 (M+H$^+$).

The following Examples were made using the general route described in Procedure 28 and are shown below in Table 18. To prepare the below Examples, different reagents/starting materials were used than some of those described in Procedure 28 and are noted in the last column of Table 18—"Changes to Procedure 28: Different Reagents/Starting Materials". A person of ordinary skill in the art will readily recognize which reagents/starting materials of Procedure 28 were replaced with the different reagents/starting materials noted below.

TABLE 18

| Example | Structure | ES/MS m/z | $^1$H-NMR | Changes to Procedure 28: Different Reagents/ Starting Materials |
|---|---|---|---|---|
| 305 | 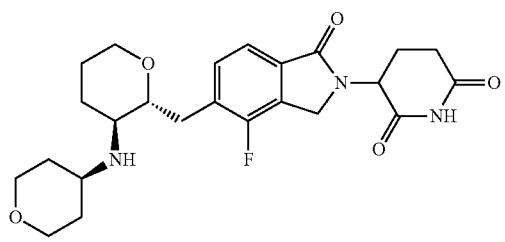<br>3-(4-fluoro-1-oxo-5-(((2R,3S)-3-((tetrahydro-2H-pyran-4-yl)amino)tetrahydro-2H-pyran-2-yl)methyl)isoindolin-2-yl)piperidine-2,6-dione | 460.4 | $^1$H NMR (400 MHz, DMSO-d6) δ 11.01 (s, 1H), 8.73 (s, 1H), 8.35 (s, 1H), 7.67-7.33 (m, 2H), 5.11 (dd, J = 13.3, 5.1 Hz, 1H), 4.65-4.30 (m, 2H), 3.93 (dd, J = 11.8, 4.2 Hz, 2H), 3.86-3.71 (m, 2H), 3.42-3.18 (m, 5H), 3.10-2.85 (m, 2H), 2.66-2.55 (m, 1H), 2.42 (td, J = 13.2, 4.6 Hz, 1H), 2.30-2.16 (m, 1H), 2.07-1.89 (m, 3H), 1.80-1.47 (m, 5H). | Step 1: tetrahydropyran-4-one |

TABLE 18-continued

| Example | Structure | ES/MS m/z | ¹H-NMR | Changes to Procedure 28: Different Reagents/ Starting Materials |
|---|---|---|---|---|
| 306 | 3-(4-fluoro-5-(((2R,3S)-3-((3-methylbutan-2-yl)amino)tetrahydro-2H-pyran-2-yl)methyl)-1-oxoisoindolin-2-yl)piperidine-2,6-dione | 446.4 | ¹H NMR (400 MHz, DMSO-d6) δ 11.01 (s, 1H), 8.03 (s, 2H), 7.62-7.49 (m, 2H), 5.11 (dd, J = 13.3, 5.1 Hz, 1H), 4.56 (dd, J = 17.3, 5.0 Hz, 1H), 4.38 (dd, J = 17.4, 3.0 Hz, 1H), 3.87 (t, J = 7.8 Hz, 1H), 3.79 (d, J = 11.5 Hz, 1H), 3.35-3.18 (m, 3H), 3.09-2.97 (m, 1H), 2.99-2.85 (m, 1H), 2.61 (d, J = 17.7 Hz, 1H), 2.42 (td, J = 13.2, 4.5 Hz, 1H), 2.25-2.20 (m, 2H), 2.08-1.95 (m, 2H), 1.76-1.53 (m, 2H), 1.25-1.16 (m, 4H), 1.01-0.87 (m, 6H). | Step 1: 3-methyl-butan-2-one |
| 307 | 3-(5-(((1R,2S)-2-(sec-butylamino)cyclohexyl)methyl)-4-fluoro-1-oxoisoindolin-2-yl)piperidine-2,6-dione | 430.3 | ¹H NMR (400 MHz, DMSO-d6) δ 11.01 (s, 1H), 8.33 (s, 1H), 8.21 (s, 1H), 7.94 (s, 1H), 7.59 (d, J = 7.6 Hz, 1H), 7.54-7.44 (m, 1H), 5.11 (dd, J = 13.3, 5.1 Hz, 1H), 4.56 (dd, J = 17.4, 3.8 Hz, 1H), 4.39 (dd, J = 17.4, 3.6 Hz, 1H), 3.31-3.19 (m, 2H), 3.13 (s, 1H), 2.99 2.85 (m, 1H), 2.60 (dd, J = 18.4, 6.7 Hz, 2H), 2.50-2.35 (m, 1H), 2.14-1.96 (m, 2H), 1.94-1.68 (m, 3H), 1.60-1.32 (m, 4H), 1.27 (dd, J = 16.8, 6.4 Hz, 3H), 1.15-1.02 (m, 2H), 0.94 (q, J = 7.7 Hz, 3H). | Step 1: I-14; 2-butanone |
| 308 | 3-(4-fluoro-1-oxo-5-(((2R,3S)-3-((1-(2,2,2-trifluoroethyl)piperidin-4-yl)amino)tetrahydro-2H-pyran-2-yl)methyl)isoindolin-2-yl)piperidine-2,6-dione | 541.4 | ¹H NMR (400 MHz, DMSO-d6) δ 11.01 (s, 1H), 8.69 (s, 1H), 8.28 (s, 1H), 7.61-7.37 (m, 3H), 5.11 (dd, J = 13.3, 5.1 Hz, 1H), 4.61-4.48 (m, 1H), 4.38 (d, J = 17.4 Hz, 1H), 3.82-3.72 (m, 2H), 3.28-3.16 (m, 5H), 3.07-2.94 (m, 3H), 2.98-2.85 (m, 1H), 2.61 (d, J = 17.1 Hz, 1H), 2.43 (q, J = 12.6, 12.0 Hz, 3H), 2.27-2.18 (m, 1H), 2.06-1.92 (m, 3H), 1.76-1.55 (m, 5H). | Step 1: 1-(2,2,2-trifluoro-ethyl)piperidin-4-one |
| 309 | 3-(5-(((2R,3S)-3-((1-(2,2-difluoroethyl)piperidin-4-yl)amino)tetrahydro-2H-pyran-2-yl)methyl)-4-fluoro-1-oxoisoindolin-2-yl)piperidine-2,6-dione | 523.4 | ¹H NMR (400 MHz, DMSO-d6) δ 11.01 (s, 1H), 8.70 (s, 1H), 8.39 (s, 1H), 7.61-7.48 (m, 2H), 6.22 (t, J = 55.1 Hz, 1H), 5.11 (dd, J = 13.3, 5.1 Hz, 1H), 4.55 (d, J = 17.4 Hz, 1H), 4.38 (d, J = 17.3 Hz, 1H), 3.71 (d, J = 52.3 Hz, 5H), 3.39-2.85 (m, 8H), 2.65-2.56 (m, 1H), 2.41 (td, J = 13.2, 4.6 Hz, 1H), 2.21 (d, J = 7.7 Hz, 1H), 2.10-1.97 (m, 3H), 1.76-1.56 (m, 5H). | Step 1: 1-(2,2-difluoro-ethyl)piperidin-4-one |

Procedure 29, Example 310

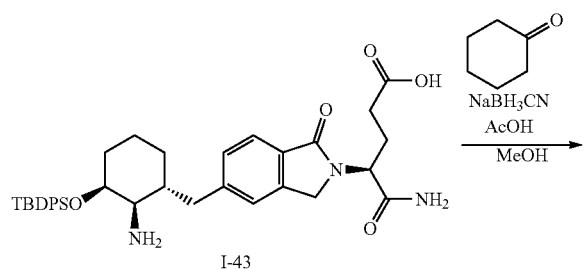

I-43

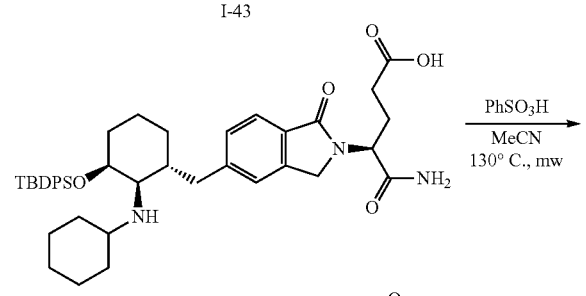

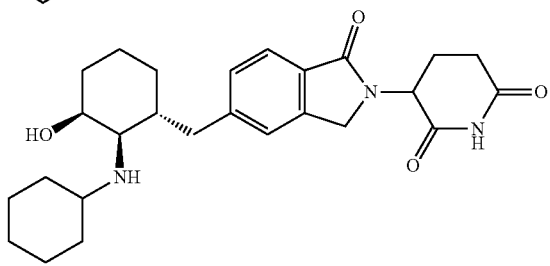

Example 310

Step 1: Preparation of (S)-5-amino-4-(5-(((1R,2R,3S)-rel-3-((tert-butyldiphenylsilyl)oxy)-2-(cyclohexylamino)cyclohexyl)methyl)-1-oxoisoindolin-2-yl)-5-oxopentanoic acid. I-43

(120 mg, 0.190 mmol) was taken up in methanol (1.5 mL) and cyclohexanone (60.4 mg, 0.616 mmol) was added followed by acetic acid (272 µL, 4.76 mmol). NaBH$_3$CN (60.0 mg, 0.952 mmol) was then added to the reaction and the mixture heated to 50° C. overnight. Following this time, the reaction was complete by LC/MS analysis and the reaction mixture was concentrated in vacuo then purified directly by RP-HPLC (eluent: MeCN/water gradient with 0.1% TFA) to yield (S)-5-amino-4-(5-(((1R,2R,3S)-3-((tert-butyldiphenylsilyl)oxy)-2-(cyclohexylamino)cyclohexyl)methyl)-1-oxoisoindolin-2-yl)-5-oxopentanoic acid. ES/MS: 710.3 (M+H$^+$).

Step 2: Preparation of 3-(5-(((1R,2R,3S)-rel-2-(cyclohexylamino)-3-hydroxycyclohexyl)methyl)-1-oxoisoindolin-2-yl)piperidine-2,6-dione (Example 310)

(S)-5-Amino-4-(5-(((1R,2R,3S)-rel-3-((tert-butyldiphenylsilyl)oxy)-2-(cyclohexylamino)cyclohexyl) methyl)-1-oxoisoindolin-2-yl)-5-oxopentanoic acid (56.2 mg, 79.2 µmol) was taken up in MeCN (1.5 mL) and benzenesulfonic acid (75.1 mg, 0.475 mmol) was added. The reaction was heated to 130° C. under microwave irradiation for 1 hour and then the reaction mixture was concentrated in vacuo and the residue purified directly by RP-HPLC (eluent: MeCN/water gradient with 0.1% TFA) to yield the product (Example 310) as the trifluoracetate salt. ES/MS: 454.2 (M+H$^+$). $^1$H NMR (400 MHz, DMSO-d6) δ 10.99 (s, 1H), 8.12 (s, 1H), 8.01 (s, 1H), 7.71 (d, J=7.8 Hz, 1H), 7.46 (s, 1H), 7.38 (dd, J=7.8, 1.3 Hz, 1H), 5.12 (dd, J=13.2, 5.2 Hz, 1H), 4.46 (d, J=17.3 Hz, 1H), 4.33 (d, J=17.3 Hz, 1H), 4.09 (s, 1H), 3.21 (s, 1H), 2.93 (ddd, J=17.3, 13.6, 5.4 Hz, 1H), 2.74-2.55 (m, 1H), 2.44-2.25 (m, 1H), 2.16 (d, J=10.7 Hz, 1H), 2.09-1.94 (m, 2H), 1.94-0.85 (m, 13H).

Procedure 30, Examples 313 and 314

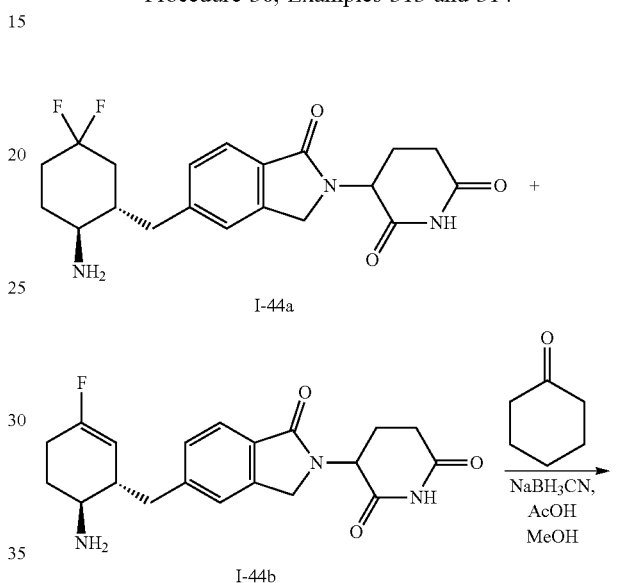

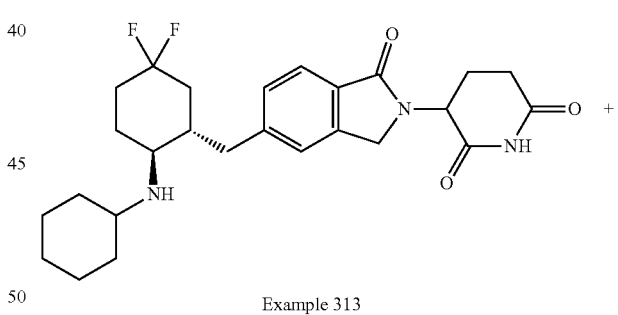

Example 313

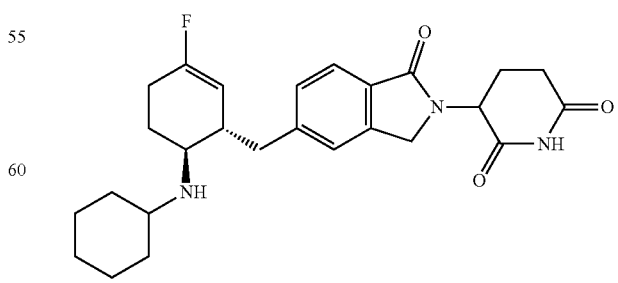

Example 314

3-(5-(((1S,2S)-2-(cyclohexylamino)-5,5-difluorocyclohexyl)methyl)-1-oxoisoindolin-2-yl)piperidine-2,6-dione (Example 313) and 3-(5-(((1S,6S)-6-(cyclohexylamino)-3-fluorocyclohex-2-en-1-yl)methyl)-1-oxoisoindolin-2-yl)piperidine-2,6-dione (Example 314)

A vial was charged with a mixture of I-44a and I-44b (50 mg, 0.128 mmol), cyclohexanone (39.7 μL, 0.383 mmol), sodium cyanoborohydride (24.1 mg, 0.383 mmol), MeOH (0.5 mL), and acetic acid (7.3 μL, 0.128 mmol). The reaction was heated to 50° C. and stirred for 1 h, adding additional cyclohexanone as needed to reach full conversion. Upon completion, the mixture was concentrated in vacuo and the residue taken up in DMSO and purified by RP-HPLC (eluent: MeCN/water gradient with 0.1% TFA) to afford 3-(5-(((1S,2S)-2-(cyclohexylamino)-5,5-difluorocyclohexyl)methyl)-1-oxoisoindolin-2-yl)piperidine-2,6-dione (Example 313) and 3-(5-(((1S,6S)-6-(cyclohexylamino)-3-fluorocyclohex-2-en-1-yl)methyl)-1-oxoisoindolin-2-yl)piperidine-2,6-dione (Example 314) as the trifluoroacetate salts. Example 314: ES/MS: 474.3 (M+H$^+$). $^1$H NMR (400 MHz, DMSO-d$_6$) δ 11.00 (s, 1H), 8.59 (s, 1H), 8.23 (s, 1H), 7.72 (d, J=7.7 Hz, 1H), 7.46 (s, 1H), 7.42-7.33 (m, 1H), 5.12 (dd, J=13.3, 5.1 Hz, 1H), 4.47 (d, J=17.3 Hz, 1H), 4.34 (dd, J=17.5, 2.1 Hz, 1H), 3.39-3.27 (m, 2H), 3.23 (s, 1H), 2.92 (ddd, J=17.2, 13.6, 5.4 Hz, 1H), 2.65-2.56 (m, 1H), 2.40 (qd, J=13.4, 4.6 Hz, 1H), 2.20 (t, J=8.3 Hz, 1H), 2.09 (d, J=10.1 Hz, 1H), 2.00 (ddd, J=12.5, 5.5, 2.2 Hz, 1H), 1.93 (dt, J=12.4, 4.2 Hz, 1H), 1.85-1.74 (m, 2H), 1.74-1.61 (m, 3H), 1.55 (ddd, J=13.3, 10.3, 3.6 Hz, 3H), 1.48 (ddd, J=9.1, 5.3, 3.3 Hz, 1H), 1.37 (dddt, J=15.8, 9.2, 5.6, 2.8 Hz, 4H), 1.30-1.19 (m, 1H), 1.13 (pd, J=12.8, 10.6, 3.6 Hz, 1H). Example 315: ES/MS: 454.3 (M+H$^+$). $^1$H NMR (400 MHz, DMSO-d$_6$) δ 10.99 (s, 1H), 8.25 (s, 1H), 8.08 (s, 1H), 7.71 (d, J=7.8 Hz, 1H), 7.50 (s, 1H), 7.41 (d, J=7.7 Hz, 1H), 5.24 (d, J=16.3 Hz, 1H), 5.12 (dd, J=13.3, 5.1 Hz, 1H), 4.45 (dd, J=18.1, 5.8 Hz, 1H), 4.32 (d, J=17.5 Hz, 1H), 3.21 (s, 2H), 2.93 (ddd, J=23.5, 13.1, 5.7 Hz, 2H), 2.73-2.53 (m, 3H), 2.47-2.34 (m, 1H), 2.33-2.21 (m, 2H), 2.11-1.87 (m, 3H), 1.75 (s, 2H), 1.67-1.55 (m, 2H), 1.26 (t, J=9.4 Hz, 3H), 1.23-1.01 (m, 3H).

The following Examples were made using the general route described in Procedure 30 and are shown below in Table 19. To prepare the below Examples, different reagents/starting materials were used than some of those described in Procedure 30 and are noted in the last column of Table 19—"Changes to Procedure 30: Different Reagents/Starting Materials". A person of ordinary skill in the art will readily recognize which reagents/starting materials of Procedure 30 were replaced with the different reagents/starting materials noted below.

TABLE 19

| Example | Structure | ES/MS m/z | $^1$H-NMR | Changes to Procedure 30: Different Reagents/Starting Materials |
|---|---|---|---|---|
| 315 | F F cyclohexyl-isoindolinone-piperidine-2,6-dione structure with isopropylamino group; 3-(5-(((1S,2S)-5,5-difluoro-2-(isopropylamino)cyclohexyl)methyl)-1-oxoisoindolin-2-yl)piperidine-2,6-dione | 434.3 | $^1$H NMR (400 MHz, DMSO-d6) δ 11.00 (s, 1H), 8.52 (s, 1H), 8.15 (d, J = 11.6 Hz, 1H), 7.73 (dd, J = 7.8, 1.3 Hz, 1H), 7.46 (s, 1H), 7.38 (dt, J = 7.8, 1.6 Hz, 1H), 5.12 (dd, J = 13.3, 5.1 Hz, 1H), 4.48 (dd, J = 17.5, 1.9 Hz, 1H), 4.34 (dd, J = 17.4, 3.9 Hz, 1H), 3.58-3.49 (m, 2H), 3.33 (d, J = 14.1 Hz, 2H), 2.92 (ddd, J = 17.3, 13.6, 5.4 Hz, 1H), 2.65-2.56 (m, 1H), 2.47-2.31 (m, 1H), 2.18 (t, J = 18.0 Hz, 3H), 2.05-1.89 (m, 2H), 1.73 (tdd, J = 29.6, 11.1, 3.7 Hz, 3H), 1.33 (d, J = 6.4 Hz, 3H), 1.29 (d, J = 6.4 Hz, 3H). | acetone |

Procedure 31, Examples 316 and 317

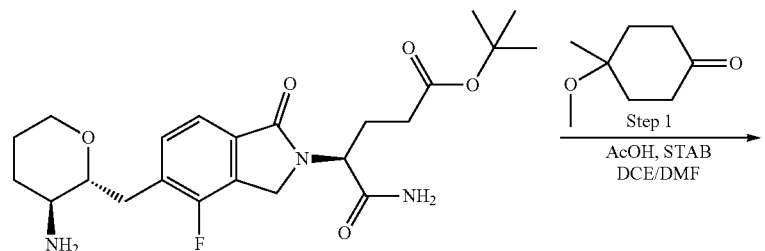

I-41

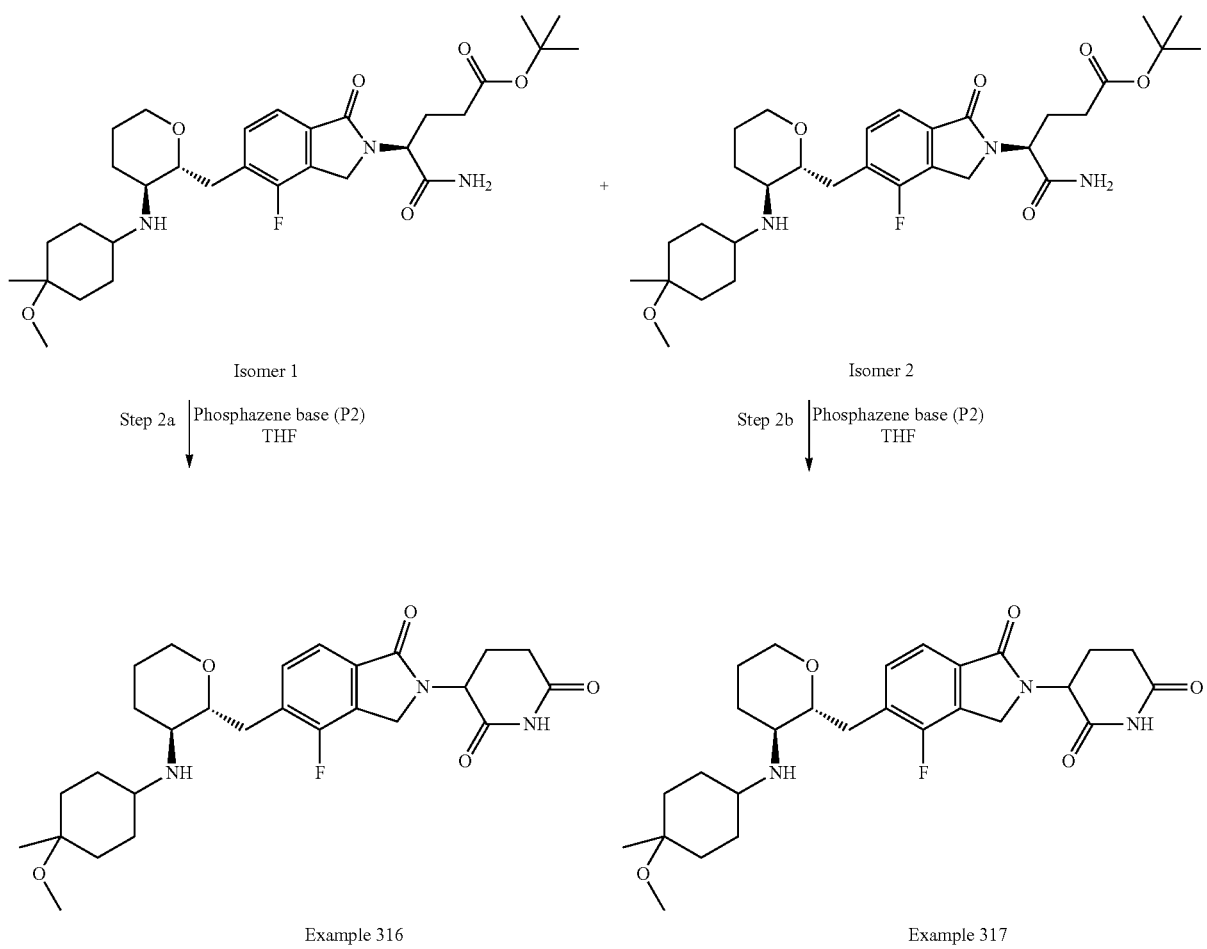

Example 316

Example 317

Step 1: Preparation of tert-butyl (S)-5-amino-4-(4-fluoro-5-(((2R,3S)-3-((4-methoxy-4-methylcyclohexyl)amino)tetrahydro-2H-pyran-2-yl)methyl)-1-oxoisoindolin-2-yl)-5-oxopentanoate (Isomer 1) and tert-butyl (S)-5-amino-4-(4-fluoro-5-(((2R,3S)-3-((4-methoxy-4-methylcyclohexyl)amino)tetrahydro-2H-pyran-2-yl)methyl)-1-oxoisoindolin-2-yl)-5-oxopentanoate (Isomer 2)

To a solution of I-41 (150 mg, 0.33 mmol) in MeOH (2 mL) was added 2-4-methoxy-4-methylcyclohexan-1-one (142 mg, 1.0 mmol) followed by acetic acid (57 µL, 1.0 mmol) and sodium cyanoborohydride (63 mg, 1.0 mmol). The reaction was stirred at r.t overnight. Following this time, the reaction was quenched with sat. aqueous NaHCO$_3$ and extracted with CH$_2$Cl$_2$(×2). The combined organics were washed with water and brine, dried over Na$_2$SO$_4$ and concentrated in vacuo to give the crude product which was purified by RP-HPLC (eluent: MeCN/water gradient with 0.1% TFA) to give tert-butyl (S)-5-amino-4-(4-fluoro-5-(((2R,3S)-3-((4-methoxy-4-methylcyclohexyl)amino)tetrahydro-2H-pyran-2-yl)methyl)-1-oxoisoindolin-2-yl)-5-oxopentanoate (Isomer 1) and tert-butyl (S)-5-amino-4-(4-fluoro-5-(((2R,3S)-3-((4-methoxy-4-methylcyclohexyl)amino)tetrahydro-2H-pyran-2-yl)methyl)-1-oxoisoindolin-2-yl)-5-oxopentanoate (Isomer 2).

Step 2a: Preparation of 3-(4-fluoro-5-(((2R,3S)-3-((4-methoxy-4-methylcyclohexyl)amino)tetrahydro-2H-pyran-2-yl)methyl)-1-oxoisoindolin-2-yl)piperidine-2,6-dione (Example 316)

To a solution of tert-butyl (S)-5-amino-4-(4-fluoro-5-(((2R,3S)-3-((4-methoxy-4-methylcyclohexyl)amino)tetrahydro-2H-pyran-2-yl)methyl)-1-oxoisoindolin-2-yl)-5-oxopentanoate (Isomer 1, 15 mg, 0.03 mmol) in THF (1.0 mL) was added 1-tert-butyl-2,2,4,4,4-pentakis(dimethylamino)-2λ5,4λ5-catenadi(phosphazene) (phosphazene P2 base, 68 µL, 0.14 mmol) and the reaction mixture was stirred at r.t. for 5 hours. Following this time, the reaction was quenched by addition of TFA (0.5 mL) and the mixture was diluted with DMSO and purified by RP-HPLC (eluent: MeCN/water gradient with 0.1% TFA) to afford 3-(4-fluoro-5-(((2R,3S)-3-((4-methoxy-4-methylcyclohexyl)amino)tetrahydro-2H-pyran-2-yl)methyl)-1-oxoisoindolin-2-yl)piperidine-2,6-dione (Example 316) as a trifluoroacetate salt. ES/MS: 502.4 (M+H$^+$). $^1$H NMR (400 MHz, DMSO-d6) δ 11.01 (s, 1H), 8.49 (s, 1H), 8.08 (s, 1H), 7.58 (d, J=7.7 Hz, 1H), 7.55-7.50 (m, 1H), 5.12 (dd, J 13.3, 5.2 Hz, 1H), 4.60-4.33 (m, 2H), 3.76 (s, 2H), 3.12 (s, 3H), 3.07-2.85 (m, 3H), 2.71-2.57 (m, 3H), 2.43 (dd, J=13.2, 4.7 Hz, 2H), 2.21 (s, 1H), 2.08-1.88 (m, 3H), 1.72 (s, 3H), 1.60 (d, J=10.2 Hz, 3H), 1.46 (d, J=8.3 Hz, 3H), 1.17 (s, 3H).

Step 2b: Preparation of 3-(4-fluoro-5-(((2R,3S)-3-((4-methoxy-4-methylcyclohexyl)amino)tetrahydro-2H-pyran-2-yl)methyl)-1-oxoisoindolin-2-yl)piperidine-2,6-dione (Example 317)

To a solution of tert-butyl (S)-5-amino-4-(4-fluoro-5-(((2R,3S)-3-((4-methoxy-4-methylcyclohexyl)amino)tetrahydro-2H-pyran-2-yl)methyl)-1-oxoisoindolin-2-yl)-5-oxopentanoate (Isomer 2, 16 mg, 0.03 mmol) in THF (1.0 mL) was added 1-tert-butyl-2,2,4,4,4-pentakis(dimethylamino)-2λ5,4λ5-catenadi(phosphazene) (phosphazene P2 base, 68 µL, 0.14 mmol) and the reaction mixture was stirred at r.t. for 5 hours. Following this time, the reaction was quenched by addition of TFA (0.5 mL) and the mixture was diluted with DMSO and purified by RP-HPLC (eluent: MeCN/water gradient with 0.1% TFA) to afford 3-(4-fluoro-5-(((2R,3S)-3-((4-methoxy-4-methylcyclohexyl)amino)tetrahydro-2H-pyran-2-yl)methyl)-1-oxoisoindolin-2-yl)piperidine-2,6-dione (Example 317) as a trifluoroacetate salt. ES/MS: 502.4 (M+H$^+$). $^1$H NMR (400 MHz, DMSO-d6) δ 11.01 (s, 1H), 8.46 (s, 1H), 8.16 (s, 1H), 7.58 (d, J=7.7 Hz, 1H), 7.55-7.45 (m, 1H), 5.11 (dd, J=13.3, 5.1 Hz, 1H), 4.62-4.33 (m, 2H), 3.84-3.67 (m, 3H), 3.25 (s, 2H), 3.10 (s, 3H), 3.03-2.85 (m, 2H), 2.70-2.56 (m, 2H), 2.46-2.37 (m, 1H), 2.21 (s, 1H), 2.07-1.95 (m, 1H), 1.84 (d, J=12.3 Hz, 3H), 1.71 (t, J=15.0 Hz, 3H), 1.57 (d, J=14.8 Hz, 3H), 1.33 (t, J=12.5 Hz, 2H), 1.07 (s, 3H).

The following Examples were made using the general route described in Procedure 31 and are shown below in Table 20. To prepare the below Examples, different reagents/starting materials were used than some of those described in Procedure 31 and are noted in the last column of Table 20—"Changes to Procedure 31: Different Reagents/Starting Materials". A person of ordinary skill in the art will readily recognize which reagents/starting materials of Procedure 31 were replaced with the different reagents/starting materials noted below.

TABLE 20

| Example | Structure | ES/MS m/z | $^1$H-NMR | Changes to Procedure 31: Different Reagents/Starting Materials |
|---|---|---|---|---|
| Example 318 | 3-(4-fluoro-5-(((2R,3S)-3-((1-(oxetan-3-yl)ethyl)amino)tetrahydro-2H-pyran-2-yl)methyl)-1-oxoisoindolin-2-yl)piperidine-2,6-dione (Isomer 1) | 460.2 | $^1$H NMR (400 MHz, DMSO-d6) δ 11.01 (s, 1H), 8.35 (s, 1H), 8.05 (s, 1H), 7.66-7.55 (m, 1H), 7.51 (dt, J = 13.9, 7.5 Hz, 1H), 5.11 (dd, J = 13.3, 5.1 Hz, 1H), 4.74-4.51 (m, 3H), 4.51-4.32 (m, 3H), 3.77 (dt, J = 20.3, 9.0 Hz, 3H), 3.27 (q, J = 14.4, 13.3 Hz, 2H), 3.17-3.06 (m, 1H), 3.04-2.82 (m, 2H), 2.70-2.55 (m, 1H), 2.46-2.35 (m, 1H), 2.35-2.16 (m, 1H), 2.10-1.91 (m, 1H), 1.74 (d, J = 18.7 Hz, 2H), 1.61 (d, J = 8.4 Hz, 1H), 1.30 (d, J = 6.5 Hz, 1H), 1.27-1.15 (m, 2H). | Step 1: 1-(oxetan-3-yl)ethanone |
| 319 | 3-(4-fluoro-5-(((2R,3S)-3-((1-(oxetan-3-yl)ethyl)amino)tetrahydro-2H-pyran-2-yl)methyl)-1-oxoisoindolin-2-yl)piperidine-2,6-dione (Isomer 1) | 460.2 | $^1$H NMR (400 MHz, DMSO-d6) δ 11.01 (s, 1H), 8.35 (s, 1H), 8.05 (s, 1H), 7.66-7.55 (m, 1H), 7.51 (dt, J = 13.9, 7.5 Hz, 1H), 5.11 (dd, J = 13.3, 5.1 Hz, 1H), 4.74-4.51 (m, 3H), 4.51-4.32 (m, 3H), 3.77 (dt, J = 20.3, 9.0 Hz, 3H), 3.27 (q, J = 14.4, 13.3 Hz, 2H), 3.17-3.06 (m, 1H), 3.04-2.82 (m, 2H), 2.70-2.55 (m, 1H), 2.46-2.35 (m, 1H), 2.35-2.16 (m, 1H), 2.10-1.91 (m, 1H), 1.74 (d, J = 18.7 Hz, 2H), 1.61 (d, J = 8.4 Hz, 1H), 1.30 (d, J = 6.5 Hz, 1H), 1.27-1.15 (m, 2H). | Step 1: 1-(oxetan-3-yl)ethanone |

Procedure 32, Examples 320

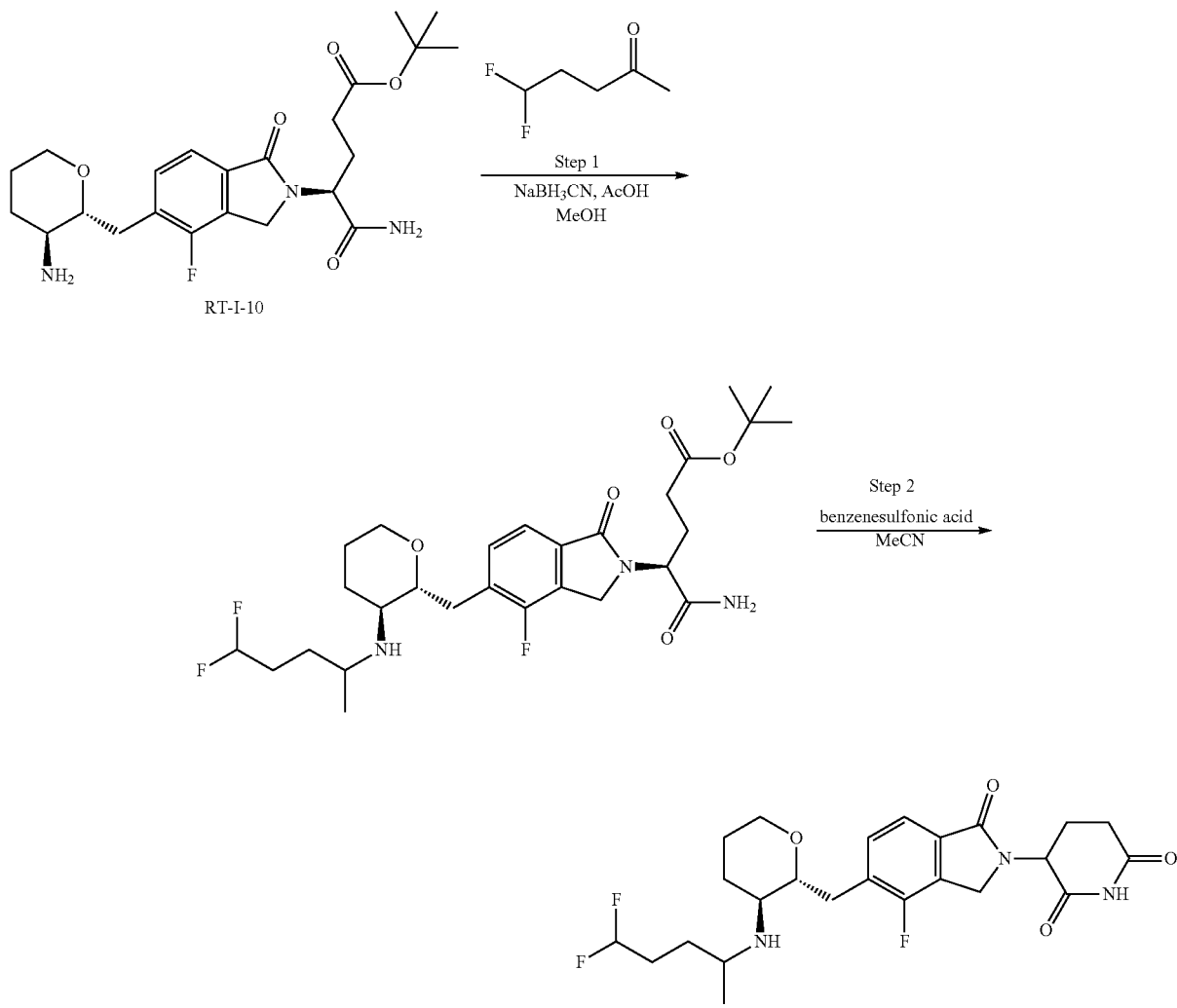

Step 1: Preparation of tert-butyl (4S)-5-amino-4-(5-(((2R,3S)-3-((5,5-difluoropentan-2-yl)amino)tetrahydro-2H-pyran-2-yl)methyl)-4-fluoro-1-oxoisoindolin-2-yl)-5-oxopentanoate A vial was charged with tert-butyl (S)-5-amino-4-(5-(((2R,3S)-3-aminotetrahydro-2H-pyran-2-yl)methyl)-4-fluoro-1-oxoisoindolin-2-yl)-5-oxopentanoate (I-41) (150 mg, 0.334 mmol), 5,5-difluoropentan-2-one (122 mg, 1.00 mmol), sodium cyanoborohydride (62.9 mg, 1.00 mmol), MeOH (1.50 mL), and acetic acid (0.0191 mL, 0.334 mmol) and the reaction mixture was stirred at r.t. for 4 h. Following this time, the mixture was concentrated in vacuo and purified directly by column chromatography (eluent: MeOH/DCM gradient) to afford tert-butyl (4S)-5-amino-4-(5-(((2R,3S)-3-(((rac)-5,5-difluoropentan-2-yl)amino)tetrahydro-2H-pyran-2-yl)methyl)-4-fluoro-1-oxoisoindolin-2-yl)-5-oxopentanoate as an oil. The oil was triturated with hexanes, followed by $CH_2Cl_2$, to generate tert-butyl (4S)-5-amino-4-(5-(((2R,3S)-3-((5,5-difluoropentan-2-yl)amino)tetrahydro-2H-pyran-2-yl)methyl)-4-fluoro-1-oxoisoindolin-2-yl)-5-oxopentanoate as a solid. ES/MS: 556.3 (M+H$^+$).

Step 2: Preparation of 3-(5-(((2R,3S)-3-((5,5-difluoropentan-2-yl)amino)tetrahydro-2H-pyran-2-yl)methyl)-4-fluoro-1-oxoisoindolin-2-yl)piperidine-2,6-dione (Example 320)

A vial was charged with tert-butyl (4S)-5-amino-4-(5-(((2R,3S)-3-((5,5-difluoropentan-2-yl)amino)tetrahydro-2H-pyran-2-yl)methyl)-4-fluoro-1-oxoisoindolin-2-yl)-5-oxopentanoate (50 mg, 0.0900 mmol), MeCN (1.50 mL) and benzenesulfonic acid (42.7 mg, 0.270 mmol). The reaction was heated to 130° C. under microwave irradiation for 30 min. Following this time, the reaction was concentrated in vacuo and the residue was then taken up in DMSO and purified directly by RP-HPLC (eluent: MeCN/water gradient with 0.1% TFA) to yield the product (Example 320) as the trifluoroacetate salt. ES/MS: 482.3 (M+H$^+$). $^1$H NMR (400 MHz, DMSO-$d_6$) δ 11.01 (s, 1H), 8.81-8.57 (m, 1H), 8.38 (d, J=10.2 Hz, 1H), 7.57 (d, J=7.6 Hz, 1H), 7.52 (q, J=7.3 Hz, 1H), 6.15 (tq, J=56.8, 4.0 Hz, 1H), 5.11 (dd, J=13.3, 5.1 Hz, 1H), 4.60-4.51 (m, 1H), 4.38 (d, J=17.3 Hz, 1H), 3.77 (dq, J=10.4, 7.4, 5.1 Hz, 2H), 3.43 (d, J=10.3 Hz, 1H), 3.33-3.13 (m, 3H), 3.08-2.85 (m, 2H), 2.61 (dt, J=17.4, 3.1 Hz, 1H), 2.43 (tt, J=13.2, 6.7 Hz, 1H), 2.21 (dt, J=8.2, 4.5 Hz, 1H), 2.06-1.83 (m, 4H), 1.77-1.51 (m, 4H), 1.29 (dd, J=16.3, 6.4 Hz, 3H).

The following Examples were made using the general route described in Procedure 32 and are shown below in Table 21. To prepare the below Examples, different reagents/starting materials were used than some of those described in Procedure 32 and are noted in the last column of Table 21—"Changes to Procedure 32: Different Reagents/Starting Materials". A person of ordinary skill in the art will readily recognize which reagents/starting materials of Procedure 32 were replaced with the different reagents/starting materials noted below.

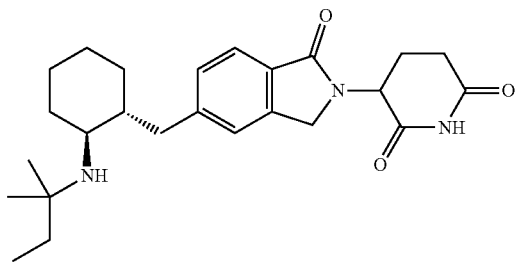

Example 322

TABLE 21

| Example | Structure | ES/MS m/z | ¹H-NMR | Changes to Procedure 32: Different Reagents/Starting Materials |
|---|---|---|---|---|
| 321 | 3-(4-fluoro-1-oxo-5-(((2R,3S)-3-((6,6,6-trifluorohexan-2-yl)amino)tetrahydro-2H-pyran-2-yl)methyl)isoindolin-2-yl)piperidine-2,6-dione | 514.3 | ¹H NMR (400 MHz, DMSO-d6) δ 11.01 (s, 1H), 8.61 (d, J = 51.2 Hz, 1H), 8.30 (s, 1H), 7.57 (d, J = 7.7 Hz, 1H), 7.52 (q, J = 7.2, 6.1 Hz, 1H), 5.11 (dd, J = 13.3, 5.1 Hz, 1H), 4.56 (dd, J = 17.3, 5.5 Hz, 1H), 4.38 (dd, J = 17.4, 3.7 Hz, 1H), 3.77 (td, J = 7.3, 3.7 Hz, 2H), 3.42 (s, 1H), 3.36-3.16 (m, 3H), 3.06-2.83 (m, 2H), 2.66-2.57 (m, 1H), 2.48-2.39 (m, 1H), 2.38-2.26 (m, 2H), 2.22 (d, J = 10.5 Hz, 1H), 2.01 (dtd, J = 12.8, 5.5, 2.2 Hz, 1H), 1.92-1.78 (m, 1H), 1.77-1.67 (m, 1H), 1.60 (ddd, J = 23.1, 13.3, 9.3 Hz, 5H), 1.31 (d, J = 6.4 Hz, 1H), 1.26 (d, J = 6.4 Hz, 2H). | Step 1: 6,6,6-trifluoro-hexan-2-one |

Procedure 33, Examples 322

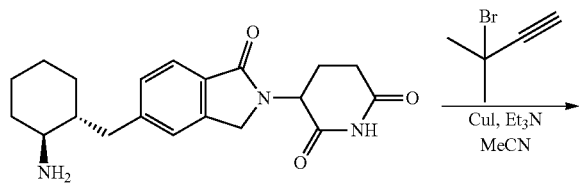

Example 1

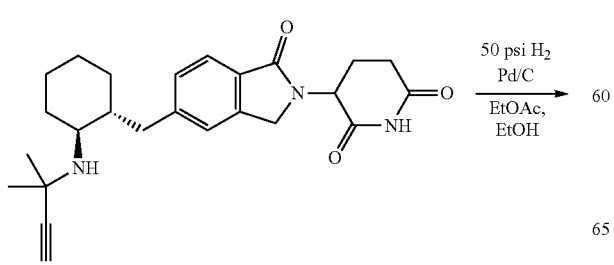

Example 322

Step 1: 3-(5-(((1R,2S)-2-((2-methylbut-3-yn-2-yl)amino)cyclohexyl)methyl)-1-oxoisoindolin-2-yl)piperidine-2,6-dione Example 1 (87.0 mg, 0.245 mmol), 3-bromo-3-methyl-but-1-yne (54.0 mg, 0.367 mmol), copper (1) iodide (4.66 mg, 0.0245 mmol) and triethylamine (37.2 mg, 0.367 mmol) were taken up in MeCN (2 mL) and the resulting mixture was stirred at r.t. for 1 h. Following this time, the mixture was concentrated in vacuo and the resulting residue was purified directly by SiO₂ column chromatography (eluent: CH2Cl2/MeOH) to afford the title product.

Step 2: 3-(1-oxo-5-(((1R,2S)-2-(tert-pentylamino)cyclohexyl)methyl)isoindolin-2-yl)piperidine-2,6-dione (Example 322)

3-(5-(((1R,2S)-2-((2-methylbut-3-yn-2-yl)amino) cyclohexyl)methyl)-1-oxoisoindolin-2-yl)piperidine-2,6-dione (53 mg, 0.126 mmol) and palladium on charcoal (53 mg, 10%) were combined in a 1:1 EtOAc/EtOH (10 mL) in a Parr shaker flask. The flask was pressurized with 50 psi of hydrogen gas and allowed to shake for 4 h. Following this time, the reaction mixture was filtered to remove solids, concentrated in vacuo, and purified by RP-HPLC (eluent: MeCN/water gradient with 0.1% TFA:) to afford 3-(1-oxo-5-(((1R,2S)-2-(tert-pentylamino)cyclohexyl)methyl)isoindolin-2-yl)piperidine-2,6-dione (Example 322) as the trifluoroacetate salt. ES/MS: 426.3 (M+H+)¹H NMR (400 MHz, DMSO-d6) δ 10.99 (s, 1H), 8.01 (d, J=13.6 Hz, 1H), 7.77 (d, J=13.6 Hz, 1H), 7.69 (d, J=7.8 Hz, 1H), 7.48 (s, 1H), 7.38 (d, J=7.8 Hz, 1H), 5.11 (dd, J=13.2, 5.1 Hz, 1H), 4.51-4.25 (m, 2H), 3.28 (dd, J=12.9, 4.0 Hz, 2H), 2.92 (ddd, J=17.2, 13.6, 5.4 Hz, 1H), 2.67-2.55 (m, 1H), 2.40 (ttd, J=13.0, 9.9, 8.8, 4.5 Hz, 2H), 2.00 (dtd, J=12.2, 7.2, 5.9, 3.4 Hz, 2H), 1.77 (d, J=28.5 Hz, 1H), 1.73-1.57 (m, 3H), 1.57-1.34 (m, 2H), 1.29 (s, 6H), 1.12 (t, J=9.0 Hz, 2H), 0.90 (t, J=7.4 Hz, 3H).

Procedure 34, Example 323

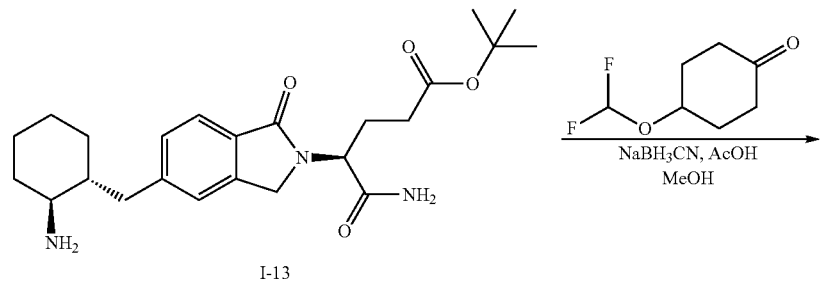

I-13

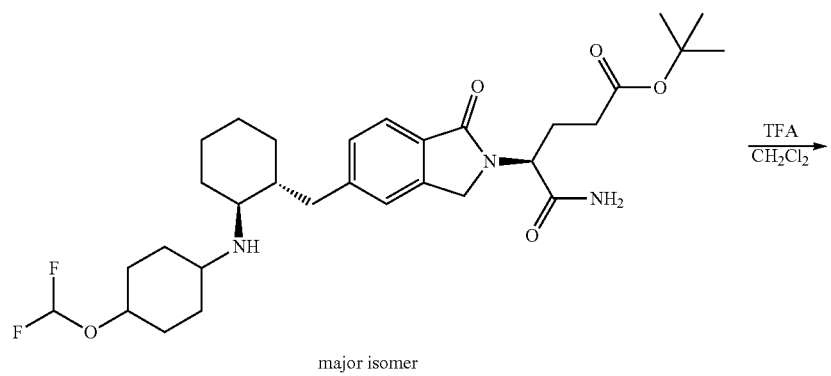

major isomer

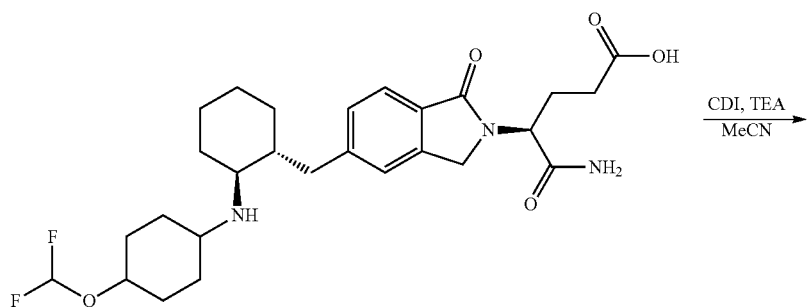

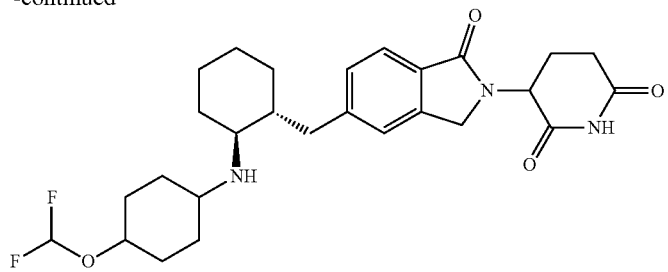

Example 323

Step 1: Preparation of tert-butyl (S)-5-amino-4-(5-(((1R,2S)-2-((4-(difluoromethoxy)cyclohexyl)amino)cyclohexyl)methyl)-1-oxoisoindolin-2-yl)-5-oxopentanoate To a solution of I-13 (120 mg, 0.279 mmol) in methanol (3 mL) was added 4-(difluoromethoxy)cyclohexan-1-one (186 mg, 1.13 mmol), followed by a few drops of acetic acid. The reaction mixture was heated to 50° C. for 15 min and then sodium cyanoborohydride (48 mg, 0.764 mmol) was added in a single portion. The reaction mixture was stirred at r.t. for 35 min and them concentrated in vacuo. The residue was purified by $SiO_2$ column chromatography to give the title product a single major stereoisomer. ES/MS: 578.2 (M+H$^+$).

Step 2: Preparation of (S)-5-amino-4-(5-(((1R,2S)-2-((4-(difluoromethoxy)cyclohexyl)amino)cyclohexyl)methyl)-1-oxoisoindolin-2-yl)-5-oxopentanoic acid tert-Butyl (S)-5-amino-4-(5-(((1R,2S)-2-((4-(difluoromethoxy)cyclohexyl) amino)cyclohexyl)methyl)-1-oxoisoindolin-2-yl)-5-oxopentanoate (29 mg, 0.053 mmol) was taken up in dichloromethane (2 mL) and trifluoroacetic acid (200 µL, 2.61 mmol) was added. The reaction mixture was stirred at room temperature for 30 min and concentrated to give crude (S)-5-amino-4-(5-(((1R,2S)-2-((4-(difluoromethoxy)cyclohexyl)amino)cyclohexyl)methyl)-1-oxoisoindolin-2-yl)-5-oxopentanoic acid which was used in the subsequent transformation without additional purification. ES/MS: 522.2 (M+H$^+$).

Step 3: Preparation of 3-(5-(((1R,2S)-2-((4-(difluoromethoxy)cyclohexyl) amino)cyclohexyl)methyl)-1-oxoisoindolin-2-yl)piperidine-2,6-dione (Example 323)

(S)-5-Amino-4-(5-(((1R,2S)-2-((4-(difluoromethoxy)cyclohexyl)amino)cyclohexyl) methyl)-1-oxoisoindolin-2-yl)-5-oxopentanoic acid (20 mg, 0.038 mmol) was taken up in acetonitrile (2 mL) and triethylamine (10 µL, 0.072 mmol) was added followed by 1,1'-carbonyldiimidazole (25 mg, 0.154 mmol). The reaction mixture was heated to 60° C. for 90 min. After cooling to room temperature, the reaction mixture was concentrated in vacuo and the residue was purified by RP-HPLC (eluent: MeCN/water gradient with 0.1% TFA) to give 3-(5-(((1R,2S)-2-((4-(difluoromethoxy)cyclohexyl)amino)cyclohexyl)methyl)-1-oxoisoindolin-2-yl)piperidine-2,6-dione (Example 323) as the trifluoroacetate salt. ES/MS: 504.4 (M+H$^+$). $^1$H NMR (400 MHz, Methanol-d4) δ 7.79 (d, J=7.8 Hz, 1H), 7.52-7.36 (m, 2H), 6.44 (t, J=75.5 Hz, 1H), 5.17 (dd, J=13.3, 5.2 Hz, 1H), 4.58-4.42 (m, 2H), 4.12 (dt, J=10.6, 5.2 Hz, 1H), 3.23-3.10 (m, 2H), 2.98-2.86 (m, 1H), 2.81 (ddd, J=17.6, 4.7, 2.4 Hz, 1H), 2.60-2.45 (m, 2H), 2.30-2.07 (m, 6H), 2.01-1.78 (m, 2H), 1.74-1.43 (m, 8H), 1.19 (q, J=12.6, 11.7 Hz, 2H).

Procedure 35, Examples 324

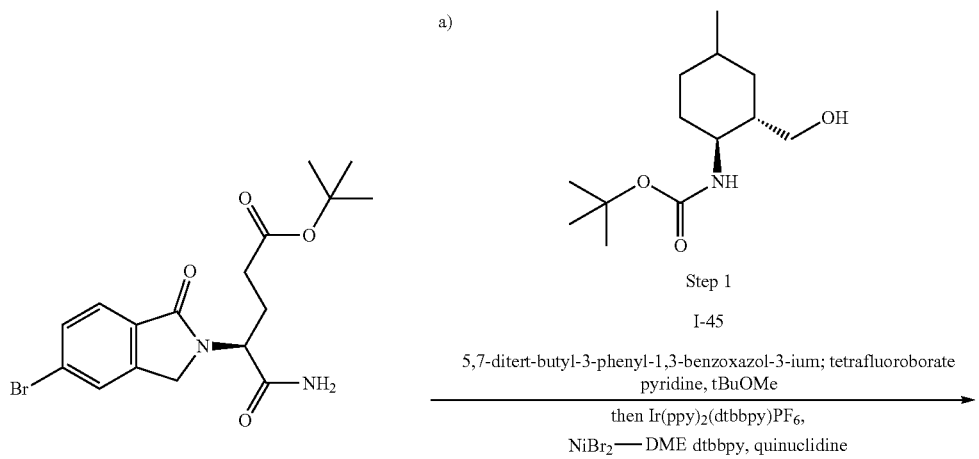

a)

Step 1
I-45

5,7-ditert-butyl-3-phenyl-1,3-benzoxazol-3-ium; tetrafluoroborate
pyridine, tBuOMe
then Ir(ppy)$_2$(dtbbpy)PF$_6$,
NiBr$_2$—DME dtbbpy, quinuclidine
DMA, 456 nm Blue LED b) Chiral SFC separation -continued

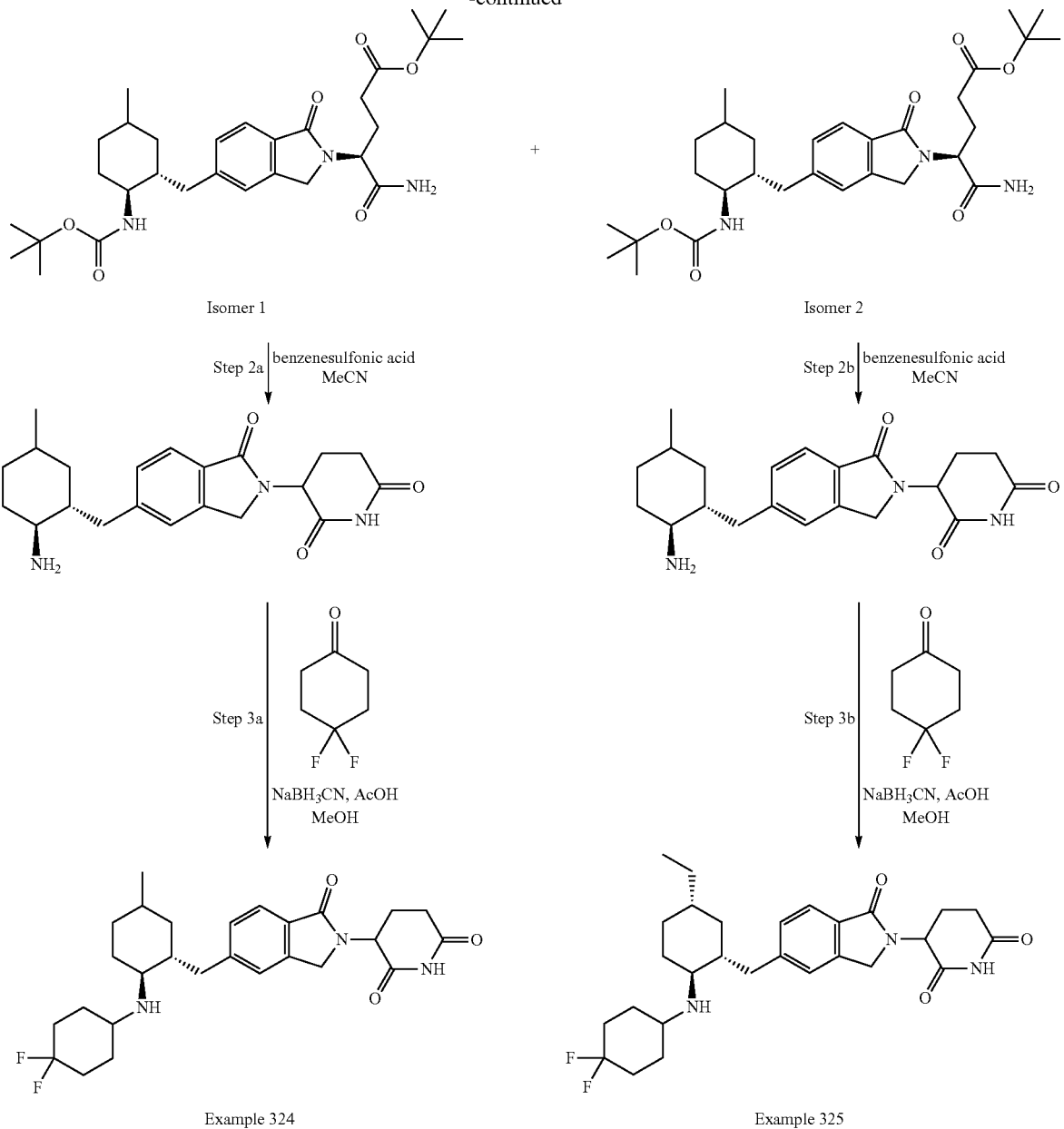

Step 1: Preparation of tert-butyl (4S)-5-amino-4-(5-(((1R,2S)-2-((tert-butoxycarbonyl)amino)-5-methyl-cyclohexyl)methyl)-1-oxoisoindolin-2-yl)-5-oxopentanoate (Isomer 1) and tert-butyl (4S)-5-amino-4-(5-(((1R,2S)-2-((tert-butoxycarbonyl)amino)-5-methylcyclohexyl)methyl)-1-oxoisoindolin-2-yl)-5-oxopentanoate (Isomer 2)

A vial was charged tert-butyl (S)-5-amino-4-(5-bromo-1-oxoisoindolin-2-yl)-5-oxopentanoate ([prepared according to the procedure described in WO2021/101919] 240 mg, 0.604 mmol), [Ir(dtbbpy)(ppy)$_2$]PF$_6$ (8.3 mg, 9.06 μmol), NiBr$_2$-DME (9.3 mg, 30.2 μmol), 4,4'-di-tert-butyl-2,2'-dipyridyl (9.7 mg, 36.2 μmol), and quinuclidine (118 mg, 1.06 mmol). The headspace was purged while in a second vial, tert-butyl ((1S,2S)-2-(hydroxymethyl)-4-methylcyclohexyl)carbamate (I-45) (206 mg, 0.846 mmol), 5,7-ditert-butyl-3-phenyl-1,3-benzoxazol-3-ium; tetrafluoroborate (382 mg, 0.967 mmol) and pyridine (0.0782 mL, 0.967 mmol) were combined in MTBE (6.04 mL). This mixture was stirred for 10 minutes. DMA (6.04 mL) was added to the first vial and the activated alcohol suspension was then transferred to a syringe fitted with a syringe filter and needle. The suspension was filtered into the solution of aryl bromide and the mixture sparged with nitrogen for 5 min. The reaction was then stirred under irradiation by blue light irradiation (Kessil Lamp/450 nm Blue LED combined with a small fan to increase air circulation) for 91 h. Following this time, the reaction was quenched by addition of sat. aqueous NaHCO$_3$ and diluted with water and EtOAc. The reaction was transferred to a separatory funnel and the layers were separated. The aqueous layer was back-extracted with EtOAc (2×) and the combined organics were then washed with water and brine and concentrated in vacuo. The residue was purified directly by column chromatography (eluent: EtOAc/hexanes gradient) to afford a solid. The solid was further purified by chiral SFC chromatography (column: AD-H 4.6×100 mm 5 μm, co-solvent: 20% EtOH) to afford tert-butyl (4S)-5-amino-4-(5-(((1R,2S)-2-((tert-butoxycarbonyl)amino)-5-methylcyclohexyl)methyl)-1-oxoisoindolin-2-yl)-5-oxopentanoate (Isomer 1) and tert-butyl (4S)-5-amino-4-(5-(((1R,2S)-2-((tert-butoxycarbonyl) amino)-5-methylcyclohexyl)methyl)-1-oxoisoindolin-2-yl)-5-oxopentanoate (Isomer 2). ES/MS: 544.3 (M+H$^+$, Isomer 1) and 544.3 (M+H$^+$, Isomer 2).

Step 2a: Preparation of 3-(5-(((1R,2S)-2-amino-5-methylcyclohexyl)methyl)-1-oxoisoindolin-2-yl)piperidine-2,6-dione (Isomer 1)

A vial was charged with tert-butyl (4S)-5-amino-4-(5-(((1R,2S)-2-((tert-butoxycarbonyl)amino)-5-methylcyclohexyl)methyl)-1-oxoisoindolin-2-yl)-5-oxopentanoate (Isomer 1, 78 mg, 0.143 mmol), MeCN (2.35 mL), and benzenesulfonic acid (68.1 mg, 0.430 mmol). The reaction was heated to 130° C. under microwave irradiation for 30 min. Following this time, the reaction was concentrated in vacuo to yield 3-(5-(((1R,2S)-2-amino-5-methylcyclohexyl)methyl)-1-oxoisoindolin-2-yl)piperidine-2,6-dione (Isomer 1) which was used in the subsequent reaction without further purification. ES/MS: 370.2 (M+H$^+$)

Step 2b: Preparation of 3-(5-(((1R,2S)-2-amino-5-methylcyclohexyl)methyl)-1-oxoisoindolin-2-yl)piperidine-2,6-dione (Isomer 2)

A vial was charged with tert-butyl (4S)-5-amino-4-(5-(((1R,2S)-2-((tert-butoxycarbonyl)amino)-5-methylcyclohexyl)methyl)-1-oxoisoindolin-2-yl)-5-oxopentanoate (Isomer 2, 38.7 mg, 0.0712 mmol), MeCN (1.16 mL), and benzenesulfonic acid (33.8 mg, 0.214 mmol). The reaction was heated to 130° C. under microwave irradiation for 30 min. Following this time, the reaction was concentrated in vacuo to yield 3-(5-(((1R,2S)-2-amino-5-methylcyclohexyl)methyl)-1-oxoisoindolin-2-yl)piperidine-2,6-dione (Isomer 2) which was used in the subsequent reaction without further purification. ES/MS: 370.2 (M+H$^+$).

Step 3a: Preparation of 3-(5-(((1R,2S)-2-((4,4-difluorocyclohexyl)amino)-5-methylcyclohexyl)methyl)-1-oxoisoindolin-2-yl)piperidine-2,6-dione (Example 324)

A vial was charged with 3-(5-(((1R,2S)-2-amino-5-methylcyclohexyl)methyl)-1-oxoisoindolin-2-yl)piperidine-2,6-dione (Isomer 1, 53 mg, 0.143 mmol), 4,4-difluorocyclohexan-1-one (192 mg, 1.43 mmol), sodium cyanoborohydride (27 mg, 0.430 mmol), MeOH (0.53 mL), and acetic acid (8.2 μL, 0.143 mmol). The reaction was heated to 50° C. and stirred for 1.5 h. Following this time, the mixture was concentrated in vacuo and the residue was taken up in DMSO and purified directly by RP-HPLC (eluent: MeCN/water gradient with 0.1% TFA) to yield the product (Example 324) as the trifluoroacetate salt. ES/MS: 488.4 (M+H$^+$). $^1$H NMR (400 MHz, DMSO-d$_6$) δ 11.00 (s, 1H), 8.62 (s, 1H), 8.14 (s, 1H), 7.70 (d, J=7.8 Hz, 1H), 7.43 (s, 1H), 7.35 (d, J=7.8 Hz, 1H), 5.11 (dd, J=13.3, 5.1 Hz, 1H), 4.46 (dd, J=17.3, 7.1 Hz, 1H), 4.32 (dd, J=17.3, 8.4 Hz, 1H), 3.06 (s, 1H), 2.92 (ddd, J=18.0, 13.6, 5.4 Hz, 1H), 2.66-2.56 (m, 1H), 2.46-2.36 (m, 1H), 2.34 (s, 1H), 2.12 (ddd, J=16.7, 11.2, 5.2 Hz, 5H), 2.07-1.88 (m, 6H), 1.88-1.75 (m, 1H), 1.75-1.60 (m, 2H), 1.47-1.35 (m, 2H), 1.29-1.16 (m, 1H), 1.00 (qd, J=13.0, 3.2 Hz, 1H), 0.76 (d, J=6.4 Hz, 3H), 0.69 (d, J=12.1 Hz, 1H).

Step 3b: 3-(5-(((1R,2S)-2-((4,4-difluorocyclohexyl)amino)-5-methylcyclohexyl) methyl)-1-oxoisoindolin-2-yl)piperidine-2,6-dione (Example 325)

A vial was charged with 3-(5-(((1R,2S)-2-amino-5-methylcyclohexyl)methyl)-1-oxoisoindolin-2-yl)piperidine-2,6-dione (Isomer 2, 26.3 mg, 0.0712 mmol), 4,4-difluorocyclohexan-1-one (95.5 mg, 0.712 mmol), sodium cyanoborohydride (13.4 mg, 0.214 mmol), MeOH (0.26 mL), and acetic acid (4.1 μL, 71.2 μmol). The reaction was heated to 50° C. and stirred for 1.5 h, adding additional 4,4-difluorocyclohexan-1-one as needed to reach full conversion. Upon completion, the mixture was concentrated in vacuo and the residue was taken up in DMSO and purified directly by RP-HPLC (eluent: MeCN/water gradient with 0.1% TFA) to yield the product (Example 325) as the trifluoroacetate salt. ES/MS: 488.4 (M+H$^+$) $^1$H NMR (400 MHz, DMSO-d$_6$) δ 10.99 (s, 1H), 8.43-8.29 (m, 1H), 8.28-8.11 (m, 1H), 7.69 (d, J=7.8 Hz, 1H), 7.47 (d, J=3.4 Hz, 1H), 7.38 (d, J=7.9 Hz, 1H), 5.11 (dd, J=13.3, 5.1 Hz, 1H), 4.44 (d, J=17.3 Hz, 1H), 4.31 (d, J=17.3 Hz, 1H), 3.24-3.10 (m, 1H), 3.03 (dd, J=13.5, 6.1 Hz, 1H), 2.92 (ddd, J=18.0, 13.6, 5.4 Hz, 1H), 2.72 (dd, J=13.4, 9.2 Hz, 1H), 2.67-2.56 (m, 1H), 2.39 (ddd, J=23.6, 11.9, 7.2 Hz, 1H), 2.25-2.16 (m, 1H), 2.14-2.04 (m, 3H), 2.03-1.96 (m, 5H), 1.96-1.84 (m, 2H), 1.82-1.66 (m, 1H), 1.56 (pd, J=9.7, 6.7, 4.3 Hz, 3H), 1.33 (ddtd, J=26.0, 16.2, 12.0, 10.7, 6.1 Hz, 3H), 0.84 (d, J=6.6 Hz, 3H).

Procedure 36, Examples 326

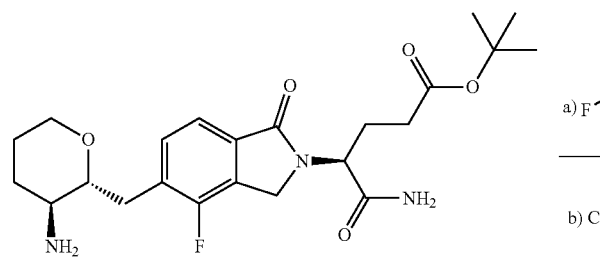

I-41

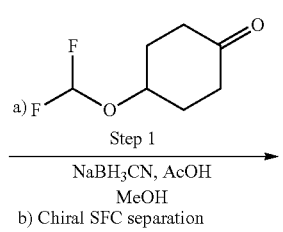

Step 1
a) NaBH$_3$CN, AcOH
MeOH
b) Chiral SFC separation

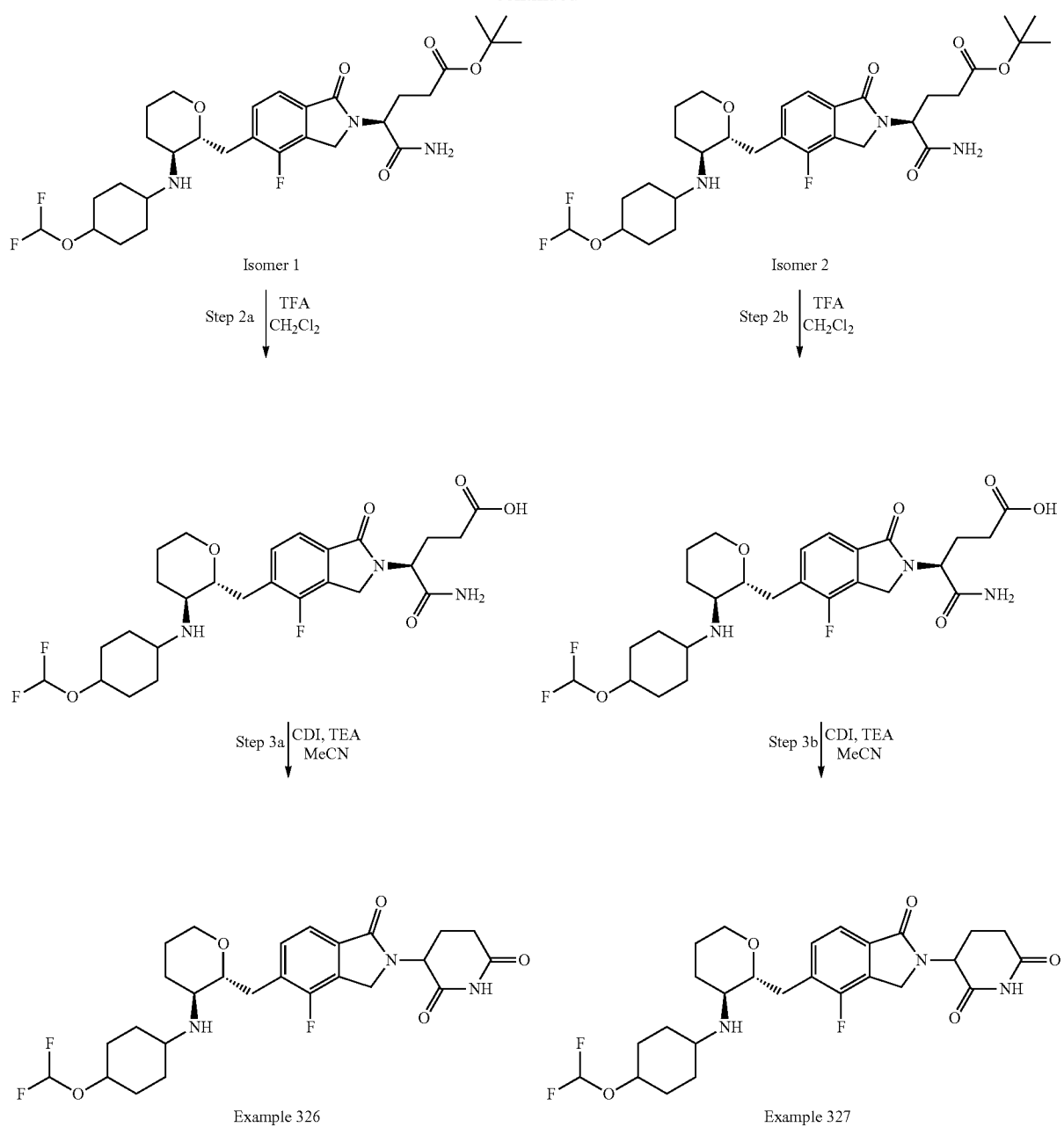

Step 1: Preparation of tert-butyl (S)-5-amino-4-(5-((((2R,3S)-3-((4-(difluoromethoxy)cyclohexyl)amino)tetrahydro-2H-pyran-2-yl)methyl)-4-fluoro-1-oxoisoindolin-2-yl)-5-oxopentanoate (Isomer 1) and tert-butyl (S)-5-amino-4-(5-(((2R,3S)-3-((4-(difluoromethoxy)cyclohexyl)amino)tetrahydro-2H-pyran-2-yl)methyl)-4-fluoro-1-oxoisoindolin-2-yl)-5-oxopentanoate (Isomer 2)

I-41 (150 mg, 0.334 mmol) was taken up in in methanol (3 mL) and 4-(difluoromethoxy)cyclohexan-1-one (230 mg, 1.40 mmol) was added followed by a few drops of acetic acid. The reaction mixture was heated to 50° C. for 15 min. After cooling to room temperature, sodium cyanoborohydride (57 mg, 0.907 mmol) was added. The reaction mixture was stirred at r.t. for 20 minutes then concentrated in vacuo and the residue was purified directly by $SiO_2$ column chromatography (eluent: $CH_2Cl_2$/MeOH). The mixture of isomers was submitted to chiral SFC separation (column: IG 4.6×100 mm, 5 μm, co-solvent: 40% MeOH) to give tert-butyl (S)-5-amino-4-(5-(((2R,3S)-3-((4-(difluoromethoxy)cyclohexyl)amino)tetrahydro-2H-pyran-2-yl)methyl)-4-fluoro-1-oxoisoindolin-2-yl)-5-oxopentanoate (Isomer 1) and tert-butyl (S)-5-amino-4-(5-(((2R,3S)-3-((4-(difluoromethoxy)cyclohexyl)amino)tetrahydro-2H-pyran-2-yl)methyl)-4-fluoro-1-oxoisoindolin-2-yl)-5-oxopentanoate (Isomer 2). ES/MS: 598.2 (M+H+) for both isomers.

593

Step 2a and 2b: Preparation of (S)-5-amino-4-(5-(((2R,3S)-3-((4-(difluoromethoxy)cyclohexyl)amino)tetrahydro-2H-pyran-2-yl)methyl)-4-fluoro-1-oxoisoindolin-2-yl)-5-oxopentanoic acid (Isomer 1) and S)-5-amino-4-(5-(((2R,3S)-3-((4-(difluoromethoxy)cyclohexyl)amino)tetrahydro-2H-pyran-2-yl)methyl)-4-fluoro-1-oxoisoindolin-2-yl)-5-oxopentanoic acid (Isomer 1)

The title compounds were prepared in the same manner as Example 323, step 2. ES/MS: 542.1 (M+H$^+$) for both isomers.

Step 3a and 3b: Preparation of 3-(5-(((2R,3S)-3-((4-(difluoromethoxy)cyclohexyl)amino)tetrahydro-2H-pyran-2-yl)methyl)-4-fluoro-1-oxoisoindolin-2-yl)piperidine-2,6-dione (Example 326) and 3-(5-(((2R,3S)-3-((4-(difluoromethoxy)cyclohexyl)amino)tetrahydro-2H-pyran-2-yl)methyl)-4-fluoro-1-oxoisoindolin-2-yl)piperidine-2,6-dione (Example 327)

The title compounds were prepared in the same manner as Example 323, step 3. Example 326: ES/MS: 524.2 (M+H$^+$). $^1$H NMR (400 MHz, Methanol-d$_4$) δ 7.62 (d, J=7.8 Hz, 1H), 7.55 (dd, J=7.8, 6.2 Hz, 1H), 6.47 (t, J=75.9 Hz, 1H), 5.17 (dd, J 13.3, 5.1 Hz, 1H), 4.66-4.50 (m, 2H), 4.45 (t, J=2.8 Hz, 1H), 3.96-3.81 (m, 2H), 3.48-3.36 (m, 3H), 3.15 (dd, J=14.4, 9.7 Hz, 1H), 2.98-2.88 (m, 1H), 2.81 (ddd, J=17.6, 4.7, 2.4 Hz, 1H), 2.55 (td, J=13.2, 4.8 Hz, 1H), 2.39 (d, J=12.6 Hz, 1H), 2.21 (ddq, J=10.5, 5.3, 2.7 Hz, 1H), 2.07 (dd, J=27.6, 13.0 Hz, 3H), 1.94 (td, J=10.8, 9.9, 3.5 Hz, 2H), 1.90-1.67 (m, 6H). Example 327: ES/MS: 524.2 (M+H$^+$). $^1$H NMR (400 MHz, Methanol-d4) δ 7.62 (d, J=7.7 Hz, 1H), 7.58-7.51 (m, 1H), 6.44 (t, J=75.5 Hz, 2H), 5.17 (dd, J=13.3, 5.1 Hz, 1H), 4.66-4.50 (m, 2H), 4.12 (p, J=6.1 Hz, 1H), 3.97-3.80 (m, 2H), 3.51-3.37 (m, 2H), 3.27 (dd, J=14.2, 3.6 Hz, 1H), 3.19-3.11 (m, 1H), 2.96-2.86 (m, 1H), 2.81 (ddd, J=17.6, 4.7, 2.4 Hz, 1H), 2.55 (td, J=13.2, 4.7 Hz, 1H), 2.37 (s, 1H), 2.30-2.15 (m, 4H), 1.90-1.71 (m, 3H), 1.70-1.47 (m, 4H).

Procedure 37, Examples 328 and 329

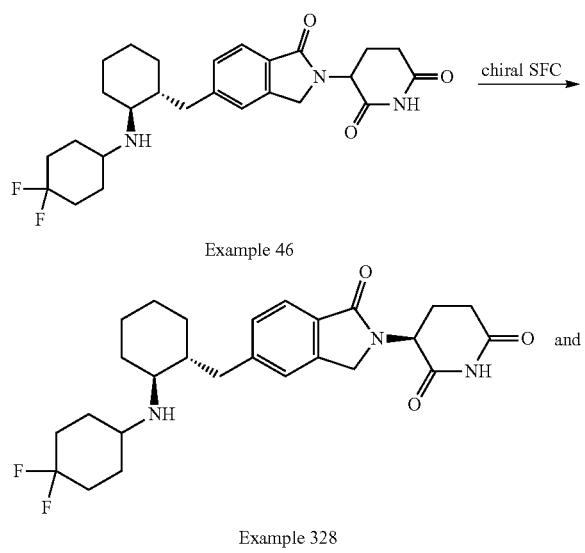

Example 46

Example 328

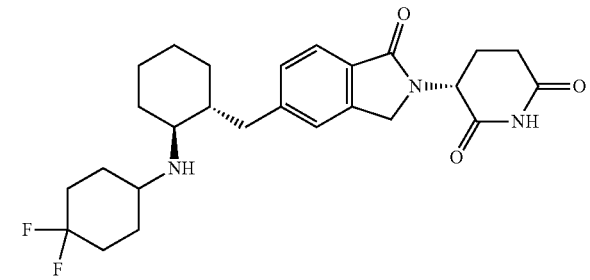

Example 329

(S)-3-(5-(((1R,2S)-2-((4,4-difluorocyclohexyl)amino)cyclohexyl)methyl)-1-oxoisoindolin-2-yl)piperidine-2,6-dione (Example 328) and (R)-3-(5-(((1R,2S)-2-((4,4-difluorocyclohexyl)amino)cyclohexyl)methyl)-1-oxoisoindolin-2-yl)piperidine-2,6-dione (Example 329). Example 46

(56.2 mg, 79.2 μmol) was subjected to chiral SFC (Column: CCO-F2 250 mm×21 mm, 5 μm, eluent: 25% MeOH) to afford two peaks. Fractions corresponding to the first peak were concentrated in vacuo to afford the product assigned as (S)-3-(5-(((1R,2S)-2-((4,4-difluorocyclohexyl)amino)cyclohexyl)methyl)-1-oxoisoindolin-2-yl)piperidine-2,6-dione (Example 328). Fractions corresponding to the second peak were concentrated in vacuo to afford the product assigned as (R)-3-(5-(((1R,2S)-2-((4,4-difluorocyclohexyl)amino)cyclohexyl)methyl)-1-oxoisoindolin-2-yl)piperidine-2,6-dione (Example 329). Example 328: ES/MS: 474.2 (M+H$^+$). $^1$H NMR (400 MHz, DMSO-d6) δ 10.98 (s, 1H), 7.63 (d, J=7.8 Hz, 1H), 7.39 (s, 1H), 7.31 (dd, J=7.8, 1.3 Hz, 1H), 5.11 (dd, J=13.3, 5.1 Hz, 1H), 4.42 (d, J=17.2 Hz, 1H), 4.30 (d, J=17.2 Hz, 1H), 3.55-3.44 (m, 1H), 2.99-2.78 (m, 2H), 2.60 (ddd, J=17.3, 4.5, 2.4 Hz, 1H), 2.39 (qd, J=13.3, 4.5 Hz, 1H), 2.23 (dd, J=13.1, 10.0 Hz, 1H), 2.17-1.94 (m, 5H), 1.94-1.71 (m, 4H), 1.66 (d, J=12.4 Hz, 1H), 1.60-1.28 (m, 5H), 1.28-1.09 (m, 1H), 1.09-0.84 (m, 3H). Example 329: ES/MS: 474.2 (M+H$^+$). $^1$H NMR (400 MHz, DMSO-d6) δ 10.98 (s, 1H), 7.62 (d, J=7.7 Hz, 1H), 7.39 (s, 1H), 7.31 (d, J=7.8 Hz, 1H), 5.10 (dd, J=13.3, 5.1 Hz, 1H), 4.43 (d, J=17.2 Hz, 1H), 4.36-4.19 (m, 1H), 3.50 (d, J=11.8 Hz, 1H), 3.05-2.72 (m, 2H), 2.71-2.56 (m, 1H), 2.46-2.27 (m, 1H), 2.27-1.94 (m, 5H), 1.77 (d, J=11.5 Hz, 4H), 1.66 (d, J=12.5 Hz, 1H), 1.60-1.27 (m, 5H), 1.27-1.09 (m, 2H), 0.96 (dp, J=24.5, 12.8, 11.4 Hz, 3H).

The following Examples were made using the general route described in Procedure 37 and are shown below in Table 22. To prepare the below Examples, different reagents/starting materials were used than some of those described in Procedure 37 and are noted in the last column of Table 22—"Changes to Procedure 37: Different Reagents/Starting Materials". A person of ordinary skill in the art will readily recognize which reagents/starting materials of Procedure 37

TABLE 22

| Example | Structure | ES/MS m/z | ¹H-NMR | Changes to Procedure 37: Different Reagents/Starting Materials |
|---|---|---|---|---|
| 330 | (S)-3-(5-(((2R,3S)-3-((4-(difluoromethyl)cyclohexyl)amino)tetrahydro-2H-pyran-2-yl)methyl)-4-fluoro-1-oxoisoindolin-2-yl)piperidine-2,6-dione | 508.0 | ¹H NMR (400 MHz, DMSO-d6) δ 11.02 (s, 1H), 8.68 (s, 1H), 8.32 (s, 1H), 7.62-7.42 (m, 2H), 5.90 (td, J = 56.6, 3.7 Hz, 1H), 5.12 (dd, J = 13.3, 5.1 Hz, 1H), 4.56 (d, J = 17.4 Hz, 1H), 4.39 (d, J = 17.4 Hz, 1H), 3.77 (ddt, J = 10.4, 7.4, 3.6 Hz, 2H), 3.32-3.13 (m, 4H), 3.12-2.82 (m, 2H), 2.78-2.56 (m, 1H), 2.49-2.29 (m, 1H), 2.30-2.07 (m, 3H), 2.02 (ddq, J = 10.3, 5.3, 3.1, 2.6 Hz, 1H), 1.94-1.15 (m, 10H). | Example 283 Chiral SFC conditions: CCO-F2 5 μm-21 × 250 mm, co-solvent: MeOH (25%) [peak 1] |
| 331 | (R)-3-(5-(((2R,3S)-3-((4-(difluoromethyl)cyclohexyl)amino)tetrahydro-2H-pyran-2-yl)methyl)-4-fluoro-1-oxoisoindolin-2-yl)piperidine-2,6-dione | 508.0 | ¹H NMR (400 MHz, DMSO-d6) δ 11.01 (s, 1H), 8.55 (s, 1H), 8.22 (s, 1H), 7.69-7.33 (m, 2H), 6.21-5.62 (m, 1H), 5.12 (dd, J = 13.3, 5.1 Hz, 1H), 4.56 (dd, J = 17.4, 5.2 Hz, 1H), 4.38 (d, J = 17.4 Hz, 1H), 3.78 (d, J = 11.0 Hz, 2H), 3.25 (d, J = 14.7 Hz, 5H), 3.10-2.78 (m, 2H), 2.78-2.55 (m, 1H), 2.46-2.30 (m, 1H), 2.30-1.94 (m, 4H), 1.94-1.06 (m, 8H). | Example 283 Chiral SFC conditions: CCO-F2 5 μm-21 × 250 mm, co-solvent: MeOH (25%) [peak 2] |
| 332 | (S)-3-(5-(((2R,3S)-3-((4,4-difluorocyclohexyl)amino)tetrahydro-2H-pyran-2-yl)methyl)-4-fluoro-1-oxoisoindolin-2-yl)piperidine-2,6-dione | 494.0 | ¹H NMR (400 MHz, DMSO-d6) δ 11.02 (s, 1H), 7.58 (d, J = 7.7 Hz, 1H), 7.52 (dd, J = 7.7, 6.2 Hz, 1H), 5.12 (dd, J = 13.3, 5.0 Hz, 1H), 4.56 (d, J = 17.4 Hz, 1H), 4.39 (d, J = 17.3 Hz, 1H), 3.78 (td, J = 11.6, 9.5, 6.1 Hz, 2H), 3.34-3.19 (m, 3H), 3.11-2.82 (m, 2H), 2.74-2.56 (m, 1H), 2.50-2.36 (m, 2H), 2.36-1.84 (m, 8H), 1.84-1.51 (m, 6H). | Example 94 Chiral SFC conditions: CCO-F2 5 μm-21 × 250 mm, co-solvent: MeOH (30%) [peak 1] |
| 333 | (R)-3-(5-(((2R,3S)-3-((4,4-difluorocyclohexyl)amino)tetrahydro-2H-pyran-2-yl)methyl)-4-fluoro-1-oxoisoindolin-2-yl)piperidine-2,6-dione | 494.0 | ¹H NMR (400 MHz, DMSO-d6) δ 11.01 (s, 1H), 8.80 (d, J = 14.0 Hz, 1H), 8.34 (s, 1H), 7.58 (d, J = 7.7 Hz, 1H), 7.55-7.43 (m, 1H), 5.12 (dd, J = 13.3, 5.1 Hz, 1H), 4.57 (d, J = 17.4 Hz, 1H), 4.38 (d, J = 17.3 Hz, 1H), 3.93-3.64 (m, 3H), 3.26 (d, J = 13.2 Hz, 3H), 3.09-2.82 (m, 2H), 2.71-2.58 (m, 1H), 2.50-2.34 (m, 1H), 2.34-1.86 (m, 7H), 1.85-1.44 (m, 6H). | Example 94 Chiral SFC conditions: CCO-F2 5 μm-21 × 250 mm, co-solvent: MeOH (30%) [peak 2] |

TABLE 22-continued

| Example | Structure | ES/MS m/z | ¹H-NMR | Changes to Procedure 37: Different Reagents/Starting Materials |
|---|---|---|---|---|
| 334 | (S)-3-(5-(((1R,2S)-2-((4,4-difluorocyclohexyl)amino)cyclohexyl)methyl)-4-fluoro-1-oxoisoindolin-2-yl)piperidine-2,6-dione | 492.0 | ¹H NMR (400 MHz, DMSO-d6) δ 11.02 (s, 1H), 8.71 (s, 1H), 8.21 (s, 1H), 7.59 (d, J = 7.7 Hz, 1H), 7.49 (dd, J = 7.7, 6.3 Hz, 1H), 5.12 (dd, J = 13.3, 5.1 Hz, 1H), 4.56 (d, J = 17.4 Hz, 1H), 4.40 (d, J = 17.3 Hz, 1H), 3.34-3.02 (m, 1H), 2.93 (ddd, J = 17.2, 13.6, 5.4 Hz, 1H), 2.75-2.53 (m, 2H), 2.49-2.30 (m, 1H), 2.26-1.21 (m, 17H), 1.08 (q, J = 10.5, 9.4 Hz, 2H). | Example 84 Chiral SFC conditions: CCO-F2 5 μm- 21 × 250 mm, co-solvent: MeOH (25%) [peak 1] |
| 335 | (R)-3-(5-(((1R,2S)-2-((4,4-difluorocyclohexyl)amino)cyclohexyl)methyl)-4-fluoro-1-oxoisoindolin-2-yl)piperidine-2,6-dione | 492.0 | ¹H NMR (400 MHz, DMSO-d6) δ 11.02 (s, 1H), 7.60 (d, J = 7.6 Hz, 1H), 7.49 (t, J = 7.0 Hz, 1H), 5.12 (dd, J = 13.3, 5.1 Hz, 1H), 4.58 (d, J = 17.4 Hz, 1H), 4.39 (d, J = 17.4 Hz, 1H), 3.34-3.11 (m, 2H), 2.93 (ddd, J = 17.2, 13.6, 5.4 Hz, 1H), 2.73-2.52 (m, 2H), 2.46-2.27 (m, 1H), 2.27-1.20 (m, 17H), 1.18-0.89 (m, 2H). | Example 84 Chiral SFC conditions: CCO-F2 5 μm- 21 × 250 mm, co-solvent: MeOH (25%) [peak 2] |
| 336 | (S)-3-(5-(((1R,2S)-2-(cyclohexylamino)cyclohexyl)methyl)-1-oxoisoindolin-2-yl)piperidine-2,6-dione | 438.1 | ¹H NMR (400 MHz, Methanol-d4) δ 7.79 (d, J = 7.8 Hz, 1H), 7.47 (s, 1H), 7.45-7.39 (m, 1H), 5.18 (dd, J = 13.3, 5.1 Hz, 1H), 4.57-4.44 (m, 2H), 3.27 (d, J = 4.4 Hz, 2H), 3.19 (d, J = 9.7 Hz, 2H), 2.97-2.88 (m, 1H), 2.81 (ddd, J = 17.7, 4.8, 2.5 Hz, 1H), 2.60-2.47 (m, 2H), 2.27-2.14 (m, 3H), 2.08 (d, J = 11.4 Hz, 1H), 1.93 (d, J = 10.7 Hz, 3H), 1.85 (s, 1H), 1.77 (d, J = 12.9 Hz, 1H), 1.65 (d, J = 15.5 Hz, 2H), 1.55-1.39 (m, 5H), 1.31-1.14 (m, 3H). | Example 53 Chiral SFC conditions: CCO-F2 5 μm- 21 × 250 mm, co-solvent: MeOH (25%) [peak 1] |
| 337 | (R)-3-(5-(((1R,2S)-2-(cyclohexylamino)cyclohexyl)methyl)-1-oxoisoindolin-2-yl)piperidine-2,6-dione | 438.0 | ¹H NMR (400 MHz, Methanol-d4) δ 7.79 (d, J = 7.9 Hz, 1H), 7.47 (s, 1H), 7.44-7.39 (m, 1H), 5.18 (dd, J = 13.3, 5.2 Hz, 1H), 4.57-4.44 (m, 2H), 3.27 (d, J = 4.3 Hz, 2H), 3.20 (d, J = 8.5 Hz, 1H), 2.96-2.89 (m, 1H), 2.85-2.77 (m, 1H), 2.59-2.45 (m, 2H), 2.26-2.13 (m, 3H), 2.09 (d, J = 11.1 Hz, 1H), 1.93 (d, J = 11.1 Hz, 3H), 1.84 (d, J = 11.0 Hz, 1H), 1.77 (d, J = 13.1 Hz, 1H), 1.64 (d, J = 16.1 Hz, 2H), 1.52-1.39 (m, 4H), 1.31-1.13 (m, 3H). | Example 53 Chiral SFC conditions: CCO-F2 5 μm- 21 × 250 mm, co-solvent: MeOH (25%) [peak 2] |

TABLE 22-continued

| Example | Structure | ES/MS m/z | ¹H-NMR | Changes to Procedure 37: Different Reagents/Starting Materials |
|---|---|---|---|---|
| 338 | (S)-3-(5-(((2R,3S)-3-(cyclohexylamino)tetrahydro-2H-pyran-2-yl)methyl)-4-fluoro-1-oxoisoindolin-2-yl)piperidine-2,6-dione | 458.0 | ¹H NMR (400 MHz, Methanol-d4) δ 7.62 (d, J = 7.7 Hz, 1H), 7.60-7.52 (m, 1H), 5.18 (dd, J = 13.4, 5.1 Hz, 1H), 4.65-4.49 (m, 2H), 3.97-3.78 (m, 2H), 3.42 (dd, J = 10.0, 6.3 Hz, 1H), 3.26 (d, J = 3.6 Hz, 1H), 3.21-3.10 (m, 1H), 2.94 (ddd, J = 18.5, 13.5, 5.4 Hz, 1H), 2.81 (ddd, J = 17.7, 4.7, 2.4 Hz, 1H), 2.58-2.48 (m, 1H), 2.41-2.32 (m, 1H), 2.25-2.15 (m, 2H), 2.09 (d, J = 10.6 Hz, 1H), 1.93 (d, J = 10.8 Hz, 2H), 1.77 (q, J = 16.0, 11.1 Hz, 3H), 1.45 (dt, J = 26.0, 12.0 Hz, 3H), 1.27 (t, J = 13.8 Hz, 1H). | Example 181 Chiral SFC conditions: CCO-F2 5 μm-21 × 250 mm, co-solvent: MeOH (25%) [peak 1] |
| 339 | (R)-3-(5-(((2R,3S)-3-(cyclohexylamino)tetrahydro-2H-pyran-2-yl)methyl)-4-fluoro-1-oxoisoindolin-2-yl)piperidine-2,6-dione | 458.0 | ¹H NMR (400 MHz, Methanol-d4) δ 7.62 (d, J = 7.8 Hz, 1H), 7.58-7.52 (m, 1H), 5.18 (dd, J = 13.4, 5.1 Hz, 1H), 4.58 (q, J = 17.2 Hz, 2H), 4.18 (ddd, J = 12.1, 9.0, 3.7 Hz, 1H), 3.97-3.81 (m, 2H), 3.55 (dt, J = 11.8, 2.8 Hz, 1H), 3.49-3.39 (m, 1H), 3.12 (d, J = 4.1 Hz, 1H), 2.95-2.87 (m, 1H), 2.84-2.75 (m, 1H), 2.52 (td, J = 13.2, 4.7 Hz, 1H), 2.36 (d, J = 3.9 Hz, 1H), 2.24-2.14 (m, 2H), 2.09 (d, J = 10.8 Hz, 2H), 1.89 (dd, J = 28.1, 13.5 Hz, 3H), 1.75 (q, J = 10.1, 9.2 Hz, 3H), 1.45 (dt, J = 25.8, 12.4 Hz, 4H), 1.33-1.20 (m, 2H). | Example 181 Chiral SFC conditions: CCO-F2 5 μm-21 × 250 mm, co-solvent: MeOH (25%) [peak 2] |

Example 328 can alternatively be prepared according to the procedure described below:

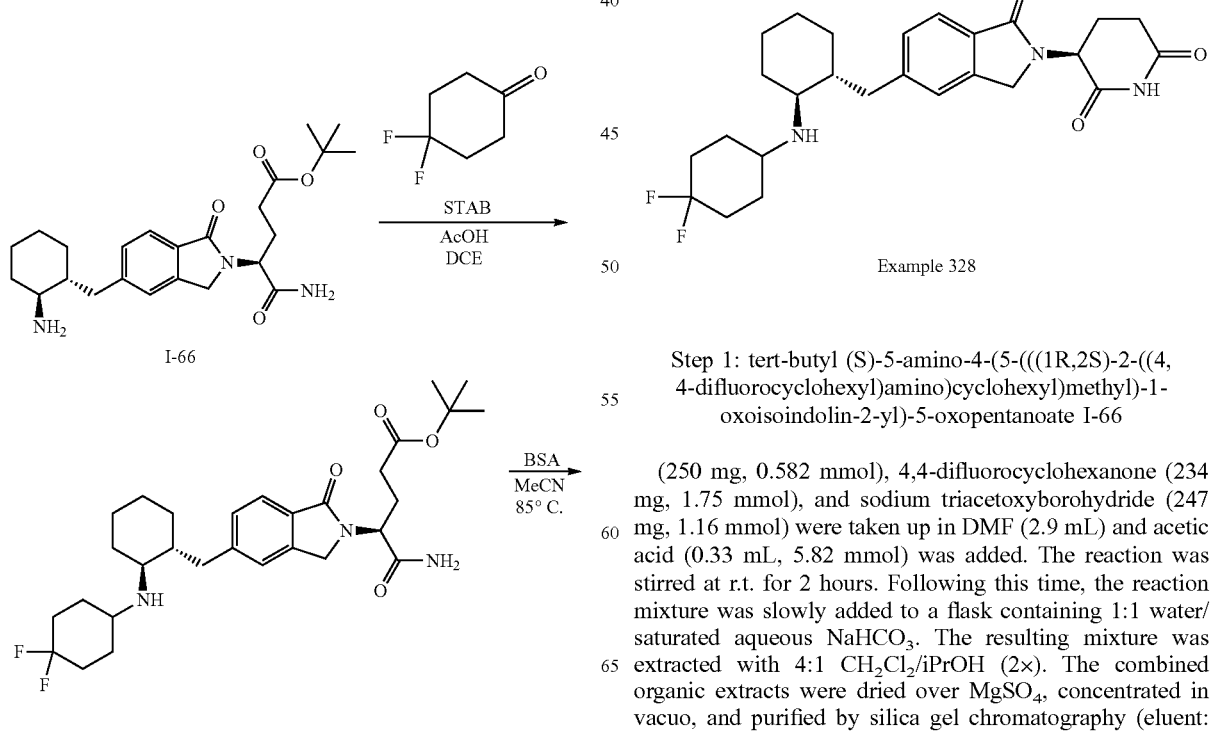

Example 328

Step 1: tert-butyl (S)-5-amino-4-(5-(((1R,2S)-2-((4,4-difluorocyclohexyl)amino)cyclohexyl)methyl)-1-oxoisoindolin-2-yl)-5-oxopentanoate I-66

(250 mg, 0.582 mmol), 4,4-difluorocyclohexanone (234 mg, 1.75 mmol), and sodium triacetoxyborohydride (247 mg, 1.16 mmol) were taken up in DMF (2.9 mL) and acetic acid (0.33 mL, 5.82 mmol) was added. The reaction was stirred at r.t. for 2 hours. Following this time, the reaction mixture was slowly added to a flask containing 1:1 water/saturated aqueous NaHCO₃. The resulting mixture was extracted with 4:1 CH₂Cl₂/iPrOH (2×). The combined organic extracts were dried over MgSO₄, concentrated in vacuo, and purified by silica gel chromatography (eluent:

CH₂Cl₂/MeOH) to afford tert-butyl (S)-5-amino-4-(5-(((1R,2S)-2-((4,4-difluorocyclohexyl)amino)cyclohexyl)methyl)-1-oxoisoindolin-2-yl)-5-oxopentanoate. (ES/MS m/z: 548.1 (M+H)⁺

Step 2: (S)-3-(5-(((1R,2S)-2-((4,4-difluorocyclohexyl)amino)cyclohexyl)methyl)-1-oxoisoindolin-2-yl)piperidine-2,6-dione (Example 328)

tert-butyl (S)-5-amino-4-(5-(((1R,2S)-2-((4,4-difluorocyclohexyl)amino)cyclohexyl)methyl)-1-oxoisoindolin-2-yl)-5-oxopentanoate (200 mg, 0.365 mmol) was taken up in MeCN (3.6 mL) and benzenesulfonic acid (86.6 mg, 0.548 mmol) was added. The reaction was then heated to 85° C. for 12 hours. Following this time, the mixture was cooled to r.t., diluted with 4:1 CH₂Cl₂/iPrOH, and washed with 1:1 water/saturated aqueous NaHCO₃. The aqueous phase was extracted with additional 4:1 CH₂Cl₂/iPrOH (2×) and then the combined organic extracts were dried over MgSO₄ and concentrated in vacuo. The material was purified by silica gel chromatography (eluent: CH₂Cl₂/MeOH) to afford Example 328. ES/MS: 474.2 (M+H⁺). ¹H NMR (400 MHz, DMSO-d6) δ 11.00 (s, 1H), 8.53 (s, 1H), 8.14 (s, 1H), 7.71 (d, J=7.8 Hz, 1H), 7.45 (s, 1H), 7.37 (dd, J=7.7, 1.3 Hz, 1H), 5.12 (dd, J=13.3, 5.1 Hz, 1H), 4.45 (d, J=17.3 Hz, 1H), 4.33 (d, J=17.3 Hz, 1H), 3.28 (dd, J=13.2, 3.4 Hz, 1H), 3.11 (s, 1H), 2.93 (ddd, J=17.3, 13.6, 5.4 Hz, 1H), 2.75-2.55 (m, 1H), 2.45-2.25 (m, 2H), 2.25-1.20 (m, 9H), 1.04 (dt, J=11.4, 5.3 Hz, 2H).

The following Examples were made using the general routes described in Procedures 3, 7, 22, 23, 24, 25, 28, or 32 (as indicated) and are shown below in Table 23. To prepare the below Examples, different reagents/starting materials were used than some of those described in indicated Procedures and are noted in the last column of Table 23—"Changes to Procedures: Different Reagents/Starting Materials". A person of ordinary skill in the art will readily recognize which reagents/starting materials of indicated Procedures were replaced with the different reagents/starting materials noted below.

TABLE 23

| Example | Structure | ES/MS m/z: | 1H NMR | Procedure | Changes to Procedure: Different Reagents/ Starting Materials |
|---|---|---|---|---|---|
| 340 | 3-(5-(((1R,2S)-2-((4,4-difluorocyclohexyl)amino)cycloheptyl)methyl)-1-oxoisoindolin-2-yl)piperidine-2,6-dione | 488.0 | ¹H NMR (400 MHz, Methanol-d4) δ 7.81 (dd, J = 7.9, 2.3 Hz, 1H), 7.56-7.42 (m, 2H), 5.18 (dt, J = 13.4, 5.3 Hz, 1H), 4.58-4.42 (m, 2H), 3.24 (d, J = 11.0 Hz, 1H), 3.12-3.03 (m, 1H), 2.96-2.75 (m, 3H), 2.58-2.45 (m, 1H), 2.28-2.06 (m, 6H), 2.03-1.82 (m, 5H), 1.66 (ddd, J = 56.9, 23.0, 12.6 Hz, 9H). | 3 | I-47; 4,4-difluorocyclohexanone |
| 341 | 3-(5-(((1S,2S,5S)-2-((4,4-difluorocyclohexyl)amino)-5-fluorocyclohexyl)methyl)-1-oxoisoindolin-2-yl)piperidine-2,6-dione | 492.4 | ¹H NMR (400 MHz, DMSO-d6) δ 10.99 (s, 1H), 8.79-8.65 (m, 1H), 8.36-8.21 (m, 1H), 7.71 (d, J = 7.8 Hz, 1H), 7.45(s, 1H), 7.37 (d, J = 7.8 Hz, 1H), 5.12 (ddd, J = 13.2, 5.2, 1.7 Hz, 1H), 4.84-4.51 (m, 2H), 4.51-4.39 (m, 2H), 4.39-4.27 (m, 1H), 3.73-3.64 (m, 2H), 3.52-3.39 (m, 2H), 3.36-3.26 (m, 1H), 3.25-3.13 (m, 1H), 2.92 (ddd, J = 18.1, 13.7, 5.4 Hz, 1H), 2.65-2.55 (m, 1H), 2.47-1.45 (m, 12H), 1.32 (p, J = 10.8 Hz, 1H). | 3 | I-51; 4,4-difluorocyclohexanone |

TABLE 23-continued

| Example | Structure | ES/MS m/z: | 1H NMR | Procedure | Changes to Procedure: Different Reagents/ Starting Materials |
|---|---|---|---|---|---|
| 342 | 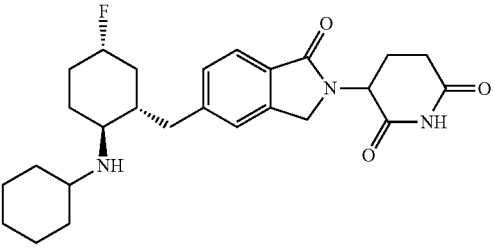<br>3-(5-(((1S,2S,5S)-2-(cyclohexylamino)-5-fluorocyclohexyl)methyl)-1-oxoisoindolin-2-yl)piperidine-2,6-dione | 456.4 | $^1$H NMR (400 MHz, DMSO-d6) δ 10.99 (s, 1H), 8.43-8.33 (m, 1H), 8.11-8.00 (m, 1H), 7.71 (d, J = 7.8 Hz, 1H), 7.46 (s, 1H), 7.37 (d, J = 7.7 Hz, 1H), 5.12 (dd, J = 13.3, 5.1 Hz, 1H), 4.60-4.39 (m, 2H), 4.33 (dd, J = 17.3, 10.7 Hz, 1H), 3.33-3.24 (m, 1H), 3.24-3.11 (m, 2H), 2.92 (ddd, J = 17.9, 13.6, 5.4 Hz, 1H), 2.65-2.56 (m, 1H), 2.46-2.31 (m, 2H), 2.20-1.90 (m, 6H), 1.84-1.22 (m, 11H), 1.18-1.05 (m, 1H). | 3 | I-51; cyclohexanone |
| 343 | 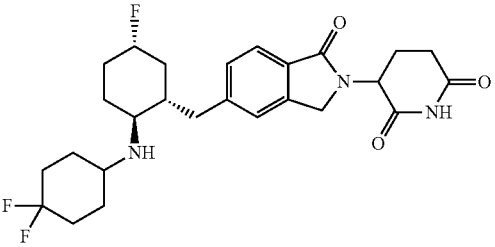<br>3-(5-(((1R,2S,4S-rel-)-2-((4,4-difluorocyclohexyl)amino)-4-hydroxycyclohexyl)methyl)-1-oxoisoindolin-2-yl)piperidine-2,6-dione | 490.0 | $^1$H NMR (400 MHz, DMSO-d6) δ 11.00 (s, 1H), 8.58 (s, 1H), 8.19 (s, 1H), 7.70 (d, J = 7.8 Hz, 1H), 7.44 (s, 1H), 7.36 (dd, J = 7.8, 1.3 Hz, 1H), 5.12 (dd, J = 13.3, 5.1 Hz, 1H), 4.96 (s, 1H), 4.46 (dd, J = 17.5, 2.6 Hz, 1H), 4.32 (dd, J = 17.4, 2.3 Hz, 1H), 3.70 (td, J = 7.1, 3.7 Hz, 0H), 3.25 (dd, J = 13.3, 3.4 Hz, 1H), 3.19 (s, 1H), 3.00-2.86 (m, 1H), 2.74 (s, 0H), 2.61 (d, J = 17.7 Hz, 1H), 2.40 (qd, J = 12.1, 10.7, 4.5 Hz, 2H), 2.22 (d, J = 12.3 Hz, 0H), 2.15 (s, 4H), 2.13-2.01 (m, 1H), 2.05-1.88 (m, 2H), 1.88-1.80 (m, 0H), 1.80 (s, 3H), 1.79-1.60 (m, 1H), 1.58-1.50 (m, 1H), 1.42 (q, J = 10.8 Hz, 1H), 1.05 (q, J = 10.3 Hz, 2H). | 3 | I-54; 4,4-difluorocyclohexanone |
| 344 | 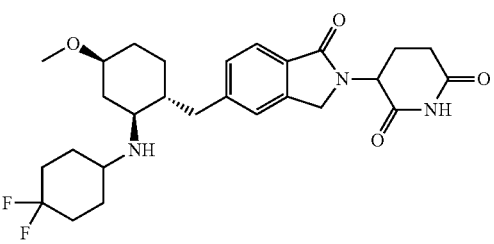<br>3-(5-(((1R,2S,4S)-rel-2-((4,4-difluorocyclohexyl)amino)-4-methoxycyclohexyl)methyl)-1-oxoisoindolin-2-yl)piperidine-2,6-dione | 504.0 | $^1$H NMR (400 MHz, DMSO-d6) δ 11.00 (s, 1H), 8.69 (s, 1H), 8.25 (s, 1H), 7.70 (d, J = 7.8 Hz, 1H), 7.45 (s, 1H), 7.36 (dd, J = 7.8, 1.3 Hz, 1H), 6.80 (s, 2H), 5.12 (dd, J = 13.3, 5.1 Hz, 1H), 4.46 (dd, J = 17.5, 2.6 Hz, 1H), 4.32 (dd, J = 17.4, 3.0 Hz, 1H), 3.26 (s, 5H), 3.19 (d, J = 9.9 Hz, 2H), 2.92 (ddd, J = 17.2, 13.6, 5.4 Hz, 1H), 2.61 (d, J = 17.6 Hz, 1H), 2.48-2.27 (m, 4H), 2.19-2.08 (m, 4H), 2.13-1.95 (m, 9H), 1.99-1.87 (m, 2H), 1.82 (t, J = 11.0 Hz, 1H), 1.66 (h, J = 8.8 Hz, 1H), 1.54 (t, J = 5.3 Hz, 1H), 1.39 (q, J = 10.5 Hz, 1H), 1.03 (q, J = 10.6, 9.2 Hz, 2H). | 3 | I-56; 4,4-difluorocyclohexanone |

TABLE 23-continued

| Example | Structure | ES/MS m/z: | 1H NMR | Procedure | Changes to Procedure: Different Reagents/ Starting Materials |
|---|---|---|---|---|---|
| 345 | 3-(5-(((1R,2S)-2-((4,4-difluorocyclohexyl)amino)-4,4-difluorocyclohexyl)methyl)-1-oxoisoindolin-2-yl)piperidine-2,6-dione | 510.2 | $^1$H NMR (400 MHz, DMSO-d6) δ 10.99 (s, 1H), 8.96-8.80 (m, 1H), 8.50-8.37 (m, 1H), 7.71 (d, J = 7.8 Hz, 1H), 7.46 (s, 1H), 7.38 (d, J = 7.8 Hz, 1H), 5.11 (dd, J = 13.3, 5.1 Hz, 1H), 4.45 (dd, J = 17.3, 8.1 Hz, 1H), 4.32 (dd, J = 17.3, 8.1 Hz, 1H), 3.55-3.44 (m, 1H), 3.31 (d, J = 14.3 Hz, 2H), 2.92 (ddd, J = 17.9, 13.5, 5.4 Hz, 1H), 2.72-2.56 (m, 2H), 2.47-2.31 (m, 2H), 2.21-1.53 (m, 14H), 1.33-1.20 (m, 1H). | 3 | I-58; 4,4-difluoro-cyclo-hexanone |
| 346 | 3-(5-(((1R,2S)-2-(cyclohexylamino)-4,4-difluorocyclohexyl)methyl)-1-oxoisoindolin-2-yl)piperidine-2,6-dione | 474.2 | $^1$H NMR (400 MHz, DMSO-d6) δ 10.99 (s, 1H), 8.73-8.62 (m, 1H), 8.34-8.24 (m, 1H), 7.71 (d, J = 7.7 Hz, 1H), 7.47 (s, 1H), 7.38 (d, J = 7.8 Hz, 1H), 5.11 (dd, J = 13.3, 5.1 Hz, 1H), 4.45 (dd, J = 17.3, 7.1 Hz, 1H), 4.32 (dd, J = 17.3, 7.1 Hz, 1H), 3.36-3.19 (m, 3H), 2.92 (ddd, J = 18.0, 13.6, 5.4 Hz, 1H), 2.68-2.55 (m, 2H), 2.53-2.31 (m, 2H), 2.20-1.90 (m, 6H), 1.84-1.20 (m, 10H), 1.18-1.04 (m, 1H). | 3 | I-58; cyclo-hexanone |
| 347 | 3-(5-(((1R,2S)-2-((4,4-difluorocyclohexyl)amino)cyclohexyl)methyl)-7-fluoro-1-oxoisoindolin-2-yl)piperidine-2,6-dione | 492.2 | $^1$H NMR (400 MHz, DMSO-d6) δ 11.01 (s, 1H), 8.59 (d, J = 11.0 Hz, 1H), 8.20 (d, J = 11.9 Hz, 1H), 7.28 (s, 1H), 7.16 (d, J = 10.5 Hz, 1H), 5.08 (dd, J = 13.3, 5.1 Hz, 1H), 4.58-4.28 (m, 2H), 3.44 (s, 1H), 3.25 (dd, J = 13.3, 3.4 Hz, 1H), 3.19-3.01 (m, 1H), 2.91 (ddd, J = 18.0, 13.6, 5.4 Hz, 1H), 2.71-2.55 (m, 1H), 2.45-2.28 (m, 2H), 2.23-1.64 (m, 6H), 1.64-1.44 (m, 2H), 1.34 (dh, J = 26.2, 14.3, 12.9 Hz, 2H), 1.05 (q, J = 10.6 Hz, 2H). | 25 | Step 1: I-59; 4,4-difluoro-cyclo-hexanone Step 2: Conventional heating at 80° C. for 12 h |
| 348 | 3-(5-(((1R,2S)-4,4-difluoro-2-(isopropylamino)cyclohexyl)methyl)-1-oxoisoindolin-2-yl)piperidine-2,6-dione | 434.1 | $^1$H NMR (400 MHz, DMSO-d6) δ 10.99 (s, 1H), 8.63 (s, 1H), 8.27 (s, 1H), 7.71 (d, J = 7.8 Hz, 1H), 7.47 (s, 1H), 7.39 (d, J = 7.8 Hz, 1H), 5.12 (dd, J = 13.3, 5.1 Hz, 1H), 4.45 (dd, J = 17.3, 7.8 Hz, 1H), 4.32 (dd, J = 17.3, 7.8 Hz, 1H), 3.62-3.50 (m, 1H), 3.35-3.20 (m, 2H), 2.92 (ddd, J = 18.0, 13.6, 5.4 Hz, 1H), 2.66-2.55 (m, 2H), 2.54-2.24 (m, 2H), 2.18-1.91 (m, 4H), 1.85-1.65 (m, 1H), 1.63-1.53 (m, 1H), 1.32 (d, J = 6.4 Hz, 3H), 1.27 (d, J = 6.4 Hz, 3H). | 3 | I-58, acetone |

TABLE 23-continued

| Example | Structure | ES/MS m/z: | 1H NMR | Procedure | Changes to Procedure: Different Reagents/ Starting Materials |
|---|---|---|---|---|---|
| 349 | 3-(5-(((1R,2S)-4,4-difluoro-2-((1-(tetrahydro-2H-pyran-4-yl)ethyl)amino)cyclohexyl)methyl)-1-oxoisoindolin-2-yl)piperidine-2,6-dione | 504.2 | ¹H NMR (400 MHz, DMSO-d6) δ 10.99 (s, 1H), 8.24-8.11 (m, 2H), 7.71 (d, J = 7.8 Hz, 1H), 7.50-7.44 (m, 1H), 7.39 (d, J = 7.9 Hz, 1H), 5.11 (dd, J = 13.3, 5.1 Hz, 1H), 4.45 (dd, J = 17.3, 6.1 Hz, 1H), 4.32 (dd, J = 17.3, 6.5 Hz, 1H), 3.97-3.86 (m, 2H), 3.44-3.21 (m, 5H), 2.92 (ddd, J = 18.0, 13.6, 5.5 Hz, 1H), 2.71-2.53 (m, 2H), 2.40 (qd, J = 13.2, 4.4 Hz, 1H), 2.29-1.47 (m, 10H), 1.44-1.19 (m, 6H). | 3 | I-58; 1-tetrahydro-pyran-4-ylethanone |
| 350 | 3-(5-(((1R,2S)-2-((4,4-difluorocyclohexyl)amino)cyclohexyl)methyl)-6-fluoro-1-oxoisoindolin-2-yl)piperidine-2,6-dione | 492.0 | ¹H NMR (400 MHz, DMSO-d6) δ 11.01 (s, 1H), 8.85 (t, J = 8.4 Hz, 1H), 8.52 (s, 0H), 8.34 (t, J = 9.9 Hz, 1H), 7.60 (d, J = 6.2 Hz, 1H), 7.52 (d, J = 8.6 Hz, 1H), 5.12 (dd, J = 13.3, 5.1 Hz, 1H), 4.45 (d, J = 17.2 Hz, 1H), 4.32 (dd, J = 17.3, 2.3 Hz, 1H), 3.62-3.37 (m, 1H), 3.37-3.07 (m, 2H), 3.07-2.69 (m, 1H), 2.41 (qd, J = 13.2, 4.4 Hz, 1H), 2.29-1.61 (m, 15H), 1.61-1.23 (m, 4H), 1.08 (q, J = 10.4, 9.6 Hz, 2H). | 3 | I-3; 4,4-difluoro-cyclo-hexanone |
| 351 | 3-(1-oxo-5-(((1R,2S)-2-((4,5,6,7-tetrahydro-1H-indazol-5-yl)amino)cyclohexyl)methyl)iso-indolin-2-yl)piperidine-2,6-dione | 476.2 | ¹H NMR (400 MHz, DMSO-d6) δ 10.99 (s, 1H), 8.60 (s, 1H), 8.29 (d, J = 10.4 Hz, 1H), 7.69 (t, J = 8.6 Hz, 1H), 7.46 (d, J = 3.4 Hz, 1H), 7.43-7.32 (m, 2H), 5.11 (dd, J = 13.3, 5.1 Hz, 1H), 4.52-4.25 (m, 2H), 3.67-3.52 (m, 2H), 3.30 (d, J = 13.3 Hz, 1H), 3.18 (d, J = 11.8 Hz, 1H), 3.13-2.86 (m, 3H), 2.86-2.56 (m, 3H), 2.47-2.20 (m, 3H), 2.20-1.78 (m, 5H), 1.73 (d, J = 12.4 Hz, 1H), 1.63-1.26 (m, 4H), 1.07 (s, 1H). | 7 | Example 1; 1,4,6,7-tetrahydro-indazol-5-one |
| 352 | 3-(1-oxo-5-(((1R,2S)-2-((3-(trifluoromethyl)-4,5,6,7-tetrahydro-1H-indazol-5-yl)amino)cyclohexyl)methyl)iso-indolin-2-yl)piperidine-2,6-dione | 544.2 | ¹H NMR (400 MHz, DMSO-d6) δ 13.33 (s, 1H), 10.99 (s, 1H), 8.63 (s, 1H), 8.29 (s, 1H), 7.70 (d, J = 7.8 Hz, 1H), 7.46 (s, 1H), 7.37 (d, J = 7.8 Hz, 1H), 5.12 (dd, J = 13.3, 5.1 Hz, 1H), 4.39 (ddd, J = 53.0, 17.5, 2.6 Hz, 2H), 3.33-3.18 (m, 1H), 3.13 (dd, J = 15.0, 4.8 Hz, 1H), 3.00-2.71 (m, 3H), 2.70-2.56 (m, 3H), 2.47-2.31 (m, 1H), 2.21 (dd, J = 45.1, 11.1 Hz, 2H), 2.05-1.81 (m, 3H), 1.73 (d, J = 12.2 Hz, 1H), 1.64-1.27 (m, 5H), 1.07 (s, 3H) | 7 | Example 1; 3-(trifluoro-methyl)-1,4,6,7-tetrahydro-indazol-5-one |

TABLE 23-continued

| Example | Structure | ES/MS m/z: | 1H NMR | Procedure | Changes to Procedure: Different Reagents/ Starting Materials |
|---|---|---|---|---|---|
| 353 | 3-(1-oxo-5-(((1R,2S)-2-((4,5,6,7-tetrahydro-1H-indazol-7-yl)amino)cyclohexyl)methyl)iso-indolin-2-yl)piperidine-2,6-dione | 476.2 | ¹H NMR (400 MHz, DMSO-d6) δ 10.99 (s, 1H), 8.75 (s, 1H), 8.61 (s, 1H), 7.68 (d, J = 7.8 Hz, 1H), 7.61 (s, 1H), 7.46 (s, 1H), 7.38 (d, J = 7.9 Hz, 1H), 5.11 (dd, J = 13.3, 5.1 Hz, 1H), 4.63 (s, 1H), 4.51-4.27 (m, 2H), 3.43-3.26 (m, 2H), 2.92 (ddd, J = 17.9, 13.6, 5.4 Hz, 1H), 2.65-2.54 (m, 2H), 2.41 (dd, J = 14.0, 10.2 Hz, 2H), 2.24 (ddd, J = 16.6, 12.6, 5.3 Hz, 2H), 1.99 (dd, J = 11.9, 6.7 Hz, 3H), 1.86 (q, J = 11.2 Hz, 1H), 1.73 (t, J = 14.5 Hz, 2H), 1.51 (dd, J = 17.0, 8.2 Hz, 4H), 1.32 (d, J = 10.7 Hz, 1H), 1.03 (d, J = 11.4 Hz, 2H). | 7 | Example 1; 1,4,5,6-tetrahydro-indazol-7-one |
| 354 | 3-(5-(((1R,2S,4R-rel)-2-((4,4-difluorocyclohexyl)amino)-4-fluorocyclohexyl)methyl)-1-oxoisoindolin-2-yl)piperidine-2,6-dione | 492.3 | 1H NMR (400 MHz, DMSO-d6) δ 10.99 (s, 1H), 8.62 (s, 1H), 8.23 (d, J = 12.7 Hz, 1H), 7.71 (d, J = 7.7 Hz, 1H), 7.46 (s, 1H), 7.38 (d, J = 7.9 Hz, 1H), 5.16-5.05 (m, 2H), 4.97 (s, 1H), 4.39 (ddd, J = 53.1, 17.3, 6.6 Hz, 2H), 3.34-3.21 (m, 4H), 3.01-2.83 (m, 1H), 2.63 (dd, J = 18.6, 14.9 Hz, 2H), 2.47-2.25 (m, 4H), 2.21-1.85 (m, 4H), 1.85-1.75 (m, 1H), 1.75-1.59 (m, 1H), 1.57-1.26 (m, 3H); 1H NMR (400 MHz, DMSO-d6) δ 10.99 (s, 1H), 8.41 (s, 1H), 8.09 (s, 1H), 7.71 (d, J = 7.8 Hz, 1H), 7.46 (s, 1H), 7.38 (d, J = 7.8 Hz, 1H), 5.20-4.85 (m, 2H), 4.39 (ddd, J = 53.3, 17.3, 5.6 Hz, 2H), 3.35-3.10 (m, 4H), 2.92 (ddd, J = 18.1, 13.5, 5.4 Hz, 1H), 2.73-2.55 (m, 1H), 2.43-2.29 (m, 2H), 2.25 (t, J = 6.6 Hz, 1H), 2.10-1.86 (m, 4H), 1.86-1.71 (m, 3H), 1.71-1.54 (m, 1H), 1.54-1.20 (m, 6H), 1.20-0.99 (m, 1H). | 7 | I-61; 4,4-difluoro-cyclo-hexanone |
| 355 | 3-(5-(((1R,2S,4R-rel)-2-(cyclohexylamino)-4-fluorocyclohexyl)methyl)-1-oxoisoindolin-2-yl)piperidine-2,6-dione | 456.2 | 1H NMR (400 MHz, DMSO-d6) δ 10.99 (s, 1H), 8.62 (s, 1H), 8.23 (d, J = 12.7 Hz, 1H), 7.71 (d, J = 7.7 Hz, 1H), 7.46 (s, 1H), 7.38 (d, J = 7.9 Hz, 1H), 5.16-5.05 (m, 2H), 4.97 (s, 1H), 4.39 (ddd, J = 53.1, 17.3, 6.6 Hz, 2H), 3.34-3.21 (m, 4H), 3.01-2.83 (m, 1H), 2.63 (dd, J = 18.6, 14.9 Hz, 2H), 2.47-2.25 (m, 4H), 2.21-1.85 (m, 4H), 1.85-1.75 (m, 1H), 1.75-1.59 (m, 1H), 1.57-1.26 (m, 3H); 1H NMR (400 MHz, DMSO-d6) δ 10.99 (s, 1H), 8.41 (s, 1H), 8.09 (s, 1H), 7.71 (d, J = 7.8 Hz, 1H), 7.46 (s, 1H), 7.38 (d, J = 7.8 Hz, 1H), 5.20-4.85 (m, 2H), 4.39 (ddd, J = 53.3, 17.3, 5.6 Hz, 2H), 3.35-3.10 (m, 4H), 2.92 (ddd, J = 18.1, 13.5 , 5.4 Hz, 1H), 2.73-2.55 (m, 1H), 2.43-2.29 (m, 2H), 2.25 (t, J = 6.6 Hz, 1H), 2.10-1.86 (m, 4H), 1.86-1.71 (m, 3H), 1.71-1.54 (m, 1H), 1.54-1.20 (m, 6H), 1.20-0.99 (m, 1H). | 7 | I-61; cyclo-hexanone |

TABLE 23-continued

| Example | Structure | ES/MS m/z: | 1H NMR | Procedure | Changes to Procedure: Different Reagents/Starting Materials |
|---|---|---|---|---|---|
| 356 | 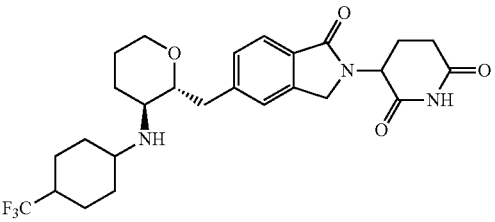<br>3-(1-oxo-5-(((2R,3S)-3-((4-(trifluoromethyl)cyclohexyl)amino)tetrahydro-2H-pyran-2-yl)methyl)isoindolin-2-yl)piperidine-2,6-dione Isomer 1 | 508.3 | 1H NMR (400 MHz, DMSO-d6) δ 10.99 (s, 1H), 8.56-8.45 (m, 1H), 8.33-8.22 (m, 1H), 7.68 (d, J = 7.8 Hz, 1H), 7.49 (s, 1H), 7.42 (d, J = 7.9 Hz, 1H), 5.11 (dd, J = 13.3, 5.1 Hz, 1H), 4.48-4.39 (m, 1H), 4.31 (d, J = 17.2 Hz, 1H), 3.83-3.74 (m, 2H), 3.39 (s, 1H), 3.31-3.16 (m, 3H), 2.98-2.86 (m, 2H), 2.65-2.56 (m, 1H), 2.39 (qd, J = 13.3, 4.6 Hz, 1H), 2.27-2.16 (m, 1H), 2.04-1.96 (m, 1H), 1.96-1.63 (m, 11H), 1.63-1.50 (m, 1H). | 22 | Step 1: I-62, 4-(trifluoromethyl)cyclohexanone Chiral SFC conditions: AD-H 5 μm-21 × 250 mm, co-solvent: MeOH—Et₂NH (25%) [peak 1] |
| 357 | 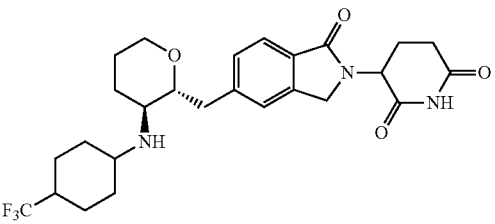<br>3-(1-oxo-5-(((2R,3S)-3-((4-(trifluoromethyl)cyclohexyl)amino)tetrahydro-2H-pyran-2-yl)methyl)isoindolin-2-yl)piperidine-2,6-dione Isomer 2 | 508.4 | 1H NMR (400 MHz, DMSO-d6) δ 10.99 (s, 1H), 8.79-8.68 (m, 1H), 8.44-8.33 (m, 1H), 7.67 (d, J = 7.8 Hz, 1H), 7.48 (s, 1H), 7.41 (d, J = 7.8 Hz, 1H), 5.11 (dd, J = 13.3, 5.1 Hz, 1H), 4.48-4.40 (m, 1H), 4.35-4.25 (m, 1H), 3.81-3.69 (m, 2H), 3.35-3.13 (m, 4H), 2.97-2.81 (m, 2H), 2.65-2.56 (m, 1H), 2.46-2.08 (m, 5H), 2.05-1.89 (m, 3H), 1.75-1.34 (m, 7H). | 22 | Step 1: I-62; 4-(trifluoromethyl)cyclohexanone Chiral SFC conditions: AD-H 5 μm-21 × 250 mm, co-solvent: MeOH—Et₂NH (25%) [peak 2] |
| 358 | 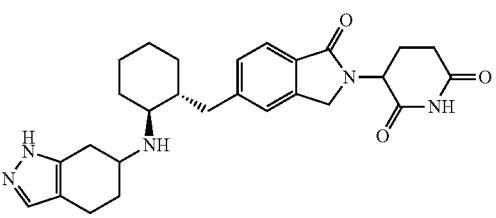<br>3-(1-oxo-5-(((1R,2S)-2-((4,5,6,7-tetrahydro-1H-indazol-6-yl)amino)cyclohexyl)methyl)isoindolin-2-yl)piperidine-2,6-dione (Isomer 1) | 476.4 | 1H NMR (400 MHz, DMSO-d6) δ 10.99 (s, 1H), 8.58 (s, 1H), 8.27 (s, 1H), 7.71 (d, J = 7.8 Hz, 1H), 7.46 (s, 1H), 7.43-7.36 (m, 2H), 5.12 (dd, J = 13.3, 5.1 Hz, 1H), 4.51-4.27 (m, 2H), 3.35-3.13 (m, 3H), 2.92 (ddd, J = 17.8, 13.5, 5.4 Hz, 1H), 2.78-2.53 (m, 4H), 2.47-2.29 (m, 3H), 2.16 (d, J = 13.9 Hz, 3H), 2.07-1.95 (m, 1H), 1.86 (dd, J = 12.0, 5.4 Hz, 1H), 1.72 (d, J = 12.1 Hz, 1H), 1.45 (ddd, J = 47.3, 20.8, 11.4 Hz, 5H), 1.07 (s, 2H).; 1H NMR (400 MHz, DMSO-d6) δ 10.99 (s, 1H), 8.60 (s, 1H), 8.26 (s, 1H), 7.70 (d, J = 7.7 Hz, 1H), 7.46 (s, 1H), 7.39 (d, J = 8.8 Hz, 2H), 5.11 (dd, J = 13.2, 5.1 Hz, 1H), 4.53-4.24 (m, 2H), 3.30 (d, J = 13.6 Hz, 2H), 3.17 (dd, J = 14.9, 5.4 Hz, 2H), 2.92 (ddd, J = 18.3, 13.6, 5.5 Hz, 1H), 2.79 (dd, J = 15.1, 10.4 Hz, 1H), 2.74-2.56 (m, 3H), 2.47-2.24 (m, 3H), 2.14 (d, J = 11.7 Hz, 1H), 2.06-1.96 (m, 1H), 1.90 (d, J = 8.5 Hz, 1H), 1.73 (d, J = 5.7 Hz, 3H), 1.62-1.27 (m, 4H), 1.23 (s, 0H), 1.06 (s, 2H). | 22 | I-13; 1,4,5,7-tetrahydroindazol-6-one Chiral SFC conditions: condition: ADH 5 μm-21 × 250 mm, co-solvent: IPA-NH₃ (40%) [peak 1] |

TABLE 23-continued

| Example | Structure | ES/ MS m/z: | 1H NMR | Procedure | Changes to Procedure: Different Reagents/ Starting Materials |
|---|---|---|---|---|---|
| 359 | 3-(1-oxo-5-(((1R,2S)-2-((4,5,6,7-tetrahydro-1H-indazol-6-yl)amino)cyclohexyl)methyl)isoindolin-2-yl)piperidine-2,6-dione (Isomer 2) | 476.4 | 1H NMR (400 MHz, DMSO-d6) δ 10.99 (s, 1H), 8.58 (s, 1H), 8.27 (s, 1H), 7.71 (d, J = 7.8 Hz, 1H), 7.46 (s, 1H), 7.43-7.36 (m, 2H), 5.12 (dd, J = 13.3, 5.1 Hz, 1H), 4.51-4.27 (m, 2H), 3.35-3.13 (m, 3H), 2.92 (ddd, J = 17.8, 13.5, 5.4 Hz, 1H), 2.78-2.53 (m, 4H), 2.47-2.29 (m, 3H), 2.16 (d, J = 13.9 Hz, 3H), 2.07-1.95 (m, 1H), 1.86 (dd, J = 12.0, 5.4 Hz, 1H), 1.72 (d, J = 12.1 Hz, 1H), 1.45 (ddd, J = 47.3, 20.8, 11.4 Hz, 5H), 1.07 (s, 2H).; 1H NMR (400 MHz, DMSO-d6) δ 10.99 (s, 1H), 8.60 (s, 1H), 8.26 (s, 1H), 7.70 (d, J = 7.7 Hz, 1H), 7.46 (s, 1H), 7.39 (d, J = 8.8 Hz, 2H), 5.11 (dd, J = 13.2, 5.1 Hz, 1H), 4.53-4.24 (m, 2H), 3.30 (d, J = 13.6 Hz, 2H), 3.17 (dd, J = 14.9, 5.4 Hz, 2H), 2.92 (ddd, J = 18.3, 13.6, 5.5 Hz, 1H), 2.79 (dd, J = 15.1, 10.4 Hz, 1H), 2.74-2.56 (m, 3H), 2.47-2.24 (m, 3H), 2.14 (d, J = 11.7 Hz, 1H), 2.06-1.96 (m, 1H), 1.90 (d, J = 8.5 Hz, 1H), 1.73 (d, J = 5.7 Hz, 3H), 1.62-1.27 (m, 4H), 1.23 (s, 0H), 1.06 (s, 2H). | 22 | I-13; 1,4,5,7-tetrahydroindazol-6-one Chiral SFC conditions: ADH 5 μm-21 × 250 mm, co-solvent: IPA-NH₃ (40%) [peak 2] |
| 360 | 3-(4-fluoro-1-oxo-5-(((2R,3S)-3-((4,5,6,7-tetrahydro-1H-indazol-6-yl)amino)tetrahydro-2H-pyran-2-yl)methyl)isoindolin-2-yl)piperidine-2,6-dione (Isomer 1) | 496.3 | 1H NMR (400 MHz, DMSO-d6) δ 11.01 (s, 1H), 8.83 (s, 1H), 8.52 (s, 1H), 7.63-7.50 (m, 2H), 7.40 (s, 1H), 5.12 (dd, J = 13.3, 5.1 Hz, 1H), 4.60-4.34 (m, 2H), 3.44 (s, 2H), 3.35-3.04 (m, 6H), 2.92 (ddd, J = 17.7, 13.6, 5.4 Hz, 1H), 2.83-2.55 (m, 4H), 2.42 (td, J = 13.2, 4.5 Hz, 1H), 2.37-2.21 (m, 3H), 2.05-1.96 (m, 1H), 1.82-1.52 (m, 4H).; 1H NMR (400 MHz, DMSO-d6) δ 11.01 (s, 1H), 8.84 (s, 1H), 8.52 (s, 1H), 7.62-7.50 (m, 2H), 7.41 (s, 1H), 5.12 (dd, J = 13.3, 5.1 Hz, 1H), 4.61-4.34 (m, 2H), 3.87-3.76 (m, 2H), 3.40 (s, 1H), 3.26 (ddd, J = 30.5, 14.7, 3.8 Hz, 4H), 3.07 (dd, J = 14.3, 10.4 Hz, 1H), 2.92 (ddd, J = 18.0, 13.5, 5.4 Hz, 1H), 2.77-2.56 (m, 4H), 2.42 (td, J = 13.2, 4.5 Hz, 1H), 2.35-2.15 (m, 2H), 2.06-1.96 (m, 1H), 1.92-1.52 (m, 4H). | 22 | Step 1: I-41; 1,4,5,7-tetrahydroindazol-6-one Chiral SFC Conditions: IA 5 μm-21 × 250 mm, co-solvent: IPA-NH₃ (30%) [peak 1] |
| 361 | 3-(4-fluoro-1-oxo-5-(((2R,3S)-3-((4,5,6,7-tetrahydro-1H-indazol-6-yl)amino)tetrahydro-2H-pyran-2-yl)methyl)isoindolin-2-yl)piperidine-2,6-dione (Isomer 2) | 496.3 | 1H NMR (400 MHz, DMSO-d6) δ 11.01 (s, 1H), 8.83 (s, 1H), 8.52 (s, 1H), 7.63-7.50 (m, 2H), 7.40 (s, 1H), 5.12 (dd, J = 13.3, 5.1 Hz, 1H), 4.60-4.34 (m, 2H), 3.44 (s, 2H), 3.35-3.04 (m, 6H), 2.92 (ddd, J = 17.7, 13.6, 5.4 Hz, 1H), 2.83-2.55 (m, 4H), 2.42 (td, J = 13.2, 4.5 Hz, 1H), 2.37-2.21 (m, 3H), 2.05-1.96 (m, 1H), 1.82-1.52 (m, 4H).; 1H NMR (400 MHz, DMSO-d6) δ 11.01 (s, 1H), 8.84 (s, 1H), 8.52 (s, 1H), 7.62-7.50 (m, 2H), 7.41 (s, 1H), 5.12 (dd, J = 13.3, 5.1 Hz, 1H), 4.61-4.34 (m, 2H), 3.87-3.76 (m, 2H), 3.40 (s, 1H), 3.26 (ddd, J = 30.5, 14.7, 3.8 Hz, 4H), 3.07 (dd, J = 14.3, 10.4 Hz, | 22 | Step 1: I-41; 1,4,5,7-tetrahydroindazol-6-one Chiral SFC Conditions: IA 5 μm-21 × 250 mm, co-solvent: IPA-NH₃ (30%) [peak 2] |

TABLE 23-continued

| Example | Structure | ES/MS m/z: | 1H NMR | Procedure | Changes to Procedure: Different Reagents/ Starting Materials |
|---|---|---|---|---|---|
| | | | 1H), 2.92 (ddd, J = 18.0, 13.5, 5.4 Hz, 1H), 2.77-2.56 (m, 4H), 2.42 (td, J = 13.2, 4.5 Hz, 1H), 2.35-2.15 (m, 2H), 2.06-1.96 (m, 1H), 1.92-1.52 (m, 4H). | | |
| 362 | 3-(1-oxo-5-(((1R,2S)-2-((3-(trifluoromethyl)-4,5,6,7-tetrahydro-1H-indazol-6-yl)amino)cyclohexyl)methyl)isoindolin-2-yl)piperidine-2,6-dione (Isomer 1) | 544.2 | 1H NMR (400 MHz, DMSO-d6) δ 13.34 (s, 1H), 10.99 (s, 1H), 8.72 (s, 1H), 8.33 (s, 1H), 7.71 (d, J = 7.7 Hz, 1H), 7.46 (s, 1H), 7.38 (d, J = 7.8 Hz, 1H), 5.11 (dd, J = 13.3, 5.1 Hz, 1H), 4.49-4.28 (m, 2H), 3.74 (s, 2H), 3.33-3.18 (m, 4H), 2.91 (ddt, J = 20.0, 14.9, 7.6 Hz, 2H), 2.80-2.57 (m, 2H), 2.48-2.26 (m, 3H), 2.14 (d, J = 12.1 Hz, 1H), 2.06-1.95 (m, 1H), 1.96-1.78 (m, 1H), 1.74 (d, J = 13.0 Hz, 1H), 1.44 (ddd, J = 54.9, 29.0, 13.6 Hz, 4H), 1.06 (d, J = 8.9 Hz, 2H). | 22 | Step 1: I-13; 3-(trifluoromethyl)-1,4,5,7-tetrahydroindazol-6-one Chiral SFC Conditions: IA 5 μm-21 × 250 mm, co-solvent: IPA-NH₃ (35%) [peak 1] |
| 363 | 3-(1-oxo-5-(((1R,2S)-2-((3-(trifluoromethyl)-4,5,6,7-tetrahydro-1H-indazol-6-yl)amino)cyclohexyl)methyl)isoindolin-2-yl)piperidine-2,6-dione (Isomer 2) | 544.2 | 1H NMR (400 MHz, DMSO-d6) δ 13.34 (s, 1H), 10.99 (s, 1H), 8.66 (s, 1H), 8.40 (s, 1H), 7.71 (d, J = 7.7 Hz, 1H), 7.46 (s, 1H), 7.38 (d, J = 7.8 Hz, 1H), 5.12 (dd, J = 13.3, 5.1 Hz, 1H), 4.51-4.28 (m, 2H), 3.74 (s, 2H), 3.27 (td, J = 16.5, 15.8, 7.4 Hz, 3H), 2.92 (ddd, J = 17.9, 13.6, 5.5 Hz, 1H), 2.77 (dd, J = 14.9, 10.4 Hz, 2H), 2.64 (td, J = 16.9, 14.0, 9.4 Hz, 2H), 2.47-2.36 (m, 1H), 2.21 (dd, J = 33.1, 11.1 Hz, 2H), 2.05-1.83 (m, 3H), 1.72 (d, J = 11.9 Hz, 1H), 1.62-1.27 (m, 4H), 1.07 (s, 2H). | 22 | Step 1: I-13; 3-(trifluoromethyl)-1,4,5,7-tetrahydroindazol-6-one Chiral SFC Conditions: IA 5 μm-21 × 250 mm, co-solvent: IPA-NH₃ (35%) [peak 1] |
| 364 | 3-(5-(((2R,3S)-3-((1,1-difluorospiro[2.5]octan-6-yl)amino)tetrahydro-2H-pyran-2-yl)methyl)-4-fluoro-1-oxoisoindolin-2-yl)piperidine-2,6-dione (Isomer 1) | 520.0 | 1H NMR (400 MHz, DMSO-d6) δ 11.02 (s, 1H), 7.58 (d, J = 7.7 Hz, 1H), 7.57-7.44 (m, 1H), 5.12 (dd, J = 13.3, 5.1 Hz, 1H), 4.57 (dd, J = 17.4, 5.8 Hz, 1H), 4.38 (dd, J = 17.4, 3.8 Hz, 1H), 3.85-3.72 (m, 5H), 3.29 (td, J = 20.9, 17.7, 12.1 Hz, 4H), 3.10-2.81 (m, 2H), 2.70-2.56 (m, 1H), 2.47-2.32 (m, 1H), 2.30-1.94 (m, 3H), 1.93-1.55 (m, 4H), 1.55-1.36 (m, 3H), 1.29 (t, J = 8.5 Hz, 2H). | 23 | Step 1: I-41, 2,2-difluorospiro[2.5]octan-6-one Chiral SFC conditions: AD-H 5 μm-21 × 250 mm, co-solvent: IPA-NH₃ (20%) [peak 1] |

TABLE 23-continued

| Example | Structure | ES/MS m/z: | 1H NMR | Procedure | Changes to Procedure: Different Reagents/Starting Materials |
|---|---|---|---|---|---|
| 365 | 3-(5-(((2R,3S)-3-((1,1-difluorospiro[2.5]octan-6-yl)amino)tetrahydro-2H-pyran-2-yl)methyl)-4-fluoro-1-oxoisoindolin-2-yl)piperidine-2,6-dione (Isomer 2) | 520.0 | 1H NMR (400 MHz, DMSO-d6) δ 11.01 (s, 1H), 7.65-7.55 (m, 1H), 7.55-7.46 (m, 1H), 5.12 (dd, J = 13.3, 5.1 Hz, 1H), 4.57 (dd, J = 17.4, 5.4 Hz, 1H), 4.38 (dd, J = 17.4, 3.3 Hz, 1H), 3.83-3.64 (m, 4H), 3.40 (s, 1H), 3.33-3.06 (m, 3H), 3.06-2.87 (m, 2H), 2.67-2.55 (m, 1H), 2.42 (td, J = 13.2, 4.5 Hz, 1H), 2.35-1.95 (m, 3H), 1.91-1.47 (m, 7H), 1.48-1.18 (m, 2H). | 23 | Step 1: I-41, 2,2-difluorospiro[2.5]octan-6-one Chiral SFC conditions: AD-H 5 μm-21 × 250 mm, co-solvent: IPA-NH$_3$ (20%) [peak 2] |
| 366 | 3-(5-(((2R,3S)-3-((4-fluorocyclohexyl)amino)tetrahydro-2H-pyran-2-yl)methyl)-1-oxoisoindolin-2-yl)piperidine-2,6-dione (Isomer 1) | 458.3 | 1H NMR (400 MHz, DMSO-d6) δ 10.99 (s, 1H), 8.70-8.56 (m, 1H), 8.32-8.20 (m, 1H), 7.68 (d, J = 7.7 Hz, 1H), 7.48 (s, 1H), 7.40 (d, J = 7.7 Hz, 1H), 5.11 (dd, J = 13.3, 5.1 Hz, 1H), 4.66-4.39 (m, 2H), 4.31 (d, J = 17.3 Hz, 1H), 3.82-3.67 (m, 2H), 3.33-3.11 (m, 4H), 2.97-2.82 (m, 2H), 2.64-2.55 (m, 1H), 2.39 (qd, J = 13.3, 4.5 Hz, 1H), 2.2-2.18 (m, 1H), 2.18-1.96 (m, 5H), 1.72-1.37 (m, 7H). | 24 | Step 1: I-62; 4-fluorocyclohexanone [peak 1] |
| 367 | 3-(5-(((2R,3S)-3-((4-fluorocyclohexyl)amino)tetrahydro-2H-pyran-2-yl)methyl)-1-oxoisoindolin-2-yl)piperidine-2,6-dione (Isomer 2) | 458.4 | 1H NMR (400 MHz, DMSO-d6) δ 10.99 (s, 1H), 8.69-8.60 (m, 1H), 8.33-8.24 (m, 1H), 7.68 (d, J = 7.8 Hz, 1H), 7.48 (s, 1H), 7.41 (d, J = 7.8 Hz, 1H), 5.11 (dd, J = 13.3, 5.1 Hz, 1H), 4.94-4.77 (m, 1H), 4.48-4.40 (m, 1H), 4.34-4.27 (m, 1H), 3.82-3.68 (m, 2H), 3.40-3.15 (m, 4H), 2.98-2.81 (m, 2H), 2.64-2.56 (m, 1H), 2.39 (qd, J = 13.3, 4.5 Hz, 1H), 2.28-2.20 (m, 1H), 2.07-1.85 (m, 5H), 1.81-1.51 (m, 7H). | 24 | Step 1: I-62; 4-fluorocyclohexanone [peak 2] |

TABLE 23-continued

| Example | Structure | ES/MS m/z: | 1H NMR | Procedure | Changes to Procedure: Different Reagents/ Starting Materials |
|---|---|---|---|---|---|
| 368 | (S)-3-(5-(((2R,3S)-3-(((1s,4R)-4-(difluoromethyl)cyclohexyl)amino)tetrahydro-2H-pyran-2-yl)methyl)-4-fluoro-1-oxoisoindolin-2-yl)piperidine-2,6-dione | 508.2 | 1H NMR (400 MHz, DMSO-d6) δ 11.01 (s, 1H), 8.38 (d, J = 130.1 Hz, 2H), 7.62-7.48 (m, 2H), 6.07 (td, J = 56.7, 5.1 Hz, 1H), 5.11 (dd, J = 13.3, 5.1 Hz, 1H), 4.60 4.33 (m, 2 H), 3.79 (td, J = 8.6, 7.8, 3.6 Hz, 2H), 3.37 (s, 1H), 3.33-3.17 (m, 4H), 3.03 (dd, J = 14.2, 10.4 Hz, 1H), 2.92 (ddd, J = 18.0, 13.6, 5.5 Hz, 1H), 2.65-2.55 (m, 1H), 2.42 (td, J = 13.2, 4.5 Hz, 1H), 2.21 (d, J = 12.0 Hz, 2H), 2.10-1.96 (m, 2H), 1.96-1.77 (m, 3H), 1.77-1.68 (m, 2H), 1.63 (q, J = 10.3, 8.1 Hz, 4H). | 24 | Step 1: I-41; 4-(difluoromethyl)cyclohexanone Step 2: Conventional heating at 80° C. for 12 h |
| 369 | (S)-3-(4-fluoro-5-(((2R,3S)-3-(((1r,4S)-4-fluorocyclohexyl)amino)tetrahydro-2H-pyran-2-yl)methyl)-1-oxoisoindolin-2-yl)piperidine-2,6-dione | 476.4 | 1H NMR (400 MHz, DMSO-d6) δ 11.01 (s, 2H), 8.63 (s, 2H), 8.25 (s, 2H), 7.61-7.48 (m, 4H), 7.40 (s, 0H), 5.11 (dd, J = 13.3, 5.1 Hz, 2H), 4.93 (s, 1H), 4.81 (s, 1H), 4.61-4.50 (m, 2H), 4.38 (dd, J = 17.4, 3.5 Hz, 2H), 3.76 (qd, J = 9.4, 7.7, 5.1 Hz, 4H), 3.36 (s, 2H), 3.31-3.20 (m, 6H), 3.05-2.85 (m, 4H), 2.63 (s, 1H), 2.54 (s, 2H), 2.50-2.35 (m, 2H), 2.24 (d, J = 10.0 Hz, 2H), 2.07-1.86 (m, 4H), 1.83-1.72 (m, 1H), 1.73 (d, J = 8.9 Hz, 4H), 1.59 (dd, J = 15.4, 5.6 Hz, 6H), 1.23 (s, 3H). | 25 | Step 1: I-41; 4-fluorocyclohexanone Step 2: Conventional heating at 80° C. for 12 h |
| 370 | 3-(5-(((1R,2S)-2-((1-(1,1-dioxidotetrahydro-2H-thiopyran-4-yl)ethyl)amino)cyclohexyl)methyl)-1-oxoisoindolin-2-yl)piperidine-2,6-dione (Isomer 1) | 516.0 | 1H NMR (400 MHz, Methanol-d4) δ 7.80 (d, J = 7.8 Hz, 1H), 7.50 (s, 1H), 7.44 (dd, J = 8.0, 1.4 Hz, 1H), 5.18 (dd, J = 13.3, 5.2 Hz, 1H), 4.58-4.45 (m, 2H), 3.58-3.48 (m, 1H), 3.25-3.05 (m, 5H), 2.94 (ddd, J = 17.6, 13.4, 5.4 Hz, 1H), 2.81 (ddd, J = 17.6, 4.7, 2.4 Hz, 1H), 2.60 (dd, J = 13.4, 10.3 Hz, 1H), 2.49 (td, J = 13.2, 4.7 Hz, 1H), 2.30-1.92 (m, 8H), 1.85 (d, J = 12.8 Hz, 1H), 1.69 (d, J = 10.0 Hz, 2H), 1.63-1.45 (m, 2H), 1.37 (d, J = 6.8 Hz, 3H), 1.24 (q, J = 9.5 Hz, 2H). | 25 | Step 1: I-13; 1-(1,1-dioxothian-4-yl)ethenone Chiral SFC conditions: AD-H 5 μm-21 × 250 mm, co-solvent: EtOH (35%) |
| 371 | 3-(5-(((1R,2S)-2-((1-(1,1-dioxidotetrahydro-2H-thiopyran-4-yl)ethyl)amino)cyclohexyl)methyl)-1-oxoisoindolin-2-yl)piperidine-2,6-dione (Isomer 2) | 516.0 | 1H NMR (400 MHz, Methanol-d4) δ 7.80 (d, J = 7.7 Hz, 1H), 7.49 (d, J = 5.3 Hz, 1H), 7.43 (d, J = 7.9 Hz, 1H), 5.19 (dd, J = 13.3, 5.2 Hz, 1H), 4.57-4.44 (m, 2H), 3.66-3.58 (m, 1H), 3.19 (d, J = 18.6 Hz, 5H), 2.96-2.87 (m, 1H), 2.81 (ddd, J = 17.7, 4.7, 2.4 Hz, 1H), 2.66-2.56 (m, 1H), 2.55-2.47 (m, 1H), 2.30-2.14 (m, 3H), 2.01 (dd, J = 28.8, 15.9 Hz, 5H), 1.86 (d, J = 12.5 Hz, 2H), 1.76-1.43 (m, 5H), 1.38 (dd, J = 6.8, 3.7 Hz, 3H), 1.31-1.13 (m, 3H). | 25 | Step 1: I-13; 1-(1,1-dioxothian-4-yl)ethenone Chiral SFC conditions: AD-H 5 μm-21 × 250 mm, co-solvent: EtOH (35%) |

TABLE 23-continued

| Example | Structure | ES/MS m/z: | 1H NMR | Procedure | Changes to Procedure: Different Reagents/ Starting Materials |
|---|---|---|---|---|---|
| 372 | (R)-3-(4-fluoro-5-(((2R,3S)-3-(((1s,4R)-4-fluorocyclohexyl)amino)tetrahydro-2H-pyran-2-yl)methyl)-1-oxoisoindolin-2-yl)piperidine-2,6-dione | 476.0 | 1H NMR (400 MHz, Methanol-d4) δ 7.62 (d, J = 7.7 Hz, 1H), 7.58-7.52 (m, 1H), 5.18 (dd, J = 13.4, 5.2 Hz, 1H), 4.65-4.45 (m, 3H), 3.92 (dt, J = 11.4, 4.1 Hz, 1H), 3.85 (ddd, J = 10.1, 6.6, 3.5 Hz, 1H), 3.42 (td, J = 13.1, 12.4, 6.0 Hz, 2H), 3.29-3.22 (m, 1H), 3.20-3.11 (m, 1H), 2.96-2.87 (m, 1H), 2.81 (ddd, J = 17.5, 4.6, 2.4 Hz, 1H), 2.58-2.48 (m, 1H), 2.38 (q, J = 7.6, 6.5 Hz, 1H), 2.30-2.14 (m, 5H), 1.89-1.70 (m, 3H), 1.63 (t, J = 9.3 Hz, 3H), 1.52 (p, J = 11.5, 10.5 Hz, 2H). | 28 | Step 1: I-63; 4-fluorocyclohexanone Chiral SFC conditions: IG 5 μm- 21 × 250 mm, co-solvent: EtOH/NH₃ (35%) [peak 1] |
| 373 | (R)-3-(4-fluoro-5-(((2R,3S)-3-(((1r,4S)-4-fluorocyclohexyl)amino)tetrahydro-2H-pyran-2-yl)methyl)-1-oxoisoindolin-2-yl)piperidine-2,6-dione | 476.0 | 1H NMR (400 MHz, Methanol-d4) δ 7.62 (d, J = 7.7 Hz, 1H), 7.58-7.51 (m, 1H), 5.18 (dd, J = 13.3, 5.2 Hz, 1H), 4.65-4.50 (m, 2H), 3.95-3.82 (m, 2H), 3.42 (ddd, J = 18.0, 8.9, 4.6 Hz, 3H), 3.14 (dd, J = 14.2, 10.2 Hz, 1H), 2.97-2.87 (m, 1H), 2.81 (ddd, J = 17.6, 4.7, 2.4 Hz, 1H), 2.53 (qd, J = 13.2, 4.7 Hz, 1H), 2.39 (d, J = 12.5 Hz, 1H), 2.25-2.13 (m, 3H), 2.04 (d, J = 7.2 Hz, 1H), 1.95 (d, J = 4.3 Hz, 1H), 1.91-1.71 (m, 6H), 1.71-1.57 (m, 1H). | 28 | Step 1: I-63; 4-fluorocyclohexanone Chiral SFC conditions: IG 5 μm- 21 × 250 mm, co-solvent: EtOH/NH₃ (35%) [peak 2] Step 2: Conventional heating at 80° C. for 12 h |
| 374 | 3-(4-fluoro-1-oxo-5-(((2R,3S)-3-((4,5,6,7-tetrahydro-1H-indazol-6-yl)amino)tetrahydro-2H-pyran-2-yl)methyl)isoindolin-2-yl)piperidine-2,6-dione | 496.3 | 1H NMR (400 MHz, DMSO-d6) δ 11.01 (s, 1H), 8.81 (s, 1H), 8.50 (s, 1H), 7.65-7.50 (m, 2H), 7.40 (s, 1H), 5.12 (dd, J = 13.3, 5.1 Hz, 1H), 4.62-4.33 (m, 2H), 3.81 (d, J = 11.9 Hz, 2H), 3.35-3.01(m, 4H), 2.92 (ddd, J = 18.1, 13.5, 5.3 Hz, 1H), 2.82-2.56 (m, 4H), 2.43 (dd, J = 13.2, 4.6 Hz, 1H), 2.36-2.17 (m, 3H), 2.08-1.94 (m, 1H), 1.90-1.52 (m, 5H). | 32 | Step 1: I-41; 1,4,5,7-tetrahydro-indazol-6-one |
| 375 | 3-(1-oxo-5-(((1R,2S)-2-((3-(trifluoromethyl)-4,5,6,7-tetrahydro-1H-indazol-6-yl)amino)cyclohexyl)methyl)isoindolin-2-yl)piperidine-2,6-dione | 544.4 | 1H NMR (400 MHz, DMSO-d6) δ 13.35 (s, 1H), 10.99 (s, 1H), 8.56 (d, J = 101.1 Hz, 2H), 7.69 (dd, J = 11.4, 7.7 Hz, 1H), 7.46 (s, 1H), 7.38 (d, J = 7.8 Hz, 1H), 5.12 (dd, J = 13.3, 5.1 Hz, 1H), 4.50-4.27 (m, 2H), 3.35-3.13 (m, 5H), 2.92 (ddd, J = 17.9, 13.5, 5.3 Hz, 1H), 2.78 (dd, J = 15.2, 10.5 Hz, 2H), 2.72-2.56 (m, 2H), 2.46-2.31 (m, 3H), 2.31-2.12 (m, 3H), 2.06 1.81 (m, 1H), 1.72 (d, J = 12.5 Hz, 1H), 1.63-1.22 (m, 3H), 1.06 (s, 2H). | 32 | Step 1: I-13; 3-(trifluoromethyl)-1,4,5,7-tetrahydro-indazol-6-one |

TABLE 23-continued

| Example | Structure | ES/MS m/z: | 1H NMR | Procedure | Changes to Procedure: Different Reagents/ Starting Materials |
|---|---|---|---|---|---|
| 376 | 3-(4-fluoro-5-(((2R,3S)-3-((4-fluoro-4-methylcyclohexyl)amino)tetrahydro-2H-pyran-2-yl)methyl)-1-oxoisoindolin-2-yl)piperidine-2,6-dione | 505.4 | 1H NMR (400 MHz, DMSO-d6) δ 11.01 (s, 1H), 8.67 (d, J = 10.9 Hz, 1H), 8.31 (s, 1H), 7.64-7.46 (m, 2H), 5.32 (s, 1H), 5.11 (dd, J = 13.3, 5.1 Hz, 1H), 4.60-4.31 (m, 2H), 3.79 (dp, J = 10.9, 3.9, 3.0 Hz, 2H), 3.26 (td, J = 11.7, 10.7, 6.7 Hz, 4H), 3.10-2.84 (m, 2H), 2.63 (td, J = 16.7, 15.0, 2.9 Hz, 1H), 2.47-2.29 (m, 2H), 2.29-1.93 (m, 6H), 1.82-1.48 (m, 8H). | 32 | Step 1: I-41; 4-fluoro-4-methyl-cyclohexanone |
| 377 | 3-(5-(((1R,2S)-2-((1-methyl-4,5,6,7-tetrahydro-1H-indazol-5-yl)amino)cyclohexyl)methyl)-1-oxoisoindolin-2-yl)piperidine-2,6-dione | 490.4 | 1H NMR (400 MHz, DMSO-d6) δ 11.00 (d, J = 2.2 Hz, 1H), 8.56 (s, 1H), 8.24 (s, 1H), 7.70 (d, J = 7.8 Hz, 1H), 7.45 (dd, J = 10.8, 3.7 Hz, 2H), 7.38 (dd, J = 8.3, 3.6 Hz, 1H), 5.17-5.06 (m, 1H), 4.50-4.27 (m, 2H), 3.74 (s, 3H), 3.35-3.23 (m, 1H), 3.19 (s, 1H), 3.12-2.85 (m, 3H), 2.80-2.56 (m, 5H), 2.46-2.28 (m, 2H), 2.27-2.06 (m, 2H), 2.06-1.75 (m, 3H), 1.74 (s, 1H), 1.65-1.26 (m, 4H), 1.06 (d, J = 5.5 Hz, 1H). | 32 | Step 1: I-13; 1-methyl-6,7-dihydro-4H-indazol-5-one |
| 378 | 3-(5-(((1R,2S)-2-((3-methyl-4,5,6,7-tetrahydro-1H-indazol-5-yl)amino)cyclohexyl)methyl)-1-oxoisoindolin-2-yl)piperidine-2,6-dione | 490.4 | 1H NMR (400 MHz, DMSO-d6) δ 10.99 (s, 1H), 8.58 (s, 1H), 8.26 (d, J = 26.1 Hz, 1H), 7.70 (dd, J = 7.8, 2.9 Hz, 1H), 7.46 (d, J = 3.5 Hz, 1H), 7.43-7.32 (m, 1H), 5.11 (dd, J = 13.3, 5.1 Hz, 1H), 4.51-4.26 (m, 2H), 3.40-3.12 (m, 2H), 2.92 (dtd, J = 34.6, 16.3, 14.8, 5.1 Hz, 2H), 2.81-2.55 (m, 3H), 2.49-2.36 (m, 2H), 2.35-2.05 (m, 6H), 2.05-1.67 (m, 4H), 1.64-1.26 (m, 4H), 1.07 (d, J = 9.9 Hz, 3H). | 32 | Step 1: I-13; 3-methyl-1,4,6,7-tetra-hydro-indazol-5-one |
| 379 | 3-(1-oxo-5-(((1R,2S)-2-((4-(pyridin-2-yl)cyclohexyl)amino)cyclohexyl)methyl)isoindolin-2-yl)piperidine-2,6-dione | 515.4 | 1H NMR (400 MHz, DMSO-d6) δ 10.99 (s, 1H), 8.60 (dd, J = 5.1, 1.7 Hz, 1H), 8.18 (s, 1H), 7.98-7.82 (m, 2H), 7.68 (d, J = 7.8 Hz, 1H), 7.52 (d, J = 8.0 Hz, 1H), 7.43 (s, 1H), 7.33 (dd, J = 14.6, 7.3 Hz, 2H), 5.11 (dd, J = 13.3, 5.1 Hz, 1H), 4.51-4.26 (m, 2H), 3.39 (s, 1H), 3.22 (dd, J = 13.2, 3.5 Hz, 1H), 3.09 (t, J = 4.5 Hz, 1H), 2.92 (ddd, J = 18.1, 13.6, 5.5 Hz, 1H), 2.70-2.56 (m, 1H), 2.38 (dq, J = 15.9, 9.9, 6.9 Hz, 4H), 2.14-1.96 (m, 2H), 1.82 (d, J = 13.0 Hz, 5H), 1.77-1.60 (m, 3H), 1.60-1.26 (m, 5H), 1.13-0.91 (m, 2H). | 32 | Step 1: I-13; 4-(2-pyridyl)cyclo-hexanone |

TABLE 23-continued

| Example | Structure | ES/ MS m/z: | 1H NMR | Procedure | Changes to Procedure: Different Reagents/ Starting Materials |
|---|---|---|---|---|---|
| 380 | 3-(5-(((1R,2S)-2-((4-(4H-1,2,4-triazol-4-yl)cyclohexyl)amino)cyclohexyl)methyl)-1-oxoisoindolin-2-yl)piperidine-2,6-dione | 505.4 | 1H NMR (400 MHz, DMSO-d6) δ 10.99 (s, 1H), 8.82 (s, 1H), 8.71 (s, 1H), 8.22 (dd, J = 138.8, 82.4 Hz, 2H), 7.70 (dd, J = 7.7, 6.1 Hz, 1H), 7.44 (d, J = 12.7 Hz, 1H), 7.36 (dd, J = 13.2, 7.8 Hz, 1H), 5.11 (ddd, J = 13.3, 5.2, 2.2 Hz, 1H), 4.52-4.25 (m, 4H), 3.50-3.18 (m, 2H), 3.10 (d, J = 25.7 Hz, 1H), 3.00-2.82 (m, 1H), 2.70-2.56 (m, 1H), 2.47-2.29 (m, 3H), 2.15 (ddd, J = 33.6, 21.8, 15.5 Hz, 3H), 2.05-1.65 (m, 6H), 1.65-1.25 (m, 5H), 1.02 (d, J = 10.6 Hz, 2H). | 32 | Step 1: I-13; 4-(1,2,4-triazol-4-yl)cyclohexanone |

Procedure 38, Example 381

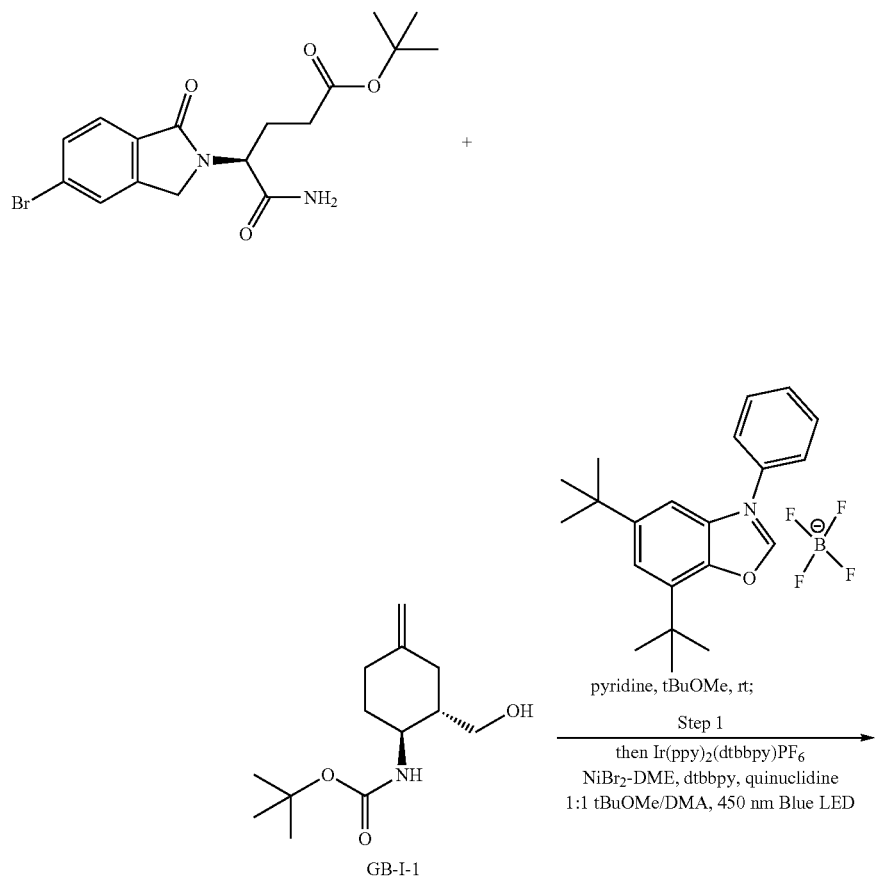

GB-I-1

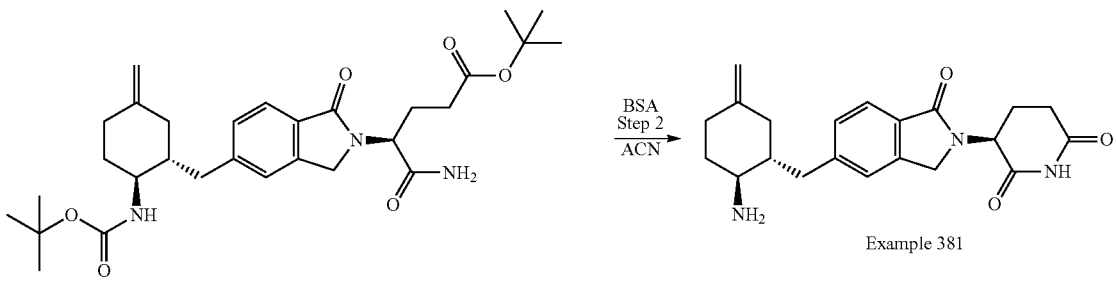

Example 381

Step 1: Preparation of tert-butyl (S)-5-amino-4-(5-(((1R,2S)-2-((tert-butoxycarbonyl)amino)-5-methylenecyclohexyl)methyl)-1-oxoisoindolin-2-yl)-5-oxopentanoate In a 40 mL vial, I-64 (0.11 g, 0.47 mmol) and 5,7-di-tert-butyl-3-phenylbenzo[d]oxazol-3-ium tetrafluoroborate (0.17 g, 0.43 mmol) were taken up in MTBE (2.3 mL) and stirred for 5 min. Pyridine (38 uL, 0.47 mmol) was then added. This mixture was stirred at room temperature for 10 minutes. Meanwhile, in a second 40 mL vial, tert-butyl (S)-5-amino-4-(5-bromo-1-oxoisoindolin-2-yl)-5-oxopentanoate (0.13 g, 0.33 mmol), [Ir(ppy)$_2$(dtbbpy)]PF$_6$ (4.5 mg, 0.005 mmol), quinuclidine (0.064 g, 0.57 mmol), NiBr$_2$-DME (5.1 mg, 0.016 mmol), and 4,4'-Di-tert-butyl-2,2'-dipyridyl (5.3 mg, 0.02 mmol) were combined. The vial was purged with N$_2$ then DMA (2.3 mL) was added. The activated alcohol suspension from the first vial was transferred to a syringe fitted with a syringe filter and needle. The suspension was filtered into the solution of aryl bromide and the mixture sparged with N$_2$ for 5 min. The reaction was then stirred under irradiation by 450 nm light in a photoreactor for 22 hours. The mixture was cooled to 0° C. and quenched with water. The product was extracted into EtOAc (×3). Combined organics were washed with water (×2) to remove DMA. Following a brine wash, the organic layer was dried (Na$_2$SO$_4$), filtered and concentrated in vacuo. The crude product was purified by silica gel column chromatography (eluent: EtOAc/hexanes then MeOH/EtOAc) yield the title compound. ES/MS m/z: 542.3 (M+H)$^+$.

Step 2: Preparation of 3-(5-(((1R,2S)-2-amino-5-methylenecyclohexyl)methyl)-1-oxoisoindolin-2-yl)piperidine-2,6-dione tert-butyl (S)-5-amino-4-(5-(((1R,2S)-2-((tert-butoxycarbonyl)amino)-5-methylenecyclohexyl)methyl)-1-oxoisoindolin-2-yl)-5-oxopentanoate (14.8 mg, 0.027 mmol) was taken up in MeCN (1.0 mL) and treated with benzenesulfonic acid (12.6 mg, 0.544 mmol). The mixture was stirred at 130° C. under microwave irradiation for 30 min, then cooled to r.t. and concentrated under reduced pressure. The resulting crude residue was purified purified by RP-HPLC (eluent: MeCN/water gradient with 0.1% TFA) to afford the product (Example 381) as the trifluoroacetate salt. ES/MS m/z: 368.3 (M+H)$^+$; $^1$H NMR (400 MHz, DMSO-d6) δ 11.00 (s, 1H), 7.96 (d, J=4.6 Hz, 2H), 7.88 (s, 1H), 7.70 (dd, J=7.8, 4.4 Hz, 1H), 7.43 (d, J=7.7 Hz, 1H), 7.35 (t, J=7.2 Hz, 1H), 5.12 (dd, J=13.3, 5.1 Hz, 1H), 4.64 (d, J=2.1 Hz, 1H), 4.53 (d, J=2.1 Hz, 1H), 4.50-4.26 (m, 2H), 3.12 (d, J=13.2 Hz, 1H), 2.92 (ddd, J=18.1, 13.6, 5.4 Hz, 1H), 2.67 (p, J=1.8 Hz, 1H), 2.61 (d, J=16.9 Hz, 1H), 2.45-2.36 (m, 1H), 2.33 (p, J=1.9 Hz, 1H), 2.16-1.93 (m, 4H), 1.89-1.74 (m, 2H), 1.59 (d, J=19.5 Hz, 1H), 1.48-1.33 (m, 1H).

Procedure 39, Examples 382 and 383

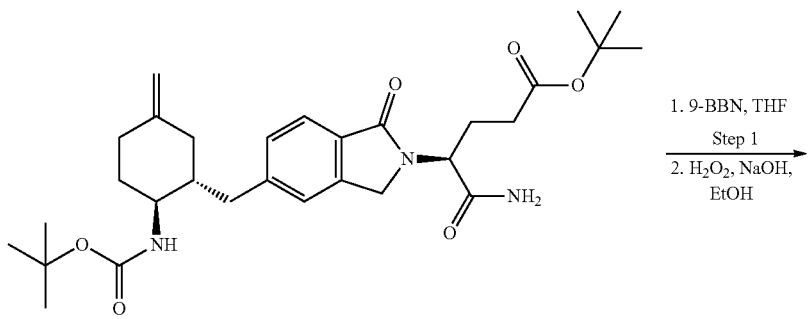

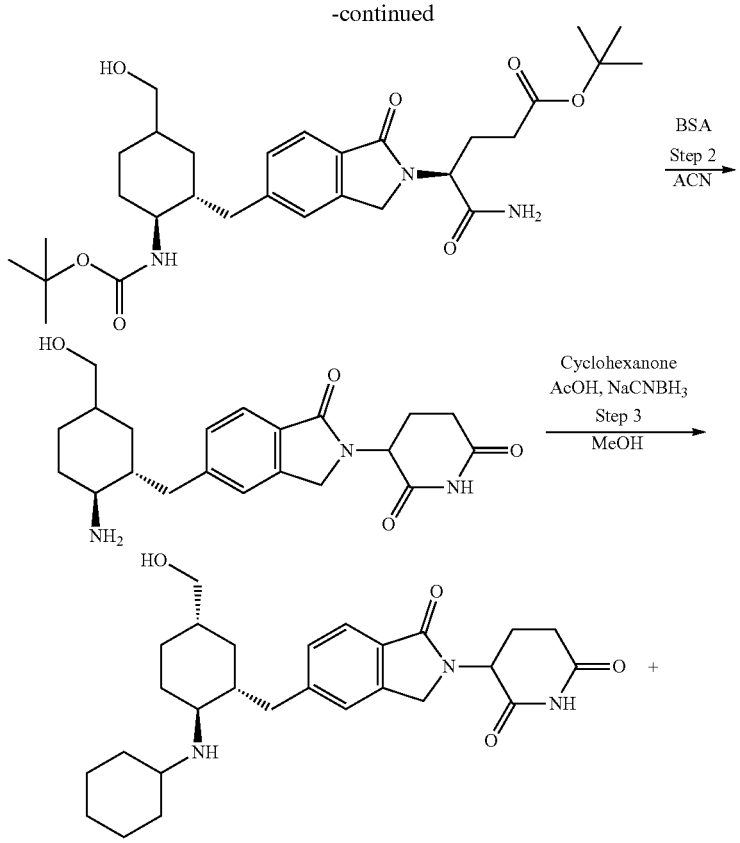

Example 382

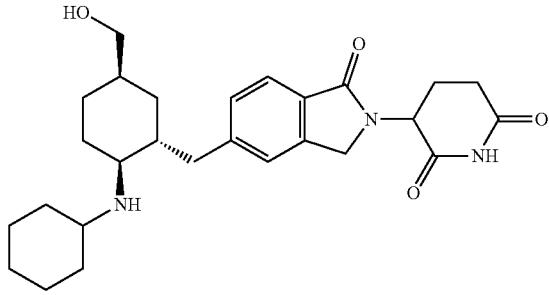

Example 383

Step 1: Preparation of tert-butyl (4S)-5-amino-4-(5-(((1R,2S)-2-((tert-butoxycarbonyl)amino)-5-(hydroxymethyl)cyclohexyl)methyl)-1-oxoisoindolin-2-yl)-5-oxopentanoate tert-butyl (S)-5-amino-4-(5-(((1R,2S)-2-((tert-butoxycarbonyl)amino)-5-methylenecyclohexyl)methyl)-1-oxoisoindolin-2-yl)-5-oxopentanoate (0.075 g, 0.14 mmol) was taken in THF (1 mL) and cooled to 0° C. A solution of 9-BBN in THF (0.5M in THF, 0.33 mL) was added dropwise under an atmosphere of nitrogen. The reaction was allowed to warm to room temperature and stirred overnight. It was then cooled back to 0° C. and more 9-BBN (0.5M in THF, 0.9 mL) was added. After another overnight stirring at room temperature, LC/MS showed consumption of starting material. The reaction was cooled again to 0° C. and treated with a solution of sodium hydroxide (0.016 g, 0.42 mmol) in THF (1 mL) and EtOH (0.5 mL) followed by 30% aq. $H_2O_2$ (24 uL, 0.21 mmol). After stirring for about two hours the reaction mix was diluted with EtOAc and water. Layers were separated and product extracted once more with EtOAc. Combined organics were washed with brine, dried ($Na_2SO_4$) and concentrated. The crude product was purified by silica gel chromatography eluting with MeOH/EtOAc/Hexane to afford the title compound as a white solid (0.041 g, 53%). ES/MS m/z: 560.3 (M+H)+

Step 2: Preparation of 3-(5-(((1R,2S)-2-amino-5-(hydroxymethyl)cyclohexyl)methyl)-1-oxoisoindolin-2-yl)piperidine-2,6-dione To tert-butyl (4S)-5-amino-4-(5-(((1R,2S)-2-((tert-butoxycarbonyl)amino)-5-(hydroxymethyl) cyclohexyl) methyl)-1-oxoisoindolin-2-yl)-5-oxopentanoate (0.041 g, 0.073 mmol) in ACN (1 mL) was added BSA (0.035 g, 0.22 mmol). The reaction was heated in the microwave at 110° C. for 20 mins. The reaction mix was then diluted with DMSO and purified on reverse phase HPLC (eluent: MeCN/water gradient with 0.1% TFA). Desired fractions were dried on the lyophilizer to yield the title product (0.01 mg, 36%). ES/MS m/z: 386.2 (M+H)+

Step 3: Preparation of 3-(5-((((1R,2S)-2-(cyclohexylamino)-5-(hydroxymethyl)cyclohexyl)methyl)-1-oxoisoindolin-2-yl)piperidine-2,6-dione, Isomer 1) and 3-(5-((((1R,2S)-2-(cyclohexylamino)-5-(hydroxymethyl)cyclohexyl)methyl)-1-oxoisoindolin-2-yl)piperidine-2,6-dione, Isomer 2)

To 3-(5-((((1R,2S)-2-amino-5-(hydroxymethyl)cyclohexyl)methyl)-1-oxoisoindolin-2-yl)piperidine-2,6-dione (0.01 g, 0.026 mmol) and cyclohexanone (8 uL, 0.078 mmol) in methanol (1 mL) was added acetic acid (4.5 uL, 0.078 mmol) followed by sodium cyanoborohydride (0.005 g, 0.078 mmol). The reaction was heated at 50° C. for about 4 hours. The reaction mix was diluted with DMSO and purified on reverse HPLC (eluent: MeCN/water gradient with 0.1% TFA) to yield Example 382 (peak 1) and Example 383 (peak 2).Example 382: ES/MS m/z: 468.4 (M+H)+; $^1$H NMR (400 MHz, DMSO-d6) δ 10.98 (t, J=4.2 Hz, 1H), 8.29 (s, 1H), 7.93 (d, J=31.7 Hz, 1H), 7.75-7.64 (m, 1H), 7.46 (d, J=18.4 Hz, 1H), 7.41-7.30 (m, 1H), 6.53 (s, 1H), 5.12 (dd, J=13.2, 5.1 Hz, 1H), 4.56-4.24 (m, 2H), 3.28-3.18 (m, 1H), 3.11 (dd, J=17.4, 6.1 Hz, 2H), 3.04-2.84 (m, 2H), 2.79-2.57 (m, 4H), 2.44-2.27 (m, 1H), 2.18 (s, 2H), 2.08-1.87 (m, 3H), 1.76 (d, J=24.4 Hz, 4H), 1.65-1.30 (m, 5H), 1.29-1.15 (m, 3H), 1.07 (d, J=12.6 Hz, 1H). Example 383: ES/MS m/z: 468.4 (M+H)+; $^1$H NMR (400 MHz, DMSO-d6) δ 10.99 (s, 1H), 8.28 (s, 1H), 7.92 (s, 1H), 7.71 (d, J=7.8 Hz, 1H), 7.44 (s, 1H), 7.36 (d, J=7.8 Hz, 1H), 5.11 (dd, J=13.2, 5.1 Hz, 1H), 4.51-4.27 (m, 2H), 3.21 (s, 1H), 3.11 (ddd, J=28.3, 10.5, 6.1 Hz, 2H), 2.92 (ddd, J=18.1, 13.5, 5.4 Hz, 1H), 2.69-2.57 (m, 2H), 2.43-2.27 (m, 2H), 2.20-1.93 (m, 4H), 1.88-1.69 (m, 5H), 1.65 (d, J=12.7 Hz, 1H), 1.51 (t, J=11.2 Hz, 2H), 1.47-1.06 (m, 6H), 1.01 (t, J=12.7 Hz, 1H), 0.72 (q, J=12.5 Hz, 1H).

REFERENCE COMPOUNDS

In the below examples, (Reference Compound A-1, B-1, B-2, B-3, B-4, and C-1),
Reference Compound A-1, disclosed as Example I-57 in WO2019/038717 has the structure

A-1

Reference Compound B-1, disclosed in WO2020/012334 has the structure

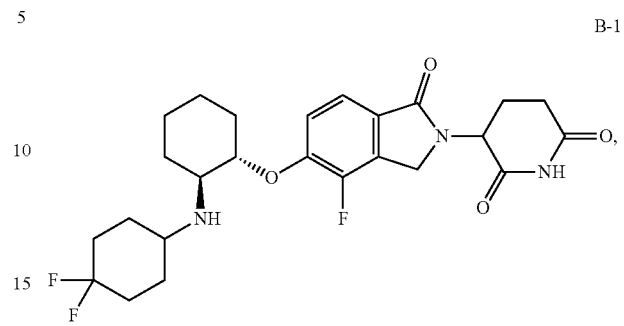

B-1

Reference Compound B-2, disclosed as I-79 in WO2020/012334 has the structure

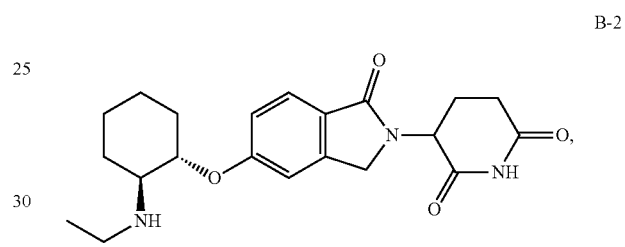

B-2

Reference Compound B-3, disclosed as I-22 in WO2020/012334 has the structure

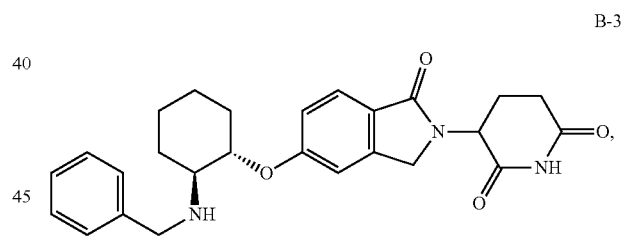

B-3

Reference Compound B-4, disclosed as I-115 in WO2020/012334 has the structure

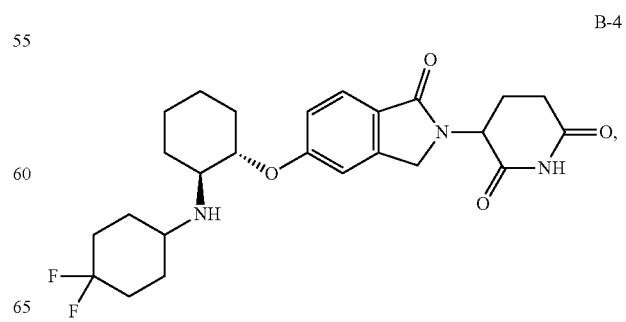

B-4

Reference Compound C-1, disclosed as I-3 in WO2020/012337 has the structure

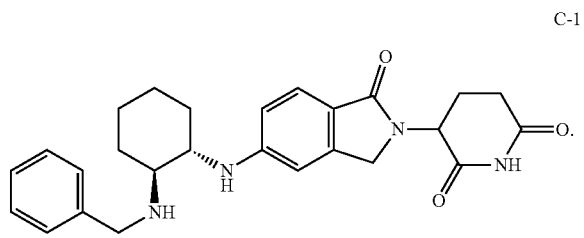 [SMILES: O=C1CCC(N2Cc3cc(N[C@H]4CCCC[C@@H]4NCc4ccccc4)ccc3C2=O)C(=O)N1]

Biological Assays and Data
HEK293 Degradation

In vitro degradation of IKZF1, IKZF2, and SALL4 was measured using HiBiT protein tagging and detection technology (Promega).

HiBit technology was used to develop the quantitative assays to measure the cellular IKZFs level by tagging an 11 amino acid HiBit peptides VSGWRLFKKIS to the protein of interest. Reporter plasmids were generated by fusing a linker sequence (GSSGGSSG) followed by the HiBit tag at the C-terminus of IKZF1, IKZF2, and SALL4. The fusion fragments were subsequently cloned into pcDNA5 pcDNA™5/FRT/TO plasmids (Thermo Fisher, cat #V652020) downstream of the tetracycline operator. The resulting plasmids were co-transfected with pOG44 Flp-Recombinase Expression Vector (Thermo Fisher, cat #V600520) into Flp-In™ T-REx HEK293 line (Thermo Fisher, cat #R78077) and a stable cell pool was selected by adding 100 pg/ml of Hygromycin (Thermo Fisher, cat #10687010). The reporter cell enabled Tet-On inducible reporter expression from a single copy of the integrated gene.

On Day 1, Cells were grown to ~80% confluency in tissue culture medium (DMEM Glutamax (Gibco10569), 10% Tet free FBS (Takara 631106), and PenStrep Glutamin (Gibco 10378)) in tissue culture flasks. Doxycycline was then added to a final concentration of 1 pg/ml to induce reporter expression at 37° C. overnight.

On Day 2, 125 nL of serially-diluted solution of testing compounds were dispensed into 384-well white solid assay plates via ECHO acoustic liquid handler. Cells were lifted by 0.25% Trypsin (Gibco 25200) then pelleted by centrifugation (Beckman Avanti J-E) at 500×g for 5 min. Cell pellets were resuspended in TC medium at the concentration of 3e5/mL and 25 μL of cell suspension were added into each well of compound-spotted plates. The plates were returned to a 37° C. incubator overnight (18-24 hr).

On Day 3, assay plates were removed from the tissue culture incubator and 25 μL of Nano-Glo lytic detection system (Promega, cat #N3030) was added to each well. Plates were incubated at r.t. for 3 min with shaking, and luminescence was read using an Envision reader (Perkin Elmer).

All raw data was normalized to DMSO control (final concentration: 0.5%) wells as percentage of control (POC) and plotted out for $EC_{50}$ and $D_{max}$ (Maximum degradation at the highest concentration tested in the assay).

To assess the IKZF1, IKZF2, and SALL4 degrader potential of exemplified compounds of this disclosure and certain Reference Compounds $EC_{50}$ and $D_{max}$ values were determined for the compounds of Examples 1 to 383 and Reference Compounds A-1, B-1, B-2, B-3, B-4, and C-1 in the HiBiT assays. Results are shown in Table 24. Asterisks (*) indicate examples for which the data shown represents an average of n≥3.

The results shown in Table 24 illustrate that the molecular glue-type IKZF family degraders provided herein, which include a 3-(1-oxoisoindolin-2-yl)piperidine-2,6-dione head group connected via a methylene linker to a Ring A of Formula (I), can form potent and efficacious degraders of IKZF2 (Helios). Exemplified compounds generally mediated selective degradation of IKZF2 (Helios) relative to IKZF1 (Ikaros). Numerous compounds of this disclosure were tested for their ability to mediate SALL4 degradation, and the vast majority of tested compounds was found to be inactive towards SALL4.

The results of Table 24 provide evidence for a differentiated SAR of the methylene-linked IKZF2 (Helios) compounds provided herein relative to the molecular glue type degrader compounds of WO2019/038717, WO2020/012334, and WO2020/012337), in which a 3-(1-oxoisoindolin-2-yl)piperidine-2,6-dione head group is linked either directly to a Ring A (WO2019/038717), or via an ether linker (WO2020/012334), or amine linker (WO2020/012337). For example, methylene degrader compounds of Examples 2, 35, 46, and 84 were found to degrade IKZF2 (Helios) with 3 to 10-fold greater potency than ether-linked Reference Compounds B-3, B-2, B-4, and B-1 respectively. These results illustrate the impact of differentiated linker chemistries on the distinctive SAR of ether-linker and methylene-linked helios degraders.

TABLE 24

In vitro IKZF1, IKZF2, and SALL4 degradation (HEK293)

| Example No. | IKZF2 $EC_{50}$ (μM) | IKZF2 $D_{max}$ (%) | IKZF1 $EC_{50}$ (μM) | IKZF1 $D_{max}$ (%) | SALL4 $EC_{50}$ (μM) | SALL4 $D_{max}$ (%) |
|---|---|---|---|---|---|---|
| 1 | 0.225 | 82 | 0.933 | 30 | | |
| 2* | 0.018 | 88 | >10 | | | |
| 3 | 0.019 | 94 | 0.034 | 38 | | |
| 4 | 0.058 | 92 | 0.130 | 26 | | |
| 5 | 0.353 | 92 | >1 | | | |
| 6 | 0.030 | 90 | 0.122 | 32 | | |
| 7* | 0.004 | 99 | 0.462 | 36 | | |
| 8 | 0.047 | 94 | 0.229 | 34 | | |
| 9 | 0.019 | 92 | >1 | | | |
| 10* | 0.013 | 96 | 0.388 | 46 | | |
| 11* | 0.007 | 98 | >1 | | | |
| 12 | 0.106 | 85 | >1 | | | |
| 13 | 0.079 | 68 | >1 | | | |
| 14 | 0.027 | 88 | >1 | | | |
| 15 | 0.020 | 95 | >1 | | | |
| 16 | 0.042 | 87 | >1 | | | |
| 17 | 0.070 | 77 | >1 | | | |
| 18 | 0.042 | 89 | >1 | | | |
| 19 | 0.030 | 89 | >1 | | | |
| 20 | 0.019 | 94 | 0.099 | 35 | | |
| 21 | 0.409 | 49 | >1 | | | |
| 22 | 0.034 | 86 | >1 | | | |
| 23 | 0.006 | 95 | 0.374 | 14 | | |
| 24* | 0.010 | 91 | 0.345 | 25 | | |
| 25 | 0.023 | 87 | >1 | | | |
| 26 | 0.530 | 57 | >1 | | | |
| 27 | 0.003 | 97 | 0.070 | 27 | | |
| 28 | 0.002 | 97 | 0.327 | 56 | | |
| 29 | 0.005 | 96 | 0.574 | 39 | | |
| 30 | 0.029 | 81 | 0.042 | 34 | | |
| 31 | 0.030 | 85 | >1 | | | |
| 32 | 0.021 | 90 | >1 | | | |
| 33 | 0.018 | 82 | >1 | | | |
| 34 | 0.028 | 80 | 0.051 | 29 | | |
| 35 | 0.029 | 94 | 0.261 | 31 | | |

TABLE 24-continued

In vitro IKZF1, IKZF2, and SALL4 degradation (HEK293)

| Example No. | IKZF2 EC$_{50}$ (μM) | IKZF2 D$_{max}$ (%) | IKZF1 EC$_{50}$ (μM) | IKZF1 D$_{max}$ (%) | SALL4 EC$_{50}$ (μM) | SALL4 D$_{max}$ (%) |
|---|---|---|---|---|---|---|
| 36 | 0.046 | 89 | 0.101 | 33 | | |
| 37 | 0.172 | 69 | >1 | | | |
| 38 | 0.192 | 97 | >1 | | | |
| 39 | 0.047 | 86 | 0.265 | 34 | | |
| 40 | 0.045 | 81 | >1 | | | |
| 41 | 0.024 | 90 | 0.216 | 44 | | |
| 42 | 0.126 | 78 | >1 | | | |
| 43 | 0.091 | 45 | >1 | | | |
| 44 | 0.067 | 60 | >1 | | | |
| 45 | 0.131 | 71 | >1 | | | |
| 46* | 0.001 | 94 | 0.033 | 29 | >10 | |
| 47 | 0.006 | 93 | >1 | | | |
| 48 | 0.024 | 96 | >1 | | | |
| 49 | 0.088 | 66 | >1 | | | |
| 50 | 0.111 | 57 | >1 | | | |
| 51 | 0.045 | 80 | >1 | | | |
| 52* | 0.006 | 96 | >1 | | | |
| 53* | 0.003 | 96 | >1 | | | |
| 54 | 0.031 | 86 | >1 | | | |
| 55 | 0.025 | 87 | >1 | | | |
| 56* | 0.014 | 96 | 0.068 | 44 | | |
| 57 | 0.025 | 89 | >1 | | | |
| 58 | 0.046 | 75 | 0.206 | 34 | | |
| 59 | 0.075 | 77 | >1 | | | |
| 60 | 0.065 | 63 | >1 | | | |
| 61 | 0.023 | 95 | >1 | | | |
| 62 | 0.056 | 79 | >1 | | | |
| 63* | 0.019 | 89 | >1 | | | |
| 64 | 0.055 | 73 | >1 | | | |
| 65 | 0.048 | 64 | >1 | | | |
| 66 | 0.017 | 89 | >1 | | | |
| 67 | 0.030 | 74 | >1 | | | |
| 68 | 0.031 | 91 | >1 | | | |
| 69 | 0.019 | 91 | >1 | | | |
| 70 | 0.080 | 48 | >1 | | | |
| 71 | 0.037 | 89 | >1 | | | |
| 72 | 0.035 | 83 | >1 | | | |
| 73* | 0.007 | 95 | >1 | | | |
| 74* | 0.004 | 96 | 0.226 | 55 | | |
| 75 | 0.007 | 95 | 0.888 | 51 | | |
| 76 | 0.034 | 84 | >1 | | | |
| 77 | 0.011 | 90 | >1 | | | |
| 78 | 0.016 | 92 | >1 | | | |
| 79 | 0.005 | 94 | 0.098 | 33 | | |
| 80 | 0.033 | 95 | 0.299 | 32 | | |
| 81 | 0.004 | 96 | 0.028 | 41 | | |
| 82* | 0.007 | 94 | 0.327 | 28 | | |
| 83 | 0.037 | 92 | >1 | | | |
| 84* | 0.001 | 97 | 0.028 | 68 | | |
| 85 | 0.002 | 97 | 0.070 | 40 | | |
| 86 | 0.012 | 97 | 0.141 | 34 | | |
| 87* | 0.002 | 98 | 0.062 | 39 | | |
| 88* | 0.001 | 99 | 0.101 | 38 | | |
| 89 | 0.006 | 97 | 0.064 | 28 | | |
| 90 | 0.069 | 75 | >1 | | | |
| 91 | 0.017 | 97 | 0.160 | 47 | | |
| 92 | 0.044 | 82 | >1 | | | |
| 93 | 0.023 | 91 | 0.039 | 22 | | |
| 94* | 0.010 | 96 | >10 | | | |
| 95* | 0.016 | 88 | >10 | | | |
| 96 | 0.009 | 95 | 0.173 | 35 | | |
| 97 | 0.036 | 92 | 0.085 | 30 | | |
| 98 | 0.041 | 87 | >1 | | | |
| 99 | 0.014 | 94 | 0.068 | 37 | | |
| 100 | 0.012 | 94 | 0.061 | 34 | | |
| 101 | 0.005 | 98 | 0.039 | 32 | | |
| 102* | 0.006 | 96 | 0.242 | 27 | | |
| 103* | 0.003 | 95 | >1 | | | |
| 104 | 0.016 | 92 | 0.075 | 37 | | |
| 105 | 0.004 | 96 | 0.076 | 31 | | |
| 106 | 0.010 | 95 | 0.079 | 24 | | |
| 107 | 0.003 | 96 | 0.081 | 36 | | |
| 108 | 0.055 | 96 | >1 | | | |
| 109* | 0.005 | 96 | 0.103 | 34 | | |
| 110* | 0.005 | 96 | 0.163 | 32 | | |
| 111 | 0.091 | 81 | >1 | | | |
| 112 | 0.003 | 97 | 0.056 | 30 | | |
| 113 | 0.006 | 98 | >1 | | | |
| 114* | 0.008 | 98 | 0.088 | 28 | | |
| 115* | 0.008 | 96 | 0.078 | 37 | | |
| 116* | 0.002 | 98 | 0.044 | 34 | | |
| 117* | 0.002 | 97 | 0.039 | 46 | | |
| 118* | 0.002 | 97 | 0.057 | 44 | | |
| 119* | 0.002 | 98 | 0.046 | 54 | | |
| 120 | 0.033 | 90 | 0.100 | 29 | | |
| 121 | 0.003 | 97 | 0.068 | 26 | | |
| 122 | 0.002 | 96 | 0.057 | 45 | | |
| 123 | 0.026 | 88 | >1 | | | |
| 124 | 0.016 | 94 | >10 | | | |
| 125* | 0.017 | 96 | 0.126 | 26 | | |
| 126 | 0.114 | 80 | >1 | | | |
| 127 | 0.015 | 68 | 0.015 | 72 | | |
| 128 | 0.018 | 98 | 0.094 | 19 | | |
| 129 | 0.013 | 95 | 0.093 | 25 | | |
| 130 | 0.148 | 76 | >1 | | | |
| 131 | 0.004 | 96 | 0.078 | 45 | | |
| 132 | 0.004 | 97 | 0.066 | 45 | | |
| 133 | 0.032 | 96 | 0.132 | 30 | | |
| 134 | 0.061 | 97 | >1 | | | |
| 135 | 0.016 | 93 | 0.077 | 24 | | |
| 136 | 0.004 | 97 | >1 | | | |
| 137 | 0.001 | 97 | 0.054 | 34 | | |
| 138 | 0.004 | 98 | >1 | | | |
| 139 | 0.001 | 98 | 0.035 | 43 | | |
| 140 | 0.003 | 98 | 0.038 | 60 | | |
| 141 | 0.002 | 98 | 0.058 | 53 | | |
| 142 | 0.005 | 95 | 0.074 | 33 | | |
| 143 | 0.033 | 94 | >1 | | | |
| 144 | 0.007 | 97 | >1 | | | |
| 145 | 0.002 | 96 | 0.055 | 44 | | |
| 146 | 0.002 | 95 | 0.168 | 34 | | |
| 147 | 0.037 | 75 | >1 | | | |
| 148* | 0.007 | 94 | >1 | | | |
| 149 | 0.046 | 71 | 0.045 | 36 | | |
| 150 | 0.051 | 73 | >0.5 | | | |
| 151 | 0.022 | 87 | >1 | | | |
| 152 | 0.026 | 78 | >0.5 | | | |
| 153 | 0.017 | 93 | >1 | | | |
| 154 | 0.114 | 90 | >0.5 | | | |
| 155* | 0.030 | 97 | 0.226 | 27 | | |
| 156 | 0.006 | 98 | >1 | | | |
| 157 | 0.008 | 92 | 0.061 | 35 | | |
| 158 | 0.011 | 91 | 0.072 | 50 | | |
| 159* | 0.006 | 100 | >1 | | | |
| 160 | 0.044 | 95 | 0.524 | 56 | | |
| 161 | 0.095 | 88 | >1 | | | |
| 162 | 0.058 | 93 | 0.226 | 42 | | |
| 163 | 0.014 | 95 | 0.328 | 45 | | |
| 164 | 0.017 | 83 | >1 | | | |
| 165 | 0.020 | 98 | 0.270 | 28 | | |
| 166 | 0.023 | 96 | >1 | | | |
| 167* | 0.002 | 97 | 0.077 | 36 | | |
| 168* | 0.003 | 97 | 0.246 | 39 | | |
| 169* | 0.001 | 97 | 0.079 | 42 | >10 | |
| 170 | 0.044 | 62 | >1 | | | |
| 171 | 0.026 | 98 | 0.198 | 37 | | |
| 172 | 0.019 | 98 | 0.203 | 28 | | |
| 173 | 0.009 | 95 | >1 | >10 | | |
| 174 | 0.067 | 86 | >1 | | | |
| 175 | 0.024 | 96 | 0.189 | 46 | | |
| 176 | 0.003 | 96 | >1 | | | |
| 177 | 0.004 | 97 | 0.078 | 42 | | |
| 178 | 0.168 | 72 | >1 | | | |
| 179* | 0.016 | 88 | >10 | | | |
| 180 | 0.039 | 85 | >1 | | | |
| 181* | 0.006 | 96 | >1 | | | |

TABLE 24-continued

In vitro IKZF1, IKZF2, and SALL4 degradation (HEK293)

| Example No. | IKZF2 EC$_{50}$ (μM) | IKZF2 D$_{max}$ (%) | IKZF1 EC$_{50}$ (μM) | IKZF1 D$_{max}$ (%) | SALL4 EC$_{50}$ (μM) | SALL4 D$_{max}$ (%) |
|---|---|---|---|---|---|---|
| 182* | 0.009 | 94 | 0.043 | 34 | | |
| 183 | 0.091 | 81 | >1 | | | |
| 184 | 0.003 | 97 | 0.056 | 30 | | |
| 185 | 0.006 | 98 | >1 | | | |
| 186* | 0.008 | 98 | 0.088 | 28 | | |
| 187* | 0.008 | 96 | 0.078 | 37 | | |
| 188* | 0.002 | 98 | 0.044 | 34 | | |
| 189* | 0.002 | 97 | 0.039 | 46 | | |
| 190* | 0.002 | 97 | 0.057 | 44 | | |
| 191 | 0.002 | 97 | 0.063 | 30 | | |
| 192 | 0.006 | 94 | >10 | | | |
| 193 | 0.007 | 96 | >1 | | | |
| 194 | 0.020 | 92 | >1 | | | |
| 195 | 0.009 | 96 | >1 | | | |
| 196* | 0.003 | 97 | 0.060 | 23 | | |
| 197 | 0.005 | 97 | 0.068 | 22 | | |
| 198 | 0.016 | 97 | >1 | | | |
| 199 | 0.010 | 95 | >10 | | | |
| 200* | 0.004 | 96 | >1 | | | |
| 201 | 0.007 | 96 | >1 | | | |
| 202 | 0.008 | 95 | >1 | | | |
| 203 | 0.013 | 95 | >1 | | | |
| 204 | 0.004 | 97 | >1 | | | |
| 205 | 0.003 | 98 | >1 | | | |
| 206 | 0.006 | 95 | >1 | | | |
| 207 | 0.002 | 94 | >1 | | | |
| 208* | 0.002 | 98 | 0.076 | 26 | | |
| 209 | 0.001 | 97 | 0.035 | 62 | >10 | |
| 210 | 0.001 | 97 | 0.030 | 68 | | |
| 211 | 0.001 | 98 | 0.054 | 37 | | |
| 212 | 0.001 | 98 | 0.045 | 42 | | |
| 213 | 0.002 | 98 | 0.041 | 45 | | |
| 214 | 0.005 | 96 | 0.065 | 22 | | |
| 215 | 0.002 | 97 | 0.174 | 29 | | |
| 216 | 0.002 | 98 | 0.051 | 34 | | |
| 217* | 0.003 | 97 | 0.085 | 44 | | |
| 218* | 0.002 | 95 | 0.626 | 34 | | |
| 219* | 0.006 | 95 | >1 | | | |
| 220 | 0.002 | 96 | >1 | | | |
| 221 | 0.002 | 98 | >1 | | | |
| 222 | 0.018 | 96 | >1 | | | |
| 223 | 0.012 | 96 | >1 | | | |
| 224 | 0.002 | 96 | >1 | | | |
| 225 | 0.011 | 94 | >0.5 | | | |
| 226 | 0.014 | 93 | 0.017 | 84 | | |
| 227 | 0.020 | 86 | >0.5 | | | |
| 228 | 0.009 | 94 | >1 | | | |
| 229 | 0.008 | 97 | >1 | | | |
| 230 | 0.003 | 96 | 0.066 | 30 | | |
| 231 | 0.003 | 96 | >1 | | | |
| 232 | 0.021 | 93 | >1 | | | |
| 233 | 0.003 | 97 | >1 | | | |
| 234 | 0.011 | 98 | >1 | | | |
| 235* | 0.009 | 97 | >1 | | | |
| 236 | 0.006 | 98 | 0.122 | 34 | | |
| 237 | 0.002 | 96 | 0.208 | 39 | | |
| 238* | 0.002 | 97 | 0.038 | 32 | | |
| 239* | 0.003 | 97 | 0.055 | 28 | | |
| 240 | 0.004 | 97 | 0.095 | 48 | | |
| 241 | 0.003 | 96 | >1 | | | |
| 242 | 0.002 | 97 | >1 | | | |
| 243 | 0.002 | 98 | 0.028 | 61 | | |
| 244 | 0.002 | 97 | 0.025 | 61 | | |
| 245 | 0.002 | 97 | 0.110 | 37 | | |
| 246 | 0.002 | 98 | 0.060 | 37 | | |
| 247 | 0.005 | 97 | >1 | | | |
| 248 | 0.021 | 92 | >1 | | | |
| 249 | 0.004 | 97 | >1 | | | |
| 250 | 0.002 | 97 | 0.117 | 30 | | |
| 251 | 0.001 | 98 | 0.213 | 35 | | |
| 252* | 0.003 | 98 | 0.105 | 31 | | |
| 253 | 0.009 | 96 | >1 | | | |
| 254 | 0.033 | 84 | >1 | | | |
| 255 | 0.032 | 87 | >1 | | | |
| 256 | 0.183 | 59 | >1 | | | |
| 256 | 0.014 | 97 | >1 | | | |
| 257* | 0.003 | 99 | 0.069 | 34 | | |
| 258 | 0.004 | 97 | 0.078 | 30 | | |
| 259 | 0.011 | 96 | 0.068 | 25 | | |
| 260 | 0.005 | 96 | >1 | | | |
| 261 | 0.006 | 96 | >1 | | | |
| 262 | 0.072 | 85 | >1 | | | |
| 263 | 0.095 | 85 | >1 | | | |
| 264 | 0.006 | 96 | >1 | | | |
| 265 | 0.003 | 96 | >1 | | >10 | |
| 266 | 0.004 | 97 | 0.055 | 32 | | |
| 267 | 0.004 | 98 | 0.109 | 44 | | |
| 268 | 0.006 | 98 | 0.076 | 62 | | |
| 269 | 0.003 | 96 | 0.266 | 40 | | |
| 270 | 0.008 | 98 | 0.179 | 22 | | |
| 271 | 0.002 | 98 | 0.045 | 44 | | |
| 272 | 0.001 | 98 | 0.040 | 54 | | |
| 273 | 0.023 | 93 | >1 | | | |
| 274 | 0.012 | 97 | 0.102 | 35 | | |
| 275 | 0.004 | 96 | >1 | | | |
| 276 | 0.003 | 97 | >1 | | | |
| 277 | 0.003 | 98 | 0.114 | 37 | | |
| 278 | 0.004 | 98 | 0.125 | 37 | | |
| 279 | 0.003 | 95 | 0.051 | 30 | | |
| 280 | 0.003 | 98 | 0.070 | 29 | | |
| 281 | 0.002 | 96 | 0.043 | 30 | | |
| 282 | 0.007 | 95 | >1 | | | |
| 283* | 0.004 | 98 | 0.092 | 26 | >10 | |
| 284 | 0.005 | 97 | >1 | | | |
| 285 | 0.008 | 94 | 0.124 | 37 | | |
| 286 | 0.027 | 96 | 0.223 | 33 | | |
| 287* | 0.001 | 95 | 0.066 | 47 | >10 | |
| 288* | 0.006 | 97 | 0.399 | 32 | | |
| 289* | 0.005 | 97 | 0.632 | 31 | >10 | |
| 290 | 0.004 | 98 | 0.138 | 27 | >10 | |
| 291* | 0.010 | 94 | >1 | | >10 | |
| 292 | 0.007 | 94 | >1 | | | |
| 293 | 0.008 | 94 | >1 | | | |
| 294 | 0.002 | 97 | 0.912 | 59 | | |
| 295 | 0.001 | 97 | 0.283 | 43 | | |
| 296 | 0.105 | 86 | >1 | | | |
| 297 | 0.101 | 84 | >1 | | | |
| 298 | 0.055 | 76 | >1 | | | |
| 299 | 0.002 | 98 | >1 | | | |
| 300 | 0.004 | 97 | >1 | | | |
| 302 | 0.015 | 89 | >1 | | | |
| 303 | 0.086 | 82 | >1 | | | |
| 304 | 0.003 | 97 | >1 | | | |
| 305 | 0.014 | 96 | >1 | | | |
| 306 | 0.010 | 95 | >1 | | | |
| 307 | 0.001 | 96 | 0.111 | 40 | | |
| 308 | 0.012 | 96 | >1 | | >10 | |
| 309 | 0.016 | 96 | >1 | | >10 | |
| 310 | 0.027 | 90 | >0.5 | | | |
| 311 | 0.011 | 95 | >1 | | | |
| 312 | 0.009 | 95 | >1 | | | |
| 313 | 0.027 | 88 | >1 | | | |
| 314 | 0.090 | 70 | 0.653 | 30 | | |
| 315 | 0.028 | 88 | >1 | | | |
| 316 | 0.007 | 95 | >1 | | >10 | |
| 317 | 0.006 | 94 | 0.243 | 33 | | |
| 318 | 0.020 | 96 | >1 | | | |
| 319 | 0.024 | 95 | >1 | | | |
| 320 | 0.011 | 93 | >1 | | | |
| 321 | 0.006 | 94 | 0.371 | 44 | | |
| 322 | 0.054 | 72 | >1 | | | |
| 323* | 0.003 | 96 | 0.050 | 45 | | |
| 324* | 0.003 | 95 | 0.016 | 71 | >10 | |
| 325* | 0.005 | 95 | >1 | | >10 | |
| 326 | 0.007 | 95 | 0.261 | 40 | | |
| 327* | 0.003 | 96 | 0.535 | | >10 | |

TABLE 24-continued

In vitro IKZF1, IKZF2, and SALL4 degradation (HEK293)

| Example No. | IKZF2 EC$_{50}$ (μM) | IKZF2 D$_{max}$ (%) | IKZF1 EC$_{50}$ (μM) | IKZF1 D$_{max}$ (%) | SALL4 EC$_{50}$ (μM) | SALL4 D$_{max}$ (%) |
|---|---|---|---|---|---|---|
| 328* | 0.001 | 98 | 0.022 | 62 | >10 | |
| 329* | 0.002 | 98 | 0.050 | 53 | >10 | |
| 330* | 0.003 | 94 | 0.037 | 28 | >10 | |
| 331* | 0.004 | 96 | 0.448 | | | |
| 332 | 0.006 | 95 | >1 | | >10 | |
| 333 | 0.009 | 94 | 0.210 | | >10 | |
| 334 | 0.001 | 97 | 0.013 | 59 | >10 | |
| 335 | 0.001 | 97 | 0.016 | 62 | >10 | |
| 336 | 0.003 | 97 | >1 | | | |
| 337 | 0.005 | 95 | >1 | | | |
| 338 | 0.006 | 92 | >1 | | | |
| 339 | 0.011 | 93 | >1 | | | |
| 340 | 0.076 | 55 | >1 | | | |
| 341 | 0.021 | 87 | >1 | | | |
| 342 | 0.018 | 86 | >1 | | | |
| 343 | 0.091 | 84 | >1 | | | |
| 344 | 0.006 | 93 | 0.041 | 51 | >10 | |
| 345 | 0.004 | 97 | 0.174 | 56 | | |
| 346 | 0.002 | 96 | 0.080 | 62 | | |
| 347 | 0.038 | 75 | >1 | | | |
| 348 | 0.002 | 97 | 0.062 | 39 | | |
| 349 | 0.011 | 92 | 0.089 | 42 | | |
| 350 | 0.010 | 94 | 0.124 | 50 | | |
| 351 | 0.019 | 98 | 0.423 | 34 | | |
| 352 | 0.003 | 99 | 0.323 | 47 | 3.1 | 47 |
| 353 | 0.071 | 94 | 0.121 | 38 | >10 | |
| 354 | 0.003 | 93 | 0.030 | 32 | | |
| 355 | 0.005 | 91 | >1 | | | |
| 356 | 0.049 | 76 | >1 | | | |
| 357 | 0.023 | 89 | 0.465 | 40 | | |
| 358 | 0.018 | 100 | 0.231 | 34 | | |
| 359 | 0.009 | 101 | 0.249 | 43 | | |
| 360 | 0.139 | 90 | >1 | | | |
| 361 | 0.034 | 102 | >1 | | | |
| 362 | 0.011 | 97 | 0.114 | 39 | >10 | |
| 363 | 0.001 | 97 | 0.050 | 56 | >10 | |
| 364 | 0.003 | 96 | 0.045 | 37 | >10 | |
| 365 | 0.003 | 95 | 0.122 | 43 | | |
| 366 | 0.017 | 85 | >1 | | >10 | |
| 367 | 0.015 | 87 | >1 | | >10 | |
| 368 | 0.008 | 96 | >1 | | | |
| 369 | 0.005 | 97 | >1 | | >10 | |
| 370 | 0.010 | 95 | 0.117 | 53 | | |
| 371 | 0.062 | 94 | 0.461 | 50 | | |
| 372 | 0.005 | 94 | >1 | | | |
| 373 | 0.007 | 94 | >1 | | | |
| 374 | 0.058 | 98 | >1 | | | |
| 375 | 0.004 | 99 | 0.048 | 65 | | |
| 376 | 0.003 | 95 | >1 | | 0.094 | 28 |
| 377* | 0.005 | 97 | 0.073 | 48 | >10 | |
| 378* | 0.040 | 95 | 0.326 | 25 | | |
| 379 | 0.003 | 96 | 0.044 | 62 | | |
| 380 | 0.400 | 71 | >1 | | | |
| 381 | 0.207 | 65 | 0.108 | 29 | | |
| 382 | 0.629 | 48 | >1 | | | |
| 383 | 0.226 | 77 | >1 | | | |
| A-1* | 0.012 | 82 | >50 | | 0.007 | 63 |
| B-1 | 0.006 | 97 | >1 | | | |
| B-2 | 0.098 | 93 | >10 | | | |
| B-3* | 0.057 | 84 | >50 | | | |
| B-4* | 0.010 | 98 | >1 | | >10 | |
| C-1* | 0.159 | 64 | >50 | | | |

HEK293 IKZF2 Degradation Kinetics

The assay technology and principles for evaluating IKZF2 degradation kinetics in HEK293 cells was identical to the HEK293 degradation assay as described above. Additional details are briefly described below.

On Day 1, Cells were grown and induced the same as described above. On Days 2 and 3, compounds for testing were dispensed via ECHO and cells were lifted and plated into compound-spotted assay plates as above. Plates were returned to the 37° C. incubator until addition of Nano-Glo lytic reagent at 1, 2, 3, 4.5, and 24 hour timepoints. At these timepoints, plates were read on Envision reader as above.

All raw data was normalized to DMSO control (final concentration: 0.5%) wells as POC and plotted out as a function of time to generate the degradation rate constant (K) value. The maximum degradation rate (K$_{inact}$) was determined by plotting the K value as a function of concentration for each compound tested. K$_{inact}$ values are shown in Table 25 and the degradation rate plots as well as timecourse of degradation are shown for select compounds in FIG. 1A, FIG. 1B, FIG. 2A and FIG. 2B. Results from the IKZF2 degradation kinetics studies further demonstrate that methylene linked compounds provided herein, such as the compounds of Example 2 or 46, can promote faster degradation of IKZF2 than directly-linked Reference Compound A-1, ether-linked Reference Compounds B-3 or B-4, or amine-linked Reference Compounds C-1.

Without wishing to be bound by theory, it is believed that the faster IKZF2 degradation mediated by exemplified compounds of this disclosure is evidence of the formation of a differentiated conformation of a ternary IKZF2-degrader-ubiquitin ligase complex that can be induced by exemplified methylene-linked degrader compound and that can promote a highly efficient ubiquitinylation and proteasomal degradation of IKZF2.

TABLE 25

Kinetics of IKF2 degradation (HEK293)

| Example No. | Maximum degradation rate K$_{inact}$ (hr$^{-1}$) |
|---|---|
| 2 | 0.53 |
| 46 | 0.57 |
| 53 | 0.53 |
| 87 | 0.50 |
| 116 | 0.54 |
| 181 | 0.38 |
| 218 | 0.47 |
| 238 | 0.53 |
| 242 | 0.54 |
| 257 | 0.48 |
| 283 | 0.34 |
| 287 | 0.68 |
| 289 | 0.47 |
| 291 | 0.31 |
| 325 | 0.39 |
| 328 | 0.63 |
| 329 | 0.57 |
| 369 | 0.38 |
| 373 | 0.40 |
| A-1 | 0.14 |
| B-3 | 0.20 |
| B-4 | 0.52 |
| C-1 | 0.03 |

Human Whole Blood IKZF2 Degradation

In vitro IKZF2 potency was assessed in human whole blood using a fluorescence activated cell sorting assay. 50 μL of freshly collected blood from healthy human volunteers was incubated with Immunocult CD3/CD28 activator (Stemcell Technologies) and solution of testing compounds (serially-diluted) for 24 hrs hours at 37° C. in 384 well plates. The treated red blood cells were removed by adding lysis buffer (BD cat #558049) then the cells were fixed, permeabilized, and stained with anti-CD4 (BD cat #564419), anti-Foxp3 (Invitrogen cat #48-4777-42), anti-IKZF1 (Cell Signaling Tech. cat #33462S), and anti-IKZF2

(Cell Signaling Tech. cat #65432S) antibodies. The median fluorescent intensity (MFI) of IKZF2 signal from CD4/CD25/Foxp3+ Treg cells and MFI of IKZF1 signal from CD4+ T cells were quantified in the same samples by flow cytometry using an Attune instrument. $EC_{50}$ and $D_{max}$ of each compound was determined by plotting the MFI and DMSO treated wells were used as control. Data for IKZF2 degradation is presented in Table 26. Asterisks (*) indicate examples for which data represents an average of n≥3 repeat experiments.

The results of Table 26 further confirm the observation that the methylene-linker chemistry exemplified in the compounds provided herein can result in more potent IKZF2 degraders (see, e.g., Example 46 and Reference Compound B-4).

TABLE 26

Human whole blood degradation

| Example No. | IKZF2 $EC_{50}$ (μM) | $D_{max}$ (%) |
|---|---|---|
| 7 | 0.002 | 98 |
| 23 | 0.006 | 98 |
| 24 | 0.008 | 89 |
| 28 | 0.003 | 99 |
| 46 | 0.003 | 96 |
| 52 | 0.005 | 95 |
| 53 | 0.004 | 96 |
| 56 | 0.008 | 97 |
| 63 | 0.019 | 91 |
| 74 | 0.003 | 93 |
| 79 | 0.005 | 93 |
| 82 | 0.004 | 89 |
| 84 | 0.001 | 93 |
| 85 | 0.002 | 96 |
| 87 | 0.003 | 95 |
| 89 | 0.005 | 97 |
| 94 | 0.007 | 90 |
| 95 | 0.011 | 89 |
| 101 | 0.006 | 95 |
| 103 | 0.004 | 96 |
| 109 | 0.001 | 97 |
| 110 | 0.003 | 98 |
| 114 | 0.005 | 98 |
| 115 | 0.006 | 90 |
| 116 | 0.001 | 89 |
| 117 | 0.001 | 92 |
| 118 | 0.001 | 91 |
| 119 | 0.002 | 92 |
| 122 | 0.002 | 97 |
| 124 | 0.023 | 91 |
| 125 | 0.003 | 91 |
| 129 | 0.009 | 91 |
| 136 | 0.006 | 97 |
| 137 | 0.002 | 99 |
| 138 | 0.003 | 96 |
| 142 | 0.005 | 94 |
| 145 | 0.004 | 100 |
| 148 | 0.006 | 92 |
| 155 | 0.012 | 91 |
| 159 | 0.005 | 94 |
| 181 | 0.008 | 99 |
| 196 | 0.003 | 98 |
| 206 | 0.010 | 101 |
| 208 | 0.003 | 97 |
| 214 | 0.003 | 98 |
| 217 | 0.002 | 89 |
| 218 | 0.004 | 97 |
| 219 | 0.010 | 97 |
| 220 | 0.003 | 98 |
| 221 | 0.004 | 101 |
| 222 | 0.006 | 95 |
| 223 | 0.003 | 95 |
| 238 | 0.003 | 90 |
| 239 | 0.003 | 90 |
| 240 | 0.002 | 99 |
| 242 | 0.002 | 98 |
| 244 | 0.002 | 95 |
| 246 | 0.003 | 99 |
| 247 | 0.004 | 95 |
| 250 | 0.004 | 100 |
| 251 | 0.002 | 98 |
| 252 | 0.001 | 97 |
| 256 | 0.010 | 95 |
| 257 | 0.005 | 93 |
| 266 | 0.006 | 98 |
| 267 | 0.002 | 97 |
| 272 | 0.002 | 97 |
| 277 | 0.002 | 95 |
| 281 | 0.005 | 98 |
| 283 | 0.005 | 96 |
| 287 | 0.002 | 92 |
| 288 | 0.005 | 92 |
| 289 | 0.005 | 90 |
| 290 | 0.006 | 96 |
| 291 | 0.005 | 96 |
| 299 | 0.002 | 96 |
| 305 | 0.004 | 95 |
| 328 | 0.002 | 94 |
| 329 | 0.004 | 97 |
| A-1 | 0.013 | 82 |
| B-4 | 0.017 | 97 |

Jurkat IKZF2 Degradation and IL-2 Functional Assays

Jurkat cell line (ATCC, Clone E6-1), highly expresses IKZF2 and lends it an appropriate system to screen degradation along with a functional readout. Jurkat cells were grown to 80% confluency in TC medium (RPMI containing glutamax, 10% FBS, 1% NEAA, and 1% Pen/Strep Glutamin in tissue culture flasks.

The cells were spun down at 400 g for 5 mins and counted. 100 K cells per well were added to a 96-well plate. The compounds were introduced starting at 10 μM and dilutions were made 1:10 for each compound. 100 μL of compound was added to each well for a 12-point titration. The cells were incubated at 37° C. with 5% $CO_2$ overnight.

The following day, supernatants were collected for a functional readout using ELISA. The supernatants were diluted 1:2 and added to appropriate Human IL-2 plates for IL-2 functional readout.

Cells were stained with appropriate surface and intracellular antibodies and acquired by flow cytometry and analysed for degradation.

Figure 3A:
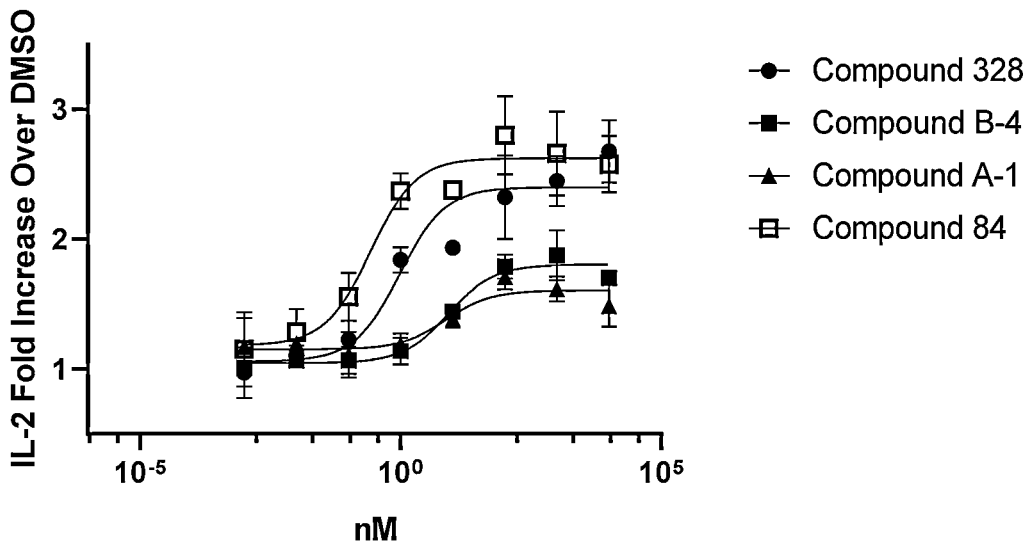
FIG. 3A shows titration curves of IL-2 production in Jurkat cells IKZF2 (Helios) for the compounds of Example 328 (Compound 328; solid circle) and Example 84 (Compound 84; open square), and Reference Compounds A-1 (Compound A-1; solid triangle), and B-4 (Compound B-4; solid square).
Figure 3B:
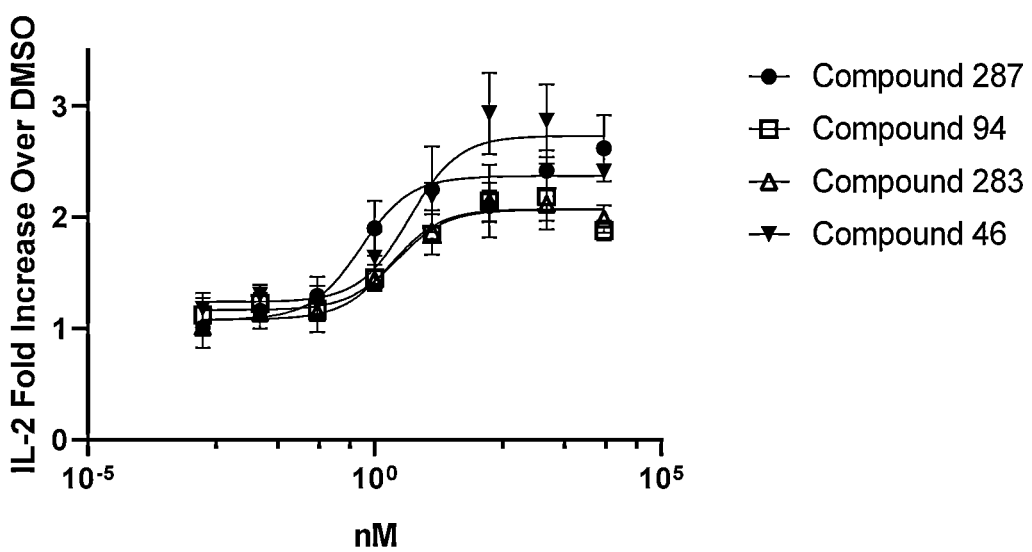
FIG. 3B shows titration curves of IL-2 production in Jurkat cells IKZF2 (Helios) for the compounds of Example 287 (Compound 287; solid circle), Example 94 (Compound 94; open square), Example 283 (Compound 283; open triangle), and Example 46 (Compound 46; solid triangle).
Figure 3C:
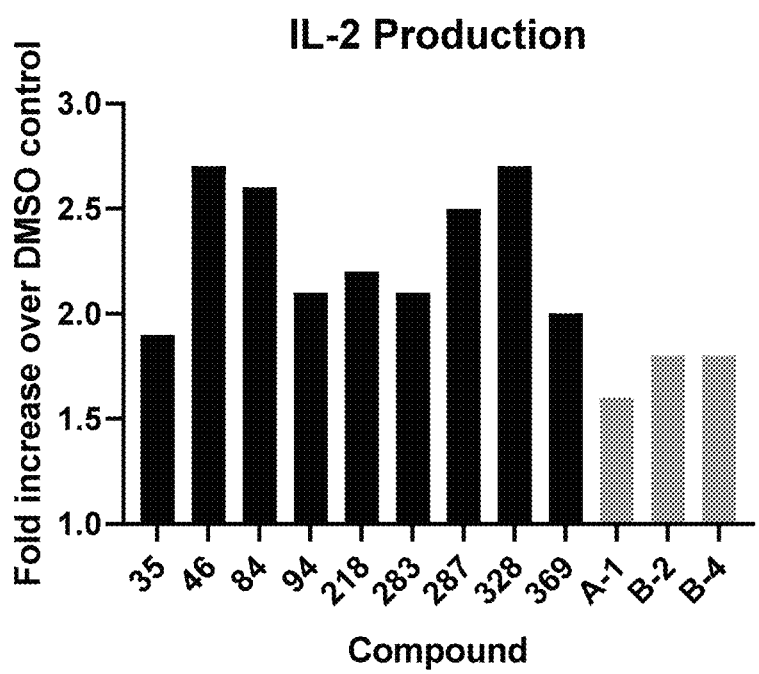
FIG. 3C shows a bar diagram illustrating the Jurkat IL-2 production levels (relative to a DMSO control) achieved at saturating compound concentrations for the IKZF2 (Helios) degrader compounds of Examples 35, 46, 84, 94, 218, 283, 287, 328, and 369, and Reference Compounds A-1, B-2, and B-4.

All raw data was normalized to DMSO control and plotted out for IKZF2 degradation [$EC_{50}$ and $D_{max}$ (Maximum degradation at the highest concentration tested in the assay)] and IL-2 production ($EC_{50}$ and IL-2 fold increase over DMSO control) as shown in Table 27 and FIG. 3A, FIG. 3B, and FIG. 3C. The top of the curve fit for each compound is reported as the IL-2 'fold increase over DMSO control.'

Reference Compounds A-1, B-2, and B-4 induced a 1.6-fold to 1-8 fold increase in IL-2 production in Jurkat cells relative to DMSO control. In contrast, the compounds of Examples 35, 46, 84, 94, 218, 283, 287, 328, 369 provided herein induced ≥1.9-fold increase in IL-2 production, with compounds of Examples 46, 84, 287, demonstrating >2.5-fold increase in IL-2 production. The ability of these compounds to illicit increased IL-2 response offers the potential for enhanced proinflammatory cytokine production by T cells in the tumor microenvironment and robust tumor killing.

TABLE 27

Jurkat IKZF2 degradation and IL-2 production

| Example No. | IKZF2 Degradation | | IL-2 Production | |
|---|---|---|---|---|
| | $EC_{50}$ (nM) | $D_{max}$ (%) | $EC_{50}$ (nM) | Fold increase over DMSO control |
| 35 | 3.9 | 83 | 141 | 1.9 |
| 46 | 2.0 | 95 | 3.5 | 2.7 |
| 84 | 0.05 | 97 | 0.2 | 2.6 |
| 94 | 2.0 | 88 | 2.3 | 2.1 |
| 218 | 0.8 | 93 | 8.0 | 2.2 |
| 283 | 1.4 | 90 | 1.9 | 2.1 |
| 287 | 0.6 | 96 | 0.6 | 2.5 |
| 328 | 0.4 | 96 | 3.4 | 2.7 |
| 369 | 0.1 | 90 | 0.03 | 2.0 |
| A-1 | 7.5 | 61 | 10 | 1.6 |
| B-2 | 6.1 | 83 | 18 | 1.8 |
| B-4 | 5.8 | 94 | 7.8 | 1.8 |

In Vitro Tumor Lysis Assay

Assessment of Treg functional activity following IKZF2 degradation can be determined by running a tumor lysis assay in the presence or absence of Tregs. In some forms of the assay, Tregs can be pretreated or simultaneously treated with an IKZF2 (Helios) degrader compound provided herein or Reference Compound while mixed with purified naïve CD8 T cells and tumor cells derived from tumor cell lines such as MDA-MB-231 (breast cancer). In other forms of the assay, purified naïve CD8 T cells and tumor cells derived from tumor cell lines such as MDA-MB-231 can be simultaneously treated with an IKZF2 (Helios) degrader compound provided herein or Reference Compound in the absence of Tregs. Lysis of tumor cells by CD8 effector T cells in the presence of suppressive Tregs can be measured, and compound activity ranked based on the reversal of Treg suppression and enhancement of tumor lysis. In various forms of the assay, cytokine production from supernatants, or direct measurement of tumor cell death can be used to identify compounds having reduced Treg suppressive function, improved CD8 effector T cell activation and/or tumor lysis activity and therefore increased potential as anticancer therapeutics.

Ubiquitin Modified Peptide Analysis

Ubiquitin analysis of IKZF2 (Helios) is performed by mass spectrometry to identify lysine residues in IKZF2 (Helios) that are ubiquitinated following degrader compound treatment or using DMSO as control. An observation of differentiated ubiquitinylation patterns in IKZF2 (Helios) following treatment with either methylene-linked IKFZ2 (Helios) degrader compounds provided herein or with Reference Compounds containing differentiated structural features (e.g., directly linked, ether-linked, or amide-linked IKFZ2 degrader Reference Compounds) can further elucidate distinct modes of action by which different compound series mediate IKZF2 (Helios) degradation at the molecular level.

In brief, $1 \times 10^8$ of IKZF2 (Helios) expressing HEK293 T cells are harvested and lysed in 1 ml urea lysis buffer (9 M urea, 20 mM HEPES pH 8.0, 1 mM sodium orthovanadate, 2.5 mM sodium pyrophosphate, 1 mM b-glycerophosphate). Samples are sonicated at 15 W with 3 bursts of 15 sec each. Then the cell lysate is cleared by centrifugation at 20,000×g for 15 min at room temperature and the supernatant is transferred to a new tube and quantified by BCA assay. 3.6 µl 1.25 M DTT, 100 µl iodoacetamide, and 3 ml 20 mM HEPES pH 8.0 is added to 1 mL of lysate and incubated at room temperature for 60 minutes at room temperature in the dark for reduction and alkylation of proteins. Protein samples are further digested with trypsin followed by lysate peptide purification from C18 reversed-phase Sep-Pak columns from Waters (#WAT054955) according to the manufacturer's instruction. Immunoaffinity purification is then performed using a PTMScan® Ubiquitin Remnant Motif (K-ε-GG) Kit (Cell signaling technology cat #5562) according to the manufacturer's instruction. Ubiquitinated peptides are identified and quantified by liquid chromatography-mass spectrometry (LC-MS). Searches are performed against the most recent update of the UniProt *Homo sapiens* database with a mass accuracy of +1-50 ppm for precursor ions and 0.02 Da for product ions. Ubiquitin-modified peptide are confirmed with mass accuracy of +/−5 ppm on precursor ions and the presence of the intended motif.

SUMMARY

The data presented herein demonstrates that the methylene-linked IKZF2 (Helios) degraders of this disclosure are characterized by a SAR that is distinct from the SAR of previously described IKZF2 degraders. The discovery of a distinct SAR further enabled the identification of IKZF2 degrader compounds with improved degradation properties and improved therapeutic potential.

Unless otherwise defined, all technical and scientific terms used herein have the same meaning as commonly understood by one of ordinary skill in the art to which this disclosure belongs.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

SEQUENCE LISTING

```
Sequence total quantity: 2
SEQ ID NO: 1            moltype = AA   length = 11
FEATURE                 Location/Qualifiers
source                  1..11
                        mol_type = protein
                        organism = synthetic construct
SEQUENCE: 1
VSGWRLFKKI S                                                                    11

SEQ ID NO: 2            moltype = AA   length = 8
FEATURE                 Location/Qualifiers
source                  1..8
                        mol_type = protein
                        organism = synthetic construct
SEQUENCE: 2
GSSGGSSG                                                                         8
```

The invention claimed is:

1. A compound of the formula:

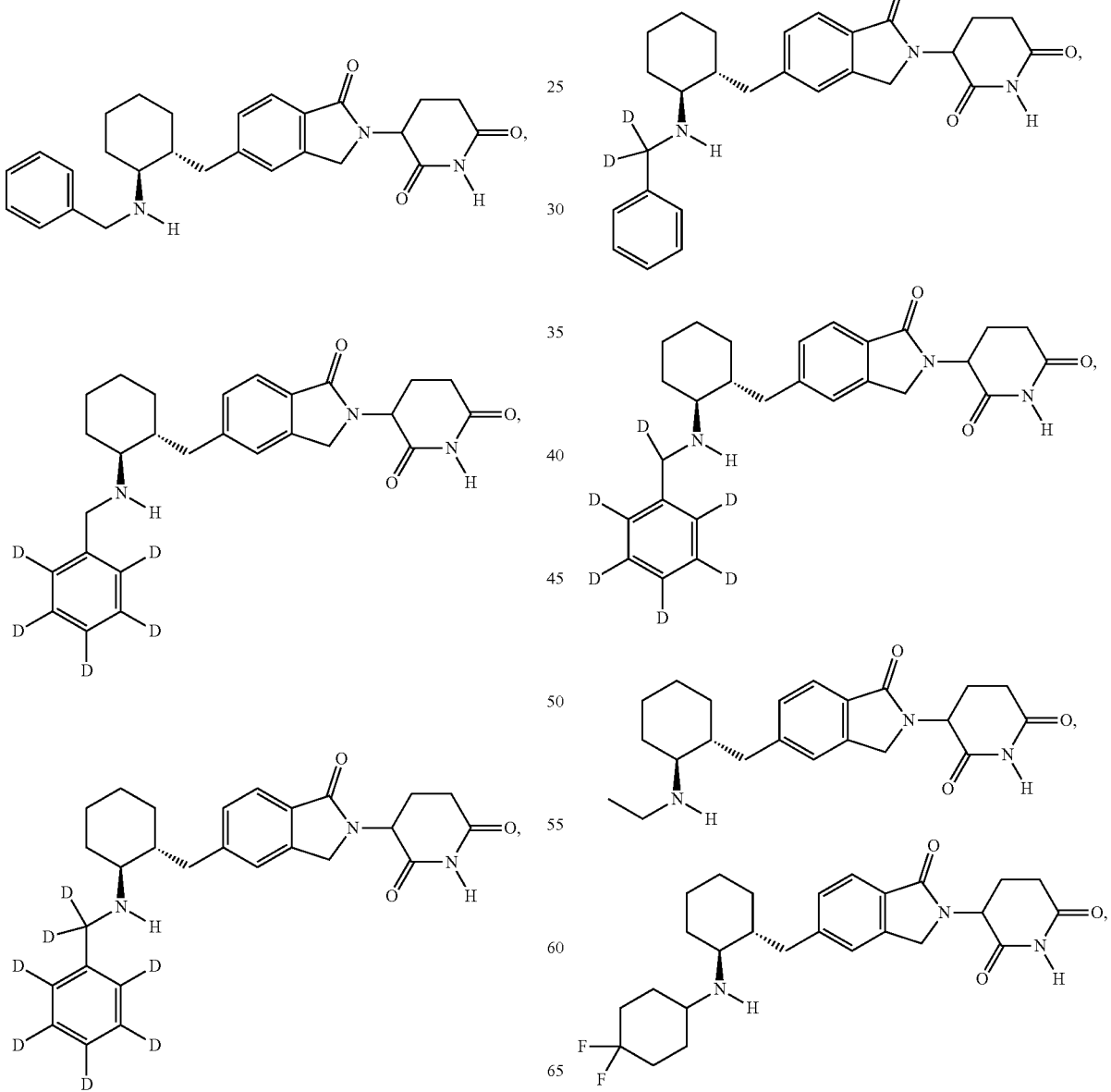

647
-continued
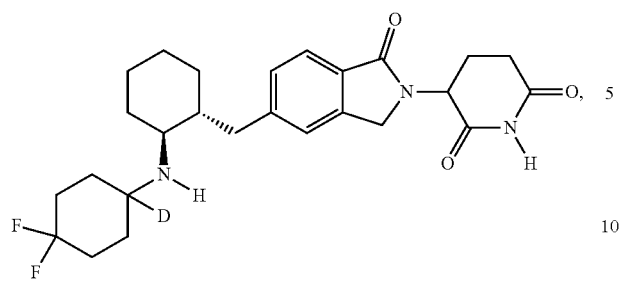
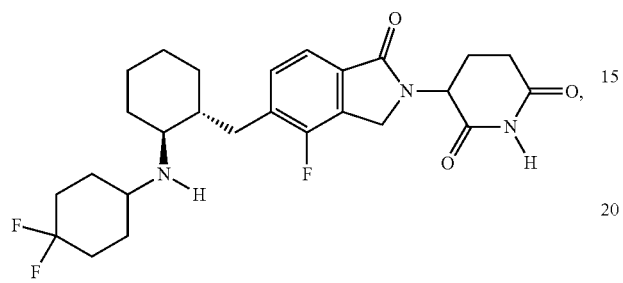
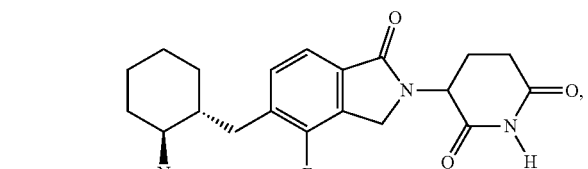
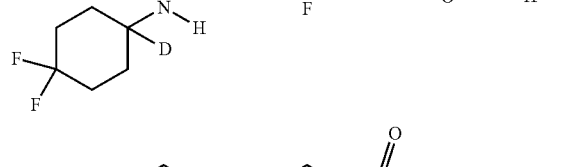
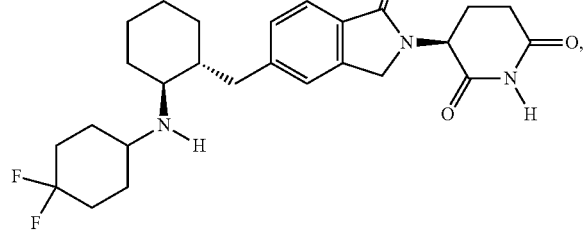
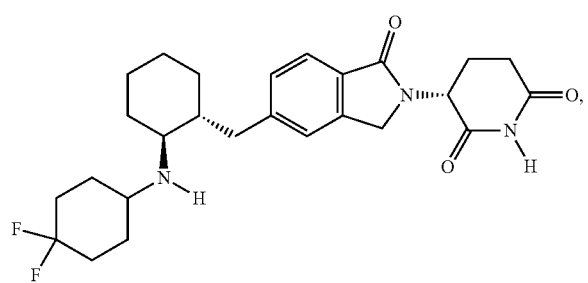
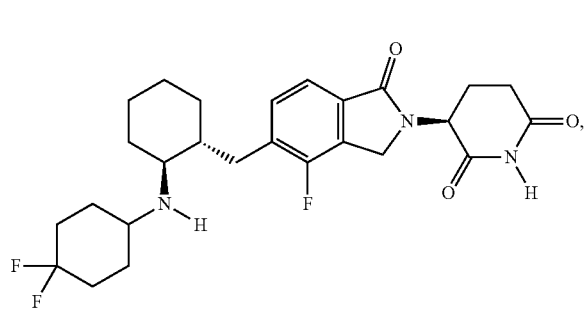
648
-continued
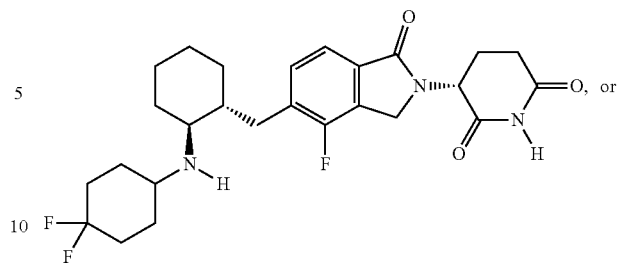, or
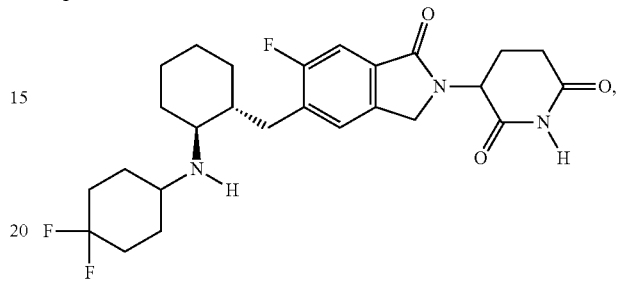
or a pharmaceutically acceptable salt thereof.
2. The compound or pharmaceutically acceptable salt thereof of claim 1, wherein the compound is
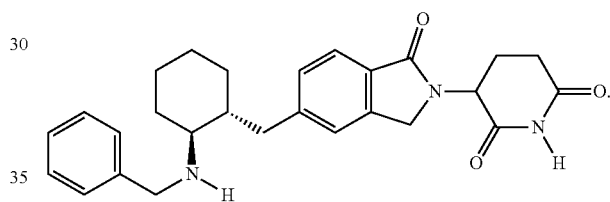
3. The compound or pharmaceutically acceptable salt thereof of claim 1, wherein the compound is
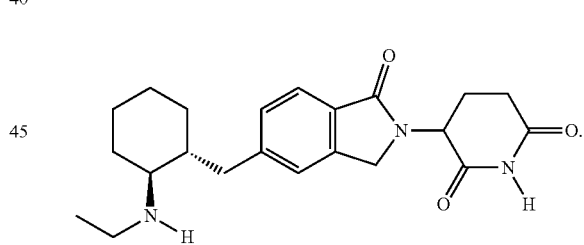
4. The compound or pharmaceutically acceptable salt thereof of claim 1, wherein the compound is
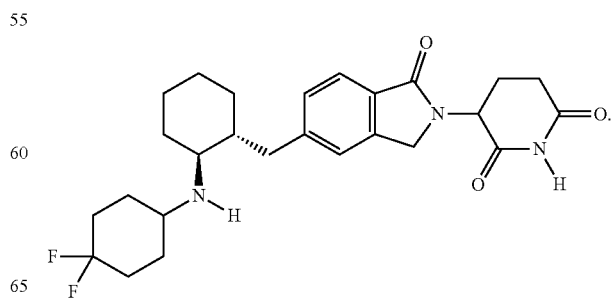

5. The compound or pharmaceutically acceptable salt thereof of claim 1, wherein the compound is

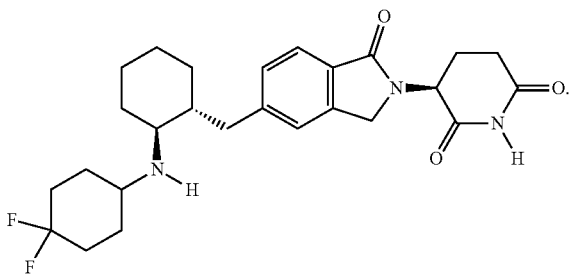 [SMILES: O=C1CC[C@H](N2Cc3cc(C[C@H]4CCCC[C@@H]4NC4CCC(F)(F)CC4)ccc3C2=O)C(=O)N1]

6. The compound or pharmaceutically acceptable salt thereof of claim 1, wherein the compound is

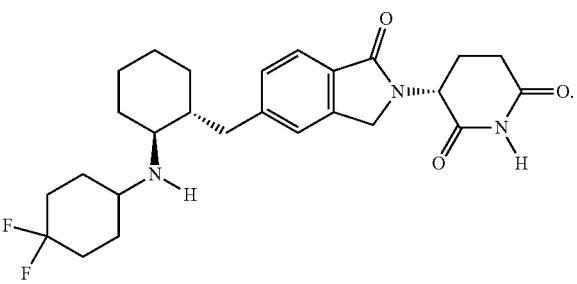 [SMILES: O=C1CC[C@@H](N2Cc3cc(C[C@H]4CCCC[C@@H]4NC4CCC(F)(F)CC4)ccc3C2=O)C(=O)N1]

7. The compound or pharmaceutically acceptable salt thereof of claim 1, wherein the compound is

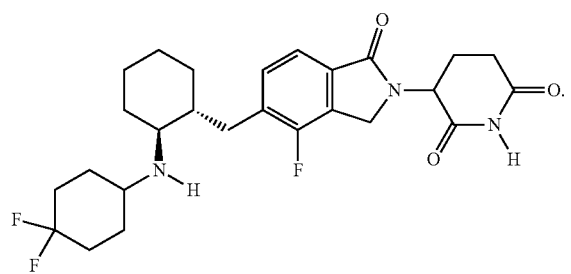 [SMILES: O=C1CCC(N2Cc3c(ccc(C[C@H]4CCCC[C@@H]4NC4CCC(F)(F)CC4)c3F)C2=O)C(=O)N1]

8. The compound or pharmaceutically acceptable salt thereof of claim 1, wherein the compound is

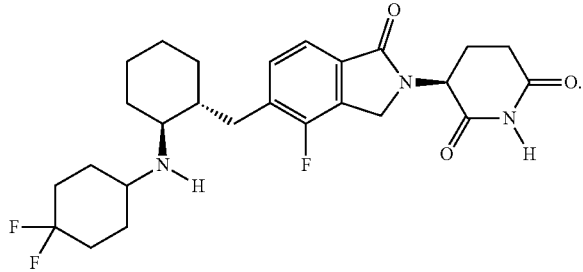 [SMILES: O=C1CC[C@H](N2Cc3c(ccc(C[C@H]4CCCC[C@@H]4NC4CCC(F)(F)CC4)c3F)C2=O)C(=O)N1]

9. The compound or pharmaceutically acceptable salt thereof of claim 1, wherein the compound is

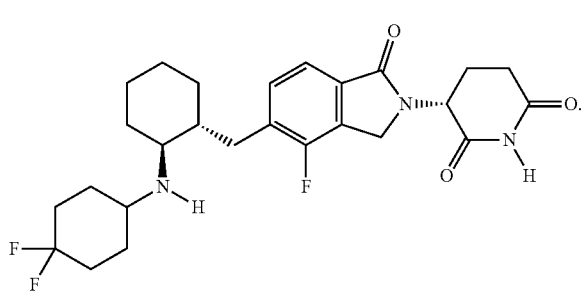 [SMILES: O=C1CC[C@@H](N2Cc3c(ccc(C[C@H]4CCCC[C@@H]4NC4CCC(F)(F)CC4)c3F)C2=O)C(=O)N1]

10. The compound or pharmaceutically acceptable salt thereof of claim 1, wherein the compound is

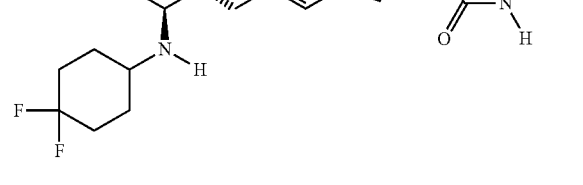

* * * * *